(12) United States Patent
Bignan et al.

(10) Patent No.: US 8,399,681 B2
(45) Date of Patent: Mar. 19, 2013

(54) SUBSTITUTED AMINOTHIAZOLONE INDAZOLES AS ESTROGEN RELATED RECEPTOR-ALPHA MODULATORS

(75) Inventors: Gilles Bignan, Bridgewater, NJ (US); Micheal Gaul, Yardley, PA (US); Guozhang Xu, Bensalem, PA (US); Bao-Ping Zhao, West Windsor, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/566,214

(22) Filed: Aug. 3, 2012

(65) Prior Publication Data

US 2012/0302544 A1  Nov. 29, 2012

Related U.S. Application Data

(62) Division of application No. 12/969,984, filed on Dec. 16, 2010, now Pat. No. 8,263,781.

(60) Provisional application No. 61/287,740, filed on Dec. 18, 2009.

(51) Int. Cl.
| | |
|---|---|
| C07D 277/14 | (2006.01) |
| C07D 211/32 | (2006.01) |
| C07D 513/00 | (2006.01) |
| C07D 413/14 | (2006.01) |
| C07D 223/02 | (2006.01) |
| C07D 243/08 | (2006.01) |
| C07D 295/04 | (2006.01) |
| A61K 31/397 | (2006.01) |
| A61K 31/55 | (2006.01) |
| A61K 31/535 | (2006.01) |
| A61K 31/50 | (2006.01) |
| A61K 31/497 | (2006.01) |
| A61K 31/445 | (2006.01) |

(52) U.S. Cl. ......... 548/184; 546/199; 546/235; 544/18; 544/62; 544/133; 544/368; 540/484; 540/492; 540/582; 514/210.01; 514/217.1; 514/226.2; 514/232.8; 514/249; 514/254.02; 514/278; 514/321; 514/365

(58) Field of Classification Search .......................... None
See application file for complete search history.

(56) References Cited

U.S. PATENT DOCUMENTS
6,518,268 B1  2/2003  Chin et al.
2006/0014812 A1  1/2006  Player et al.

FOREIGN PATENT DOCUMENTS
| EP | 0537300 B1 | 4/1995 |
| EP | 1398029 A1 | 3/2004 |
| WO | WO 98/27113 A2 | 6/1998 |
| WO | WO 2006/047269 A2 | 5/2006 |
| WO | WO 2008/071451 A1 | 6/2008 |
| WO | WO 2008/109737 A1 | 9/2008 |

OTHER PUBLICATIONS

Aranda et al., "Nuclear Hormone Receptors and Gene Expression.", Physiol. Rev., 2001, pp. 1269-1304, vol. 81(3).
Ariazi et al., "Estrogen-related Receptor α and Estrogen-related Receptor γ Associate with Unfavorable and Favorable Biomarkers, Respectively, in Human Breast Cancer 1.", Cancer Res., 2002, pp. 6510-6518, vol. 62.
Berge et al., "Pharmaceutical Salts.", J. Pharm. Sci., 1977, pp. 1-19, vol. 66(1).
Bonnelye et al., "Estrogen Receptor-Related Receptor α Impinges on the Estrogen Axis in Bone: Potential Function in Osteoporsis.", Endocrinology, 2002, pp. 2658-3670, vol. 143(9).
Bonnelye et al., "The ERR-1 Orphan Receptor Is a Transcriptional Activator Expressed During Bone Development.", Mol. Endocrin, 1997, pp. 905-916, vol. 11.

(Continued)

Primary Examiner — Kamal Saeed
Assistant Examiner — Nyeemah A Grazier
(74) Attorney, Agent, or Firm — Jeremy K. McKown

(57) ABSTRACT

The present invention relates to compounds of Formula (I),

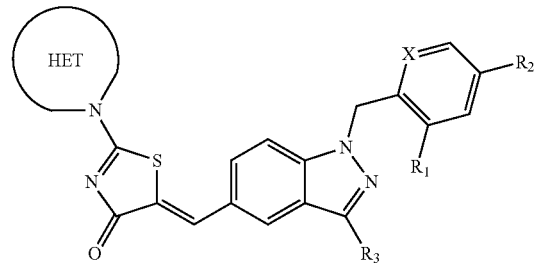

(I)

methods for preparing these compounds, compositions, intermediates and derivatives thereof and for treating a condition including but not limited to ankylosing spondylitis, artherosclerosis, arthritis (such as rheumatoid arthritis, infectious arthritis, childhood arthritis, psoriatic arthritis, reactive arthritis), bone-related diseases (including those related to bone formation), breast cancer (including those unresponsive to anti-estrogen therapy), cardiovascular disorders, cartilage-related disease (such as cartilage injury/loss, cartilage degeneration, and those related to cartilage formation), chondrodysplasia, chondrosarcoma, chronic back injury, chronic bronchitis, chronic inflammatory airway disease, chronic obstructive pulmonary disease, diabetes, disorders of energy homeostasis, gout, pseudogout, lipid disorders, metabolic syndrome, multiple myeloma, obesity, osteoarthritis, osteogenesis imperfecta, osteolytic bone metastasis, osteomalacia, osteoporosis, Paget's disease, periodontal disease, polymyalgia rheumatica, Reiter's syndrome, repetitive stress injury, hyperglycemia, elevated blood glucose level, and insulin resistance.

14 Claims, No Drawings

OTHER PUBLICATIONS

Bonnelye, et al., "The Orphan Nuclear Estrogen Receptor—related Receptor α (ERRα) Is Expressed throughout Osteoblast Differentiation and Regulates Bone Formation in Vitro.", J. Cell Biol. 2001, pp. 971-984, vol. 153.

Giguere et al., "Identification of a new class of steroid hormone receptors.", Nature, 1988, pp. 91-94, vol. 331.

Giguere, V., "Orphan Nuclear Receptors: From Gene to Function*.", Endocrine Rev., 1999, pp. 689-725, vol. 20(5).

Giguere, V., "To ERR in the estrogen pathway.", Trends in Endocrinol. Metab., 2002, pp. 220-225, vol. 13.

Gould P.L., "Salt Selection for Basic Drugs.", International J. Pharm., 1986, pp. 201-217, vol. 33.

Grundy et al., "Definition of Metabolic Syndrome: Report of the National Heart, Lung, and Blood Institute/American Heart Association Conference on Scientific Issues Related to Definition.", Circulation, 2004, pp. 433-438, vol. 109(3).

Hong et al., "Hormone-independent Transcriptional Activation and Coactivator Binding by Novel Orphan Nuclear Receptor ERR3*,", J. Biol. Chem. 1999. 22618-22626, vol. 274.

Jinbo, Y. et al., "Synthesis and Antibacterial Activity of Thiazolopyrazine-Incorporated Tetracyclic Quinolone Antibacterial Agents. 2.", J. Med. Chem. 1994, pp. 2791-2796, vol. 37.

Jones, P.L. and Y.B. Shi., "N-CoR-HDAC Corepressor Complexes: Roles in Transcriptional Regulation by Nuclear Hormone Receptors.", Curr. Top. Microbiol. Immunol., 2003, pp. 237-268, vol. 274.

Kamei et al., "PPARγ coactivator 1β ERR ligand 1 is an ERR protein ligand, whose expression induces a high-energy expenditure and antagonizes obesity.", Proc. Natl. Acad. Sci., 2003, pp. 12378-12383, vol. 100(21), USA.

Kodair, A.I., "A Convenient Synthesis of 2-Aryidene-5H-thiazolo[2,3-b]quinazoline-3,5[2H]diones and Their Benzoquinazoline Derivatives.", J. Heterocyclic Chem., Nov.-Dec. 2002, pp. 1153-1160, vol. 39.

Korach, K. S., "Insights from the Study of Animals Lacking Functional Estrogen Receptor.", Science, Jan. 1994, pp. 1524-1527, vol. 266.

Kraus et al., "Estrogen-related Receptor α1 Actively Antagonizes Estrogen Receptor-regulated Transcription in MCF-7 Mammary Cells*.", J. Biol. Chem., 2002, pp. 24826-24834, vol. 272.

Luo et al., "Reduced Fat Mass in Mice Lacking Orphan Nuclear Receptor Estrogen-Relatedα.", Mol. Cell. Biol., 2003, pp. 7947-7956, vol. 23(22).

McKenna et al., "Nuclear Receptor Coregulators: Cellular and Molecular Biology.", Endocrine Rev., 1999, pp. 321-344, vol. 20.

Olefsky, J.M., "Minireview Prologue. Nuclear Receptor Minireview Series*.", J. Biol. Chem., 2001, pp. 36863-36864, vol. 276(40).

Pacifici, R.J., "Estrogen, Cytokines, and Pathogenesis of Postmenopausal Osteoporosis.", Bone Miner. Res., 1996, pp. 1043-1051, vol. 11(8).

Rochette-Egly et al., "Retinoic Acid Receptor β: Immunodetection and Phosphorylation on Tyrosine Residues.", Mol. Endocrinol., 1992, pp. 2197-2209, vol. 6.

Rochette-Egly et al., "Stimulation of RARa Activation Function AF-1 through Binding to the General Transcription Factor TFIIH and Phosphorylation by CDK7.", Cell, 1997, pp. 97-107, vol. 90.

Sladek et al., "The Orphan Nuclear Receptor Estrogen-Related Receptor α Is a Transcriptional Regulator of the Human Medium-Chain Acyl Coenzyme A Dehydrogenase Gene.", Mol. Cell. Biol. 1997, pp. 5400-5409, vol. 17.

Sumi, D. and L.J. Ignarro, "Estrogen-related receptor α1 up-regulates endothelial nitric oxide synthase expression.", Proc Natl. Acad. Sci. 2003, pp. 14451-14456, vol. 100.

Turner et al., "Skeletal Effects of Estrogen.", Endocrine Rev. 1994, pp. 275-300, vol. 15(3).

Vanacker, "Transcriptional targets shared by estrogen receptor-related receptors (ERRs) and estrogen receptor (ER) α, but not by ERβ.", The EMBO Journal, 1999, pp. 4270-4279, vol. 18.

Vega, R.B. and D.P. Kelly, "A Role for Estrogen-related Receptor α in the Control of Mitochondrial Fatty Acid β-Oxidation during Brown Adipocyte Differentiation*.", J. Biol. Chem. 1997, pp. 31693-31699, vol. 272.

Windahl et al., "Increased cortical bone mineral content but unchanged trabecular bone mineral density in female ERβ / mice.", J. Clin. Invest., 1999, pp. 895-901, vol. 104(7).

Wurtz et al., "A canonical structure for ligand-binding domain of nuclear receptors.", Nat. Struct. Biol.,1996, pp. 87-94, vol. 3.

Xu et al., "Structural basis for antagonist mediated recruitment of nuclear co-repressors by PPARa.", Nature 2002, pp. 813-817, vol. 415 (6873).

Zhang, Z. and C.T. Teng, "Estrogen Receptor-related Receptor α1 Interacts with Coactivator and Constitutively Activates the Estrogen Response Elements of the Human Lactoferrin Gene*.", J. Biol. Chem., 2000, pp. 20837-20846, vol. 275.

International Search Report relating to International Patent Application No. PCT/US2010/060720. Date of Mailing of International Search Report: Feb. 21, 2011.

Written Opinion of the International Searching Authority relating to International Patent Application No. PCT/US2010/060720. Date of Mailing of Written Opinion: Feb. 21, 2011.

SUBSTITUTED AMINOTHIAZOLONE INDAZOLES AS ESTROGEN RELATED RECEPTOR-ALPHA MODULATORS

CROSS REFERENCE TO RELATED APPLICATIONS

This Application is a divisional application of U.S. Application Ser. No. 12/969,984, filed Dec. 16, 2010, which claims priority to U.S. Provisional Application 61/287,740, filed on Dec. 18, 2009 the disclosures of which are hereby incorporated by reference in their entireties.

FIELD OF THE INVENTION

The present invention relates to certain novel compounds, methods for preparing compounds, compositions, intermediates and derivatives thereof and for treating conditions such as cancer, arthritis, inflammatory airway disease, and metabolic disorders. More particularly, the compounds of the present invention are Estrogen Related Receptor alpha (ERR-α) modulators useful for treating, ameliorating, preventing or inhibiting the progression of disease states, disorders, and conditions mediated by ERR-α activity.

BACKGROUND OF THE INVENTION

Nuclear receptors are members of a superfamily of transcription factors. The members of this family share structural similarities and regulate a diverse set of biological effects (Olefsky, J. M. J. Biol. Chem. 2001, 276(40), 36863-36864). Ligands activate or repress these transcription factors that control genes involved in metabolism, differentiation and reproduction (Laudet, V. and H. Gronmeyer. The Nuclear Receptor Factbooks. 2002, San Diego: Academic Press). Presently, the human genome project has identified about 48 members for this family and cognate ligands have been identified for about 28 of them (Giguere, V. Endocrine Rev. 1999, 20(5), 689-725). This protein family is composed of modular structural domains that can be interchanged within the members of the family without loss of function. A typical nuclear receptor contains a hypervariable N-terminus, a conserved DNA binding domain (DBD), a hinge region, and a conserved ligand-binding domain (LBD). The function of the DBD is targeting of the receptor to specific DNA sequences (Nuclear Hormone Receptor (NHR) response elements or NREs), and the function of the LBD is recognition of its cognate ligand. Within the sequence of the nuclear receptor there are regions involved in transcriptional activation. The Activation Function 1 (AF-1) domain is situated at the N-terminus and constitutively activates transcription (Rochette-Egly, C. et al. Cell 1997, 90, 97-107; Rochette-Egly, C. et al. Mol. Endocrinol. 1992, 6, 2197-2209), while the Activation Function 2 (AF-2) domain is embedded within the LBD and its transcriptional activation is ligand dependent (Wurtz, J. M. et al. Nat. Struct. Biol. 1996, 3, 87-94). Nuclear receptors can exist as monomers, homodimers or heterodimers and bind to direct or inverted nucleotide repeats (Laudet and Gronmeyer, 2002; Aranda, A. and A. Pascual. Physiol. Rev. 2001, 81(3), 1269-1304).

The members of this family exist either in an activated or repressed basal biological state. The basic mechanism of gene activation involves ligand dependent exchange of co-regulatory proteins. These co-regulatory proteins are referred to as co-activators or co-repressors (McKenna, L. J. et al. Endocrine Rev. 1999, 20, 321-344). A nuclear receptor in the repressed state is bound to its DNA response element and is associated with co-repressor proteins that recruit histone de-acetylases (HDACs) (Jones, P. L. and Y. B. Shi. Curr. Top. Microbiol. Immunol. 2003, 274, 237-268). In the presence of an agonist there is an exchange of co-repressors with co-activators that in turn recruit transcription factors that assemble into an ATP dependent chromatin-remodeling complex. Histones are hyper-acetylated, causing the nucleosome to unfold, and repression is alleviated. The AF-2 domain acts as the ligand dependent molecular switch for the exchange of co-regulatory proteins. In the presence of an agonist the AF-2 domain undergoes a conformational transition and presents a surface on the LBD for interaction with co-activator proteins. In the absence of an agonist or in the presence of an antagonist the AF-2 domain presents a surface that promotes interactions with co-repressor proteins. The interaction surfaces on the LBD for both co-activators, and co-repressors overlap and provide a conserved molecular mechanism for gene activation or repression that is shared by the members of this family of transcription factors (Xu, H. E. et al. Nature 2002, 415 (6873), 813-817).

Natural ligands that modulate the biological activity of nuclear receptors have been identified for only approximately one half of known nuclear receptors. Receptors for which no natural ligand has been identified are termed "orphan receptors." The discovery of ligands or compounds that interact with an orphan receptor will accelerate the understanding of the role of the nuclear receptors in physiology and disease and facilitate the pursuit of new therapeutic approachesEstrogen related receptors (ERRs) constitutes a sub-class of these receptors where no ligand has been identified.

ERR-α (also known as ERR-1), an orphan receptor, is the first of the three identified members of the estrogen receptor related subfamily of orphan nuclear receptors (ERR-α, β, γ). The ERR subfamily is closely related to the estrogen receptors (ER-α and ER-β). ERR-α and ERR-β were first isolated by a low stringency hybridization screen (Giguere, V. et al. Nature 1988, 331, 91-94) followed later with the discovery of ERR-γ (Hong, H. et al. J. Biol. Chem. 1999, 274, 22618-22626). The ERRs and ERs share sequence similarity with the highest homology observed in their DBDs, approximately 60%, and all interact with the classical DNA estrogen response element. Recent biochemical evidence suggested that the ERRs and ERs share target genes, including pS2, lactoferin, aromatase and osteopontin, and share co-regulator proteins (Giguere, V. Trends in Endocrinol. Metab. 2002, 13, 220-225; Vanacker, J. M. et al. EMBO J. 1999, 18, 4270-4279; Kraus, R. J. et al. J. Biol. Chem. 2002, 272, 24286-24834; Hong et al., 1999; Zhang, Z. and C. T. Teng. J. Biol. Chem. 2000, 275, 20387-20846). Therefore, one of the main functions of ERR is to regulate the response of estrogen responsive genes. The effect of the steroid hormone estrogen is primarily mediated in the breast, bone and endometrium. Thus, the identification of compounds that will interact with ERRs should provide a benefit for the treatment of bone related disease, breast cancer and reproduction.

ERR-α is shown to be present both in normal and breast cancer tissue (Ariazi, E. A. et al. Cancer Res. 2002, 62, 6510-6518). It has been reported that the main function of ERR-α in normal breast tissue is that of a repressor for estrogen responsive genes. In breast cancers or cell lines that are non-estrogen responsive (ER-α negative), ERR-α has been reported to be in an activated state (Ariazi et al., 2002). Therefore, compounds that will interact with ERR-α may be useful agents for the treatment of breast cancer that is ER-α negative and non-responsive to classical anti-estrogenic therapy, or may be used as an adjunct agent for anti-estrogen responsive breast cancers. These agents may act as antagonists by reducing the biological activity of ERR-α in these particular tissues.

Many post-menopausal women experience osteoporosis, a condition that is a result of the reduction of estrogen production. Reduction of estrogen levels results in an increase of bone loss (Turner, R. T. et al. Endocrine Rev. 1994, 15(3), 275-300). An anabolic effect on bone development has been observed on the administration of estrogens to postmenopausal patients with osteoporosis (Pacifici, R. J. Bone Miner. Res. 1996, 11(8), 1043-1051) but the molecular mechanism is unknown since ER-a and ER-b knock-out animals have minor skeletal defects, where the action of estrogens is typically mediated (Korach, K. S. Science 1994, 266, 1524-1527; Windahl, S. H. et al. J. Clin. Invest. 1999, 104(7), 895-901). Expression of ERR-α in bone is regulated by estrogen (Bonnelye, E. et al. Mol. Endocrin. 1997, 11, 905-916; Bonnelye, E. et al. J. Cell Biol. 2001, 153, 971-984). ERR-α is maintained throughout osteoblast differentiation stages. Over-expression of ERR-α in rat calvaria osteoblasts, an accepted model of bone differentiation, results in an increase of bone nodule formation, while treatment of rat calvaria osteoblasts with ERR-α antisense results in a decrease of bone nodule formation. ERR-α also regulates osteopontin, a protein believed to be involved in bone matrix formation. Therefore compounds that will modulate ERR-α by increasing its activity can have an anabolic effect for the regeneration of bone density and provide a benefit over current approaches that prevent bone loss, but have no anabolic effect. Such compounds can enhance the activity of the receptor by two possible mechanisms: i) enhancing the association of the receptor with proteins that enhance its activity or improve the stability of the receptor; and ii) increasing the intracellular concentrations of the receptor and consequently increasing its activity. Conversely, with respect to bone diseases that are a result of abnormal bone growth, compounds that will interact with ERR-α and decrease its biological activity may provide a benefit for the treatment of these diseases by retarding bone growth. Antagonism of the association of the receptor with co-activator proteins decreases the activity of the receptor.

ERR-α is also present in cardiac, adipose, and muscle tissue and forms a transcriptional active complex with the PGC-1 co-activator family, co-activators implicated with energy homeostasis, mitochondria biogenesis, hepatic gluconeogenesis and in the regulation of genes involved in fatty acid beta-oxidation (Kamei, Y. et al. Proc. Natl. Acad. Sci. USA 2003, 100(21), 12378-12383). ERR-α regulates the expression of the medium chain acyl-CoA dehydrogenase promoter (MCAD). Medium chain acyl-CoA dehydrogenase is a gene involved in the initial reaction in fatty acid beta-oxidation. It is believed that in the adipose tissue ERR-α regulates energy expenditure through the regulation of MCAD (Sladek, R. et al. Mol. Cell. Biol. 1997, 17, 5400-5409; Vega, R. B. and D. P. Kelly. J. Biol. Chem. 1997, 272, 31693-31699). In antisense experiments in rat calvaria osteoblasts, in addition to the inhibition of bone nodule formation, there was an increase in adipocyte differentiation markers including aP2 and PPAR-γ (Bonnelye, E. et al. Endocrinology 2002, 143, 3658-3670). Recently an ERR-α knockout model has been described that exhibited reduced fat mass relative to the wild type and DNA chip analysis data indicated alteration of the expression levels of genes involved in adipogenesis and energy metabolism (Luo, J. et al. Mol. Cell. Biol. 2003, 23(22), 7947-7956). More recently it has been shown that ERR-α regulates the expression of endothelial nitric oxide synthase, a gene that has a protective mechanism against arteriosclerosis (Sumi, D. and L. J. Ignarro. Proc Natl. Acad.

Sci. 2003, 100, 14451-14456). The biochemical evidence supports the involvement of ERR-α in metabolic homeostasis and differentiation of cells into adipocytes. Therefore, compounds interacting with ERR-α can affect energy homeostasis and may therefore provide a benefit for the treatment of obesity and metabolic syndrome related disease indications, including arteriosclerosis and diabetes (Grundy, S. M. et al. Circulation 2004, 109(3), 433-438).

There is a continuing need for new ERR-α modulators. There is also a need for ERR-α modulators useful for the treatment of conditions including but not limited to ankylosing spondylitis, artherosclerosis, arthritis (such as rheumatoid arthritis, infectious arthritis, childhood arthritis, psoriatic arthritis, reactive arthritis), bone-related diseases (including those related to bone formation), breast cancer (including those unresponsive to anti-estrogen therapy), cardiovascular disorders, cartilage-related disease (such as cartilage injury/loss, cartilage degeneration, and those related to cartilage formation), chondrodysplasia, chondrosarcoma, chronic back injury, chronic bronchitis, chronic inflammatory airway disease, chronic obstructive pulmonary disease, diabetes, disorders of energy homeostasis, gout, pseudogout, lipid disorders, metabolic syndrome, multiple myeloma, obesity, osteoarthritis, osteogenesis imperfecta, osteolytic bone metastasis, osteomalacia, osteoporosis, Paget's disease, periodontal disease, polymyalgia rheumatica, Reiter's syndrome, repetitive stress injury, hyperglycemia, elevated blood glucose level, and insulin resistance.

SUMMARY OF THE INVENTION

In its many embodiments, the present invention provides novel compounds useful as, for example, ERR-α modulators, methods of preparing such compounds, pharmaceutical compositions comprising one or more such compounds, methods of preparing pharmaceutical compositions comprising one or more such compounds, and methods of treatment, prevention, inhibition or amelioration of one or more diseases associated with ERR-α using such compounds or pharmaceutical compositions.

One aspect of the present invention features a compound of Formula (I)

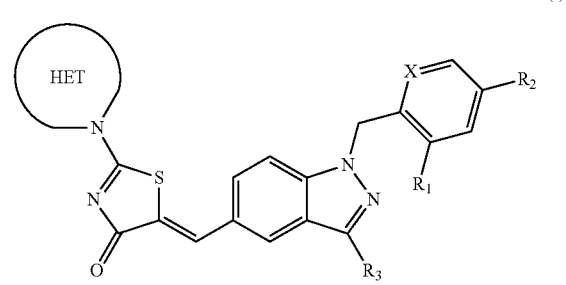

wherein

X is —CH— or N;

$R_1$ is $C_{1-3}$alkyl, halo, cycloalkyl, or —C(O)—$C_{1-4}$alkyl; wherein said $C_{1-3}$alkyl may be substituted with halo;

$R_2$ is —H, halo, cyano, $C_{1-3}$alkyl, $C_{2-4}$alkenyl, $C_{1-4}$alkoxy, hydroxyl, cycloalkyl, —C(O)O—$C_{1-4}$alkyl, —C(O)NH$_2$, —OS(O$_2$)—$C_{1-4}$alkyl, —O—$C_{1-4}$alkyl-O—$C_{1-4}$alkyl, heterocyclyl, heteroaryl, or —S(O$_2$)—C$_{1-4}$alkyl; wherein said C$_{1-3}$alkyl may be substituted with halo or hydroxyl, R$_3$ is —H, halo, cyano, or C$_{1-3}$alkyl; and

is a 4 to 9 membered heterocyclyl bonded to the rest of the molecule through a ring nitrogen atom and optionally containing 1-2 heteroatoms in addition to said ring nitrogen atom, wherein the optional 1-2 additional heteroatoms are independently selected from the group consisting of N, O and S;

wherein said 4 to 9 membered heterocyclyl may be substituted with C$_{1-4}$alkyl, C$_{2-4}$alkenyl, C$_{2-4}$alkynyl, halo, oxo, cyano, hydroxyl, —OR$^5$, —O—C$_{1-4}$alkyl-C(O)OR$^5$, cycloalkyl, heteroaryl, heterocyclyl, —C(O)OR$^5$, —C(O)N(R$^5$)(R$^6$), —C(O)N(R$^5$)(OR$^6$), —C(O)R$^5$, —C(O)—C$_{1-4}$alkyl-N(R$^5$)(R$^6$), —C(O)—C$_{1-4}$alkyl-O—C$_{1-4}$alkyl, —C(O)N(R$^5$)—S(O)$_2$(R$^6$), —C(O)N(R$^5$)—OR$^6$, —C(O)N(R$^5$)S(O)$_2$N(R$^5$)(R$^6$), —C(O)N(R$^5$)—C$_{1-4}$alkyl-C(O)OR$^6$, —N(R$^5$)(R$^6$), —N(R$^5$)—C$_{1-4}$alkyl-OR$^6$, —N(R$^5$)C(O)R$^6$, —N(R$^5$)C(O)OR$^6$, —N(R$^5$)S(O)$_2$R$^6$, —N(R$^5$)C(O)—NH(R$^6$), —N(R$^5$)—C$_{1-4}$alkyl-C(O)—NH(R$^6$), —SR$^5$, —S(O)$_2$R$^5$, or —S(O)$_2$—N(R$^5$)(R$^6$);

wherein said C$_{1-4}$alkyl may be substituted with —OH, —O—C$_{1-4}$alkyl, —C(O)OR$^5$, —C(O)N(R$^5$)(R$^6$), —N(R$^5$)(R$^6$), —N(R$^5$)C(O)OR$^6$, heterocyclyl, heteroaryl, cycloalkyl, or halo;

wherein said heteroaryl may be substituted with C$_{1-4}$alkyl, halo, cyano, —CF$_3$, alkoxy or hydroxyl;

wherein said heterocyclyl may be substituted with C$_{1-4}$alkyl, oxo, halo, amino, alkoxy, or hydroxyl;

wherein said C$_{2-4}$alkenyl and said C$_{2-4}$alkynyl may be independently substituted with oxo, heterocyclyl, hydroxyl, or halo;

wherein R$^5$ and R$^6$ are each independently H, C$_{1-4}$alkyl, cycloalkyl, or heterocyclyl, wherein said C$_{1-4}$alkyl may be substituted with halo or hydroxyl; or alternatively R$^5$ and R$^6$ are linked together to form a 5 to 7 membered ring;

or an optical isomer, enantiomer, diastereomer, cis-trans isomer, racemate, or pharmaceutically acceptable salt thereof.

Another aspect of the present invention features a pharmaceutical composition comprising at least one compound of Formula (I) and at least one pharmaceutically acceptable carrier.

The present invention also features a method of treating a subject suffering from or diagnosed with a disease, disorder, or condition mediated by ERR-α activity, comprising administering to the subject a therapeutically effective amount of at least one compound of Formula (I). Such disease, disorder, or condition can include, but is not limited to ankylosing spondylitis, artherosclerosis, arthritis (such as rheumatoid arthritis, infectious arthritis, childhood arthritis, psoriatic arthritis, reactive arthritis), bone-related diseases (including those related to bone formation), breast cancer (including those unresponsive to anti-estrogen therapy), cardiovascular disorders, cartilage-related disease (such as cartilage injury/loss, cartilage degeneration, and those related to cartilage formation), chondrodysplasia, chondrosarcoma, chronic back injury, chronic bronchitis, chronic inflammatory airway disease, chronic obstructive pulmonary disease, diabetes, disorders of energy homeostasis, gout, pseudogout, lipid disorders, metabolic syndrome, multiple myeloma, obesity, osteoarthritis, osteogenesis imperfecta, osteolytic bone metastasis, osteomalacia, osteoporosis, Paget's disease, periodontal disease, polymyalgia rheumatica, Reiter's syndrome, repetitive stress injury, hyperglycemia, elevated blood glucose level, and insulin resistance. The therapeutically effective amount of the compound of Formula (I) can be from about 0.1 mg/day to about 5000 mg/day.

The present invention further features a process for making a pharmaceutical composition comprising admixing any of the compounds according to Formula (I) and a pharmaceutically acceptable carrier.

Additional embodiments and advantages of the invention will become apparent from the detailed discussion, schemes, examples, and claims below.

DETAILED DESCRIPTION OF THE INVENTION

This invention relates to novel ERR-α modulators and compositions thereof for the treatment, amelioration, prevention or inhibition of numerous conditions, including but not limited to cancer, arthritis, inflammatory airway disease, bone-related diseases, metabolic disorders, and associated symptoms or complications thereof.

One aspect of the present invention features a compound of Formula (I)

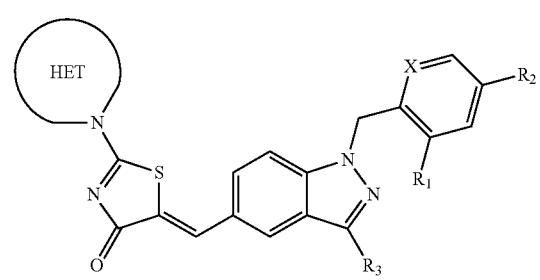

(I)

wherein
X is —CH— or N;
R$_1$ is C$_{1-3}$alkyl, halo, cycloalkyl, and —C(O)—C$_{1-4}$alkyl; wherein the C$_{1-3}$alkyl may be substituted with halo;
R$_2$ is —H, halo, cyano, C$_{1-3}$alkyl, C$_{2-3}$alkenyl, C$_{1-4}$alkoxy, hydroxyl, cycloalkyl, —C(O)O—C$_{1-4}$alkyl, —C(O)NH$_2$, —OS(O$_2$)—C$_{1-4}$alkyl, —O—C$_{1-4}$alkyl-O—C$_{1-4}$alkyl, heterocyclyl, heteroaryl, or —S(O$_2$)—C$_{1-4}$alkyl; wherein the C$_{1-3}$alkyl may be substituted with halo or hydroxyl;
R$_3$ is —H, halo, cyano, or C$_{1-3}$alkyl; and

is a 4 to 9 membered heterocyclyl bonded to the rest of the molecule through a ring nitrogen atom and optionally containing 1-2 heteroatoms in addition to said ring nitrogen atom, wherein the optional 1-2 additional heteroatoms are independently selected from the group consisting of N, O and S;

wherein said 4 to 9 membered heterocyclyl may be substituted with C$_{1-4}$alkyl, C$_{2-4}$alkenyl, C$_{2-4}$alkynyl, halo, oxo, cyano, hydroxyl, —OR$^5$, —O—C$_{1-4}$alkyl-C(O)OR$^5$, cycloalkyl, heteroaryl, heterocyclyl, —C(O)OR$^5$, —C(O)N $(R^5)(R^6)$, —C(O)N($R^5$)(O$R^6$), —C(O)$R^5$, —C(O)—C$_{1-4}$alkyl-N($R^5$)($R^6$), —C(O)—C$_{1-4}$alkyl-O—C$_{1-4}$alkyl, —C(O)N($R^5$)—S(O)$_2$($R^6$), —C(O)N($R^5$)—O$R^6$, —C(O)N($R^5$)S(O)$_2$N($R^5$)($R^6$), —C(O)N($R^5$)—C$_{1-4}$alkyl-C(O)O$R^6$, —N($R^5$)($R^6$), —N($R^5$)—C$_{1-4}$alkyl-O$R^6$, —N($R^5$)C(O)$R^6$, —N($R^5$)C(O)O$R^6$, —N($R^5$)S(O)$_2$$R^6$, —N($R^5$)C(O)—NH($R^6$), —N($R^5$)—C$_{1-4}$alkyl-C(O)—NH($R^6$), —S$R^5$, —S(O)$_2$$R^5$, or —S(O)$_2$—N($R^5$)($R^6$);

wherein said —C$_{1-4}$alkyl may be substituted with —OH, —O—C$_{1-4}$alkyl, —C(O)O$R^5$, —C(O)N($R^5$)($R^6$), —N($R^5$)($R^6$), —N($R^5$)C(O)O$R^6$, heterocyclyl, heteroaryl, cycloalkyl, or halo;

wherein said heteroaryl may be substituted with C$_{1-4}$alkyl, halo, cyano, —CF$_3$, alkoxy or hydroxyl;

wherein said heterocyclyl may be substituted with C$_{1-4}$alkyl, oxo, halo, amino, alkoxy, or hydroxyl;

wherein said C$_{2-4}$alkenyl and said C$_{2-4}$alkynyl may be independently substituted with oxo, heterocyclyl, hydroxyl, or halo;

wherein $R^5$ and $R^6$ are each independently —H, C$_{1-4}$alkyl, cycloalkyl, or heterocyclyl, wherein said C$_{1-4}$alkyl may be substituted with halo or hydroxyl; or alternatively $R^5$ and $R^6$ are linked together to form a 5 to 7 membered ring;

or an optical isomer, enantiomer, diastereomer, cis-trans isomer, racemate or pharmaceutically acceptable salt thereof.

In particular, the present invention includes a cis-trans isomer of the compound of Formula (I), which has the following structure, wherein X, $R_1$, $R_2$, $R_3$ and

are as described above:

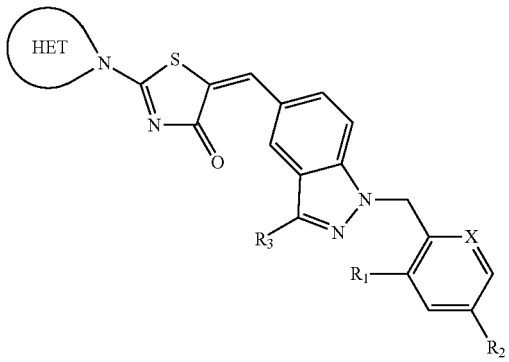

Particularly, X is N. More particularly, X is —CH—.

Particularly, $R_1$ is —C(O)—C$_{1-2}$alkyl, —Cl, —Br, —I, C$_{1-3}$alkyl, or C$_{3-5}$cycloalkyl; wherein the C$_{1-3}$alkyl may be substituted with halo. More particularly, $R_1$ is —C(O)—CH$_3$, —Cl, —Br, —I, —CF$_3$, or cyclopropyl.

Particularly, $R_2$ is —F, —Cl, —Br, cyclopropyl, C$_{1-3}$alkyl, C$_{1-2}$alkoxy, or hydroxyl; wherein the C$_{1-3}$alkyl may be substituted with halo or hydroxyl. More particularly, $R_2$ is —CF$_3$, hydroxyl, —OCH$_3$, or —Cl. More particularly, $R_2$ is —CF$_3$, —OCH$_3$, or —Cl. Even more particularly, $R_2$ is —CF$_3$, or —Cl. Particularly, $R_2$ is —CF$_3$.

Particularly, $R_3$ is —H, halo, or cyano. More particularly, $R_3$ is —H.

Particularly,

is an N-containing heterocyclyl.
Particularly,

is a 4 to 9 membered heterocyclyl bonded to the rest of the molecule through a ring nitrogen atom and containing 0-2 heteroatoms in addition to said ring nitrogen atom, wherein the 0-2 additional heteroatoms are independently selected from the group consisting of N, O and S;

wherein said 4 to 9 membered heterocyclyl may be substituted with C$_{1-4}$alkyl, C$_{2-4}$alkenyl, C$_{2-4}$alkynyl, halo, oxo, cyano, hydroxyl, —O$R^5$, —O—C$_{1-4}$alkyl-C(O)O$R^5$, cycloalkyl, heteroaryl, heterocyclyl, —C(O)O$R^5$, —C(O)N($R^5$)($R^6$), —C(O)N($R^5$)(O$R^6$), —C(O)$R^5$, —C(O)—C$_{1-4}$alkyl-N($R^5$)($R^6$), —C(O)—C$_{1-4}$alkyl-O—C$_{1-4}$alkyl, —C(O)N($R^5$)—S(O)$_2$($R^6$), —C(O)N($R^5$)—O$R^6$, —C(O)N($R^5$)S(O)$_2$N($R^5$)($R^6$), —C(O)N($R^5$)—C$_{1-4}$alkyl-C(O)O$R^6$, —N($R^5$)($R^6$), —N($R^5$)—C$_{1-4}$alkyl-O$R^6$, —N($R^5$)C(O)$R^6$, —N($R^5$)C(O)O$R^6$, —N($R^5$)S(O)$_2$$R^6$, —N($R^5$)C(O)—NH($R^6$), —N($R^5$)—C$_{1-4}$alkyl-C(O)—NH($R^6$), —S$R^5$, —S(O)$_2$$R^5$, or —S(O)$_2$—N($R^5$)($R^6$);

wherein said —C$_{1-4}$alkyl may be substituted with —OH, —O—C$_{1-4}$alkyl, —C(O)O$R^5$, —C(O)N($R^5$)($R^6$), —N($R^5$)($R^6$), —N($R^5$)C(O)O$R^6$, heterocyclyl, heteroaryl, cycloalkyl, or halo;

wherein said heteroaryl may be substituted with C$_{1-4}$alkyl, halo, cyano, —CF$_3$, alkoxy or hydroxyl;

wherein said heterocyclyl may be substituted with C$_{1-4}$alkyl, oxo, halo, amino, alkoxy, or hydroxyl;

wherein said C$_{2-4}$alkenyl and said C$_{2-4}$alkynyl may be independently substituted with oxo, heterocyclyl, hydroxyl, or halo;

wherein $R^5$ and $R^6$ are each independently H, C$_{1-4}$alkyl, cycloalkyl, or heterocyclyl, wherein said C$_{1-4}$alkyl may be substituted with halo or hydroxyl; or alternatively, $R^5$ and $R^6$ are linked together to form a 5 to 7 membered ring.

Particularly,

is a 4 to 9 membered heterocyclyl bonded to the rest of the molecule through a ring nitrogen atom and containing 0 heteroatoms in addition to said ring nitrogen atom, wherein said 4 to 9 membered heterocyclyl may be substituted with C$_{1-4}$alkyl, C$_{2-4}$alkenyl, C$_{2-4}$alkynyl, halo, oxo, cyano, hydroxyl, —O$R^5$, —O—C$_{1-4}$alkyl-C(O)O$R^5$, cycloalkyl, heteroaryl, heterocyclyl, —C(O)O$R^5$, —C(O)N($R^5$)($R^6$), —C(O)N($R^5$)(O$R^6$), —C(O)$R^5$, —C(O)—C$_{1-4}$alkyl-N($R^5$)($R^6$), —C(O)—C$_{1-4}$alkyl-O—C$_{1-4}$alkyl, —C(O)N($R^5$)—S(O)$_2$($R^6$), —C(O)N($R^5$)—O$R^6$, —C(O)N($R^5$)S(O)$_2$N($R^5$)($R^6$), —C(O)N($R^5$)—C$_{1-4}$alkyl-C(O)O$R^6$, —N(R$^5$)(R$^6$), —N(R$^5$)—C$_{1-4}$alkyl-OR$^6$, —N(R$^5$)C(O)R$^6$, —N(R$^5$)C(O)OR$^6$, —N(R$^5$)S(O)$_2$R$^6$, —N(R$^5$)C(O)—NH(R$^6$), —N(R$^5$)—C$_{1-4}$alkyl-C(O)—NH(R$^6$), —SR$^5$, —S(O)$_2$R$^5$, or —S(O)$_2$—N(R$^5$)(R$^6$);

wherein said C$_{1-4}$alkyl may be substituted with —OH, —O—C$_{1-4}$alkyl, —C(O)OR$^5$, —C(O)N(R$^5$)(R$^6$), —N(R$^5$)(R$^6$), —N(R$^5$)C(O)OR$^6$, heterocyclyl, heteroaryl, cycloalkyl, or halo;

wherein said heteroaryl may be substituted with C$_{1-4}$alkyl, halo, cyano, —CF$_3$, alkoxy or hydroxyl;

wherein said heterocyclyl may be substituted with C$_{1-4}$alkyl, oxo, halo, amino, alkoxy, or hydroxyl;

wherein said C$_{2-4}$alkenyl and said C$_{2-4}$alkynyl may be independently substituted with oxo, heterocyclyl, hydroxyl, or halo;

wherein R$^5$ and R$^6$ are each independently H, C$_{1-4}$alkyl, cycloalkyl, or heterocyclyl, wherein said C$_{1-4}$alkyl may be substituted with halo or hydroxyl; or alternatively R$^5$ and R$^6$ are linked together to form a 5 to 7 membered ring.

Particularly,

is a 4 to 9 membered heterocyclyl bonded to the rest of the molecule through a ring nitrogen atom and containing 1 heteroatom in addition to said ring nitrogen atom, wherein the 1 additional heteroatom is independently selected from the group consisting of N, O and S;

wherein said 4 to 9 membered heterocyclyl may be substituted with C$_{1-4}$alkyl, C$_{2-4}$alkenyl, C$_{2-4}$alkynyl, halo, oxo, cyano, hydroxyl, —OR$^5$, —O—C$_{1-4}$alkyl-C(O)OR$^5$, cycloalkyl, heteroaryl, heterocyclyl, —C(O)OR$^5$, —C(O)N(R$^5$)(R$^6$), —C(O)N(R$^5$)(OR$^6$), —C(O)R$^5$, —C(O)—C$_{1-4}$alkyl-N(R$^5$)(R$^6$), —C(O)—C$_{1-4}$alkyl-O—C$_{1-4}$alkyl, —C(O)N(R$^5$)—S(O)$_2$(R$^6$), —C(O)N(R$^5$)—OR$^6$, —C(O)N(R$^5$)S(O)$_2$N(R$^5$)(R$^6$), —C(O)N(R$^5$)—C$_{1-4}$alkyl-C(O)OR$^6$, —N(R$^5$)(R$^6$), —N(R$^5$)—C$_{1-4}$alkyl-OR$^6$, —N(R$^5$)C(O)R$^6$, —N(R$^5$)C(O)OR$^6$, —N(R$^5$)S(O)$_2$R$^6$, —N(R$^5$)C(O)—NH(R$^6$), —N(R$^5$)—C$_{1-4}$alkyl-C(O)—NH(R$^6$), —SR$^5$, —S(O)$_2$R$^5$, or —S(O)$_2$—N(R$^5$)(R$^6$);

wherein said C$_{1-4}$alkyl may be substituted with —OH, —O—C$_{1-4}$alkyl, —C(O)OR$^5$, —C(O)N(R$^5$)(R$^6$), —N(R$^5$)(R$^6$), —N(R$^5$)C(O)OR$^6$, heterocyclyl, heteroaryl, cycloalkyl, or halo;

wherein said heteroaryl may be substituted with C$_{1-4}$alkyl, halo, cyano, —CF$_3$, alkoxy or hydroxyl;

wherein said heterocyclyl may be substituted with C$_{1-4}$alkyl, oxo, halo, amino, alkoxy, or hydroxyl;

wherein said C$_{2-4}$alkenyl and said C$_{2-4}$alkynyl may be independently substituted with oxo, heterocyclyl, hydroxyl, or halo;

wherein R$^5$ and R$^6$ are each independently —H, C$_{1-4}$alkyl, cycloalkyl, or heterocyclyl, wherein said C$_{1-4}$alkyl may be substituted with halo or hydroxyl; or alternatively R$^5$ and R$^6$ are linked together to form a 5 to 7 membered ring.

Particularly,

is a 4 to 9 membered heterocyclyl bonded to the rest of the molecule through a ring nitrogen atom and containing 2 heteroatoms in addition to said ring nitrogen atom, wherein the 2 additional heteroatom are independently selected from the group consisting of N, O and S;

wherein said 4 to 9 membered heterocyclyl may be substituted with C$_{1-4}$alkyl, C$_{2-4}$alkenyl, C$_{2-4}$alkynyl, halo, oxo, cyano, hydroxyl, —OR$^5$, —O—C$_{1-4}$alkyl-C(O)OR$^5$, cycloalkyl, heteroaryl, heterocyclyl, —C(O)OR$^5$, —C(O)N(R$^5$)(R$^6$), —C(O)N(R$^5$)(OR$^6$), —C(O)R$^5$, —C(O)—C$_{1-4}$alkyl-N(R$^5$)(R$^6$), —C(O)—C$_{1-4}$alkyl-O—C$_{1-4}$alkyl, —C(O)N(R$^5$)—S(O)$_2$(R$^6$), —C(O)N(R$^5$)—OR$^6$, —C(O)N(R$^5$)S(O)$_2$N(R$^5$)(R$^6$), —C(O)N(R$^5$)—C$_{1-4}$alkyl-C(O)OR$^6$, —N(R$^5$)(R$^6$), —N(R$^5$)—C$_{1-4}$alkyl-OR$^6$, —N(R$^5$)C(O)R$^6$, —N(R$^5$)C(O)OR$^6$, —N(R$^5$)S(O)$_2$R$^6$, —N(R$^5$)C(O)—NH(R$^6$), —N(R$^5$)—C$_{1-4}$alkyl-C(O)—NH(R$^6$), —SR$^5$, —S(O)$_2$R$^5$, or —S(O)$_2$—N(R$^5$)(R$^6$);

wherein said C$_{1-4}$alkyl may be substituted with —OH, —O—C$_{1-4}$alkyl, —C(O)OR$^5$, —C(O)N(R$^5$)(R$^6$), —N(R$^5$)(R$^6$), —N(R$^5$)C(O)OR$^6$, heterocyclyl, heteroaryl, cycloalkyl, or halo;

wherein said heteroaryl may be substituted with C$_{1-4}$alkyl, halo, cyano, —CF$_3$, alkoxy or hydroxyl;

wherein said heterocyclyl may be substituted with C$_{1-4}$alkyl, oxo, halo, amino, alkoxy, or hydroxyl;

wherein said C$_{2-4}$alkenyl and said C$_{2-4}$alkynyl may be independently substituted with oxo, heterocyclyl, hydroxyl, or halo;

wherein R$^5$ and R$^6$ are each independently —H, C$_{1-4}$alkyl, cycloalkyl, or heterocyclyl, wherein said C$_{1-4}$alkyl may be substituted with halo or hydroxyl; or alternatively, R$^5$ and R$^6$ are linked together to form a 5 to 7 membered ring.

Particularly,

is a 4 to 9 membered heterocyclyl bonded to the rest of the molecule through a ring nitrogen atom and containing 0 heteroatoms in addition to said ring nitrogen atom, wherein said 4 to 9 membered heterocyclyl is selected from

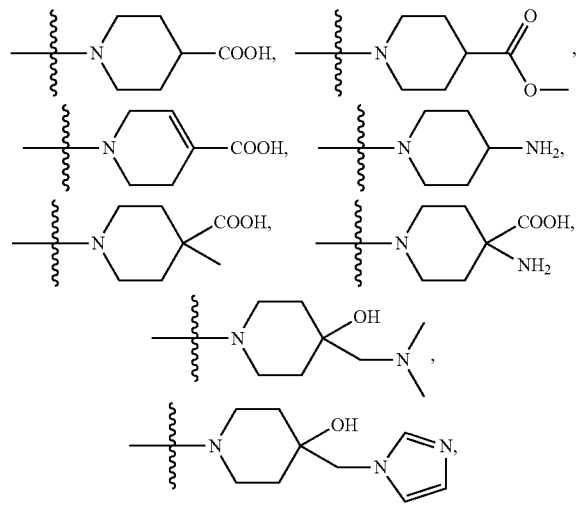

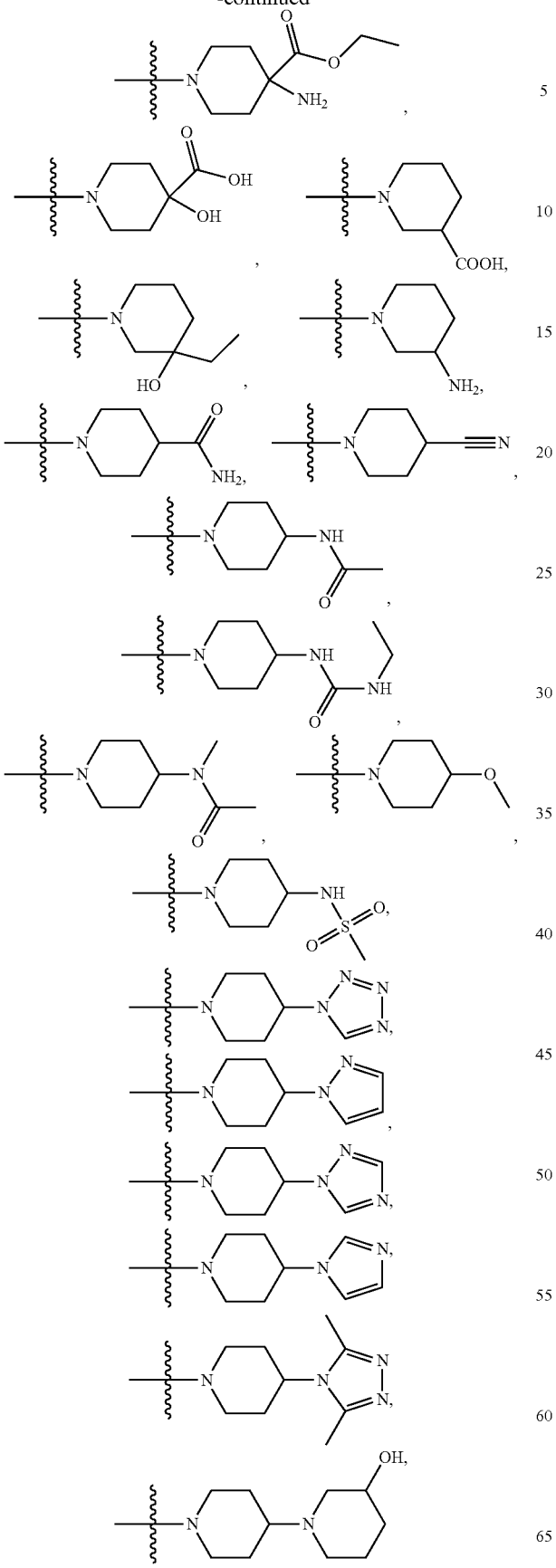
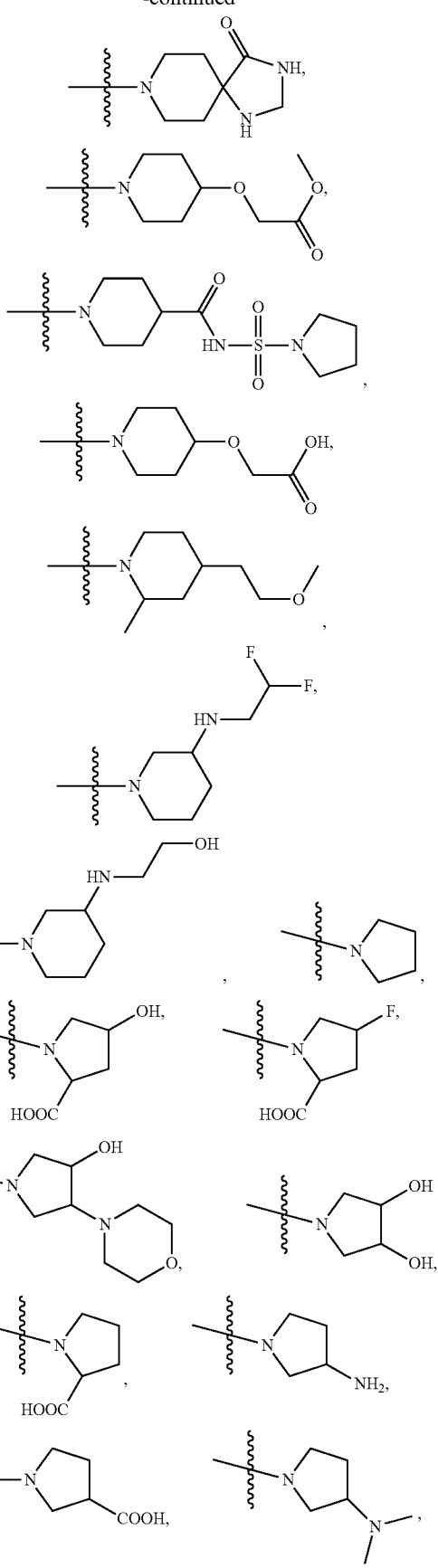

-continued
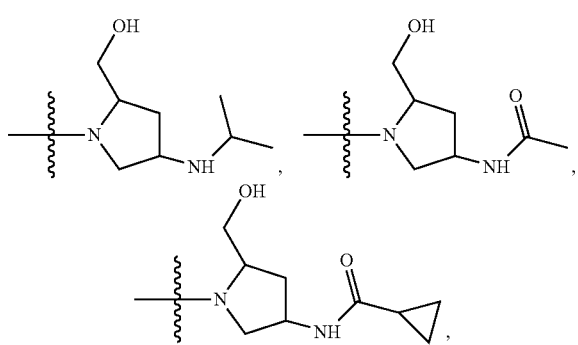
Particularly,
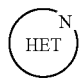
is a 4 to 9 membered heterocyclyl bonded to the rest of the molecule through a ring nitrogen atom and containing 1 heteroatom in addition to said ring nitrogen atom, wherein the 1 additional heteroatom is independently selected from the group consisting of N, O and S;
wherein said 4 to 9 membered heterocyclyl is selected from -continued
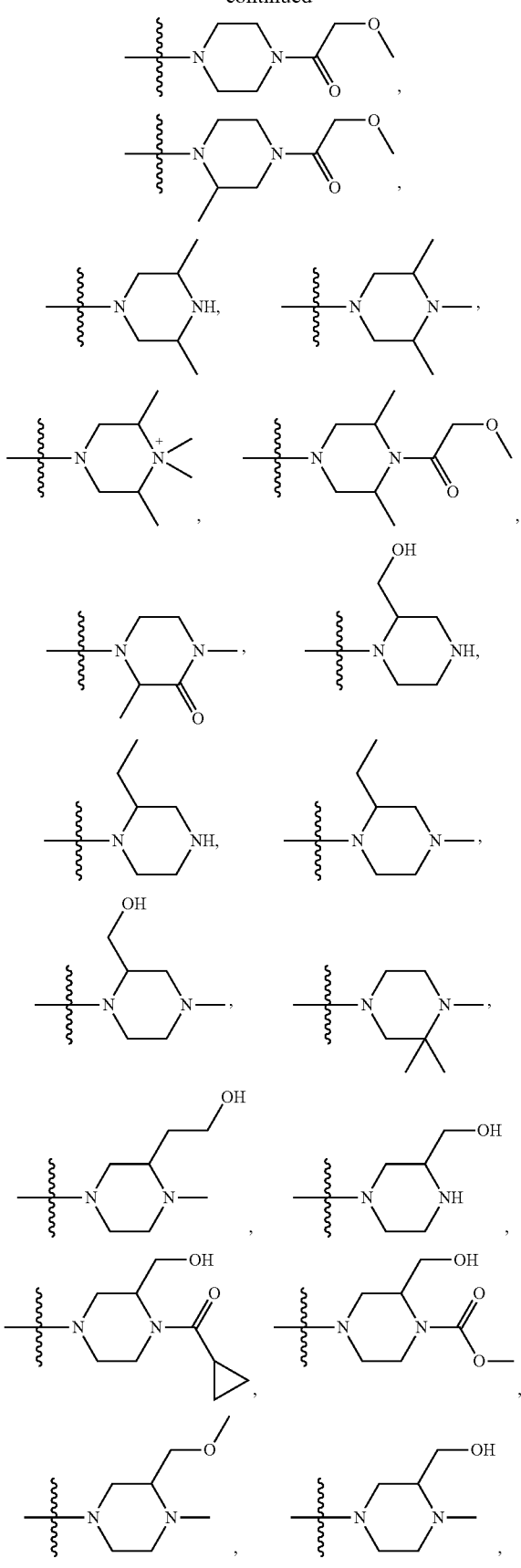
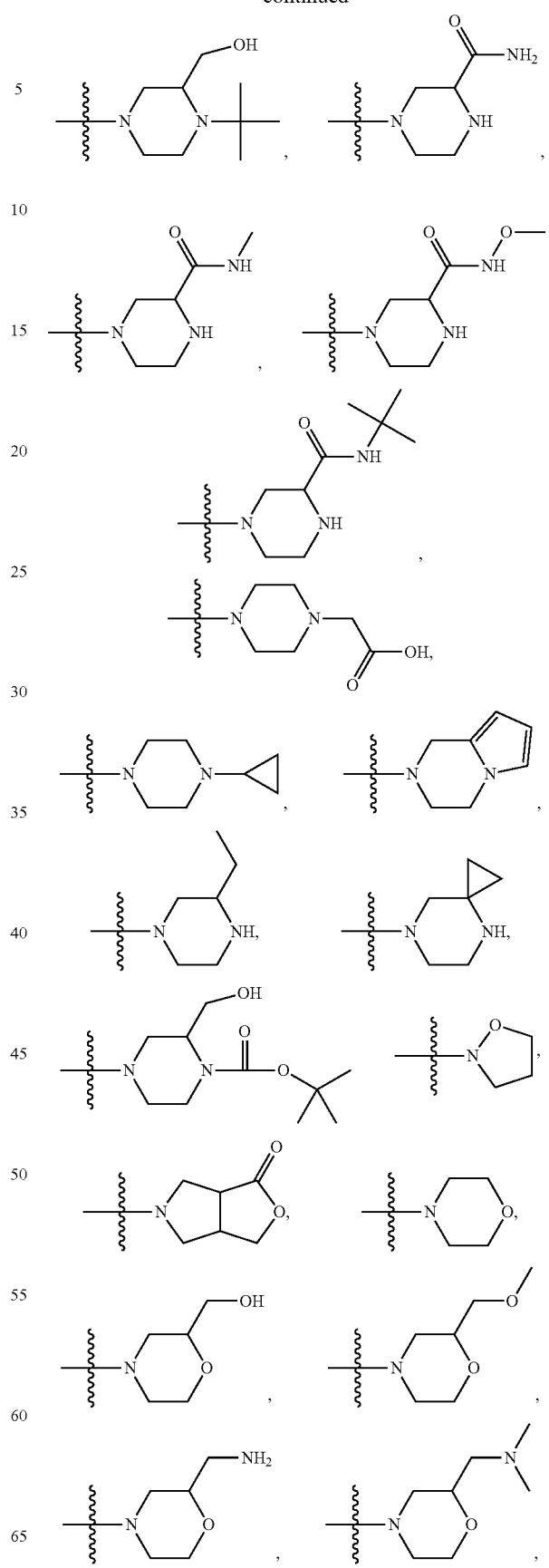

-continued

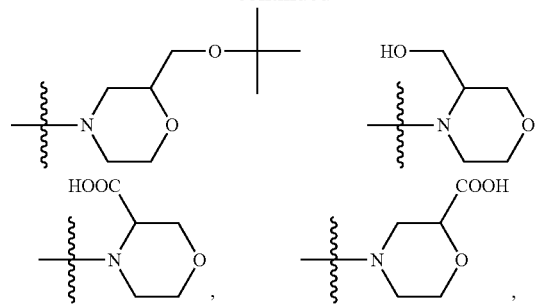
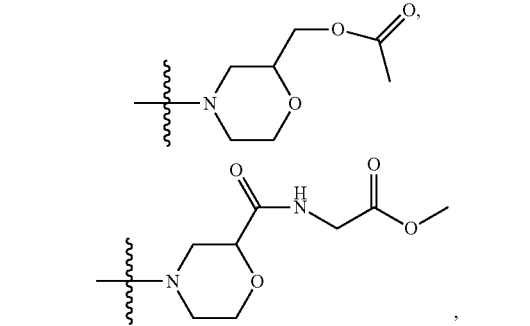
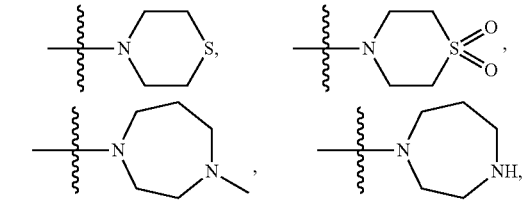
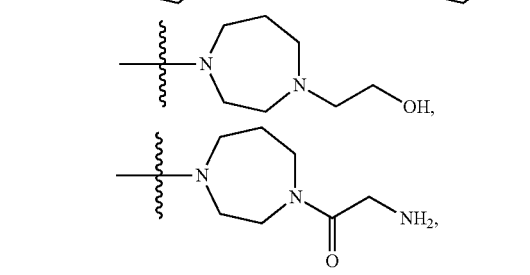
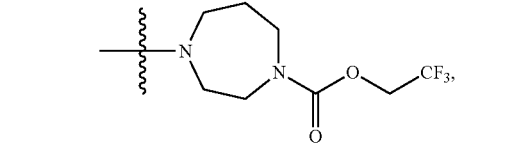
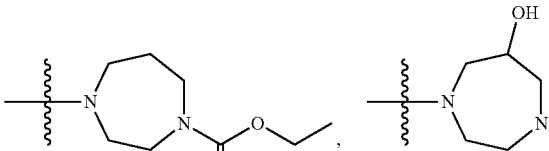
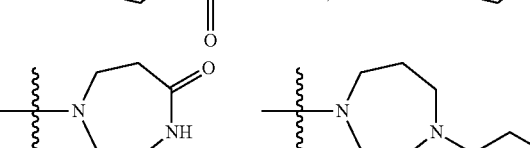
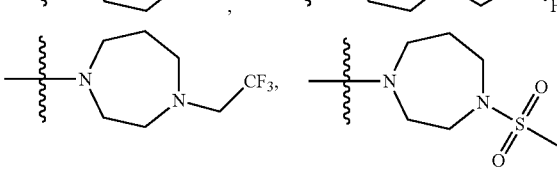

-continued

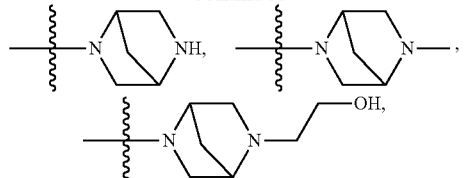

Particularly,

is a 4 to 9 membered heterocyclyl bonded to the rest of the molecule through a ring nitrogen atom and containing 2 heteroatoms in addition to said ring nitrogen atom, wherein the 2 additional heteroatom are independently selected from the group consisting of N, O and S;

wherein said 4 to 9 membered heterocyclyl is

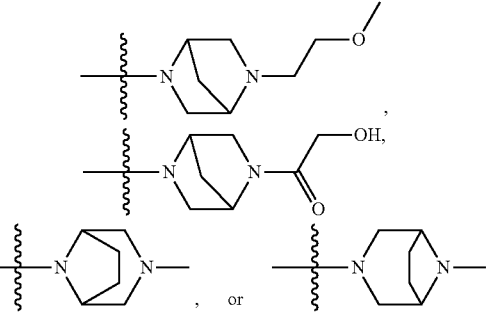

More particularly, the N-containing heterocyclyl is independently selected from:

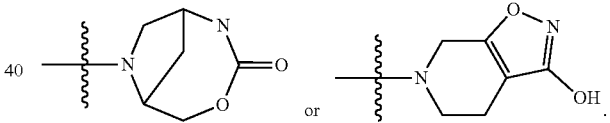
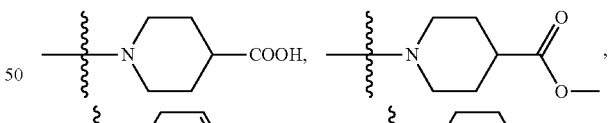
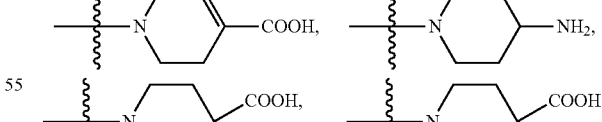
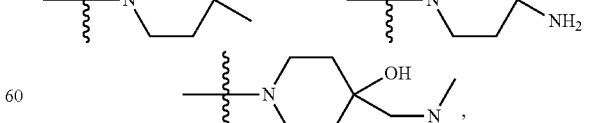
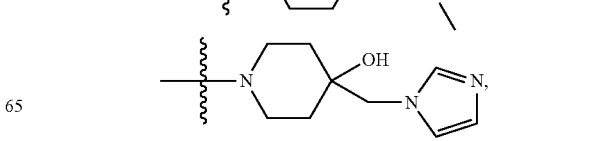

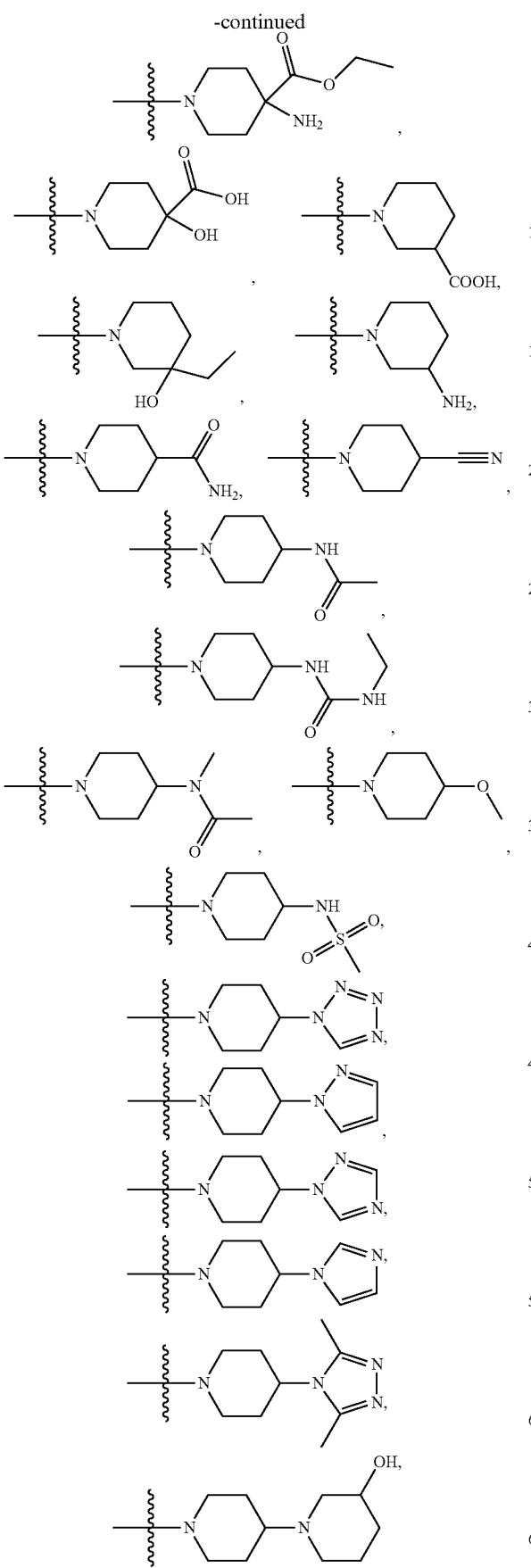
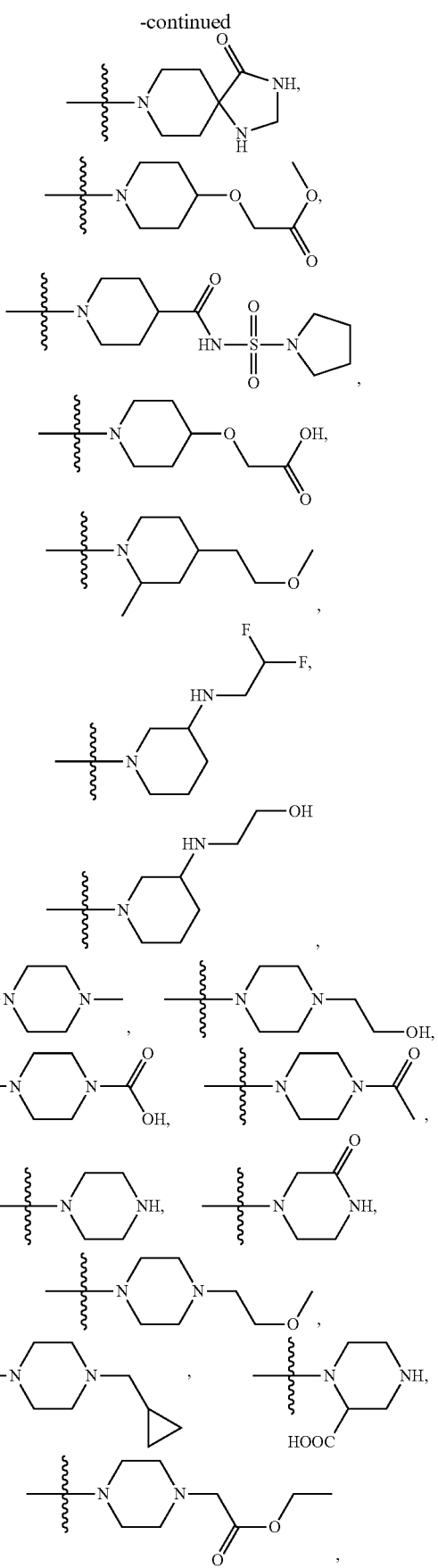

-continued

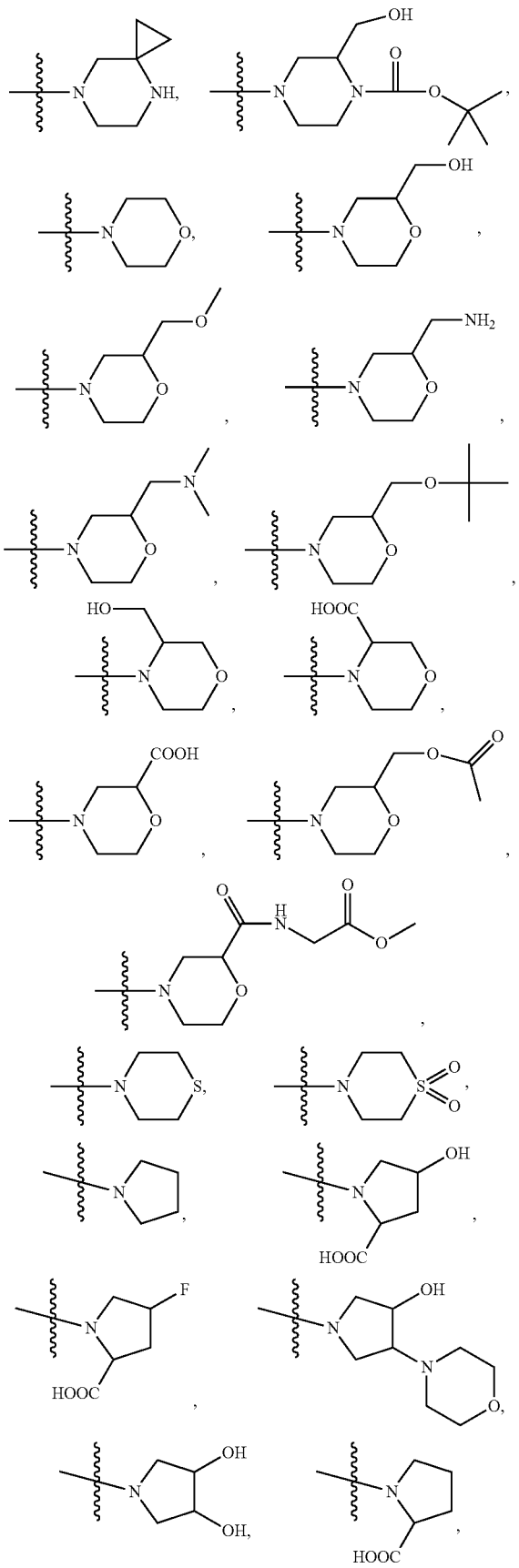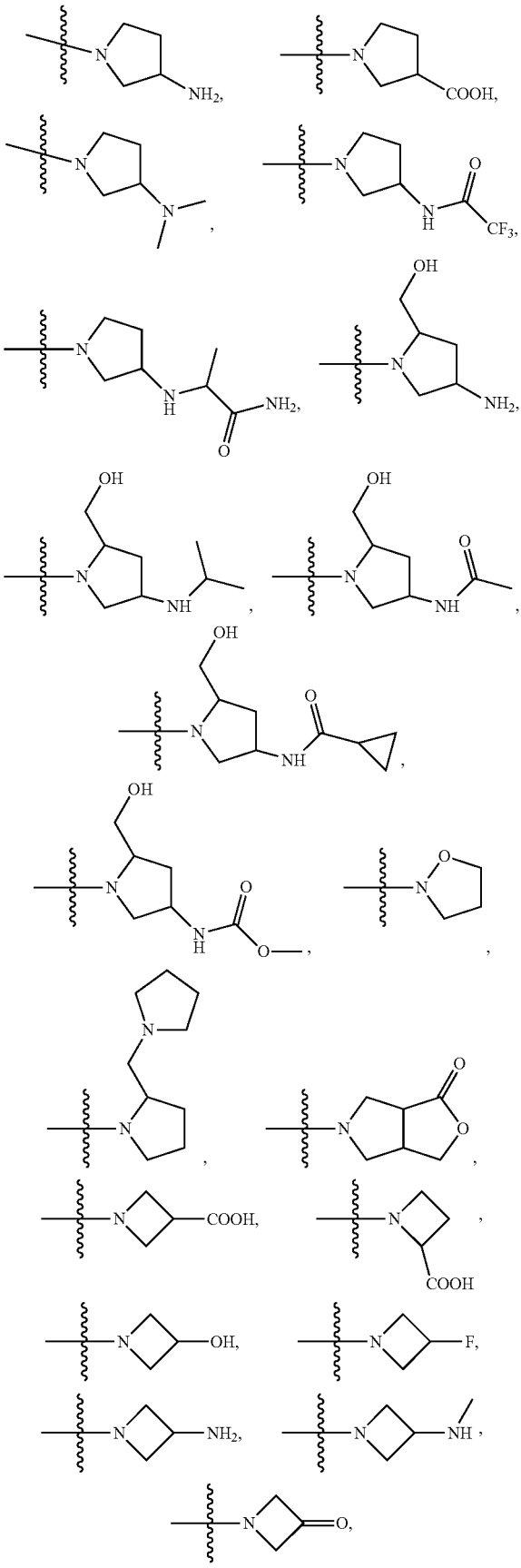

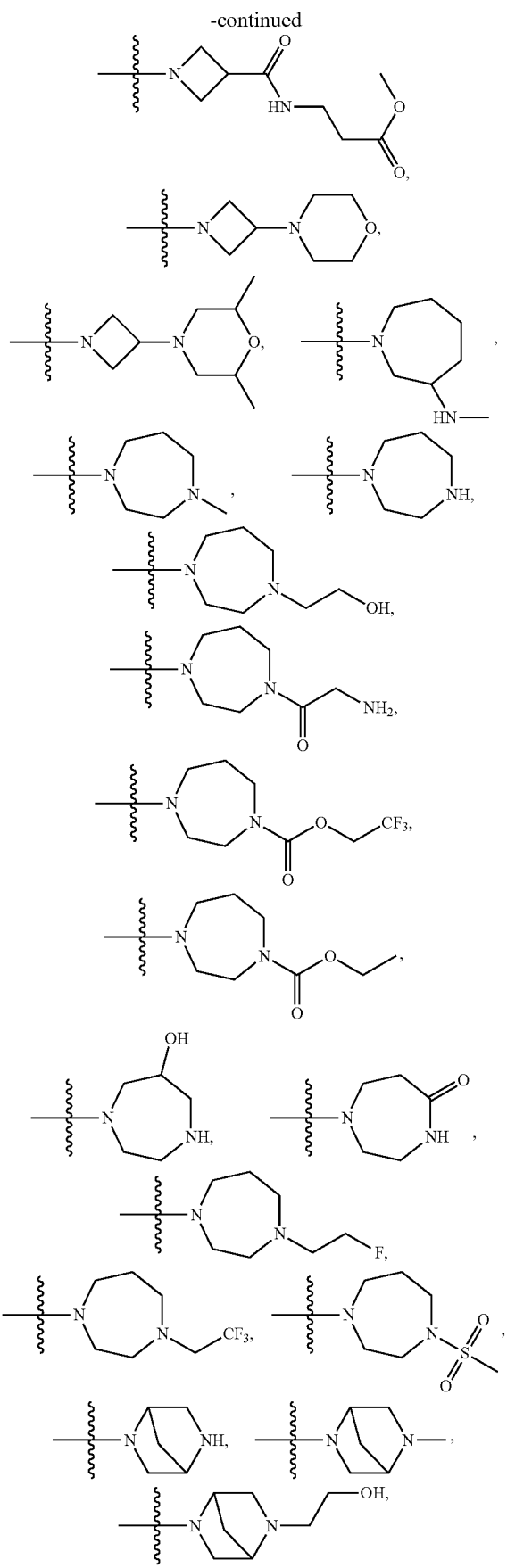

Particularly, the present invention includes a compound of Formula (I) wherein
X is —CH—;
$R_1$ is —CF$_3$, —Br, or —I;
$R_2$ is —CF$_3$, hydroxyl, —OCH$_3$, or —Cl; and
$R_3$ is —H, halo, or cyano.

Particularly, the present invention includes a compound of Formula (I) wherein
X is —CH—;
$R_1$ is —CF$_3$, —Br, or —I;
$R_2$ is —CF$_3$, hydroxyl, —OCH$_3$, or —Cl; and
$R_3$ is halo, or cyano.

Particularly, the present invention includes a compound of Formula (I) wherein
X is —CH—;
$R_1$ is —CF$_3$, —Br, or —I;
$R_2$ is —CF$_3$, hydroxyl, —OCH$_3$, or —Cl; and
$R_3$ is —H.

Particularly, the present invention includes a compound of Formula (I) wherein
X is —CH—;
$R_1$ is —CF$_3$;
$R_2$ is —CF$_3$, —OCH$_3$, or —Cl; and
$R_3$ is —H.

More particularly, an example of the present invention includes compounds of Formula (I) wherein
X is —CH—;
$R_1$ is —C(O)—C$_{1-2}$alkyl, —Cl, —Br, —I, C$_{1-3}$alkyl, or C$_{3-5}$cycloalkyl; wherein
said —C$_{1-3}$alkyl may be substituted with halo;
$R_2$ is —F, —Cl, —Br, cyclopropyl, C$_{1-2}$alkoxy or hydroxyl; wherein
said C$_{1-3}$alkyl may be substituted with halo or hydroxyl;
$R_3$ is —H, halo, or cyano; and

is selected from

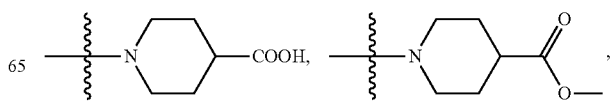

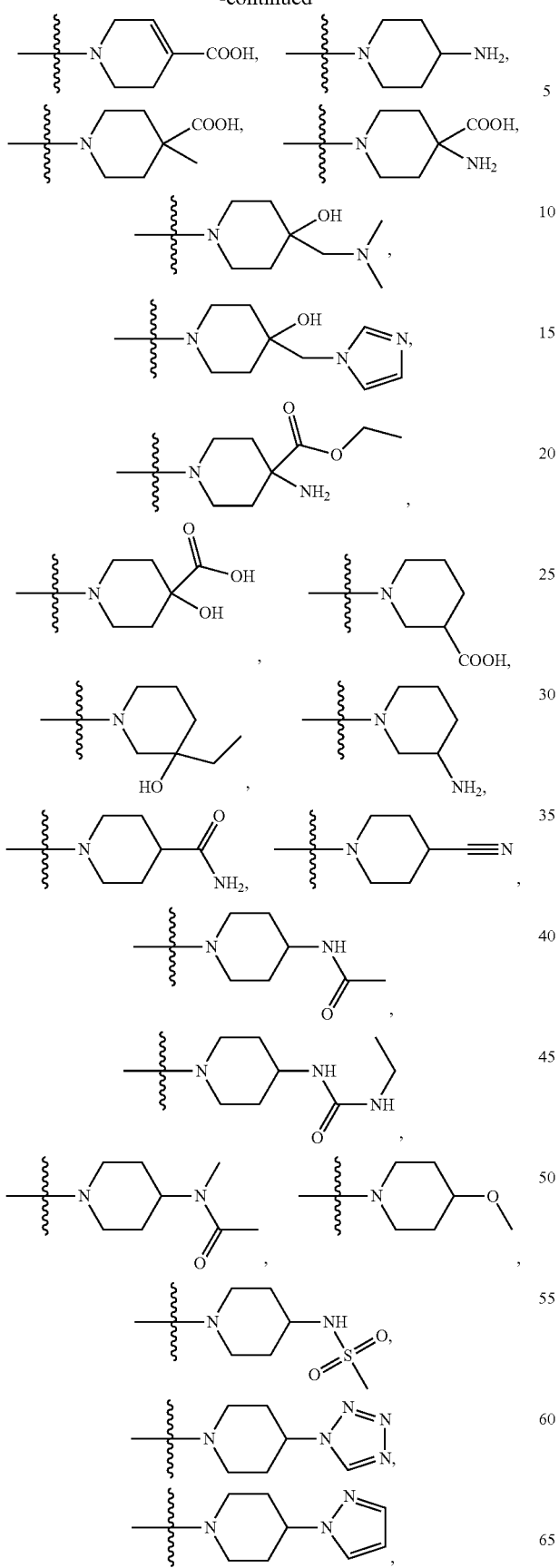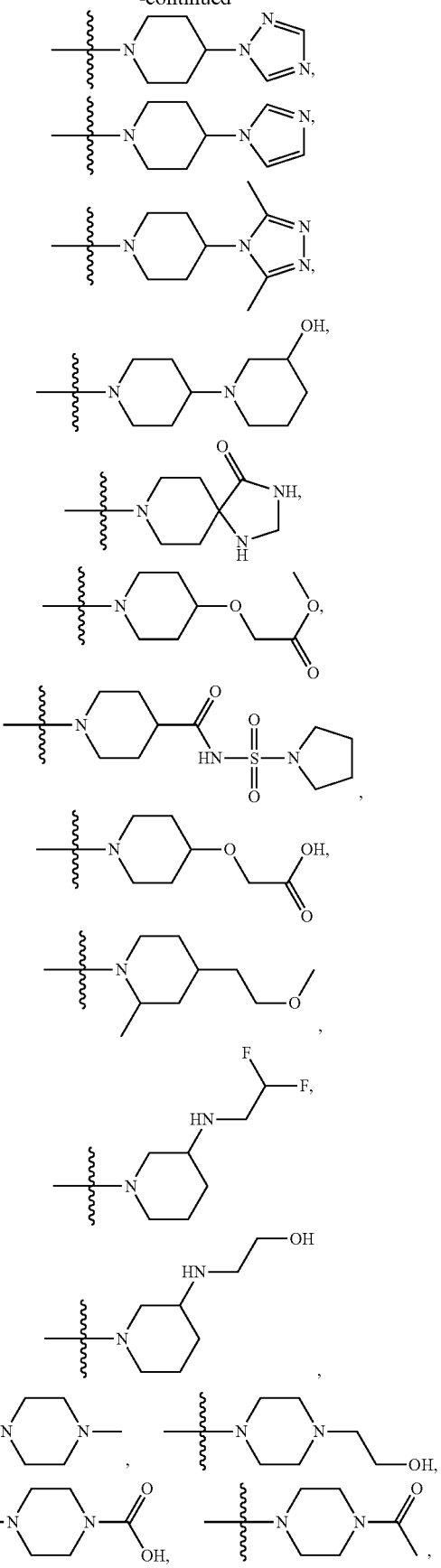

-continued
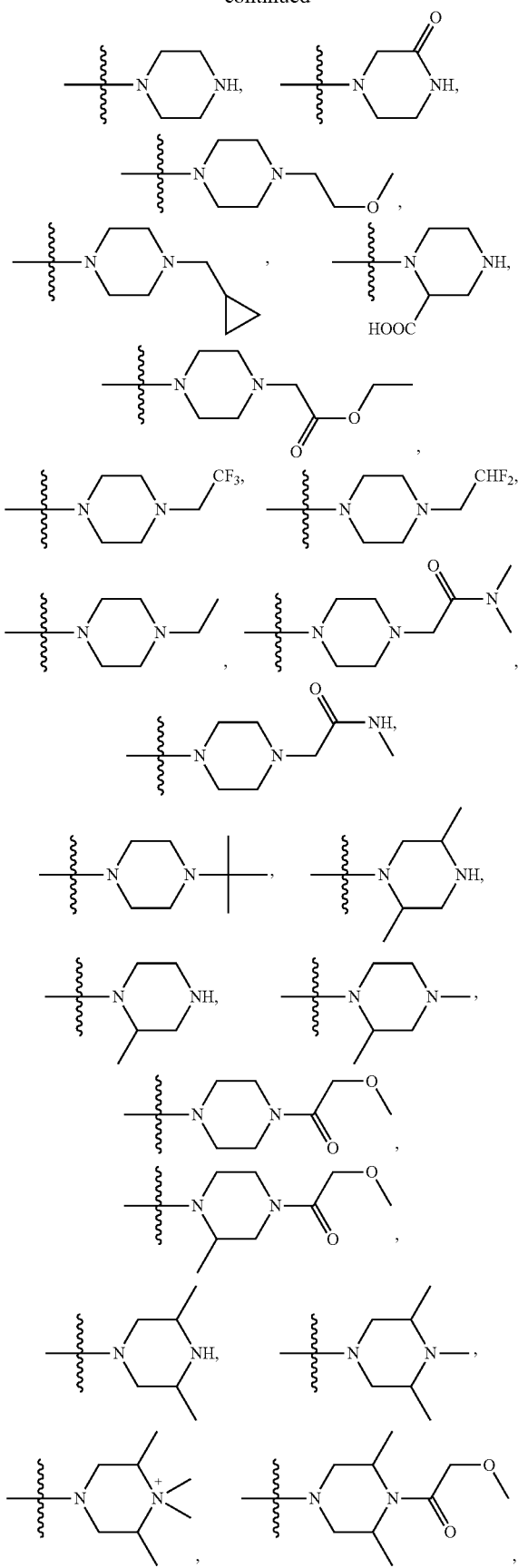
-continued
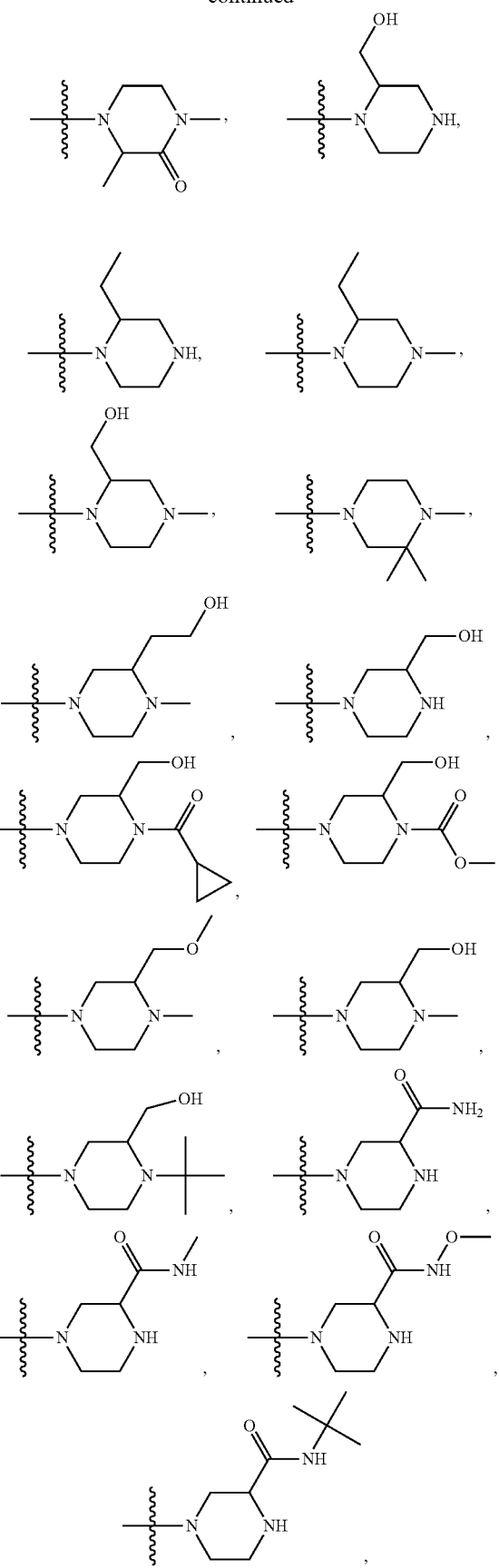

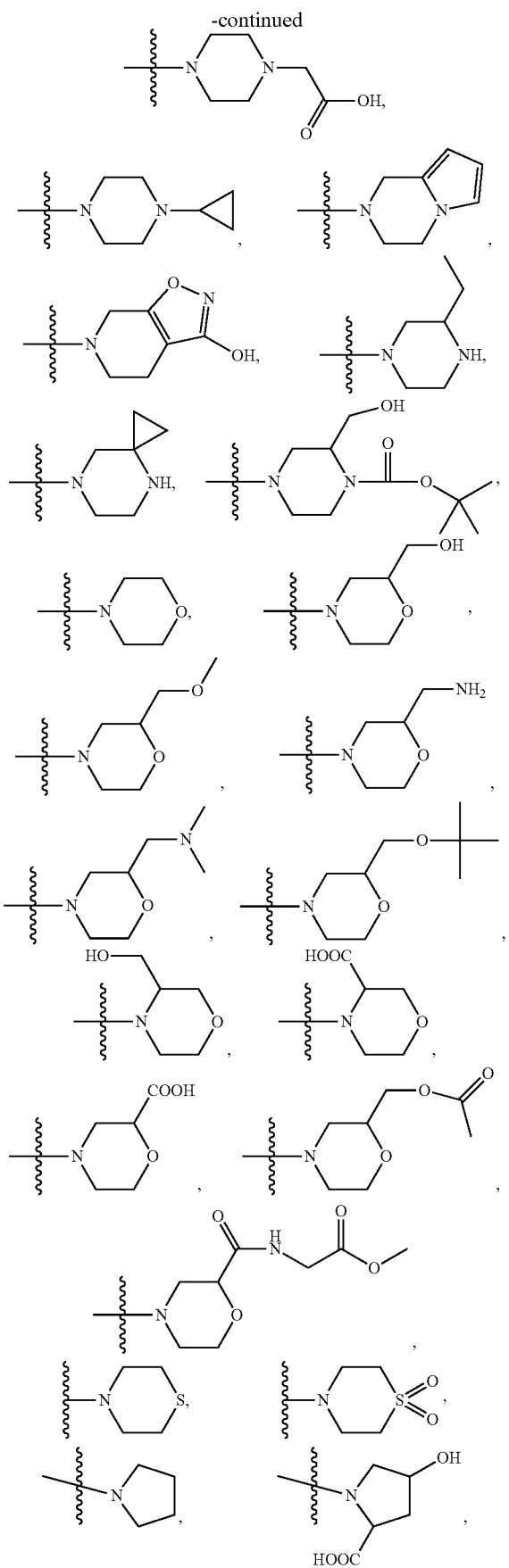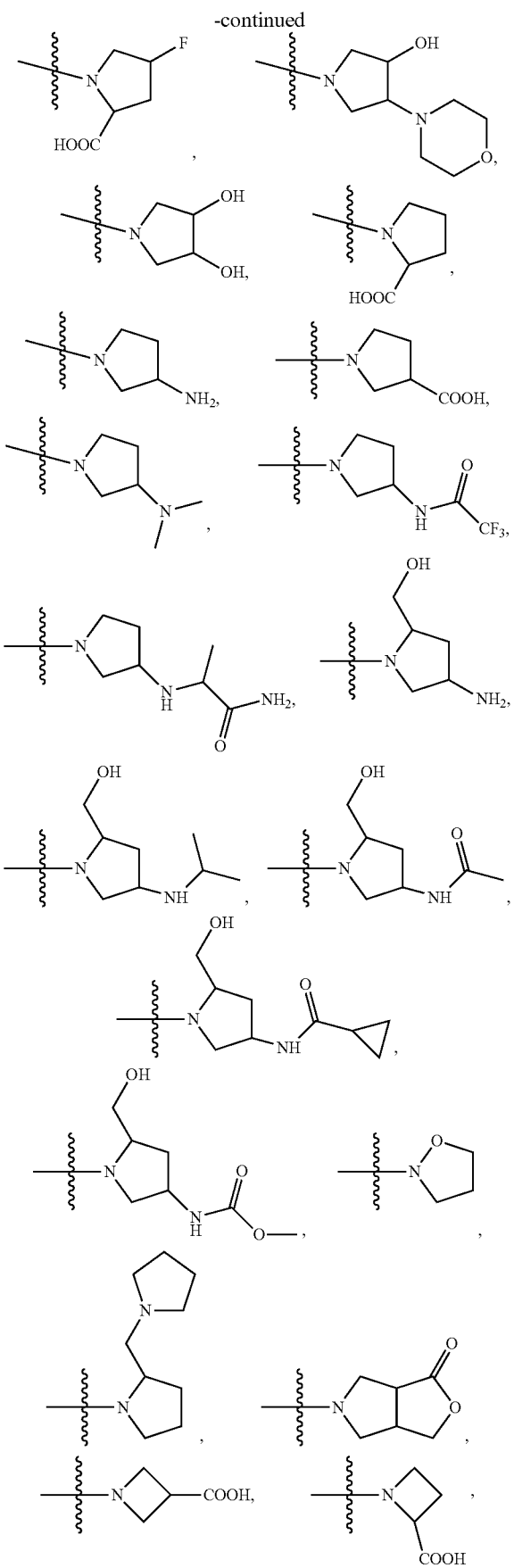

-continued
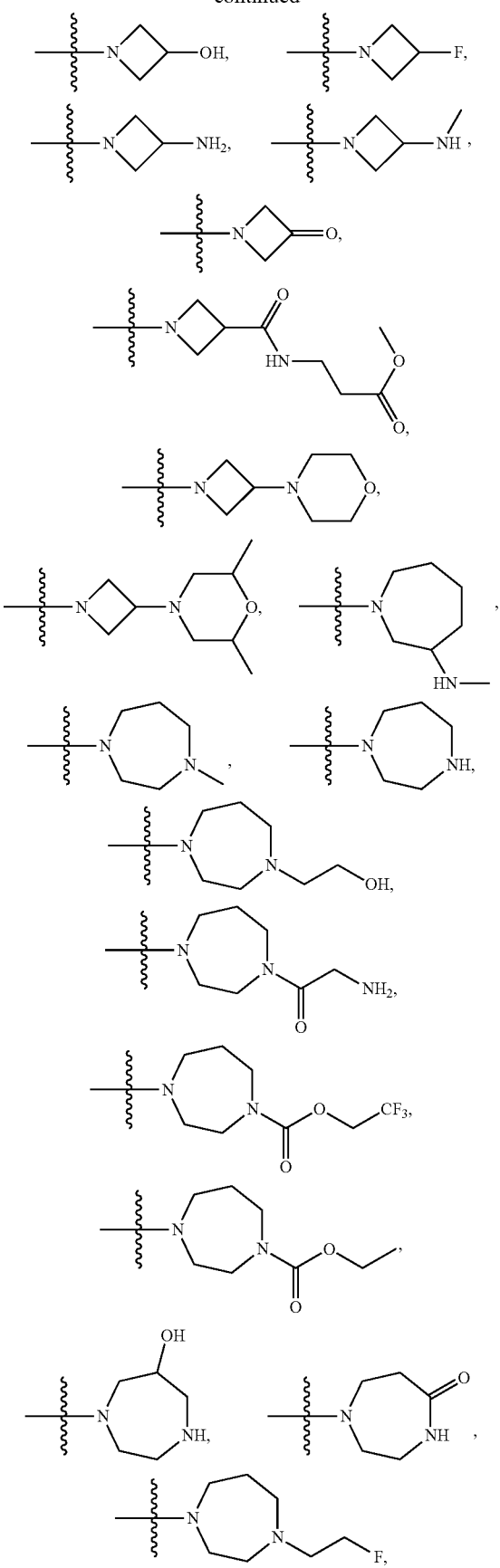
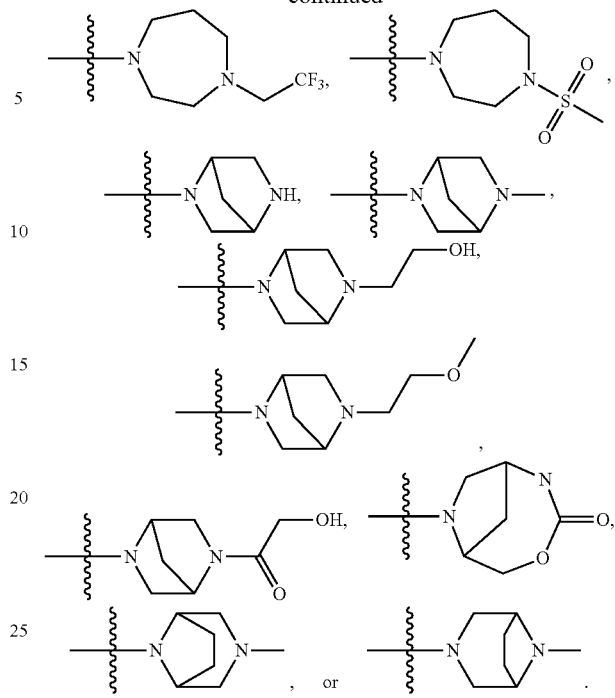
More particularly, an example of the present invention includes compounds of Formula (I) wherein
X is —CH—;
$R_1$ is —C(O)—CH$_3$, —Cl, —Br, —I, —CF$_3$, or cyclopropyl;
$R_2$ is —F, —Cl, —Br, cyclopropyl, $C_{1-3}$alkyl, $C_{1-2}$alkoxy or hydroxyl; wherein
said $C_{1-3}$alkyl may be substituted with hydroxyl or halo;
$R_3$ is —H, halo, or cyano; and
is selected from
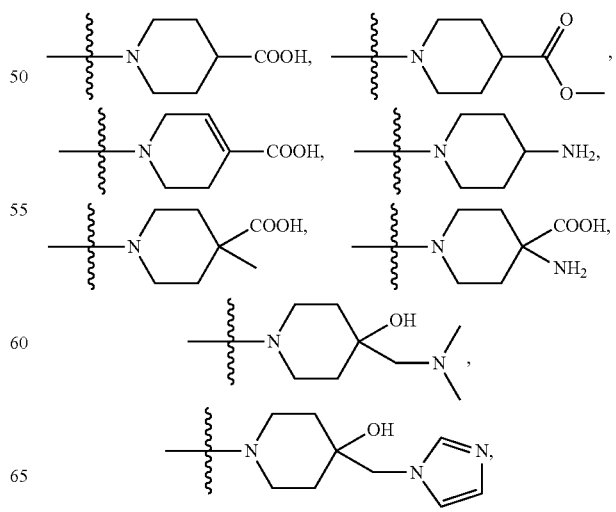

-continued
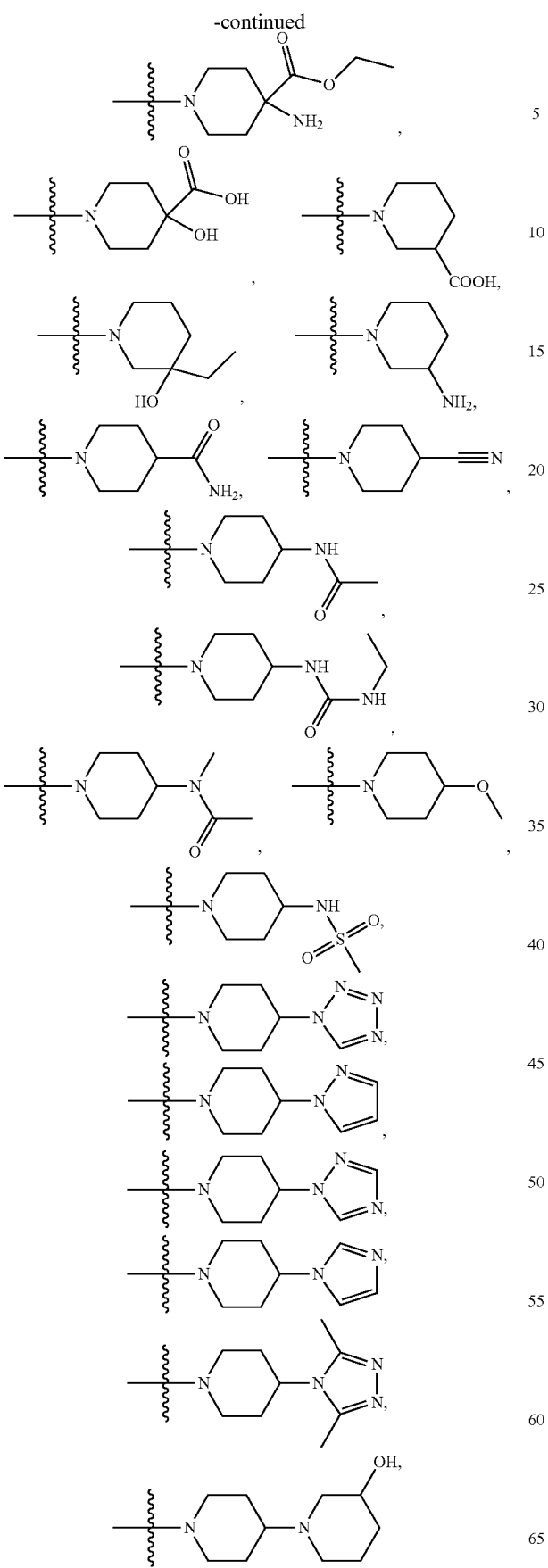
-continued
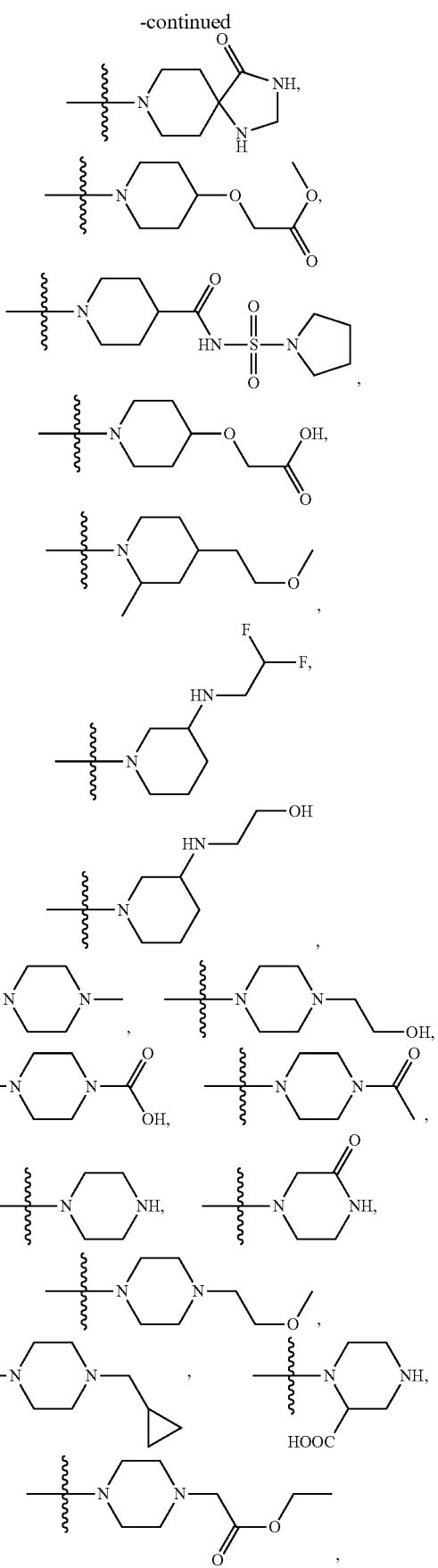

-continued

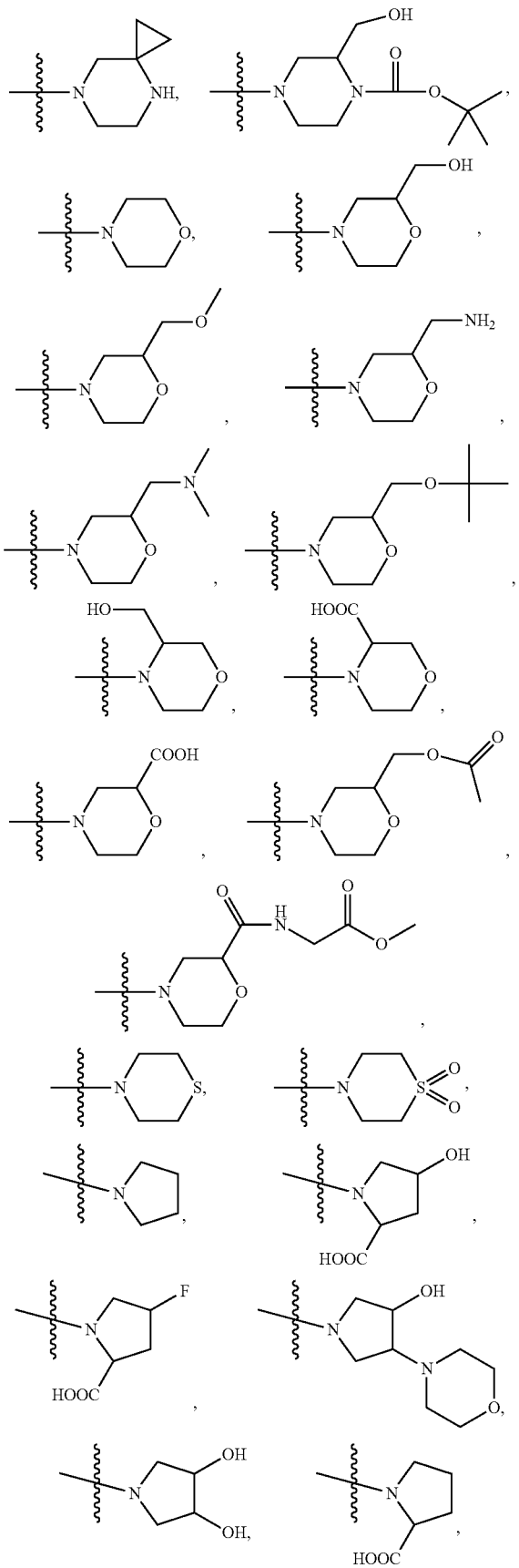
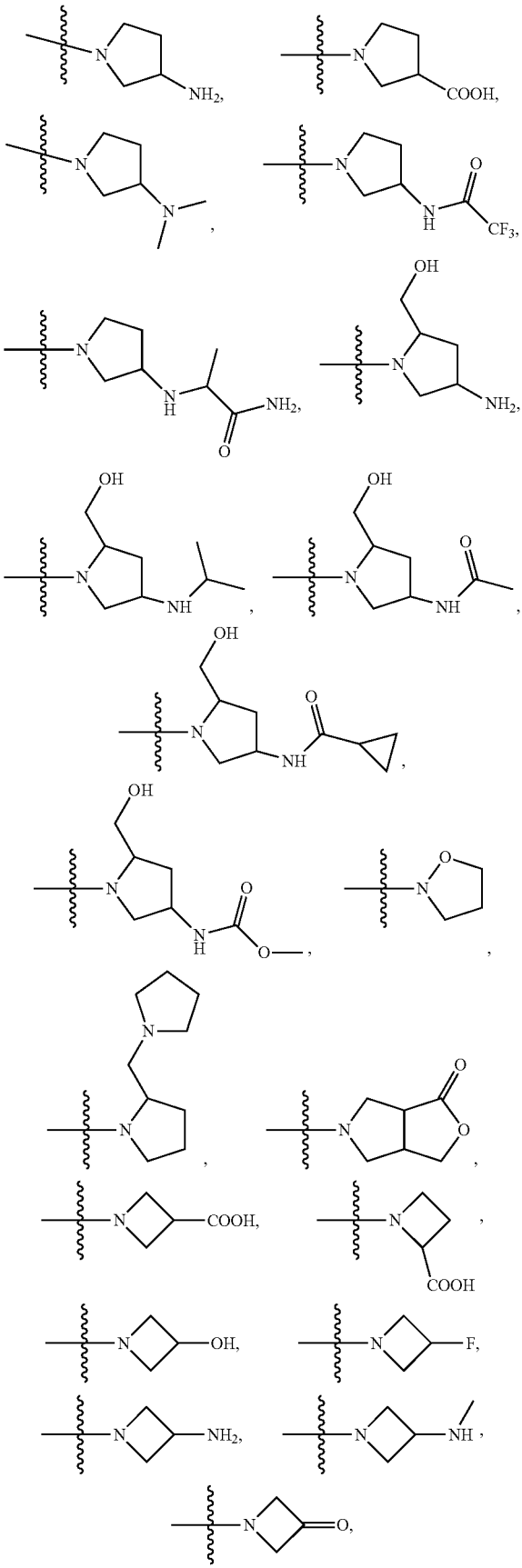

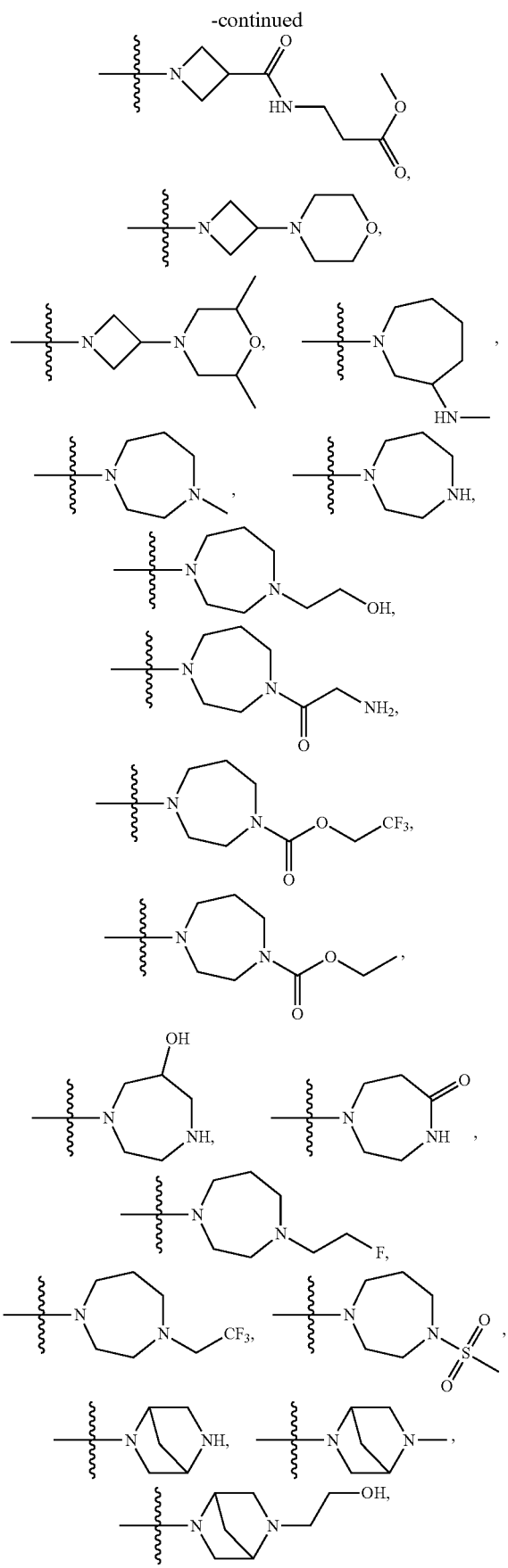
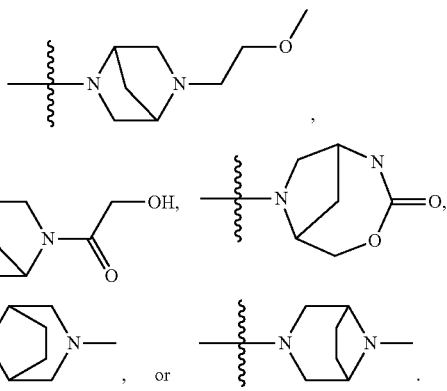
More particularly, an example of the present invention includes compounds of Formula (I) wherein
X is —CH—;
$R_1$ is —CF$_3$, —Br, or —I;
$R_2$ is —CF$_3$, hydroxyl, —OCH$_3$, or —Cl;
$R_3$ is —H, halo, or cyano; and
is selected from
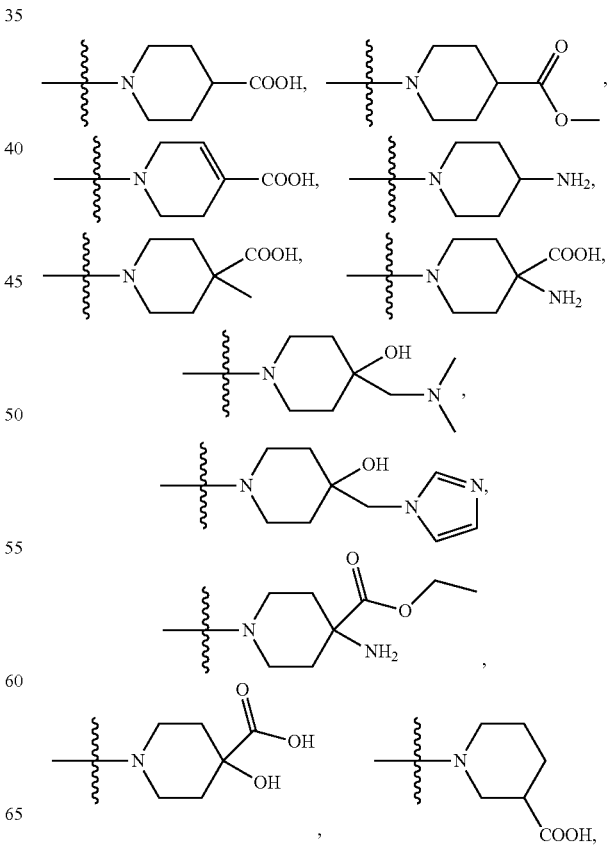

-continued
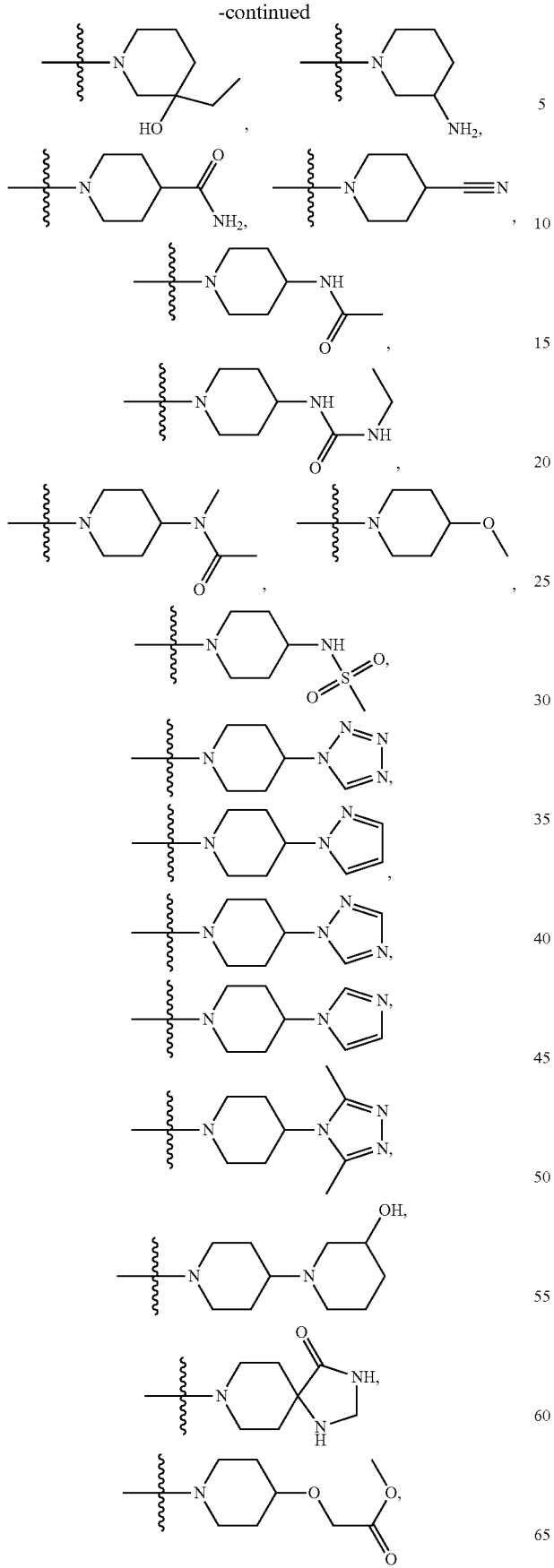
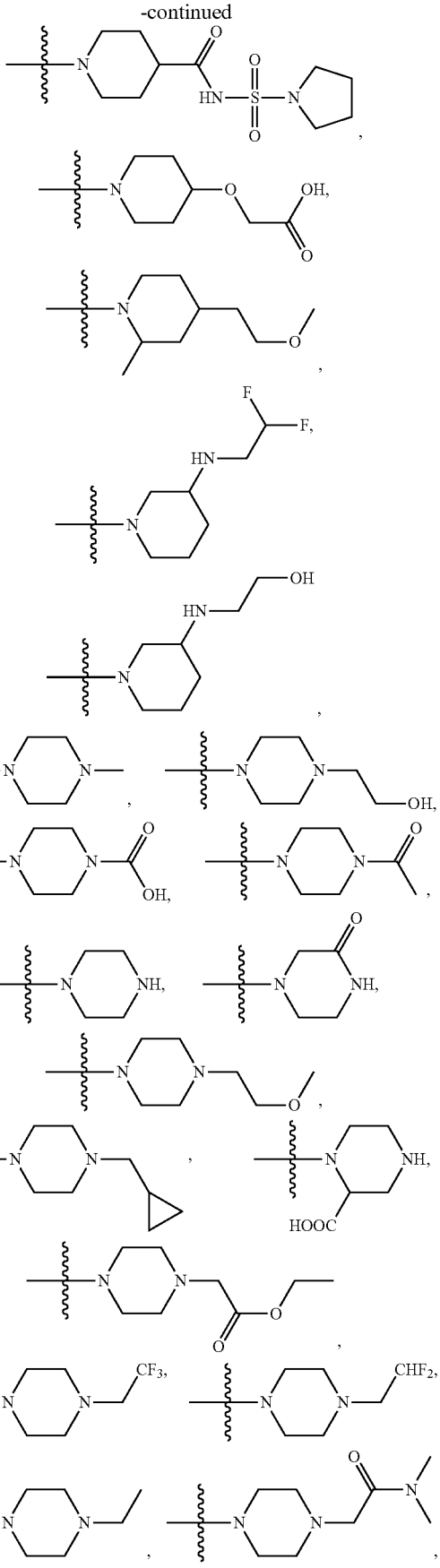

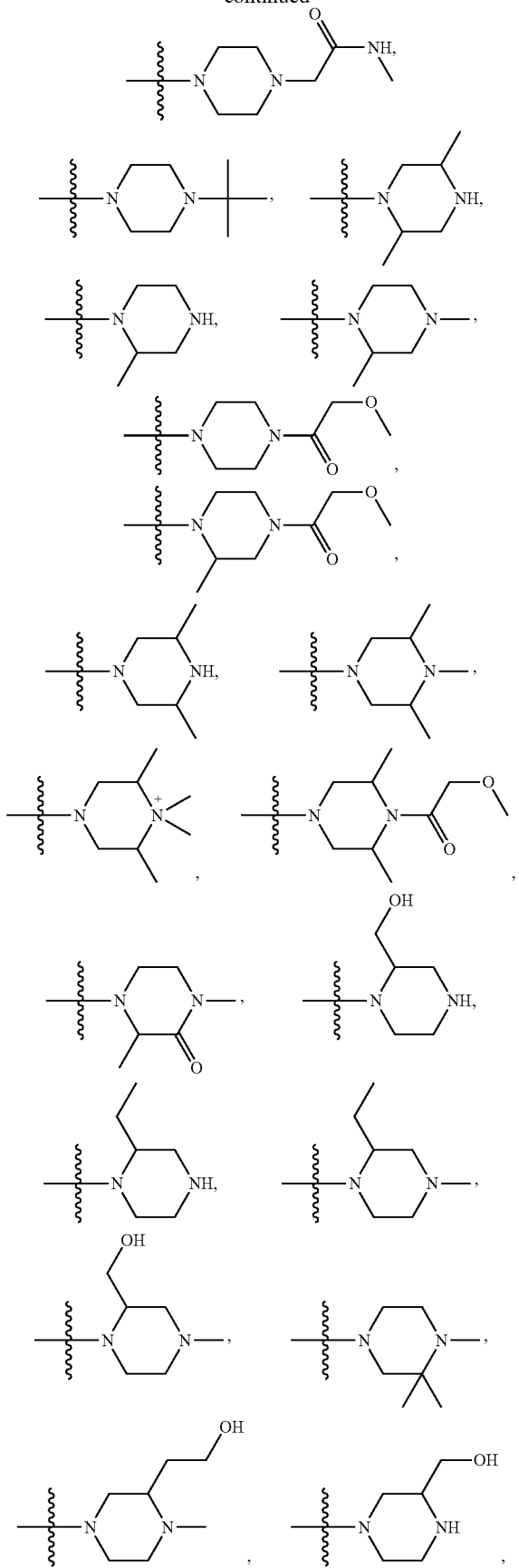
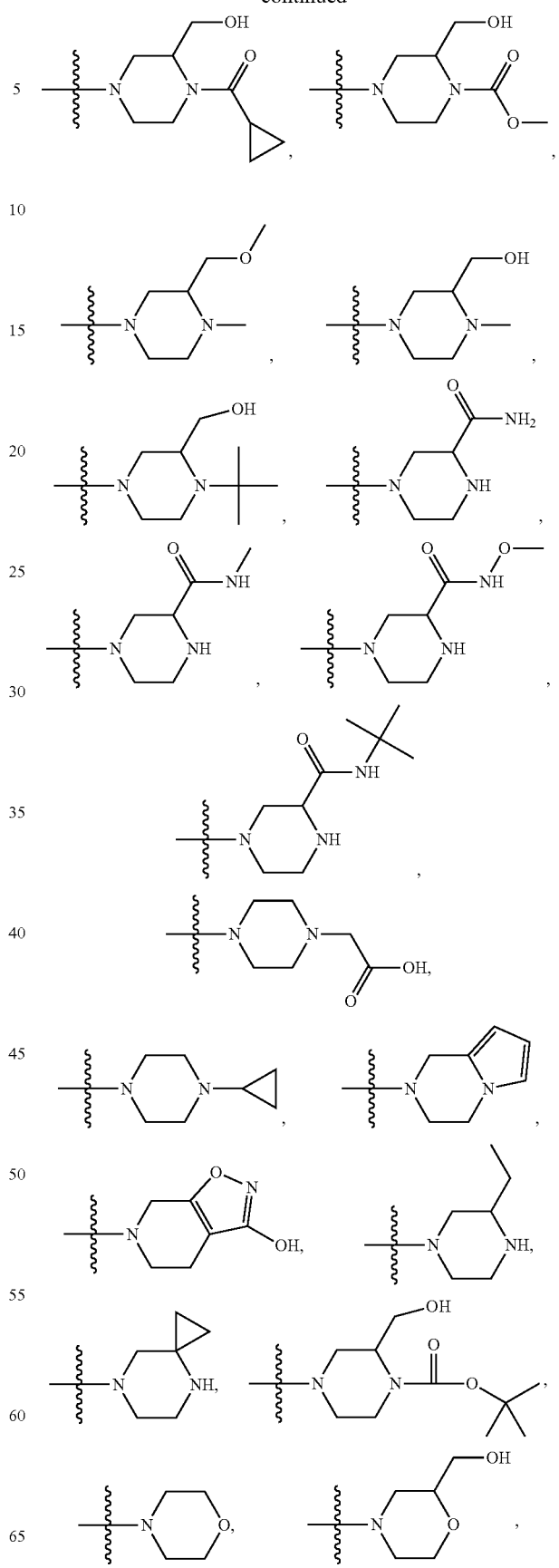

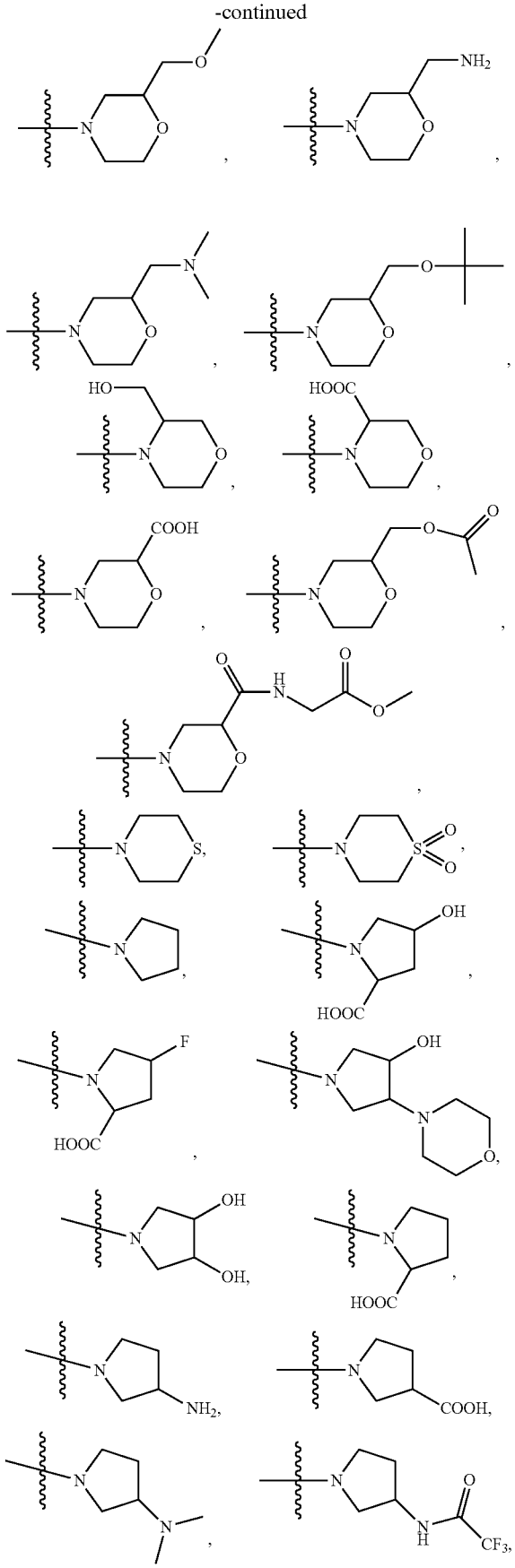
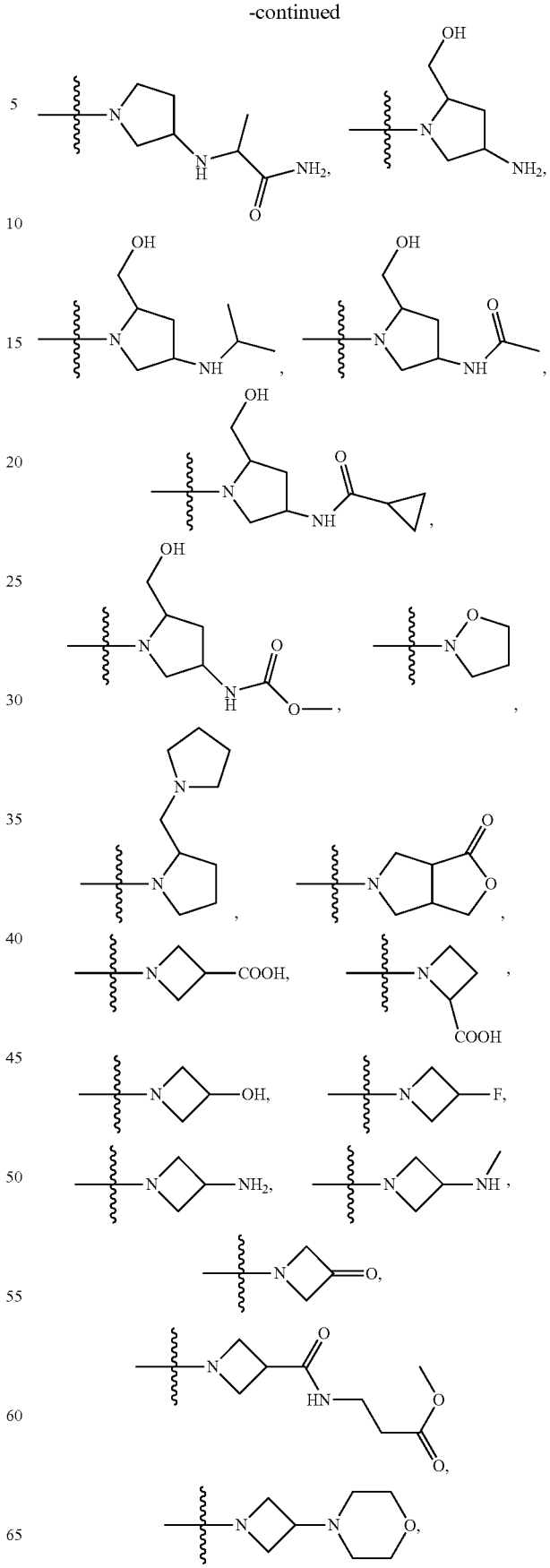

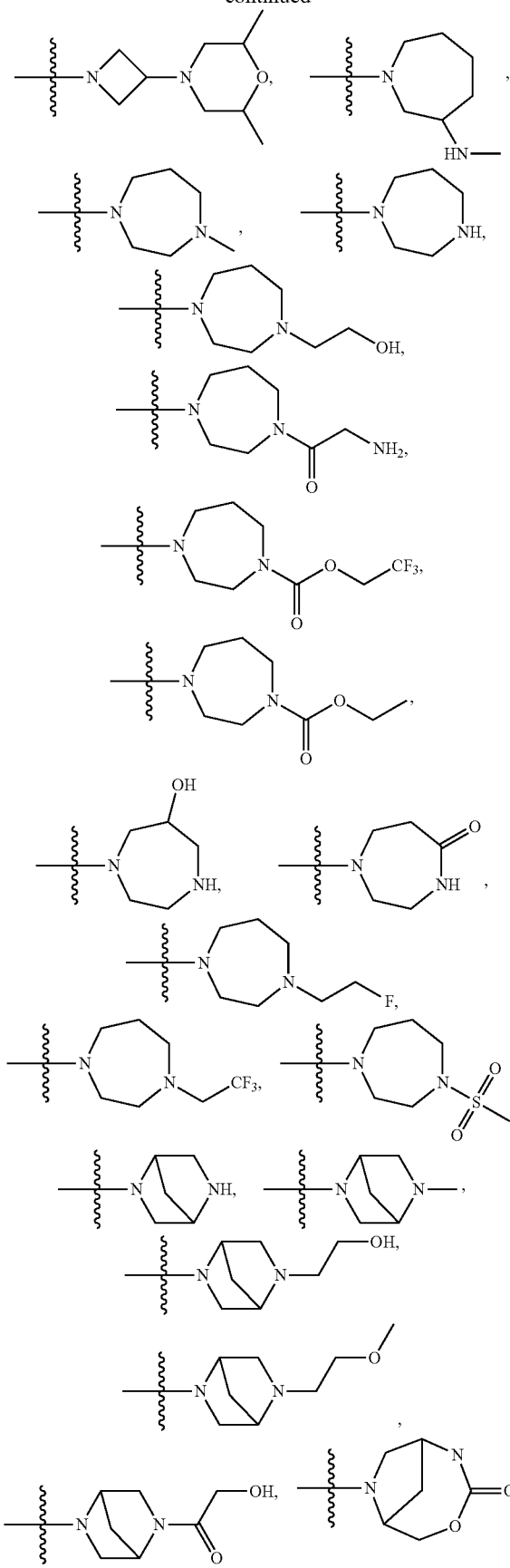
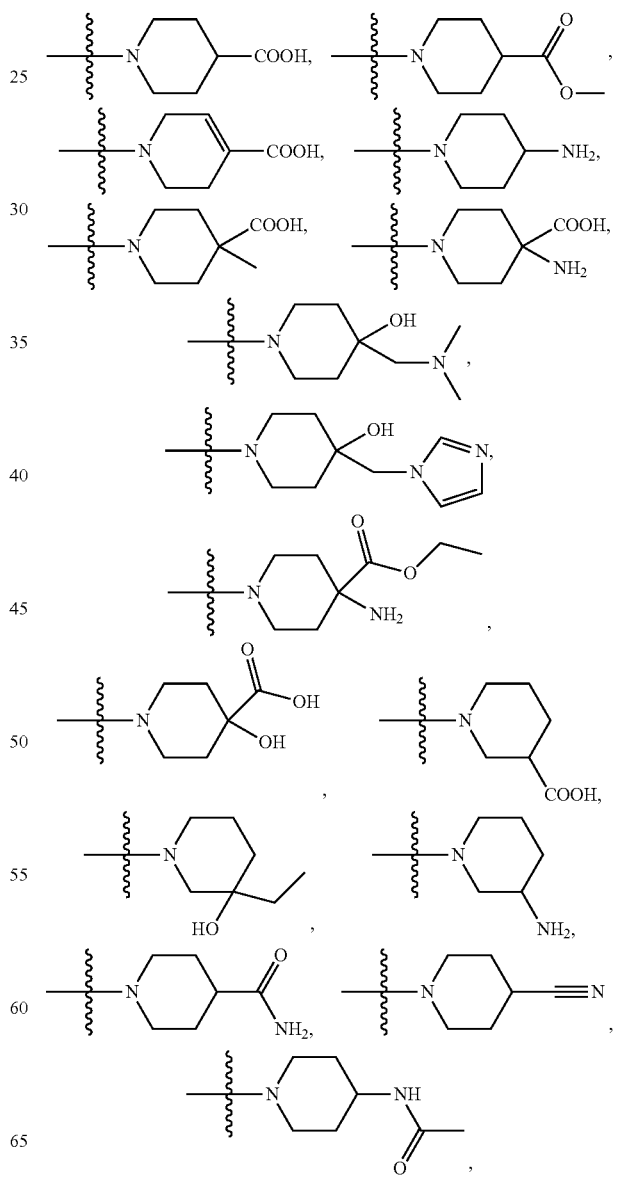
More particularly, an example of the present invention includes compounds of Formula (I) wherein
X is —CH—;
$R_1$ is —$CF_3$;
$R_2$ is —$CF_3$, —$OCH_3$, or —Cl;
$R_3$ is —H; and
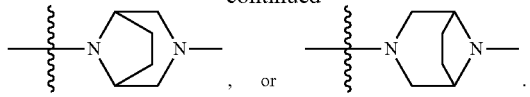
is selected from

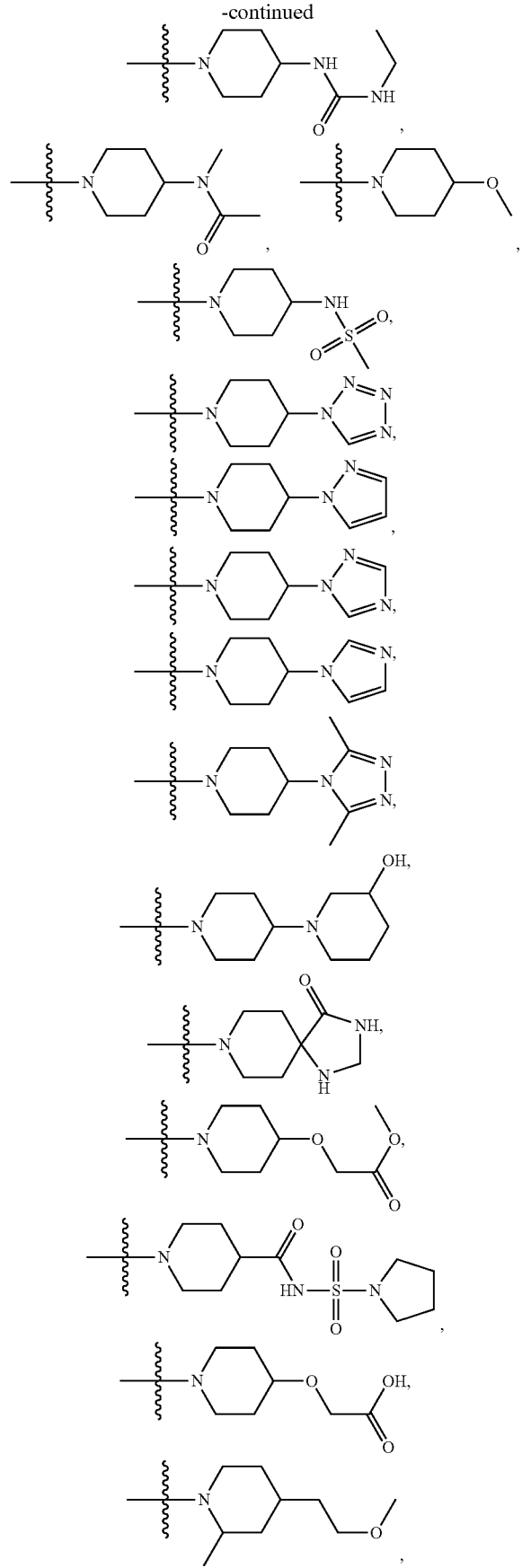
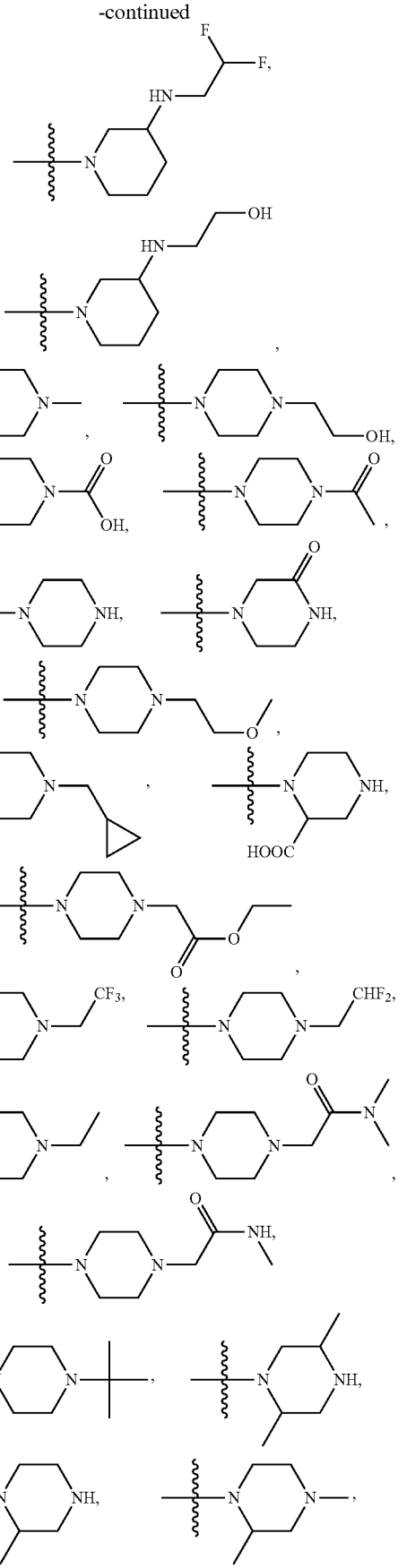

-continued
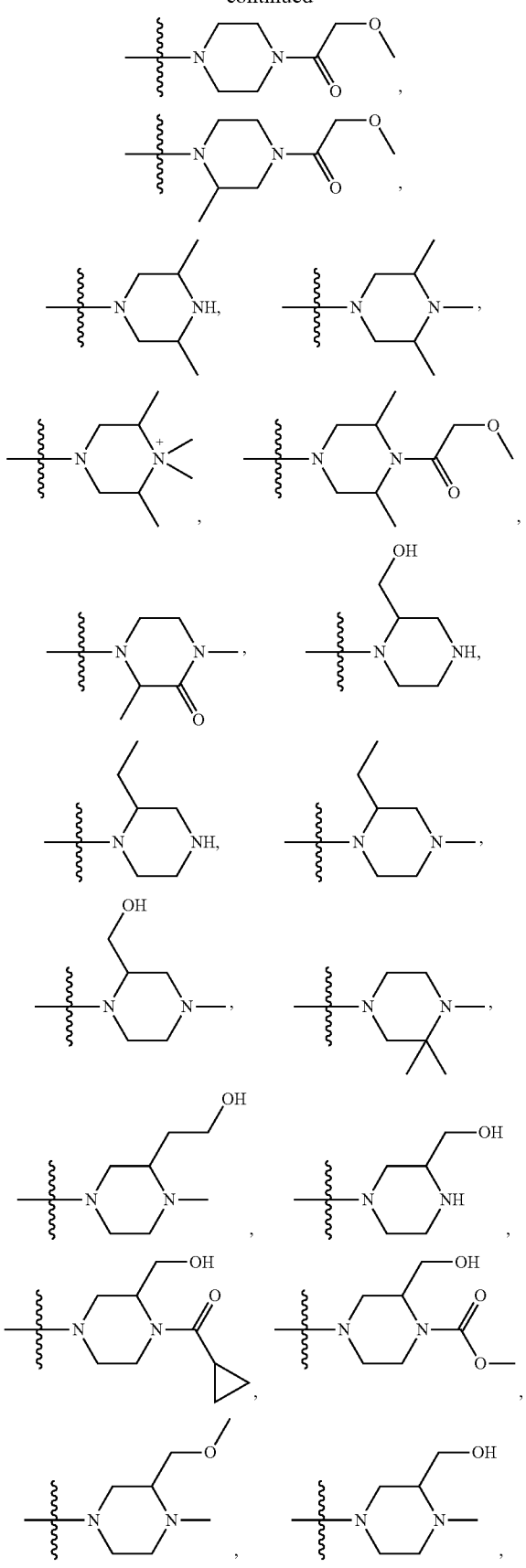
-continued
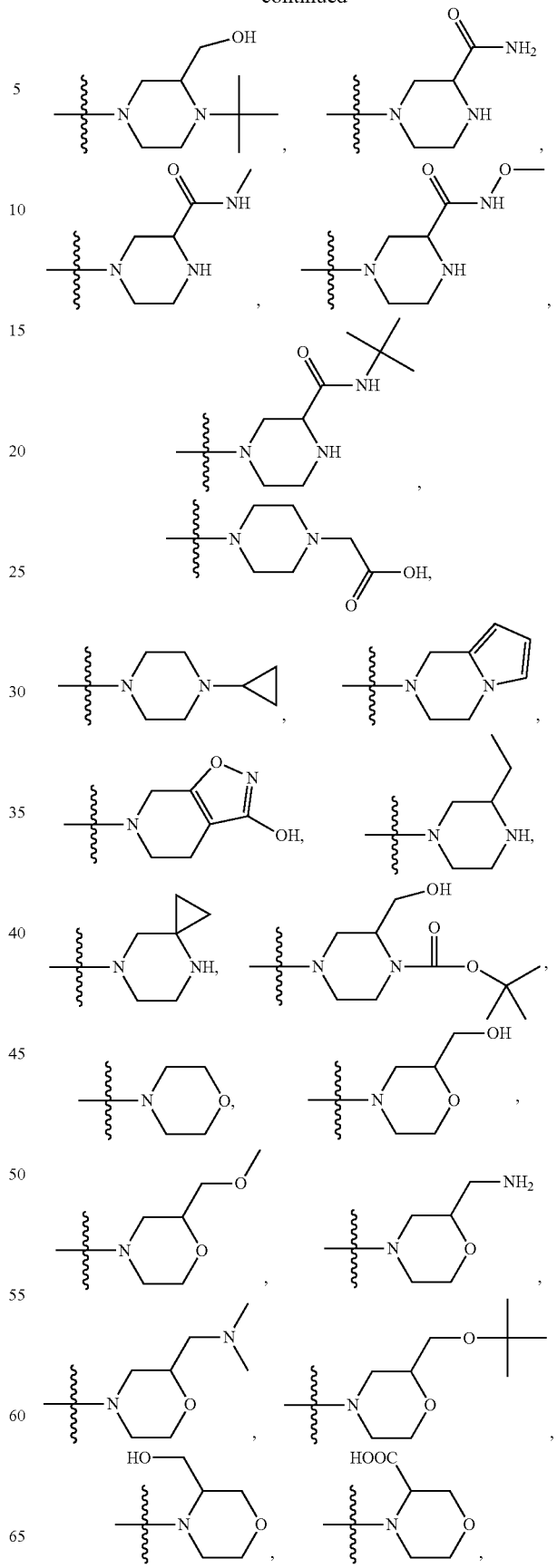

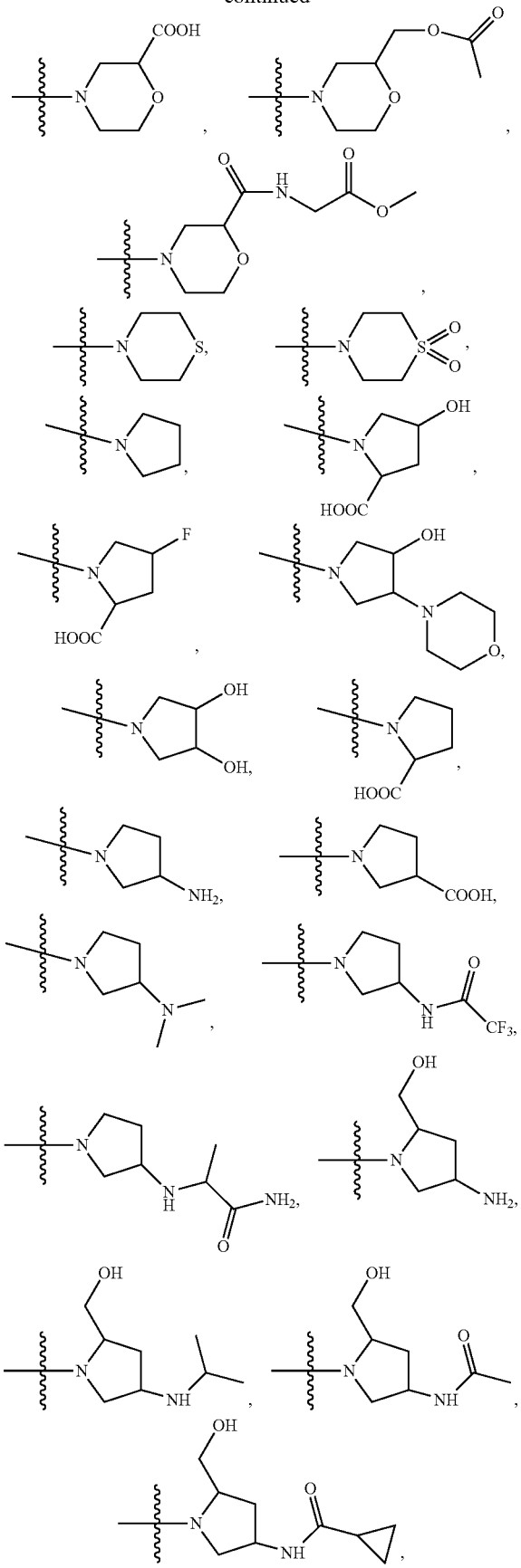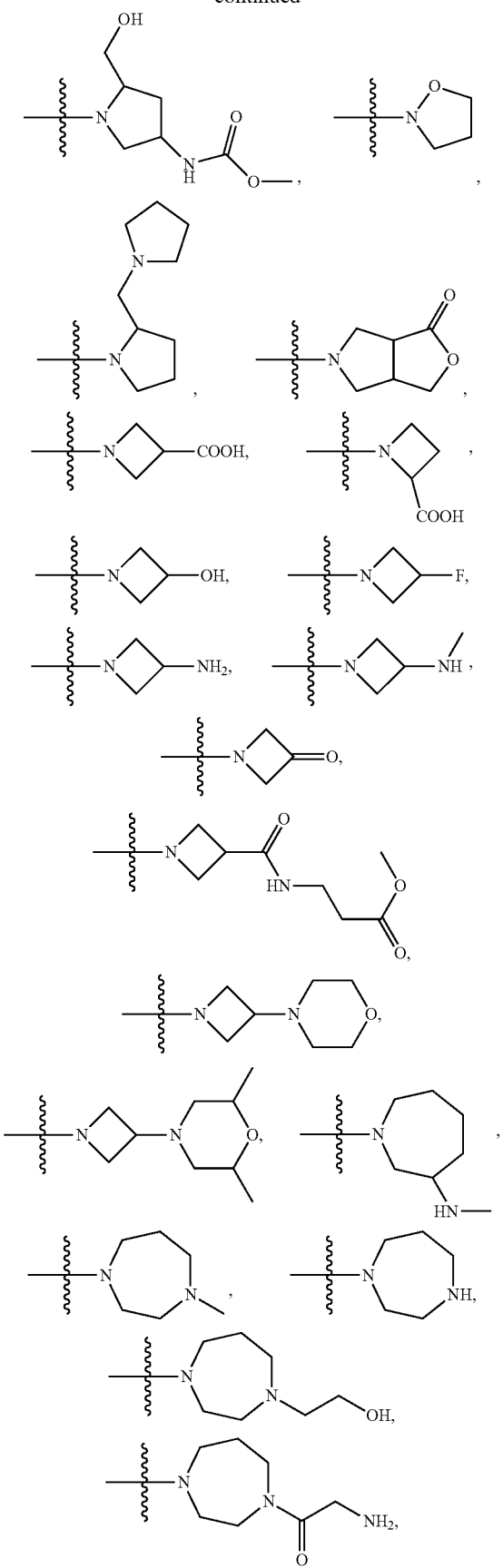

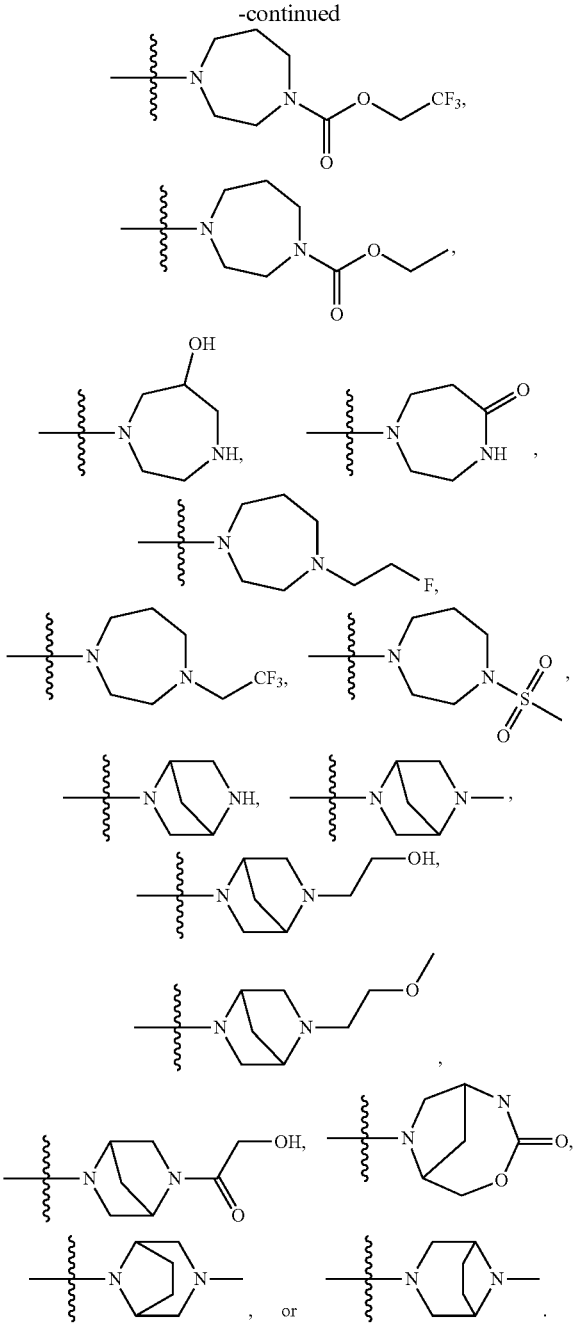
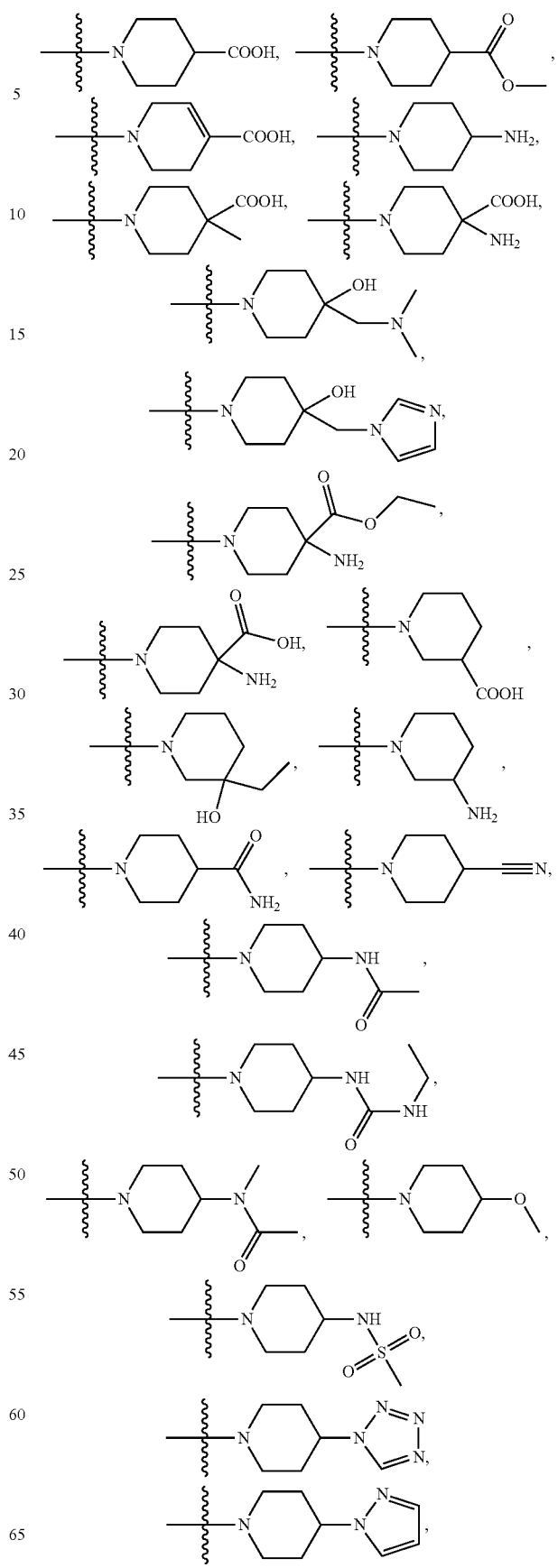
More particularly, an example of the present invention includes compounds of Formula (I) wherein
X is —CH;
R$_1$ is —CF$_3$;
R$_2$ is —CF$_3$ or —Cl;
R$_3$ is —H; and
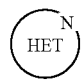
is selected from

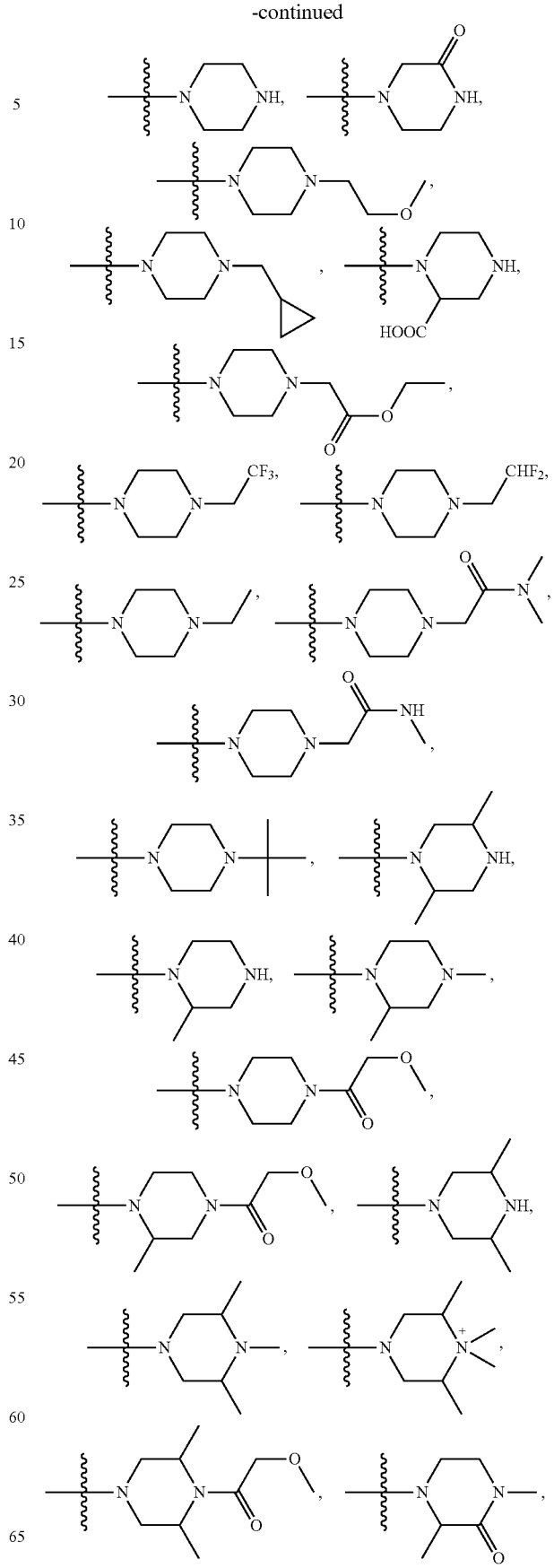

-continued
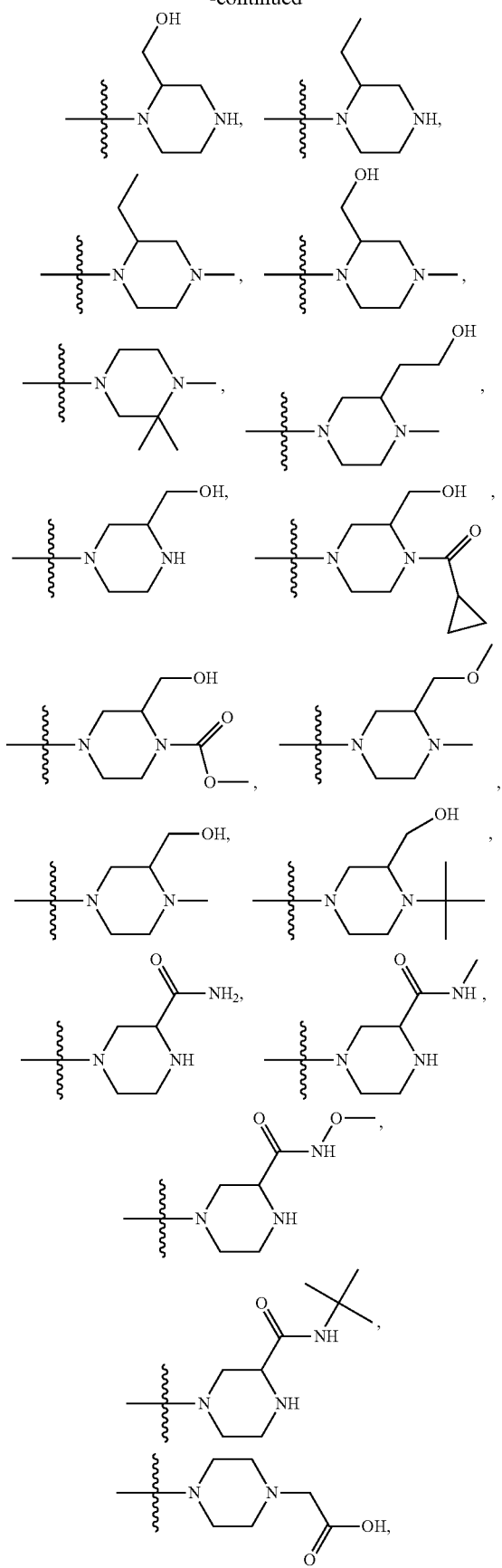
-continued
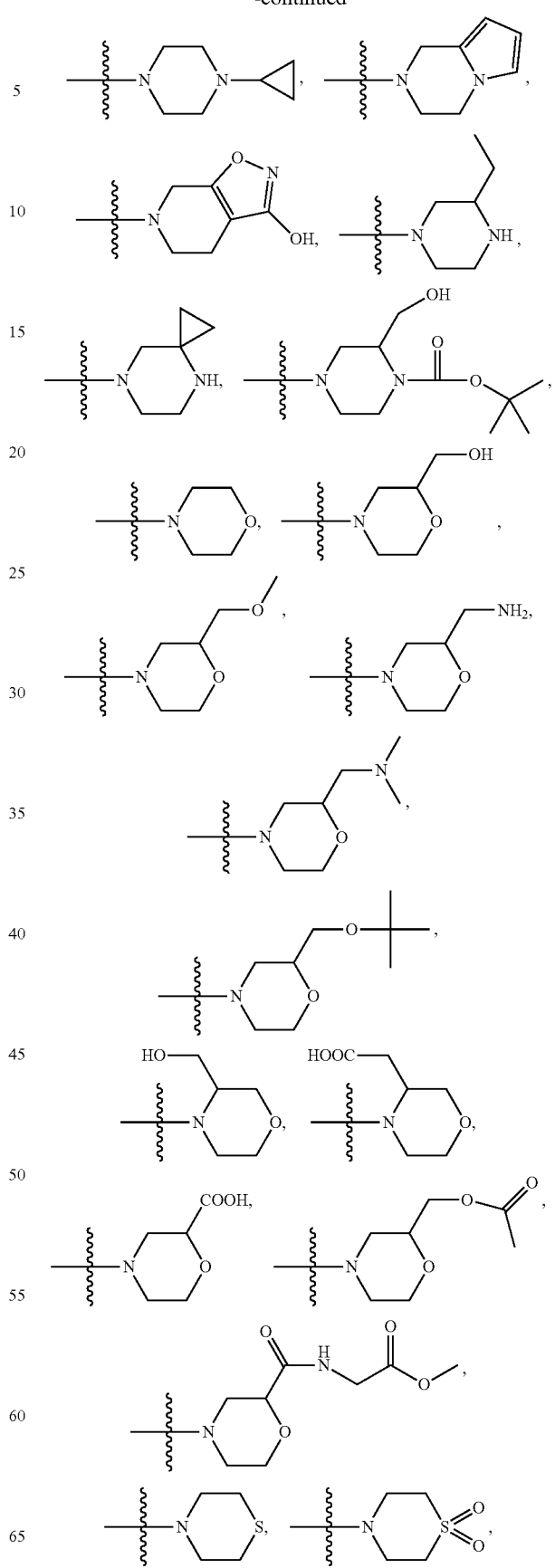

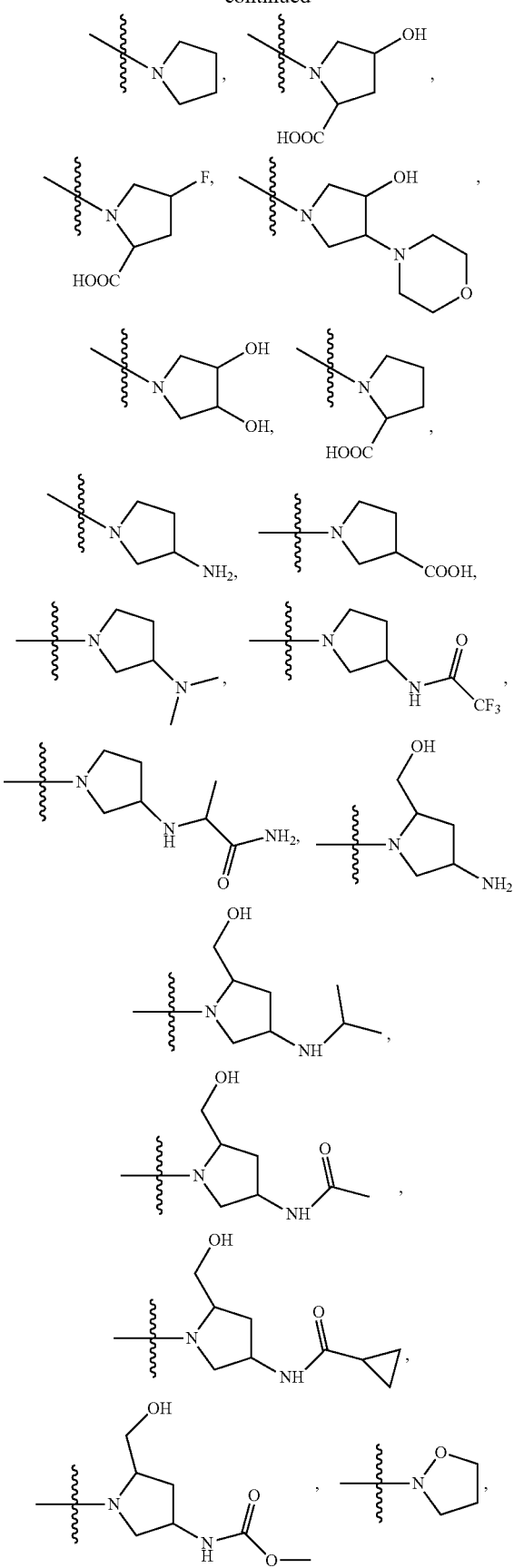
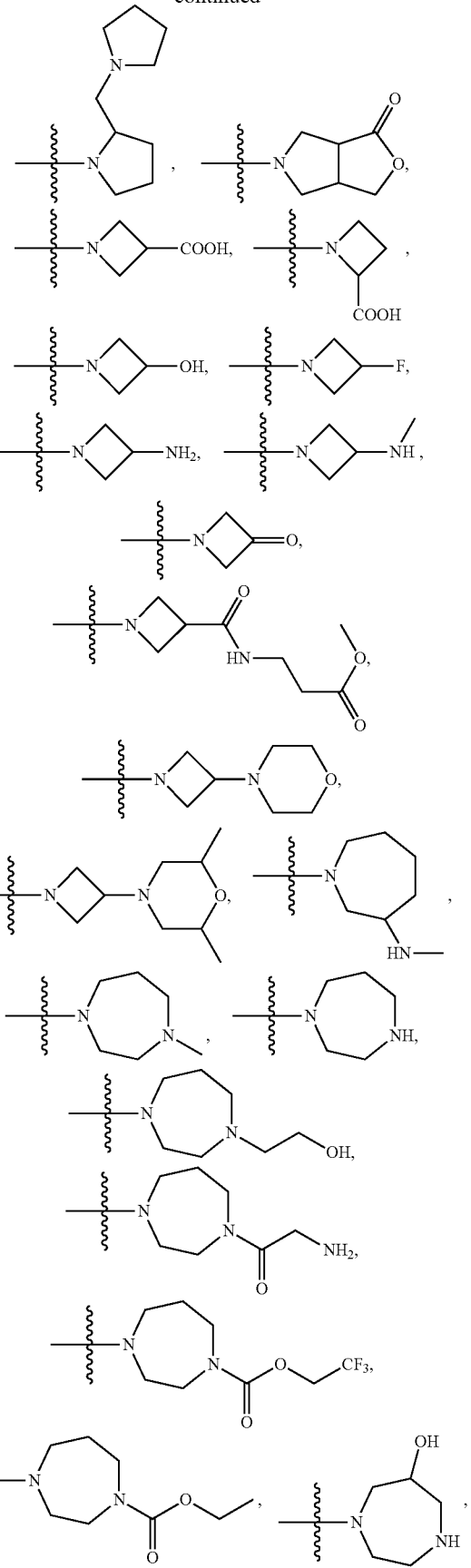

-continued
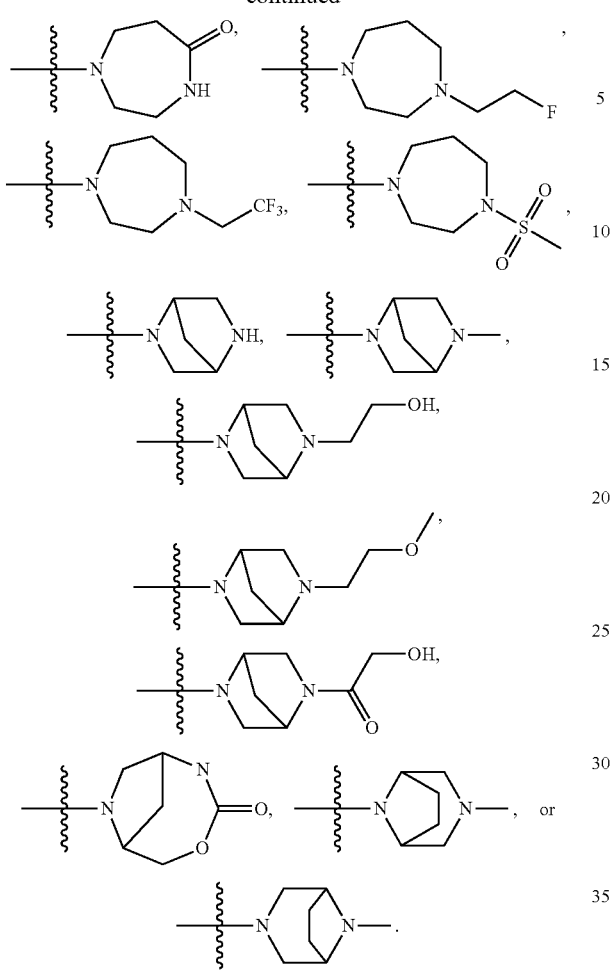
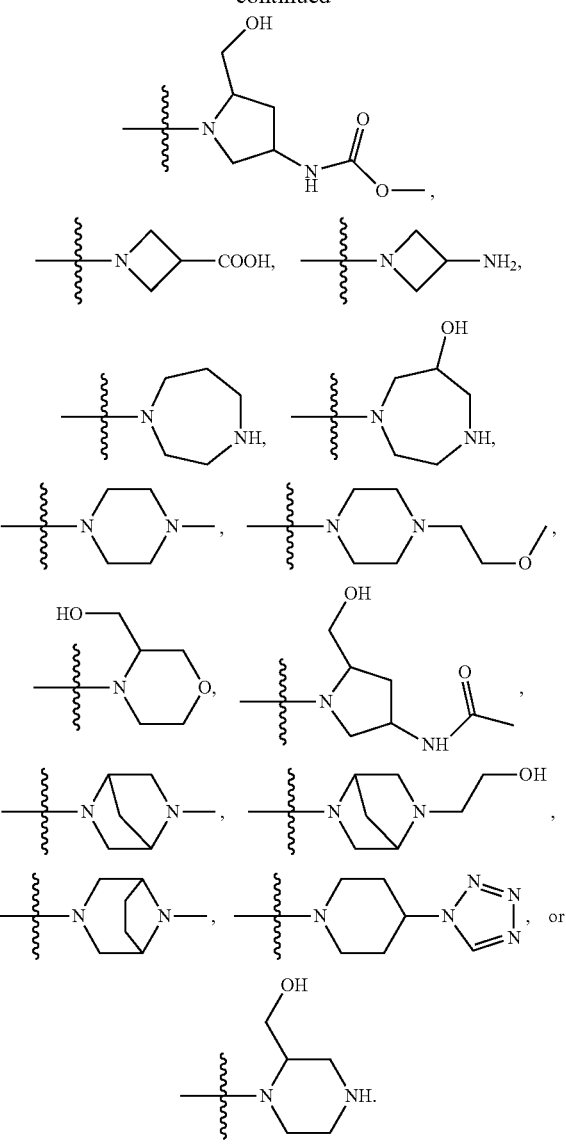
Preferred embodiments of the present invention include compounds of Formula (I) wherein
is selected from
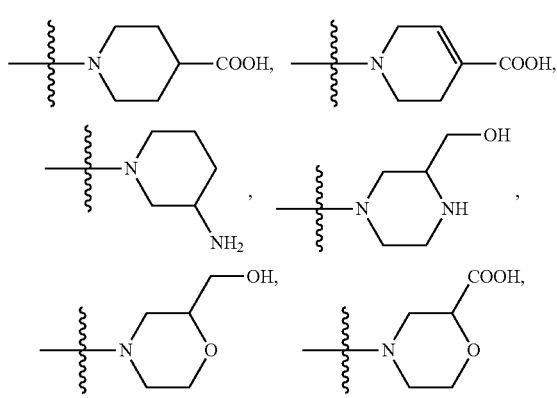
More preferred embodiments of the present invention include compounds of Formula (I) wherein
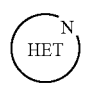
is selected from
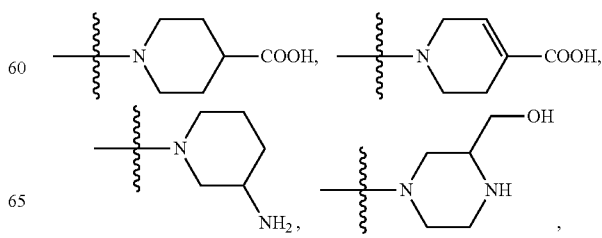

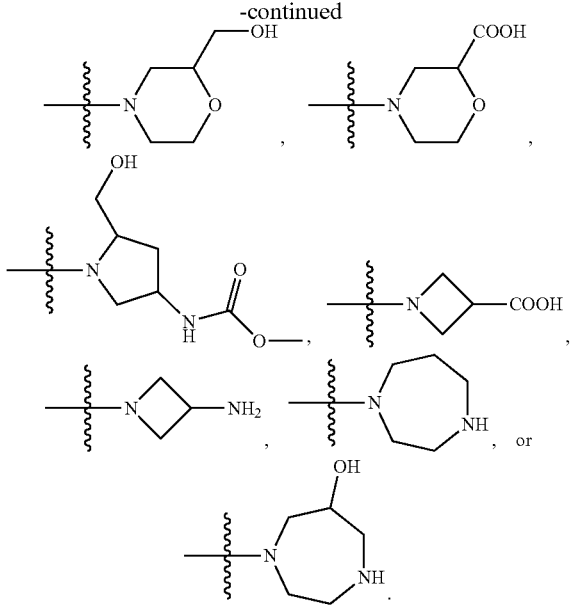

More particularly, an example of the present invention includes compounds of Formula (I) wherein X is —CH—;

$R_1$ is —C(O)—$C_{1-2}$alkyl, —Cl, —Br, —I, $C_{1-3}$alkyl, or $C_{3-5}$cycloalkyl; wherein
said $C_{1-3}$alkyl may be substituted with halo;

$R_2$ is —F, —Cl, —Br, cyclopropyl, $C_{1-3}$alkyl, $C_{1-2}$alkoxy or hydroxyl; wherein
said $C_{1-3}$alkyl may be substituted with halo or hydroxyl;

$R_3$ is —H, halo, or cyano; and

is selected from

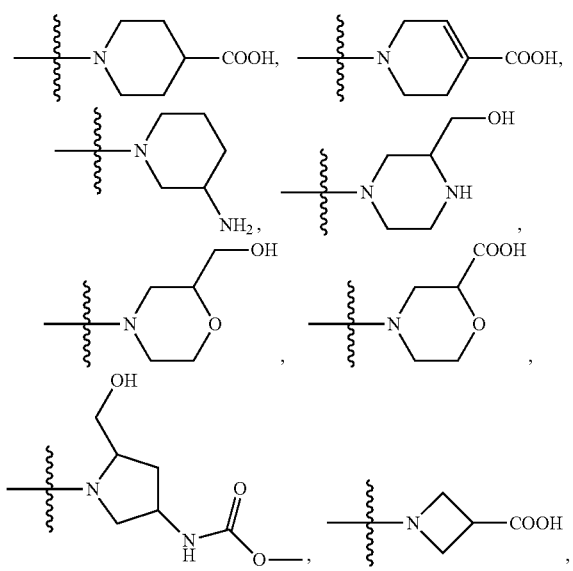

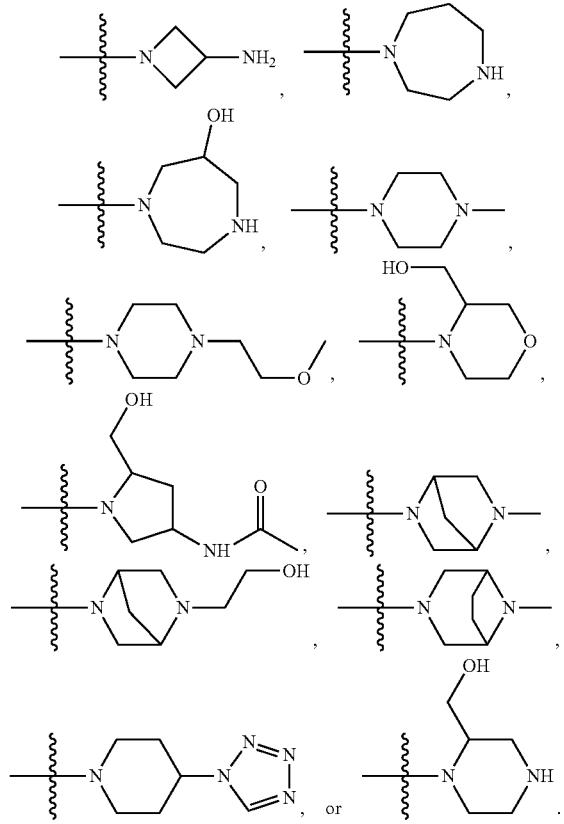

More particularly, an example of the present invention includes compounds of Formula (I) wherein X is —CH—;

$R_1$ is —C(O)—$CH_3$, —Cl, —Br, —I, —$CF_3$, or cyclopropyl;

$R_2$ is —F, —Cl, —Br, cyclopropyl, $C_{1-3}$alkyl, $C_{1-2}$alkoxy or hydroxyl; wherein said $C_{1-3}$alkyl may be substituted with halo or hydroxyl;

$R_3$ is —H, halo, or cyano; and

is selected from

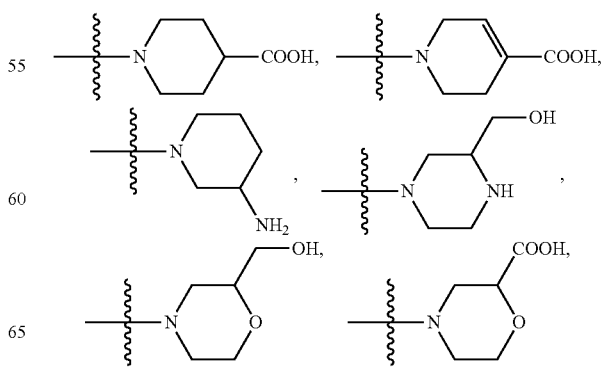

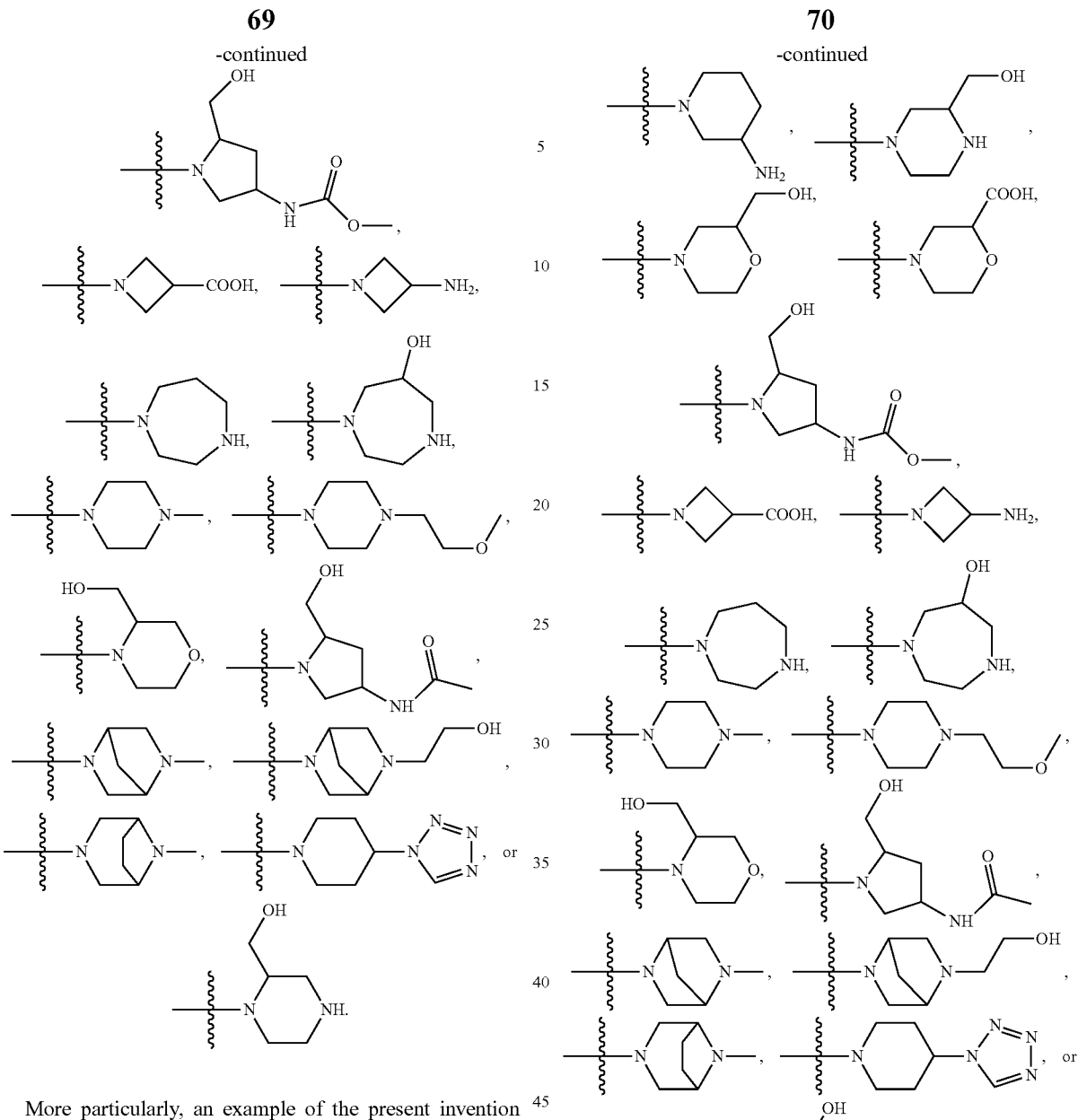
More particularly, an example of the present invention includes compounds of Formula (I) wherein
X is —CH—;
R₁ is —CF₃, —Br, or —I;
R₂ is —CF₃, hydroxyl, —OCH₃, or —Cl;
R₃ is —H, halo, or cyano; and
and
is selected from
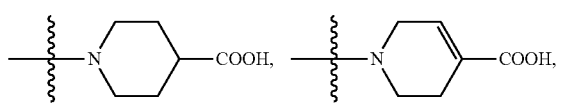
More particularly, an example of the present invention includes compounds of Formula (I) wherein
X is —CH;
R₁ is —CF₃;
R₂ is —CF₃, —OCH₃, or —Cl;
R₃ is —H; and
is selected from $R_2$ is —$CF_3$ or —Cl;
$R_3$ is —H; and (HET with N) is selected from

[chemical structures]

More particularly, an example of the present invention includes compounds of Formula (I) wherein X is —CH—;

$R_1$ is —$CF_3$;

More particularly, an example of the present invention includes compounds of Formula (I) wherein X is —CH—;

R$_1$ is —C(O)—C$_{1-2}$alkyl, —Cl, —Br, —I, C$_{1-3}$alkyl, or C$_{3-5}$cycloalkyl; wherein
said C$_{1-3}$alkyl may be substituted with halo;

R$_2$ is —F, —Cl, —Br, cyclopropyl, C$_{1-3}$alkyl, C$_{1-2}$alkoxy or hydroxyl; wherein
said C$_{1-3}$alkyl may be substituted with halo or hydroxyl;

R$_3$ is —H, halo, or cyano; and

is selected from

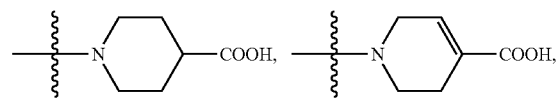

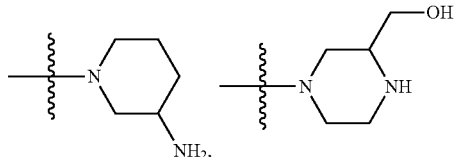

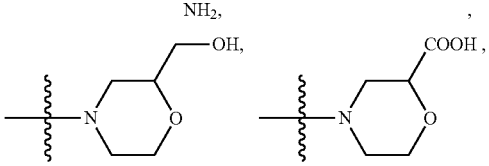

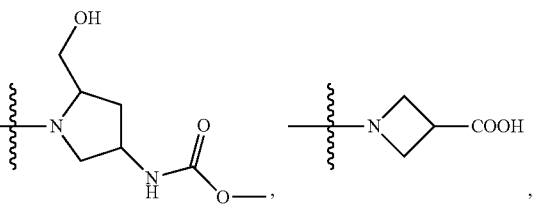

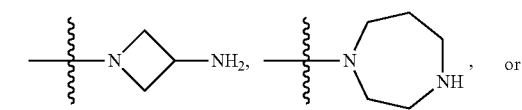

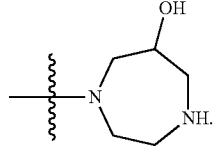

More particularly, an example of the present invention includes compounds of Formula (I) wherein X is —CH—;

R$_1$ is —C(O)—CH$_3$, —Cl, —Br, —I, —CF$_3$, or cyclopropyl;

R$_2$ is —F, —Cl, —Br, cyclopropyl, C$_{1-3}$alkyl, C$_{1-2}$alkoxy or hydroxyl; wherein
said C$_{1-3}$alkyl may be substituted with halo or hydroxyl;

R$_3$ is —H, halo, or cyano; and

is selected from

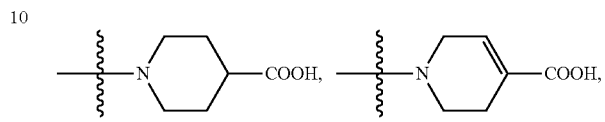

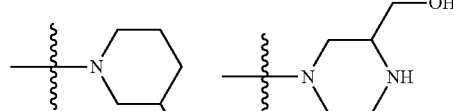

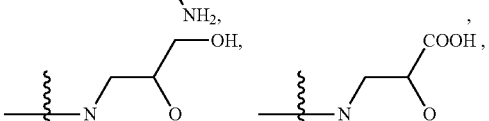

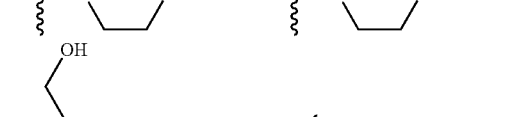

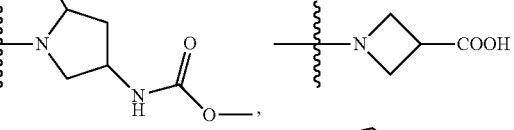

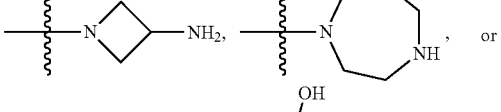

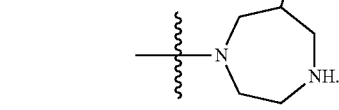

More particularly, an example of the present invention includes compounds of Formula (I) wherein X is —CH—;

R$_1$ is —CF$_3$, —Br, or —I;

R$_2$ is —CF$_3$, hydroxyl, —OCH$_3$, or —Cl;

R$_3$ is —H, halo, or cyano; and

is selected from

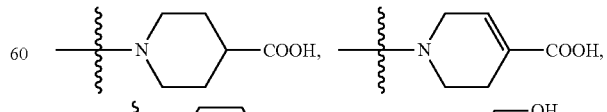

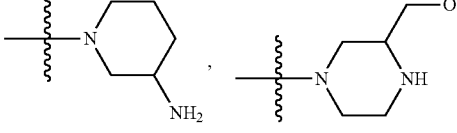

-continued

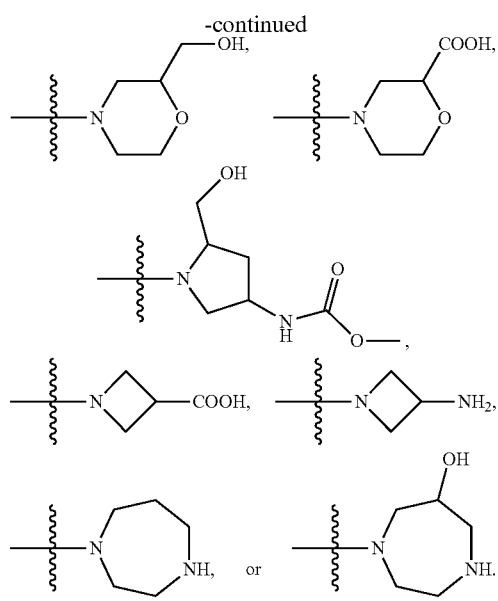

More particularly, an example of the present invention includes compounds of Formula (I) wherein
X is —CH—;
R₁ is —CF₃;
R₂ is —CF₃, —OCH₃, or —Cl;
R₃ is —H; and

is selected from

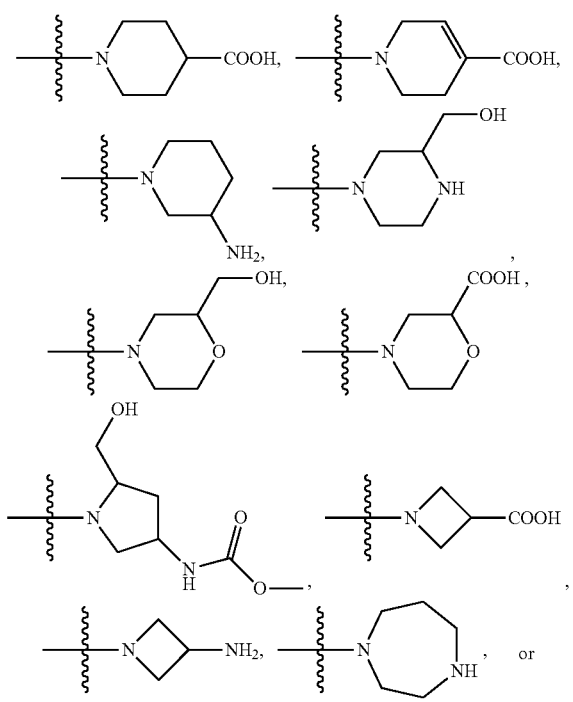

-continued

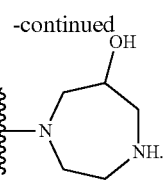

More particularly, an example of the present invention includes compounds of Formula (I) wherein
X is —CH—;
R₁ is —CF₃;
R₂ is —CF₃ or —Cl;
R₃ is —H; and

is selected from

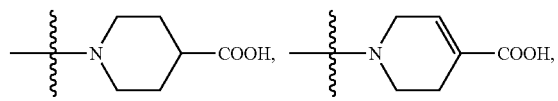
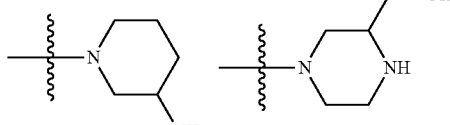
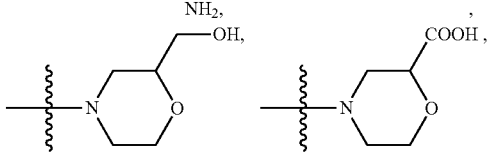
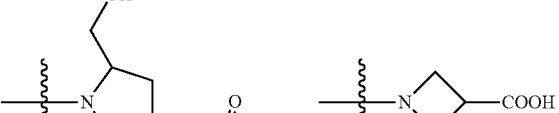
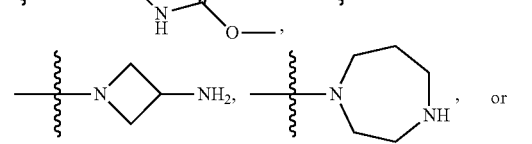
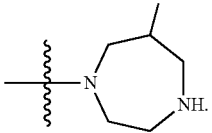

It is an embodiment of the present invention to provide a compound selected from:
1-{5-[1-(2,4-Bis-trifluoromethyl-benzyl)-1H-indazol-5-yl-methylene]-4-oxo-4,5-dihydro-thiazol-2-yl}-piperidine-4-carboxylic acid;
5-[1-(2,4-Bis-trifluoromethyl-benzyl)-1H-indazol-5-ylm-ethylene]-2-(4-methyl-piperazin-1-yl)-thiazol-4-one;
1-{5-[1-(2,4-Bis-trifluoromethyl-benzyl)-1H-indazol-5-yl-methylene]-4-oxo-4,5-dihydro-thiazol-2-yl}-azetidine-3-carboxylic acid;

1-{5-[1-(4-Chloro-2-trifluoromethyl-benzyl)-1H-indazol-5-ylmethylene]-4-oxo-4,5-dihydro-thiazol-2-yl}-piperidine-4-carboxylic acid;

1-{5-[1-(4-Chloro-2-trifluoromethyl-benzyl)-1H-indazol-5-ylmethylene]-4-oxo-4,5-dihydro-thiazol-2-yl}-azetidine-3-carboxylic acid;

2-(3-(S)-Amino-piperidin-1-yl)-5-[1-(2,4-bis-trifluoromethyl-benzyl)-1H-indazol-5-ylmethylene]-thiazol-4-one;

5-[1-(4-Chloro-2-trifluoromethyl-benzyl)-1H-indazol-5-ylmethylene]-2-[1,4]diazepan-1-yl-thiazol-4-one;

5-[1-(4-Chloro-2-trifluoromethyl-benzyl)-1H-indazol-5-ylmethylene]-2-[4-(2-methoxy-ethyl)-piperazin-1-yl]-thiazol-4-one;

2-(3-(R)-Amino-pyrrolidin-1-yl)-5-[1-(4-chloro-2-trifluoromethyl-benzyl)-1H-indazol-5-ylmethylene]-thiazol-4-one;

5-[1-(4-Chloro-2-trifluoromethyl-benzyl)-1H-indazol-5-ylmethylene]-2-(S)-(2-pyrrolidin-1-ylmethyl-pyrrolidin-1-yl)-thiazol-4-one;

5-[1-(2,4-Bis-trifluoromethyl-benzyl)-1H-indazol-5-ylmethylene]-2-[4-(2-methoxy-ethyl)-piperazin-1-yl]-thiazol-4-one;

5-[1-(2,4-Bis-trifluoromethyl-benzyl)-1H-indazol-5-ylmethylene]-2-(5-methyl-2S,5S-diaza-bicyclo[2.2.1]hept-2-yl)-thiazol-4-one;

5-[1-(2,4-Bis-trifluoromethyl-benzyl)-1H-indazol-5-ylmethylene]-2-[5-(2-hydroxy-ethyl)-2S,5S-diaza-bicyclo[2.2.1]hept-2-yl]-thiazol-4-one;

2-(4-{5-[1-(4-Chloro-2-trifluoromethyl-benzyl)-1H-indazol-5-ylmethylene]-4-oxo-4,5-dihydro-thiazol-2-yl}-piperazin-1-yl)-N,N-dimethyl-acetamide;

2-(3-Amino-azetidin-1-yl)-5-[1-(4-chloro-2-trifluoromethyl-benzyl)-1H-indazol-5-ylmethylene]-thiazol-4-one;

5-[1-(4-Chloro-2-trifluoromethyl-benzyl)-1H-indazol-5-ylmethylene]-2-(8-methyl-3,8-diaza-bicyclo[3.2.1]oct-3-yl)-thiazol-4-one;

5-[1-(2,4-Bis-trifluoromethyl-benzyl)-1H-indazol-5-ylmethylene]-2-(2-hydroxymethyl-piperazin-1-yl)-thiazol-4-one;

5-[1-(4-Chloro-2-trifluoromethyl-benzyl)-1H-indazol-5-ylmethylene]-2-[4-(1H-tetrazol-5-yl)-piperidin-1-yl]-thiazol-4-one;

5-[1-(4-Chloro-2-trifluoromethyl-benzyl)-1H-indazol-5-ylmethylene]-2-(6-hydroxy-[1,4]diazepan-1-yl)-thiazol-4-one;

5-[1-(2,4-Bis-trifluoromethyl-benzyl)-1H-indazol-5-ylmethylene]-2-(3-(R)-hydroxymethyl-piperazin-1-yl)-thiazol-4-one;

5-[1-(2,4-Bis-trifluoromethyl-benzyl)-1H-indazol-5-ylmethylene]-2-((2S)-hydroxymethyl-morpholin-4-yl)-thiazol-4-one;

5-[1-(2,4-Bis-trifluoromethyl-benzyl)-1H-indazol-5-ylmethylene]-2-(3(R)-hydroxymethyl-morpholin-4-yl)-thiazol-4-one;

5-[1-(4-Chloro-2-trifluoromethyl-benzyl)-1H-indazol-5-ylmethylene]-2-(3(R)-hydroxymethyl-morpholin-4-yl)-thiazol-4-one;

5-[1-(2,4-Bis-trifluoromethyl-benzyl)-3-methyl-1H-indazol-5-ylmethylene]-2-(3-(R)-hydroxymethyl-piperazin-1-yl)-thiazol-4-one;

5-[1-(2,4-Bis-trifluoromethyl-benzyl)-3-chloro-1H-indazol-5-ylmethylene]-2 (3-(R)-hydroxymethyl-piperazin-1-yl)-thiazol-4-one;

4-[5-({1-[2,4-Bis(trifluoromethyl)benzyl]-1H-indazol-5-yl}methylidene)-4-oxo-4,5-dihydro-1,3-thiazol-2-yl]morpholine-2-carboxylic acid;

1-[5-({1-[4-Chloro-2-(trifluoromethyl)benzyl]-1H-indazol-5-yl}methylidene)-4-oxo-4,5-dihydro-1,3-thiazol-2-yl]-1,2,3,6-tetrahydropyridine-4-carboxylic acid;

Methyl{1-[5-({1-[2,4-bis(trifluoromethyl)benzyl]-1H-indazol-5-yl}methylidene)-4-oxo-4,5-dihydro-1,3-thiazol-2-yl]-5-(R)-(hydroxymethyl)pyrrolidin-3-(R)-yl}carbamate;

1-[4-Chloro-2-(trifluoromethyl)benzyl]-5-{[2-(4-methylpiperazin-1-yl)-4-oxo-1,3-thiazol-5(4H)-ylidene]methyl}-1H-indazole-3-carbonitrile;

N-{1-[(3R,5R)-5-({1-[2,4-Bis(trifluoromethyl)benzyl]-1H-indazol-5-yl}methylidene)-4-oxo-4,5-dihydro-1,3-thiazol-2-yl]-5-(hydroxymethyl)pyrrolidin-3-yl}acetamide; and 5-[1-(2,4-Bis-trifluoromethyl-benzyl)-1H-indazol-5-ylmethylene]-2-(3-(S)-hydroxymethyl-piperazin-1-yl)-thiazol-4-one.

Particularly, the present invention provides a compound selected from:

1-{5-[1-(2,4-Bis-trifluoromethyl-benzyl)-1H-indazol-5-ylmethylene]-4-oxo-4,5-dihydro-thiazol-2-yl}-piperidine-4-carboxylic acid;

5-[1-(2,4-Bis-trifluoromethyl-benzyl)-1H-indazol-5-ylmethylene]-2-(4-methyl-piperazin-1-yl)-thiazol-4-one;

1-{5-[1-(4-Chloro-2-trifluoromethyl-benzyl)-1H-indazol-5-ylmethylene]-4-oxo-4,5-dihydro-thiazol-2-yl}-piperidine-4-carboxylic acid;

1-{5-[1-(4-Chloro-2-trifluoromethyl-benzyl)-1H-indazol-5-ylmethylene]-4-oxo-4,5-dihydro-thiazol-2-yl}-azetidine-3-carboxylic acid;

2-(3-(S)-Amino-piperidin-1-yl)-5-[1-(2,4-bis-trifluoromethyl-benzyl)-1H-indazol-5-ylmethylene]-thiazol-4-one;

5-[1-(4-Chloro-2-trifluoromethyl-benzyl)-1H-indazol-5-ylmethylene]-2-[1,4]diazepan-1-yl-thiazol-4-one;

5-[1-(4-Chloro-2-trifluoromethyl-benzyl)-1H-indazol-5-ylmethylene]-2-[4-(2-methoxy-ethyl)piperazin-1-yl]-thiazol-4-one;

2-(3-(R)-Amino-pyrrolidin-1-yl)-5-[1-(4-chloro-2-trifluoromethyl-benzyl)-1H-indazol-5-ylmethylene]-thiazol-4-one;

5-[1-(2,4-Bis-trifluoromethyl-benzyl)-1H-indazol-5-ylmethylene]-2-(5-methyl-2S,5S-diaza-bicyclo[2.2.1]hept-2-yl)-thiazol-4-one;

5-[1-(2,4-Bis-trifluoromethyl-benzyl)-1H-indazol-5-ylmethylene]-2-[5-(2-hydroxy-ethyl)-2S,5S-diaza-bicyclo[2.2.1]hept-2-yl]-thiazol-4-one;

2-(3-Amino-azetidin-1-yl)-5-[1-(4-chloro-2-trifluoromethyl-benzyl)-1H-indazol-5-ylmethylene]-thiazol-4-one;

5-[1-(4-Chloro-2-trifluoromethyl-benzyl)-1H-indazol-5-ylmethylene]-2-(6-hydroxy-[1,4]diazepan-1-yl)-thiazol-4-one;

5-[1-(2,4-Bis-trifluoromethyl-benzyl)-1H-indazol-5-ylmethylene]-2-(3-(R)-hydroxymethyl-piperazin-1-yl)-thiazol-4-one;

5-[1-(2,4-Bis-trifluoromethyl-benzyl)-1H-indazol-5-ylmethylene]-2-((2S)-hydroxymethyl-morpholin-4-yl)-thiazol-4-one;

5-[1-(2,4-Bis-trifluoromethyl-benzyl)-1H-indazol-5-ylmethylene]-2-(3(R)-hydroxymethyl-morpholin-4-yl)-thiazol-4-one;

5-[1-(4-Chloro-2-trifluoromethyl-benzyl)-1H-indazol-5-ylmethylene]-2-(3(R)-hydroxymethyl-morpholin-4-yl)-thiazol-4-one;

5-[1-(2,4-Bis-trifluoromethyl-benzyl)-3-methyl-1H-indazol-5-ylmethylene]-2-(3-(R)-hydroxymethyl-piperazin-1-yl)-thiazol-4-one;

5-[1-(2,4-Bis-trifluoromethyl-benzyl)-3-chloro-1H-indazol-5-ylmethylene]-2 (3-(R)-hydroxymethyl-piperazin-1-yl)-thiazol-4-one;

4-[5-({1-[2,4-Bis(trifluoromethyl)benzyl]-1H-indazol-5-yl}methylidene)-4-oxo-4,5-dihydro-1,3-thiazol-2-yl]morpholine-2-carboxylic acid;

1-[5-({1-[4-Chloro-2-(trifluoromethyl)benzyl]-1H-indazol-5-yl}methylidene)-4-oxo-4,5-dihydro-1,3-thiazol-2-yl]-1,2,3,6-tetrahydropyridine-4-carboxylic acid;

Methyl{1-[5-({1-[2,4-bis(trifluoromethyl)benzyl]-1H-indazol-5-yl}methylidene)-4-oxo-4,5-dihydro-1,3-thiazol-2-yl]-5-(R)-(hydroxymethyl)pyrrolidin-3-(R)-yl}carbamate;

1-[4-Chloro-2-(trifluoromethyl)benzyl]-5-{[2-(4-methylpiperazin-1-yl)-4-oxo-1,3-thiazol-5(4H)-ylidene]methyl}-1H-indazole-3-carbonitrile;

N-{1-[(3R,5R)-5-({1-[2,4-Bis(trifluoromethyl)benzyl]-1H-indazol-5-yl}methylidene)-4-oxo-4,5-dihydro-1,3-thiazol-2-yl]-5-(hydroxymethyl)pyrrolidin-3-yl}acetamide; and 5-[1-(2,4-Bis-trifluoromethyl-benzyl)-1H-indazol-5-ylmethylene]-2-(3-(S)-hydroxymethyl-piperazin-1-yl)-thiazol-4-one.

More particularly, the present invention provides a compound selected from:

1-{5-[1-(2,4-Bis-trifluoromethyl-benzyl)-1H-indazol-5-ylmethylene]-4-oxo-4,5-dihydro-thiazol-2-yl}-piperidine-4-carboxylic acid;

1-{5-[1-(4-Chloro-2-trifluoromethyl-benzyl)-1H-indazol-5-ylmethylene]-4-oxo-4,5-dihydro-thiazol-2-yl}-azetidine-3-carboxylic acid;

2-(3-(S)-Amino-piperidin-1-yl)-5-[1-(2,4-bis-trifluoromethyl-benzyl)-1H-indazol-5-ylmethylene]-thiazol-4-one;

5-[1-(4-Chloro-2-trifluoromethyl-benzyl)-1H-indazol-5-ylmethylene]-2-[1,4]diazepan-1-yl-thiazol-4-one;

2-(3-Amino-azetidin-1-yl)-5-[1-(4-chloro-2-trifluoromethyl-benzyl)-1H-indazol-5-ylmethylene]-thiazol-4-one;

5-[1-(4-Chloro-2-trifluoromethyl-benzyl)-1H-indazol-5-ylmethylene]-2-(6-hydroxy-[1,4]diazepan-1-yl)thiazol-4-one;

5-[1-(2,4-Bis-trifluoromethyl-benzyl)-1H-indazol-5-ylmethylene]-2-(3-(R)-hydroxymethyl-piperazin-1-yl)-thiazol-4-one;

5-[1-(2,4-Bis-trifluoromethyl-benzyl)-1H-indazol-5-ylmethylene]-2-((2S)-hydroxymethyl-morpholin-4-yl)-thiazol-4-one;

5-[1-(4-Chloro-2-trifluoromethyl-benzyl)-1H-indazol-5-ylmethylene]-2-(3(R)-hydroxymethyl-morpholin-4-yl)-thiazol-4-one;

5-[1-(2,4-Bis-trifluoromethyl-benzyl)-3-methyl-1H-indazol-5-ylmethylene]-2-(3-(R)-hydroxymethyl-piperazin-1-yl)-thiazol-4-one;

5-[1-(2,4-Bis-trifluoromethyl-benzyl)-3-chloro-1H-indazol-5-ylmethylene]-2 (3-(R)-hydroxymethyl-piperazin-1-yl) thiazol-4-one;

4-[5-({1-[2,4-Bis(trifluoromethyl)benzyl]-1H-indazol-5-yl}methylidene)-4-oxo-4,5-dihydro-1,3-thiazol-2-yl]morpholine-2-carboxylic acid;

1-[5-({1-[4-Chloro-2-(trifluoromethyl)benzyl]-1H-indazol-5-yl}methylidene)-4-oxo-4,5-dihydro-1,3-thiazol-2-yl]-1,2,3,6-tetrahydropyridine-4-carboxylic acid;

Methyl{1-[5-({1-[2,4-bis(trifluoromethyl)benzyl]-1H-indazol-5-yl}methylidene)-4-oxo-4,5-dihydro-1,3-thiazol-2-yl]-5-(R)-(hydroxymethyl)pyrrolidin-3-(R)-yl}carbamate;

1-[4-Chloro-2-(trifluoromethyl)benzyl]-5-{[2-(4-methylpiperazin-1-yl)-4-oxo-1,3-thiazol-5(4H)-ylidene]methyl}-1H-indazole-3-carbonitrile; and 5-[1-(2,4-Bis-trifluoromethyl-benzyl)-1H-indazol-5-ylmethylene]-2-(3-(S)-hydroxymethyl-piperazin-1-yl)-thiazol-4-one.

Another aspect of the present invention features a pharmaceutical composition comprising at least one compound of Formula (I) and at least one pharmaceutically acceptable carrier. Particularly, a pharmaceutical composition of the present invention can further comprise at least one additional agent, drug, medicament, antibody and/or inhibitor for treating, ameliorating or preventing the progression of an ERR-α mediated disease.

A pharmaceutical composition of the present invention comprises a compound selected from:

1-{5-[1-(2,4-Bis-trifluoromethyl-benzyl)-1H-indazol-5-ylmethylene]-4-oxo-4,5-dihydro-thiazol-2-yl}-piperidine-4-carboxylic acid;

5-[1-(2,4-Bis-trifluoromethyl-benzyl)-1H-indazol-5-ylmethylene]-2-(4-methyl-piperazin-1-yl)-thiazol-4-one;

1-{5-[1-(2,4-Bis-trifluoromethyl-benzyl)-1H-indazol-5-ylmethylene]-4-oxo-4,5-dihydro-thiazol-2-yl}-azetidine-3-carboxylic acid;

1-{5-[1-(4-Chloro-2-trifluoromethyl-benzyl)-1H-indazol-5-ylmethylene]-4-oxo-4,5-dihydro-thiazol-2-yl}-piperidine-4-carboxylic acid;

1-{5-[1-(4-Chloro-2-trifluoromethyl-benzyl)-1H-indazol-5-ylmethylene]-4-oxo-4,5-dihydro-thiazol-2-yl}-azetidine-3-carboxylic acid;

2-(3-(S)-Amino-piperidin-1-yl)-5-[1-(2,4-bis-trifluoromethyl-benzyl)-1H-indazol-5-ylmethylene]-thiazol-4-one;

5-[1-(4-Chloro-2-trifluoromethyl-benzyl)-1H-indazol-5-ylmethylene]-2-[1,4]diazepan-1-yl-thiazol-4-one;

5-[1-(4-Chloro-2-trifluoromethyl-benzyl)-1H-indazol-5-ylmethylene]-2-[4-(2-methoxy-ethyl)-piperazin-1-yl]-thiazol-4-one;

2-(3-(R)-Amino-pyrrolidin-1-yl)-5-[1-(4-chloro-2-trifluoromethyl-benzyl)-1H-indazol-5-ylmethylene]-thiazol-4-one;

5-[1-(4-Chloro-2-trifluoromethyl-benzyl)-1H-indazol-5-ylmethylene]-2-(S)-(2-pyrrolidin-1-ylmethyl-pyrrolidin-1-yl)-thiazol-4-one;

5-[1-(2,4-Bis-trifluoromethyl-benzyl)-1H-indazol-5-ylmethylene]-2-[4-(2-methoxy-ethyl)-piperazin-1-yl]-thiazol-4-one;

5-[1-(2,4-Bis-trifluoromethyl-benzyl)-1H-indazol-5-ylmethylene]-2-(5-methyl-2S,5S-diaza-bicyclo[2.2.1]hept-2-yl)-thiazol-4-one;

5-[1-(2,4-Bis-trifluoromethyl-benzyl)-1H-indazol-5-ylmethylene]-2-[5-(2-hydroxy-ethyl)-2S,5S-diaza-bicyclo[2.2.1]hept-2-yl]-thiazol-4-one;

2-(4-{5-[1-(4-Chloro-2-trifluoromethyl-benzyl)-1H-indazol-5-ylmethylene]-4-oxo-4,5-dihydro-thiazol-2-yl}-piperazin-1-yl)-N,N-dimethyl-acetamide;

2-(3-Amino-azetidin-1-yl)-5-[1-(4-chloro-2-trifluoromethyl-benzyl)-1H-indazol-5-ylmethylene]-thiazol-4-one;

5-[1-(4-Chloro-2-trifluoromethyl-benzyl)-1H-indazol-5-ylmethylene]-2-(8-methyl-3,8-diaza-bicyclo[3.2.1]oct-3-yl)-thiazol-4-one;

5-[1-(2,4-Bis-trifluoromethyl-benzyl)-1H-indazol-5-ylmethylene]-2-(2-hydroxymethyl-piperazin-1-yl)-thiazol-4-one;

5-[1-(4-Chloro-2-trifluoromethyl-benzyl)-1H-indazol-5-ylmethylene]-2-[4-(1H-tetrazol-5-yl)-piperidin-1-yl]-thiazol-4-one;

5-[1-(4-Chloro-2-trifluoromethyl-benzyl)-1H-indazol-5-yl-methylene]-2-(6-hydroxy-[1,4]diazepan-1-yl)-thiazol-4-one;

5-[1-(2,4-Bis-trifluoromethyl-benzyl)-1H-indazol-5-ylmethylene]-2-(3-(R)-hydroxymethyl-piperazin-1-yl)-thiazol-4-one;

5-[1-(2,4-Bis-trifluoromethyl-benzyl)-1H-indazol-5-ylmethylene]-2-((2S)-hydroxymethyl-morpholin-4-yl)-thiazol-4-one;

5-[1-(2,4-Bis-trifluoromethyl-benzyl)-1H-indazol-5-ylmethylene]-2-(3(R)-hydroxymethyl-morpholin-4-yl)-thiazol-4-one;

5-[1-(4-Chloro-2-trifluoromethyl-benzyl)-1H-indazol-5-ylmethylene]-2-(3(R)-hydroxymethyl-morpholin-4-yl)-thiazol-4-one;

5-[1-(2,4-Bis-trifluoromethyl-benzyl)-3-methyl-1H-indazol-5-ylmethylene]-2-(3-(R)-hydroxymethyl-piperazin-1-yl)-thiazol-4-one;

5-[1-(2,4-Bis-trifluoromethyl-benzyl)-3-chloro-1H-indazol-5-ylmethylene]-2 (3-(R)-hydroxymethyl-piperazin-1-yl)-thiazol-4-one;

4-[5-({1-[2,4-Bis(trifluoromethyl)benzyl]-1H-indazol-5-yl}methylidene)-4-oxo-4,5-dihydro-1,3-thiazol-2-yl]morpholine-2-carboxylic acid;

1-[5-({1-[4-Chloro-2-(trifluoromethyl)benzyl]-1H-indazol-5-yl}methylidene)-4-oxo-4,5-dihydro-1,3-thiazol-2-yl]-1,2,3,6-tetrahydropyridine-4-carboxylic acid;

Methyl{1-[5-({1-[2,4-bis(trifluoromethyl)benzyl]-1H-indazol-5-yl}methylidene)-4-oxo-4,5-dihydro-1,3-thiazol-2-yl]-5-(R)-(hydroxymethyl)pyrrolidin-3-(R)-yl}carbamate;

1-[4-Chloro-2-(trifluoromethyl)benzyl]-5-{[2-(4-methylpiperazin-1-yl)-4-oxo-1,3-thiazol-5(4H)-ylidene]methyl}-1H-indazole-3-carbonitrile;

N-{1-[(3R,5R)-5-({1-[2,4-Bis(trifluoromethyl)benzyl]-1H-indazol-5-yl}methylidene)-4-oxo-4,5-dihydro-1,3-thiazol-2-yl]-5-(hydroxymethyl)pyrrolidin-3-yl}acetamide; and 5-[1-(2,4-Bis-trifluoromethyl-benzyl)-1H-indazol-5-ylmethylene]-2-(3-(S)-hydroxymethyl-piperazin-1-yl)-thiazol-4-one.

Particularly, a pharmaceutical composition of the present invention comprises at least a compound selected from:

1-{5-[1-(2,4-Bis-trifluoromethyl-benzyl)-1H-indazol-5-ylmethylene]-4-oxo-4,5-dihydro-thiazol-2-yl}-piperidine-4-carboxylic acid;

5-[1-(2,4-Bis-trifluoromethyl-benzyl)-1H-indazol-5-ylmethylene]-2-(4-methyl-piperazin-1-yl)-thiazol-4-one;

1-{5-[1-(4-Chloro-2-trifluoromethyl-benzyl)-1H-indazol-5-ylmethylene]-4-oxo-4,5-dihydro-thiazol-2-yl}-piperidine-4-carboxylic acid;

1-{5-[1-(4-Chloro-2-trifluoromethyl-benzyl)-1H-indazol-5-ylmethylene]-4-oxo-4,5-dihydro-thiazol-2-yl}-azetidine-3-carboxylic acid;

2-(3-(S)-Amino-piperidin-1-yl)-5-[1-(2,4-bis-trifluoromethyl-benzyl)-1H-indazol-5-ylmethylene]-thiazol-4-one;

5-[1-(4-Chloro-2-trifluoromethyl-benzyl)-1H-indazol-5-ylmethylene]-2-[1,4]diazepan-1-yl-thiazol-4-one;

5-[1-(4-Chloro-2-trifluoromethyl-benzyl)-1H-indazol-5-ylmethylene]-2-[4-(2-methoxy-ethyl)-piperazin-1-yl]-thiazol-4-one;

2-(3-(R)-Amino-pyrrolidin-1-yl)-5-[1-(4-chloro-2-trifluoromethyl-benzyl)-1H-indazol-5-ylmethylene]-thiazol-4-one;

5-[1-(2,4-Bis-trifluoromethyl-benzyl)-1H-indazol-5-ylmethylene]-2-(5-methyl-2S,5S-diaza-bicyclo[2.2.1]hept-2-yl)-thiazol-4-one;

5-[1-(2,4-Bis-trifluoromethyl-benzyl)-1H-indazol-5-ylmethylene]-2-[5-(2-hydroxy-ethyl)-2S,5S-diaza-bicyclo[2.2.1]hept-2-yl]-thiazol-4-one;

2-(3-Amino-azetidin-1-yl)-5-[1-(4-chloro-2-trifluoromethyl-benzyl)-1H-indazol-5-ylmethylene]-thiazol-4-one;

5-[1-(4-Chloro-2-trifluoromethyl-benzyl)-1H-indazol-5-ylmethylene]-2-(6-hydroxy-[1,4]diazepan-1-yl)-thiazol-4-one;

5-[1-(2,4-Bis-trifluoromethyl-benzyl)-1H-indazol-5-ylmethylene]-2-(3-(R)-hydroxymethyl-piperazin-1-yl)-thiazol-4-one;

5-[1-(2,4-Bis-trifluoromethyl-benzyl)-1H-indazol-5-ylmethylene]-2-((2S)-hydroxymethyl-morpholin-4-yl)-thiazol-4-one;

5-[1-(2,4-Bis-trifluoromethyl-benzyl)-1H-indazol-5-ylmethylene]-2-(3(R)-hydroxymethyl-morpholin-4-yl)-thiazol-4-one;

5-[1-(4-Chloro-2-trifluoromethyl-benzyl)-1H-indazol-5-ylmethylene]-2-(3(R)-hydroxymethyl-morpholin-4-yl)-thiazol-4-one;

5-[1-(2,4-Bis-trifluoromethyl-benzyl)-3-methyl-1H-indazol-5-ylmethylene]-2-(3-(R)-hydroxymethyl-piperazin-1-yl)-thiazol-4-one;

5-[1-(2,4-Bis-trifluoromethyl-benzyl)-3-chloro-1H-indazol-5-ylmethylene]-2 (3-(R)-hydroxymethyl-piperazin-1-yl)-thiazol-4-one;

4-[5-({1-[2,4-Bis(trifluoromethyl)benzyl]-1H-indazol-5-yl}methylidene)-4-oxo-4,5-dihydro-1,3-thiazol-2-yl]morpholine-2-carboxylic acid;

1-[5-({1-[4-Chloro-2-(trifluoromethyl)benzyl]-1H-indazol-5-yl}methylidene)-4-oxo-4,5-dihydro-1,3-thiazol-2-yl]-1,2,3,6-tetrahydropyridine-4-carboxylic acid;

Methyl{1-[5-({1-[2,4-bis(trifluoromethyl)benzyl]-1H-indazol-5-yl}methylidene)-4-oxo-4,5-dihydro-1,3-thiazol-2-yl]-5-(R)-(hydroxymethyl)pyrrolidin-3-(R)-yl}carbamate;

1-[4-Chloro-2-(trifluoromethyl)benzyl]-5-{[2-(4-methylpiperazin-1-yl)-4-oxo-1,3-thiazol-5(4H)-ylidene]methyl}-1H-indazole-3-carbonitrile;

N-{1-[(3R,5R)-5-({1-[2,4-Bis(trifluoromethyl)benzyl]-1H-indazol-5-yl}methylidene)-4-oxo-4,5-dihydro-1,3-thiazol-2-yl]-5-(hydroxymethyl)pyrrolidin-3-yl}acetamide; and 5-[1-(2,4-Bis-trifluoromethyl-benzyl)-1H-indazol-5-ylmethylene]-2-(3-(S)-hydroxymethyl-piperazin-1-yl)-thiazol-4-one.

More particularly, a pharmaceutical composition of the present invention comprises at least a compound selected from:

1-{5-[1-(2,4-Bis-trifluoromethyl-benzyl)-1H-indazol-5-ylmethylene]-4-oxo-4,5-dihydro-thiazol-2-yl}-piperidine-4-carboxylic acid;

1-{5-[1-(4-Chloro-2-trifluoromethyl-benzyl)-1H-indazol-5-ylmethylene]-4-oxo-4,5-dihydro-thiazol-2-yl}-azetidine-3-carboxylic acid;

2-(3-(S)-Amino-piperidin-1-yl)-5-[1-(2,4-bis-trifluoromethyl-benzyl)-1H-indazol-5-ylmethylene]-thiazol-4-one;

5-[1-(4-Chloro-2-trifluoromethyl-benzyl)-1H-indazol-5-ylmethylene]-2-[1,4]diazepan-1-yl-thiazol-4-one;

2-(3-Amino-azetidin-1-yl)-5-[1-(4-chloro-2-trifluoromethyl-benzyl)-1H-indazol-5-ylmethylene]-thiazol-4-one;

5-[1-(4-Chloro-2-trifluoromethyl-benzyl)-1H-indazol-5-ylmethylene]-2-(6-hydroxy-[1,4]diazepan-1-yl)-thiazol-4-one;

5-[1-(2,4-Bis-trifluoromethyl-benzyl)-1H-indazol-5-ylmethylene]-2-(3-(R)-hydroxymethyl-piperazin-1-yl)-thiazol-4-one;

5-[1-(2,4-Bis-trifluoromethyl-benzyl)-1H-indazol-5-ylm-ethylene]-2-((2S)-hydroxymethyl-morpholin-4-yl)-thiazol-4-one;

5-[1-(4-Chloro-2-trifluoromethyl-benzyl)-1H-indazol-5-yl-methylene]-2-(3(R)-hydroxymethyl-morpholin-4-yl)-thiazol-4-one;

5-[1-(2,4-Bis-trifluoromethyl-benzyl)-3-methyl-1H-indazol-5-ylmethylene]-2-(3-(R)-hydroxymethyl-piperazin-1-yl)-thiazol-4-one;

5-[1-(2,4-Bis-trifluoromethyl-benzyl)-3-chloro-1H-indazol-5-ylmethylene]-2 (3-(R)-hydroxymethyl-piperazin-1-yl)-thiazol-4-one;

4-[5-({1-[2,4-Bis(trifluoromethyl)benzyl]-1H-indazol-5-yl}methylidene)-4-oxo-4,5-dihydro-1,3-thiazol-2-yl]morpholine-2-carboxylic acid;

1-[5-({1-[4-Chloro-2-(trifluoromethyl)benzyl]-1H-indazol-5-yl}methylidene)-4-oxo-4,5-dihydro-1,3-thiazol-2-yl]-1,2,3,6-tetrahydropyridine-4-carboxylic acid;

Methyl{1-[5-({1-[2,4-bis(trifluoromethyl)benzyl]-1H-indazol-5-yl}methylidene)-4-oxo-4,5-dihydro-1,3-thiazol-2-yl]-5-(R)-(hydroxymethyl)pyrrolidin-3-(R)-yl}carbamate;

1-[4-Chloro-2-(trifluoromethyl)benzyl]-5-{[2-(4-methylpiperazin-1-yl)-4-oxo-1,3-thiazol-5(4H)-ylidene]methyl}-1H-indazole-3-carbonitrile; and 5-[1-(2,4-Bis-trifluoromethyl-benzyl)-1H-indazol-5-ylm-ethylene]-2-(3-(S)-hydroxymethyl-piperazin-1-yl)-thiazol-4-one.

It is an embodiment of the present invention to provide a compound selected from:

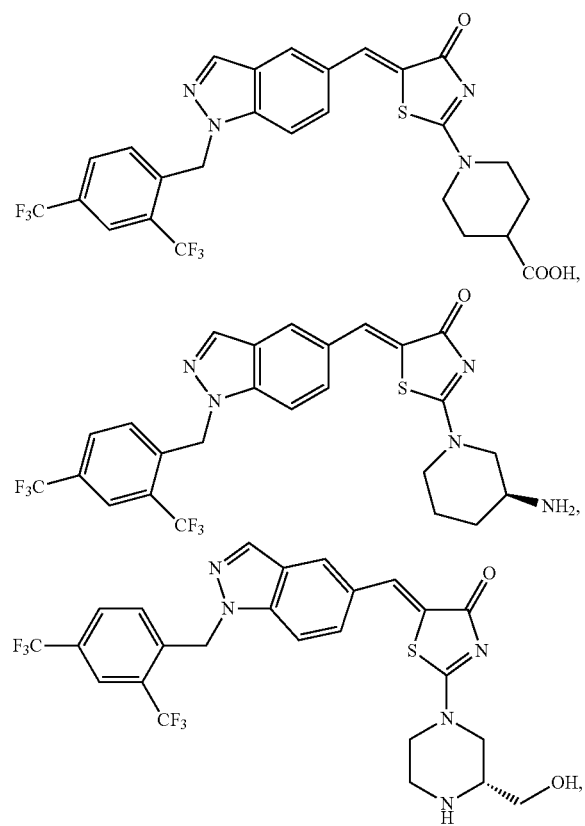

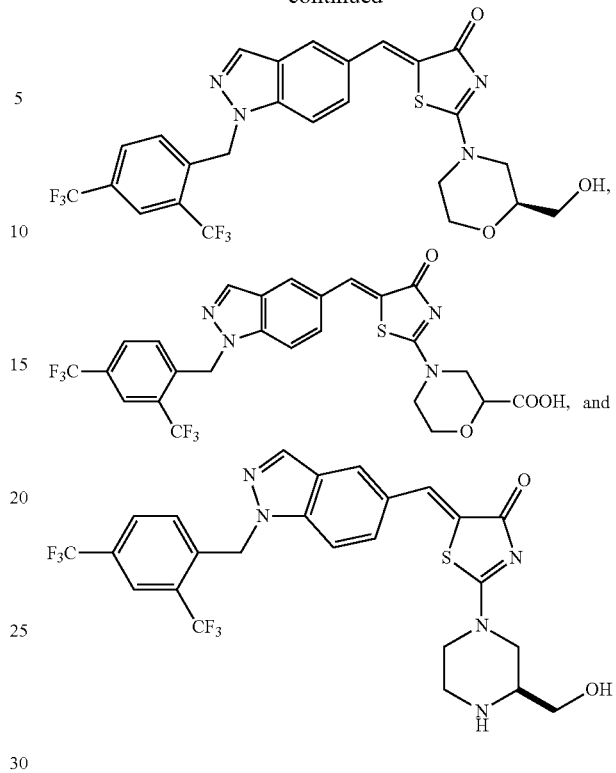

The present invention also features a method of treating a subject suffering from or diagnosed with a disease, disorder, or condition mediated by ERR-α activity, comprising administering to the subject a therapeutically effective amount of at least one compound of Formula (I).

The present invention also features a method for preventing or inhibiting the progression of an ERR-α-mediated condition in a subject in need thereof, comprising administering to said subject a therapeutically effective amount of at least one compound of Formula (I).

The present invention also features a method for treating a prediabetic condition in a subject in need thereof, comprising administering to said subject a therapeutically effective amount of at least one compound of Formula (I).

Such disease, disorder, or condition can include, but is not limited to ankylosing spondylitis, artherosclerosis, arthritis (such as rheumatoid arthritis, infectious arthritis, childhood arthritis, psoriatic arthritis, reactive arthritis), bone-related diseases (including those related to bone formation), breast cancer (including those unresponsive to anti-estrogen therapy), cardiovascular disorders, cartilage-related disease (such as cartilage injury/loss, cartilage degeneration, and those related to cartilage formation), chondrodysplasia, chondrosarcoma, chronic back injury, chronic bronchitis, chronic inflammatory airway disease, chronic obstructive pulmonary disease, diabetes, disorders of energy homeostasis, gout, pseudogout, lipid disorders, metabolic syndrome, multiple myeloma, obesity, osteoarthritis, osteogenesis imperfecta, osteolytic bone metastasis, osteomalacia, osteoporosis, Paget's disease, periodontal disease, polymyalgia rheumatica, Reiter's syndrome, repetitive stress injury, hyperglycemia, elevated blood glucose level, and insulin resistance.

According to one aspect of the invention, the disclosed compounds and compositions are useful for the amelioration of symptoms associated with, the treatment of, and preventing and/or inhibiting the progression of, the following conditions and diseases: bone-related disease, bone formation, cartilage formation, cartilage loss, cartilage degeneration, cartilage injury, ankylosing spondylitis, chronic back injury, gout, osteoporosis, osteolytic bone metastasis, multiple myeloma, chondrosarcoma, chondrodysplasia, osteogenesis imperfecta, osteomalacia, Paget's disease, polymyalgia rheumatica, pseudogout, arthritis, rheumatoid arthritis, infectious arthritis, osteoarthritis, psoriatic arthritis, reactive arthritis, childhood arthritis, Reiter's syndrome, and repetitive stress injury.

According to another aspect of the invention, the disclosed compounds and compositions are useful for the amelioration of symptoms associated with, the treatment of, and preventing and/or inhibiting the progression of, the following conditions and diseases: periodontal disease, chronic inflammatory airway disease, chronic bronchitis, and chronic obstructive pulmonary disease.

According to a further aspect of the invention, the disclosed compounds and compositions are useful for the amelioration of symptoms associated with, the treatment of, and preventing and/or inhibiting the progression of breast cancer.

According to yet another aspect of the invention, the disclosed compounds and compositions are useful for the amelioration of symptoms associated with, the treatment of, and preventing and/or inhibiting the progression of, the following conditions and diseases: metabolic syndrome, obesity, disorders of energy homeostasis, diabetes, lipid disorders, cardiovascular disorders, artherosclerosis, hyperglycemia, elevated blood glucose level, and insulin resistance.

Particularly, a method of the present invention comprises administering to the subject a therapeutically effective amount of (a) at least one compound of Formula (I); and (b) at least one additional agent selected from an anti-diabetic agent, an anti-obesity agent, a lipid lowering agent, an anti-thrombotic agent, direct thrombin inhibitor, and a blood pressure lowering agent, said administration being in any order. More particularly, the additional agent in (b) is an anti-obesity agent selected from CB1 antagonists, monoamine reuptake inhibitors, MTP inhibitors and lipase inhibitors. More particularly, the additional agent in (b) is an anti-diabetic agent selected from metformin, DPP-IV inhibitors, GLP-1 mimetics, glucokinase modulators, glucagon antagonists, SGLT2 inhibitors, PPARγ agonists and GPR119 modulators. More particularly, the additional agent in (b) is selected from Metformin, Sitagliptin and Pioglitazone.

The present invention also features a method for treating or inhibiting the progression of one or more ERR-α-mediated conditions, said method comprising administering to a patient in need of treatment a pharmaceutically effective amount of a composition of the invention.

It is a further embodiment of the invention to provide a process for making a pharmaceutical composition comprising admixing any of the compounds according to Formula (I) and a pharmaceutically acceptable carrier.

The invention also features pharmaceutical compositions which include, without limitation, one or more of the disclosed compounds, and pharmaceutically acceptable carriers or excipients.

In a further embodiment of the invention, a method for treating or ameliorating an ERR-α-mediated condition in a subject in need thereof comprises administering to the subject a therapeutically effective amount of at least one compound of Formula (I), wherein the therapeutically effective amount of the compound of Formula (I) is from about 0.1 mg/dose to about 5000 mg/dose. In particular, the therapeutically effective amount of the compound of Formula (I) is from about 0.5 mg/dose to about 1000 mg/dose. More particularly, the therapeutically effective amount of the compound of Formula (I) is from about 1 mg/dose to about 100 mg/dose. In a further embodiment of the invention, the number of doses per day of a compound of Formula (I) is from 1 to 3 doses. In a further embodiment of the invention, the therapeutically effective amount of the compound of Formula (I) is from about 0.001 mg/kg/day to about 30 mg/kg/day. More particularly, the therapeutically effective amount of the compound of Formula (I) is from about 0.01 mg/kg/day to about 2 mg/kg/day.

In a further embodiment of the invention, a method for preventing or inhibiting the progression of an ERR-α-mediated condition in a subject in need thereof comprises administering to the subject a therapeutically effective amount of at least one compound of Formula (I), wherein the therapeutically effective amount of the compound of Formula (I) is from about 0.1 mg/dose to about 5000 mg/dose. In particular, the therapeutically effective amount of the compound of Formula (I) is from about 1 mg/dose to about 100 mg/dose. In a further embodiment of the invention, the number of doses per day of a compound of Formula (I) is from 1 to 3 doses. In a further embodiment of the invention, the therapeutically effective amount of the compound of Formula (I) is from about 0.001 mg/kg/day to about 30 mg/kg/day. More particularly, the therapeutically effective amount of the compound of Formula (I) is from about 0.01 mg/kg/day to about 2 mg/kg/day.

In yet another embodiment of the invention, a method for treating a prediabetic condition in a subject in need thereof, comprises administering to said subject a therapeutically effective amount of at least one compound of Formula (I), wherein the therapeutically effective amount of the compound of Formula (I) is from about 0.1 mg/dose to about 5000 mg/dose. In particular, the therapeutically effective amount of the compound of Formula (I) is from about 1 mg/dose to about 100 mg/dose. In a further embodiment of the invention, the number of doses per day of a compound of Formula (I) is from 1 to 3 doses. In a further embodiment of the invention, the therapeutically effective amount of the compound of Formula (I) is from about 0.001 mg/kg/day to about 30 mg/kg/day. More particularly, the therapeutically effective amount of the compound of Formula (I) is from about 0.01 mg/kg/day to about 2 mg/kg/day.

The invention is further described below.

A) Terms

Some terms are defined below and by their usage throughout this disclosure.

Unless otherwise noted, "alkyl" as used herein, whether used alone or as part of a substituent group, refers to a saturated, branched, or straight-chain monovalent hydrocarbon radical derived by the removal of one hydrogen atom from a single carbon atom of a parent alkane. Typical alkyl groups include, but are not limited to, methyl; ethyls such as ethanyl; propyls such as propan-1-yl, propan-2-yl, cyclopropan-1-yl; butyls such as butan-1-yl, butan-2-yl, 2-methyl-propan-1-yl, 2-methyl-propan-2-yl, cyclobutan-1-yl and the like. In preferred embodiments, the alkyl groups are $C_{1-6}$alkyl, $C_{1-4}$alkyl, with $C_{1-3}$ being particularly preferred. "Alkoxy" radicals are oxygen ethers formed from the previously described straight or branched chain alkyl groups.

The term "cycloalkyl", as used herein, refers to a stable, saturated or partially saturated monocyclic or bicyclic ring system containing from 3 to 10 ring carbons. preferably 5 to 7 ring carbons, and more preferably 3 to 5 ring carbons. Examples of such cyclic alkyl rings include cyclopropyl, cyclobutyl, cyclopentyl, cyclohexyl or cycloheptyl.

The term "alkenyl" refers to an unsaturated branched, straight-chain or cyclic monovalent hydrocarbon radical, which has at least one carbon-carbon double bond, derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, 1-methylethenyl, etc.; and the like.

The term "alkynyl" refers to an unsaturated branched, straight-chain or cyclic monovalent hydrocarbon radical, which has at least one carbon-carbon triple bond, derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

The term "heteroaryl" refers to a monovalent heteroaromatic radical derived by the removal of one hydrogen atom from a single atom of a parent heteroaromatic ring system. Typical heteroaryl groups include monocyclic and bicyclic systems where one or both rings are heteroaromatic. Heteroaromatic rings may contain 1-4 heteroatoms selected from O, N, and S. Examples include but are not limited to, radicals derived from carbazole, imidazole, indazole, indole, indolizine, isoindole, isoquinoline, isothiazole, isoxazole, naphthyridine, oxadiazole, oxazole, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

The term "aryl", as used herein, refers to carbocyclic aromatic groups comprising 6- to 14-carbon atoms. Typical aryl groups include but are not limited to, a stable six-membered monocyclic, a ten-membered bicyclic or a fourteen-membered tricyclic aromatic ring system. Examples of aryl groups include, but are not limited to, phenyl or naphthalenyl.

The term "heterocyclyl" or "heterocycle" is a 3- to 12-member saturated, or partially saturated single or fused ring system and preferably a 4 to 9 member saturated, or partially saturated single or fused ring system, which consists of carbon atoms and from 1 to 4 heteroatoms selected from N, O and S. The heterocyclyl group may be attached at any heteroatom or carbon atom, which results in the creation of a stable structure. Example of heterocyclyl groups include, but are not limited to, 2-imidazoline, imidazolidine; azetidine, morpholine, oxazoline, 2-pyrroline, 3-pyrroline, pyrrolidine, pyridone, pyrimidone, piperazine, piperidine, indoline, tetrahydrofuran, 2-pyrroline, 3-pyrroline, 2-imidazoline, 2-pyrazoline, indolinone, tetrahydroquinoline, tetrahydroquinazoline, and the like.

For the purpose of clarification, in this application

means N-containing heterocyclyl.

As used herein, "halo" or "halogen" shall mean chlorine, bromine, fluorine and iodine. "Halo substituted" shall mean a group substituted with at least one halogen atom, preferably substituted with a least one fluoro atom. Suitable examples include, but are not limited to —$CF_3$, —$CH_2$—$CHF_2$, —$CH_2$—$CF_3$, and the like.

The term "oxo" whether used alone or as part of a substituent group refers to an O= to either a carbon or a sulfur atom. For example, phthalimide and saccharin are examples of compounds with oxo substituents.

The term "cis-trans isomer" refers to stereoisomeric olefins or cycloalkanes (or hetero-analogues), which differ in the positions of atoms (or groups) relative to a reference plane: in the cis-isomer the atoms are on the same side; in the trans-isomer they are on opposite sides.

The term "substituted" refers to a radical in which one or more hydrogen atoms are each independently replaced with the same or different substituent(s). A substituted group comprising alkyl, cycloalkyl, aryl, heteroaryl, heterocyclyl may have one or more substituents, preferably from one to five substituents, more preferably from one to three substituents, most preferably from one to two substituents, independently selected from the list of substituents.

With reference to substituents, the term "independently" means that when more than one of such substituent is possible, such substituents may be the same or different from each other.

The term "composition" is intended to encompass a product comprising the specified ingredients in the specified amounts, as well as any product which results, directly or indirectly, from combinations of the specified ingredients in the specified amounts.

The term "subject" as used herein, refers to an animal, preferably a mammal, most preferably a human, who is the object of treatment, observation or experiment.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Metabolic disorders, diseases, or conditions include, but are not limited to, diabetes, obesity, and associated symptoms or complications thereof. They include such conditions as IDDM (insulin-dependent diabetes mellitus), NIDDM (non insulin-dependent diabetes mellitus), IGT (Impaired Glucose Tolerance), IFG (Impaired Fasting Glucose), Syndrome X (or Metabolic Syndrome), hyperglycemia, elevated blood glucose level, and insulin resistance. A condition such as IGT or IFG is also known as a "prediabetic condition" or "prediabetic state."

Methods are known in the art for determining effective doses for therapeutic and prophylactic purposes for the disclosed pharmaceutical compositions or the disclosed drug combinations, whether or not formulated in the same composition. For therapeutic purposes, the term "therapeutically effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the progression of a disorder), the term "therapeutically effective amount" refers to that amount of each active compound or pharmaceutical agent, alone or in combination, that treats or inhibits in a subject the progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

The term "pharmaceutically acceptable salt" refers to nontoxic pharmaceutically acceptable salts (Ref. International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

B) Compounds

Representative compounds of the present invention are listed in Table I below:

TABLE I

| STRUCTURE | COMPOUND # | NAME |
|---|---|---|
| 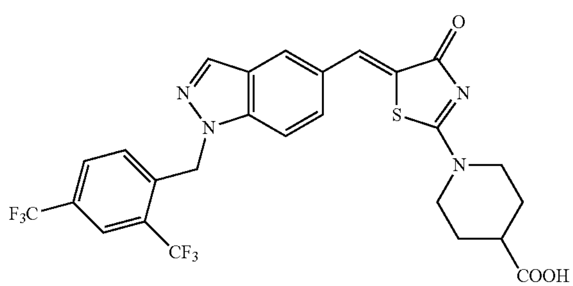 [SMILES: O=C1N=C(N2CCC(C(=O)O)CC2)S/C1=C\c1ccc2c(cnn2Cc2ccc(C(F)(F)F)cc2C(F)(F)F)c1] | 1 | 1-{5-[1-(2,4-Bis-trifluoromethyl-benzyl-1H-indazol-5-ylmethylene]-4-oxo-4,5-dihydro-2-yl}-piperidine-4-carboxylic acid |
| 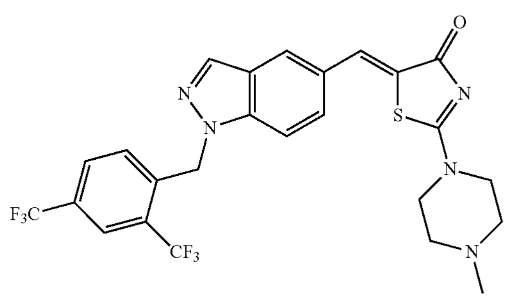 [SMILES: CN1CCN(C2=NC(=O)/C(=C/c3ccc4c(cnn4Cc4ccc(C(F)(F)F)cc4C(F)(F)F)c3)S2)CC1] | 2 | 5-[1-(2,4-Bis-trifluoromethyl-benzyl)-1H-indazol-5-ylmethylene]-2-(4-methyl-piperazin-1-yl)-thiazol-4-one |
| 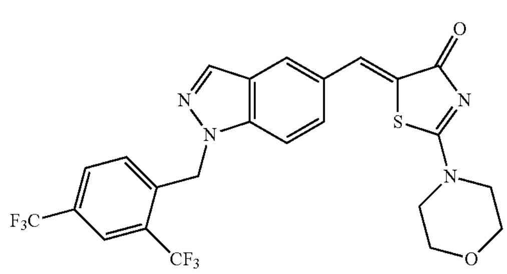 [SMILES: O=C1N=C(N2CCOCC2)S/C1=C\c1ccc2c(cnn2Cc2ccc(C(F)(F)F)cc2C(F)(F)F)c1] | 3 | 5-[1-(2,4-Bis-trifluoromethyl-benzyl)-1H-indazol-5-ylmethylene]-2-morpholin-4-yl-thiazol-4-one |

TABLE I-continued

| STRUCTURE | COMPOUND # | NAME |
|---|---|---|
| 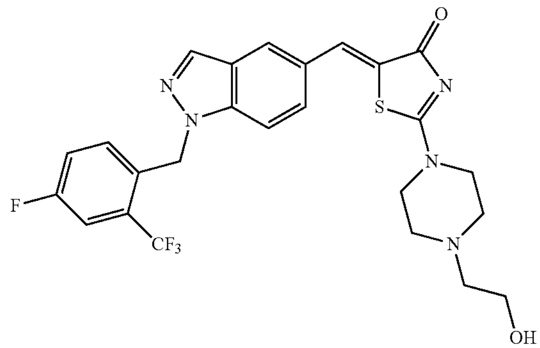 [SMILES: O=C1N=C(N2CCN(CCO)CC2)S/C1=C\c1ccc2c(cnn2Cc2ccc(F)cc2C(F)(F)F)c1] | 4 | 5-[1-(4-Fluoro-2-trifluoromethyl-benzyl)-1H-indazol-5-ylmethylene]-2-[4-(2-hydroxy-ethyl)-piperazin-1-yl]-thiazol-4-one |
| 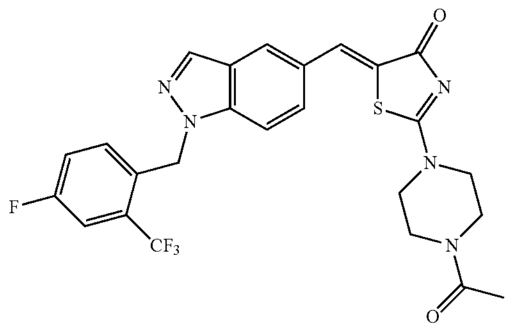 [SMILES: CC(=O)N1CCN(C2=NC(=O)/C(=C/c3ccc4c(cnn4Cc4ccc(F)cc4C(F)(F)F)c3)S2)CC1] | 5 | 2-(4-Acetyl-piperazin-1-yl)-5-[1-(4-fluoro-2-trifluoromethyl-benzyl)-1H-indazol-5-ylmethylene]-thiazol-4-one |
| 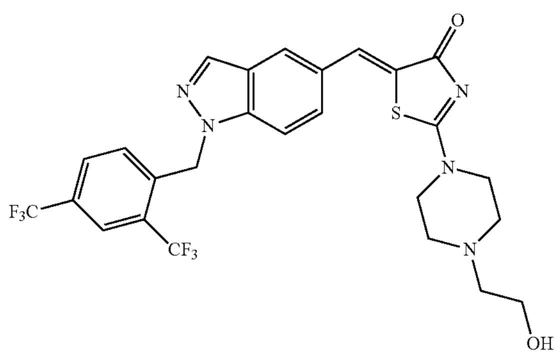 [SMILES: O=C1N=C(N2CCN(CCO)CC2)S/C1=C\c1ccc2c(cnn2Cc2ccc(C(F)(F)F)cc2C(F)(F)F)c1] | 6 | 5-[1-(2,4-Bis-trifluoromethyl-benzyl)-1H-indazol-5-ylmethylene]-2-[4-(2-hydroxy-ethyl)-piperazin-1-yl]-thiazol-4-one |
| 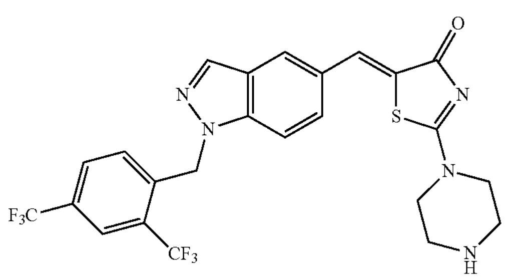 [SMILES: O=C1N=C(N2CCNCC2)S/C1=C\c1ccc2c(cnn2Cc2ccc(C(F)(F)F)cc2C(F)(F)F)c1] | 7 | 5-[1-(2,4-Bis-trifluoromethyl-benzyl)-1H-indazol-5-ylmethylene]-2-piperazin-1-yl-thiazol-4-one |

TABLE I-continued

| STRUCTURE | COMPOUND # | NAME |
|---|---|---|
| 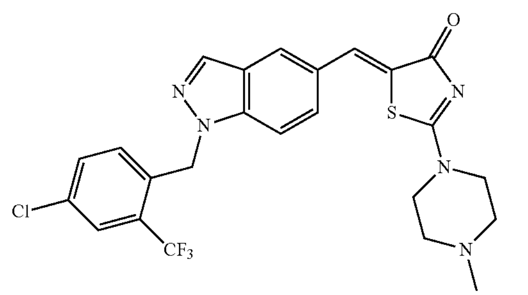 | 8 | 5-[1-(4-Chloro-2-trifluoromethyl-benzyl)-1H-indazol-5-ylmethylene]-2-(4-methyl-piperazin-1-yl)-thiazol-4-one |
| 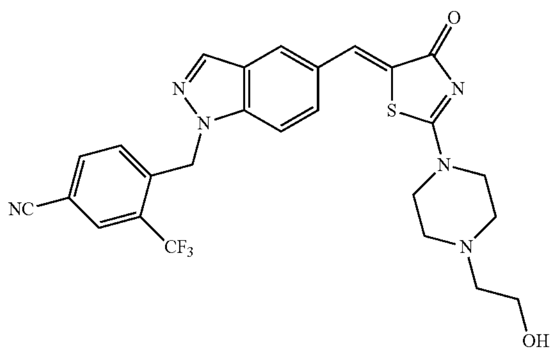 [SMILES: N#Cc1ccc(Cn2ncc3cc(/C=C4\SC(N5CCN(CCO)CC5)=NC4=O)ccc32)c(C(F)(F)F)c1] | 9 | 4-(5-{2-[4-(2-Hydroxy-ethyl)-piperazin-1-yl]-4-oxo-4H-thiazol-5-ylidenemethyl}-indazol-1-ylmethyl)-3-trifluoromethyl-benzonitrile |
| 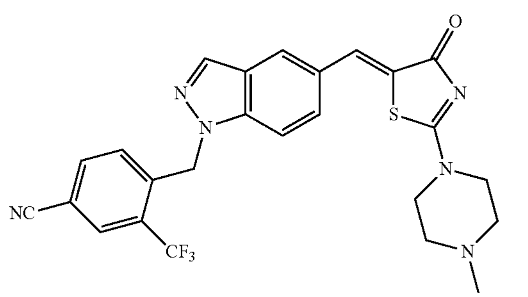 | 10 | 4-{5-[2-(4-Methyl-piperazin-1-yl)-4-oxo-4H-thiazol-5-ylidenemethyl]-indazol-1-ylmethyl}-3-trifluoromethyl-benzonitrile |
| 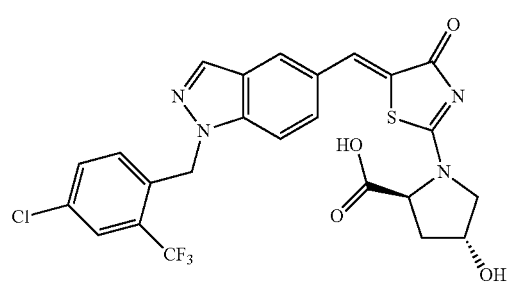 [SMILES: O=C1N=C(N2C[C@H](O)C[C@H]2C(=O)O)S/C1=C\c1ccc2c(cnn2Cc2ccc(Cl)cc2C(F)(F)F)c1] | 11 | 1-{5-[1-(4-Chloro-2-trifluoromethyl-benzyl)-1H-indazol-5-ylmethylene]-4-oxo-4,5-dihydro-thiazol-2-yl}-4-(R)-hydroxy-pyrrolidine-2-(S)-carboxylic acid |
| 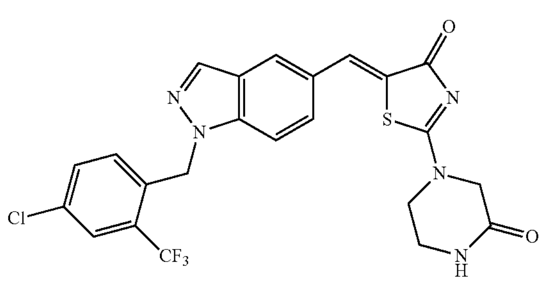 [SMILES: O=C1CN(C2=NC(=O)/C(=C/c3ccc4c(cnn4Cc4ccc(Cl)cc4C(F)(F)F)c3)S2)CCN1] | 12 | 4-{5-[1-(4-Chloro-2-trifluoromethyl-benzyl)-1H-indazol-5-ylmethylene]-4-oxo-4,5-dihydro-thiazol-2-yl}-piperazin-2-one |

TABLE I-continued

| STRUCTURE | COMPOUND # | NAME |
|---|---|---|
| 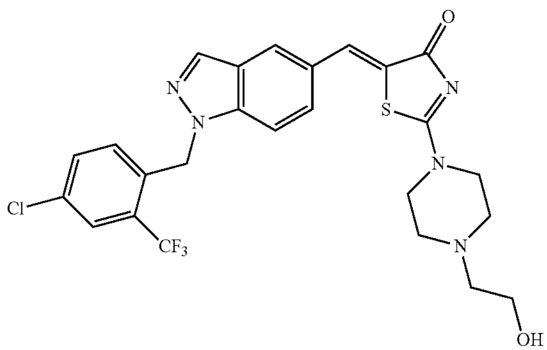 | 13 | 5-[1-(4-Chloro-2-trifluoromethyl-benzyl)-1H-indazol-5-ylmethylene]-2-[4-(2-hydroxy-ethyl)-piperazin-1-yl]-thiazol-4-one |
| 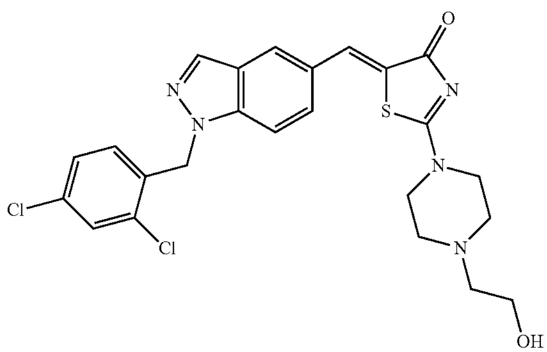 [SMILES: O=C1N=C(N2CCN(CCO)CC2)S/C1=C\c1ccc2c(cnn2Cc2ccc(Cl)cc2Cl)c1] | 14 | 5-[1-(2,4-Dichloro-benzyl)-1H-indazol-5-ylmethylene]-2-[4-(2-hydroxy-ethyl)-piperazin-1-yl]-thiazol-4-one |
| 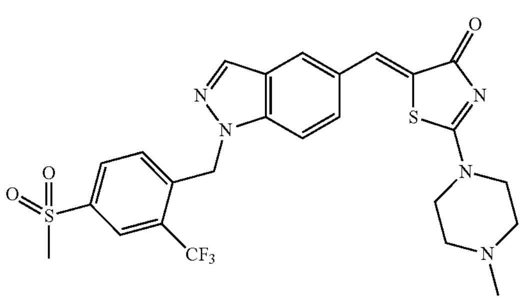 [SMILES: CN1CCN(C2=NC(=O)/C(=C/c3ccc4c(cnn4Cc4ccc(S(C)(=O)=O)cc4C(F)(F)F)c3)S2)CC1] | 15 | 5-[1-(4-Methanesulfonyl-2-trifluoromethyl-benzyl)-1H-indazol-5-ylmethylene]-2-(4-methyl-piperazin-1-yl)-thiazol-4-one |
| 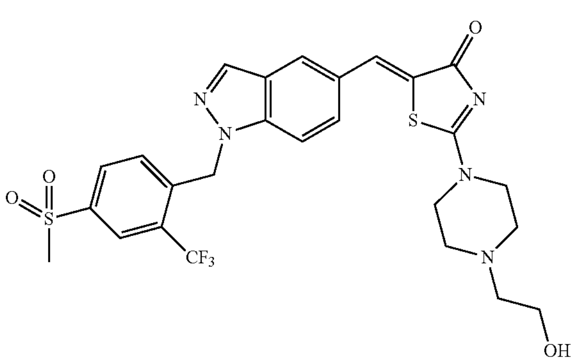 [SMILES: CS(=O)(=O)c1ccc(Cn2ncc3cc(/C=C4\SC(N5CCN(CCO)CC5)=NC4=O)ccc32)c(C(F)(F)F)c1] | 16 | 2-[4-(2-Hydroxy-ethyl)-piperazin-1-yl]-5-[1-(4-methanesulfonyl-2-trifluoromethyl-benzyl)-1H-indazol-5-ylmethylene]-thiazol-4-one |

TABLE I-continued

| STRUCTURE | COMPOUND # | NAME |
|---|---|---|
| 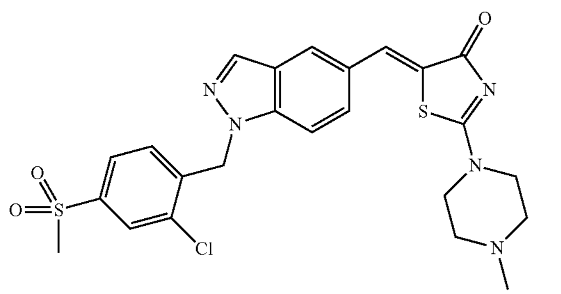 [SMILES: CN1CCN(C2=NC(=O)/C(=C/c3ccc4c(cnn4Cc4ccc(S(C)(=O)=O)cc4Cl)c3)S2)CC1] | 17 | 5-[1-(2-Chloro-4-methanesulfonyl-benzyl)-1H-indazol-5-ylmethylene]-2-(4-methyl-piperazin-1-yl)-thiazol-4-one |
| 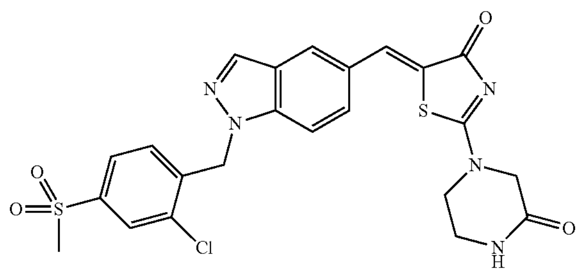 [SMILES: CS(=O)(=O)c1ccc(Cn2ncc3cc(/C=C4\SC(N5CCNC(=O)C5)=NC4=O)ccc32)c(Cl)c1] | 18 | 4-{5-[1-(2-Chloro-4-methanesulfonyl-benzyl)-1H-indazol-5-ylmethylene]-4-oxo-4,5-dihydro-thiazol-2-yl}-2-piperazin-2-one |
| 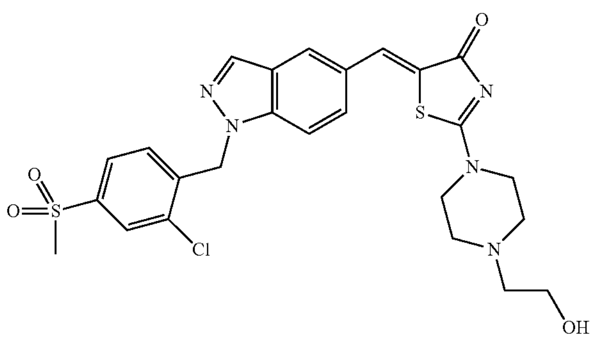 [SMILES: CS(=O)(=O)c1ccc(Cn2ncc3cc(/C=C4\SC(N5CCN(CCO)CC5)=NC4=O)ccc32)c(Cl)c1] | 19 | 5-[1-(2-Chloro-4-methanesulfonyl-benzyl)-1H-indazol-5-ylmethylene]-2-[4-(2-hydroxy-ethyl)-piperazin-1-yl]-thiazol-4-one |
| 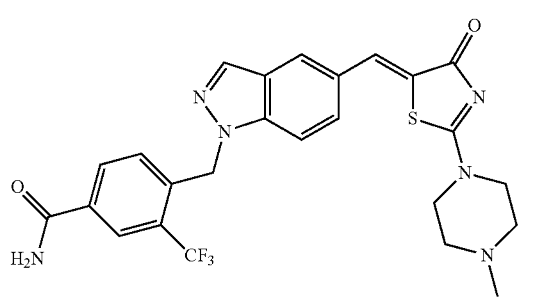 [SMILES: CN1CCN(C2=NC(=O)/C(=C/c3ccc4c(cnn4Cc4ccc(C(N)=O)cc4C(F)(F)F)c3)S2)CC1] | 20 | 4-{5-[2-(4-Methyl-piperazin-1-yl)-4-oxo-4H-thiazol-5-ylidenemethyl]-indazol-1-ylmethyl}-3-trifluoromethyl-benzamide |
| 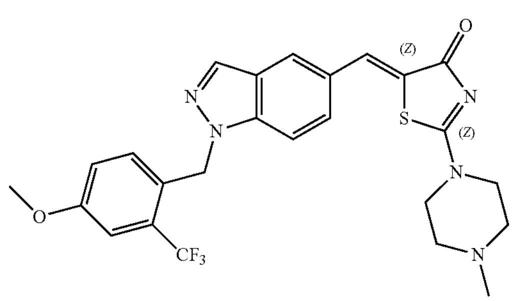 [SMILES: COc1ccc(Cn2ncc3cc(/C=C4\SC(N5CCN(C)CC5)=NC4=O)ccc32)c(C(F)(F)F)c1] | 21 | 5-[1-(4-Methoxy-2-trifluoromethyl-benzyl)-1H-indazol-5-ylmethylene]-2-(4-methyl-piperazin-1-yl)-thiazol-4-one |

TABLE I-continued

| STRUCTURE | COMPOUND # | NAME |
|---|---|---|
| 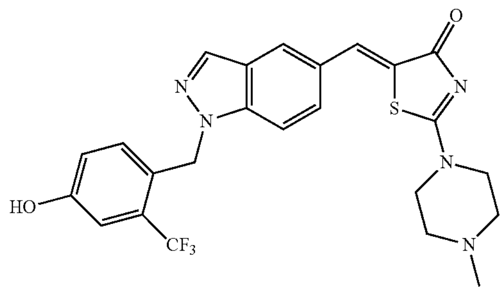 | 22 | 5-[1-(4-Hydroxy-2-trifluoromethyl-benzyl)-1H-indazol-5-ylmethylene]-2-(4-methyl-piperazin-1-yl)-thiazol-4-one |
| 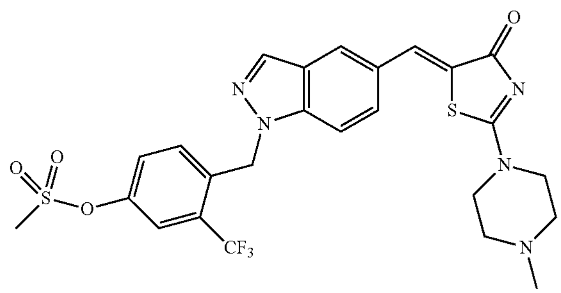 [SMILES: CN1CCN(C2=NC(=O)/C(=C/c3ccc4c(cnn4Cc4ccc(OS(C)(=O)=O)cc4C(F)(F)F)c3)S2)CC1] | 23 | Methanesulfonic acid 4-{5-[2-(4-methyl-piperazin-1-yl)-4-oxo-4H-thiazol-5-ylidenemethyl]-indazol-1-ylmethyl}-3-trifluoromethyl-phenyl ester |
| 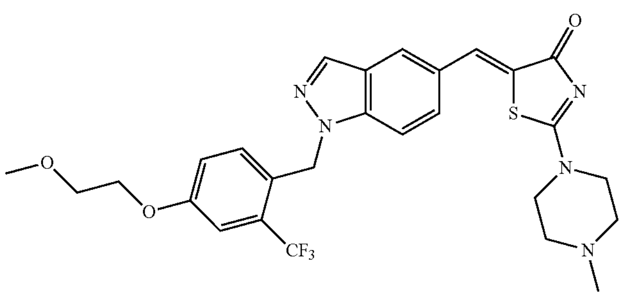 [SMILES: COCCOc1ccc(Cn2ncc3cc(/C=C4\SC(N5CCN(C)CC5)=NC4=O)ccc32)c(C(F)(F)F)c1] | 24 | 5-{1-[4-(2-Methoxy-ethoxy)-2-trifluoromethyl-benzyl]-1H-indazol-5-ylmethylene}-2-(4-methyl-piperazin-1-yl)-thiazol-4-one |
| 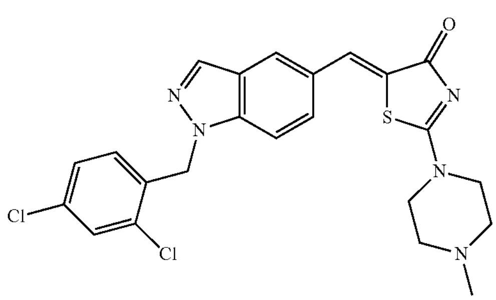 | 25 | 5-[1-(2,4-Dichloro-benzyl)-1H-indazol-5-ylmethylene]-2-(4-methyl-piperazin-1-yl)-thiazol-4-one |
| 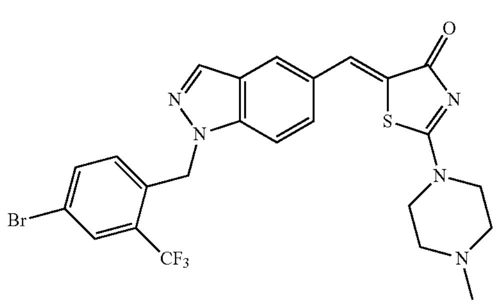 [SMILES: CN1CCN(C2=NC(=O)/C(=C/c3ccc4c(cnn4Cc4ccc(Br)cc4C(F)(F)F)c3)S2)CC1] | 26 | 5-[1-(4-Bromo-2-trifluoromethyl-benzyl)-1H-indazol-5-ylmethylene]-2-(4-methyl-piperazin-1-yl)-thiazol-4-one |

TABLE I-continued

| STRUCTURE | COMPOUND # | NAME |
|---|---|---|
| 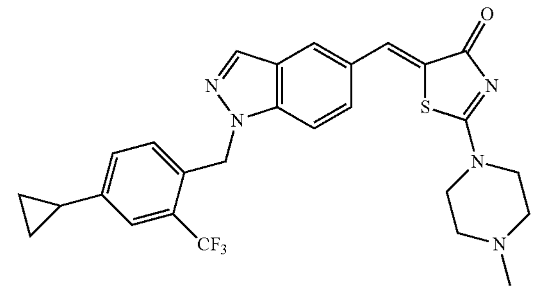 [SMILES: CN1CCN(C2=NC(=O)/C(=C/c3ccc4c(cnn4Cc4ccc(C5CC5)cc4C(F)(F)F)c3)S2)CC1] | 27 | 5-[1-(4-Cyclopropyl-2-trifluoromethyl-benzyl)-1H-indazol-5-ylmethylene]-2-(4-methyl-piperazin-1-yl)-thiazol-4-one |
| 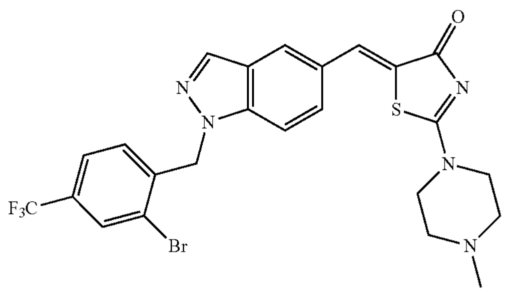 [SMILES: CN1CCN(C2=NC(=O)/C(=C/c3ccc4c(cnn4Cc4ccc(C(F)(F)F)cc4Br)c3)S2)CC1] | 28 | 5-[1-(2-Bromo-4-trifluoromethyl-benzyl)-1H-indazol-5-ylmethylene]-2-(4-methyl-piperazin-1-yl)-thiazol-4-one |
| 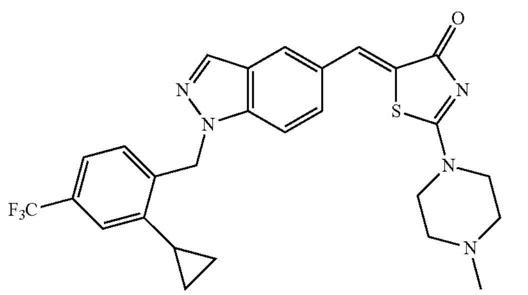 [SMILES: CN1CCN(C2=NC(=O)/C(=C/c3ccc4c(cnn4Cc4ccc(C(F)(F)F)cc4C4CC4)c3)S2)CC1] | 29 | 5-[1-(2-Cyclopropyl-4-trifluoromethyl-benzyl)-1H-indazol-5-ylmethylene]-2-(4-methyl-piperazin-1-yl)-thiazol-4-one |
| 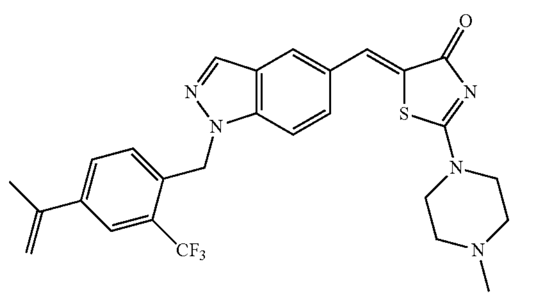 [SMILES: C=C(C)c1ccc(Cn2ncc3cc(/C=C4\SC(N5CCN(C)CC5)=NC4=O)ccc32)c(C(F)(F)F)c1] | 30 | 5-[1-(4-Isopropenyl-2-trifluoromethyl-benzyl)-1H-indazol-5-ylmethylene]-2-(4-methyl-piperazin-1-yl)-thiazol-4-one |
| 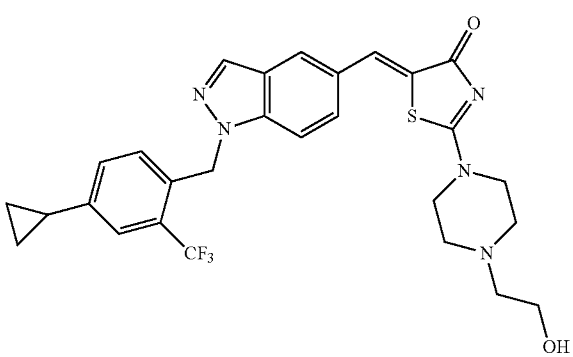 [SMILES: O=C1N=C(N2CCN(CCO)CC2)S/C1=C\c1ccc2c(cnn2Cc2ccc(C3CC3)cc2C(F)(F)F)c1] | 31 | 5-[1-(4-Cyclopropyl-2-trifluoromethyl-benzyl)-1H-indazol-5-ylmethylene]-2-[4-(2-hydroxy-ethyl)-piperazin-1-yl]-thiazol-4-one |

TABLE I-continued

| STRUCTURE | COMPOUND # | NAME |
|---|---|---|
| 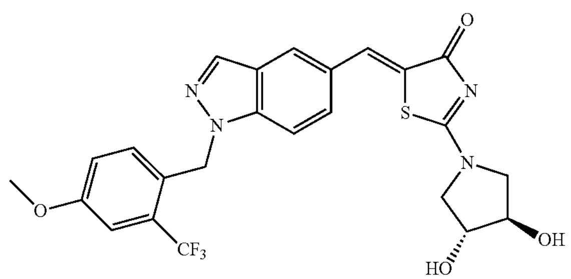 [SMILES: COc1ccc(Cn2ncc3cc(/C=C4\SC(N5C[C@@H](O)[C@H](O)C5)=NC4=O)ccc32)c(C(F)(F)F)c1] | 32 | 2-(3R,4R-Dihydroxy-pyrrolidin-1-yl)-5-[1-(4-methoxy-2-trifluoromethyl-benzyl)-1H-indazol-5-ylmethylene]-thiazol-4-one |
| 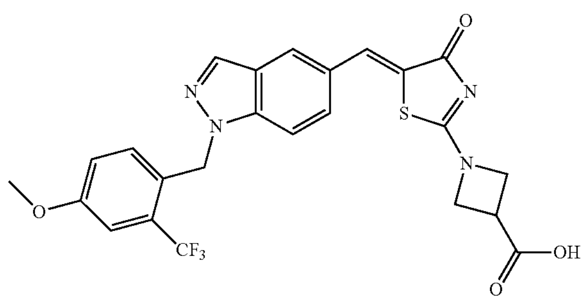 [SMILES: COc1ccc(Cn2ncc3cc(/C=C4\SC(N5CC(C(=O)O)C5)=NC4=O)ccc32)c(C(F)(F)F)c1] | 33 | 1-{5-[1-(4-Methoxy-2-trifluoromethyl-benzyl)-1H-indazol-5-ylmethylene]-4-oxo-4,5-dihydro-thiazol-2-yl}-azetidine-3-carboxylic acid |
| 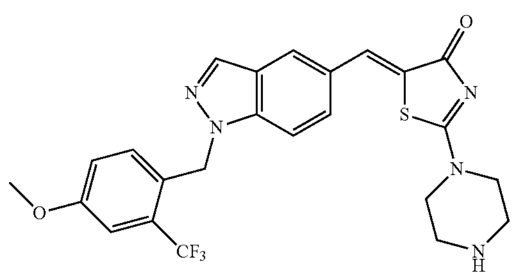 [SMILES: COc1ccc(Cn2ncc3cc(/C=C4\SC(N5CCNCC5)=NC4=O)ccc32)c(C(F)(F)F)c1] | 34 | 5-[1-(4-Methoxy-2-trifluoromethyl-benzyl)-1H-indazol-5-ylmethylene]-2-piperazin-1-yl-thiazol-4-one |
| 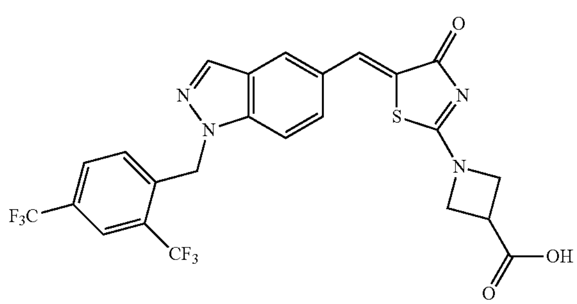 [SMILES: O=C1N=C(N2CC(C(=O)O)C2)S/C1=C\c1ccc2c(cnn2Cc2ccc(C(F)(F)F)cc2C(F)(F)F)c1] | 35 | 1-{5-[1-(2,4-Bis-trifluoromethyl-benzyl)-1H-indazol-5-ylmethylene]-4-oxo-4,5-dihydro-thiazol-2-yl}-azetidine-3-carboxylic acid |
| 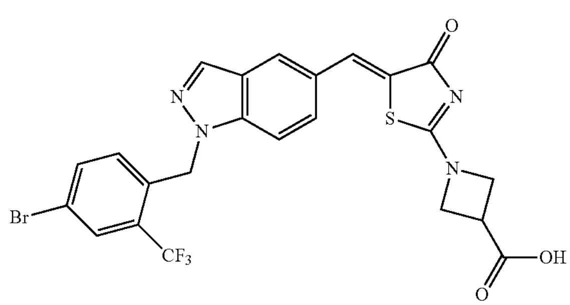 [SMILES: O=C1N=C(N2CC(C(=O)O)C2)S/C1=C\c1ccc2c(cnn2Cc2ccc(Br)cc2C(F)(F)F)c1] | 36 | 1-{5-[1-(4-Bromo-2-trifluoromethyl-benzyl)-1H-indazol-5-ylmethylene]-4-oxo-4,5-dihydro-thiazol-2-yl}-azetidine-3-carboxylic acid |

TABLE I-continued

| STRUCTURE | COMPOUND # | NAME |
|---|---|---|
| 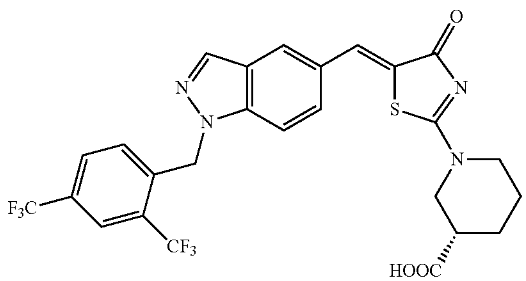 [SMILES: O=C1N=C(N2CCC[C@H](C(=O)O)C2)S/C1=C\c1ccc2c(cnn2Cc2ccc(C(F)(F)F)cc2C(F)(F)F)c1] | 37 | 1-{5-[1-(2,4-Bis-trifluoromethyl-benzyl)-1H-indazol-5-ylmethylene]-4-oxo-4,5-dihydro-thiazol-2-yl}-piperidine-3-(S)-carboxylic acid |
| 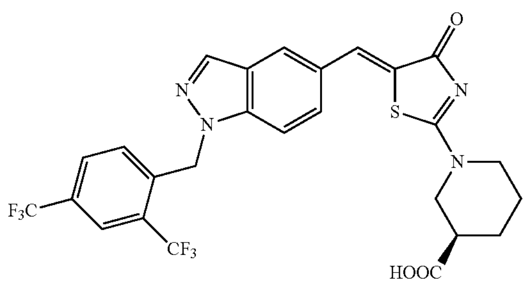 [SMILES: O=C1N=C(N2CCC[C@@H](C(=O)O)C2)S/C1=C\c1ccc2c(cnn2Cc2ccc(C(F)(F)F)cc2C(F)(F)F)c1] | 38 | 1-{5-[1-(2,4-Bis-trifluoromethyl-benzyl)-1H-indazol-5-ylmethylene]-4-oxo-4,5-dihydro-thiazol-2-yl}-piperidine-3-(R)-carboxylic acid |
| 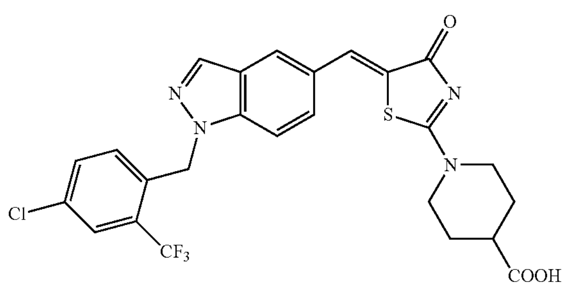 [SMILES: O=C1N=C(N2CCC(C(=O)O)CC2)S/C1=C\c1ccc2c(cnn2Cc2ccc(Cl)cc2C(F)(F)F)c1] | 39 | 1-{5-[1-(4-Chloro-2-trifluoromethyl-benzyl)-1H-indazol-5-ylmethylene]-4-oxo-4,5-dihydro-thiazol-2-yl}-piperidine-4-carboxylic acid |
| 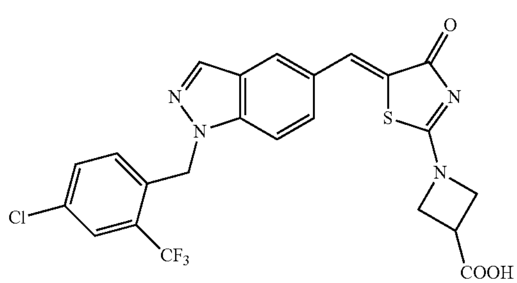 [SMILES: O=C1N=C(N2CC(C(=O)O)C2)S/C1=C\c1ccc2c(cnn2Cc2ccc(Cl)cc2C(F)(F)F)c1] | 40 | 1-{5-[1-(4-Chloro-2-trifluoromethyl-benzyl)-1H-indazol-5-ylmethylene]-4-oxo-4,5-dihydro-thiazol-2-yl}-azetidine-3-carboxylic acid |
| 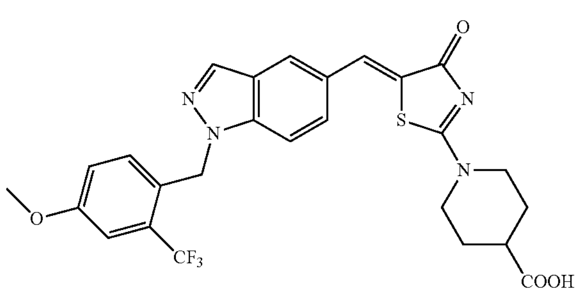 [SMILES: COc1ccc(Cn2ncc3cc(/C=C4\SC(N5CCC(C(=O)O)CC5)=NC4=O)ccc32)c(C(F)(F)F)c1] | 41 | 1-{5-[1-(4-Methoxy-2-trifluoromethyl-benzyl)-1H-indazol-5-ylmethylene]-4-oxo-4,5-dihydro-thiazol-2-yl}-piperidine-4-carboxylic acid |

| STRUCTURE | COMPOUND # | NAME |
|---|---|---|
| 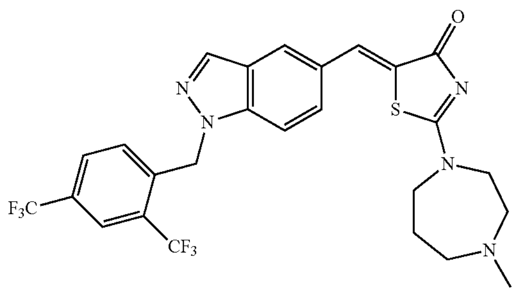 [SMILES: CN1CCCN(C2=NC(=O)/C(=C/c3ccc4c(cnn4Cc4ccc(C(F)(F)F)cc4C(F)(F)F)c3)S2)CC1] | 42 | 5-[1-(2,4-Bis-trifluoromethyl-benzyl)-1H-indazol-5-ylmethylene]-2-(4-methyl-[1,4]diazepan-1-yl)-thiazol-4-one |
| 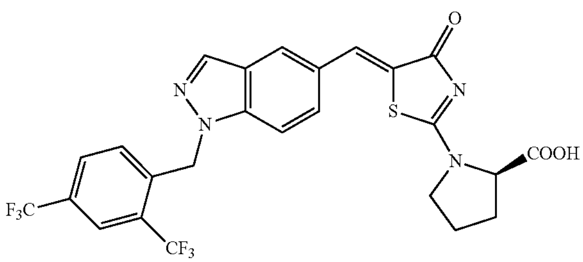 [SMILES: O=C1N=C(N2CCC[C@@H]2C(=O)O)S/C1=C\c1ccc2c(cnn2Cc2ccc(C(F)(F)F)cc2C(F)(F)F)c1] | 43 | 1-{5-[1-(2,4-Bis-trifluoromethyl-benzyl)-1H-indazol-5-ylmethylene]-4-oxo-4,5-dihydro-thiazol-2-yl}-pyrrolidine-2-(R)-carboxylic acid |
| 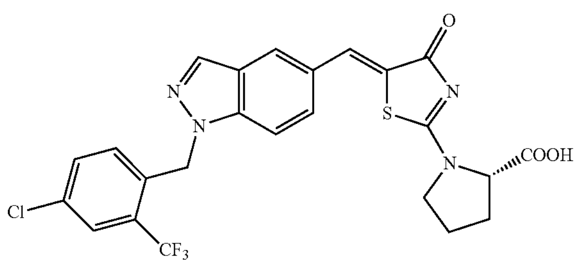 [SMILES: O=C1N=C(N2CCC[C@H]2C(=O)O)S/C1=C\c1ccc2c(cnn2Cc2ccc(Cl)cc2C(F)(F)F)c1] | 44 | 1-{5-[1-(4-Chloro-2-trifluoromethyl-benzyl)-1H-indazol-5-ylmethylene]-4-oxo-4,5-dihydro-thiazol-2-yl}-pyrrolidine-2-(S)-carboxylic acid |
| 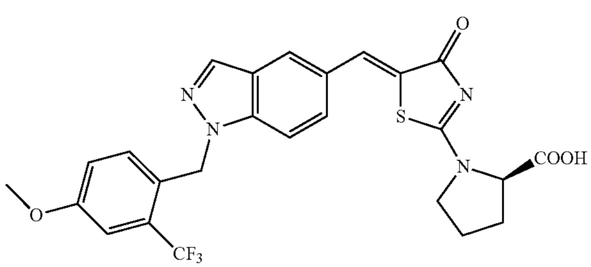 [SMILES: COc1ccc(Cn2ncc3cc(/C=C4\SC(N5CCC[C@@H]5C(=O)O)=NC4=O)ccc32)c(C(F)(F)F)c1] | 45 | 1-{5-[1-(4-Methoxy-2-trifluoromethyl-benzyl)-1H-indazol-5-ylmethylene]-4-oxo-4,5-dihydro-thiazol-2-yl}-pyrrolidine-2-(R)-carboxylic acid |
| 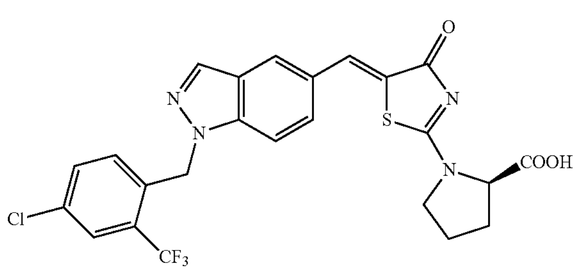 [SMILES: O=C1N=C(N2CCC[C@@H]2C(=O)O)S/C1=C\c1ccc2c(cnn2Cc2ccc(Cl)cc2C(F)(F)F)c1] | 46 | 1-{5-[1-(4-Chloro-2-trifluoromethyl-benzyl)-1H-indazol-5-ylmethylene]-4-oxo-4,5-dihydro-thiazol-2-yl}-pyrrolidine-2-(R)-carboxylic acid |

TABLE I-continued

| STRUCTURE | COMPOUND # | NAME |
|---|---|---|
| 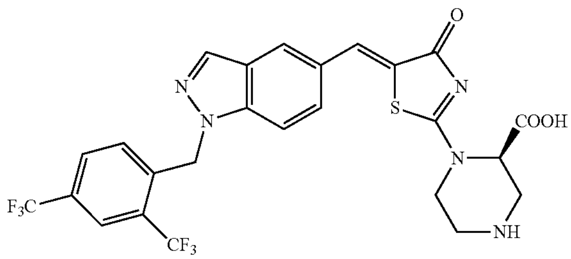 [SMILES: O=C1N=C(N2CCNC[C@@H]2C(=O)O)S/C1=C\c1ccc2c(cnn2Cc2ccc(C(F)(F)F)cc2C(F)(F)F)c1] | 47 | 1-{5-[1-(2,4-Bis-trifluoromethyl-benzyl)-1H-indazol-5-ylmethylene]-4-oxo-4,5-dihydro-thiazol-2-yl}-piperazine-2-(R)-carboxylic acid |
| 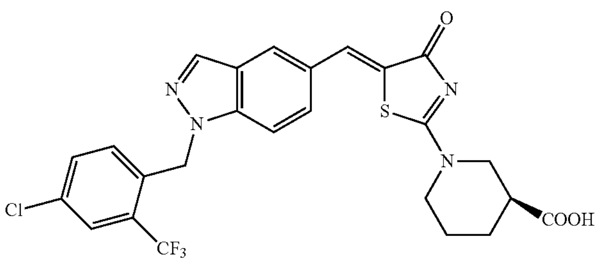 [SMILES: O=C1N=C(N2CCC[C@H](C(=O)O)C2)S/C1=C\c1ccc2c(cnn2Cc2ccc(Cl)cc2C(F)(F)F)c1] | 48 | 1-{5-[1-(4-Chloro-2-trifluoromethyl-benzyl)-1H-indazol-5-ylmethylene]-4-oxo-4,5-dihydro-thiazol-2-yl}-piperidine-3-(S)-carboxylic acid |
| 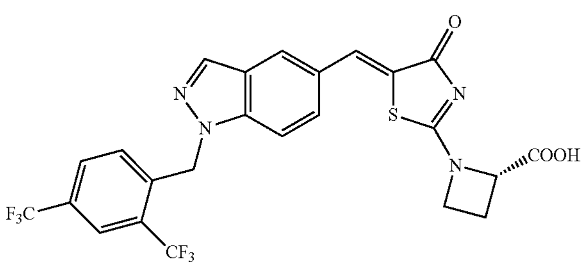 [SMILES: O=C1N=C(N2CC[C@H]2C(=O)O)S/C1=C\c1ccc2c(cnn2Cc2ccc(C(F)(F)F)cc2C(F)(F)F)c1] | 49 | 1-{5-[1-(2,4-Bis-trifluoromethyl-benzyl)-1H-indazol-5-ylmethylene]-4-oxo-4,5-dihydro-thiazol-2-yl}-azetidine-2-(S)-carboxylic acid |
| 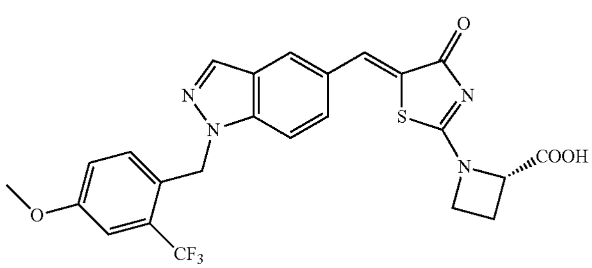 [SMILES: COc1ccc(Cn2ncc3cc(/C=C4\SC(N5CC[C@H]5C(=O)O)=NC4=O)ccc32)c(C(F)(F)F)c1] | 50 | 1-{5-[1-(4-Methoxy-2-trifluoromethyl-benzyl)-1H-indazol-5-ylmethylene]-4-oxo-4,5-dihydro-thiazol-2-yl}-azetidine-2-(S)-carboxylic acid |
| 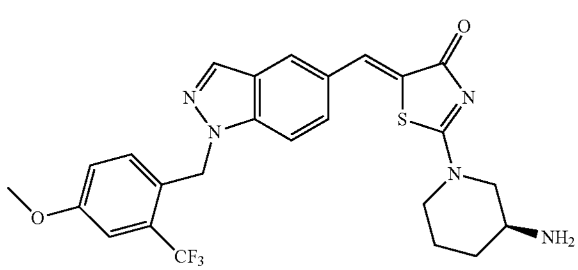 [SMILES: COc1ccc(Cn2ncc3cc(/C=C4\SC(N5CCC[C@H](N)C5)=NC4=O)ccc32)c(C(F)(F)F)c1] | 51 | 2-(3-(S)-Amino-piperidin-1-yl)-5-[1-(4-methoxy-2-trifluoromethyl-benzyl)-1H-indazol-5-ylmethylene]-thiazol-4-one |

TABLE I-continued

| STRUCTURE | COMPOUND # | NAME |
|---|---|---|
| 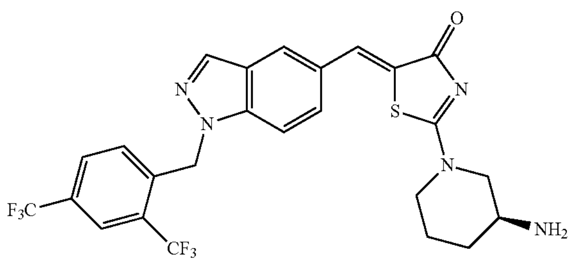 [SMILES: N[C@H]1CCCN(C2=NC(=O)/C(=C/c3ccc4c(cnn4Cc4ccc(C(F)(F)F)cc4C(F)(F)F)c3)S2)C1] | 52 | 2-(3-(S)-Amino-piperidin-1-yl)-5-[1-(2,4-bis-trifluoromethyl-benzyl)-1H-indazol-5-ylmethylene]-thiazol-4-one |
| 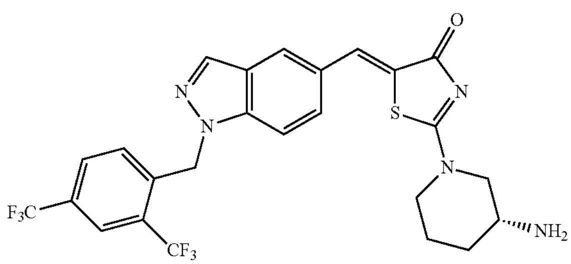 [SMILES: N[C@@H]1CCCN(C2=NC(=O)/C(=C/c3ccc4c(cnn4Cc4ccc(C(F)(F)F)cc4C(F)(F)F)c3)S2)C1] | 53 | 2-(3-(R)-Amino-piperidin-1-yl)-5-[1-(2,4-bis-trifluoromethyl-benzyl)-1H-indazol-5-ylmethylene]-thiazol-4-one |
| 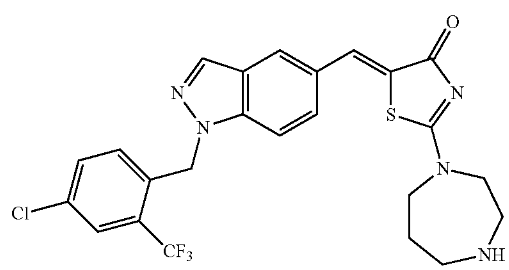 [SMILES: O=C1N=C(N2CCCNCC2)S/C1=C\c1ccc2c(cnn2Cc2ccc(Cl)cc2C(F)(F)F)c1] | 54 | 5-[1-(4-Chloro-2-trifluoromethyl-benzyl)-1H-indazol-5-ylmethylene]-2-[1,4]diazepan-1-yl-thiazol-4-one |
| 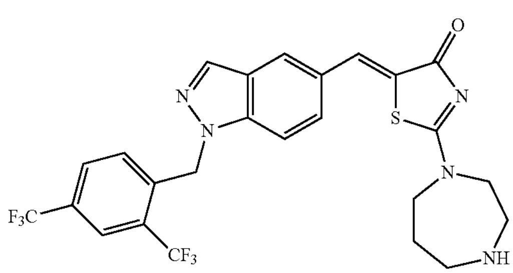 [SMILES: O=C1N=C(N2CCCNCC2)S/C1=C\c1ccc2c(cnn2Cc2ccc(C(F)(F)F)cc2C(F)(F)F)c1] | 55 | 5-[1-(2,4-Bis-trifluoromethyl-benzyl)-1H-indazol-5-ylmethylene]-2-[1,4]diazepan-1-yl-thiazol-4-one |
| 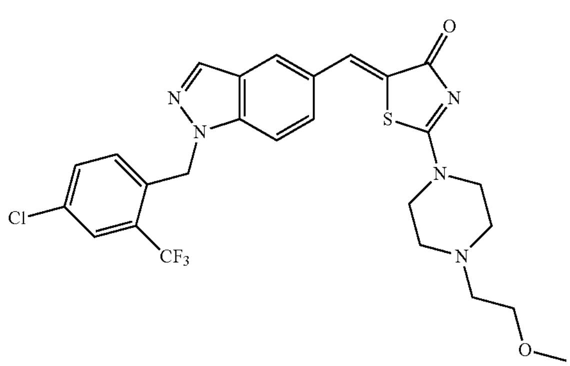 [SMILES: COCCN1CCN(C2=NC(=O)/C(=C/c3ccc4c(cnn4Cc4ccc(Cl)cc4C(F)(F)F)c3)S2)CC1] | 56 | 5-[1-(4-Chloro-2-trifluoromethyl-benzyl)-1H-indazol-5-ylmethylene]-2-[4-(2-methoxy-ethyl)-piperazin-1-yl]-thiazol-4-one |

TABLE I-continued

| STRUCTURE | COMPOUND # | NAME |
|---|---|---|
| 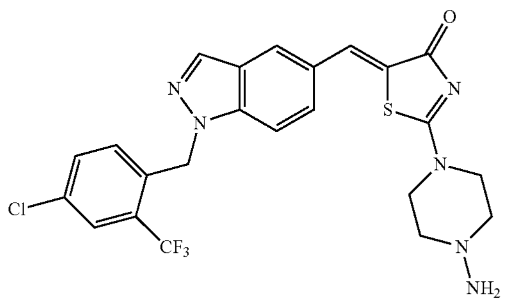 [SMILES: NN1CCN(C2=NC(=O)/C(=C/c3ccc4c(cnn4Cc4ccc(Cl)cc4C(F)(F)F)c3)S2)CC1] | 57 | 2-(4-Amino-piperidin-1-yl)-5-[1-(4-chloro-2-trifluoromethyl-benzyl)-1H-indazol-5-ylmethylene]-thiazol-4-one |
| 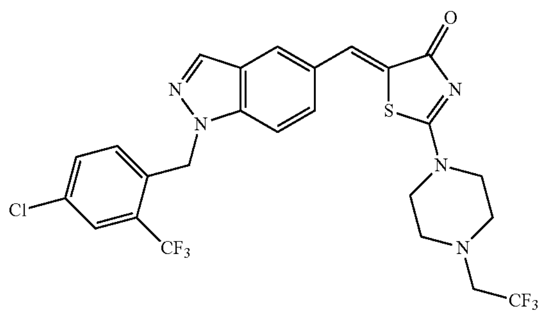 [SMILES: O=C1N=C(N2CCN(CC(F)(F)F)CC2)S/C1=C\c1ccc2c(cnn2Cc2ccc(Cl)cc2C(F)(F)F)c1] | 58 | 5-[1-(4-Chloro-2-trifluoromethyl-benzyl)-1H-indazol-5-ylmethylene]-2-[4-(2,2,2-trifluoro-ethyl)-piperazin-1-yl]-thiazol-4-one |
| 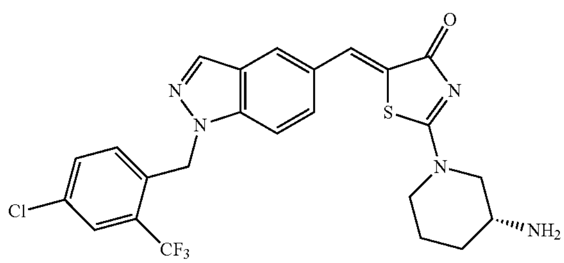 [SMILES: N[C@@H]1CCCN(C2=NC(=O)/C(=C/c3ccc4c(cnn4Cc4ccc(Cl)cc4C(F)(F)F)c3)S2)C1] | 59 | 2-(3-(R)-Amino-piperidin-1-yl)-5-[1-(4-chloro-2-trifluoromethyl-benzyl)-1H-indazol-5-ylmethylene]-thiazol-4-one |
| 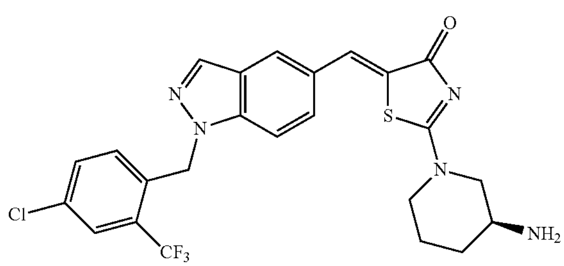 | 60 | 2-(3-(S)-Amino-piperidin-1-yl)-5-[1-(4-chloro-2-tifluoromethyl-benzyl)-1H-indazol-5-ylmethylene]-thiazol-4-one |
| 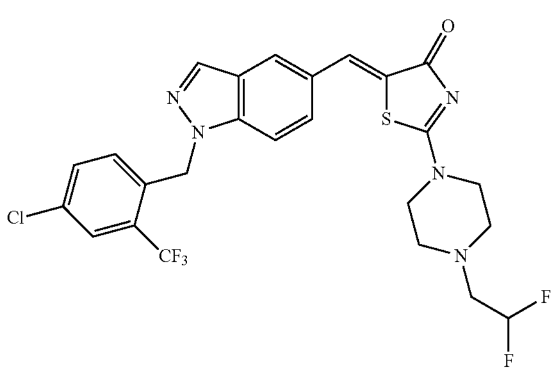 [SMILES: O=C1N=C(N2CCN(CC(F)F)CC2)S/C1=C\c1ccc2c(cnn2Cc2ccc(Cl)cc2C(F)(F)F)c1] | 61 | 5-[1-(4-Chloro-2-trifluoromethyl-benzyl)-1H-indazol-5-ylmethylene]-2-[4-(2,2,2-difluoro-ethyl)-piperazin-1-yl]-thiazol-4-one |

TABLE I-continued

| STRUCTURE | COMPOUND # | NAME |
|---|---|---|
| 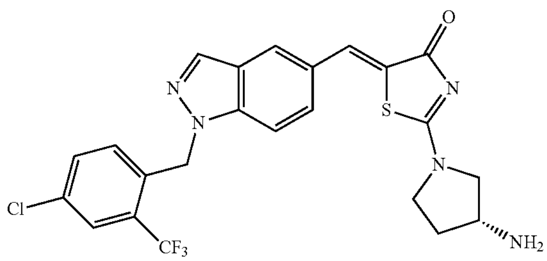 [SMILES: N[C@@H]1CCN(C2=NC(=O)/C(=C/c3ccc4c(cnn4Cc4ccc(Cl)cc4C(F)(F)F)c3)S2)C1] | 62 | 2-(3-(R)-Amino-pyrrolidin-1-yl)-5-[1-(4-chloro-2-trifluoromethyl-benzyl)-1H-indazol-5-ylmethylene]-thiazol-4-one |
| 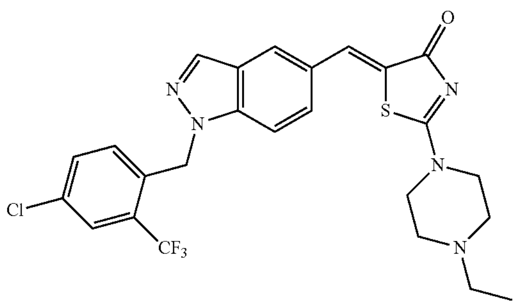 [SMILES: CCN1CCN(C2=NC(=O)/C(=C/c3ccc4c(cnn4Cc4ccc(Cl)cc4C(F)(F)F)c3)S2)CC1] | 63 | 5-[1-(4-Chloro-2-trifluoromethyl-benzyl)-1H-indazol-5-ylmethylene]-2-(4-ethyl-piperazin-1-yl)-thiazol-4-one |
| 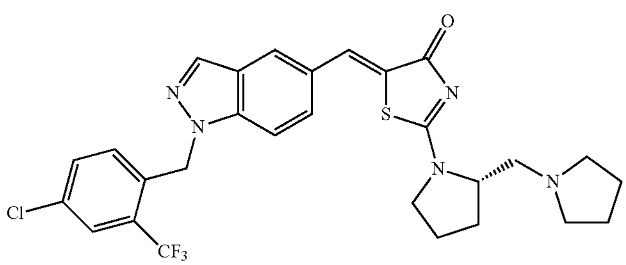 [SMILES: O=C1N=C(N2CCC[C@H]2CN2CCCC2)S/C1=C\c1ccc2c(cnn2Cc2ccc(Cl)cc2C(F)(F)F)c1] | 64 | 5-[1-(4-Chloro-2-trifluoromethyl-benzyl)-1H-indazol-5-ylmethylene]-2-(S)-(2-pyrrolidin-1-ylmethyl-pyrrolidin-1-yl)-thiazol-4-one |
| 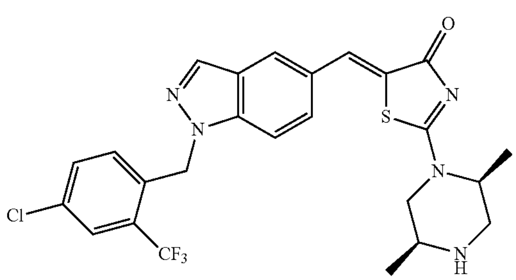 [SMILES: C[C@H]1CN(C2=NC(=O)/C(=C/c3ccc4c(cnn4Cc4ccc(Cl)cc4C(F)(F)F)c3)S2)[C@@H](C)CN1] | 65 | 5-[1-(4-Chloro-2-trifluoromethyl-benzyl)-1H-indazol-5-ylmethylene]-2-(2-(S),5-(S)-dimethyl-piperazin-1-yl)-thiazol-4-one |
| 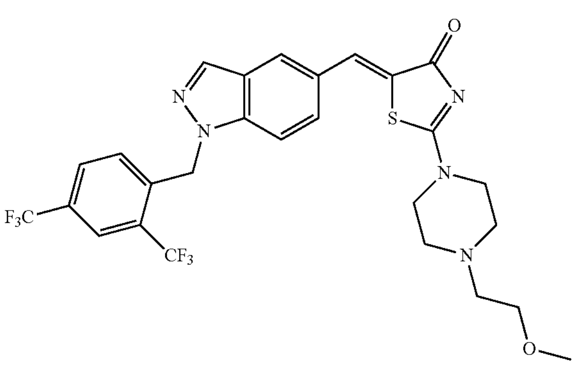 [SMILES: COCCN1CCN(C2=NC(=O)/C(=C/c3ccc4c(cnn4Cc4ccc(C(F)(F)F)cc4C(F)(F)F)c3)S2)CC1] | 66 | 5-[1-(2,4-Bis-trifluoromethyl-benzyl)-1H-indazol-5-ylmethylene]-2-[4-(2-methoxy-ethyl)-piperazin-1-yl]-thiazol-4-one |

TABLE I-continued

| STRUCTURE | COMPOUND # | NAME |
|---|---|---|
| 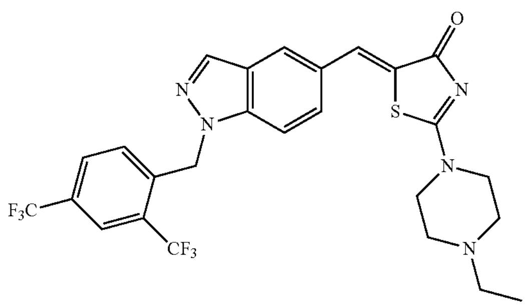 [SMILES: CCN1CCN(C2=NC(=O)/C(=C/c3ccc4c(cnn4Cc4ccc(C(F)(F)F)cc4C(F)(F)F)c3)S2)CC1] | 67 | 5-[1-(2,4-Bis-trifluoromethyl-benzyl)-1H-indazol-5-ylmethylene]-2-(4-ethyl-piperazin-1-yl)-thiazol-4-one |
| 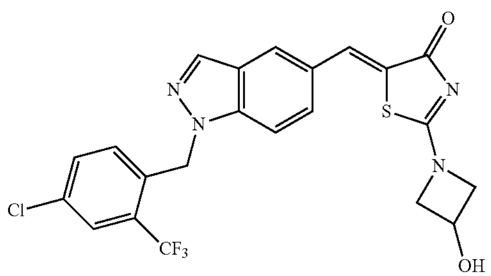 [SMILES: O=C1N=C(N2CC(O)C2)S/C1=C\c1ccc2c(cnn2Cc2ccc(Cl)cc2C(F)(F)F)c1] | 68 | 5-[1-(4-Chloro-2-trifluoromethyl-benzyl)-1H-indazol-5-ylmethylene]-2-(3-hydroxy-azetidin-1-yl)-thiazol-4-one |
| 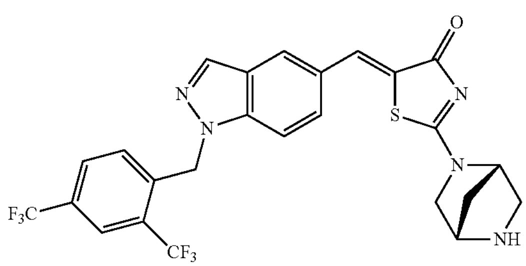 [SMILES: O=C1N=C(N2C[C@@H]3C[C@H]2CN3)S/C1=C\c1ccc2c(cnn2Cc2ccc(C(F)(F)F)cc2C(F)(F)F)c1] | 69 | 5-[1-(2,4-Bis-trifluoromethyl-benzyl)-1H-indazol-5-ylmethylene]-2-(2S,5S-diaza-bicyclo[2.2.1]hept-2-yl)-thiazol-4-one |
| 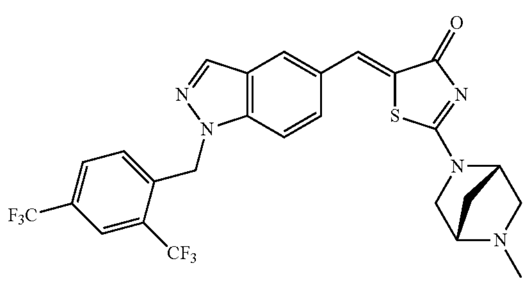 [SMILES: CN1C[C@@H]2C[C@H]1CN2C1=NC(=O)/C(=C/c2ccc3c(cnn3Cc3ccc(C(F)(F)F)cc3C(F)(F)F)c2)S1] | 70 | 5-[1-(2,4-Bis-trifluoromethyl-benzyl)-1H-indazol-5-ylmethylene]-2-(5-methyl-2S,5S-diaza-bicyclo[2.2.1]hept-2-yl)-thiazol-4-one |
| 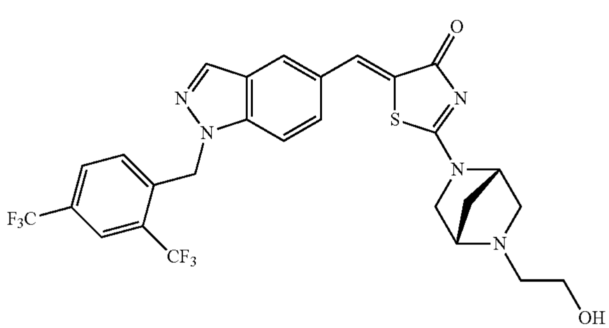 [SMILES: O=C1N=C(N2C[C@@H]3C[C@H]2CN3CCO)S/C1=C\c1ccc2c(cnn2Cc2ccc(C(F)(F)F)cc2C(F)(F)F)c1] | 71 | 5-[1-(2,4-Bis-trifluoromethyl-benzyl)-1H-indazol-5-ylmethylene]-2-[5-(2-hydroxy-ethyl)-2S,5S-diaza-bicyclo[2.2.1]hept-2-yl]-thiazol-4-one |

TABLE I-continued

| COMPOUND # | NAME |
|---|---|
| 72 | 2-(4-{5-[1-(4-Chloro-2-trifluoromethyl-benzyl)-1H-indazol-5-ylmethylene]-4-oxo-4,5-dihydro-thiazol-2-yl}-piperazin-1-yl)-N,N-dimethyl-acetamide |
| 73 | 5-[1-(2,4-Bis-trifluoromethyl-benzyl)-1H-indazol-5-ylmethylene]-2-[4-(2-ethoxy-ethyl)-piperazin-1-yl]-thiazol-4-one |
| 74 | 1-{5-[1-(2,4-Bis-trifluoromethyl-benzyl)-1H-indazol-5-ylmethylene]-4-oxo-4,5-dihydro-thiazol-2-yl}-4-methyl-piperidine-4-carboxylic acid |
| 75 | 1-{5-[1-(4-Chloro-2-trifluoromethyl-benzyl)-1H-indazol-5-ylmethylene]-4-oxo-4,5-dihydro-thiazol-2-yl}-4-methyl-piperidine-4-carboxylic acid |

TABLE I-continued

| COMPOUND # | NAME |
|---|---|
| 76 | 5-[1-(4-Chloro-2-trifluoromethyl-benzyl)-1H-indazol-5-ylmethylene]-2-[4-(2-hydroxy-ethyl)-[1,4]diazepan-1-yl]-thiazol-4-one |
| 77 | 2-(3-Amino-azetidin-1-yl)-5-[1-(2,4-bis-trifluoromethyl-benzyl)-1H-indazol-5-ylmethylene]-thiazol-4-one |
| 78 | 5-[1-(4-Chloro-2-trifluoromethyl-benzyl)-1H-indazol-5-ylmethylene]-2-(5-methyl-2S,5S-diaza-bicyclo[2.2.1]hept-2-yl)-thiazol-4-one |
| 79 | 2-(4-{5-[1-(4-Chloro-2-trifluoromethyl-benzyl)-1H-indazol-5-ylmethylene]-4-oxo-4,5-dihydro-thiazol-2-yl}-piperazin-1-yl)-acetamide |
| 80 | 5-[1-(4-Chloro-2-trifluoromethyl-benzyl)-1H-indazol-5-ylmethylene]-2-[5-(2-hydroxy-ethyl)-2S,5S-diaza-bicyclo[2.2.1]hept-2-yl]-thiazol-4-one |

TABLE I-continued

| STRUCTURE | COMPOUND # | NAME |
|---|---|---|
| 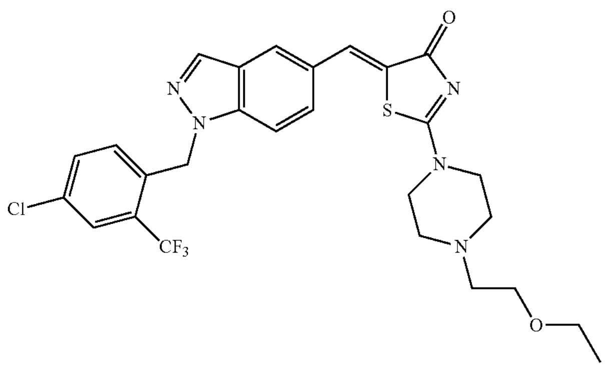 [SMILES: CCOCCN1CCN(C2=NC(=O)/C(=C/c3ccc4c(cnn4Cc4ccc(Cl)cc4C(F)(F)F)c3)S2)CC1] | 81 | 5-[1-(4-Chloro-2-trifluoromethyl-benzyl)-1H-indazol-5-ylmethylene]-2-[4-(2-ethoxy-ethyl)-piperazin-1-yl]-thiazol-4-one |
| 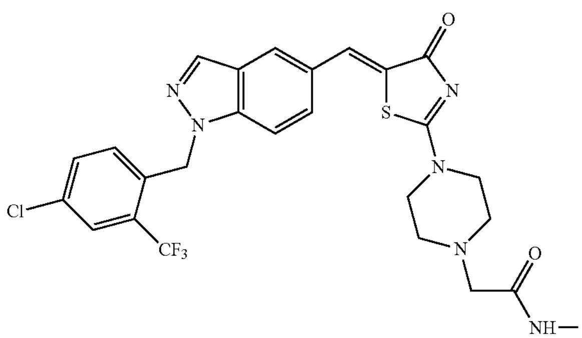 [SMILES: CNC(=O)CN1CCN(C2=NC(=O)/C(=C/c3ccc4c(cnn4Cc4ccc(Cl)cc4C(F)(F)F)c3)S2)CC1] | 82 | 2-(4-{5-[1-(4-Chloro-2-trifluoromethyl-benzyl)-1H-indazol-5-ylmethylene]-4-oxo-4,5-dihydro-thiazol-2-yl}-piperazin-1-yl)-N-methyl-acetamide |
| 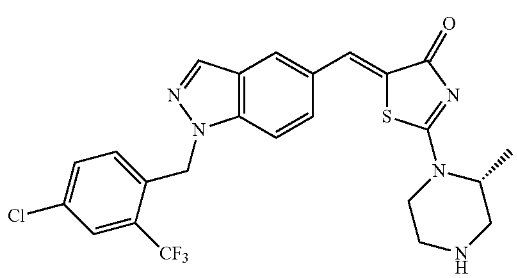 [SMILES: C[C@@H]1CNCCN1C1=NC(=O)/C(=C/c2ccc3c(cnn3Cc3ccc(Cl)cc3C(F)(F)F)c2)S1] | 83 | 5-[1-(4-Chloro-2-trifluoromethyl-benzyl)-1H-indazol-5-ylmethylene]-2-(2-(R)-methyl-piperazin-1-yl)-thiazol-4-one |
| 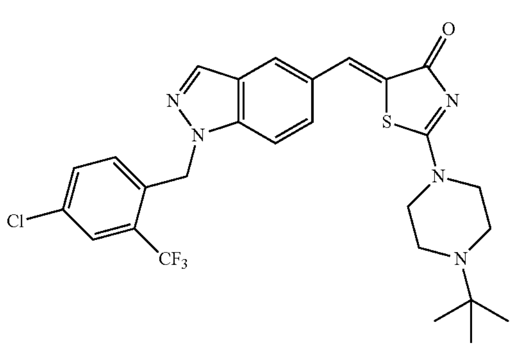 [SMILES: CC(C)(C)N1CCN(C2=NC(=O)/C(=C/c3ccc4c(cnn4Cc4ccc(Cl)cc4C(F)(F)F)c3)S2)CC1] | 84 | 2-(4-tert-Butyl-piperazin-1-yl)-5-[1-(4-chloro-2-trifluoromethyl-benzyl)-1H-indazol-5-ylmethylene]-thiazol-4-one |

TABLE I-continued

| STRUCTURE | COMPOUND # | NAME |
|---|---|---|
| 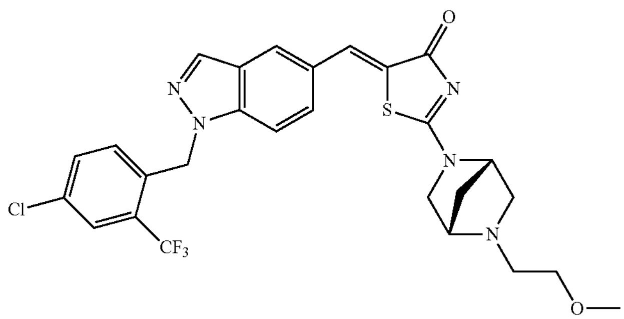 [SMILES: COCCN1C[C@@H]2C[C@H]1CN2C1=NC(=O)/C(=C/c2ccc3c(cnn3Cc3ccc(Cl)cc3C(F)(F)F)c2)S1] | 85 | 5-[1-(4-Chloro-2-trifluoromethyl-benzyl)-1H-indazol-5-ylmethylene]-2-[5-(2-methoxy-ethyl)-2S,5S-diaza-bicyclo[2.2.1]hept-2-yl]-thiazol-4-one |
| 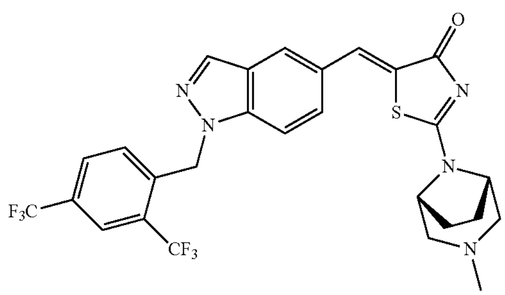 [SMILES: CN1C[C@H]2CC[C@@H](C1)N2C1=NC(=O)/C(=C/c2ccc3c(cnn3Cc3ccc(C(F)(F)F)cc3C(F)(F)F)c2)S1] | 86 | 5-[1-(2,4-Bis-trifluoromethyl-benzyl)-1H-indazol-5-ylmethylene]-2-(3-methyl-3,8-diaza-bicyclo[3.2.1]oct-8-yl)-thiazol-4-one |
| 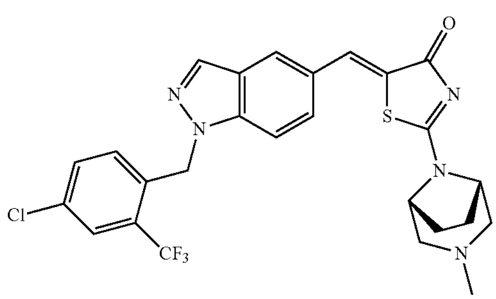 [SMILES: CN1C[C@H]2CC[C@@H](C1)N2C1=NC(=O)/C(=C/c2ccc3c(cnn3Cc3ccc(Cl)cc3C(F)(F)F)c2)S1] | 87 | 5-[1-(4-Chloro-2-trifluoromethyl-benzyl)-1H-indazol-5-ylmethylene]-2-(3-methyl-3,8-diaza-bicyclo[3.2.1]oct-8-yl)-thiazol-4-one |
| 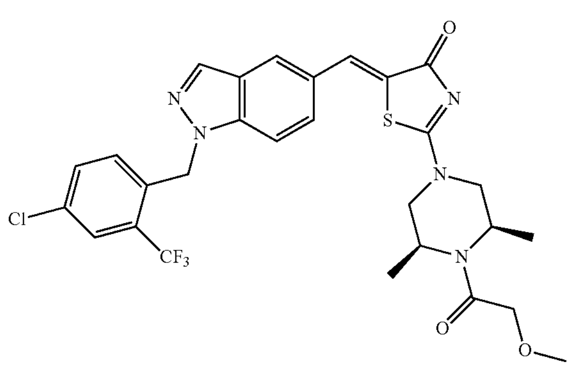 [SMILES: COCC(=O)N1[C@H](C)CN(C2=NC(=O)/C(=C/c3ccc4c(cnn4Cc4ccc(Cl)cc4C(F)(F)F)c3)S2)C[C@@H]1C] | 88 | 5-[1-(4-Chloro-2-trifluoromethyl-benzyl)-1H-indazol-5-ylmethylene]-2-[4-(2-methoxy-acetyl)-cis-3,5-dimethyl-piperazin-1-yl]-thiazol-4-one |

TABLE I-continued

| STRUCTURE | COMPOUND # | NAME |
|---|---|---|
| 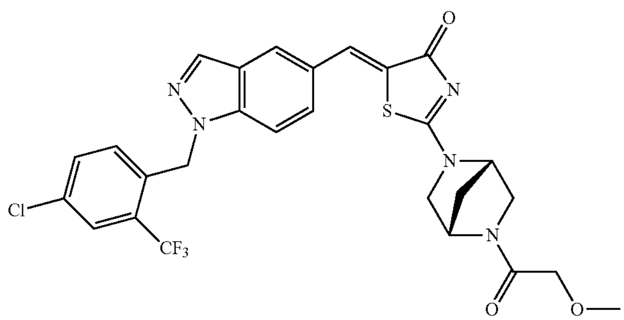 [SMILES: COCC(=O)N1C[C@@H]2C[C@H]1CN2C1=NC(=O)/C(=C/c2ccc3c(cnn3Cc3ccc(Cl)cc3C(F)(F)F)c2)S1] | 89 | 5-[1-(4-Chloro-2-trifluoromethyl-benzyl)-1H-indazol-5-ylmethylene]-2-[5-(2-methoxy-acetyl)-2S,5S-diaza-bicyclo[2.2.1]hept-2-yl]-thiazol-4-one |
| 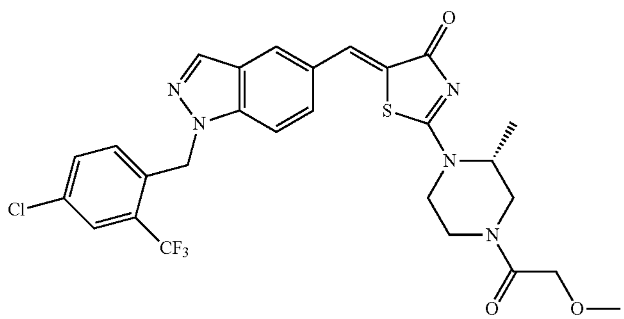 [SMILES: COCC(=O)N1CCN(C2=NC(=O)/C(=C/c3ccc4c(cnn4Cc4ccc(Cl)cc4C(F)(F)F)c3)S2)[C@H](C)C1] | 90 | 5-[1-(4-Chloro-2-trifluoromethyl-benzyl)-1H-indazol-5-ylmethylene]-2-[4-(2-methoxy-acetyl)-2-(R)-methyl-piperazin-1-yl]-thiazol-4-one |
| 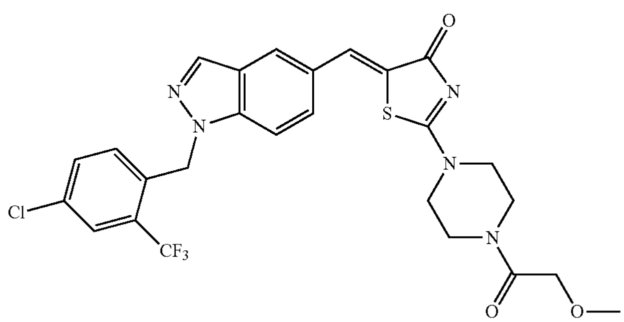 [SMILES: COCC(=O)N1CCN(C2=NC(=O)/C(=C/c3ccc4c(cnn4Cc4ccc(Cl)cc4C(F)(F)F)c3)S2)CC1] | 91 | 5-[1-(4-Chloro-2-trifluoromethyl-benzyl)-1H-indazol-5-ylmethylene]-2-[4-(2-methoxy-acetyl)-piperazin-1-yl]-thiazol-4-one |
| 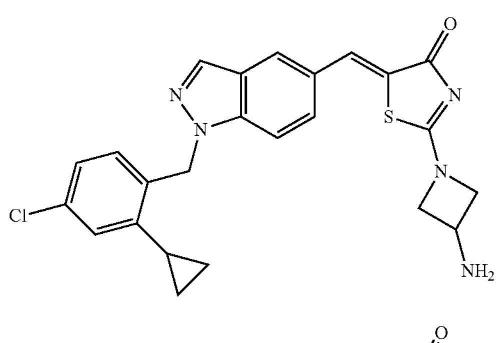 | 92 | 2-(3-Amino-azetidin-1-yl)-5-[1-(4-chloro-2-cyclopropyl-benzyl)-1H-indazol-5-ylmethylene]-thiazol-4-one |
| 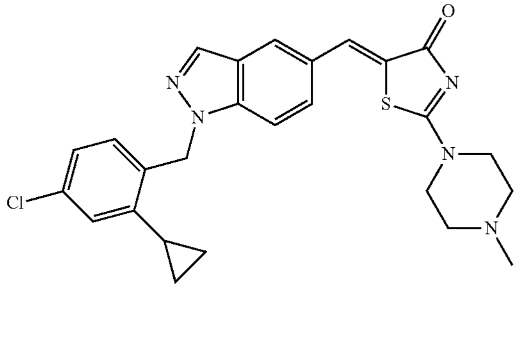 [SMILES: CN1CCN(C2=NC(=O)/C(=C/c3ccc4c(cnn4Cc4ccc(Cl)cc4C4CC4)c3)S2)CC1] | 93 | 5-[1-(4-Chloro-2-cyclopropyl-benzyl)-1H-indazol-5-ylmethylene]-2-(4-methyl-piperazin-1-yl)-thiazol-4-one |

TABLE I-continued

| STRUCTURE | COMPOUND # | NAME |
|---|---|---|
| 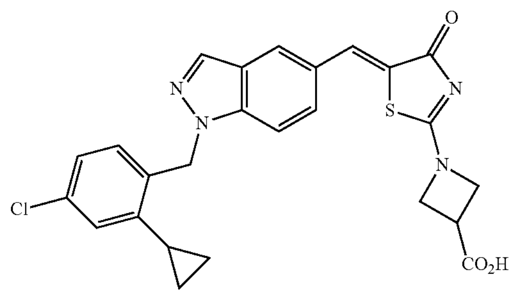 [SMILES: O=C1N=C(N2CC(C(=O)O)C2)S/C1=C\c1ccc2c(cnn2Cc2ccc(Cl)cc2C2CC2)c1] | 94 | 1-(5-[1-(4-Chloro-2-cyclopropyl-benzyl)-1H-indazol-5-ylmethylene]-4-oxo-dihydro-thiazol-2-yl)-azetidine-3-carboxylic acid |
| 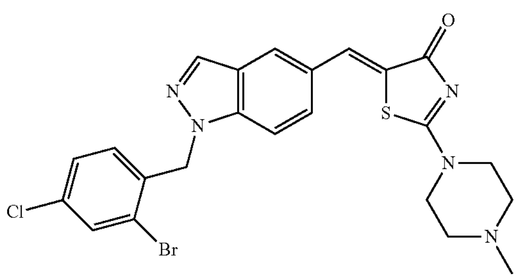 | 95 | 5-[1-(2-bromo-4-chlorobenzyl)-1H-indazol-5-ylmethylene]-2-(4-methyl-piperazin-1-yl)-thiazol-4-one |
| 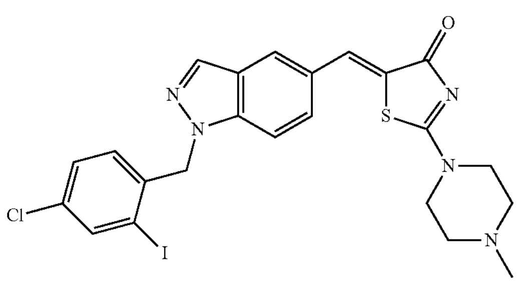 [SMILES: CN1CCN(C2=NC(=O)/C(=C/c3ccc4c(cnn4Cc4ccc(Cl)cc4I)c3)S2)CC1] | 96 | 5-[1-(4-Chloro-2-iodo-benzyl)-1H-indazol-5-ylmethylene]-2-(4-methyl-piperazin-1-yl)-thiazol-4-one |
| 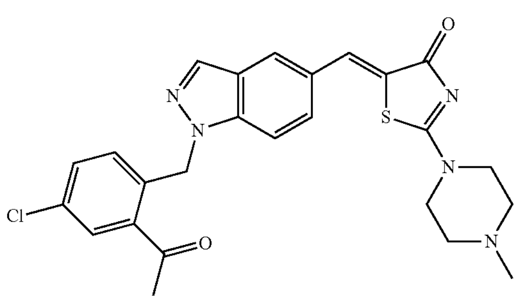 [SMILES: CC(=O)c1cc(Cl)ccc1Cn1ncc2cc(/C=C3\SC(N4CCN(C)CC4)=NC3=O)ccc21] | 97 | 5-[1-(2-Acetyl-4-chloro-benzyl)-1H-indazol-5-ylmethylene]-2-(4-methyl-piperazin-1-yl)-thiazol-4-one |
| 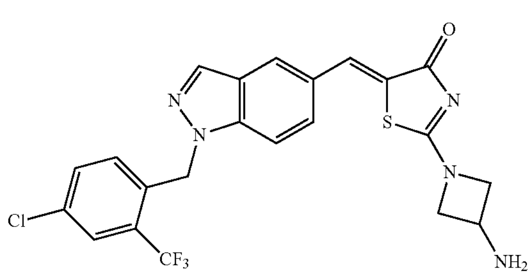 [SMILES: NC1CN(C2=NC(=O)/C(=C/c3ccc4c(cnn4Cc4ccc(Cl)cc4C(F)(F)F)c3)S2)C1] | 98 | 2-(3-Amino-azetidin-1-yl)-5-[1-(4-chloro-2-trifluoromethyl-benzyl)-1H-indazol-5-ylmethylene]-thiazol-4-one |

TABLE I-continued

| STRUCTURE | COMPOUND # | NAME |
|---|---|---|
| 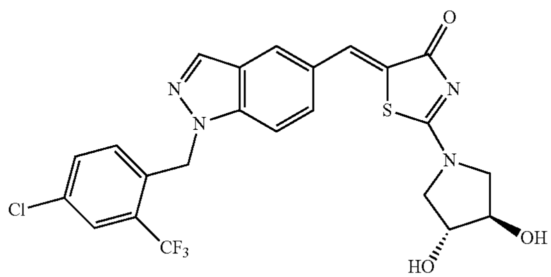 [SMILES: O=C1N=C(N2C[C@@H](O)[C@H](O)C2)S/C1=C\c1ccc2c(cnn2Cc2ccc(Cl)cc2C(F)(F)F)c1] | 99 | 5-[1-(4-Chloro-2-trifluoromethyl-benzyl)-1H-indazol-5-ylmethylene]-2-(3R,4R-dihydroxy-pyrrolidin-1-yl)-thiazol-4-one |
| 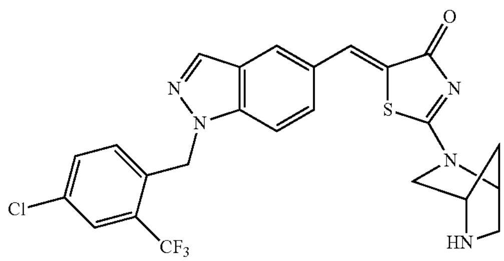 [SMILES: O=C1N=C(N2CC3CC2CN3)S/C1=C\c1ccc2c(cnn2Cc2ccc(Cl)cc2C(F)(F)F)c1] | 100 | 5-[1-(4-Chloro-2-trifluoromethyl-benzyl)-1H-indazol-5-ylmethylene]-2-(2S,5S-bicyclo[2.2.1]hept-2-yl)-thiazol-4-one |
| 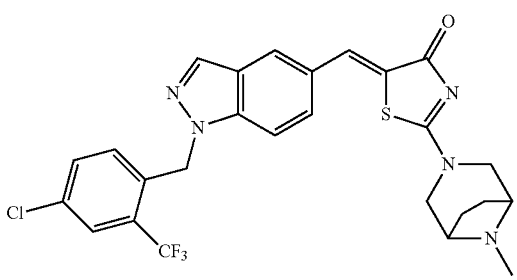 [SMILES: CN1C2CCC1CN(C1=NC(=O)/C(=C/c3ccc4c(cnn4Cc4ccc(Cl)cc4C(F)(F)F)c3)S1)C2] | 101 | 5-[1-(4-Chloro-2-trifluoromethyl-benzyl)-1H-indazol-5-ylmethylene]-2-(8-methyl-3,8-diaza-bicyclo[3.2.1]oct-3-yl)-thiazol-4-one |
| 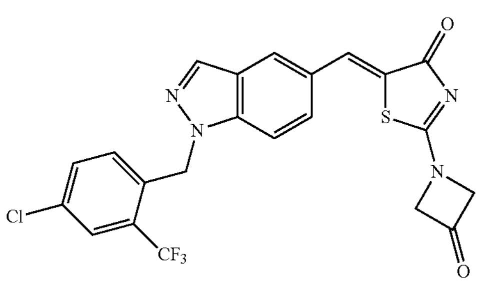 [SMILES: O=C1CN(C2=NC(=O)/C(=C/c3ccc4c(cnn4Cc4ccc(Cl)cc4C(F)(F)F)c3)S2)C1] | 102 | 5-[1-(4-Chloro-2-trifluoromethyl-benzyl)-1H-indazol-5-ylmethylene]-2-(3-oxo-azetidin-1-yl)-thiazol-4-one |
| 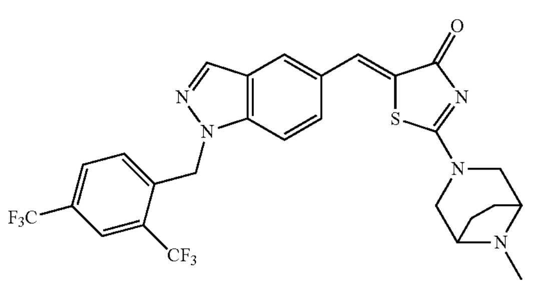 [SMILES: CN1C2CCC1CN(C1=NC(=O)/C(=C/c3ccc4c(cnn4Cc4ccc(C(F)(F)F)cc4C(F)(F)F)c3)S1)C2] | 103 | 5-[1-(2,4-Bis-trifluoromethyl-benzyl)-1H-indazol-5-ylmethylene]-2-(8-methyl-3,8-diaza-bicyclo[3.2.1]oct-3-yl)-thiazol-4-one |

TABLE I-continued

| STRUCTURE | COMPOUND # | NAME |
|---|---|---|
| 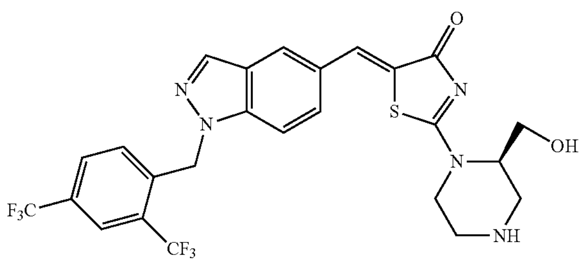 [SMILES: O=C1N=C(N2CCNC[C@@H]2CO)S/C1=C\c1ccc2c(cnn2Cc2ccc(C(F)(F)F)cc2C(F)(F)F)c1] | 104 | 5-[1-(2,4-Bis-trifluoromethyl-benzyl)-1H-indazol-5-ylmethylene]-2-(2-hydroxymethyl-piperazin-1-yl)-thiazol-4-one |
| 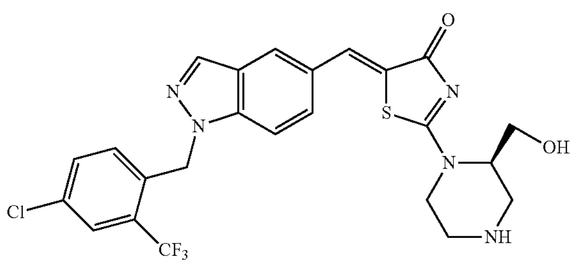 [SMILES: O=C1N=C(N2CCNC[C@@H]2CO)S/C1=C\c1ccc2c(cnn2Cc2ccc(Cl)cc2C(F)(F)F)c1] | 105 | 5-[1-(4-Chloro-2-trifluoromethyl-benzyl)-1H-indazol-5-ylmethylene]-2-(2-hydroxymethyl-piperazin-1-yl)-thiazol-4-one |
| 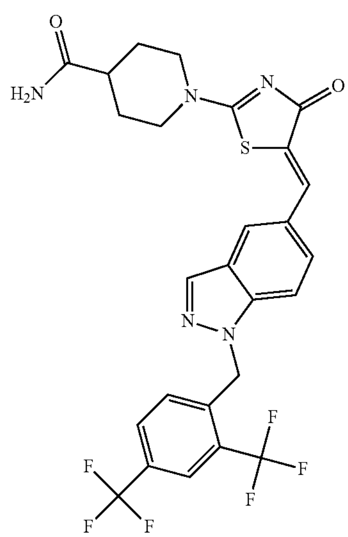 [SMILES: NC(=O)C1CCN(C2=NC(=O)/C(=C/c3ccc4c(cnn4Cc4ccc(C(F)(F)F)cc4C(F)(F)F)c3)S2)CC1] | 106 | 1-{5-[1-(2,4-Bis-trifluoromethyl-benzyl)-1H-indazol-5-ylmethylene]-4-oxo-4,5-dihydro-thiazol-2-yl}-piperidine-4-carboxylic acid amide |
| 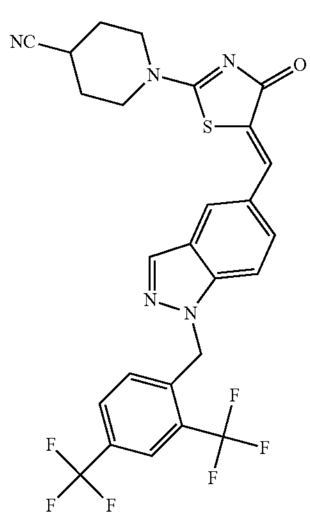 [SMILES: N#CC1CCN(C2=NC(=O)/C(=C/c3ccc4c(cnn4Cc4ccc(C(F)(F)F)cc4C(F)(F)F)c3)S2)CC1] | 107 | 5-[1-(2,4-Bis-trifluoromethyl-benzyl)-1H-indazol-5-ylmethylene]-2-(4-isocyano-piperidin-1-yl)-thiazol-4-one |

TABLE I-continued

| STRUCTURE | COMPOUND # | NAME |
|---|---|---|
| 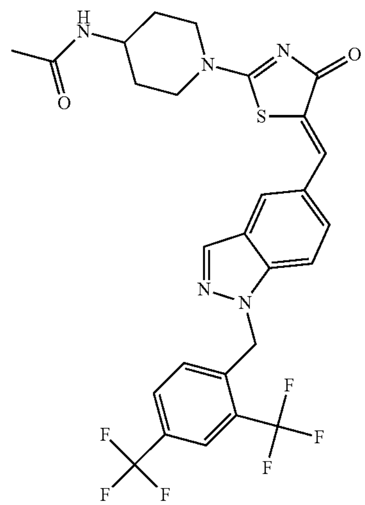 [SMILES: CC(=O)NC1CCN(C2=NC(=O)/C(=C/c3ccc4c(cnn4Cc4ccc(C(F)(F)F)cc4C(F)(F)F)c3)S2)CC1] | 108 | N-(1-{5-[1-(2,4-Bis-trifluoromethyl-benzyl)-1H-indazol-5-ylmethylene]-4-oxo-4,5-dihydro-thiazol-2-yl}-piperidin-4-yl)-acetamide |
| 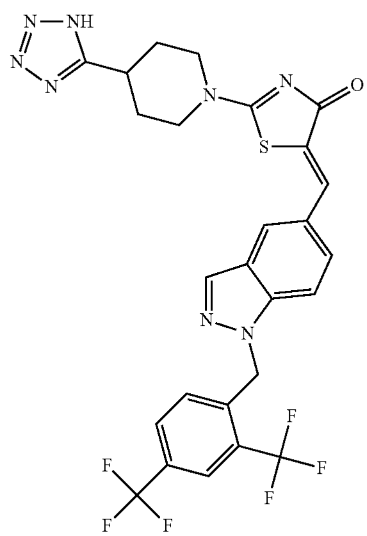 [SMILES: O=C1N=C(N2CCC(c3nnn[nH]3)CC2)S/C1=C\c1ccc2c(cnn2Cc2ccc(C(F)(F)F)cc2C(F)(F)F)c1] | 109 | 5-[1-(2,4-Bis-trifluoromethyl-benzyl)-1H-indazol-5-ylmethylene]-2-[4-(1H-tetrazol-5-yl)-piperidin-1-yl]-thiazol-4-one |
| 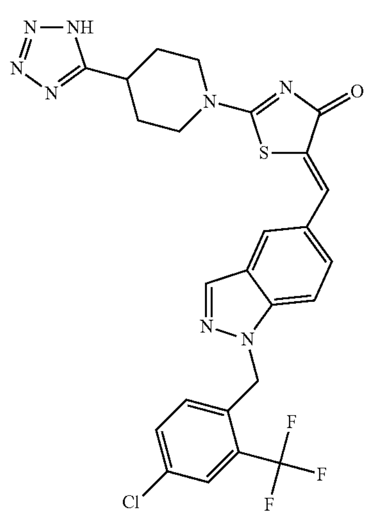 [SMILES: O=C1N=C(N2CCC(c3nnn[nH]3)CC2)S/C1=C\c1ccc2c(cnn2Cc2ccc(Cl)cc2C(F)(F)F)c1] | 110 | 5-[1-(4-Chloro-2-trifluoromethyl-benzyl)-1H-indazol-5-ylmethylene]-2-[4-(1H-tetrazol-5-yl)-piperidin-1-yl]-thiazol-4-one |

TABLE I-continued

| STRUCTURE | COMPOUND # | NAME |
|---|---|---|
| 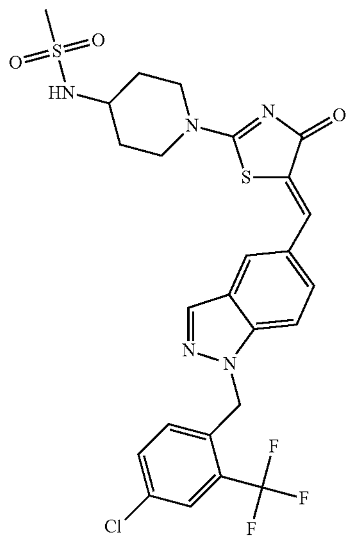 [SMILES: CS(=O)(=O)NC1CCN(C2=NC(=O)/C(=C/c3ccc4c(cnn4Cc4ccc(Cl)cc4C(F)(F)F)c3)S2)CC1] | 111 | N-(1-{5-[1-(4-Chloro-2-trifluoromethyl-benzyl)-1H-indazol-5-ylmethylene]-4-oxo-4,5-dihydro-thiazol-2-yl}-piperidin-4-yl)-methanesulfonamide |
| 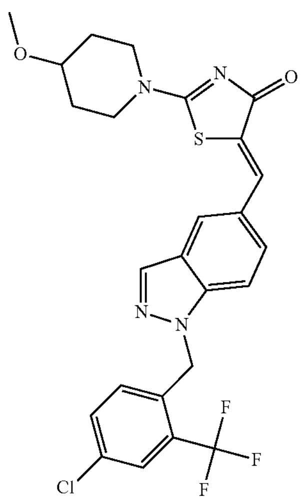 [SMILES: COC1CCN(C2=NC(=O)/C(=C/c3ccc4c(cnn4Cc4ccc(Cl)cc4C(F)(F)F)c3)S2)CC1] | 112 | 5-[1-(4-Chloro-2-trifluoromethyl-benzyl)-1H-indazol-5-ylmethylene]-2-(4-methoxy-piperidin-1-yl)-thiazol-4-one |
| 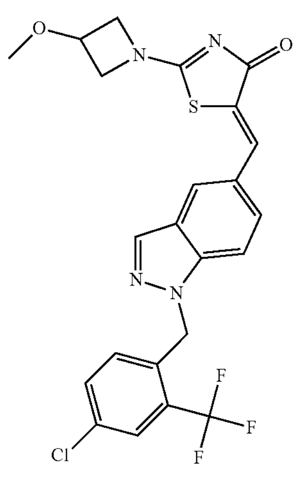 [SMILES: COC1CN(C2=NC(=O)/C(=C/c3ccc4c(cnn4Cc4ccc(Cl)cc4C(F)(F)F)c3)S2)C1] | 113 | 5-[1-(4-Chloro-2-trifluoromethyl-benzyl)-1H-indazol-5-ylmethylene]-2-(3-methoxy-azetidin-1-yl)-thiazol-4-one |

TABLE I-continued
| STRUCTURE | COMPOUND # | NAME |
|---|---|---|
| 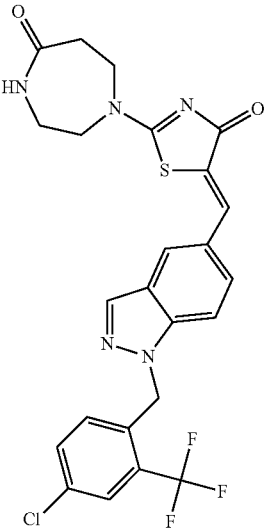 [SMILES: O=C1CCN(C2=NC(=O)/C(=C/c3ccc4c(cnn4Cc4ccc(Cl)cc4C(F)(F)F)c3)S2)CCN1] | 114 | 1-{5-[1-(4-Chloro-2-trifluoromethyl-benzyl)-1H-indazol-5-ylmethylene]-4-oxo-4,5-dihydro-thiazol-2-yl}-[1,4]diazepan-5-one |
| 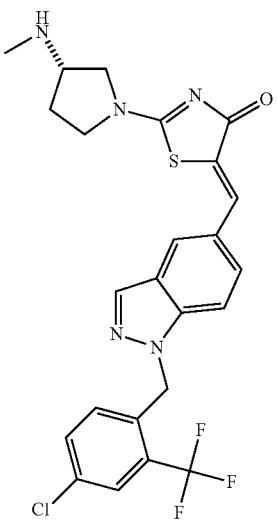 [SMILES: CN[C@H]1CCN(C2=NC(=O)/C(=C/c3ccc4c(cnn4Cc4ccc(Cl)cc4C(F)(F)F)c3)S2)C1] | 115 | 5-[1-(4-Chloro-2-trifluoromethyl-benzyl)-1H-indazol-5-ylmethylene]-2-(3-methylamino-pyrrolidin-1-yl)-thiazol-4-one |

| STRUCTURE | COMPOUND # | NAME |
|---|---|---|
| 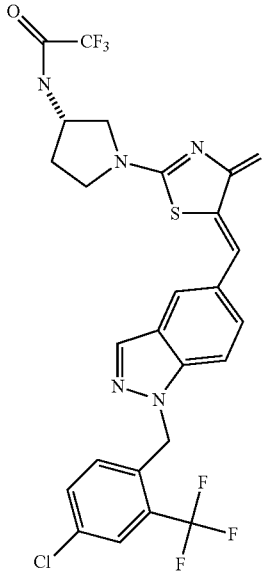 | 116 | N-(1-{5-[1-(4-Chloro-2-trifluoromethyl-benzyl)-1H-indazol-5-ylmethylene]-4-oxo-4,5-dihydro-thiazol-2-yl}-pyrrolidin-3-yl)-2,2,2-trifluoro-acetamide |
| 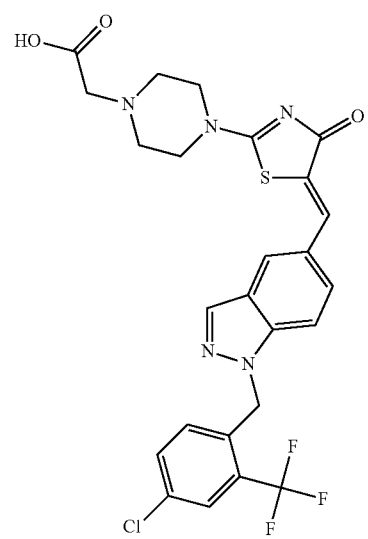 [SMILES: O=C(O)CN1CCN(C2=NC(=O)/C(=C/c3ccc4c(cnn4Cc4ccc(Cl)cc4C(F)(F)F)c3)S2)CC1] | 117 | (4-{5-[1-(4-Chloro-2-trifluoromethyl-benzyl)-1H-indazol-5-ylmethylene]-4-oxo-4,5-dihydro-thiazol-2-yl}-piperazin-1-yl)-acetic acid |

US 8,399,681 B2
143                                                                 144
TABLE I-continued
| STRUCTURE | COMPOUND # | NAME |
|---|---|---|
| 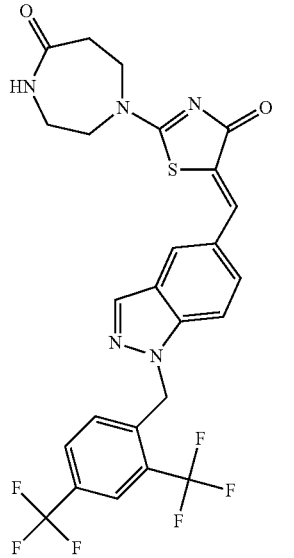 [SMILES: O=C1CCN(C2=NC(=O)/C(=C/c3ccc4c(cnn4Cc4ccc(C(F)(F)F)cc4C(F)(F)F)c3)S2)CCN1] | 118 | 1-{5-[1-(2,4-Bis-trifluoromethyl-benzyl)-1H-indazol-5-ylmethylene]-4-oxo-4,5-dihydro-thiazol-2-yl}-[1,4]diazepan-5-one |
| 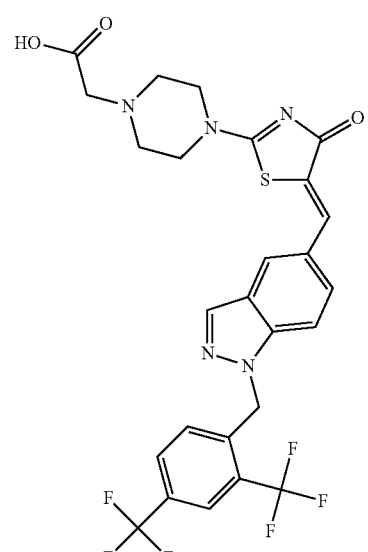 | 119 | (4-{5-[1-(2,4-Bis-trifluoromethyl-benzyl)-1H-indazol-5-ylmethylene]-4-oxo-4,5-dihydro-thiazol-2-yl}-piperazin-1-yl)-acetic acid |

| STRUCTURE | COMPOUND # | NAME |
|---|---|---|
| 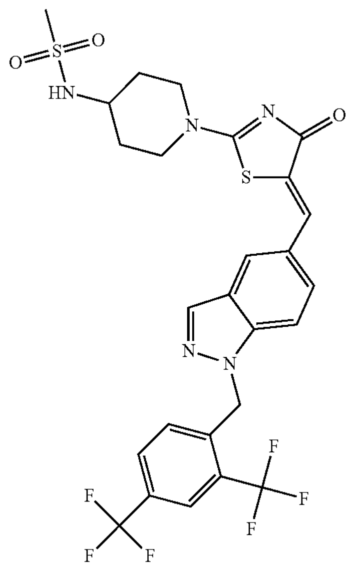 [SMILES: CS(=O)(=O)NC1CCN(C2=NC(=O)/C(=C/c3ccc4c(cnn4Cc4ccc(C(F)(F)F)cc4C(F)(F)F)c3)S2)CC1] | 120 | N-(1-{5-[1-(2,4-Bis-trifluoromethyl-benzyl)-1H-indazol-5-ylmethylene]-4-oxo-4,5-dihydro-thiazol-2-yl}-piperidin-4-yl)-methanesulfonamide |
| 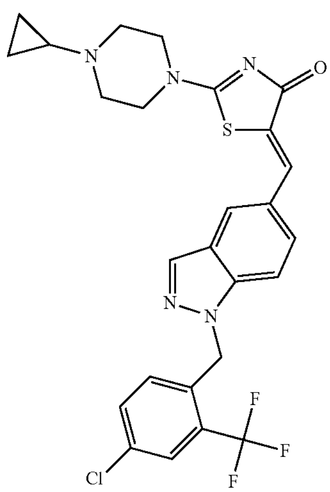 [SMILES: O=C1N=C(N2CCN(C3CC3)CC2)S/C1=C\c1ccc2c(cnn2Cc2ccc(Cl)cc2C(F)(F)F)c1] | 121 | 5-[1-(4-Chloro-2-trifluoromethyl-benzyl)-1H-indazol-5-ylmethylene]-2-(4-cyclopropyl-piperazin-1-yl)-thiazol-4-one |
| 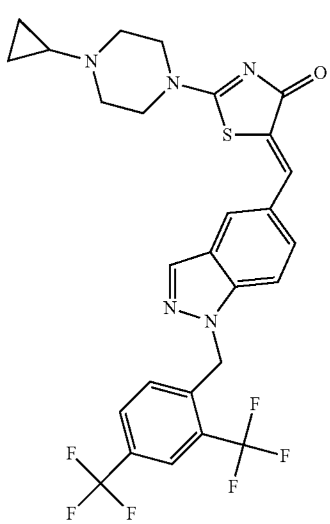 [SMILES: O=C1N=C(N2CCN(C3CC3)CC2)S/C1=C\c1ccc2c(cnn2Cc2ccc(C(F)(F)F)cc2C(F)(F)F)c1] | 122 | 5-[1-(2,4-Bis-trifluoromethyl-benzyl)-1H-indazol-5-ylmethylene]-2-(4-cyclopropyl-piperazin-1-yl)-thiazol-4-one |

TABLE I-continued
| STRUCTURE | COMPOUND # | NAME |
|---|---|---|
| 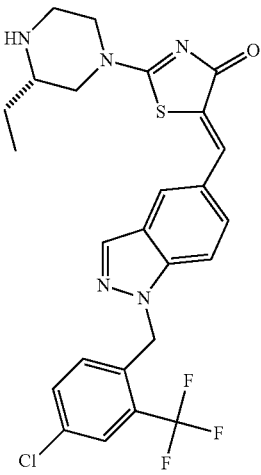 [SMILES: CC[C@H]1CN(C2=NC(=O)/C(=C/c3ccc4c(cnn4Cc4ccc(Cl)cc4C(F)(F)F)c3)S2)CCN1] | 123 | 5-[1-(4-Chloro-2-trifluoromethyl-benzyl)-1H-indazol-5-ylmethylene]-2-(3-ethyl-piperazin-1-yl)-thiazol-4-one |
| 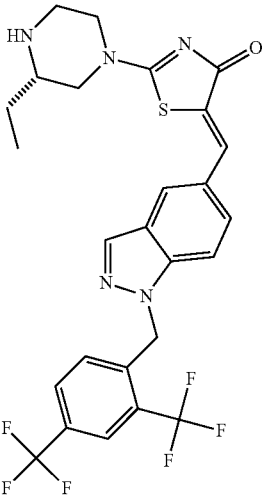 [SMILES: CC[C@H]1CN(C2=NC(=O)/C(=C/c3ccc4c(cnn4Cc4ccc(C(F)(F)F)cc4C(F)(F)F)c3)S2)CCN1] | 124 | 5-[1-(2,4-Bis-trifluoromethyl-benzyl)-1H-indazol-5-ylmethylene]-2-(3-ethyl-piperazin-1-yl)-thiazol-4-one |
| 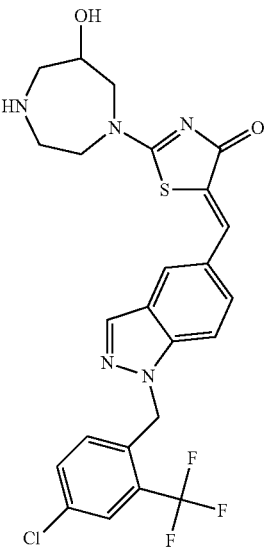 [SMILES: O=C1N=C(N2CCNCC(O)C2)S/C1=C\c1ccc2c(cnn2Cc2ccc(Cl)cc2C(F)(F)F)c1] | 125 | 5-[1-(4-Chloro-2-trifluoromethyl-benzyl)-1H-indazol-5-ylmethylene]-2-(6-hydroxy-[1,4]diazepan-1-yl)-thiazol-4-one |

| STRUCTURE | COMPOUND # | NAME |
|---|---|---|
| 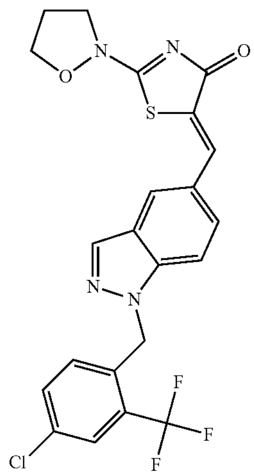 [SMILES: O=C1N=C(N2CCCO2)S/C1=C\c1ccc2c(cnn2Cc2ccc(Cl)cc2C(F)(F)F)c1] | 126 | 5-[1-(4-Chloro-2-trifluoromethyl-benzyl)-1H-indazol-5-ylmethylene]-2-isoxazolidin-2-yl-thiazol-4-one |
| 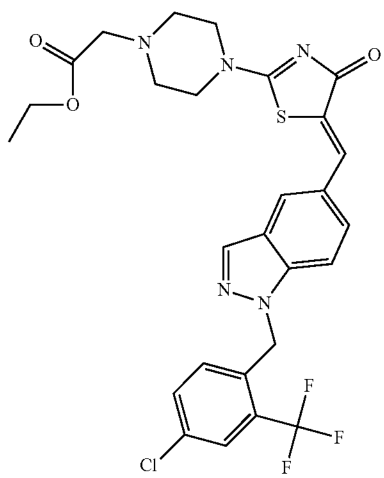 [SMILES: CCOC(=O)CN1CCN(C2=NC(=O)/C(=C/c3ccc4c(cnn4Cc4ccc(Cl)cc4C(F)(F)F)c3)S2)CC1] | 127 | (4-{5-[1-(4-Chloro-2-trifluoromethyl-benzyl)-1H-indazol-5-ylmethylene]-4-oxo-4,5-dihydro-thiazol-2-yl}-piperazin-1-yl)-acetic acid ethyl ester |
| 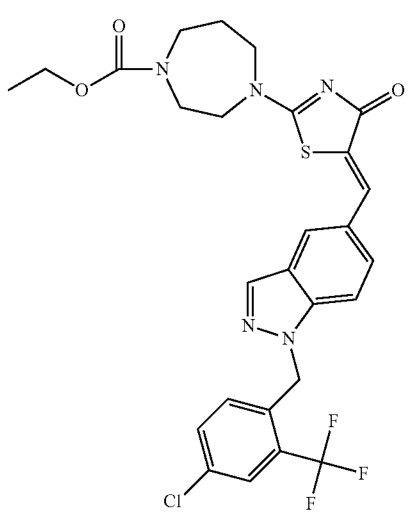 [SMILES: CCOC(=O)N1CCCN(C2=NC(=O)/C(=C/c3ccc4c(cnn4Cc4ccc(Cl)cc4C(F)(F)F)c3)S2)CC1] | 128 | 4-{5-[1-(4-Chloro-2-trifluoromethyl-benzyl)-1H-indazol-5-ylmethylene]-4-oxo-4,5-dihydro-thiazol-2-yl}-[1,4]diazepane-1-carboxylic acid ethyl ester |

TABLE I-continued

| STRUCTURE | COMPOUND # | NAME |
|---|---|---|
| 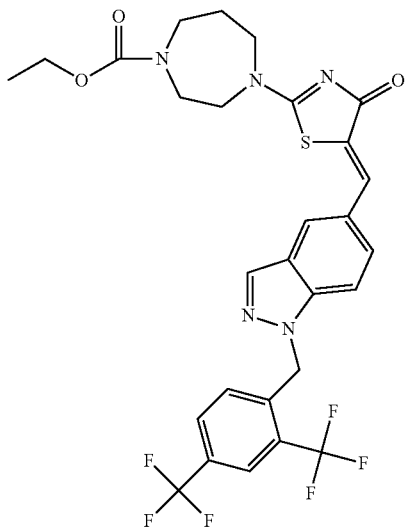 [SMILES: CCOC(=O)N1CCCN(C2=NC(=O)/C(=C/c3ccc4c(cnn4Cc4ccc(C(F)(F)F)cc4C(F)(F)F)c3)S2)CC1] | 129 | 4-{5-[1-(2,4-Bis-trifluoromethyl-benzyl)-1H-indazol-5-ylmethylene]-4-oxo-4,5-dihydro-thiazol-2-yl}-[1,4]diazepane-1-carboxylic acid ethyl ester |
| 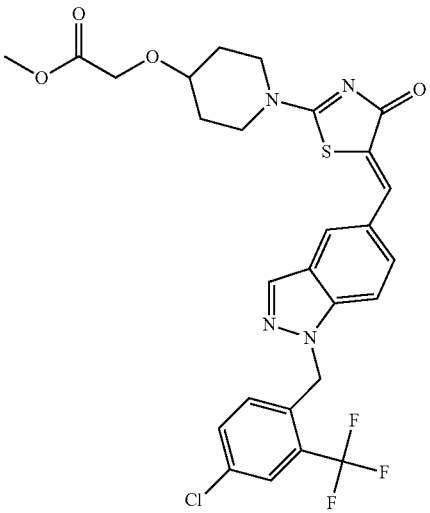 [SMILES: COC(=O)COC1CCN(C2=NC(=O)/C(=C/c3ccc4c(cnn4Cc4ccc(Cl)cc4C(F)(F)F)c3)S2)CC1] | 130 | (1-{5-[1-(4-Chloro-2-trifluoromethyl-benzyl)-1H-indazol-5-ylmethylene]-4-oxo-4,5-dihydro-thiazol-2-yl}-piperidin-4-yloxy)-acetic acid methyl ester |
| 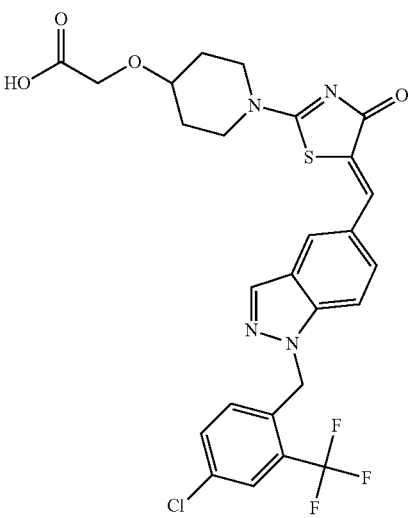 [SMILES: O=C(O)COC1CCN(C2=NC(=O)/C(=C/c3ccc4c(cnn4Cc4ccc(Cl)cc4C(F)(F)F)c3)S2)CC1] | 131 | (1-{5-[1-(4-Chloro-2-trifluoromethyl-benzyl)-1H-indazol-5-ylmethylene]-4-oxo-4,5-dihydro-thiazol-2-yl}-piperidin-4-yloxy)-acetic acid |

TABLE I-continued

| STRUCTURE | COMPOUND # | NAME |
|---|---|---|
| 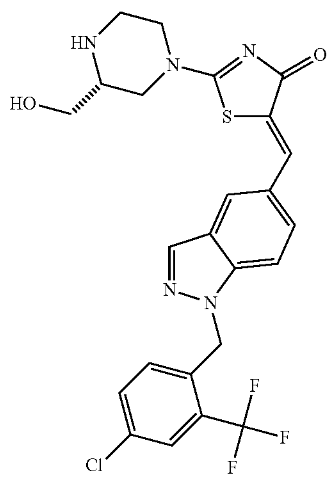 [SMILES: O=C1N=C(N2CCN[C@@H](CO)C2)S/C1=C\c1ccc2c(cnn2Cc2ccc(Cl)cc2C(F)(F)F)c1] | 132 | 5-[1-(4-Chloro-2-trifluoromethyl-benzyl)-1H-indazol-5-ylmethylene]-2-(3-(R)-hydroxymethyl-piperazin-1-yl)-thiazol-4-one |
| 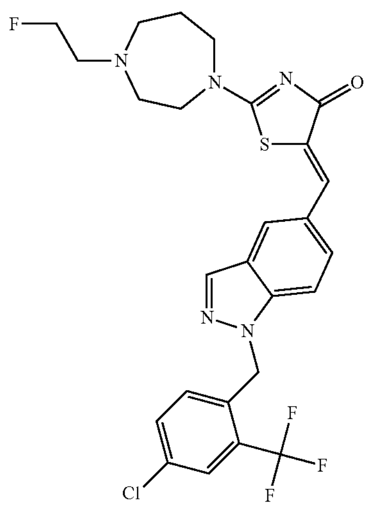 [SMILES: O=C1N=C(N2CCCN(CCF)CC2)S/C1=C\c1ccc2c(cnn2Cc2ccc(Cl)cc2C(F)(F)F)c1] | 133 | 5-[1-(4-Chloro-2-trifluoromethyl-benzyl)-1H-indazol-5-ylmethylene]-2-[4-(2-fluoro-ethyl)-[1,4]diazepan-1-yl]-thiazol-4-one |
| 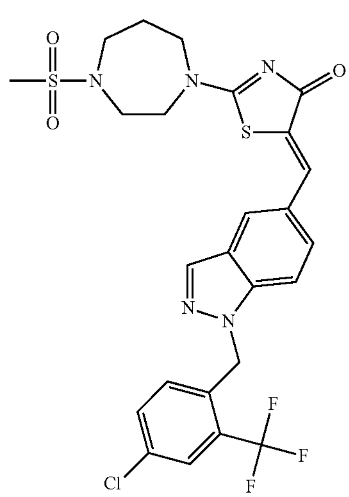 [SMILES: CS(=O)(=O)N1CCCN(C2=NC(=O)/C(=C/c3ccc4c(cnn4Cc4ccc(Cl)cc4C(F)(F)F)c3)S2)CC1] | 134 | 5-[1-(4-Chloro-2-trifluoromethyl-benzyl)-1H-indazol-5-ylmethylene]-2-(4-methanesulfonyl-[1,4]diazepan-1-yl)-thiazol-4-one |

TABLE I-continued

| STRUCTURE | COMPOUND # | NAME |
|---|---|---|
| 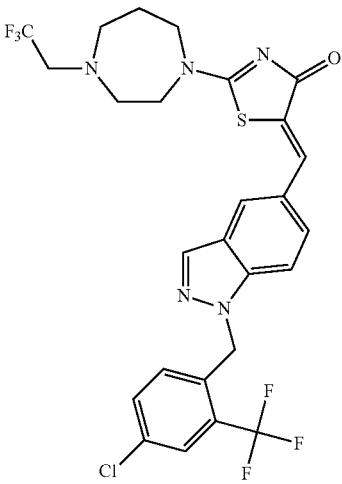 [SMILES: O=C1N=C(N2CCCN(CC(F)(F)F)CC2)S/C1=C\c1ccc2c(cnn2Cc2ccc(Cl)cc2C(F)(F)F)c1] | 135 | 5-[1-(4-Chloro-2-trifluoromethyl-benzyl)-1H-indazol-5-ylmethylene]-2-[4-(2,2,2-trifluoro-ethyl)-[1,4]diazepan-1-yl]-thiazol-4-one |
| 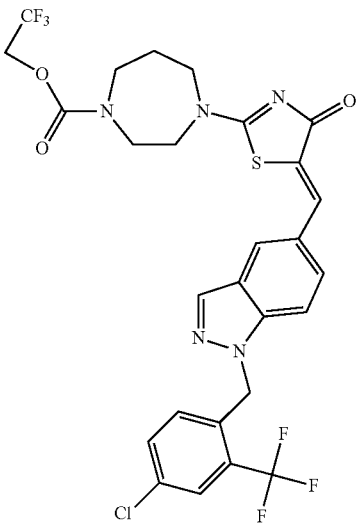 [SMILES: O=C1N=C(N2CCCN(C(=O)OCC(F)(F)F)CC2)S/C1=C\c1ccc2c(cnn2Cc2ccc(Cl)cc2C(F)(F)F)c1] | 136 | 4-{5-[1-(4-Chloro-2-trifluoromethyl-benzyl)-1H-indazol-5-ylmethylene]-4-oxo-4,5-dihydro-thiazol-2-yl}-[1,4]diazepane-1-carboxylic acid 2,2,2-trifluoro-ethyl ester |
| 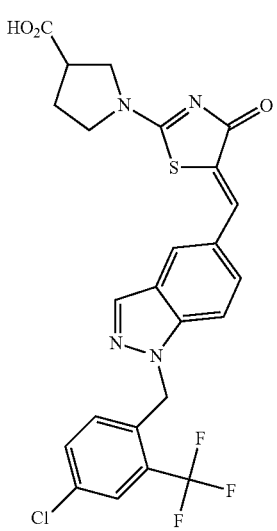 [SMILES: O=C1N=C(N2CCC(C(=O)O)C2)S/C1=C\c1ccc2c(cnn2Cc2ccc(Cl)cc2C(F)(F)F)c1] | 137 | 1-{5-[1-(4-Chloro-2-trifluoromethyl-benzyl)-1H-indazol-5-ylmethylene]-4-oxo-4,5-dihydro-thiazol-2-yl}-pyrrolidine-3-carboxylic acid |

TABLE I-continued

| STRUCTURE | COMPOUND # | NAME |
|---|---|---|
| 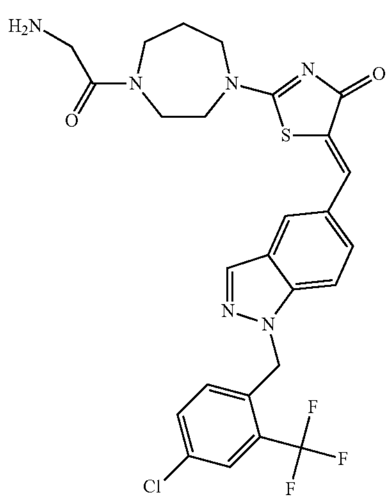 [SMILES: NCC(=O)N1CCCN(C2=NC(=O)/C(=C/c3ccc4c(cnn4Cc4ccc(Cl)cc4C(F)(F)F)c3)S2)CC1] | 138 | 2-[4-(2-Amino-acetyl)-[1,4]diazepan-1-yl]-5-[1-(4-chloro-2-trifluoromethyl-benzyl)-1H-indazol-5-ylmethylene]-thiazol-4-one |
| 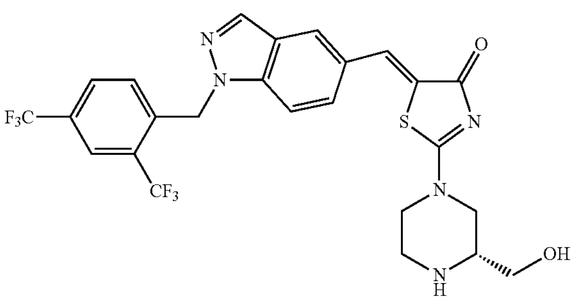 [SMILES: O=C1N=C(N2CCN[C@@H](CO)C2)S/C1=C\c1ccc2c(cnn2Cc2ccc(C(F)(F)F)cc2C(F)(F)F)c1] | 139 | 5-[1-(2,4-Bis-trifluoromethyl-benzyl)-1H-indazol-5-ylmethylene]-2-(3-(R)-hydroxymethyl-piperazin-1-yl)-thiazol-4-one |
| 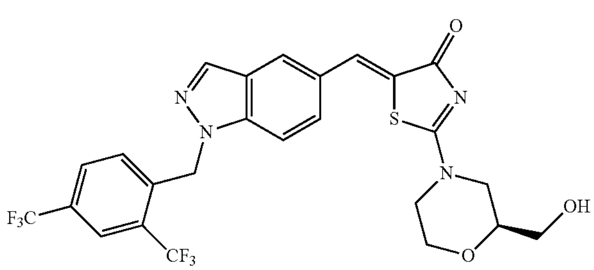 [SMILES: O=C1N=C(N2CCO[C@H](CO)C2)S/C1=C\c1ccc2c(cnn2Cc2ccc(C(F)(F)F)cc2C(F)(F)F)c1] | 140 | 5-[1-(2,4-Bis-trifluoromethyl-benzyl)-1H-indazol-5-ylmethylene]-2-((S)-hydroxymethyl-morpholin-4-yl)-thiazol-4-one |
| 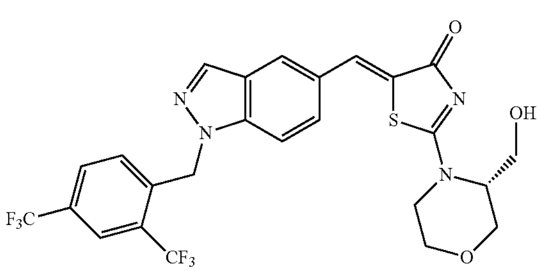 [SMILES: O=C1N=C(N2CCOC[C@H]2CO)S/C1=C\c1ccc2c(cnn2Cc2ccc(C(F)(F)F)cc2C(F)(F)F)c1] | 141 | 5-[1-(2,4-Bis-trifluoromethyl-benzyl)-1H-indazol-5-ylmethylene]-2-(3(R)-hydroxymethyl-morpholin-4-yl)-thiazol-4-one |

TABLE I-continued

| STRUCTURE | COMPOUND # | NAME |
|---|---|---|
| 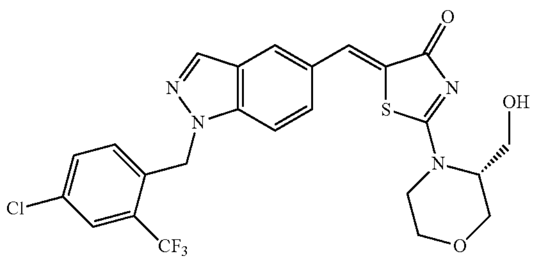 [SMILES: O=C1N=C(N2CCOC[C@H]2CO)S/C1=C\c1ccc2c(cnn2Cc2ccc(Cl)cc2C(F)(F)F)c1] | 142 | 5-[1-(4-Chloro-2-trifluoromethyl-benzyl)-1H-indazol-5-ylmethylene]-2-(3(R)-hydroxymethyl-morpholin-4-yl)-thiazol-4-one |
| 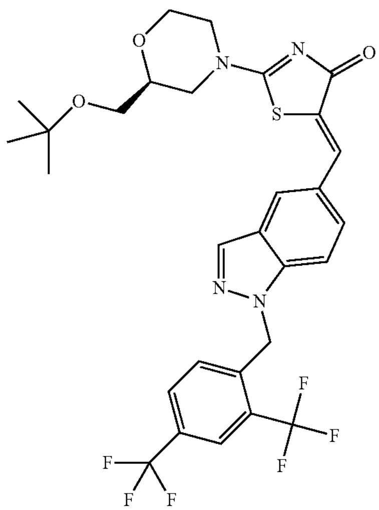 [SMILES: CC(C)(C)OC[C@@H]1CN(C2=NC(=O)/C(=C/c3ccc4c(cnn4Cc4ccc(C(F)(F)F)cc4C(F)(F)F)c3)S2)CCO1] | 143 | 5-({1-[2,4-Bis(trifluoromethyl)benzyl]-1H-indazol-5-yl}methylidene)-2-[2(S)-(tert-butoxymethyl)morpholin-4-yl]-1,3-thiazol-4(5H)-one |
| 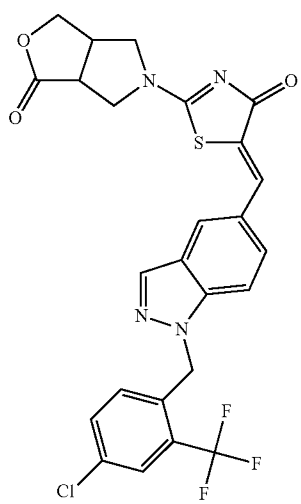 [SMILES: O=C1N=C(N2CC3COC(=O)C3C2)S/C1=C\c1ccc2c(cnn2Cc2ccc(Cl)cc2C(F)(F)F)c1] | 144 | 5-{5-[1-(4-Chloro-2-trifluoromethyl-benzyl)-1H-indazol-5-ylmethylene]-4-oxo-4,5-dihydro-thiazol-2-yl}-hexahydro-furo[3,4-c]pyrrol-1-one |

TABLE I-continued

| STRUCTURE | COMPOUND # | NAME |
|---|---|---|
| 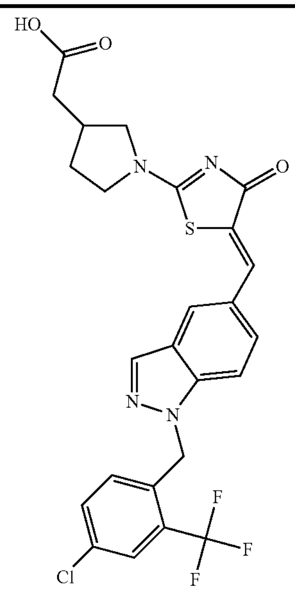 | 145 | (1-{5-[1-(4-Chloro-2-trifluoromethyl-benzyl)-1H-indazol-5-ylmethylene]-4-oxo-4,5-dihydro-thiazol-2-yl}-pyrrolidin-3-yl)-acetic acid |
| 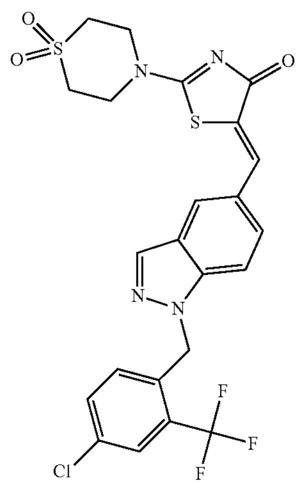 [SMILES: O=C1N=C(N2CCS(=O)(=O)CC2)S/C1=C\c1ccc2c(cnn2Cc2ccc(Cl)cc2C(F)(F)F)c1] | 146 | 5-[1-(4-Chloro-2-trifluoromethyl-benzyl)-1H-indazol-5-ylmethylene]-2-(1,1-dioxidothiomorpholin-4-yl)-thiazol-4-one |
| 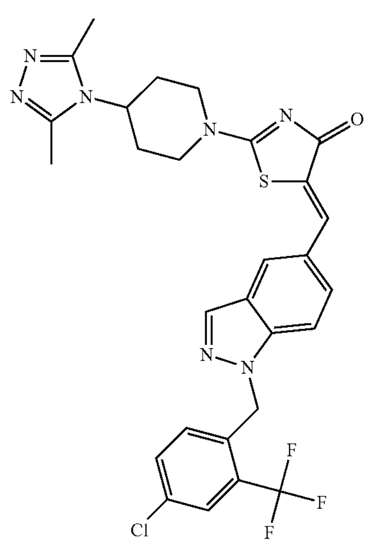 [SMILES: Cc1nnc(C)n1C1CCN(C2=NC(=O)/C(=C/c3ccc4c(cnn4Cc4ccc(Cl)cc4C(F)(F)F)c3)S2)CC1] | 147 | 5-[1-(4-Chloro-2-trifluoromethyl-benzyl)-1H-indazol-5-ylmethylene]-2-[4-(3,5-dimethyl-[1,2,4]triazol-4-yl)-piperidin-1-yl}-thiazol-4-one |

| STRUCTURE | COMPOUND # | NAME |
| --- | --- | --- |
| 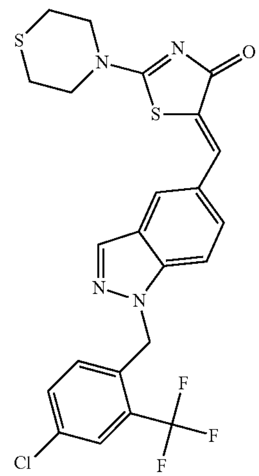 [SMILES: O=C1N=C(N2CCSCC2)S/C1=C\c1ccc2c(cnn2Cc2ccc(Cl)cc2C(F)(F)F)c1] | 148 | 5-[1-(4-Chloro-2-trifluoromethyl-benzyl)-1H-indazol-5-ylmethylene]-2-thiomorpholin-4-yl-thiazol-4-one |
| 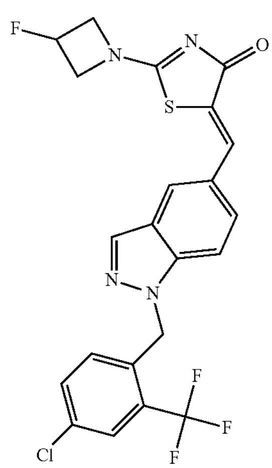 [SMILES: O=C1N=C(N2CC(F)C2)S/C1=C\c1ccc2c(cnn2Cc2ccc(Cl)cc2C(F)(F)F)c1] | 149 | 5-[1-(4-Chloro-2-trifluoromethyl-benzyl)-1H-indazol-5-ylmethylene]-2-(3-fluoro-azetidin-1-yl)-thiazol-4-one |
| 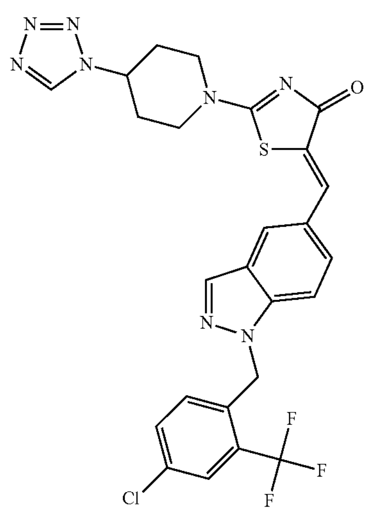 [SMILES: O=C1N=C(N2CCC(n3cnnn3)CC2)S/C1=C\c1ccc2c(cnn2Cc2ccc(Cl)cc2C(F)(F)F)c1] | 150 | 5-[1-(4-Chloro-2-trifluoromethyl-benzyl)-1H-indazol-5-ylmethylene]-2-(4-tetrazol-1-yl-piperidin-1-yl)-thiazol-4-one |

| STRUCTURE | COMPOUND # | NAME |
|---|---|---|
| 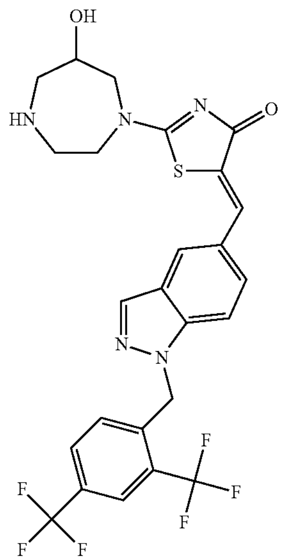 [SMILES: O=C1N=C(N2CCNCC(O)C2)S/C1=C\c1ccc2c(cnn2Cc2ccc(C(F)(F)F)cc2C(F)(F)F)c1] | 151 | 5-[1-(2,4-Bis-trifluoromethyl-benzyl)-1H-indazol-5-ylmethylene]-2-(6-hydroxy-[1,4]diazepan-1-yl)-thiazol-4-one |
| 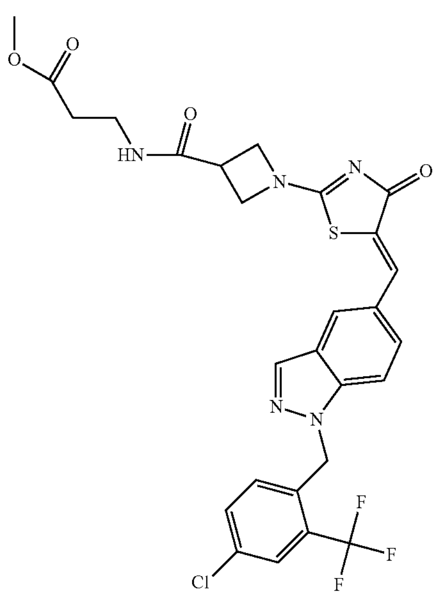 | 152 | 3-[(1-{5-[1-(4-Chloro-2-trifluoromethyl-benzyl)-1H-indazol-5-ylmethylene]-4-oxo-4,5-dihydro-thiazol-2-yl}-azetidine-3-carbonyl)-amino]-propionic acid methyl ester |

US 8,399,681 B2
167                                                                   168
TABLE I-continued
| STRUCTURE | COMPOUND # | NAME |
|---|---|---|
| 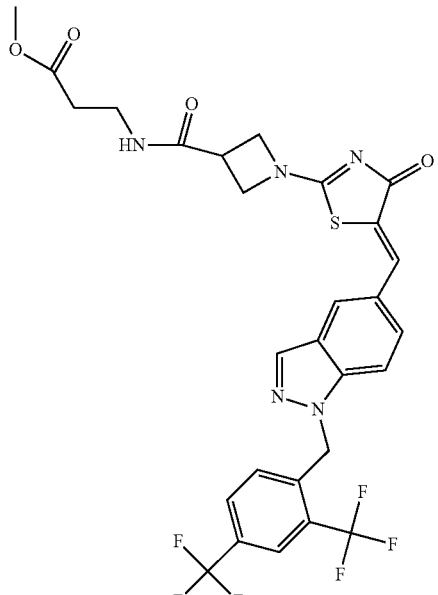 | 153 | 3-[(1-{5-[1-(2,4-Bis-trifluoromethyl-benzyl)-1H-indazol-5-ylmethylene]-4-oxo-4,5-dihydro-thiazol-2-yl}-azetidine-3-carbonyl)-amino]-propionic acid methyl ester |
| 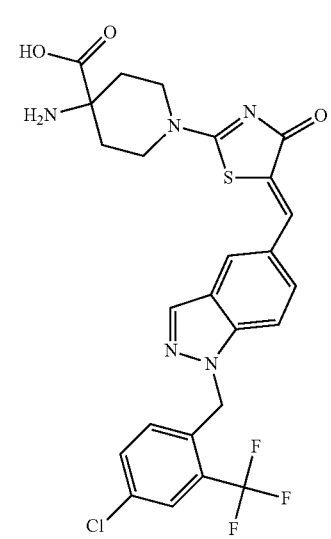 [SMILES: NC1(C(=O)O)CCN(C2=NC(=O)/C(=C/c3ccc4c(cnn4Cc4ccc(Cl)cc4C(F)(F)F)c3)S2)CC1] | 154 | 4-Amino-1-{5-[1-(4-chloro-2-trifluoromethyl-benzyl)-1H-indazol-5-ylmethylene]-4-oxo-4,5-dihydro-thiazol-2-yl}-piperidine-4-carboxylic acid |

TABLE I-continued

| STRUCTURE | COMPOUND # | NAME |
|---|---|---|
| 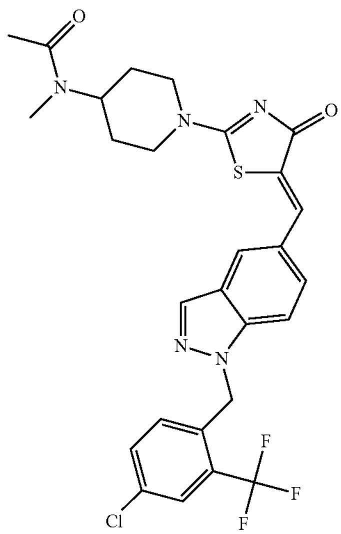 [SMILES: CC(=O)N(C)C1CCN(C2=NC(=O)/C(=C/c3ccc4c(cnn4Cc4ccc(Cl)cc4C(F)(F)F)c3)S2)CC1] | 155 | N-(1-{5-[1-(4-Chloro-2-trifluoromethyl-benzyl)-1H-indazol-5-ylmethylene]-4-oxo-4,5-dihydro-thiazol-2-yl}-piperidin-4-yl)-N-methyl-acetamide |
| 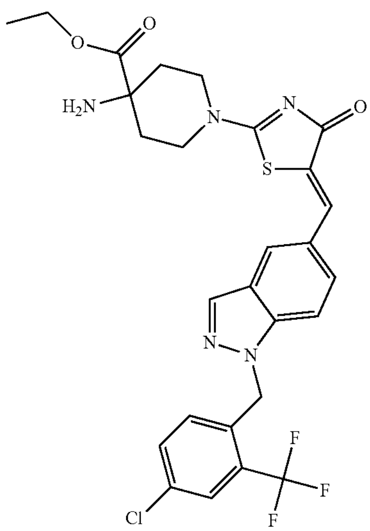 [SMILES: CCOC(=O)C1(N)CCN(C2=NC(=O)/C(=C/c3ccc4c(cnn4Cc4ccc(Cl)cc4C(F)(F)F)c3)S2)CC1] | 156 | 4-Amino-1-{5-[1-(4-chloro-2-trifluoromethyl-benzyl)-1H-indazol-5-ylmethylene]-4-oxo-4,5-dihydro-thiazol-2-yl}-piperidine-4-carboxylic acid ethyl ester |
| 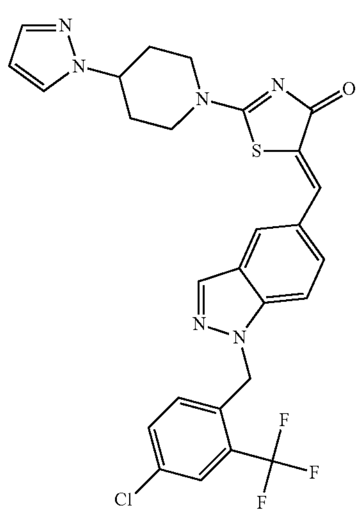 [SMILES: O=C1N=C(N2CCC(n3cccn3)CC2)S/C1=C\c1ccc2c(cnn2Cc2ccc(Cl)cc2C(F)(F)F)c1] | 157 | 5-[1-(4-Chloro-2-trifluoromethyl-benzyl)-1H-indazol-5-ylmethylene]-2-(4-pyrazol-1-yl-piperidin-1-yl)-thiazol-4-one |

TABLE I-continued

| STRUCTURE | COMPOUND # | NAME |
|---|---|---|
| 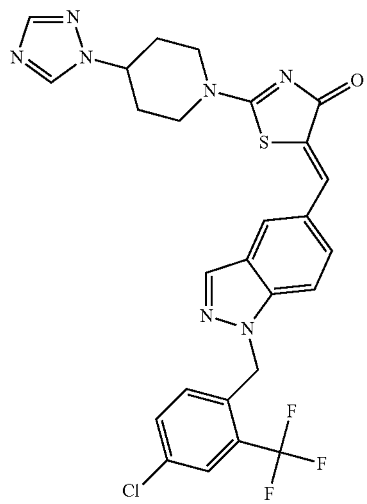 | 158 | 5-[1-(4-Chloro-2-trifluoromethyl-benzyl)-1H-indazol-5-ylmethylene]-2-(4-[1,2,4]triazol-1-yl-piperidin-1-yl)-thiazol-4-one |
| 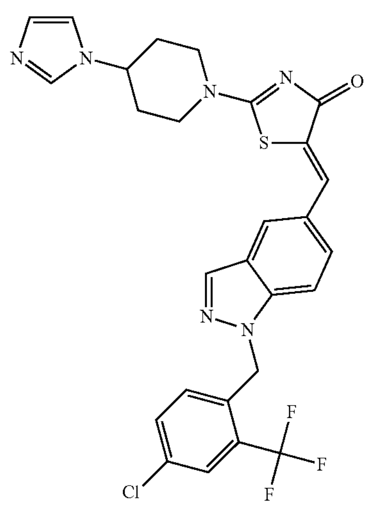 [SMILES: O=C1N=C(N2CCC(n3ccnc3)CC2)S/C1=C\c1ccc2c(cnn2Cc2ccc(Cl)cc2C(F)(F)F)c1] | 159 | 5-[1-(4-Chloro-2-trifluoromethyl-benzyl)-1H-indazol-5-ylmethylene]-2-(4-imidazol-1-yl-piperidin-1-yl)-thiazol-4-one |
| 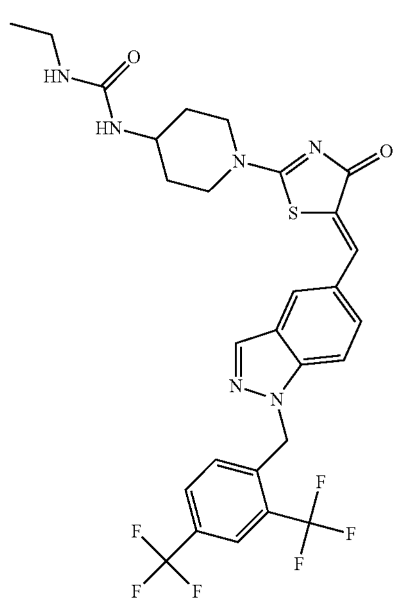 [SMILES: CCNC(=O)NC1CCN(C2=NC(=O)/C(=C/c3ccc4c(cnn4Cc4ccc(C(F)(F)F)cc4C(F)(F)F)c3)S2)CC1] | 160 | 1-(1-{5-[1-(2,4-Bis-trifluoromethyl-benzyl)-1H-indazol-5-ylmethylene]-4-oxo-4,5-dihydro-thiazol-2-yl}-piperidin-4-yl)-3-ethyl-urea |

TABLE I-continued

| STRUCTURE | COMPOUND # | NAME |
|---|---|---|
| 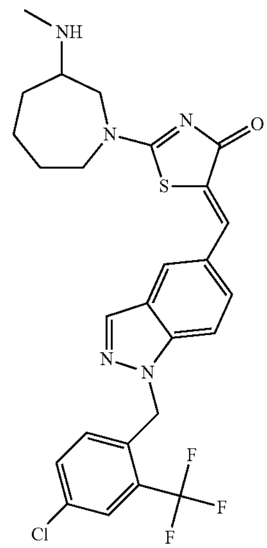 [SMILES: CNC1CCCCN(C2=NC(=O)/C(=C/c3ccc4c(cnn4Cc4ccc(Cl)cc4C(F)(F)F)c3)S2)C1] | 161 | 5-[1-(4-Chloro-2-trifluoromethyl-benzyl)-1H-indazol-5-ylmethylene]-2-(3-methylamino-azepan-1-yl)-thiazol-4-one |
| 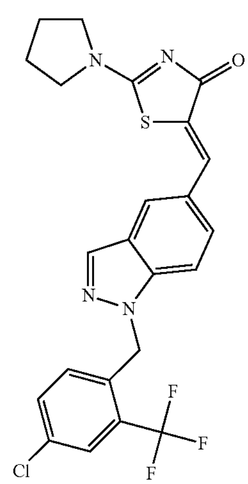 [SMILES: O=C1N=C(N2CCCC2)S/C1=C\c1ccc2c(cnn2Cc2ccc(Cl)cc2C(F)(F)F)c1] | 162 | 5-[1-(4-Chloro-2-trifluoromethyl-benzyl)-1H-indazol-5-ylmethylene]-2-pyrrolidin-1-yl-thiazol-4-one |

TABLE I-continued
| STRUCTURE | COMPOUND # | NAME |
|---|---|---|
| 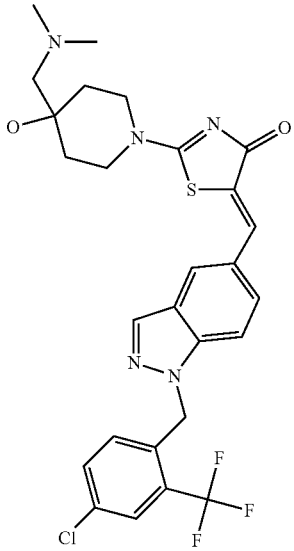 [SMILES: CN(C)CC1(O)CCN(C2=NC(=O)/C(=C/c3ccc4c(cnn4Cc4ccc(Cl)cc4C(F)(F)F)c3)S2)CC1] | 163 | 5-[1-(4-Chloro-2-trifluoromethyl-benzyl)-1H-indazol-5-ylmethylene]-2-(4-dimethylaminomethyl-4-hydroxy-piperidin-1-yl)-thiazol-4-one |
| 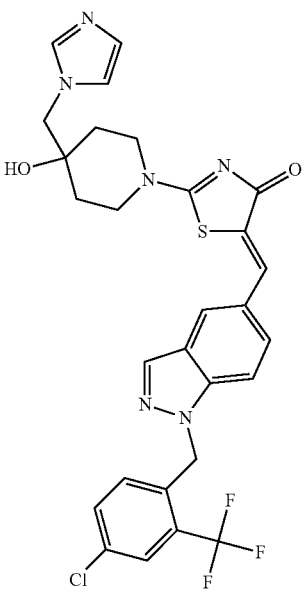 [SMILES: O=C1N=C(N2CCC(O)(Cn3ccnc3)CC2)S/C1=C\c1ccc2c(cnn2Cc2ccc(Cl)cc2C(F)(F)F)c1] | 164 | 5-[1-(4-Chloro-2-trifluoromethyl-benzyl)-1H-indazol-5-ylmethylene]-2-(4-hydroxy-4-imidazol-1-ylmethyl-piperidin-1-yl)-thiazol-4-one |

TABLE I-continued

| STRUCTURE | COMPOUND # | NAME |
|---|---|---|
| 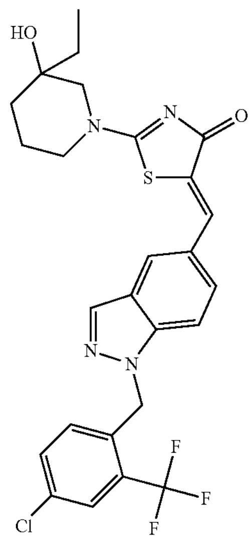 [SMILES: CCC1(O)CCCN(C2=NC(=O)/C(=C/c3ccc4c(cnn4Cc4ccc(Cl)cc4C(F)(F)F)c3)S2)C1] | 165 | 5-[1-(4-Chloro-2-trifluoromethyl-benzyl)-1H-indazol-5-ylmethylene]-2-(3-ethyl-3-hydroxy-piperidin-1-yl)-thiazol-4-one |
| 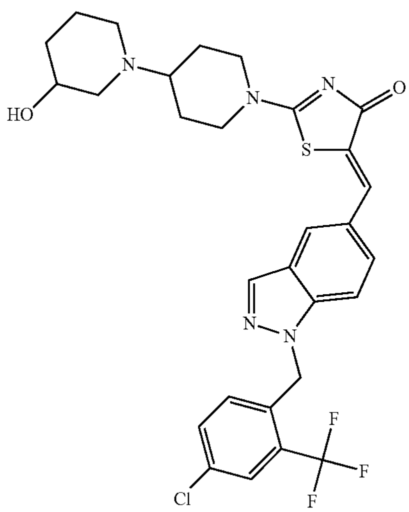 [SMILES: O=C1N=C(N2CCC(N3CCCC(O)C3)CC2)S/C1=C\c1ccc2c(cnn2Cc2ccc(Cl)cc2C(F)(F)F)c1] | 166 | 5-[1-(4-Chloro-2-trifluoromethyl-benzyl)-1H-indazol-5-ylmethylene]-2-(3-hydroxy-[1,4']bipiperidinyl-1'-yl)-thiazol-4-one |
| 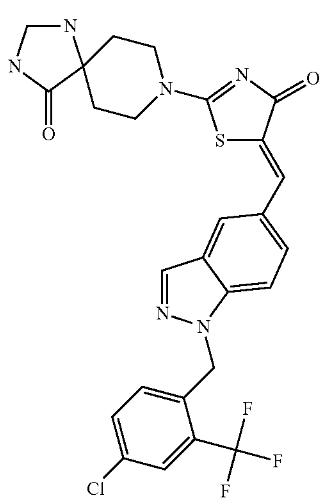 [SMILES: O=C1N=C(N2CCC3(CC2)NCNC3=O)S/C1=C\c1ccc2c(cnn2Cc2ccc(Cl)cc2C(F)(F)F)c1] | 167 | 8-{5-[1-(4-Chloro-2-trifluoromethyl-benzyl)-1H-indazol-5-ylmethylene]-4-oxo-4,5-dihydro-thiazol-2-yl}-1,3,8-triaza-spiro[4.5]decan-4-one |

TABLE I-continued
| STRUCTURE | COMPOUND # | NAME |
|---|---|---|
| 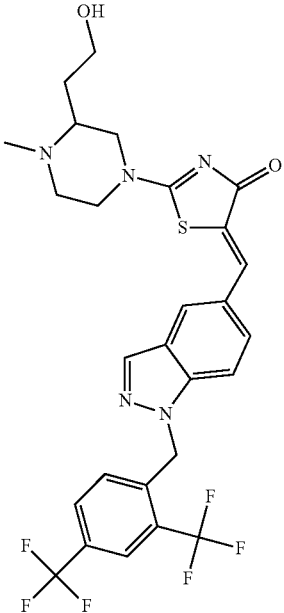 [SMILES: CN1CCN(C2=NC(=O)/C(=C/c3ccc4c(cnn4Cc4ccc(C(F)(F)F)cc4C(F)(F)F)c3)S2)CC1CCO] | 168 | 5-[1-(2,4-Bis-trifluoromethyl-benzyl)-1H-indazol-5-ylmethylene]-2-[3-(2-hydroxy-ethyl)-4-methyl-piperazin-1-yl]-thiazol-4-one |
| 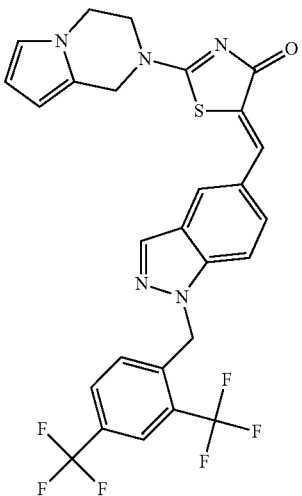 [SMILES: O=C1N=C(N2CCn3cccc3C2)S/C1=C\c1ccc2c(cnn2Cc2ccc(C(F)(F)F)cc2C(F)(F)F)c1] | 169 | 5-[1-(2,4-Bis-trifluoromethyl-benzyl)-1H-indazol-5-ylmethylene]-2-(3,4-dihydro-1H-pyrrolo[1,2-a]pyrazin-2-yl)-thiazol-4-one |

TABLE I-continued

| STRUCTURE | COMPOUND # | NAME |
|---|---|---|
| 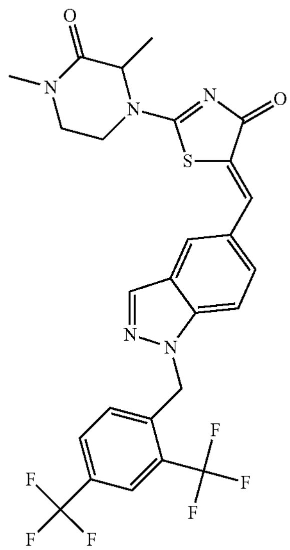 [SMILES: CC1C(=O)N(C)CCN1C1=NC(=O)/C(=C/c2ccc3c(cnn3Cc3ccc(C(F)(F)F)cc3C(F)(F)F)c2)S1] | 170 | 4-{5-[1-(2,4-Bis-trifluoromethyl-benzyl)-1H-indazol-5-ylmethylene]-4-oxo-4,5-dihydro-thiazol-2-yl}-1,3-dimethyl-piperazin-2-one |
| 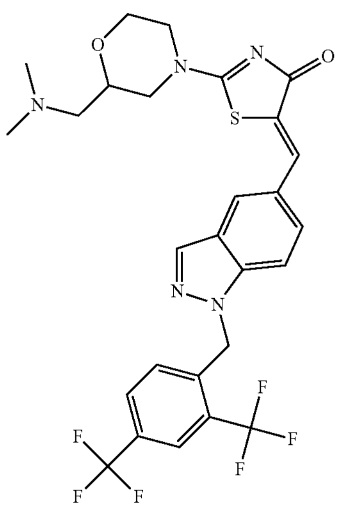 [SMILES: CN(C)CC1CN(C2=NC(=O)/C(=C/c3ccc4c(cnn4Cc4ccc(C(F)(F)F)cc4C(F)(F)F)c3)S2)CCO1] | 171 | 5-[1-(2,4-Bis-trifluoromethyl-benzyl)-1H-indazol-5-ylmethylene]-2-(2-dimethylaminomethyl-morpholin-4-yl)-thiazol-4-one |
| 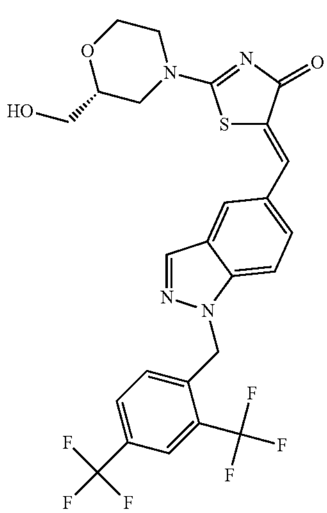 [SMILES: O=C1N=C(N2CCO[C@@H](CO)C2)S/C1=C\c1ccc2c(cnn2Cc2ccc(C(F)(F)F)cc2C(F)(F)F)c1] | 172 | 5-[1-(2,4-Bis-trifluoromethyl-benzyl)-1H-indazol-5-ylmethylene]-2(R)-(2-hydroxymethyl-morpholin-4-yl)-thiazol-4-one |

TABLE I-continued
| STRUCTURE | COMPOUND # | NAME |
|---|---|---|
| 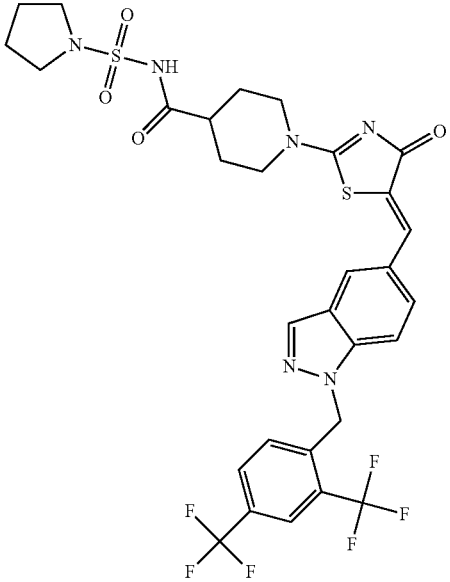 [SMILES: O=C1N=C(N2CCC(C(=O)NS(=O)(=O)N3CCCC3)CC2)S/C1=C\c1ccc2c(cnn2Cc2ccc(C(F)(F)F)cc2C(F)(F)F)c1] | 173 | Pyrrolidine-1-sulfonic acid (1-{5-[1-(2,4-bis-trifluoromethyl-benzyl)-1H-indazol-5-ylmethylene]-4-oxo-4,5-dihydro-thiazol-2-yl}-piperidine-4-carbonyl)-amide |
| 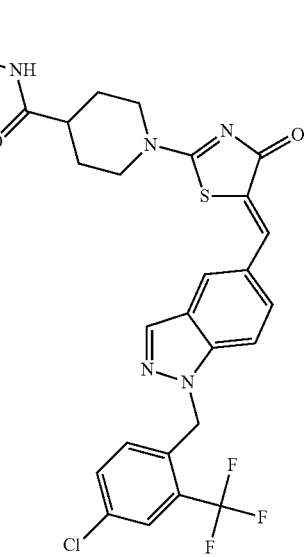 | 174 | Pyrrolidine-1-sulfonic acid (1-{5-[1-(4-chloro-2-trifluoromethyl-benzyl)-1H-indazol-5-ylmethylene]-4-oxo-4,5-dihydro-thiazol-2-yl}-piperidine-4-carbonyl)-amide |

TABLE I-continued

| STRUCTURE | COMPOUND # | NAME |
|---|---|---|
| 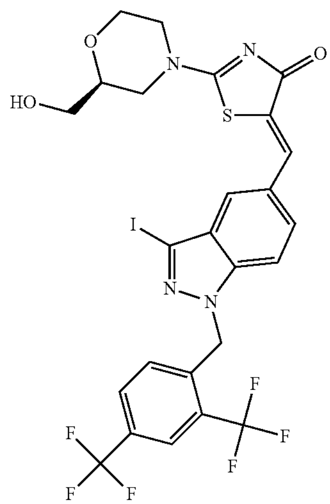 [SMILES: O=C1N=C(N2CCO[C@H](CO)C2)S/C1=C\c1ccc2c(c1)c(I)nn2Cc1ccc(C(F)(F)F)cc1C(F)(F)F] | 175 | 5-[1-(2,4-Bis-trifluoromethyl-benzyl)-3-iodo-1H-indazol-5-ylmethylene]-2(S)-(2-hydroxymethyl-morpholin-4-yl)-thiazol-4-one |
| 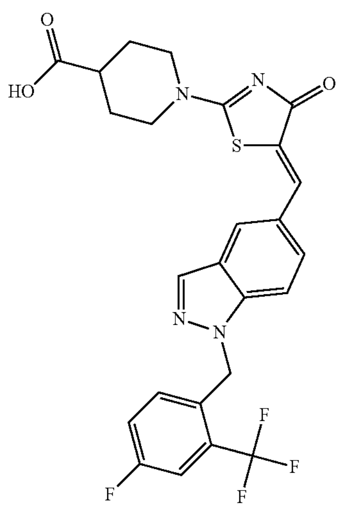 [SMILES: O=C1N=C(N2CCC(C(=O)O)CC2)S/C1=C\c1ccc2c(cnn2Cc2ccc(F)cc2C(F)(F)F)c1] | 176 | 1-{5-[1-(4-Fluoro-2-trifluoromethyl-benzyl)-1H-indazol-5-ylmethylene]-4-oxo-4,5-dihydro-thiazol-2-yl}-piperidine-4-carboxylic acid |
| 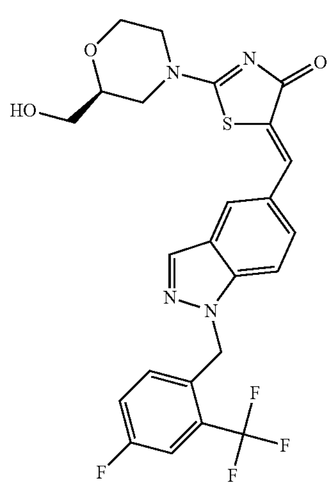 [SMILES: O=C1N=C(N2CCO[C@H](CO)C2)S/C1=C\c1ccc2c(cnn2Cc2ccc(F)cc2C(F)(F)F)c1] | 177 | 5-[1-(4-Fluoro-2-trifluoromethyl-benzyl)-1H-indazol-5-ylmethylene]-2-((2S)-2-hydroxymethyl-morpholin-4-yl)-thiazol-4-one |

TABLE I-continued

| STRUCTURE | COMPOUND # | NAME |
|---|---|---|
| 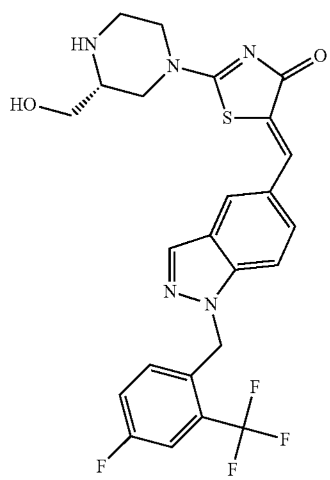 [SMILES: O=C1N=C(N2CCN[C@@H](CO)C2)S/C1=C\c1ccc2c(cnn2Cc2ccc(F)cc2C(F)(F)F)c1] | 178 | 5-[1-(4-Fluoro-2-trifluoromethyl-benzyl)-1H-indazol-5-ylmethylene]-2-((3R)-3-hydroxymethyl-piperazin-1-yl)-thiazol-4-one |
| 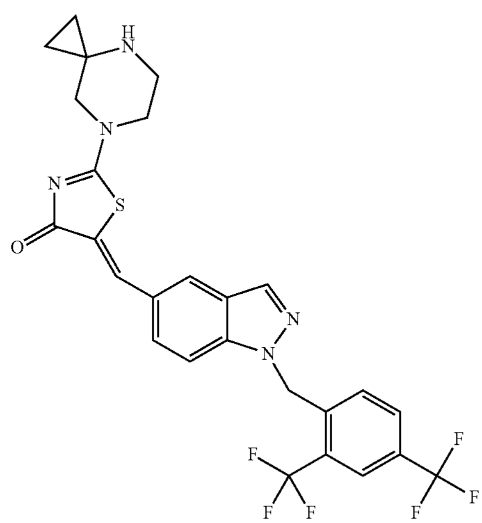 [SMILES: O=C1N=C(N2CCNC3(CC3)C2)S/C1=C\c1ccc2c(cnn2Cc2ccc(C(F)(F)F)cc2C(F)(F)F)c1] | 179 | 5-[1-(2,4-Bis-trifluoromethyl-benzyl)-1H-indazol-5-ylmethylene]-2-(4,7-diaza-spiro[2.5]oct-7-yl)-thiazol-4-one |
| 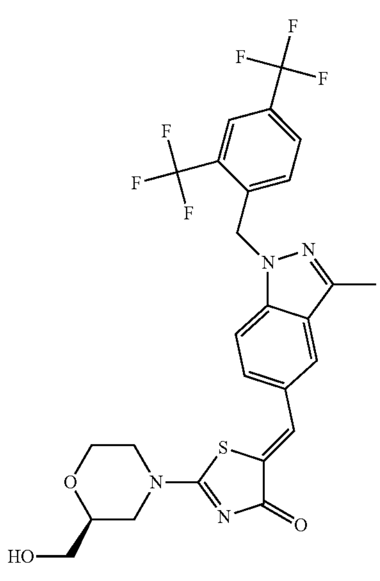 [SMILES: Cc1nn(Cc2ccc(C(F)(F)F)cc2C(F)(F)F)c2ccc(/C=C3\SC(N4CCO[C@H](CO)C4)=NC3=O)cc12] | 180 | 5-[1-(2,4-Bis-trifluoromethyl-benzyl)-3-methyl-1H-indazol-5-ylmethylene]-2-(2-(S)-hydroxymethyl-morpholin-4-yl)-thiazol-4-one |

| STRUCTURE | COMPOUND # | NAME |
|---|---|---|
| 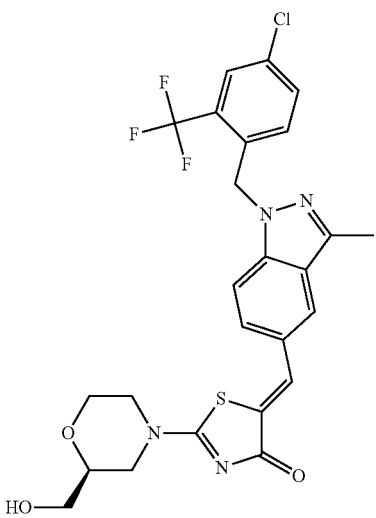 [SMILES: Cc1nn(Cc2ccc(Cl)cc2C(F)(F)F)c2ccc(/C=C3\SC(N4CCO[C@H](CO)C4)=NC3=O)cc12] | 181 | 5-[1-(4-Chloro-2-trifluoromethyl-benzyl)-3-methyl-1H-indazol-5-ylmethylene]-2-(2-(S)-hydroxymethyl-morpholin-4-yl)-thiazol-4-one |
| 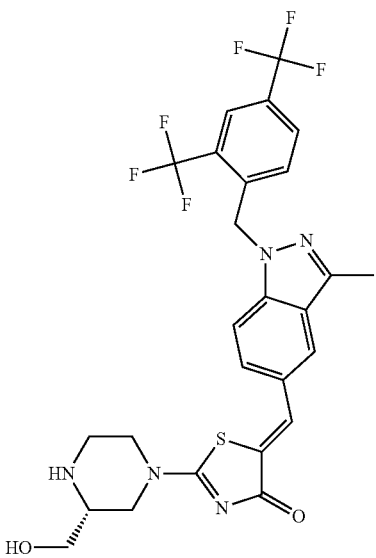 [SMILES: Cc1nn(Cc2ccc(C(F)(F)F)cc2C(F)(F)F)c2ccc(/C=C3\SC(N4CCN[C@@H](CO)C4)=NC3=O)cc12] | 182 | 5-[1-(2,4-Bis-trifluoromethyl-benzyl)-3-methyl-1H-indazol-5-ylmethylene]-2-(3-(R)-hydroxymethyl-piperazin-1-yl)-thiazol-4-one |

| STRUCTURE | COMPOUND # | NAME |
|---|---|---|
| 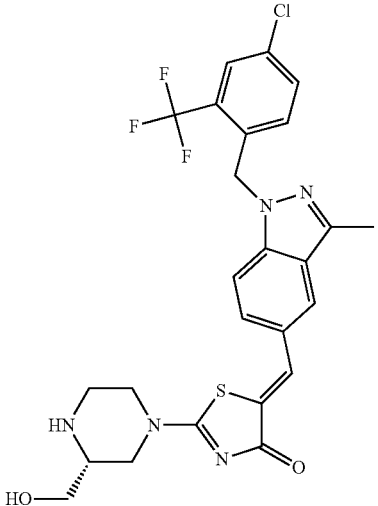 [SMILES: Cc1nn(Cc2ccc(Cl)cc2C(F)(F)F)c2ccc(/C=C3\SC(N4CCN[C@@H](CO)C4)=NC3=O)cc12] | 183 | 5-[1-(4-Chloro-2-trifluoromethyl-benzyl)-3-methyl-1H-indazol-5-ylmethylene]-2-(3-(R)-hydroxymethyl-piperazin-1-yl)-thiazol-4-one |
| 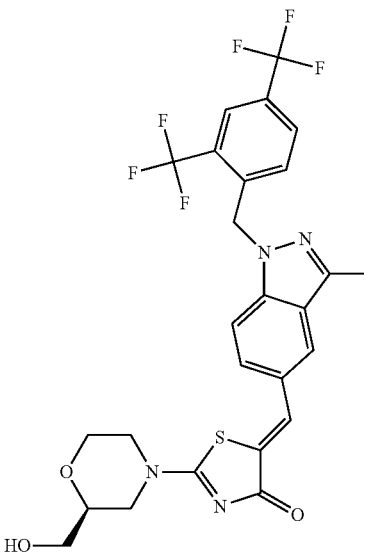 | 184 | 5-[1-(2,4-Bis-trifluoromethyl-benzyl)-3-chloro-1H-indazol-5-ylmethylene]-2-(2-(S)-hydroxymethyl-morpholin-4-yl)-thiazol-4-one |
| 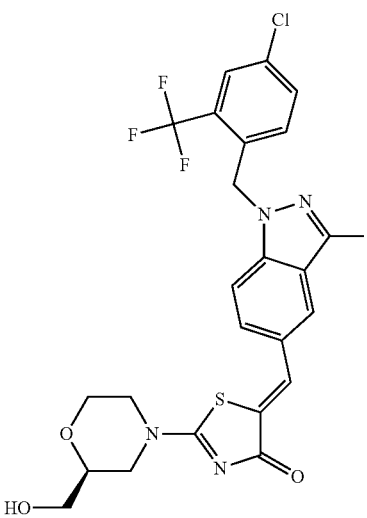 | 185 | 5-[3-Chloro-1-(4-chloro-2-trifluoromethyl-benzyl)-1H-indazol-5-ylmethylene]-2-(2-(S)-hydroxymethyl-morpholin-4-yl)-thiazol-4-one |

| STRUCTURE | COMPOUND # | NAME |
|---|---|---|
| 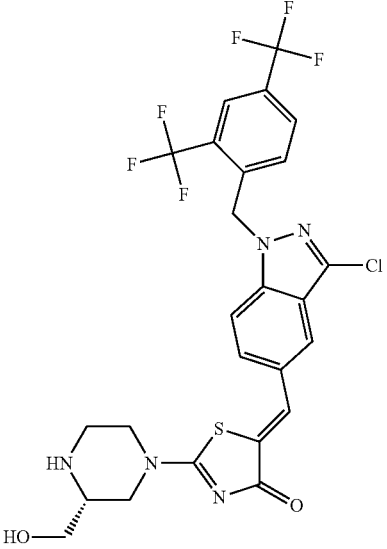 [SMILES: O=C1N=C(N2CCN[C@@H](CO)C2)S/C1=C\c1ccc2c(c1)c(Cl)nn2Cc1ccc(C(F)(F)F)cc1C(F)(F)F] | 186 | 5-[1-(2,4-Bis-trifluoromethyl-benzyl)-3-chloro-1H-indazol-5-ylmethylene]-2-(3-(R)-hydroxymethyl-piperazin-1-yl)-thiazol-4-one |
| 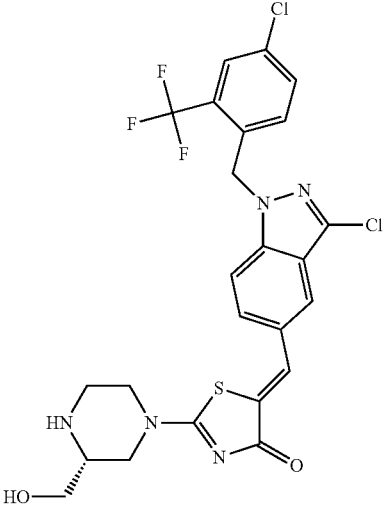 [SMILES: O=C1N=C(N2CCN[C@@H](CO)C2)S/C1=C\c1ccc2c(c1)c(Cl)nn2Cc1ccc(Cl)cc1C(F)(F)F] | 187 | 5-[3-Chloro-1-(4-chloro-2-trifluoromethyl-benzyl)-1H-indazol-5-ylmethylene]-2-(3-(R)-hydroxymethyl-piperazin-1-yl)-thiazol-4-one |
| 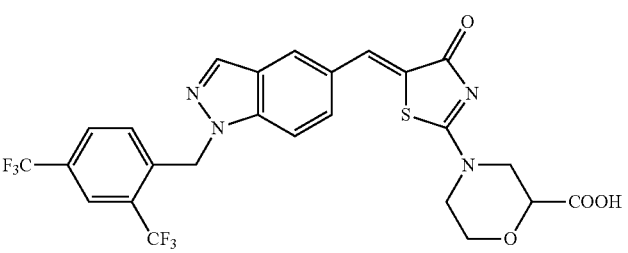 [SMILES: O=C1N=C(N2CCOC(C(=O)O)C2)S/C1=C\c1ccc2c(cnn2Cc2ccc(C(F)(F)F)cc2C(F)(F)F)c1] | 188 | 4-[5-({1-[2,4-Bis(trifluoromethyl)benzyl]-1H-indazol-5-yl}methylidene)-4-oxo-4,5-dihydro-1,3-thiazol-2-yl]morpholine-2-carboxylic acid |

TABLE I-continued

| STRUCTURE | COMPOUND # | NAME |
|---|---|---|
| 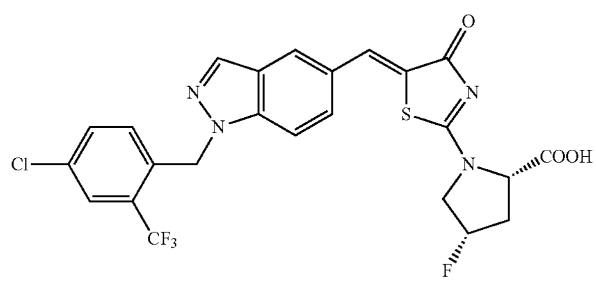 [SMILES: O=C1N=C(N2C[C@@H](F)C[C@H]2C(=O)O)S/C1=C\c1ccc2c(cnn2Cc2ccc(Cl)cc2C(F)(F)F)c1] | 189 | 1-[5-({1-[4-Chloro-2-(trifluoromethyl)benzyl]-1H-indazol-5-yl}methylidene)-4-oxo-4,5-dihydro-1,3-thiazol-2-yl]-4-(S)-fluoro-L-proline |
| 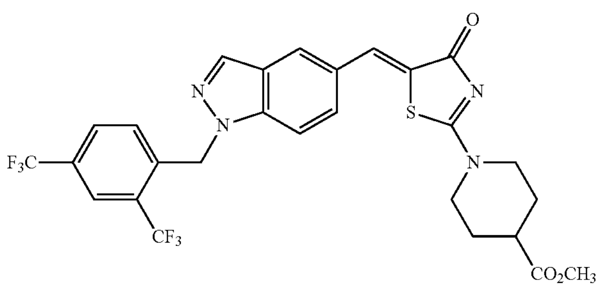 [SMILES: COC(=O)C1CCN(C2=NC(=O)/C(=C/c3ccc4c(cnn4Cc4ccc(C(F)(F)F)cc4C(F)(F)F)c3)S2)CC1] | 190 | Methyl 1-[5-({1-[2,4-bis(trifluoromethyl)benzyl]-1H-indazol-5-yl}methylidene)-4-oxo-4,5-dihydro-1,3-thiazol-2-yl]piperidine-4-carboxylate |
| 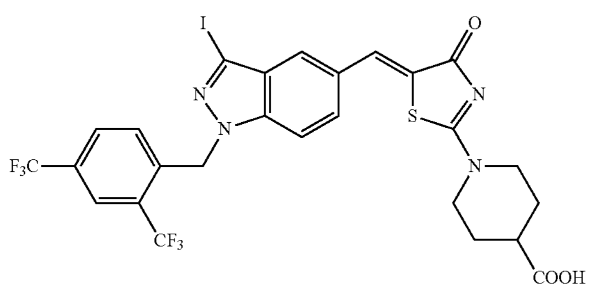 [SMILES: O=C1N=C(N2CCC(C(=O)O)CC2)S/C1=C\c1ccc2c(c1)c(I)nn2Cc1ccc(C(F)(F)F)cc1C(F)(F)F] | 191 | 1-[5-({1-[2,4-Bis(trifluoromethyl)benzyl]-3-iodo-1H-indazol-5-yl}methylidene)-4-oxo-4,5-dihydro-1,3-thiazol-2-yl]piperidine-4-carboxylic acid |
| 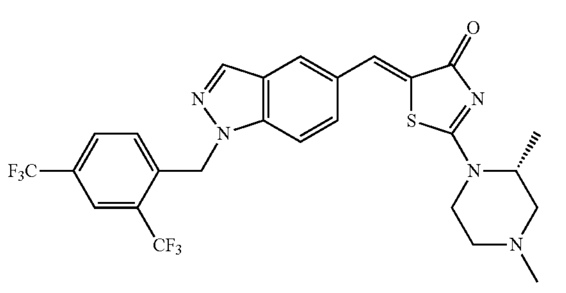 [SMILES: C[C@@H]1CN(C)CCN1C1=NC(=O)/C(=C/c2ccc3c(cnn3Cc3ccc(C(F)(F)F)cc3C(F)(F)F)c2)S1] | 192 | 5-({1-[2,4-Bis(trifluoromethyl)benzyl]-1H-indazol-5-yl}methylidene)-2-(2-(R)-4,dimethylpiperazin-1-yl)-1,3-thiazol-4(5)-one |
| 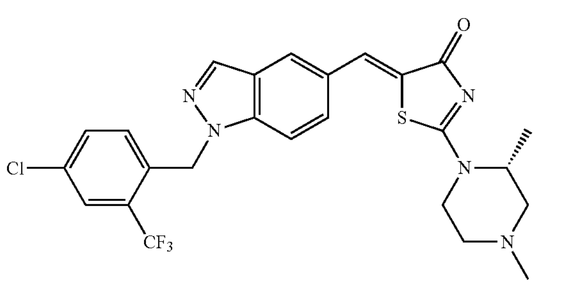 [SMILES: C[C@@H]1CN(C)CCN1C1=NC(=O)/C(=C/c2ccc3c(cnn3Cc3ccc(Cl)cc3C(F)(F)F)c2)S1] | 193 | 5-({1-[4-Chloro-2-(trifluoromethyl)benzyl]-1H-indazol-5-yl}methylidene)-2-(2-(R),4-dimethylpiperazin-1-yl)-1,3-thiazol-4(5H)-one |

TABLE I-continued

| STRUCTURE | COMPOUND # | NAME |
|---|---|---|
| 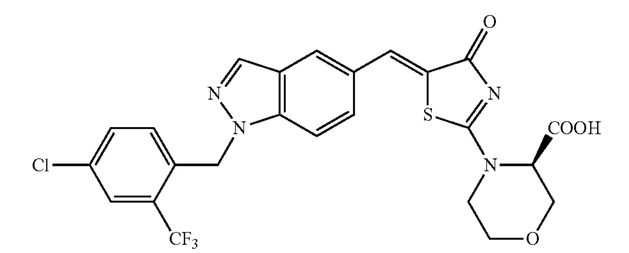 [SMILES: O=C1N=C(N2CCOC[C@@H]2C(=O)O)S/C1=C\c1ccc2c(cnn2Cc2ccc(Cl)cc2C(F)(F)F)c1] | 194 | 4-[5-({1-[4-Chloro-2-(trifluoromethyl)benzyl]-1H-indazol-5-yl}methylidene)-4-oxo-4,5-dihydro-1,3-thiazol-2-yl]morpholine-3-(R)-carboxylic acid |
| 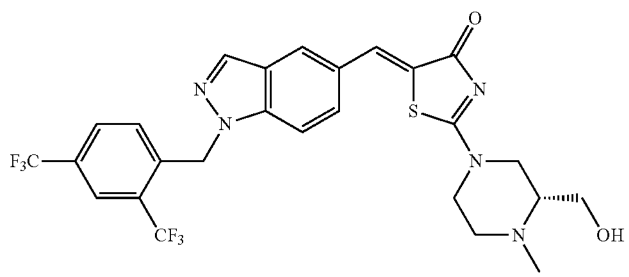 [SMILES: CN1CCN(C2=NC(=O)/C(=C/c3ccc4c(cnn4Cc4ccc(C(F)(F)F)cc4C(F)(F)F)c3)S2)C[C@@H]1CO] | 195 | 5-({1-[2,4-Bis(trifluoromethyl)benzyl]-1H-indazol-5-yl}methylidene)-2-[3-(R)-(hydroxymethyl)-4-methylpiperazin-1-yl]-1,3-thiazol-4(5H)-one |
| 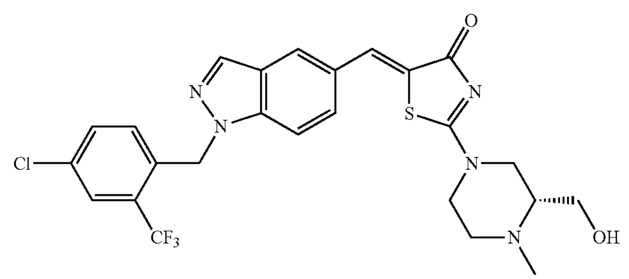 [SMILES: CN1CCN(C2=NC(=O)/C(=C/c3ccc4c(cnn4Cc4ccc(Cl)cc4C(F)(F)F)c3)S2)C[C@@H]1CO] | 196 | 5-({1-[4-Chloro-2-(trifluoromethyl)benzyl}-1H-indazol-5-yl}methylidene)-2-[3-(R)-(hydroxymethyl)-4-methylpiperazin-1-yl]-1,3-thiazol-4(5H)-one |
| 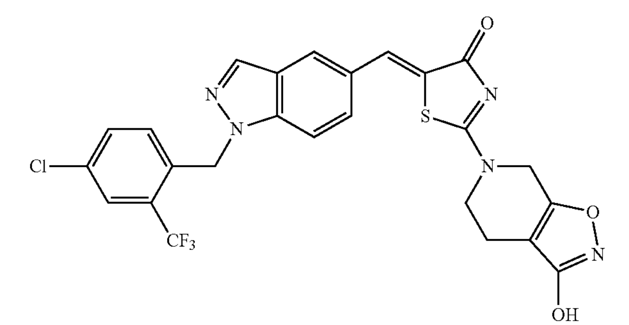 [SMILES: O=C1N=C(N2CCc3c(O)noc3C2)S/C1=C\c1ccc2c(cnn2Cc2ccc(Cl)cc2C(F)(F)F)c1] | 197 | 5-({1-[4-Chloro-2-(trifluoromethyl)benzyl]-1H-indazol-5-yl}methylidene)-2-(3-hydroxy-4,7-dihydroisoxazolo[5,4-c]pyridin-6(5H)-yl)-1,3-thiazol-4(5H)-one |
| 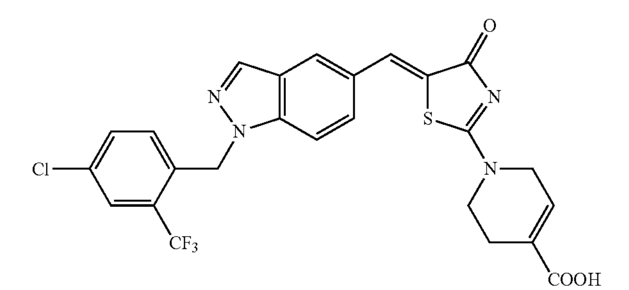 [SMILES: O=C(O)C1=CCN(C2=NC(=O)/C(=C/c3ccc4c(cnn4Cc4ccc(Cl)cc4C(F)(F)F)c3)S2)CC1] | 198 | 1-[5-({1-[4-Chloro-2-(trifluoromethyl)benzyl]-1H-indazol-5-yl}methylidene)-4-oxo-4,5-dihydro-1,3-thiazol-2-yl]-1,2,3,6-tetrahydropyridine-4-carboxylic acid |

TABLE I-continued

| STRUCTURE | COMPOUND # | NAME |
|---|---|---|
| 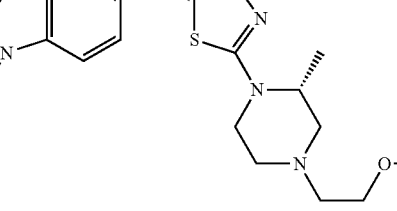 | 199 | 5-({1-[4-Chloro-2-(trifluoromethyl)benzyl]-1H-indazol-5-yl}methylidene)-2-[4-(2-methoxyethyl)-2-(R)-methylpiperazin-1-yl]-1,3-thiazol-4(5)-one |
| 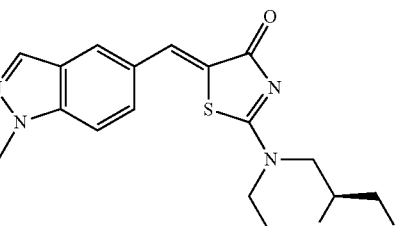 | 200 | 5-({1-[2,4-Bis(trifluoromethyl)benzyl]-1H-indazol-5-yl}methylidene)-2-[3-(S)-(hydroxymethyl)piperazin-1-yl]-1,3-thiazol-4(5H)-one |
| 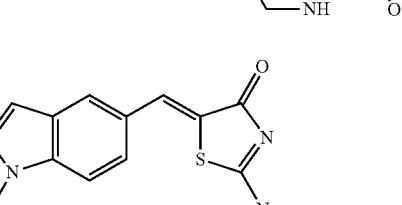 | 201 | 2-[2-(Aminomethyl)morpholin-4-yl]-5-({1-[2,4-bis(trifluoromethyl)benzyl]-1H-indazol-5-yl}methylidene)-1,3-thiazol-4(5H)-one |
| 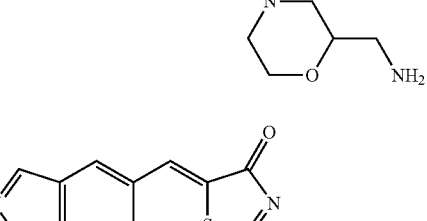 | 202 | 5-({1-[2,4-Bis(trifluoromethyl)benzyl]-1H-indazol-5-yl}methylidene)-2-[3-(2,6-cis-dimethylmorpholin-4-yl)azetidin-1-yl]-1,3-thiazol-4(5H)-one |
| 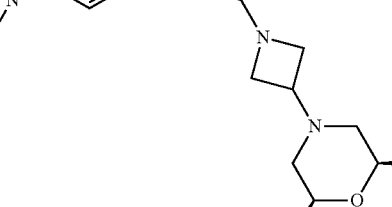 | 203 | 5-({1-[4-Chloro-2-(trifluoromethyl)benzyl]-1H-indazol-5-yl}methylidene)-2-[3-(2,6-cis-dimethylmorpholin-4-yl)azetidin-1-yl]-1,3-thiazol-4(5H)-one |

TABLE I-continued

| STRUCTURE | COMPOUND # | NAME |
|---|---|---|
| 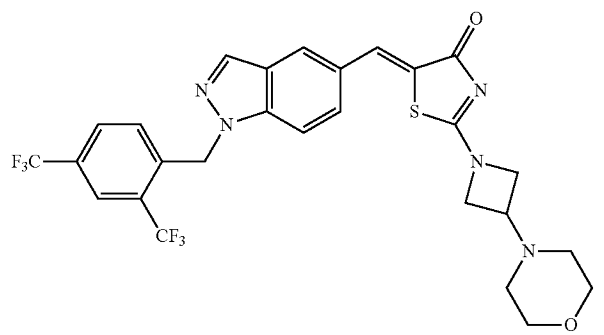 [SMILES: O=C1N=C(N2CC(N3CCOCC3)C2)S/C1=C\c1ccc2c(cnn2Cc2ccc(C(F)(F)F)cc2C(F)(F)F)c1] | 204 | 5-({1-[2,4-Bis(trifluoromethyl)benzyl]-1H-indazol-5-yl}methylidene)-2-(3-morpholin-4-ylazetidin-1-yl)-1,3-thiazol-4(5H)-one |
| 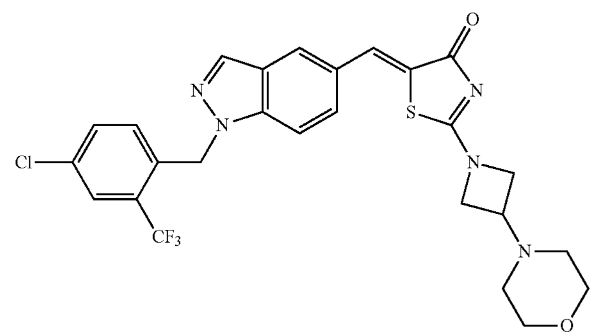 [SMILES: O=C1N=C(N2CC(N3CCOCC3)C2)S/C1=C\c1ccc2c(cnn2Cc2ccc(Cl)cc2C(F)(F)F)c1] | 205 | 5-({1-[4-Chloro-2-(trifluoromethyl)benzyl]-1H-indazol-5-yl}methylidene)-2-(3-morpholin-4-ylazetidin-1-yl)-1,3-thiazol-4(5H)-one |
| 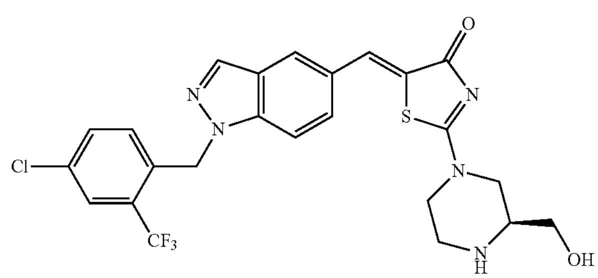 [SMILES: O=C1N=C(N2CCN[C@H](CO)C2)S/C1=C\c1ccc2c(cnn2Cc2ccc(Cl)cc2C(F)(F)F)c1] | 206 | 5-({1-[4-Chloro-2-(trifluoromethyl)benzyl]-1H-indazol-5-yl}methylidene)-2-[3-(S)-(hydroxymethyl)piperazin-1-yl]-1,3-thiazol-4(5H)-one |
| 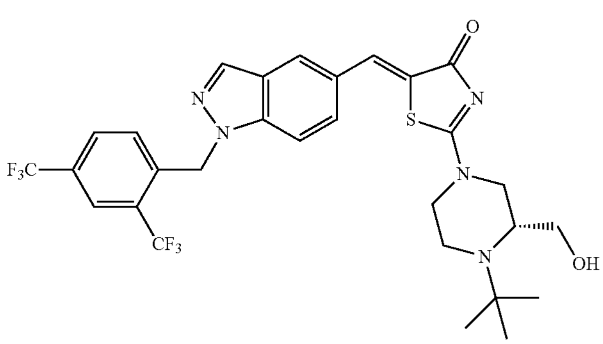 [SMILES: CC(C)(C)N1CCN(C2=NC(=O)/C(=C/c3ccc4c(cnn4Cc4ccc(C(F)(F)F)cc4C(F)(F)F)c3)S2)C[C@@H]1CO] | 207 | 5-({1-[2,4-Bis(trifluoromethyl)benzyl]-1H-indazol-5-yl}methylidene)-2-[4-tert-butyl-3-(R)-(hydroxymethyl)piperazin-1-yl]-1,3-thiazol-4(5H)-one |
| 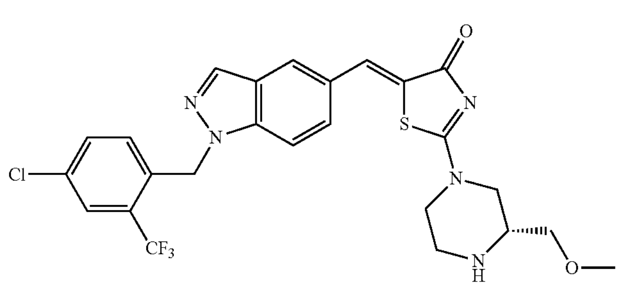 [SMILES: COC[C@H]1CN(C2=NC(=O)/C(=C/c3ccc4c(cnn4Cc4ccc(Cl)cc4C(F)(F)F)c3)S2)CCN1] | 208 | 5-({1-[4-Chloro-2-(trifluoromethyl)benzyl]-1H-indazol-5-yl}methylidene)-2-[3-(R)-(methoxymethyl)piperazin-1-yl]-1,3-thiazol-4(5H)-one |

TABLE I-continued

| STRUCTURE | COMPOUND # | NAME |
|---|---|---|
| 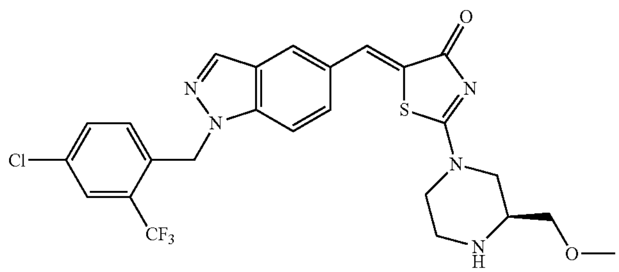 [SMILES: COC[C@@H]1CN(C2=NC(=O)/C(=C/c3ccc4c(cnn4Cc4ccc(Cl)cc4C(F)(F)F)c3)S2)CCN1] | 209 | 5-({1-[4-Chloro-2-(trifluoromethyl)benzyl]-1H-indazol-5-yl}methylidene)-2-[3-(S)-(methoxymethyl)piperazin-1-yl]-1,3-thiazol-4(5H)-one |
| 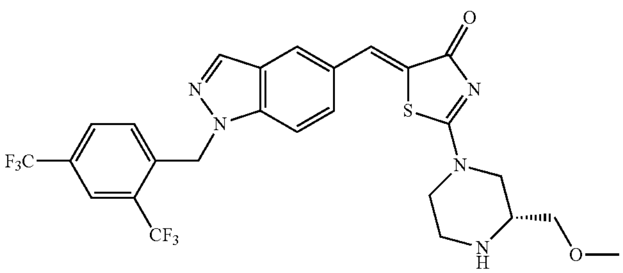 [SMILES: COC[C@H]1CN(C2=NC(=O)/C(=C/c3ccc4c(cnn4Cc4ccc(C(F)(F)F)cc4C(F)(F)F)c3)S2)CCN1] | 210 | 5-({1-[2,4-Bis(trifluoromethyl)benzyl]-1H-indazol-5-yl}methylidene)-2-[3-(R)-(methoxymethyl)piperazin-1-yl]-1,3-thiazol-4(5H)-one |
| 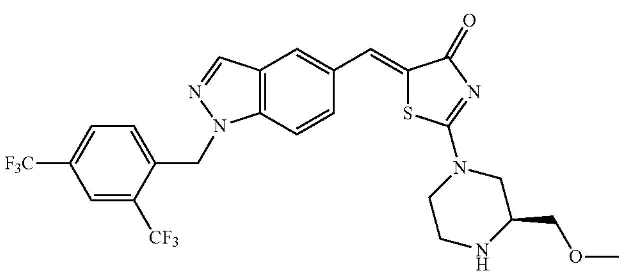 [SMILES: COC[C@@H]1CN(C2=NC(=O)/C(=C/c3ccc4c(cnn4Cc4ccc(C(F)(F)F)cc4C(F)(F)F)c3)S2)CCN1] | 211 | 5-({1-[2,4-Bis(trifluoromethyl)benzyl]-1H-indazol-5-yl}methylidene)-2-[3-(S)-(methoxymethyl)piperazin-1-yl]-1,3-thiazol-4(5H)-one |
| 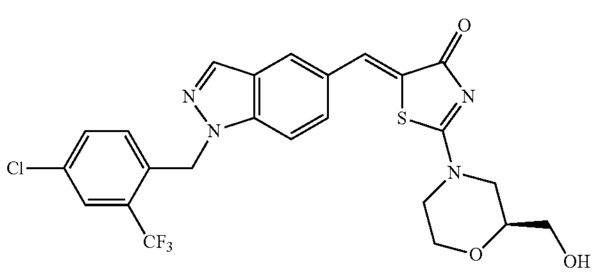 [SMILES: O=C1N=C(N2CCO[C@H](CO)C2)S/C1=C\c1ccc2c(cnn2Cc2ccc(Cl)cc2C(F)(F)F)c1] | 212 | 5-({1-[4-Chloro-2-(trifluoromethy)benzyl]-1H-indazol-5-yl}methylidene)-2-[2-(S)-(hydroxymethyl)morpholin-4-yl]-1,3-thiazol-4(5H)-one |
| 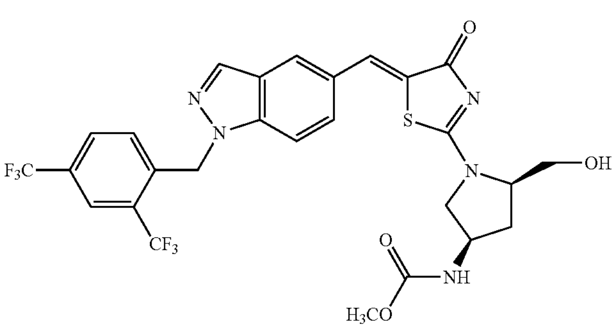 [SMILES: COC(=O)N[C@@H]1C[C@H](CO)N(C2=NC(=O)/C(=C/c3ccc4c(cnn4Cc4ccc(C(F)(F)F)cc4C(F)(F)F)c3)S2)C1] | 213 | Methyl {1-[5-({1-[2,4-bis(trifluoromethyl)benzyl]-1H-indazol-5-yl}methylidene)-4-oxo-4,5-dihydro-1,3-thiazol-2-yl]-5-(R)-(hydroxymethyl)pyrrolidin-3-(R)-yl}carbamate |

TABLE I-continued

| STRUCTURE | COMPOUND # | NAME |
|---|---|---|
| 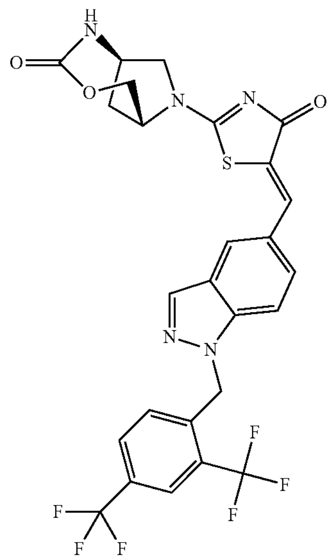 [SMILES: O=C1N[C@@H]2C[C@H](CO1)N(C1=NC(=O)/C(=C/c3ccc4c(cnn4Cc4ccc(C(F)(F)F)cc4C(F)(F)F)c3)S1)C2] | 214 | (1R,6R)-7-[5-({1-[2,4-Bis(trifluoromethyl)benzyl]-1H-indazol-5-yl}methylidene)-4-oxo-4,5-dihydro-1,3-thiazol-2-yl]-4-oxa-2,7-diazabicyclo[4.2.1]nonan-3-one |
| 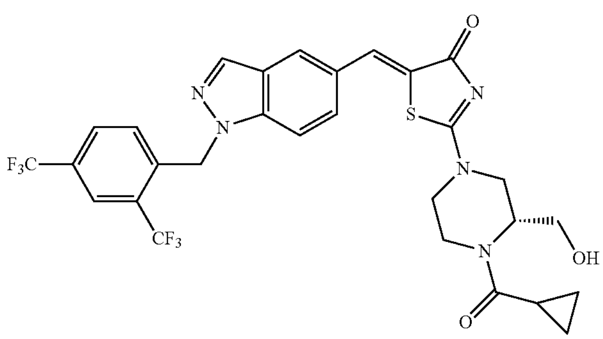 [SMILES: O=C1N=C(N2CCN(C(=O)C3CC3)[C@@H](CO)C2)S/C1=C\c1ccc2c(cnn2Cc2ccc(C(F)(F)F)cc2C(F)(F)F)c1] | 215 | 5-({1-[2,4-Bis(trifluoromethyl)benzyl]-1H-indazol-5-yl}methylidene)-2-[4-(cyclopropylcarbonyl)-3-(R)-(hydroxymethyl)piperazin-1-yl]-1,3-thiazol-4(5H)-one |
| 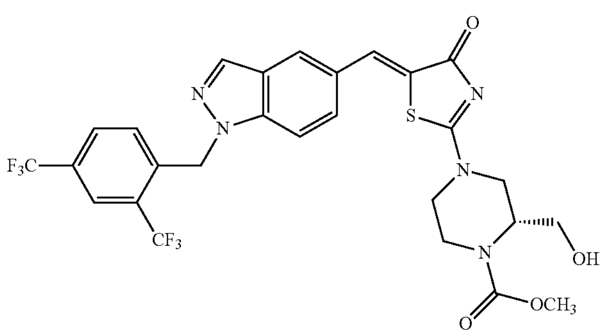 [SMILES: COC(=O)N1CCN(C2=NC(=O)/C(=C/c3ccc4c(cnn4Cc4ccc(C(F)(F)F)cc4C(F)(F)F)c3)S2)C[C@@H]1CO] | 216 | Methyl-4-[5-({1-[2,4-bis(trifluoromethyl)benzyl]-1H-indazol-5-yl}methylidene)-4-oxo-4,5-dihydro-1,3-thiazol-2-yl]-2-(R)-(hydroxymethyl)piperazine-1-carboxylate |
| 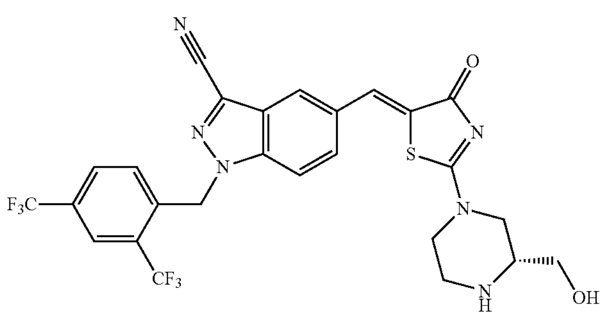 [SMILES: N#Cc1nn(Cc2ccc(C(F)(F)F)cc2C(F)(F)F)c2ccc(/C=C3\SC(N4CCN[C@@H](CO)C4)=NC3=O)cc12] | 217 | 1-[2,4-Bis(trifluoromethyl)benzyl]-5-({2-[3-(R)-(hydroxymethyl)piperazin-1-yl]-4-oxo-1,3-thiazol-5(4H)-ylidene}methyl)-1H-indazole-3-carbonitrile |

TABLE I-continued

| STRUCTURE | COMPOUND # | NAME |
|---|---|---|
| 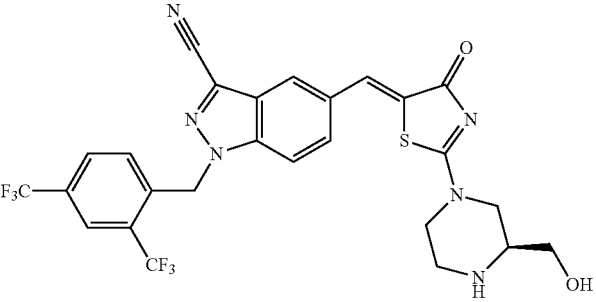 [SMILES: N#Cc1nn(Cc2ccc(C(F)(F)F)cc2C(F)(F)F)c2ccc(/C=C3\SC(N4CCN[C@H](CO)C4)=NC3=O)cc12] | 218 | 1-[2,4-Bis(trifluoromethyl)benzyl]-5-({2-[3-(S)-(hydroxymethyl)piperazin-1-yl]-4-oxo-1,3-thiazol-5(4H)-ylidene}methyl)-1H-indazole-3-carbonitrile |
| 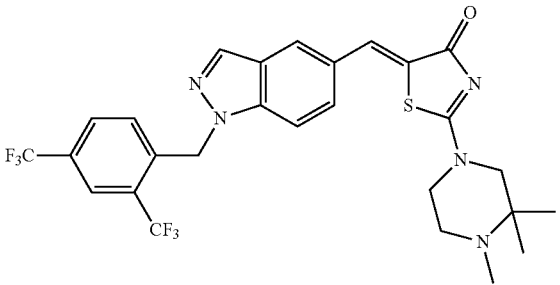 [SMILES: CN1CCN(C2=NC(=O)/C(=C/c3ccc4c(cnn4Cc4ccc(C(F)(F)F)cc4C(F)(F)F)c3)S2)CC1(C)C] | 219 | 5-({1-[2,4-Bis(trifluoromethyl)benzyl]-1H-indazol-5-yl}methylidene)-2-(3,3,4-trimethylpiperazin-1-yl)-1,3-thiazol-4(5H)-one |
| 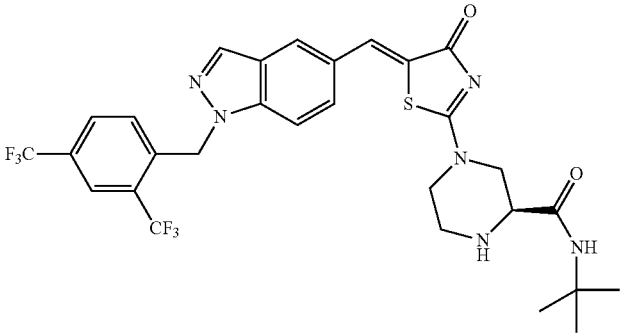 [SMILES: CC(C)(C)NC(=O)[C@@H]1CN(C2=NC(=O)/C(=C/c3ccc4c(cnn4Cc4ccc(C(F)(F)F)cc4C(F)(F)F)c3)S2)CCN1] | 220 | 4-[5-({1-[2,4-Bis(trifluoromethyl)benzyl]-1H-indazol-5-yl}methylidene)-4-oxo-4,5-dihydro-1,3-thiazol-2-yl]-N-tert-butylpiperazine-2-(S)-carboxamide |
| 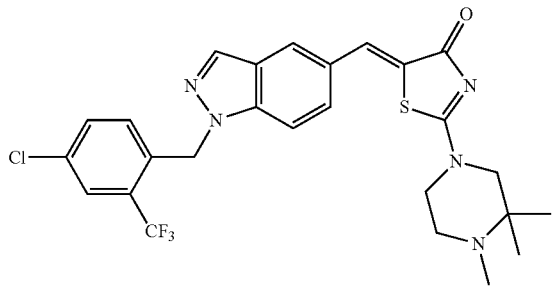 [SMILES: CN1CCN(C2=NC(=O)/C(=C/c3ccc4c(cnn4Cc4ccc(Cl)cc4C(F)(F)F)c3)S2)CC1(C)C] | 221 | 5-({1-[4-Chloro-2-(trifluoromethyl)benzyl]-1H-indazol-5-yl}methylidene)-2-(3,3,4-trimethylpiperazin-1-yl)-1,3-thiazol-4(5H)-one |
| 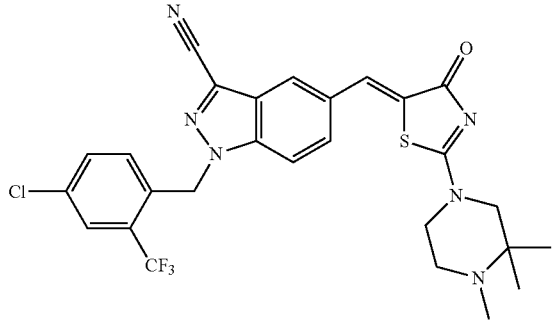 [SMILES: CN1CCN(C2=NC(=O)/C(=C/c3ccc4c(c3)c(C#N)nn4Cc3ccc(Cl)cc3C(F)(F)F)S2)CC1(C)C] | 222 | 1-[4-Chloro-2-(trifluoromethyl)benzyl]-5-{[4-oxo-2-(3,3,4-trimethylpiperazin-1-yl)-1,3-thiazol-5(4H)-ylidene]methyl}-1H-indazole-3-carbonitrile |

| STRUCTURE | COMPOUND # | NAME |
|---|---|---|
| 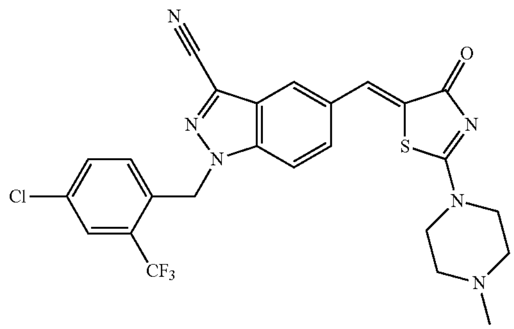 [SMILES: CN1CCN(C2=NC(=O)/C(=C/c3ccc4c(c3)c(C#N)nn4Cc3ccc(Cl)cc3C(F)(F)F)S2)CC1] | 223 | 1-[4-Chloro-2-(trifluoromethyl)benzyl]-5-{[2-(4-methylpiperazin-1-yl)-4-oxo-1,3-thiazol-5(4H)-ylidene]methyl}-1H-indazole-3-carbonitrile |
| 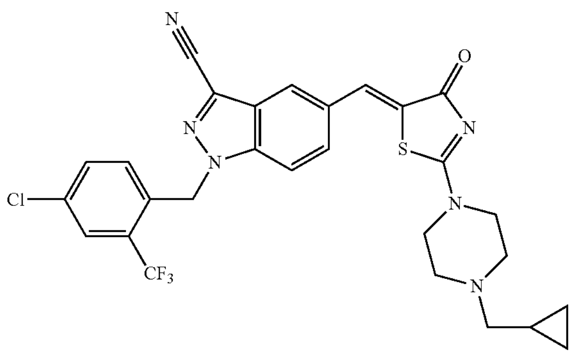 [SMILES: N#Cc1nn(Cc2ccc(Cl)cc2C(F)(F)F)c2ccc(/C=C3\SC(N4CCN(CC5CC5)CC4)=NC3=O)cc12] | 224 | 1-[4-Chloro-2-(trifluoromethyl)benzyl]-5-({2-[4-(cyclopropylmethyl)piperazin-1-yl]-4-oxo-1,3-thiazol-5(4H)-ylidene}methyl)-1H-indazole-3-carbonitrile |
| 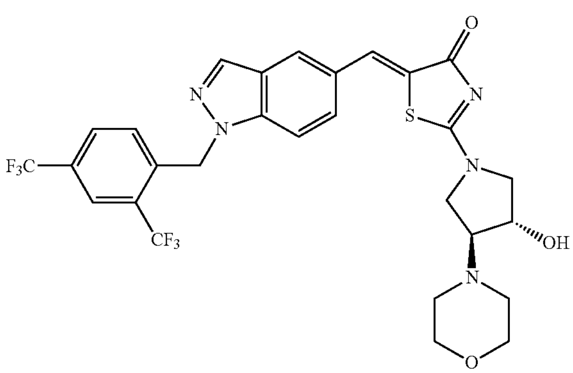 [SMILES: O=C1N=C(N2C[C@H](O)[C@@H](N3CCOCC3)C2)S/C1=C\c1ccc2c(cnn2Cc2ccc(C(F)(F)F)cc2C(F)(F)F)c1] | 225 | 5-({1-[2,4-Bis(trifluoromethyl)benzyl]-1H-indazol-5-yl}methylidene)-2-[(3S,4S)-3-hydroxy-4-morpholin-4-ylpyrrolidin-1-yl]-1,3-thiazol-4(5H)-one |
| 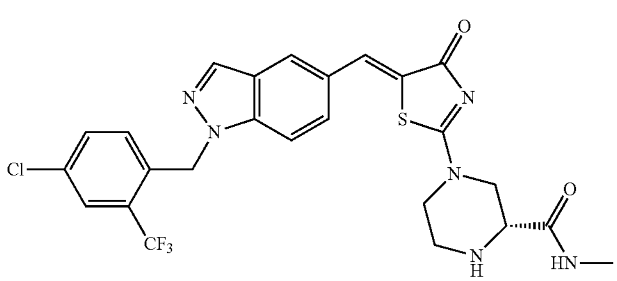 [SMILES: CNC(=O)[C@H]1CN(C2=NC(=O)/C(=C/c3ccc4c(cnn4Cc4ccc(Cl)cc4C(F)(F)F)c3)S2)CCN1] | 226 | (2R)-4-[5-({1-[4-Chloro-2-(trifluoromethyl)benzyl]-1H-indazol-5-yl}methylidene)-4-oxo-4,5-dihydro-1,3-thiazol-2-yl]-N-methylpiperazine-2-carboxamide |

TABLE I-continued

| STRUCTURE | COMPOUND # | NAME |
|---|---|---|
| 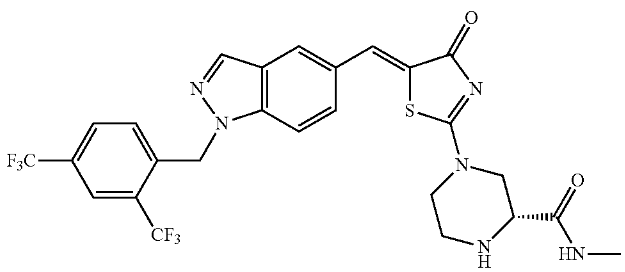 [SMILES: CNC(=O)[C@H]1CN(C2=NC(=O)/C(=C/c3ccc4c(cnn4Cc4ccc(C(F)(F)F)cc4C(F)(F)F)c3)S2)CCN1] | 227 | (2R)-4-[5-({1-[2,4-Bis(trifluoromethyl)benzyl]-1H-indazol-5-yl}methylidene)-4-oxo-4,5-dihydro-1,3-thiazol-2-yl]-N-methylpiperazine-2-carboxamide |
| 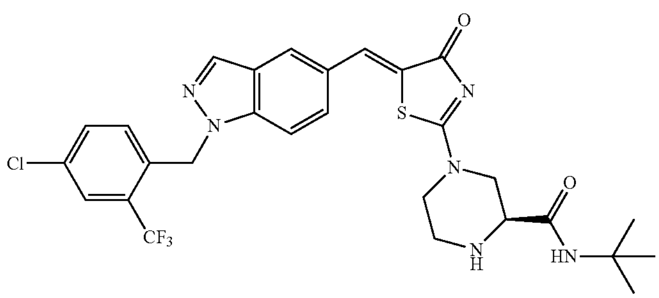 [SMILES: CC(C)(C)NC(=O)[C@@H]1CN(C2=NC(=O)/C(=C/c3ccc4c(cnn4Cc4ccc(Cl)cc4C(F)(F)F)c3)S2)CCN1] | 228 | (2S)-N-tert-Butyl-4-[5-({1-[4-chloro-2-(trifluoromethyl)benzyl]-1H-thiazol-5-yl}methylidene)-4-oxo-4,5-dihydro-1,3-thiazol-2-yl]piperazine-2-carboxamide |
| 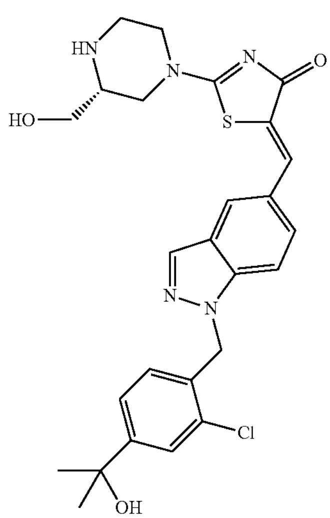 [SMILES: CC(C)(O)c1ccc(Cn2ncc3cc(/C=C4\SC(N5CCN[C@@H](CO)C5)=NC4=O)ccc32)c(Cl)c1] | 229 | 5-({1-[2-Chloro-4-(1-hydroxy-1-methylethyl)benzyl]-1H-indazol-5-yl}methylidene)-2-[3-(R)-(hydroxymethyl)piperazin-1-yl]-1,3-thiazol-4(5H)-one |

TABLE I-continued

| STRUCTURE | COMPOUND # | NAME |
|---|---|---|
| 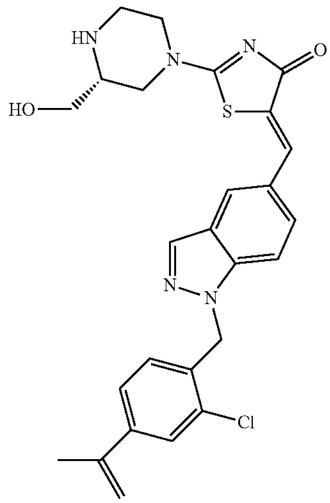 [SMILES: C=C(C)c1ccc(Cn2ncc3cc(/C=C4\SC(N5CCN[C@@H](CO)C5)=NC4=O)ccc32)c(Cl)c1] | 230 | 5-({1-[2-Chloro-4-(1-methylethenyl)benzyl]-1H-indazol-5-yl}methylidene)-2-[3-(R)-(hydroxymethyl)piperazin-1-yl]-1,3-thiazol-4(5H)-one |
| 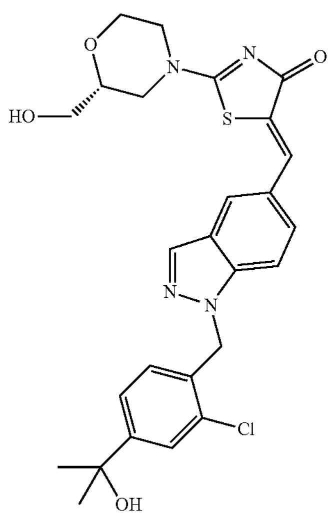 [SMILES: CC(C)(O)c1ccc(Cn2ncc3cc(/C=C4\SC(N5CCO[C@@H](CO)C5)=NC4=O)ccc32)c(Cl)c1] | 231 | 5-({1-[2-Chloro-4-(1-hydroxy-1-methylethyl)benzyl]-1H-indazol-5-yl}methylidene)-2-[2-(R)-(hydroxymethyl)morpholin-4-yl]-1,3-thiazol-4(5H)-one |
| 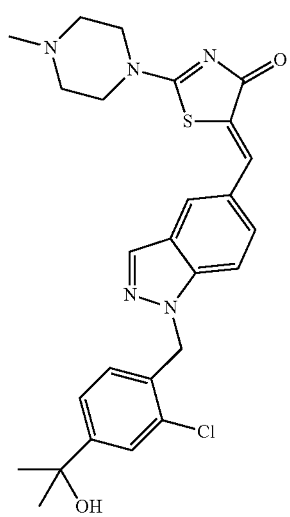 [SMILES: CN1CCN(C2=NC(=O)/C(=C/c3ccc4c(cnn4Cc4ccc(C(C)(C)O)cc4Cl)c3)S2)CC1] | 232 | 5-({1-[2-Chloro-4-(1-hydroxy-1-methylethyl)benzyl]-1H-indazol-5-yl}methylidene)-2-(4-methylpiperazin-1-yl)-1,3-thiazol-4(5H)-one |

TABLE I-continued

| STRUCTURE | COMPOUND # | NAME |
|---|---|---|
| 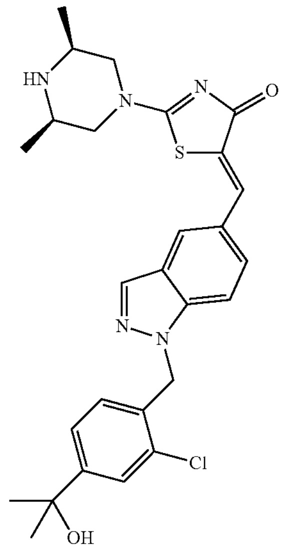 [SMILES: C[C@@H]1CN(C2=NC(=O)/C(=C/c3ccc4c(cnn4Cc4ccc(C(C)(C)O)cc4Cl)c3)S2)C[C@H](C)N1] | 233 | 5-({1-[2-Chloro-4-(1-hydroxy-1-methylethyl)benzyl]-1H-indazol-5-yl}methylidene)-2-(3,5-(cis)-dimethylpiperazin-1-yl)-1,3-thiazol-4(5H)-one |
| 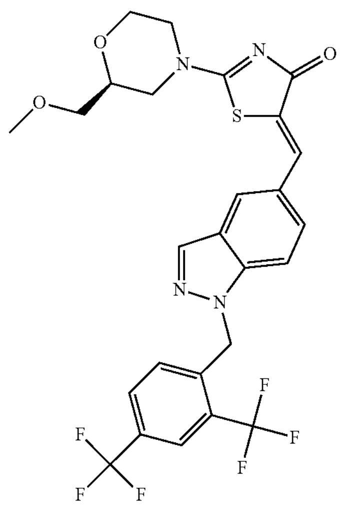 [SMILES: COC[C@@H]1CN(C2=NC(=O)/C(=C/c3ccc4c(cnn4Cc4ccc(C(F)(F)F)cc4C(F)(F)F)c3)S2)CCO1] | 234 | 5-({1-[2,4-Bis(trifluoromethyl)benzyl]-1H-indazol-5-yl}methylidene)-2-[2-(S)-(methoxymethyl)morpholin-4-yl]-1,3-thiazol-4(5H)-one |
| 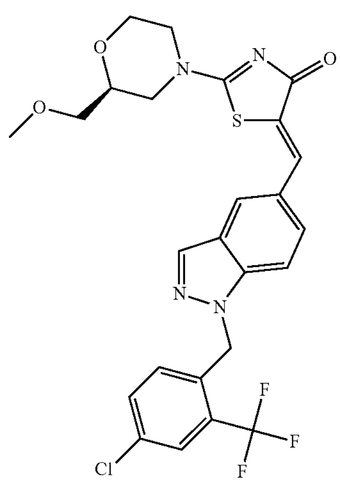 [SMILES: COC[C@@H]1CN(C2=NC(=O)/C(=C/c3ccc4c(cnn4Cc4ccc(Cl)cc4C(F)(F)F)c3)S2)CCO1] | 235 | 5-({1-[4-Chloro-2-(trifluoromethyl)benzyl]-1H-indazol-5-yl}methylidene)-2-[2-(S)-(methoxymethyl)morpholin-4-yl]-1,3-thiazol-4(5H)-one |

TABLE I-continued

| STRUCTURE | COMPOUND # | NAME |
|---|---|---|
| 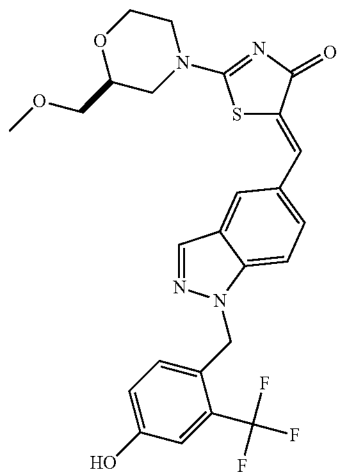 [SMILES: COC[C@@H]1CN(C2=NC(=O)/C(=C/c3ccc4c(cnn4Cc4ccc(O)cc4C(F)(F)F)c3)S2)CCO1] | 236 | 5-({1-[4-Hydroxy-2-(trifluoromethyl)benzyl]-1H-indazol-5-yl}methylidene)-2-[2(S)-(methoxymethyl)morpholin-4-yl]-1,3-thiazol-4(5H)-one |
| 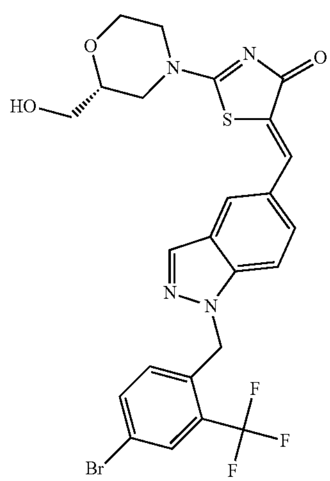 [SMILES: O=C1N=C(N2CCO[C@@H](CO)C2)S/C1=C\c1ccc2c(cnn2Cc2ccc(Br)cc2C(F)(F)F)c1] | 237 | 5-({1-[4-Bromo-2-(trifluoromethyl)benzyl]-1H-indazol-5-yl}methylidene)-2-[2-(R)-(hydroxymethyl)morpholin-4-yl]-1,3-thiazol-4(5H)-one |
| 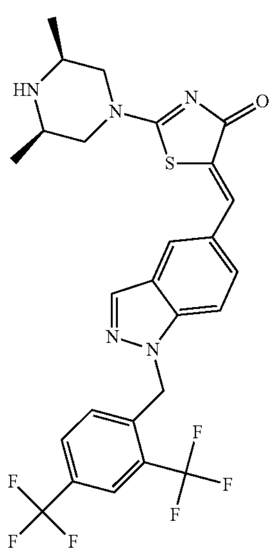 [SMILES: C[C@@H]1CN(C2=NC(=O)/C(=C/c3ccc4c(cnn4Cc4ccc(C(F)(F)F)cc4C(F)(F)F)c3)S2)C[C@H](C)N1] | 238 | 5-({1-[2,4-(trifluoromethyl)benzyl]-1H-indazol-5-yl}methylidene)-2-(3,5-(cis)-dimethylpiperazin-1-yl)-1,3-thiazol-4(5H)-one |

| STRUCTURE | COMPOUND # | NAME |
|---|---|---|
| 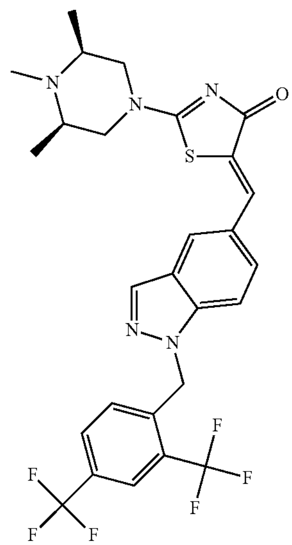 [SMILES: C[C@@H]1CN(C2=NC(=O)/C(=C/c3ccc4c(cnn4Cc4ccc(C(F)(F)F)cc4C(F)(F)F)c3)S2)C[C@H](C)N1C] | 239 | 5-({1-[2,4-Bis(trifluoromethyl)benzyl]-1H-indazol-5-yl}methylidene)-2-((3R,5S)-3,4,5-trimethylpiperazin-1-yl)-1,3-thiazol-4(5H)-one |
| 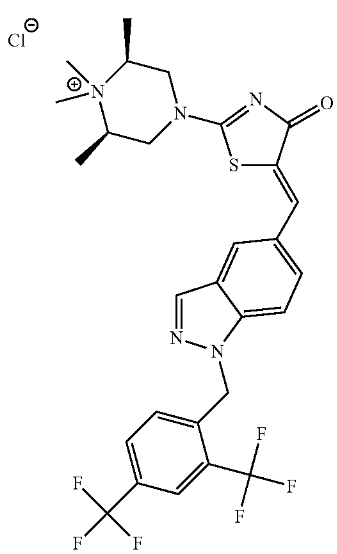 [SMILES: [Cl-] ; C[C@@H]1CN(C2=NC(=O)/C(=C/c3ccc4c(cnn4Cc4ccc(C(F)(F)F)cc4C(F)(F)F)c3)S2)C[C@H](C)[N+]1(C)C] | 240 | (2R,6S)-4-[5-({1-[2,4-Bis(trifluoromethyl)benzyl]-1H-indazol-5-yl}methylidene)-4-oxo-4,5-dihydro-1,3-thiazol-2-yl]-1,1,2,6-tetramethylpiperazin-1-ium chloride |

TABLE I-continued

| STRUCTURE | COMPOUND # | NAME |
|---|---|---|
| 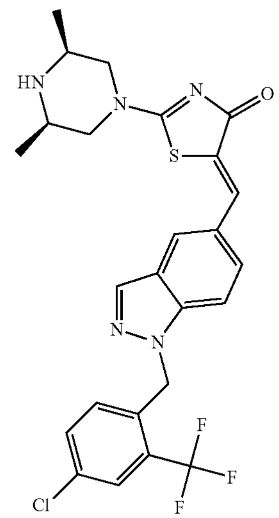 [SMILES: C[C@@H]1CN(C2=NC(=O)/C(=C/c3ccc4c(cnn4Cc4ccc(Cl)cc4C(F)(F)F)c3)S2)C[C@H](C)N1] | 241 | 5-({1-[4-Chloro-2-(trifluoromethyl)benzyl]-1H-indazol-5-yl}methylidene)-2-((3R,5S)-3,5-dimethylpiperazin-1-yl)-1,3-thiazol-4(5H)-one |
| 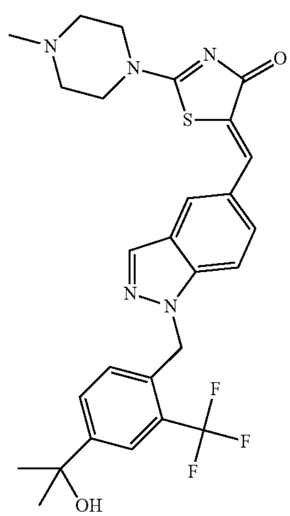 [SMILES: CN1CCN(C2=NC(=O)/C(=C/c3ccc4c(cnn4Cc4ccc(C(C)(C)O)cc4C(F)(F)F)c3)S2)CC1] | 242 | 5-({1-[4-(1-Hydroxy-1-methylethyl)-2-(trifluoromethyl)benzyl]-1H-indazol-5-yl}methylidene)-2-(4-methylpiperazin-1-yl)-1,3-thiazol-4(5H)-one |
| 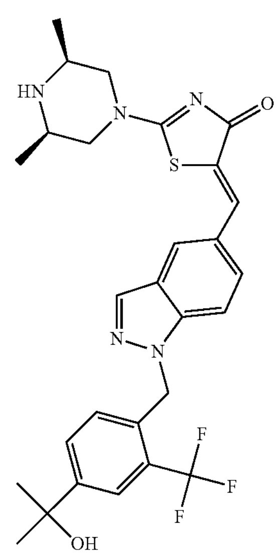 [SMILES: C[C@@H]1CN(C2=NC(=O)/C(=C/c3ccc4c(cnn4Cc4ccc(C(C)(C)O)cc4C(F)(F)F)c3)S2)C[C@H](C)N1] | 243 | 2-((3R,5S)-3,5-Dimethylpiperazin-1-yl)-5-({1-[4-(1-hydroxy-1-methylethyl)-2-(trifluoromethyl)benzyl]-1H-indazol-5-yl}methylidene)-1,3-thiazol-4(5H)-one |

TABLE I-continued

| STRUCTURE | COMPOUND # | NAME |
|---|---|---|
| 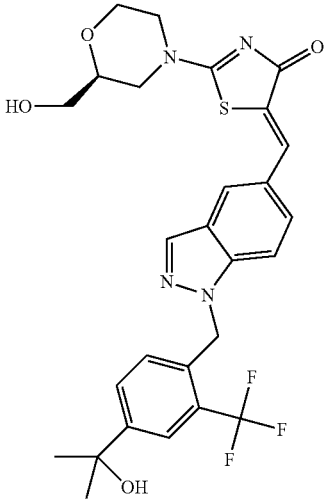 [SMILES: CC(C)(O)c1ccc(Cn2ncc3cc(/C=C4\SC(N5CCO[C@H](CO)C5)=NC4=O)ccc32)c(C(F)(F)F)c1] | 244 | 5-({1-[4-(1-Hydroxy-1-methylethyl)-2-(trifluoromethyl)benzyl]-1H-indazol-5-yl}methylidene)-2-[2-(S)-(hydroxymethyl)morpholin-4-yl]-1,3-thiazol-4(5H)-one |
| 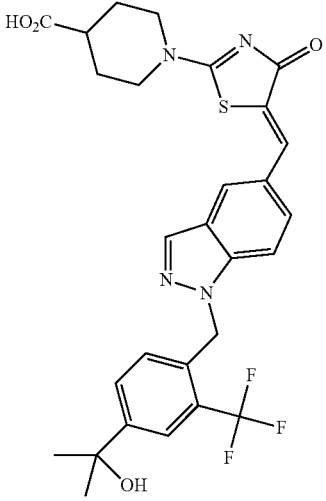 [SMILES: CC(C)(O)c1ccc(Cn2ncc3cc(/C=C4\SC(N5CCC(C(=O)O)CC5)=NC4=O)ccc32)c(C(F)(F)F)c1] | 245 | 4-[(5Z)-5-({1-[4-(1-Hydroxy-1-methylethyl)-2-(trifluoromethyl)benzyl]-1H-indazol-5-yl}methylidene)-4-oxo-4,5-dihydro-1,3-thiazol-2-yl]piperazine-1-carboxylic acid |
| 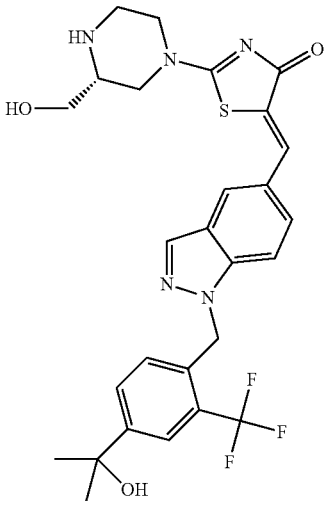 [SMILES: CC(C)(O)c1ccc(Cn2ncc3cc(/C=C4\SC(N5CCN[C@@H](CO)C5)=NC4=O)ccc32)c(C(F)(F)F)c1] | 246 | 5-({1-[4-(1-Hydroxy-1-methylethyl)-2-(trifluoromethyl)benzyl]-1H-indazol-5-yl}methylidene)-2-[3-(R)-(hydroxymethyl)piperazin-1-yl]-1,3-thiazol-4(5H)-one |

TABLE I-continued

| STRUCTURE | COMPOUND # | NAME |
|---|---|---|
| 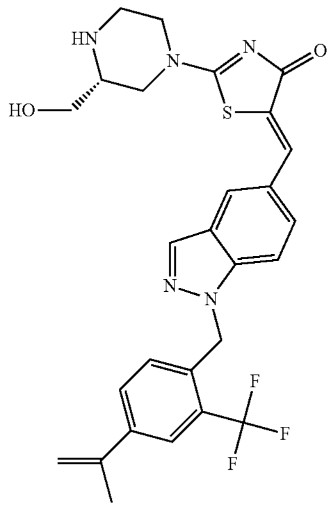 [SMILES: C=C(C)c1ccc(Cn2ncc3cc(/C=C4\SC(N5CCN[C@@H](CO)C5)=NC4=O)ccc32)c(C(F)(F)F)c1] | 247 | 2-[3-(R)-(Hydroxymethyl)piperazin-1-yl]-5-({1-[4-(1-methylethenyl)-2-(trifluoromethyl)benzyl]-1H-thiazol-5-yl}methylidene)-1,3-thiazol-4(5H)-one |
| 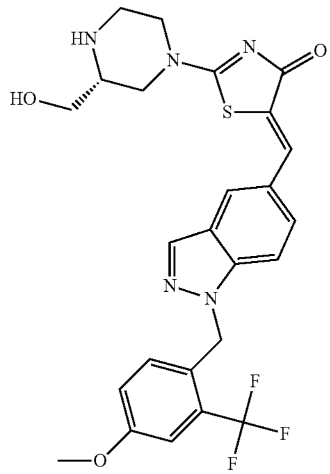 [SMILES: COc1ccc(Cn2ncc3cc(/C=C4\SC(N5CCN[C@@H](CO)C5)=NC4=O)ccc32)c(C(F)(F)F)c1] | 248 | 2-[3-(R)-(Hydroxymethyl)piperazin-1-yl]-5-({1-[4-methoxy-2-(trifluoromethyl)benzyl]-1H-indazol-5-yl}methylidene)-1,3-thiazol-4(5H)-one |
| 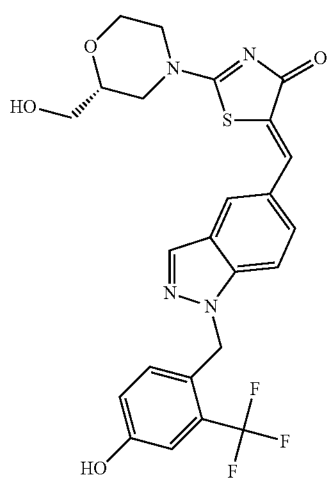 [SMILES: O=C1N=C(N2CCO[C@@H](CO)C2)S/C1=C\c1ccc2c(cnn2Cc2ccc(O)cc2C(F)(F)F)c1] | 249 | 2-[(2R)-2-(Hydroxymethyl)morpholin-4-yl]-5-({1-[4-hydroxy-2-(trifluoromethyl)benzyl]-1H-indazol-5-yl}methylidene)-1,3-thiazol-4(5H)-one |

TABLE I-continued

| STRUCTURE | COMPOUND # | NAME |
|---|---|---|
| 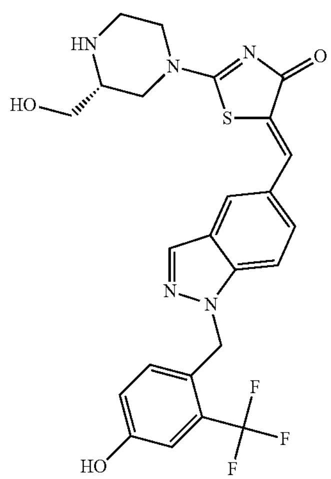 [SMILES: O=C1N=C(N2CCN[C@@H](CO)C2)S/C1=C\c1ccc2c(cnn2Cc2ccc(O)cc2C(F)(F)F)c1] | 250 | 2-[(3R)-3-(Hydroxymethyl)piperazin-1-yl]-5-({1-[4-hydroxy-2-(trifluoromethyl)benzyl]-1H-indazol-5-yl}methylidene)-1,3-thiazol-4(5H)-one |
| 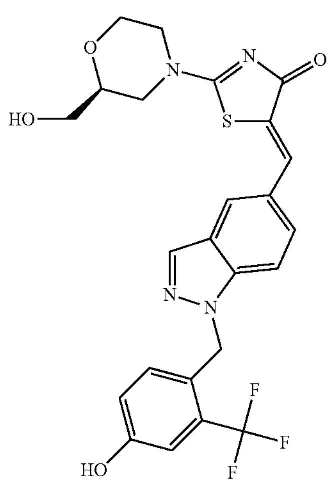 [SMILES: O=C1N=C(N2CCO[C@H](CO)C2)S/C1=C\c1ccc2c(cnn2Cc2ccc(O)cc2C(F)(F)F)c1] | 251 | (5Z)-2-[(2S)-2-(Hydroxymethyl)morpholin-4-yl]-5-({1-[4-hydroxy-2-(trifluoromethyl)benzyl]-1H-indazol-5-yl}methylidene)-1,3-thiazol-4(5H)-one |
| 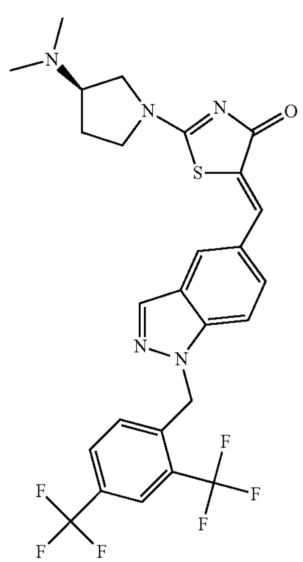 [SMILES: CN(C)[C@@H]1CCN(C2=NC(=O)/C(=C/c3ccc4c(cnn4Cc4ccc(C(F)(F)F)cc4C(F)(F)F)c3)S2)C1] | 252 | 5-({1-[2,4-Bis(trifluoromethyl)benzyl]-1H-indazol-5-yl}methylidene)-2-[(3R)-3-(dimethylamino)pyrrolidin-1-yl]-1,3-thiazol-4(5H)-one |

| STRUCTURE | COMPOUND # | NAME |
|---|---|---|
| 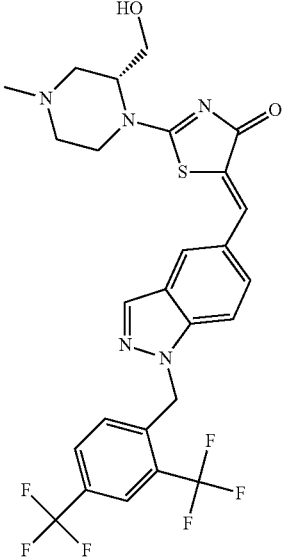 [SMILES: CN1CCN(C2=NC(=O)/C(=C/c3ccc4c(cnn4Cc4ccc(C(F)(F)F)cc4C(F)(F)F)c3)S2)[C@@H](CO)C1] | 253 | 5-({1-[2,4-Bis(trifluoromethyl)benzyl]-1H-indazol-5-yl}-methylidene)-2-[(2R)-2-(hydroxymethyl)-4-methylpiperazin-1-yl]-1,3-thiazol-4(5H)-one |
| 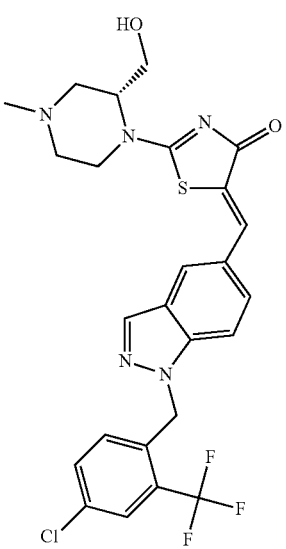 [SMILES: CN1CCN(C2=NC(=O)/C(=C/c3ccc4c(cnn4Cc4ccc(Cl)cc4C(F)(F)F)c3)S2)[C@@H](CO)C1] | 254 | 5-({1-[4-Chloro-2-(trifluoromethyl)benzyl]-1H-indazol-5-yl}methylidene)-2-[(2R)-2-(hydroxymethyl)-4-methylpiperazin-1-yl]-1,3-thiazol-4(5H)-one |

TABLE I-continued

| STRUCTURE | COMPOUND # | NAME |
|---|---|---|
| 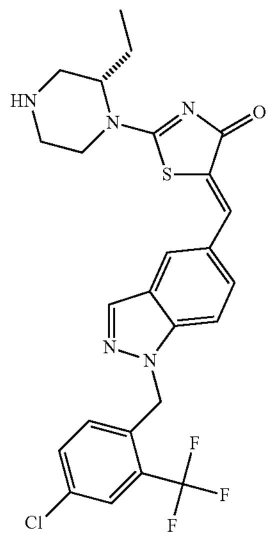 [SMILES: CC[C@H]1CNCCN1C1=NC(=O)/C(=C/c2ccc3c(cnn3Cc3ccc(Cl)cc3C(F)(F)F)c2)S1] | 255 | 5-({1-[4-Chloro-2-(trifluoromethyl)benzyl]-1H-indazol-5-yl}methylidene)-2-((2S)-2-ethylpiperazin-1-yl)-1,3-thiazol-4(5H)-one |
| 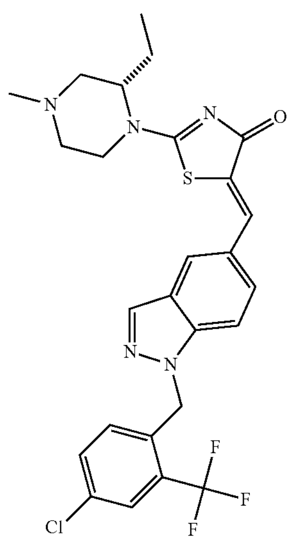 [SMILES: CC[C@H]1CN(C)CCN1C1=NC(=O)/C(=C/c2ccc3c(cnn3Cc3ccc(Cl)cc3C(F)(F)F)c2)S1] | 256 | 5-({1-[4-Chloro-2-(trifluoromethyl)benzyl]-1H-indazol-5-yl}methylidene)-2-((2S)-2-ethyl-4-methylpiperazin-1-yl)-1,3-thiazol-4(5H)-one |
| 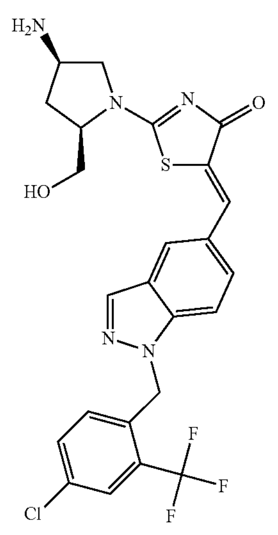 [SMILES: N[C@@H]1C[C@H](CO)N(C2=NC(=O)/C(=C/c3ccc4c(cnn4Cc4ccc(Cl)cc4C(F)(F)F)c3)S2)C1] | 257 | 2-[(2R,4R)-4-Amino-2-(hydroxymethyl)pyrrolidin-1-yl]-5-({1-[4-chloro-2-(trifluoromethyl)benzyl]-1H-indazol-5-yl}methylidene)-1,3-thiazol-4(5H)-one |

TABLE I-continued
| STRUCTURE | COMPOUND # | NAME |
|---|---|---|
| 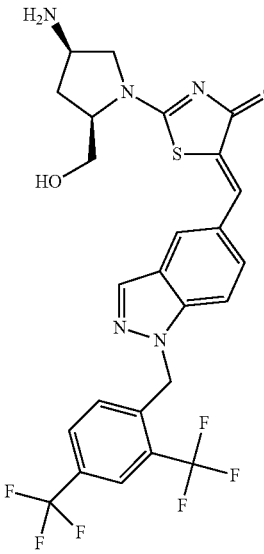 | 258 | 2-[(2R,4R)-4-Amino-2-(hydroxymethyl)pyrrolidin-1-yl]-5-({1-[2,4-bis(trifluoromethyl)benzyl]-1H-indazol-5-yl}methylidene)-1,3-thiazol-4(5H)-one |
| 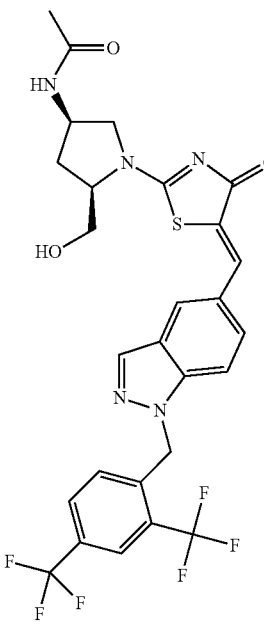 | 259 | N-{1-[(3R,5R)-5-({1-[2,4-Bis(trifluoromethyl)benzyl]-1H-indazol-5-yl}methylidene)-4-oxo-4,5-dihydro-1,3-thiazol-2-yl]-5-(hydroxymethyl)pyrrolidin-3-yl}acetamide |

| STRUCTURE | COMPOUND # | NAME |
|---|---|---|
| 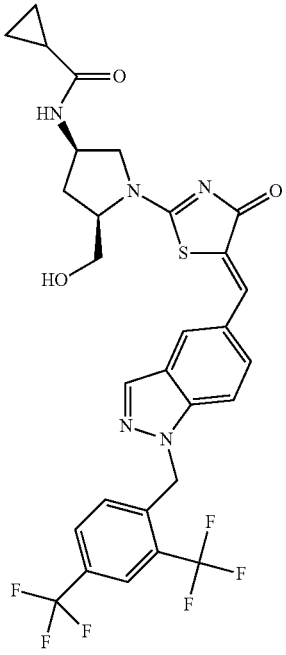 [SMILES: O=C1N=C(N2C[C@H](NC(=O)C3CC3)C[C@@H]2CO)S/C1=C\c1ccc2c(cnn2Cc2ccc(C(F)(F)F)cc2C(F)(F)F)c1] | 260 | N-{(3R,5R)-1-[5-({1-[2,4-Bis(trifluoromethyl)benzyl]-1H-indazol-5-yl}methylidene)-4-oxo-4,5-dihydro-1,3-thiazol-2-yl]-5-(hydroxymethyl)pyrrolidin-3-yl}cyclopropanecarboxamide |
| 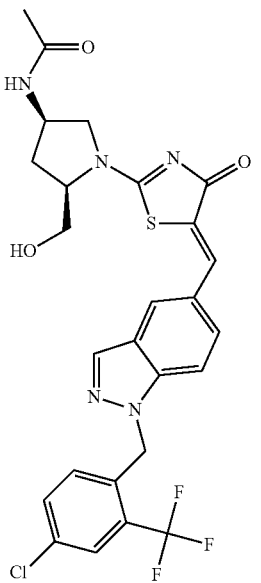 [SMILES: CC(=O)N[C@@H]1C[C@H](CO)N(C2=NC(=O)/C(=C/c3ccc4c(cnn4Cc4ccc(Cl)cc4C(F)(F)F)c3)S2)C1] | 261 | N-{(3R,5R)-1-[5-({1-[4-Chloro-2-(trifluoromethyl)benzyl]-1H-indazol-5-yl}methylidene)-4-oxo-4,5-dihydro-1,3-thiazol-2-yl]-5-(hydroxymethyl)pyrrolidin-3-yl}acetamide |

| STRUCTURE | COMPOUND # | NAME |
|---|---|---|
| 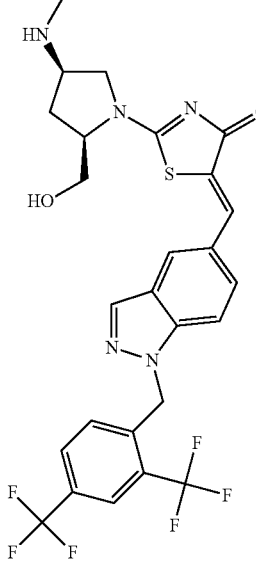 | 262 | N-{(2R,4R)-1-[2,4-Bis(trifluoromethyl)benzyl]-1H-indazol-5-yl}methylidene)-2-{2-(hydroxymethyl)-4-[(1-methylethyl)amino]pyrrolidin-1-yl}-1,3-thiazol-4(5H)-one |
| 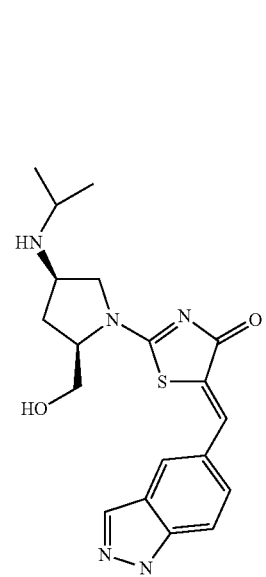 | 263 | N-{(2R,4R)-1-[4-Chloro-2-(trifluoromethyl)benzyl]-1H-indazol-5-yl}methylidene)-2-{2-(hydroxymethyl)-4-[(1-methylethyl)amino]pyrrolidin-1-yl}-1,3-thiazol-4(5H)-one |

TABLE I-continued

| STRUCTURE | COMPOUND # | NAME |
|---|---|---|
| 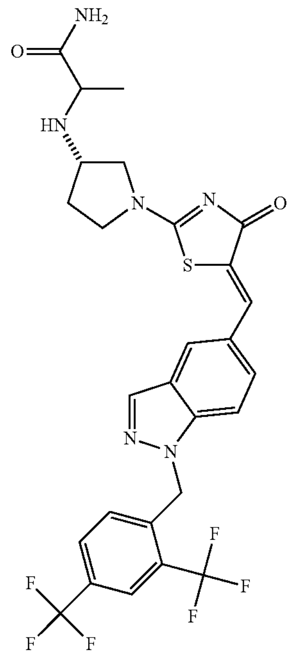 [SMILES: CC(N[C@H]1CCN(C2=NC(=O)/C(=C/c3ccc4c(cnn4Cc4ccc(C(F)(F)F)cc4C(F)(F)F)c3)S2)C1)C(N)=O] | 264 | N-2-{(3S)-1-[5-({1-[2,4-Bis(trifluoromethyl)benzyl]-1H-indazol-5-yl}methylidene)-4-oxo-4,5-dihydro-1,3-thiazol-2-yl]pyrrolidin-3-yl}alaninamide |
| 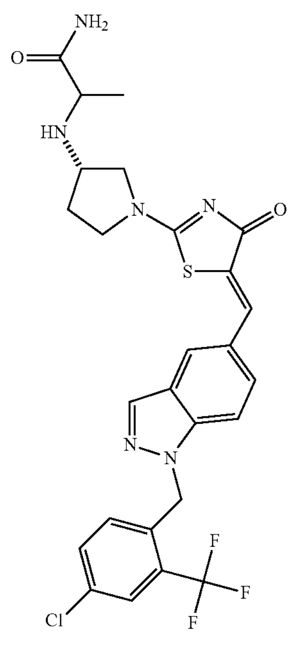 [SMILES: CC(N[C@H]1CCN(C2=NC(=O)/C(=C/c3ccc4c(cnn4Cc4ccc(Cl)cc4C(F)(F)F)c3)S2)C1)C(N)=O] | 265 | N-2-{(3S)-1-[5-({1-[4-Chloro-2-(trifluoromethyl)benzyl]-1H-indazol-5-yl}methylidene)-4-oxo-4,5-dihydro-1,3-thiazol-2-yl]pyrrolidin-3-yl}alaninamide |

TABLE I-continued

| STRUCTURE | COMPOUND # | NAME |
|---|---|---|
| 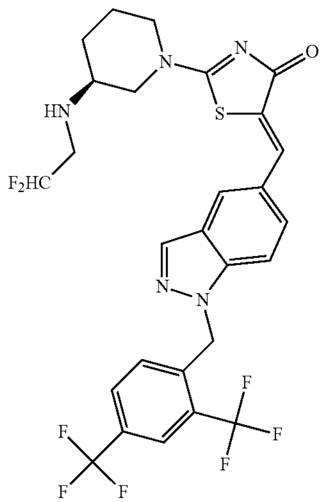 [SMILES: O=C1N=C(N2CCC[C@H](NCC(F)F)C2)S/C1=C\c1ccc2c(cnn2Cc2ccc(C(F)(F)F)cc2C(F)(F)F)c1] | 266 | 5-({1-[2,4-Bis(trifluoromethyl)benzyl]-1H-indazol-5-yl}methylidene)-2-{(3S)-3-[(2,2-difluoroethyl)amino]piperidin-1-yl}-1,3-thiazol-4(5H)-one |
| 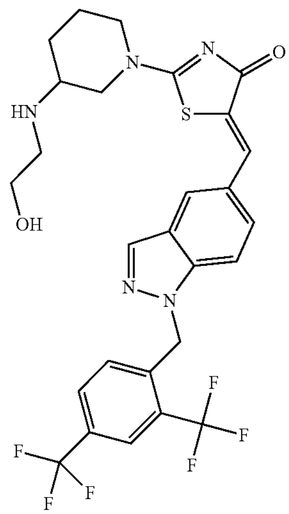 [SMILES: O=C1N=C(N2CCCC(NCCO)C2)S/C1=C\c1ccc2c(cnn2Cc2ccc(C(F)(F)F)cc2C(F)(F)F)c1] | 267 | 5-({1-[2,4-Bis(trifluoromethyl)benzyl]-1H-indazol-5-yl}methylidene)-2-{3-[(2-hydroxyethyl)amino]piperidin-1-yl}-1,3-thiazol-4(5H)-one |
| 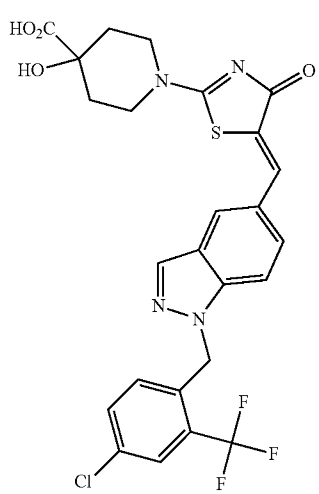 [SMILES: O=C1N=C(N2CCC(O)(C(=O)O)CC2)S/C1=C\c1ccc2c(cnn2Cc2ccc(Cl)cc2C(F)(F)F)c1] | 268 | 1-[5-({1-[4-Chloro-2-(trifluoromethyl)benzyl]-1H-indazol-5-yl}methylidene)-4-oxo-4,5-dihydro-1,3-thiazol-2-yl]-4-hydroxypiperidine-4-carboxylic acid |

TABLE I-continued

| STRUCTURE | COMPOUND # | NAME |
|---|---|---|
| 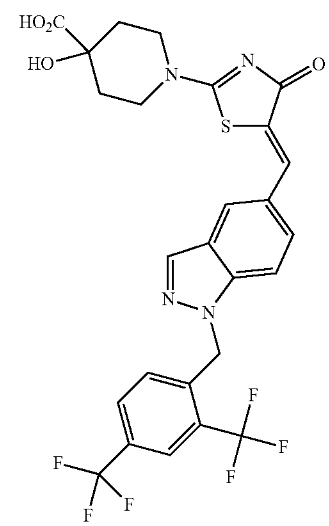 [SMILES: O=C1N=C(N2CCC(O)(C(=O)O)CC2)S/C1=C\c1ccc2c(cnn2Cc2ccc(C(F)(F)F)cc2C(F)(F)F)c1] | 269 | 1-[5-({1-[2,4-Bis(trifluoromethyl)benzyl]-1H-indazol-5-yl}methylidene)-4-oxo-4,5-dihydro-1,3-thiazol-2-yl]-4-hydroxypiperidine-4-carboxylic acid |
| 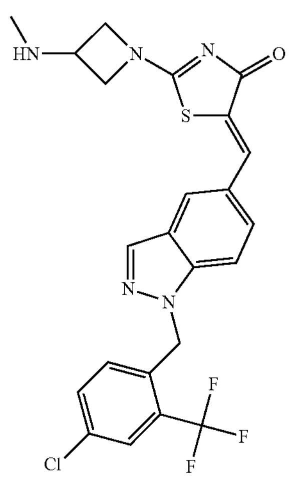 [SMILES: CNC1CN(C2=NC(=O)/C(=C/c3ccc4c(cnn4Cc4ccc(Cl)cc4C(F)(F)F)c3)S2)C1] | 270 | 5-({1-[4-Chloro-2-(trifluoromethyl)benzyl]-1H-indazol-5-yl}methylidene)-2-[3-(methylamino)azetidin-1-yl]-1,3-thiazol-4(5H)-one |
| 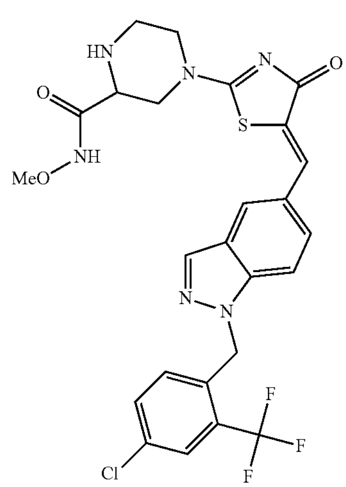 [SMILES: CONC(=O)C1CN(C2=NC(=O)/C(=C/c3ccc4c(cnn4Cc4ccc(Cl)cc4C(F)(F)F)c3)S2)CCN1] | 271 | 4-[5-({1-[4-Chloro-2-(trifluoromethyl)benzyl]-1H-indazol-5-yl}methylidene)-4-oxo-4,5-dihydro-1,3-thiazol-2-yl]-N-methoxypiperazine-2-carboxamide |

TABLE I-continued

| STRUCTURE | COMPOUND # | NAME |
|---|---|---|
| 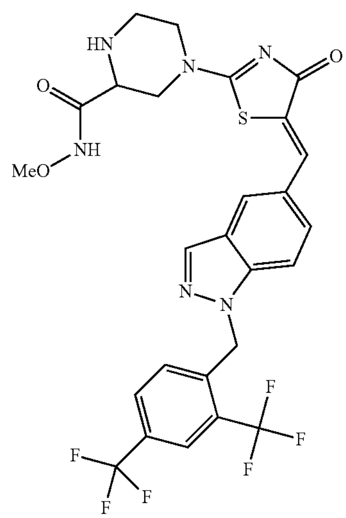 [SMILES: CONC(=O)C1CN(C2=NC(=O)/C(=C/c3ccc4c(cnn4Cc4ccc(C(F)(F)F)cc4C(F)(F)F)c3)S2)CCN1] | 272 | 4-[5-({1-[2,4-Bis(trifluoromethyl)benzyl]-1H-indazol-5-yl}methylidene)-4-oxo-4,5-dihydro-1,3-thiazol-2-yl]-N-methoxypiperazine-2-carboxamide |
| 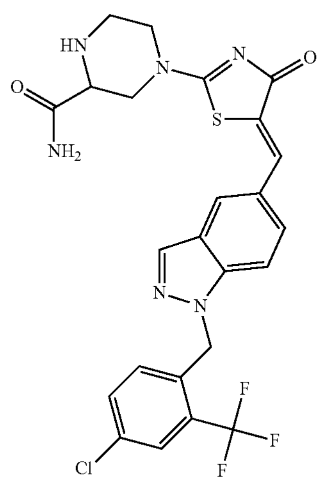 [SMILES: NC(=O)C1CN(C2=NC(=O)/C(=C/c3ccc4c(cnn4Cc4ccc(Cl)cc4C(F)(F)F)c3)S2)CCN1] | 273 | 4-[(5Z)-5-({1-[4-Chloro-2-(trifluoromethyl)benzyl]-1H-indazol-5-yl}methylidene)-4-oxo-4,5-dihydro-1,3-thiazol-2-yl]piperazine-2-carboxamide |
| 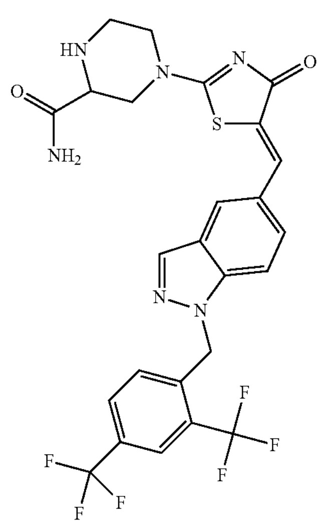 [SMILES: NC(=O)C1CN(C2=NC(=O)/C(=C/c3ccc4c(cnn4Cc4ccc(C(F)(F)F)cc4C(F)(F)F)c3)S2)CCN1] | 274 | 4-[(5Z)-4-({1-[2,4-Bis(trifluoromethyl)benzyl]-1H-indazol-5-yl}methylidene)-4-oxo-4,5-dihydro-1,3-thiazol-2-yl]piperazine-2-carboxamide |

TABLE I-continued

| STRUCTURE | COMPOUND # | NAME |
|---|---|---|
| 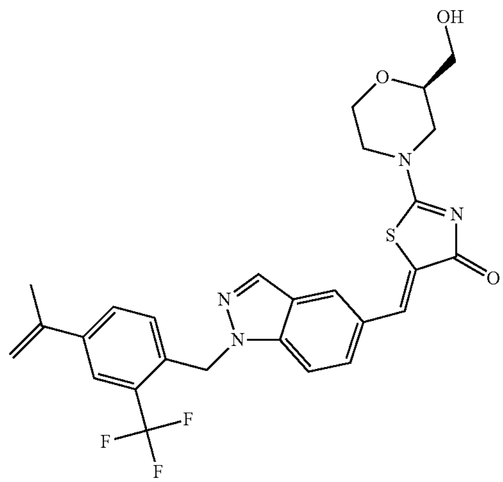 [SMILES: C=C(C)c1ccc(Cn2ncc3cc(/C=C4\SC(N5CCO[C@@H](CO)C5)=NC4=O)ccc32)c(C(F)(F)F)c1] | 275 | 2-[(2R)-2-(Hydroxymethyl)morpholin-4-yl]-5-({1-[4-(1-methylethenyl)-2-(trifluoromethyl)benzyl]-1H-indazol-5-yl}methylidene)-1,3-thiazol-4(5H)-one |
| 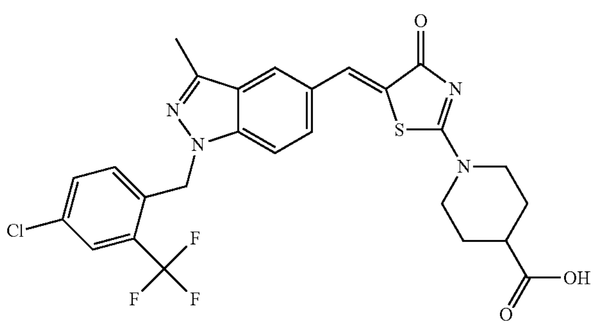 [SMILES: Cc1nn(Cc2ccc(Cl)cc2C(F)(F)F)c2ccc(/C=C3\SC(N4CCC(C(=O)O)CC4)=NC3=O)cc12] | 276 | 1-[5-({1-[4-Chloro-2-(trifluoromethyl)benzyl]-3-methyl-1H-indazol-5-yl}methylidene)-4-oxo-4,5-dihydro-1,3-thiazol-2-yl]piperidine-4-carboxylic acid |
| 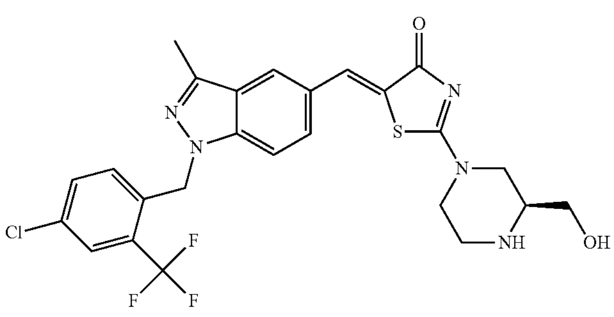 [SMILES: Cc1nn(Cc2ccc(Cl)cc2C(F)(F)F)c2ccc(/C=C3\SC(N4CCN[C@H](CO)C4)=NC3=O)cc12] | 277 | 5-({1-[4-Chloro-2-(trifluoromethyl)benzyl]-3-methyl-1H-indazol-5-yl}methylidene)-2-[(3S)-3-(hydroxymethyl)piperazin-1-yl]-1,3-thiazol-4(5H)-one |
| 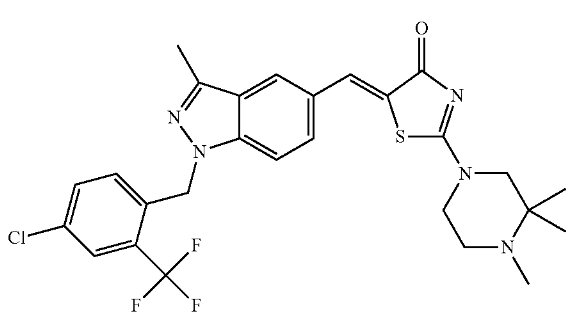 [SMILES: Cc1nn(Cc2ccc(Cl)cc2C(F)(F)F)c2ccc(/C=C3\SC(N4CCN(C)C(C)(C)C4)=NC3=O)cc12] | 278 | 5-({1-[4-Chloro-2-(trifluoromethyl)benzyl]-3-methyl-1H-indazol-5-yl}methylidene)-2-(3,3,4-trimethylpiperazin-1-yl)-1,3-thiazol-4(5H)-one |

TABLE I-continued

| STRUCTURE | COMPOUND # | NAME |
|---|---|---|
| 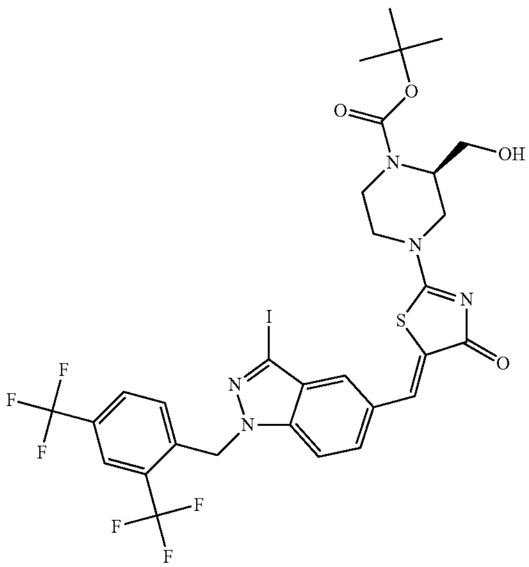 [SMILES: CC(C)(C)OC(=O)N1CCN(C2=NC(=O)/C(=C/c3ccc4c(c3)c(I)nn4Cc3ccc(C(F)(F)F)cc3C(F)(F)F)S2)C[C@@H]1CO] | 279 | tert-Butyl (2R)-4-[5-({1-[2,4-bis(trifluoromethyl)benzyl]-3-iodo-1H-indazol-5-yl}methylidene)-4-oxo-4,5-dihydro-1,3-thiazol-2-yl]-2-(hydroxymethyl)piperazine-1-carboxylate |
| 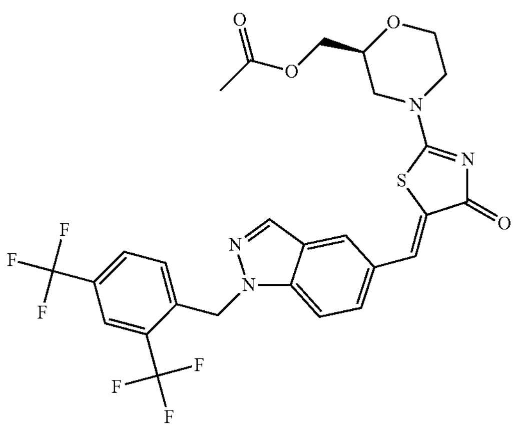 [SMILES: CC(=O)OC[C@@H]1CN(C2=NC(=O)/C(=C/c3ccc4c(cnn4Cc4ccc(C(F)(F)F)cc4C(F)(F)F)c3)S2)CCO1] | 280 | {(2S)-4-[5-({1-[2,4-Bis(trifluoromethyl)benzyl]-1H-indazol-5-yl}methylidene)-4-oxo-4,5-dihydro-1,3-thiazol-2-yl]morpholin-2-yl}methyl acetate |
| 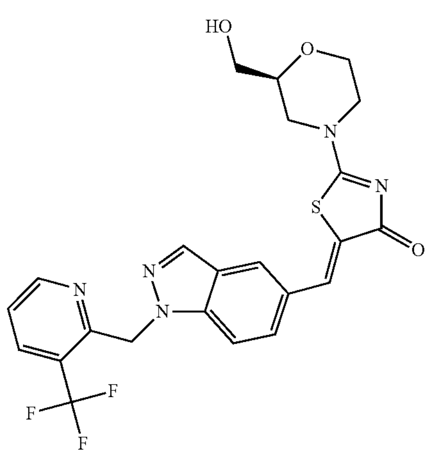 [SMILES: O=C1N=C(N2CCO[C@H](CO)C2)S/C1=C\c1ccc2c(cnn2Cc2ncccc2C(F)(F)F)c1] | 281 | 2-[(2S)-2-(Hydroxymethyl)morpholin-4-yl]-5-[(1-{[3-(trifluoromethyl)pyridin-2-yl]methyl}-1H-indazol-5-yl)methylidene]-1,3-thiazol-4(5H)-one |

TABLE I-continued

| STRUCTURE | COMPOUND # | NAME |
|---|---|---|
| 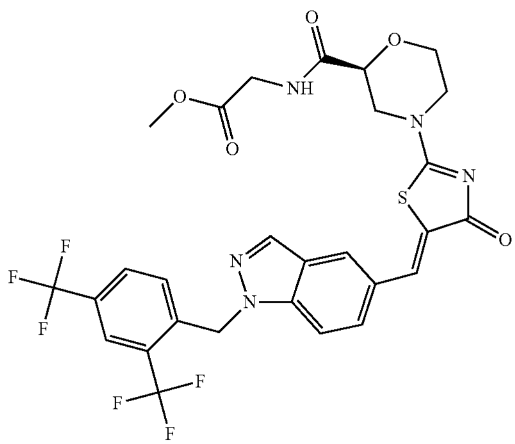 [SMILES: COC(=O)CNC(=O)[C@@H]1CN(C2=NC(=O)/C(=C/c3ccc4c(cnn4Cc4ccc(C(F)(F)F)cc4C(F)(F)F)c3)S2)CCO1] | 282 | Methyl N-({(2S)-4-[5-({1-[2,4-bis(trifluoromethyl)benzyl]-1H-indazol-5-yl}methylidene)-4-oxo-4,5-dihydro-1,3-thiazol-2-yl]morpholin-2-yl}carbonyl)glycinate |
| 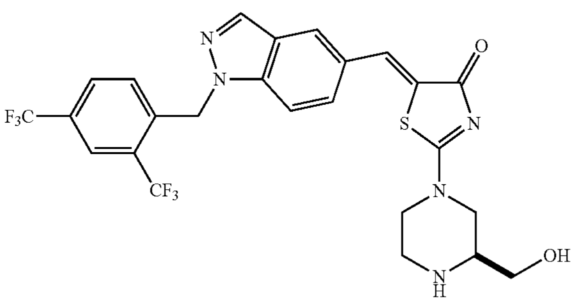 [SMILES: O=C1N=C(N2CCN[C@H](CO)C2)S/C1=C\c1ccc2c(cnn2Cc2ccc(C(F)(F)F)cc2C(F)(F)F)c1] | 283 | 5-[1-(2,4-Bis-trifluoromethyl-benzyl)-1H-indazol-5-ylmethylene]-2-(3-(S)-hydroxymethyl-piperazin-1-yl)-thiazol-4-one |

C) Synthesis

The invention provides methods of making the disclosed compounds according to traditional organic synthetic methods as well as matrix or combinatorial synthetic methods. Schemes 1 to 5 describe suggested synthetic routes. Using the scheme, the guidelines below, and the examples, a person of skill in the art may develop analogous or similar methods for a given compound that is within the invention. These methods are representative of the synthetic schemes, but are not to be construed as limiting the scope of the invention.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, geometric isomers, and enantiomers thereof are encompassed within the scope of the present invention.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Examples of the described synthetic routes include Schemes 1-5, Examples 1 through 283, and General Procedures A-I. Compounds analogous to the target compounds of these examples can be made according to similar routes. The disclosed compounds are useful as pharmaceutical agents as described herein.

Abbreviations or Acronyms Useful Herein Include:
AIBN (2,2'-Azobisisobutyronitrile)
Boc (tert butyl carbamate)
BOP (Benzotriazol-1-yloxy)tris(dimethylamino)phosphonium hexfluorophosphate)
BuLi (butyllithium)
DIBAL-H (Diisobutylaluminum hydride)
DCM (Dichloromethane)
DIEA (Diisopropylethylamine)
DMAP (4-(dimethylamino)pyridine)
DME (Ethylene glycol dimethyl ether)
DMF (dimethylformamide)
DMPU (1,3-Dimethyl-3,4,5,6-tetrahydro-2(1H)-pyrimidinone)
DMSO (methyl sulfoxide)
EDC (N-(3-Dimethylaminopropyl)-N'-ethylcarbodiimide)

EDCl (1-(3-Dimethylaminopropyl)-3-ethylcarbodiimide hydrochloride)
Et (ethyl)
EtOAc (ethyl acetate)
h or hr (hour(s))
HATU (O-(7-Azabenzotriazol-1-yl)-N,N,N',N'-tetramethyluronium hexafluorophosphate)
HCl (Hydrochloric acid)
HMPA (Hexamethylphosphoramide)
HOBt (1-Hydroxybenzotriazole monohydrate)
HPLC (High Performance Liquid Chromatography)
LCMS (high pressure liquid chroatography with mass spectrometer)
LDA (Lithium diisopropylamide)
LHMDS (lithium hexamethyl disilazide)
Me (methyl)
MeCN (acetonitrile)
MeOH (methyl alcohol)
Mg (milligram)
MOM (Methoxymethyl)
NaHMDS (sodium hexamethyl disilazide)
NaO$^t$Bu (sodium tert-butoxide)
NBS (N-Bromosuccinimide)
NMP (N-Methyl Pyrrolidinone)
N,N-DMA (N,N-dimethylacetamide)
rt or RT (room temperature)
SPE (solid phase extraction)
TBTU (O-Benzotriazol-1-yl-N,N,N',N'-tetramethyluronium hexafluorophosphate)
tBu (tert-butyl)
TEMPO (2,2,6,6-tetramethyl-1-piperidinyloxy, free radical)
TFA (trifluoroacetic acid);
THF (tetrahydrofuran)
TLC (thin layer chromatography)

General Guidance

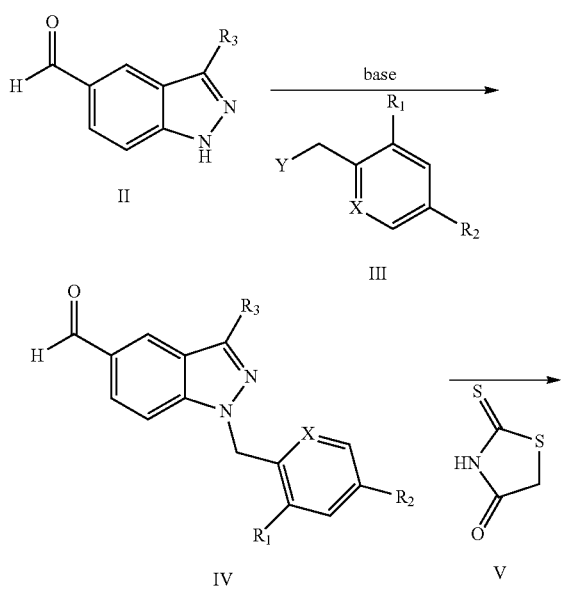

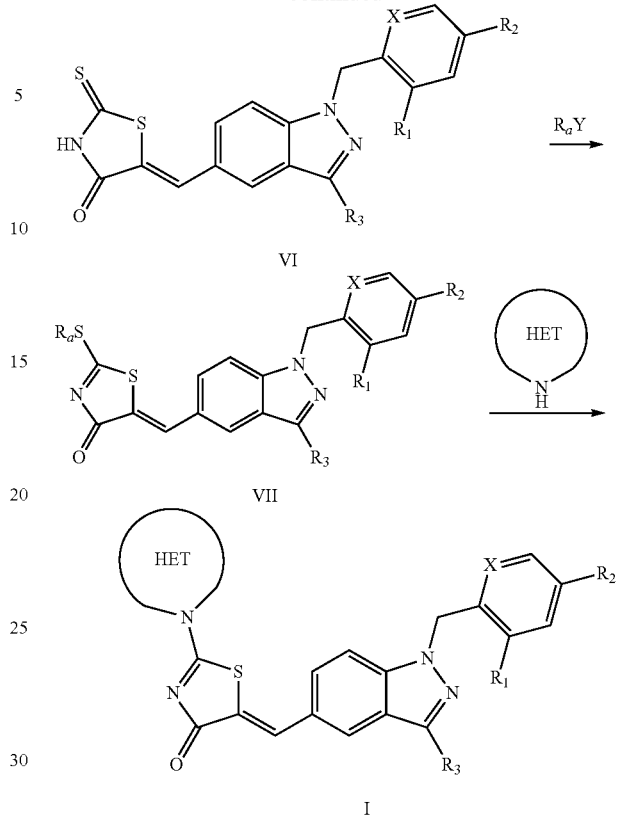

The compounds of Formula (I), wherein X, $R_1$, $R_2$, $R_3$ and are defined as in Formula I, may be synthesized as outlined by the general synthetic route illustrated in Scheme 1. Treatment of an appropriate 1H-Indazole-5-carbaldehyde II and an appropriate substituted benzyl or an appropriate substituted alkylheteroaryl ($C_1$alkylaryl) III, a known compound or compound prepared by known methods, wherein Y is a suitably selected leaving group such as Cl, Br, I, tosylate, mesylate, and the like, both of which are either commercially available or can be made from commercially available starting materials, with a base such as $K_2CO_3$, $Cs_2CO_3$, NaH, and the like, in a solvent such as NMP, DMF, THF, and the like, at a temperature preferably between 25-150° C. can provide the substituted 1-Benzyl-1H-indazole-5-carbaldehyde IV. Knoevenagel reaction of aldehyde IV with a suitably compound of formula V in the presence of a catalytic amount of base such as piperidine and an acid such as benzoic acid can provide compound VI. Alternatively, the Knoevenagel reaction of aldehyde IV with a suitable compound of formula V in the presence of DBU can provide compound VI. The Knoevenagel reaction is typically performed in an aprotic solvent such as toluene at a temperature preferably between 100-200° C. The reaction between aldehyde IV and rhodanine V may also be performed with a base such as sodium acetate in a solvent such as acetonitrile at a temperature preferably between 50-150° C., or in the presence of ammonium acetate in acetic acid at a temperature preferably between 50-150° C. The compound of formula VI is reacted with a compound of formula R$_a$Y, a known compound or compound prepared by known methods, wherein R$_a$ is a suitably selected alkyl such as methyl, ethyl, isopropyl, and the like, and Y, a suitably selected leaving group such as Cl, Br, I, tosylate, mesylate, and the like, in the presence of a base such as K$_2$CO$_3$, Et$_3$N, DIEA, and the like, in an organic solvent such as MeOH, MeCN, DCM, THF, and the like, at a temperature preferably between 25-80° C., to yield the corresponding compound of formula VII.

Treatment of VII with an appropriate amine in a solvent such as acetonitrile, MeOH, DMF, and the like, at a temperature preferably between 25-180° C. can provide compounds of Formula (I).

In the case where the cyclic amine of formula incorporates another protected nitrogen such as Boc, Cbz, and the like, this nitrogen may be deprotected under appropriate conditions known to those skilled in the art to afford a compound of formula I of the present invention. For example, Boc-protected amines may be deprotected under acidic conditions using reagents such as HCl, TFA, and the like. Likewise, Cbz-protected amines may be deprotected under acidic conditions or hydrogenolysis.

Scheme 2

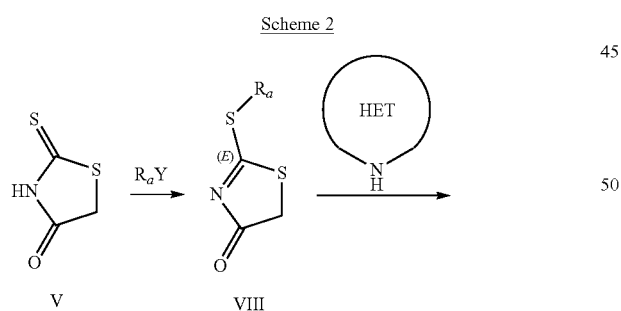

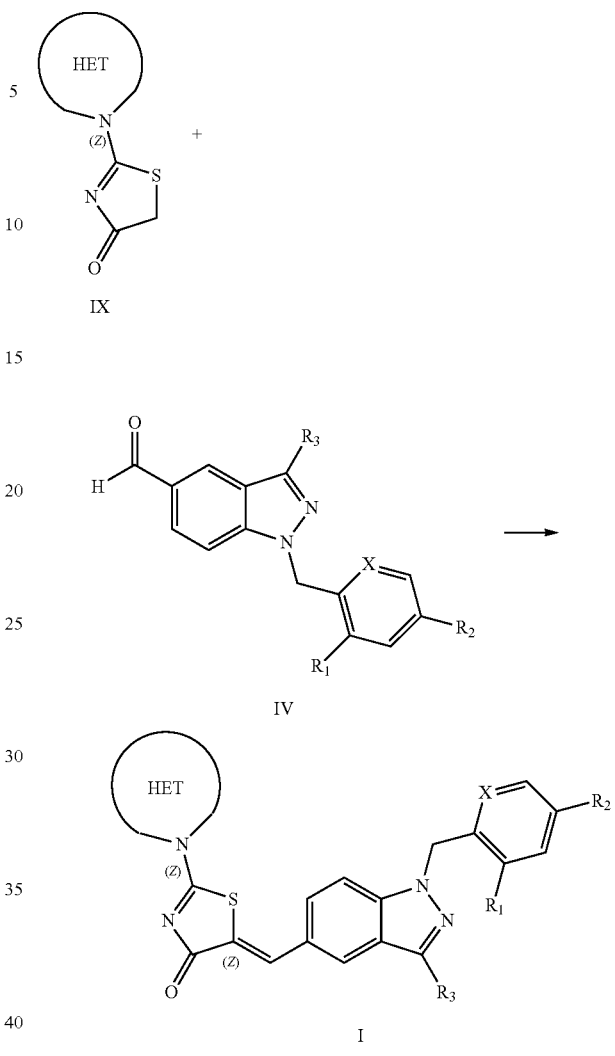

The compounds of Formula (I), wherein X, R$_1$, R$_2$, R$_3$ and are defined as in Formula I, may alternatively be synthesized as outlined by the general synthetic route illustrated in Scheme 2. Accordingly, a suitable compound of formula V, a known compound or compound prepared by known methods, is reacted with a compound of formula R$_a$Y, a known compound or compound prepared by known methods, wherein R$_a$ is a suitably selected alkyl such as methyl, ethyl, isopropyl, and the like, and Y, a suitably selected leaving group such as Cl, Br, I, tosylate, mesylate, and the like, in the presence of a base such as K$_2$CO$_3$, Et$_3$N, DIPEA, and the like, in an organic solvent such as MeOH, DCM, THF, and the like, at a temperature preferably between 25-80° C., to yield the corresponding compound of formula VIII. Treatment of VIII with an appropriate amine

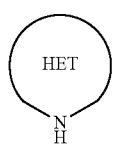

in a solvent such as acetonitrile, MeOH, DMF, and the like, at a temperature preferably between 25-150° C. can provide compounds of Formula IX. Knoevenagel reaction of aldehyde IV with a suitably compound of formula IX in the presence of a catalytic amount of base such as piperidine and an acid such as benzoic acid can provide compounds of Formula (I). Alternatively, the Knoevenagel reaction of aldehyde IV with a suitable compound of formula IX in the presence of DBU can provide compound of formula (I). The Knoevenagel reaction is typically performed in an aprotic solvent such as toluene at a temperature preferably between 100-200° C. The reaction between aldehyde IV and a suitably compound of formula IX may also be performed with a base such as sodium acetate in a solvent such as acetonitrile at a temperature preferably between 50-150° C., or in the presence of ammonium acetate in acetic acid at a temperature preferably between 50-150° C.

In the case where the cyclic amine of formula

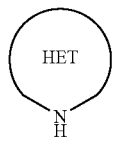

incorporates another protected nitrogen such as Boc, Cbz, and the like, this nitrogen may be deprotected under appropriate conditions known to those skilled in the art to afford a compound of formula I of the present invention. For example, Boc-protected amines may be deprotected under acidic conditions using reagents such as HCl, TFA, and the like. Likewise, Cbz-protected amines may be deprotected under acidic conditions or hydrogenolysis.

Scheme 3

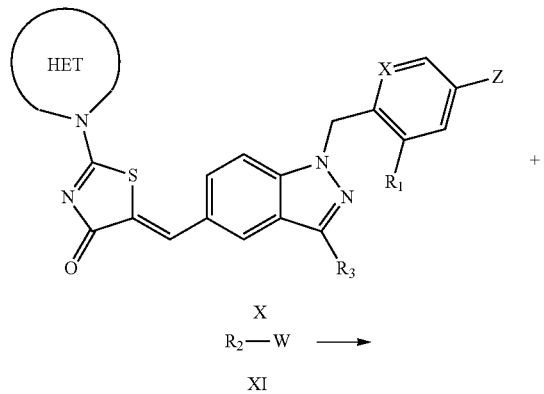

X $R_2$—W ⟶

XI

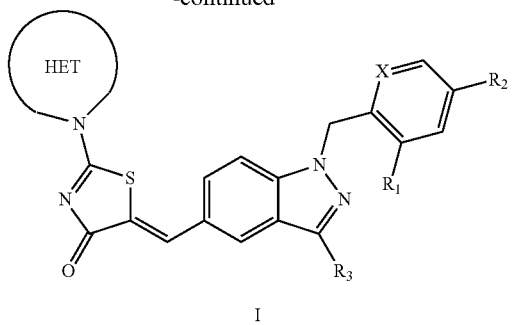

I

The compounds of Formula (I), wherein X, $R_1$, $R_2$, $R_3$ and

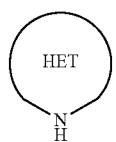

are defined as in Formula I, may alternatively be synthesized as outlined by the general synthetic route illustrated in Scheme 3. Accordingly, a suitable compound of formula X, prepared as described in Scheme 1, wherein X, $R_1$, $R_3$ and

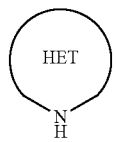

are defined as in Formula I and wherein Z is a suitably selected leaving group such as Cl, Br, I, triflate, mesylate, and the like, is reacted with a compound of formula XI, wherein $R_2$ is defined as in Formula I and W a suitably selected boronic acid, boronic ester, tin derivative, and the like, which are either commercially available or can be made from commercially available starting materials, in the presence of a transition metal catalyst such as $Pd(OAc)_2$, $Pd(Ph_3P)_4$, $Pd(dppf)Cl_2$, $Pd_2(dba)_3$ and the like, in the presence of a base, such as $K_2CO_3$, $Cs_2CO_3$, potassium phosphate, and the like, in the presence of a ligand, such as $PPh_3$, tricyclohexylphosphine, tri-t-butylphosphine, biphenyl-2-yl-di-t-butyl-phosphane, and the like, in an organic solvent such as toluene, dioxane, THF, EtOH, water, and the like, at a temperature in the range of from about 20° C. to about 180° C., to yield the corresponding compound of formula I.

Scheme 4

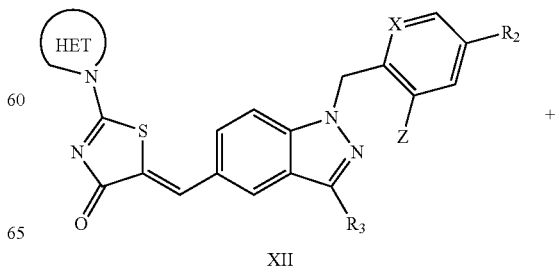

XII

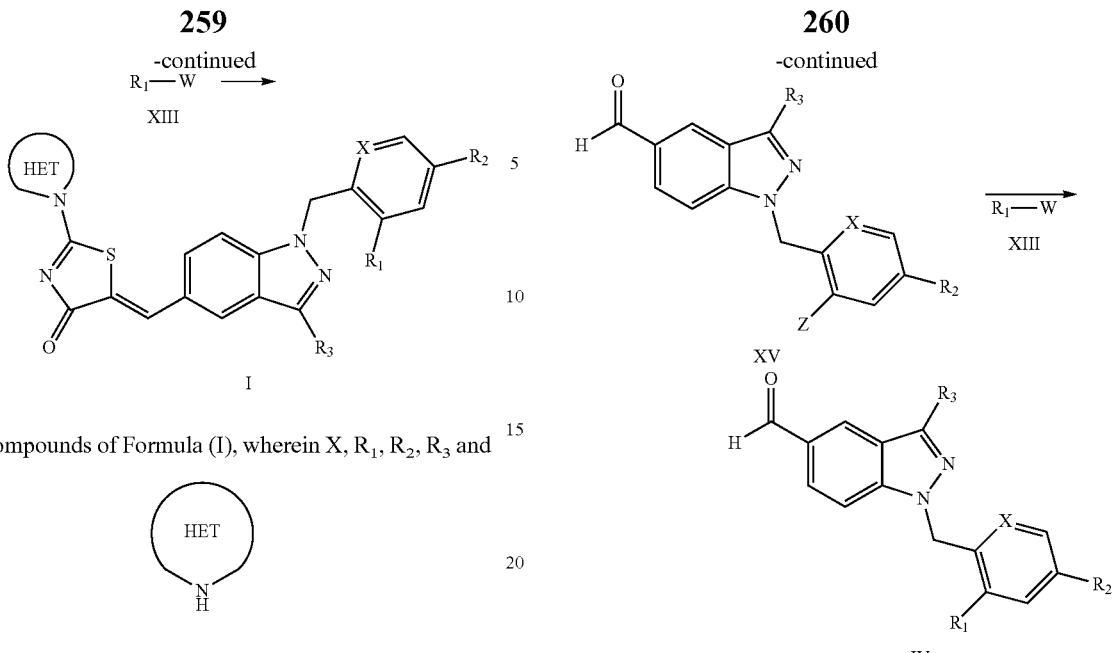

The compounds of Formula (I), wherein X, $R_1$, $R_2$, $R_3$ and

are defined as in Formula I, may alternatively be synthesized as outlined by the general synthetic route illustrated in Scheme 4. Accordingly, a suitable compound of formula XII, prepared as described in Scheme 1, wherein X, $R_2$, $R_3$ and

are defined as in Formula I and wherein Z is a suitably selected leaving group such as Cl, Br, I, triflate, mesylate, and the like, is reacted with a compound of formula XIII, wherein $R_1$ is defined as in Formula I and W a suitably selected boronic acid, boronic ester, tin derivative, and the like, which are either commercially available or can be made from commercially available starting materials, in the presence of a transition metal catalyst such as Pd(OAc)$_2$, Pd(Ph$_3$P)$_4$, Pd(dppf)Cl$_2$, Pd$_2$(dba)$_3$ and the like, in the presence of a base, such as K$_2$CO$_3$, Cs$_2$CO$_3$, potassium phosphate, and the like, in the presence of a ligand, such as PPh$_3$, tricyclohexylphosphine, tri-t-butylphosphine, biphenyl-2-yl-di-t-butyl-phosphane, and the like, in an organic solvent such as toluene, dioxane, THF, EtOH, water, and the like, at a temperature in the range of from about 20° C. to about 180° C., to yield the corresponding compound of formula I.

Scheme 5

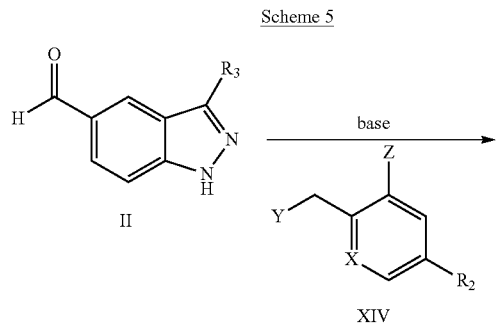

The compounds of Formula (I), wherein X, $R_1$, $R_2$, $R_3$ and

are defined as in Formula I, may be synthesized as outlined by the general synthetic route illustrated in Scheme 5. Treatment of an appropriate 1H-Indazole-5-carbaldehyde II and an appropriate substituted benzyl or an appropriate substituted alkylheteroaryl (C$_1$alkylaryl) XIV, a known compound or compound prepared by known methods, wherein Y is a suitably selected leaving group such as Cl, Br, I, tosylate, mesylate, and the like, and wherein Z is a suitably selected leaving group such as Cl, Br, I, tosylate, and the like, both of which are either commercially available or can be made from commercially available starting materials, with a base such as K$_2$CO$_3$, Cs$_2$CO$_3$, NaH, and the like, in a solvent such as NMP, DMF, THF, and the like, at a temperature preferably between 25-150° C. can provide the substituted 1-Benzyl-1H-indazole-5-carbaldehyde or the substituted 1-Pyridin-2-ylmethyl-1H-indazole-5-carbaldehyde XV.

Accordingly, a suitable compound of formula XV is reacted with a compound of formula XIII, wherein $R_1$ is defined as in Formula I and W a suitably selected boronic acid, boronic ester, tin derivative, and the like, f which are either commercially available or can be made from commercially available starting materials, in the presence of a transition metal catalyst such as Pd(OAc)$_2$, Pd(Ph$_3$P)$_4$, Pd(dppf)Cl$_2$, Pd$_2$(dba)$_3$ and the like, in the presence of a base, such as K$_2$CO$_3$, Cs$_2$CO$_3$, potassium phosphate, and the like, in the presence of a ligand, such as PPh$_3$, tricyclohexylphosphine, tri-t-butylphosphine, biphenyl-2-yl-di-t-butyl-phosphane, and the like, in an organic solvent such as toluene, dioxane, THF, EtOH, water, and the like, at a temperature in the range of from about 20° C. to about 180° C., to yield the corresponding compound of formula IV. Aldehyde IV can be transformed to provide compounds of Formula (I) as described in Scheme 1.

EXAMPLES

General Procedure A:

A solution of 1H-Indazole-5-carbaldehyde (7.6 g, 52.0 mmol) and an appropriate substituted benzyl bromide (62.1 mmol) in DMF (120 mL) was treated with $Cs_2CO_3$ (17 g, 52.1 mmol), and the mixture was heated in an oil bath at 100° C. for 16 h. The reaction was cooled to RT and partitioned between EtOAc and $H_2O$. The organic phase was washed with water (3×), brine, dried over $Na_2SO_4$ and concentrated in vacuo. Silica gel chromatography (EtOAc/hexanes) afforded the desired isomer. Recrystallization of the desired isomer from EtOAc/Hexanes afforded the desired pure aldehyde isomer.

General Procedure B:

2-thioxo-thiazolidin-4-one (0.59 g, 4.42 mmol) and aldehyde from Procedure A (4.42 mmol) were dissolved in toluene (40 mL) and treated with benzoic acid (0.22 mmol) and piperidine (0.22 mmol). The flask was equipped with a Dean-Stark trap, and the reaction was refluxed at 130° C. using an oil bath for 16 h. After cooling to RT, the product was collected by filtration and washed with toluene and water to afford the desired pure 5-[1-(substituted-benzyl)-1H-indazol-5-ylmethylene]-2-thioxo-thiazolidin-4-one product.

A mixture of 5-[1-(substituted-benzyl)-1H-indazol-5-ylmethylene]-2-thioxo-thiazolidin-4-one (0.32 mmol) and DIEA (0.63 mmol) in DCM (5 mL) was treated with an appropriate iodoalkane (1 mmol). The reaction mixture was stirred at RT for 16 h and partitioned between DCM and $H_2O$. The organic phase was washed with brine, dried over $Na_2SO_4$ and concentrated in vacuo to afford the desired pure 5-[1-(substituted-benzyl)-1H-indazol-5-ylmethylene]-2-alkylsulfanyl-thiazol-4-one product.

To a mixture of 5-[1-(substituted-benzyl)-1H-indazol-5-ylmethylene]-2-alkylsulfanyl-thiazol-4-one (0.31 mmol) and the appropriate cyclic amine (0.37 mmol) was added MeOH/DCM (2:1 v/v, 8 mL). The suspension was heated at 70° C. under reflux conditions for 4 h. The reaction was cooled to RT and the solvent concentrated in vacuo. Silica gel chromatography or reverse phase HPLC afforded the desired pure product.

General Procedure C:

To a mixture of 2-thioxo-thiazolidin-4-one (0.35 mmol) and aldehyde from Procedure A (0.32 mmol) was added acetic acid (2.0 mL) and $NH_4OAc$ (0.95 mmol). The suspension was heated at 95° C. (aluminum heating block) for 2 h. The product was collected by filtration, washed with cold ethanol and triturated with EtOAc/hexanes to afford the desired pure 5-[1-(substituted-benzyl)-1H-indazol-5-ylmethylene]-2-thioxo-thiazolidin-4-one product.

A mixture of 5-[1-(substituted-benzyl)-1H-indazol-5-ylmethylene]-2-thioxo-thiazolidin-4-one (0.32 mmol) and DIEA (0.63 mmol) in DCM (5 mL) was treated with an appropriate iodoalkane (1 mmol). The reaction mixture was stirred at RT for 16 h and partitioned between DCM and $H_2O$. The organic phase was washed with brine, dried over $Na_2SO_4$ and concentrated in vacuo to afford the desired pure 5-[1-(substituted-benzyl)-1H-indazol-5-ylmethylene]-2-alkylsulfanyl-thiazol-4-one product.

To a mixture of 5-[1-(substituted-benzyl)-1H-indazol-5-ylmethylene]-2-alkylsulfanyl-thiazol-4-one (0.31 mmol) and the appropriate cyclic amine (0.37 mmol) was added MeOH/DCM (2:1 v/v, 8 mL). The suspension was heated at 70° C. under reflux conditions for 4 h. The reaction was cooled to RT and the solvent concentrated in vacuo. Silica gel chromatography or reverse phase HPLC afforded the desired pure product.

General Procedure D:

2-thioxo-thiazolidin-4-one (10 g, 75 mmol) in aqueous 2% NaOH (200 mL) was treated with the appropriate iodoalkane (82.5 mmol). The reaction mixture was stirred at RT for 16 h and partitioned between DCM and $H_2O$. The organic phase was washed with a cold saturated $NaHCO_3$ solution, $H_2O$, dried over $Na_2SO_4$ and concentrated in vacuo to afford the desired pure 2-alkylsulfanyl-thiazol-4-one product.

To a mixture of 2-alkylsulfanyl-thiazol-4-one (2.71 mmol) and the appropriate cyclic amine (2.71 mmol) was added EtOH (15 mL). The suspension was heated at 65° C. for 16 h. The reaction was cooled to RT and the solvent concentrated in vacuo. Silica gel chromatography (MeOH/DCM) afforded the desired pure 2-cyclic amino-thiazol-4-one product.

2-Cyclic amino-thiazol-4-one (1.33 mmol) and the aldehyde from Procedure A (1.33 mmol) were dissolved in toluene (16 mL) and treated with benzoic acid (0.07 mmol) and piperidine (0.07 mmol). The flask was equipped with a Dean-Stark trap, and the reaction was refluxed at 130° C. using an oil bath for 12 h. After cooling to RT, the product was collected by filtration and triturated with hexanes to afford the desired pure product.

General Procedure E:

2-thioxo-thiazolidin-4-one (10 g, 75 mmol) in aqueous 2% NaOH (200 mL) was treated with the appropriate iodoalkane (82.5 mmol). The reaction mixture was stirred at RT for 16 h and partitioned between DCM and $H_2O$. The organic phase was washed with a cold saturated $NaHCO_3$ solution, $H_2O$, dried over $Na_2SO_4$ and concentrated in vacuo to afford the desired pure 2-alkylsulfanyl-thiazol-4-one product.

To a mixture of 2-alkylsulfanyl-thiazol-4-one (2.71 mmol) and the appropriate cyclic amine (2.71 mmol) was added EtOH (15 mL). The suspension was heated at 65° C. for 16 h. The reaction was cooled to RT and the solvent concentrated in vacuo. Silica gel chromatography (MeOH/DCM) or reverse phase HPLC afforded the desired pure 2-cyclic amino-thiazol-4-one product.

To a mixture of 2-cyclic amino-thiazol-4-one (0.18 mmol) and aldehyde from Procedure A (0.18 mmol) was added acetic acid (1.0 mL) and $NH_4OAc$ (0.1 mmol). The suspension was heated at 100° C. (aluminum heating block) for 16 h and then diluted with water. The product was collected by filtration and purified using Silica gel chromatography or reverse phase HPLC to afford the desired pure product.

General Procedure F:

To a solution of an appropriate 5-[1-(4-bromo-2-substituted-benzyl)-1H-indazol-5-ylmethylene]-2-(cyclic amino)-thiazol-4-one (0.053 mmol), an appropriate substituted boronic acid (0.074 mmol), potassium phosphate (0.24 mmol) and tricyclohexylphosphonium tetrafluoroborate (7 mg, 0.019 mmol) in toluene (1.5 mL) and water (70 µL) was added palladium acetate (2 mg, 0.003 mmol). The mixture was stirred at 100° C. under nitrogen atmosphere for 3 h and partitioned between water and ethyl acetate. The organic phase was dried over $Na_2SO_4$ and concentrated in vacuo. Silica gel chromatography (DCM/EtOAc/MeOH) or reverse phase HPLC afforded the desired pure 2-cyclic amino-thiazol-4-one product.

General Procedure G:

To a solution of an appropriate 5-[1-(4-substituted-2-bromo)-1H-indazol-5-ylmethylene]-2-(cyclic amino)-thiazol-4-one (0.053 mmol), an appropriate substituted boronic acid (0.074 mmol), potassium phosphate (0.24 mmol) and tricyclohexylphosphonium tetrafluoroborate (7 mg, 0.019 mmol) in toluene (1.5 mL) and water (70 μL) was added palladium acetate (2 mg, 0.003 mmol). The mixture was stirred at 100° C. under nitrogen atmosphere for 3 h and partitioned between water and ethyl acetate. The organic phase was dried over $Na_2SO_4$ and concentrated in vacuo. Silica gel chromatography (DCM/EtOAc/MeOH) or reverse phase HPLC afforded the desired pure 2-cyclic amino-thiazol-4-one product.

General Procedure H:

Deprotection of t-Butyl Carbamate BOC tBuOC(O)N using trifluoroacetic acid.

The BOC intermediate (1 mmol) was treated with TFA/DCM (0.3; 0.7 v/v). The mixture was stirred at room temperature for 2-4 hr and concentrated in vacuo. The residue was partitioned between EtOAc and a saturated aqueous $NaHCO_3$ solution. The organic phase was dried and evaporated to afford the desired product. Silica gel chromatography (DCM/EtOAc/MeOH) or reverse phase HPLC afforded the desired pure 2-cyclic amino-thiazol-4-one product.

General Procedure I:

Deprotection of t-Butyl Carbamate BOC tBuOC(O)N using HCl

A solution of BOC intermediate (0.05 mmol) in MeOH (2 mL) and THF (1 mL) was treated with 4.0N HCl in 1,4-dioxane (2.5 mL) and stirred at room temperature for 12 hours. The solvent was removed in vacuo and the residue recrystallized from methanol/diethyl ether to yield the desired product Silica gel chromatography (DCM/EtOAc/MeOH) or reverse phase HPLC afforded the desired pure 2-cyclic amino-thiazol-4-one product.

Example 1

1-{5-[1-(2,4-Bis-trifluoromethyl-benzyl)-1H-indazol-5-ylmethylene]-4-oxo-4,5-dihydro-thiazol-2-yl}-piperidine-4-carboxylic acid

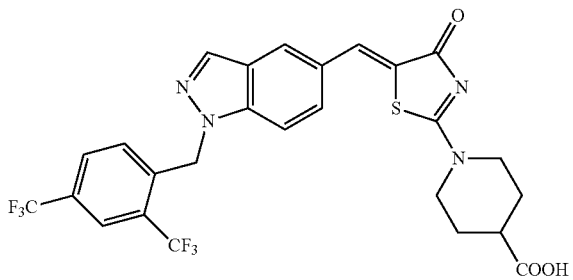 [SMILES: O=C1N=C(N2CCC(C(=O)O)CC2)S/C1=C\c1ccc2c(cnn2Cc2ccc(C(F)(F)F)cc2C(F)(F)F)c1]

A. 1-(2,4-Bis-trifluoromethyl-benzyl)-1H-indazole-5-carbaldehyde was prepared from 1H-Indazole-5-carbaldehyde and 1-bromomethyl-2,4-bis-trifluoromethyl-benzene following General Procedure A.

$^1$H NMR (400 MHz, $CDCl_3$): δ 10.08 9s, 1H), 8.34 (s, 1H), 8.31 (s, 1H), 7.99 (s, 1H), 7.95 (dd, 1H), 7.63 (d, 1H), 7.37 (d, 1H), 6.82 (d, 1H), 5.91 (s, 2H).

LC/MS: mass calcd. for $C_{17}H_{10}F_6N_2O$: 372.07. found 373.2 $[M+H]^+$.

B. 5-[1-(2,4-Bis-trifluoromethyl-benzyl)-1H-indazol-5-ylmethylene]-2-thioxo-thiazolidin-4-one was prepared from 1-(2,4-Bis-trifluoromethyl-benzyl)-1H-indazole-5-carbaldehyde and 2-thioxo-thiazolidin-4-one following General Procedure C.

LC/MS: mass calcd. for $C_{20}H_{11}F_6N_4OS_2$ (m/z), 487.0. found, 488.1 $[M+H]^+$.

C. 5-[1-(2,4-Bis-trifluoromethyl-benzyl)-1H-indazol-5-ylmethylene]-2-ethylsulfanyl-thiazol-4-one was prepared from 5-[1-(2,4-Bis-trifluoromethyl-benzyl)-1H-indazol-5-ylmethylene]-2-thioxo-thiazolidin-4-one and iodoethane following General Procedure C.

$^1$H NMR (400 MHz, $CDCl_3$): δ 8.24 (s, 1H), 7.98-8.01 (3H), 7.63 (d, 1H), 7.55 (dd, 1H), 7.34 (d, 1H), 6.83 (d, 1H), 5.89 (s, 2H), 3.46 (q, 2H), 1.50 (t, 3H).

LC/MS: mass calcd. for $C_{22}H_{15}F_6N_3OS_2$ (m/z), 515.1. found, 516.1 $[M+H]^+$.

D. 1-{5-[1-(2,4-Bis-trifluoromethyl-benzyl)-1H-indazol-5-ylmethylene]-4-oxo-4,5-dihydro-thiazol-2-yl}piperidine-4-carboxylic acid was prepared from 5-[1-(2,4-Bis-trifluoromethyl-benzyl)-1H-indazol-5-ylmethylene]-2-ethylsulfanyl-thiazol-4-one and piperidine-4-carboxylic acid following General Procedure C.

$^1$H NMR (400 MHz, $CD_3OD$): δ 8.25 (d, 1H), 8.08 (m, 1H), 8.05 (s, 1H), 7.81 (s, 1H), 7.78 (d, 1H), 7.64 (dd, 1H), 7.56 (d, 1H), 6.85 (d, 1H), 5.95 (s, 2H), 4.57 (m, 1H), 3.92 (m, 1H), 3.56 (m, 1H), 3.49 (m, 1H), 2.75 (m, 1H), 2.12 (m, 2H), 1.82 (m, 2H).

LC/MS: mass calcd. for $C_{26}H_{20}F_6N_4O_3S$ (m/z), 582.1. found, 583.3 $[M+H]^+$.

Example 2

5-[1-(2,4-Bis-trifluoromethyl-benzyl)-1H-indazol-5-ylmethylene]-2-(4-methyl-piperazin-1-yl)-thiazol-4-one

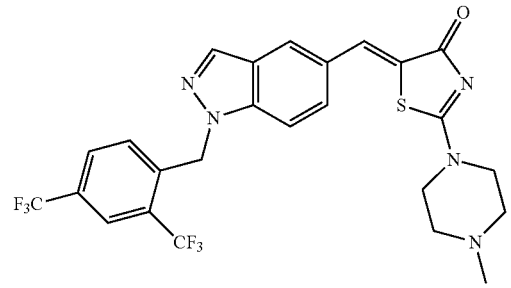 [SMILES: CN1CCN(C2=NC(=O)/C(=C/c3ccc4c(cnn4Cc4ccc(C(F)(F)F)cc4C(F)(F)F)c3)S2)CC1]

5-[1-(2,4-Bis-trifluoromethyl-benzyl)-1H-indazol-5-ylmethylene]-2-(4-methyl-piperazin-1-yl)-thiazol-4-one was prepared from 5-[1-(2,4-Bis-trifluoromethyl-benzyl)-1H-indazol-5-ylmethylene]-2-methylsulfanyl-thiazol-4-one and 1-methyl-piperazine following General Procedure C.

$^1$H NMR (400 MHz, $CD_3OD$): δ 8.28 (s, 1H), 8.15 (s, 1H), 8.06 (s, 1H), 7.96 (s, 1H), 7.80 (d, 1H), 7.69 (dd, 1H), 7.60 (d, 1H), 6.88 (d, 1H), 5.98 (s, 2H), 4.22 (br, 2H), 3.86 (br, 2H), 3.69 (br, 4H), 3.01 (s, 3H).

LC/MS: mass calcd. for $C_{25}H_{21}F_6N_5OS$ (m/z), 553.1. found, 554.4 [M+H]$^+$.

Example 3

5-[1-(2,4-Bis-trifluoromethyl-benzyl)-1H-indazol-5-ylmethylene]-2-morpholin-4-yl-thiazol-4-one

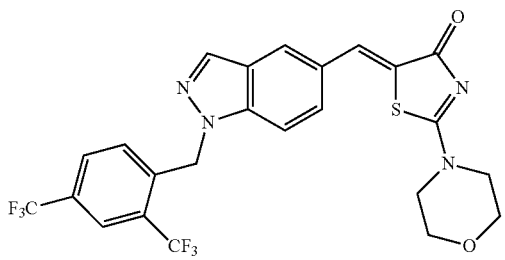 [SMILES: O=C1N=C(N2CCOCC2)S/C1=C\c1ccc2c(cnn2Cc2ccc(C(F)(F)F)cc2C(F)(F)F)c1]

5-[1-(2,4-Bis-trifluoromethyl-benzyl)-1H-indazol-5-ylmethylene]-2-morpholin-4-yl-thiazol-4-one was prepared from 5-[1-(2,4-Bis-trifluoromethyl-benzyl)-1H-indazol-5-ylmethylene]-2-methylsulfanyl-thiazol-4-one and morpholine following General Procedure C.

$^1$H NMR (400 MHz, CDCl$_3$): δ 8.21 (s, 1H), 7.99 (s, 2H), 7.96 (s, 1H), 7.63 (d, 1H), 7.56 (dd, 1H), 7.32 (d, 1H), 6.83 (d, 1H), 5.89 (s, 2H), 4.11 (t, 2H), 3.86 (t, 2H), 3.83 (t, 2H), 3.66 (t, 2H).

LC/MS: mass calcd. for $C_{24}H_{16}F_6N_4OS$ (m/z), 540.1. found, 541.4 [M+H]$^+$.

Example 4

5-[1-(4-Fluoro-2-trifluoromethyl-benzyl)-1H-indazol-5-ylmethylene]-2-[4-(2-hydroxy-ethyl)-piperazin-1-yl]-thiazol-4-one

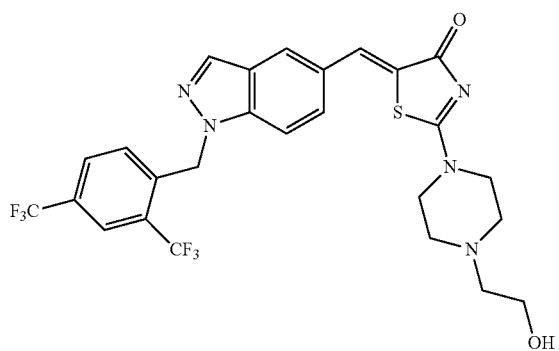 [SMILES: O=C1N=C(N2CCN(CCO)CC2)S/C1=C\c1ccc2c(cnn2Cc2ccc(C(F)(F)F)cc2C(F)(F)F)c1]

A. 1-(4-Fluoro-2-trifluoromethyl-benzyl)-1H-indazole-5-carbaldehyde was prepared following General Procedure A.

$^1$H NMR (400 MHz, CDCl$_3$): δ 10.09 (s, 1H), 8.34 (s, 1H), 8.30 (s, 1H), 7.96 (dd, 1H), 7.47 (dd, 1H), 7.40 (d, 1H), 6.77 (dd, 1H), 5.86 (s, 2H).

LC/MS: mass calcd. for $C_{16}H_{10}F_4N_2O$ (m/z), 322.2. found, 323.3 [M+H]$^+$.

B. 5-[1-(4-Fluoro-2-trifluoromethyl-benzyl)-1H-indazol-5-ylmethylene]-2-[4-(2-hydroxy-ethyl)-piperazin-1-yl]-thiazol-4-one was prepared from 1-(4-Fluoro-2-trifluoromethyl-benzyl)-1H-indazole-5-carbaldehyde and 2-piperazin-1-yl-ethanol following General Procedure C.

$^1$H NMR (400 MHz, CDCl$_3$): δ 8.21 (s, 1H), 8.00 (s, 1H), 7.96 (s, 1H), 7.57 (dd, 1H), 7.46 (dd, 1H), 7.35 (d, 1H), 7.09 (m, 1H), 6.77 (m, 1H), 5.81 (s, 2H), 4.14 (t, 2H), 3.68-3.74 (4H), 2.65-2.75 (6H), 2.40 (t, 1H).

LC/MS: mass calcd. for $C_{25}H_{23}F_4N_5O_2S$ (m/z), 533.2. found, 534.4 [M+H]$^+$.

Example 5

2-(4-Acetyl-piperazin-1-yl)-5-[1-(4-fluoro-2-trifluoromethyl-benzyl)-1H-indazol-5-ylmethylene]-thiazol-4-one

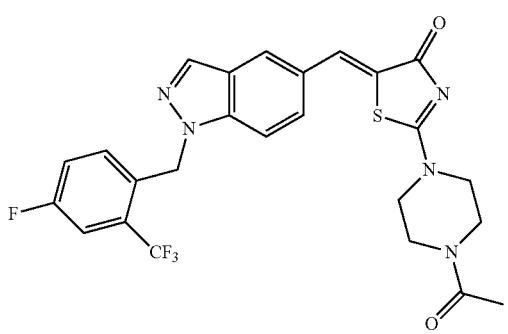 [SMILES: CC(=O)N1CCN(C2=NC(=O)/C(=C/c3ccc4c(cnn4Cc4ccc(F)cc4C(F)(F)F)c3)S2)CC1]

2-(4-Acetyl-piperazin-1-yl)-5-[1-(4-fluoro-2-trifluoromethyl-benzyl)-1H-indazol-5-ylmethylene]-thiazol-4-one was prepared from 5-[1-(4-fluoro-2-trifluoromethyl-benzyl)-1H-indazol-5-ylmethylene]-2-methylsulfanyl-thiazol-4-one and 1-piperazin-1-yl-ethanone following General Procedure C.

$^1$H NMR (400 MHz, CDCl$_3$): δ 8.12 (s, 1H), 7.91 (s, 1H), 7.47 (dd, 1H), 7.37 (dd, 1H), 7.27 (d, 1H), 7.00 (m, 1H), 6.68 (m, 1H), 5.72 (s, 2H), 4.05 9t, 1H), 4.01 (m, 1H), 3.76 (t, 1H), 3.72 (m, 1H), 3.54-3.62 (4H), 2.11 (s, 3H).

LC/MS: mass calcd. for $C_{25}H_{21}F_4N_5O_2S$ (m/z), 531.1. found, 532.4 [M+H]$^+$.

Example 6

5-[1-(2,4-Bis-trifluoromethyl-benzyl)-1H-indazol-5-ylmethylene]-2-[4-(2-hydroxy-ethyl)-piperazin-1-yl]-thiazol-4-one

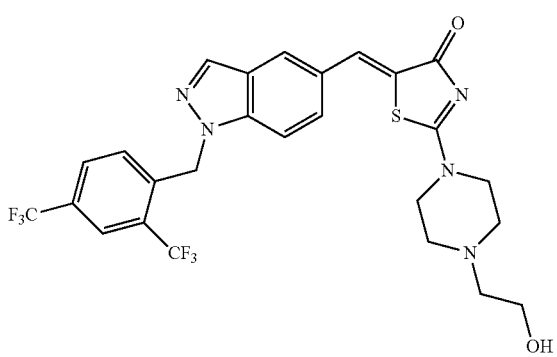 [SMILES: O=C1N=C(N2CCN(CCO)CC2)S/C1=C\c1ccc2c(cnn2Cc2ccc(C(F)(F)F)cc2C(F)(F)F)c1]

5-[1-(2,4-Bis-trifluoromethyl-benzyl)-1H-indazol-5-ylmethylene]-2-[4-(2-hydroxy-ethyl)-piperazin-1-yl]-thiazol-4-one was prepared from 5-[1-(2,4-Bis-trifluoromethyl-benzyl)-1H-indazol-5-ylmethylene]-2-methylsulfanyl-thiazol-4-one and 2-piperazin-1-yl-ethanol following General Procedure C.

$^1$H NMR (400 MHz, CDCl$_3$): δ 8.24 (s, 1H), 8.01 (s, 1H), 7.96 (s, 1H), 7.65 (d, 1H), 7.58 (dd, 1H), 7.34 (d, 1H), 6.84 (d, 1H), 5.91 (s, 2H), 4.15 (t, 2H), 3.72 (m, 4H), 2.75 (t, 2H), 2.69 (m, 4H).

LC/MS: mass calcd. for C$_{26}$H$_{23}$F$_6$N$_5$O$_2$S (m/z), 583.2. found, 584.4 [M+H]$^+$ Example 7

5-[1-(2,4-Bis-trifluoromethyl-benzyl)-1H-indazol-5-ylmethylene]-2-piperazin-1-yl-thiazol-4-one

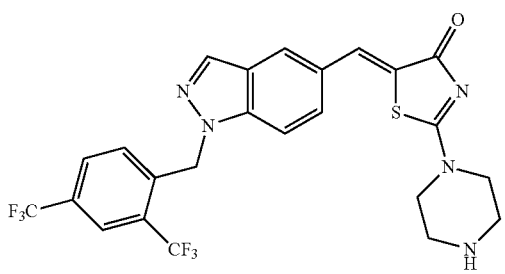 [SMILES: O=C1N=C(N2CCNCC2)S/C1=C\c1ccc2c(cnn2Cc2ccc(C(F)(F)F)cc2C(F)(F)F)c1]

5-[1-(2,4-Bis-trifluoromethyl-benzyl)-1H-indazol-5-ylmethylene]-2-piperazin-1-yl-thiazol-4-one was prepared from 5-[1-(2,4-Bis-trifluoromethyl-benzyl)-1H-indazol-5-ylmethylene]-2-methylsulfanyl-thiazol-4-one and piperazine following General Procedure C.

$^1$H NMR (400 MHz, CD$_3$OD): δ 8.28 (d, 1H), 8.14 (d, 1H), 8.05 (s, 1H), 7.88 (s, 1H), 7.79 (dd, 1H), 7.69 (dd, 1H), 7.59 (d, 1H), 6.87 (d, 1H), 5.98 (s, 2H), 3.99 (t, 2H), 3.69 (t, 2H), 3.00 (t, 2H), 2.95 (t, 2H).

LC/MS: mass calcd. for C$_{24}$H$_{19}$F$_6$N$_5$O$_2$S (m/z), 539.1. found, 540.2 [M+H]$^+$.

Example 8

5-[1-(4-Chloro-2-trifluoromethyl-benzyl)-1H-indazol-5-ylmethylene]-2-(4-methyl-piperazin-1-yl)-thiazol-4-one

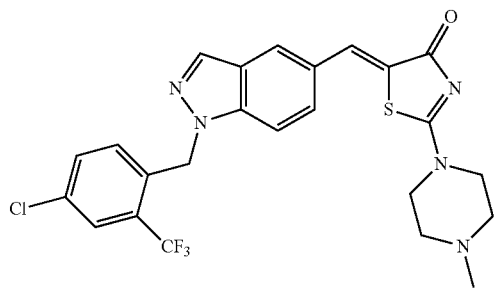

A. 1-(4-Chloro-2-trifluoromethyl-benzyl)-1H-indazole-5-carbaldehyde was prepared from 1H-indazole-5-carbaldehyde and 1-bromomethyl-4-chloro-2-trifluoromethyl-benzene following General Procedure A.

LC/MS: mass calcd. for C$_{16}$H$_{10}$ClF$_3$N$_2$O (m/z), 338.71. found, 339.1 [M+H]$^+$.

B. 5-[1-(4-Chloro-2-trifluoromethyl-benzyl)-1H-indazol-5-ylmethylene]-2-(4-methyl-piperazin-1-yl)-thiazol-4-one was prepared from 1-(4-Chloro-2-trifluoromethyl-benzyl)-1H-indazole-5-carbaldehyde and 1-methyl-piperazine following General Procedure C.

$^1$H NMR (400 MHz, CDCl$_3$): δ 8.18 (d, 1H), 7.97 (m, 1H), 7.93 (s, 1H), 7.71 (d, 1H), 7.54 (dd, 1H), 7.29-7.35 (2H), 6.66 (d, 1H), 5.79 (s, 2H), 4.09 (t, 2H), 3.66 (t, 2H), 2.58 (t, 2H), 2.54 (t, 2H), 2.37 (s, 3H).

LC/MS: mass calcd. for C$_{24}$H$_{21}$ClF$_3$N$_5$OS (m/z), 519.1. found, 520.3 [M+H]$^+$.

Example 9

4-(5-{2-[4-(2-Hydroxy-ethyl)-piperazin-1-yl]-4-oxo-4H-thiazol-5-ylidenemethyl}-indazol-1-ylmethyl)-3-trifluoromethyl-benzonitrile

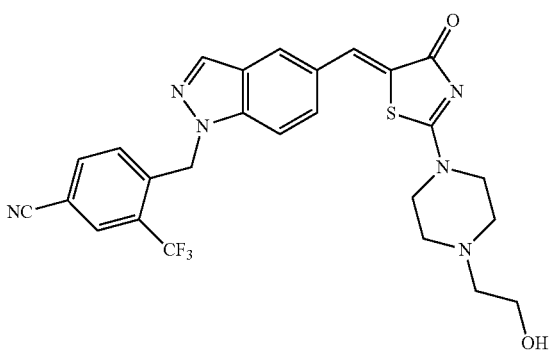 [SMILES: N#Cc1ccc(Cn2ncc3cc(/C=C4\SC(N5CCN(CCO)CC5)=NC4=O)ccc32)c(C(F)(F)F)c1]

A. 4-Bromomethyl-3-trifluoromethyl-benzonitrile

A mixture of 4-methyl-3-trifluoromethyl-benzonitrile (370 mg, 2 mmol), N-Bromosuccinimide (356 mg, 2 mmol) and benzoyl peroxide (15 mg) in CCl$_4$ (8 mL) was stirred at 85° C. for 16 hrs. The reaction mixture was then partitioned between saturated aqueous NaHCO$_3$ and DCM. DCM layer was dried over Na$_2$SO$_4$, filtered, and the solvent evaporated in vacuo to yield a crude solid which was purified via flash chromatography (15% EtOAc in n-heptane) to yield the title compound as a solid (460 mg, 85%).

$^1$H NMR (400 MHz, CDCl$_3$): δ 7.95 (s, 1H), 7.86 (dd, 1H), 7.77 (dd, 1H), 4.63 (s, 2H).

B. 4-(5-Formyl-indazol-1-ylmethyl)-3-trifluoromethyl-benzonitrile was prepared from 4-bromomethyl-3-trifluoromethyl-benzonitrile and 1H-indazole-5-carbaldehyde following General Procedure A.

LC/MS: mass calcd. for C$_{17}$H$_{10}$F$_3$N$_3$O (m/z), 329.2. found, 330.2 [M+H]$^+$.

C. 4-(5-{2-[4-(2-Hydroxy-ethyl)-piperazin-1-yl]-4-oxo-4H-thiazol-5-ylidenemethyl}-indazol-1-ylmethyl)-3-trifluoromethyl-benzonitrile was prepared from 4-(5-Formyl-indazol-1-ylmethyl)-3-trifluoromethyl-benzonitrile and 2-piperazin-1-yl-ethanol following General Procedure C.

$^1$H NMR (400 MHz, CDCl$_3$): δ 8.22 (d, 1H), 8.02 (br, 1H), 7.99 (m, 1H), 7.94 (s, 1H), 7.65 (dd, 1H), 7.56 (dd, 1H), 7.31 (d, 1H), 6.80 (d, 1H), 5.88 (s, 2H), 4.12 (t, 2H), 3.69 (m, 4H), 2.72 (t, 2H), 2.66 (m, 4H).

LC/MS: mass calcd. for $C_{26}H_{23}F_3N_6O_2S$ (m/z), 540.2. found, 541.4 [M+H]$^+$.

Example 10

4-{5-[2-(4-Methyl-piperazin-1-yl)-4-oxo-4H-thiazol-5-ylidenemethyl]-indazol-1-ylmethyl}-3-trifluoromethyl-benzonitrile

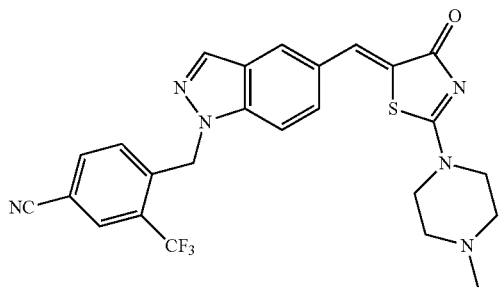

4-{5-[2-(4-Methyl-piperazin-1-yl)-4-oxo-4H-thiazol-5-ylidenemethyl]-indazol-1-ylmethyl}-3-trifluoromethyl-benzonitrile was prepared from 4-[5-(2-methylsulfanyl-4-oxo-4H-thiazol-5-ylidenemethylyindazol-1-ylmethyl]-3-trifluoromethyl-benzonitrile and 1-methyl-piperazine following General Procedure C.

$^1$H NMR (400 MHz, CDCl$_3$): δ 8.21 (d, 1H), 8.02 (br, 1H), 7.99 (m, 1H), 7.93 (s, 1H), 7.65 (dd, 1H), 7.57 (dd, 1H), 7.30 (d, 1H), 6.80 (d, 1H), 5.88 (s, 2H), 4.10 (t, 2H), 3.67 (t, 2H), 2.58 (t, 2H), 2.55 (t, 2H), 2.37 (s, 3H).

LC/MS: mass calcd. for $C_{25}H_{21}F_3N_6OS$ (m/z), 510.1. found, 511.4 [M+H]$^+$.

Example 11

1-{5-[1-(4-Chloro-2-trifluoromethyl-benzyl)-1H-indazol-5-ylmethylene]-4-oxo-4,5-dihydro-thiazol-2-yl}-4-(R)-hydroxy-pyrrolidine-2-(S)-carboxylic acid

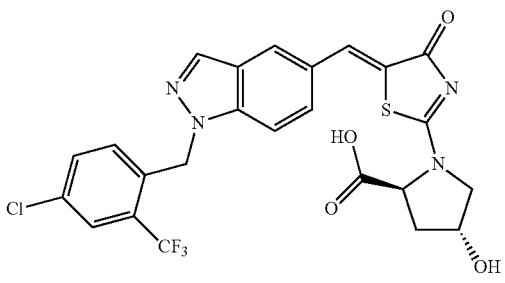 [SMILES: O=C1N=C(N2C[C@H](O)C[C@H]2C(=O)O)S/C1=C\c1ccc2c(cnn2Cc2ccc(Cl)cc2C(F)(F)F)c1]

1-{5-[1-(4-Chloro-2-trifluoromethyl-benzyl)-1H-indazol-5-ylmethylene]-4-oxo-4,5-dihydro-thiazol-2-yl}-4-(R)-hydroxy-pyrrolidine-2-(S)-carboxylic acid was prepared from 5-[1-(4-chloro-2-trifluoromethyl-benzyl)-1H-indazol-5-ylmethylene]-2-methylsulfanyl-thiazol-4-one and 4-(R)-hydroxy-pyrrolidine-2-(S)-carboxylic acid following General Procedure C.

$^1$H NMR (400 MHz, CD$_3$OD): δ 8.24 (s, 1H), 8.05 (d, 1H), 7.82 (d, 1H), 7.78 (m, 1H), 7.63 (dd, 1H), 7.55 (m, 1H), 7.47 (dd, 1H), 6.67 (d, 1H), 5.84 (s, 2H), 4.60 (m, 1H), 3.91-4.05 (1H), 3.70 (m, 1H), 2.27-2.55 (3H).

LC/MS: mass calcd. for $C_{24}H_{18}ClF_3N_4O_4S$ (m/z), 550.1. found, 551.3 [M+H]$^+$.

Example 12

4-{5-[1-(4-Chloro-2-trifluoromethyl-benzyl)-1H-indazol-5-ylmethylene]-4-oxo-4,5-dihydro-thiazol-2-yl}-piperazin-2-one

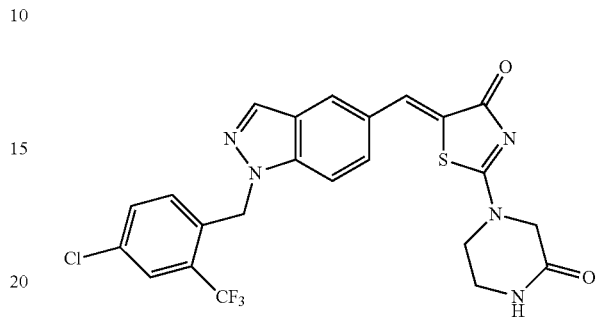

4-{5-[1-(4-Chloro-2-trifluoromethyl-benzyl)-1H-indazol-5-ylmethylene]-4-oxo-4,5-dihydro-thiazol-2-yl}-piperazin-2-one was prepared from 5-[1-(4-chloro-2-trifluoromethyl-benzyl)-1H-indazol-5-ylmethylene]-2-methylsulfanyl-thiazol-4-one and piperazin-2-one following General Procedure C.

$^1$H NMR (400 MHz, CDCl$_3$): δ 8.21 (br, 1H), 7.98 (s, 2H), 7.72 (d, 1H), 7.54 (d, 1H), 7.34 (d, 1H), 6.68 (d, 1H), 5.80 (s, 2H), 4.28-4.33 (3H), 3.88 (m, 1H), 3.56-3.65 (m, 2H).

LC/MS: mass calcd. for $C_{23}H_{17}ClF_3N_5O_2S$ (m/z), 519.1. found, 520.1 [M+H]$^+$.

Example 13

5-[1-(4-Chloro-2-trifluoromethyl-benzyl)-1H-indazol-5-ylmethylene]-2-[4-(2-hydroxy-ethyl)piperazin-1-yl]-thiazol-4-one

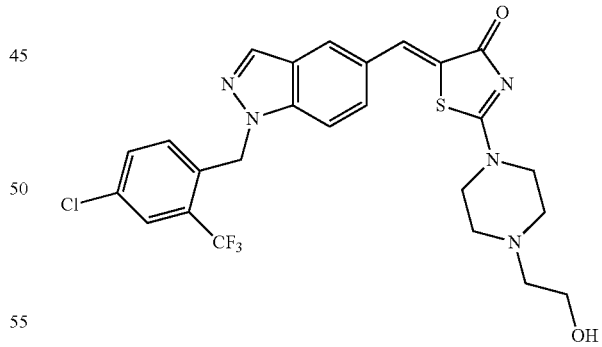

5-[1-(4-Chloro-2-trifluoromethyl-benzyl)-1H-indazol-5-ylmethylene]-2-[4-(2-hydroxy-ethyl)-piperazin-1-yl]-thiazol-4-one was prepared from 5-[1-(4-chloro-2-trifluoromethyl-benzyl)-1H-indazol-5-ylmethylene]-2-methylsulfanyl-thiazol-4-one and 2-piperazin-1-yl-ethanol following General Procedure C.

$^1$H NMR (400 MHz, CD$_3$OD): δ 8.21 (d, 1H), 8.08 (br, 1H), 7.92 (s, 1H), 7.79 (d, 1H), 7.63 (dd, 1H), 7.52 (d, 1H), 7.47 (dd, 1H), 6.69 (d, 1H), 5.82 (s, 2H), 4.17 (br, 2H), 3.95 (t, 2H), 3.81 (br, 2H), 3.41 (t, 2H).

LC/MS: mass calcd. for $C_{25}H_{23}ClF_3N_5O_2S$ (m/z), 549.1. found, 550.2 $[M+H]^+$.

Example 14

5-[1-(2,4-Dichloro-benzyl)-1H-indazol-5-ylmethylene]-2-[4-(2-hydroxy-ethyl)-piperazin-1-yl]thiazol-4-one

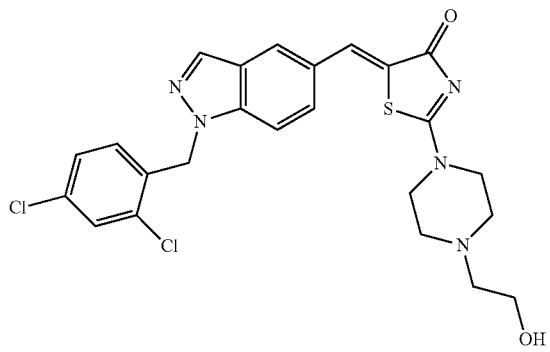 [SMILES: O=C1N=C(N2CCN(CCO)CC2)S/C1=C\c1ccc2c(cnn2Cc2ccc(Cl)cc2Cl)c1]

A. 1-(2,4-Dichloro-benzyl)-1H-indazole-5-carbaldehyde was prepared from 1H-indazole-5-carbaldehyde and 1-bromomethyl-2,4-dichloro-benzene following General Procedure A.

LC/MS: mass calcd. for $C_{15}H_{10}Cl_2N_2O$ (m/z), 305.1. found, 305.1 $[M+H]^+$.

B. 5-[1-(2,4-Dichloro-benzyl)-1H-indazol-5-ylmethylene]-2-[4-(2-hydroxy-ethyl)-piperazin-1-yl]-thiazol-4-one was prepared from 1-(2,4-Dichloro-benzyl)-1H-indazole-5-carbaldehyde and 2-piperazin-1-yl-ethanol following General Procedure C.

$^1$H NMR (400 MHz, CD$_3$OD): δ 8.16 (s, 1H), 8.03 (s, 1H), 7.91 (s, 1H), 7.60 (s, 2H), 7.51 (s, 1H), 7.23 (dd, 1H), 6.85 (d, 1H), 4.86 (br, 1H), 4.20 (br, 1H), 3.97 (t, 2H), 3.85 (br, 2H), 3.42 (t, 2H).

LC/MS: mass calcd. for $C_{24}H_{23}Cl_2N_5O_2S$ (m/z), 515.1. found, 516.2 $[M+H]^+$.

Example 15

5-[1-(4-Methanesulfonyl-2-trifluoromethyl-benzyl)-1H-indazol-5-ylmethylene]-2-(4-methyl-piperazin-1-yl)-thiazol-4-one

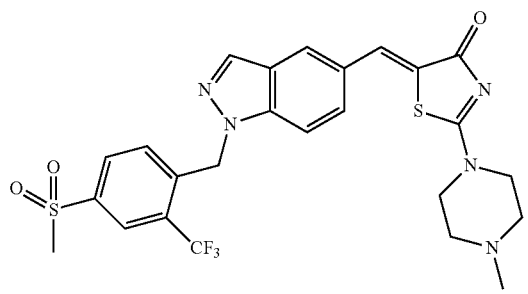 [SMILES: CN1CCN(C2=NC(=O)/C(=C/c3ccc4c(cnn4Cc4ccc(S(C)(=O)=O)cc4C(F)(F)F)c3)S2)CC1]

A. 4-Methylsulfanyl-2-trifluoromethyl-benzaldehyde

To a DMF solution (5 mL) containing 935.3 mg (4.87 mmol) of 4-fluoro-2-(trifluoromethyl)benzaldehyde was added sodium thiomethoxide (414.2 mg, 5.84 mmol). The mixture was stirred at 90° C. for 2 h, partitioned between EtOAc and water. The EtOAc extracts were washed with brine, dried over Na$_2$SO$_4$ and evaporated to afford desired product.

$^1$H NMR (400 MHz, CDCl$_3$): δ 10.30 (s, 1H), 8.05 (d, 1H), 7.54 (s, 1H), 7.46 (d, 1H), 2.58 (s, 3H).

B. (4-Methylsulfanyl-2-trifluoromethyl-phenyl)-methanol

4-Methylsulfanyl-2-trifluoromethyl-benzaldehyde (4.87 mmol) was dissolved in 5 mL of MeOH and the resulting solution was treated with NaBH$_4$ (221.1 mg, 5.84 mmol). The reaction mixture was stirred at room temperature for 2 h. The solvent was evaporated and the residue was partitioned between CH$_2$Cl$_2$ and 1N HCl solution. The combined extracts were washed with brine, dried over Na$_2$SO$_4$. A small portion of extracts was evaporated to afford the desired product.

$^1$H NMR (400 MHz, CDCl$_3$): δ 7.59 (d, 1H), 7.48 (d, 1H), 7.40 (dd, 1H), 4.80 (d, 2H), 2.51 (s, 3H).

C. (4-Methanesulfonyl-2-trifluoromethyl-phenyl)-methanol (4-Methylsulfanyl-2-trifluoromethyl-phenyl)-methanol (4.87 mmol) was dissolved in 40 mL of CH$_2$Cl$_2$ and the resulting solution was treated with mCPBA (~69.9% w/w mCPBA, 2.4 g). The reaction mixture was stirred overnight at room temperature. The excess mCPBA was quenched with aq. Na$_2$S$_2$O$_3$. The CH$_2$Cl$_2$ extracts were washed with 1N NaOH three times. The organic solvents were dried over Na$_2$SO$_4$ and evaporated to afford the desired product.

$^1$H NMR (400 MHz, CDCl$_3$): δ 8.20 (s, 1H), 8.15 (dd, 1H), 8.07 (d, 1H), 5.01 (d, 2H), 3.09 (s, 3H).

D. 1-Bromomethyl-4-methanesulfonyl-2-trifluoromethyl-benzene (4-Methanesulfonyl-2-trifluoromethyl-phenyl)-methanol (4.87 mmol) was dissolved in 40 mL of CH$_2$Cl$_2$ and the resulting solution was treated with PBr$_3$ (1 N, 4.87 mL) at 0° C. for 4 h. The mixture was partitioned between CH$_2$Cl$_2$ and water. The combined CH$_2$Cl$_2$ extracts were washed with brine, dried and evaporated. The residue was purified by flash column chromatography on silica gel (heptane/EtOAc 3:1 v/v) to afford white crystals (1.24 g, 80%).

$^1$H NMR (400 MHz, CDCl$_3$): δ 8.23 (s, 1H), 8.13 (dd, 1H), 7.25 (d, 1H), 4.66 (s, 2H), 3.11 (s, 3H).

E. 1-(4-Methanesulfonyl-2-trifluoromethyl-benzyl)-1H-indazole-5-carbaldehyde was prepared from 1H-indazole-5-carbaldehyde and 1-bromomethyl-4-methanesulfonyl-2-trifluoromethyl-benzene following General Procedure A.

$^1$H NMR (400 MHz, CDCl$_3$): δ 10.08 (s, 1H), 8.31-8.36 (3H), 7.97 (dd, 1H), 7.95 (dd, 1H), 7.38 (d, 1H), 6.91 (d, 1H), 5.94 (s, 2H), 3.06 (s, 3H).

F. 5-[1-(4-Methanesulfonyl-2-trifluoromethyl-benzyl)-1H-indazol-5-ylmethylene]-2-methylsulfanyl-thiazol-4-one was prepared from 5-[1-(4-Methanesulfonyl-2-trifluoromethyl-benzyl)-1H-indazol-5-ylmethylene]-2-thioxo-thiazolidin-4-one and methyl iodide following General Procedure C.

LC/MS: mass calcd. for $C_{21}H_{16}F_3N_3O_3S_3$ (m/z), 511.0. found, 512.1 $[M+H]^+$.

G. 5-[1-(4-Methanesulfonyl-2-trifluoromethyl-benzyl)-1H-indazol-5-ylmethylene]-2-(4-methyl-piperazin-1-yl)-thiazol-4-one was prepared from 5-[1-(4-methanesulfonyl-2-trifluoromethyl-benzyl)-1H-indazol-5-ylmethylene]-2-methylsulfanyl-thiazol-4-one and 1-methyl-piperazine following General Procedure C.

$^1$H NMR (400 MHz, CDCl$_3$): δ 8.31 (d, 1H), 8.22 (d, 1H), 7.99 (m, 1H), 7.91-7.95 (2H), 7.55 (d, 1H), 7.32 (d, 1H), 6.90 (d, 1H), 5.90 (s, 2H), 4.11 (m, 2H), 3.67 (m, 2H), 3.07 (s, 3H), 2.56 (m, 4H), 2.38 (s, 3H).

LC/MS: mass calcd. for $C_{25}H_{24}F_3N_5O_3S_2$ (m/z), 563.1. found, 564.2 [M+H]+.

Example 16

2-[4-(2-Hydroxy-ethyl)-piperazin-1-yl]-5-[1-(4-methanesulfonyl-2-trifluoromethyl-benzyl)-1H-indazol-5-ylmethylene]-thiazol-4-one

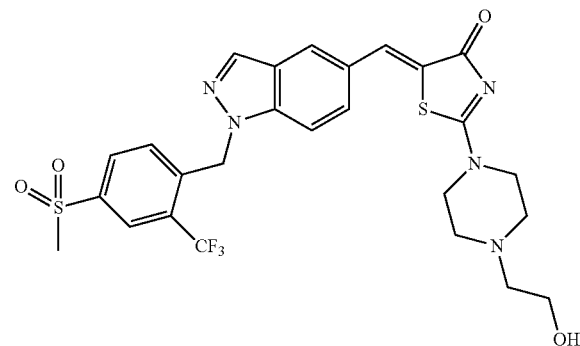 [SMILES: CS(=O)(=O)c1ccc(Cn2ncc3cc(/C=C4\SC(N5CCN(CCO)CC5)=NC4=O)ccc32)c(C(F)(F)F)c1]

2-[4-(2-Hydroxy-ethyl)-piperazin-1-yl]-5-[1-(4-methanesulfonyl-2-trifluoromethyl-benzyl)-1H-indazol-5-ylmethylene]-thiazol-4-one was prepared from 5-[1-(4-methanesulfonyl-2-trifluoromethyl-benzyl)-1H-indazol-5-ylmethylene]-2-methylsulfanyl-thiazol-4-one and 2-piperazin-1-yl-ethanol following General Procedure C.

1H NMR (400 MHz, CD3OD): δ 8.31 (br, 1H), 8.26 (s, 1H), 8.08 (m, 1H), 8.02 (d, 1H), 7.82 (s, 1H), 7.64 (d, 1H), 7.56 (d, 1H), 6.90 (d, 1H), 5.97 (s, 2H), 4.02 (m, 2H), 3.73 (m, 2H), 3.31 (m, 4H), 3.15 (s, 3H), 2.72 (t, 2H), 2.66 (t, 2H), 2.60 (t, 2H).

LC/MS: mass calcd. for $C_{26}H_{26}F_3N_5O_4S_2$ (m/z), 593.1. found, 594.2 [M+H]+.

Example 17

5-[1-(2-Chloro-4-methanesulfonyl-benzyl)-1H-indazol-5-ylmethylene]-2-(4-methyl-piperazin-1-yl)-thiazol-4-one

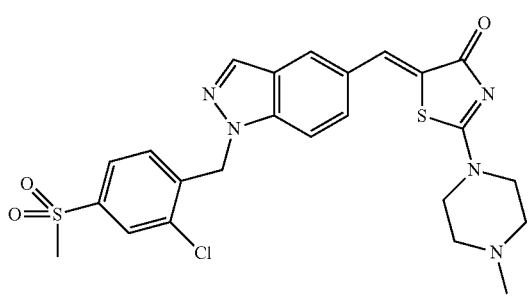 [SMILES: CN1CCN(C2=NC(=O)/C(=C/c3ccc4c(cnn4Cc4ccc(S(C)(=O)=O)cc4Cl)c3)S2)CC1]

5-[1-(2-Chloro-4-methanesulfonyl-benzyl)-1H-indazol-5-ylmethylene]-2-(4-methyl-piperazin-1-yl)-thiazol-4-one was prepared from 5-[1-(2-Chloro-4-methanesulfonyl-benzyl)-1H-indazol-5-ylmethylene]-2-methylsulfanyl-thiazol-4-one and 1-methyl-piperazine following General Procedure C.

1H NMR (400 MHz, CDCl3): δ 8.19 (d, 1H), 8.02 (d, 1H), 7.98 (m, 1H), 7.94 (s, 1H), 7.69 (dd, 1H), 7.58 (dd, 1H), 7.42 (d, 1H), 6.93 (d, 1H), 5.78 (s, 2H), 4.10 (t, 2H), 3.67 (t, 2H), 3.04 (s, 3H), 2.58 (t, 2H), 2.55 (t, 2H), 2.37 (s, 3H).

LC/MS: mass calcd. for $C_{24}H_{24}ClN_5O_3S_2$ (m/z), 529.1. found, 530.2 [M+H]+.

Example 18

4-{5-[1-(2-Chloro-4-methanesulfonyl-benzyl)-1H-indazol-5-ylmethylene]-4-oxo-4,5-dihydro-thiazol-2-yl}-piperazin-2-one 4-{5-[1-(2-Chloro-4-methanesulfonyl-benzyl)-1H-indazol-5-ylmethylene]-4-oxo-4,5-dihydro-thiazol-2-yl}-piperazin-2-one was prepared from 5-[1-(2-chloro-4-methanesulfonyl-benzyl)-1H-indazol-5-ylmethylene]-2-methylsulfanyl-thiazol-4-one and piperazin-2-one following General Procedure C.

1H NMR (400 MHz, CDCl3): δ 8.22 (s, 1H), 8.02 (d, 1H), 7.99 (s, 2H), 7.70 (dd, 1H), 7.58 (m, 1H), 7.45 (m, 1H), 6.94 (d, 1H), 5.79 (s, 2H), 4.30 (s, 2H), 3.88 (t, 1H), 3.64 (t, 1H), 3.59 (m, 2H), 3.04 (s, 3H).

LC/MS: mass calcd. for $C_{23}H_{20}ClN_5O_4S_2$ (m/z), 529.1. found, 530.3 [M+H]+.

Example 19

5-[1-(2-Chloro-4-methanesulfonyl-benzyl)-1H-indazol-5-ylmethylene]-2-[4-(2-hydroxy-ethyl)-piperazin-1-yl]-thiazol-4-one 5-[1-(2-Chloro-4-methanesulfonyl-benzyl)-1H-indazol-5-ylmethylene]-2-[4-(2-hydroxy-ethyl)-piperazin-1-yl]-thiazol-4-one was prepared from 5-[1-(2-chloro-4-methanesulfonyl-benzyl)-1H-indazol-5-ylmethylene]-2-methylsulfanyl-thiazol-4-one and 2-piperazin-1-yl-ethanol following General Procedure C.

1H NMR (400 MHz, CDCl3): δ 8.19 (d, 1H), 8.02 (d, 1H), 7.98 (m, 1H), 7.94 (s, 1H), 7.69 (dd, 1H), 7.58 (dd, 1H), 7.42

(d, 1H), 6.93 (d, 1H), 5.77 (s, 2H), 4.12 (t, 2H), 3.69 (m, 4H), 3.04 (s, 3H), 2.72 (t, 2H), 2.66 (m, 4H).

LC/MS: mass calcd. for $C_{25}H_{26}ClN_5O_4S_2$ (m/z), 559.1. found, 560.3 $[M+H]^+$.

Example 20

4-{5-[2-(4-Methyl-piperazin-1-yl)-4-oxo-4H-thiazol-5-ylidenemethyl]-indazol-1-ylmethyl}-3-trifluoromethyl-benzamide

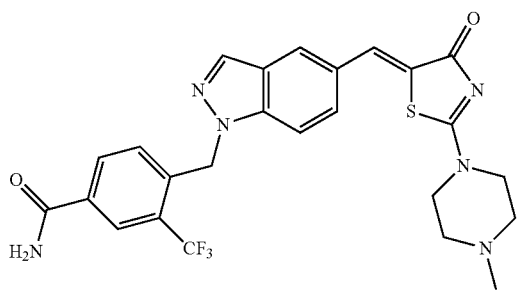 [SMILES: CN1CCN(C2=NC(=O)/C(=C/c3ccc4c(cnn4Cc4ccc(C(N)=O)cc4C(F)(F)F)c3)S2)CC1]

4-{5-[2-(4-Methyl-piperazin-1-yl)-4-oxo-4H-thiazol-5-ylidenemethyl]-indazol-1-ylmethyl}-3-trifluoromethyl-benzonitrile (Example 10) (15.2 mg, 0.03 mmol) was dissolved in 1 mL of concentrated HCl and the mixture was stirred at 45° C. for 5 h. It was neutralized with aqueous 2N NaOH and extracted with EtOAc. The EtOAc layer was dried over $Na_2SO_4$, filtered, and the solvent evaporated in vacuo to yield the desired product (10.8 mg, 68% yield).

$^1$H NMR (400 MHz, $CD_3OD$): δ 8.31 (m, 1H), 8.27 (s, 1H), 8.13 (s, 1H), 7.92 (dd, 1H), 7.87 (s, 1H), 7.67 (dd, 1H), 7.56 (d, 1H), 6.72 (d, 1H), 5.95 (s, 2H), 4.03 (t, 2H), 3.74 (t, 2H), 3.34 (s, 3H), 2.63 (t, 2H), 2.58 (t, 2H).

LC/MS: mass calcd. for $C_{25}H_{23}F_3N_6O_2S$ (m/z), 528.2. found, 529.3 $[M+H]^+$.

Example 21

5-[1-(4-Methoxy-2-trifluoromethyl-benzyl)-1H-indazol-5-ylmethylene]-2-(4-methyl-piperazin-1-yl)-thiazol-4-one

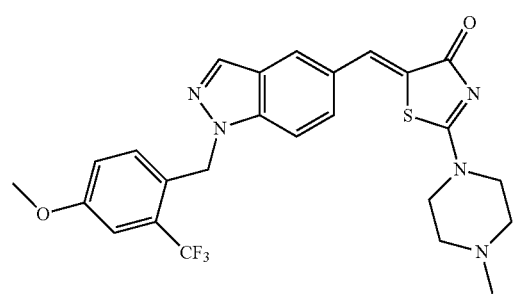 [SMILES: COc1ccc(Cn2ncc3cc(/C=C4\SC(N5CCN(C)CC5)=NC4=O)ccc32)c(C(F)(F)F)c1]

A. 1-Bromomethyl-4-methoxy-2-trifluoromethyl-benzene

A solution of (4-methoxy-2-trifluoromethyl-phenyl)-methanol (1.04 g, 5 mmol) in DCM (20 mL) was treated at 0° C. with phosphorous tribromide (1.64 g, 6 mmol). The reaction mixture was stirred for 10 minutes at 0° C., 1 h at room temperature. The solvent was evaporated in vacuo to yield a crude oil which was purified via flash chromatography (10% DCM in hexane) to yield the title compound as an oil (1.36 g, 100%)

LC/MS: mass calcd. for $C_6H_8BrF_3O$ (m/z), 269.06. found, 270 $[M+H]^+$.

B. 1-(4-Methoxy-2-trifluoromethyl-benzyl)-1H-indazole-5-carbaldehyde was prepared from 1-bromomethyl-4-methoxy-2-trifluoromethyl-benzene and 1H-indazole-5-carbaldehyde following General Procedure A.

LC/MS: mass calcd. for $C_{17}H_{13}F_3N_2O_2$ (m/z), 334.2. found, 335.2 $[M+H]^+$.

C. 5-[1-(4-Methoxy-2-trifluoromethyl-benzyl)-1H-indazol-5-ylmethylene]-2-(4-methyl-piperazin-1-yl)-thiazol-4-one was prepared from 1-(4-Methoxy-2-trifluoromethyl-benzyl)-1H-indazole-5-carbaldehyde and 1-methyl-piperazine following General Procedure C.

$^1$H NMR (400 MHz, $CD_3OD$): δ 8.22 (s, 1H), 8.12 (s, 1H), 7.94 (s, 1H), 7.63 (m, 1H), 7.52 (d, 1H), 7.27 (d, 1H), 7.00 (m, 1H), 6.72 (d, 1H), 5.79 (s, 2H), 3.81 (s, 3H), 3.20-3.70 (8H), 3.01 (s, 3H).

LC/MS: mass calcd. for $C_{25}H_{24}F_3N_5O_2S$ (m/z), 515.2. found, 516.1 $[M+H]^+$.

Example 22

5-[1-(4-Hydroxy-2-trifluoromethyl-benzyl)-1H-indazol-5-ylmethylene]-2-(4-methyl-piperazin-1-yl)-thiazol-4-one

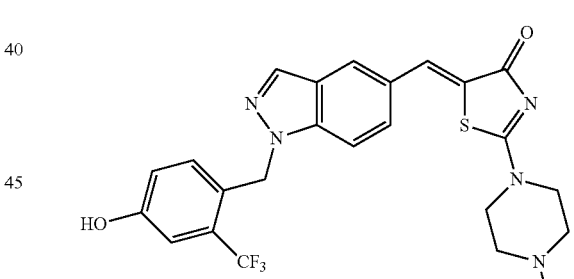

To a solution of 5-[1-(4-methoxy-2-trifluoromethyl-benzyl)-1H-indazol-5-ylmethylene]-2-(4-methyl-piperazin-1-yl)-thiazol-4-one (32 mg, 0.062 mmol) in $CH_2Cl_2$ (1 mL) was added 0.4 mL of 1M $BBr_3$ at −78° C. The mixture was stirred for 2 h at −78° C., then warmed up to room temperature. It was quenched with aqueous MeOH and $NaHCO_3$ solution, extracted with EtOAc. The combined organic extracts were evaporated and the residue was purified by flash column chromatography on silica gel (0-100% gradient $CH_2Cl_2$/EtOAc, followed by 10% MeOH/EtOAc) to afford the title compound (30 mg, 96%).

$^1$H NMR (400 MHz, $CD_3OD$): δ 8.21 (s, 1H), 8.10 (s, 1H), 7.87 (s, 1H), 7.64 (d, 1H), 7.50 (d, 1H), 7.14 (d, 1H), 6.82 (m, 1H), 6.61 (d, 1H), 5.75 (s, 2H), 4.07 (m, 2H), 3.77 (m, 2H), 2.73 (m, 2H), 2.69 (m, 2H), 2.44 (s, 3H).

LC/MS: mass calcd. for $C_{24}H_{22}F_3N_5O_2S$ (m/z), 501.1. found, 502.2 [M+H]⁺.

Example 23

Methanesulfonic acid 4-{5-[2-(4-methyl-piperazin-1-yl)-4-oxo-4H-thiazol-5-ylidenemethyl]-indazol-1-ylmethyl}-3-trifluoromethyl-phenyl ester

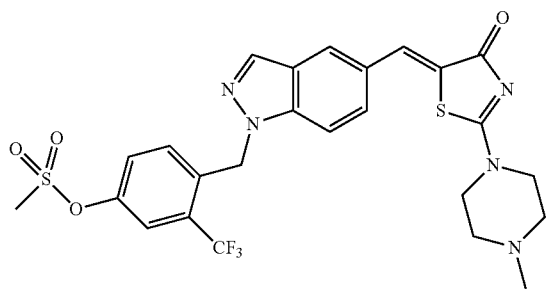 [SMILES: CN1CCN(C2=NC(=O)/C(=C/c3ccc4c(cnn4Cc4ccc(OS(C)(=O)=O)cc4C(F)(F)F)c3)S2)CC1]

To a solution of 5-[1-(4-hydroxy-2-trifluoromethyl-benzyl)-1H-indazol-5-ylmethylene]-2-(4-methyl-piperazin-1-yl)-thiazol-4-one (10 mg, 0.02 mmol) in 1 mL $CH_2Cl_2$ was added DIEA (7.7 mg, 0.06 mmol) and methanesulfonyl chloride (4 mg, 0.03 mmol). The mixture was stirred for 1 h and loaded onto a silica gel-packed column. The desired product was eluted with 0-100% gradient of $CH_2Cl_2$/EtOAc, followed by 10% MeOH/EtOAc (8.6 mg, 74%).

¹H NMR (400 MHz, CDCl₃): δ 8.20 (s, 1H), 7.97 (s, 1H), 7.94 (s, 1H), 7.64 (d, 1H), 7.56 (d, 1H), 7.34 (d, 1H), 7.30 (dd, 1H), 6.77 (d, 1H), 5.83 (s, 2H), 4.13 (br, 2H), 3.70 (br, 2H), 3.19 (s, 3H), 2.62 (m, 4H), 2.41 (s, 3H).

LC/MS: mass calcd. for $C_{25}H_{24}F_3N_5O_4S_2$ (m/z), 579.1. found, 580.2 [M+H]⁺.

Example 24

5-{1-[4-(2-Methoxy-ethoxy)-2-trifluoromethyl-benzyl]-1H-indazol-5-ylmethylene}-2-(4-methyl-piperazin-1-yl)-thiazol-4-one

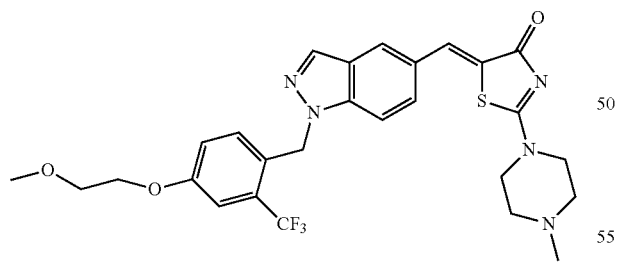

5-[1-(4-Hydroxy-2-trifluoromethyl-benzyl)-1H-indazol-5-ylmethylene]-2-(4-methyl-piperazin-1-yl)-thiazol-4-one (24.7 mg, 0.049 mmol) was dissolved in 1 mL of dry DMF. To the DMF solution was added $Cs_2CO_3$ (31.9 mg, 0.098 mmol), followed by methoxyethyl bromide (9.6 mg, 0.07 mmol). The mixture was stirred at 60° C. for 16 h and then diluted with water. It was extracted with EtOAc and the combined EtOAc extracts were washed with brine and dried over $Na_2SO_4$. The solvent was evaporated and the residue was purified by flash column chromatography on silica gel (0-100% gradient $CH_2Cl_2$/EtOAc, followed by 10% MeOH/EtOAc) to afford the title compound (21 mg, 76%).

¹H NMR (400 MHz, CDCl₃): δ 8.16 (d, 1H), 7.96 (s, 1H), 7.93 (s, 1H), 7.52 (dd, 1H), 7.31 (d, 1H), 7.28 (d, 1H), 6.89 (dd, 1H), 6.68 (d, 1H), 5.75 (s, 2H), 4.10 (m, 4H), 3.73 (m, 2H), 3.66 (t, 2H), 3.43 (s, 3H), 2.58 (t, 2H), 2.54 (t, 2H), 2.37 (s, 3H).

LC/MS: mass calcd. for $C_{27}H_{28}F_3N_5O_3S$ (m/z), 559.2. found, 560.4 [M+H]⁺.

Example 25

5-[1-(2,4-Dichloro-benzyl)-1H-indazol-5-ylmethylene]-2-(4-methyl-piperazin-1-yl)-thiazol-4-one

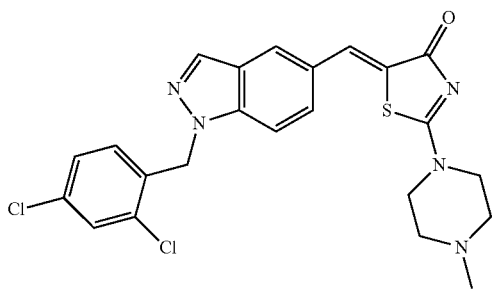 [SMILES: CN1CCN(C2=NC(=O)/C(=C/c3ccc4c(cnn4Cc4ccc(Cl)cc4Cl)c3)S2)CC1]

5-[1-(2,4-Dichloro-benzyl)-1H-indazol-5-ylmethylene]-2-(4-methyl-piperazin-1-yl)-thiazol-4-one was prepared from 5-[1-(2,4-dichloro-benzyl)-1H-indazol-5-ylmethylene]-2-ethylsulfanyl-thiazol-4-one and 1-methyl-piperazine following General Procedure C.

¹H NMR (400 MHz, CDCl₃): δ 8.15 (s, 1H), 7.95 (d, 1H), 7.93 (s, 1H), 7.55 (dd, 1H), 7.41-7.44 (2H), 7.13 (dd, 1H), 6.78 (d, 1H), 5.67 (s, 2H), 4.10 (t, 2H), 3.66 (t, 2H), 2.58 (t, 2H), 2.55 (t, 2H), 2.37 (s, 3H).

LC/MS: mass calcd. for $C_{23}H_{21}Cl_2N_5OS$ (m/z), 485.1. found, 486.1 [M+H]⁺.

Example 26

5-[1-(4-Bromo-2-trifluoromethyl-benzyl)-1H-indazol-5-ylmethylene]-2-(4-methyl-piperazin-1-yl)-thiazol-4-one

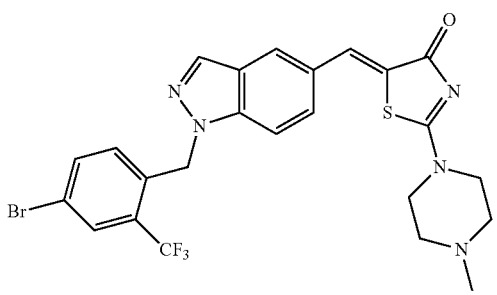

A. 4-bromo-1-bromomethyl-2-trifluoromethyl-benzene was prepared from 4-bromo-1-methyl-2-trifluoromethyl-benzene following the procedure described for Example 9 (A).

¹H NMR (400 MHz, CDCl₃): 7.78 (d, 1H), 7.68 (dd, 1H), 7.47 (d, 1H), 4.57 (s, 2H).

B. 1-(4-Bromo-2-trifluoromethyl-benzyl)-1H-indazole-5-carbaldehyde was prepared from 1H-indazole-5-carbaldehyde and 4-bromo-1-bromomethyl-2-trifluoromethyl-benzene following General Procedure A.

LC/MS: mass calcd. for $C_{16}H_{10}BrF_3N_2O$ (m/z), 383.1. found, 385.0 [M+2H]$^+$.

C. 5-[1-(4-Bromo-2-trifluoromethyl-benzyl)-1H-indazol-5-ylmethylene]-2-(4-methyl-piperazin-1-yl)-thiazol-4-one was prepared from 1-(4-Bromo-2-trifluoromethyl-benzyl)-1H-indazole-5-carbaldehyde and 1-methyl-piperazine following General Procedure C.

$^1$H NMR (400 MHz, CDCl$_3$): δ 8.19 (s, 1H), 7.97 (s, 1H), 7.93 (s, 1H), 7.86 (m, 1H), 7.55 (d, 1H), 7.49 (d, 1H), 7.31 (d, 1H), 6.59 (d, 1H), 5.77 (s, 2H), 4.10 (t, 2H), 3.66 (t, 2H), 2.58 (t, 2H), 2.55 (t, 2H), 2.37 (s, 3H).

LC/MS: mass calcd. for $C_{24}H_{21}BrF_3N_5OS$ (m/z), 563.1. found, 564.2 [M+H]$^+$.

Example 27

5-[1-(4-Cyclopropyl-2-trifluoromethyl-benzyl)-1H-indazol-5-ylmethylene]-2-(4-methyl-piperazin-1-yl)-thiazol-4-one

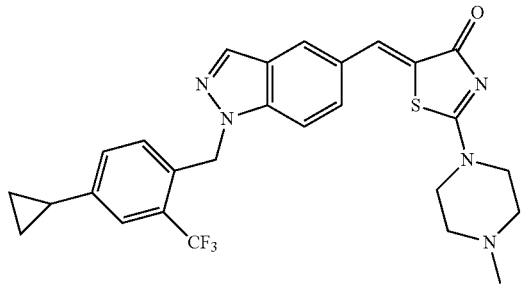 [SMILES: CN1CCN(C2=NC(=O)/C(=C/c3ccc4c(cnn4Cc4ccc(C5CC5)cc4C(F)(F)F)c3)S2)CC1]

5-[1-(4-Cyclopropyl-2-trifluoromethyl-benzyl)-1H-indazol-5-ylmethylene]-2-(4-methyl-piperazin-1-yl)-thiazol-4-one was prepared from 5-[1-(4-Bromo-2-trifluoromethyl-benzyl)-1H-indazol-5-ylmethylene]-2-(4-methyl-piperazin-1-yl)-thiazol-4-one and cyclopropyl boronic acid following General Procedure F.

$^1$H NMR (400 MHz, CD$_3$OD): δ 8.22 (s, 1H), 8.10 (s, 1H), 7.93 (s, 1H), 7.63 (d, 1H), 7.49 (d, 1H), 7.46 (m, 1H), 7.11 (d, 1H), 6.57 (d, 1H), 5.81 (s, 2H), 4.21 (br, 2H), 3.88 (br, 2H), 3.70 (br, 4H), 3.01 (s, 3H), 1.96 (m, 1H), 1.01 (m, 2H), 0.69 (m, 2H).

LC/MS: mass calcd. for $C_{27}H_{26}F_3N_5OS$ (m/z), 525.2. found, 526.3 [M+H]$^+$.

Example 28

5-[1-(2-Bromo-4-trifluoromethyl-benzyl)-1H-indazol-5-ylmethylene]-2-(4-methyl-piperazin-1-yl)-thiazol-4-one

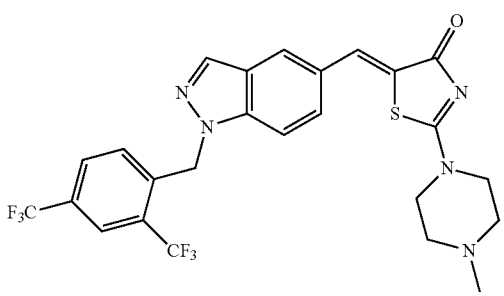

A. 2-Bromo-1-bromomethyl-4-trifluoromethyl-benzene was prepared from 2-Bromo-1-methyl-4-trifluoromethyl-benzene following the procedure described for Example 9 (A).

B. 1-(2-Bromo-4-trifluoromethyl-benzyl)-1H-indazole-5-carbaldehyde was prepared from 1H-indazole-5-carbaldehyde and 2-bromo-1-bromomethyl-4-trifluoromethyl-benzene following General Procedure A.

LC/MS: mass calcd. for $C_{16}H_{10}BrF_3N_2O$ (m/z), 383.1. found, 385.0 [M+2H]$^+$.

C. 5-[1-(2-Bromo-4-trifluoromethyl-benzyl)-1H-indazol-5-ylmethylene]-2-(4-methyl-piperazin-1-yl)-thiazol-4-one was prepared from 1-(2-Bromo-4-trifluoromethyl-benzyl)-1H-indazole-5-carbaldehyde and N-methyl piperazine following General Procedure C.

$^1$H NMR (400 MHz, CD$_3$OD): δ 8.25 (s, 1H), 8.14 (s, 1H), 7.97 (s, 1H), 7.96 (s, 1H), 7.69 (m, 2H), 7.56 (dd, 1H), 6.88 (d, 1H), 5.84 (s, 2H), 4.22 (br, 2H), 3.84 (br, 2H), 3.69 (br, 4H), 3.01 (s, 3H).

LC/MS: mass calcd. for $C_{24}H_{21}BrF_3N_5OS$ (m/z), 563.1. found, 564.2 [M+H]$^+$.

Example 29

5-[1-(2-Cyclopropyl-4-trifluoromethyl-benzyl)-1H-indazol-5-ylmethylene]-2-(4-methyl-piperazin-1-yl)-thiazol-4-one

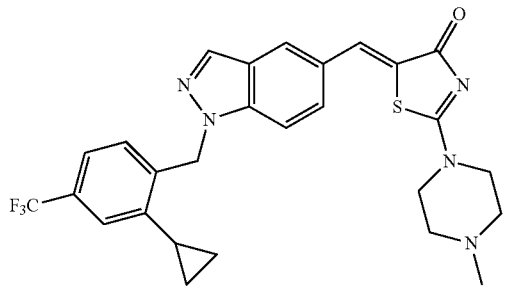 [SMILES: CN1CCN(C2=NC(=O)/C(=C/c3ccc4c(cnn4Cc4ccc(C(F)(F)F)cc4C4CC4)c3)S2)CC1]

5-[1-(2-Cyclopropyl-4-trifluoromethyl-benzyl)-1H-indazol-5-ylmethylene]-2-(4-methyl-piperazin-1-yl)-thiazol-4-one was prepared from 5-[1-(2-bromo-4-trifluoromethyl-benzyl)-1H-indazol-5-ylmethylene]-2-(4-methyl-piperazin-1-yl)-thiazol-4-one and cyclopropyl boronic acid following General Procedure G.

$^1$H NMR (400 MHz, CDCl$_3$): δ 8.19 (s, 1H), 7.96 (s, 1H), 7.93 (s, 1H), 7.88 (s, 1H), 7.55 (m, 1H), 7.42 (m, 1H), 7.34 (m, 1H), 6.79 (d, 1H), 5.73 (s, 2H), 4.13 (m, 2H), 3.70 (m, 2H), 2.61 (m, 4H), 1.99 (m, 1H), 1.05 (m, 2H), 0.76 (m, 2H).

LC/MS: mass calcd. for $C_{27}H_{26}F_3N_5OS$ (m/z), 525.2. found, 526.1 [M+H]$^+$.

Example 30

5-[1-(4-Isopropenyl-2-trifluoromethyl-benzyl)-1H-indazol-5-ylmethylene]-2-(4-methyl-piperazin-1-yl)-thiazol-4-one

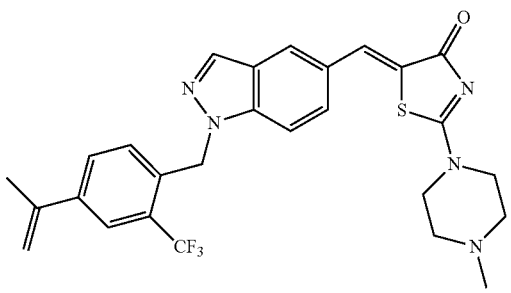 [SMILES: C=C(C)c1ccc(Cn2ncc3cc(/C=C4\SC(N5CCN(C)CC5)=NC4=O)ccc32)c(C(F)(F)F)c1]

5-[1-(4-Isopropenyl-2-trifluoromethyl-benzyl)-1H-indazol-5-ylmethylene]-2-(4-methyl-piperazin-1-yl)-thiazol-4-one was prepared from 5-[1-(4-bromo-2-trifluoromethyl-benzyl)-1H-indazol-5-ylmethylene]-2-(4-methyl-piperazin-1-yl)-thiazol-4-one and isopropenylboronic acid following General Procedure F.

$^1$H NMR (400 MHz, CDCl$_3$): δ 8.19 (d, 1H), 7.97 (m, 1H), 7.93 (s, 1H), 7.79 (d, 1H), 7.53 (dd, 1H), 7.42 (dd, 1H), 7.33 (d, 1H), 6.66 (d, 1H), 5.82 (s, 2H), 5.38 (s, 1H), 5.15 (m, 1H), 4.10 (t, 2H), 3.66 (t, 2H), 2.58 (t, 2H), 2.55 (t, 2H), 2.37 (s, 3H), 2.12 (s, 3H).

LC/MS: mass calcd. for C$_{27}$H$_{26}$F$_3$N$_5$OS (m/z), 525.2. found, 526.2 [M+H]$^+$.

Example 31

5-[1-(4-Cyclopropyl-2-trifluoromethyl-benzyl)-1H-indazol-5-ylmethylene]-2-[4-(2-hydroxy-ethyl)-piperazin-1-yl]-thiazol-4-one

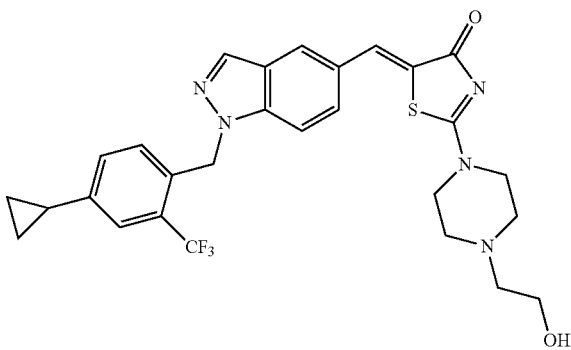 [SMILES: O=C1N=C(N2CCN(CCO)CC2)S/C1=C\c1ccc2c(cnn2Cc2ccc(C3CC3)cc2C(F)(F)F)c1]

5-[1-(4-Cyclopropyl-2-trifluoromethyl-benzyl)-1H-indazol-5-ylmethylene]-2-[4-(2-hydroxy-ethyl)-piperazin-1-yl]-thiazol-4-one was prepared from 5-[1-(4-bromo-2-trifluoromethyl-benzyl)-1H-indazol-5-ylmethylene]-2-[4-(2-hydroxy-ethyl)-piperazin-1-yl]-thiazol-4-one and cyclopropyl boronic acid following General Procedure F.

$^1$H NMR (400 MHz, CD$_3$OD): δ 8.22 (s, 1H), 8.10 (s, 1H), 7.94 (s, 1H), 7.63 (dd, 1H), 7.50 (d, 1H), 7.47 (s, 1H), 7.11 (d, 1H), 6.57 (d, 1H), 5.81 (s, 2H), 4.18 (br, 2H), 3.94 (t, 2H), 3.78 (br, 2H), 3.39 (t, 2H), 1.96 (m, 1H), 1.01 (m, 2H), 0.69 (m, 2H).

LC/MS: mass calcd. for C$_{28}$H$_{28}$F$_3$N$_6$O$_2$S (m/z), 555.2. found, 556.2 [M+H]$^+$.

Example 32

2-(3R,4R-Dihydroxy-pyrrolidin-1-yl)-5-[1-(4-methoxy-2-trifluoromethyl-benzyl)-1H-indazol-5-ylmethylene]-thiazol-4-one

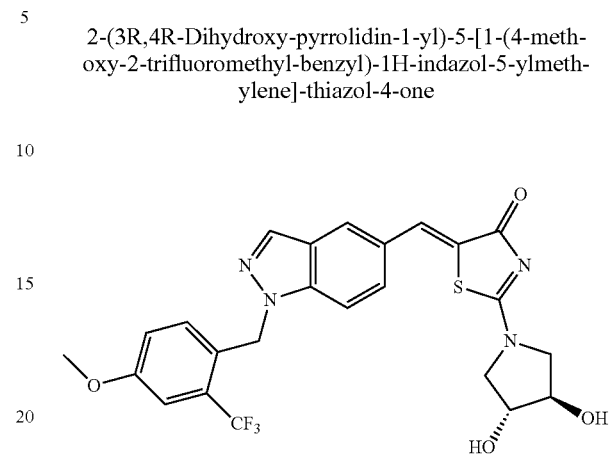

2-(3R,4R-Dihydroxy-pyrrolidin-1-yl)-5-[1-(4-methoxy-2-trifluoromethyl-benzyl)-1H-indazol-5-ylmethylene]-thiazol-4-one was prepared from 5-[1-(4-methoxy-2-trifluoromethyl-benzyl)-1H-indazol-5-ylmethylene]-2-methylsulfanyl-thiazol-4-one and pyrrolidine-3R,4R-diol following General Procedure C.

$^1$H NMR (400 MHz, DMSO-d$_6$): δ 8.29 (s, 1H), 8.10 (s, 1H), 7.76 (s, 1H), 7.71 (d, 1H), 7.65 (dd, 1H), 7.25 (d, 1H), 7.11 (dd, 1H), 6.77 (d, 1H), 5.76 (s, 2H), 5.55 (d, 1H), 5.49 (d, 1H), 4.11 (m, 2H), 3.83 (m, 2H), 3.77 (s, 3H), 3.67 (m, 1H), 3.47 (m, 1H).

LC/MS: mass calcd. for C$_{24}$H$_{21}$F$_3$N$_4$O$_4$S (m/z), 518.1. found, 519.2 [M+H]$^+$.

Example 33

1-{5-[1-(4-Methoxy-2-trifluoromethyl-benzyl)-1H-indazol-5-ylmethylene]-4-oxo-4,5-dihydro-thiazol-2-yl}-azetidine-3-carboxylic acid

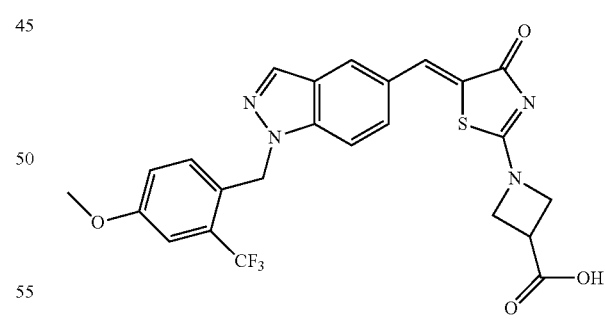

1-{5-[1-(4-Methoxy-2-trifluoromethyl-benzyl)-1H-indazol-5-ylmethylene]-4-oxo-4,5-dihydro-thiazol-2-yl}-azetidine-3-carboxylic acid was prepared from 5-[1-(4-methoxy-2-trifluoromethyl-benzyl)-1H-indazol-5-ylmethylene]-2-methylsulfanyl-thiazol-4-one and azetidine-3-carboxylic acid following General Procedure C.

$^1$H NMR (400 MHz, CD$_3$OD): δ 8.23 (d, 1H), 8.07 (s, 1H), 7.83 (s, 1H), 7.61 (dd, 1H), 7.51 (d, 1H), 7.27 (d, 1H), 7.00 (dd, 1H), 6.68 (d, 1H), 5.78 (s, 2H), 4.44-4.57 (4H), 3.81 (s, 3H), 3.55 (m, 1H).

Example 34

5-[1-(4-Methoxy-2-trifluoromethyl-benzyl)-1H-indazol-5-ylmethylene]-2-piperazin-1-yl-thiazol-4-one

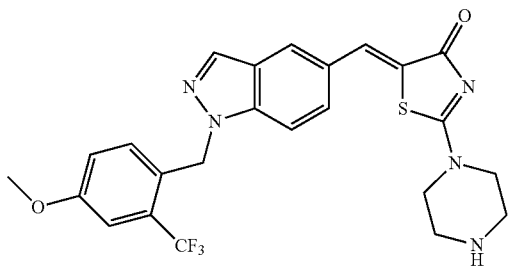 [SMILES: COc1ccc(Cn2ncc3cc(/C=C4\SC(N5CCNCC5)=NC4=O)ccc32)c(C(F)(F)F)c1]

5-[1-(4-Methoxy-2-trifluoromethyl-benzyl)-1H-indazol-5-ylmethylene]-2-piperazin-1-yl-thiazol-4-one was prepared from 5-[1-(4-methoxy-2-trifluoromethyl-benzyl)-1H-indazol-5-ylmethylene]-2-methylsulfanyl-thiazol-4-one and piperazine following General Procedure C.

$^1$H NMR (400 MHz, CDCl$_3$): δ 8.16 (d, 1H), 7.95 (s, 1H), 7.93 (s, 1H), 7.52 (dd, 1H), 7.33 (d, 1H), 7.23 (d, 1H), 6.87 (dd, 1H), 6.70 (d, 1H), 5.75 (s, 2H), 4.06 (t, 2H), 3.80 (s, 3H), 3.63 (t, 2H), 3.04 (t, 2H), 3.00 (t, 2H).

LC/MS: mass calcd. for C$_{24}$H$_{22}$F$_3$N$_5$O$_2$S (m/z), 501.1. found, 502.3 [M+H]$^+$.

Example 35

1-{5-[1-(2,4-Bis-trifluoromethyl-benzyl)-1H-indazol-5-ylmethylene]-4-oxo-4,5-dihydro-thiazol-2-yl}-azetidine-3-carboxylic acid

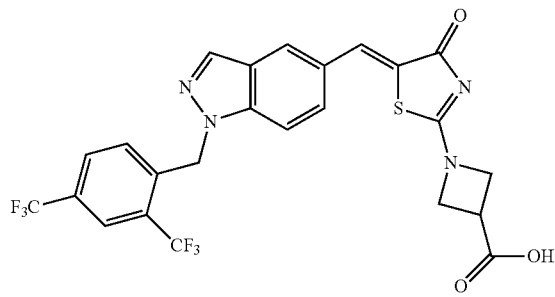 [SMILES: O=C1N=C(N2CC(C(=O)O)C2)S/C1=C\c1ccc2c(cnn2Cc2ccc(C(F)(F)F)cc2C(F)(F)F)c1]

1-{5-[1-(2,4-Bis-trifluoromethyl-benzyl)-1H-indazol-5-ylmethylene]-4-oxo-4,5-dihydro-thiazol-2-yl}-azetidine-3-carboxylic acid was prepared from 5-[1-(2,4-bis-trifluoromethyl-benzyl)-1H-indazol-5-ylmethylene]-2-methylsulfanyl-thiazol-4-one and azetidine-3-carboxylic acid following General Procedure C.

$^1$H NMR (400 MHz, CD$_3$OD): δ 8.25 (s, 1H), 8.05 (s, 1H), 8.04 (s, 1H), 7.81 (s, 1H), 7.78 (d, 1H), 7.61 (dd, 1H), 7.56 (d, 1H), 6.84 (d, 1H), 5.95 (s, 2H), 4.54 (m, 2H), 4.49 (m, 2H), 3.69 (m, 1H).

LC/MS: mass calcd. for C$_{24}$H$_{16}$F$_6$N$_4$O$_3$S (m/z), 554.1. found, 555.3 [M+H]$^+$.

Example 36

1-{5-[1-(4-Bromo-2-trifluoromethyl-benzyl)-1H-indazol-5-ylmethylene]-4-oxo-4,5-dihydro-thiazol-2-yl}-azetidine-3-carboxylic acid

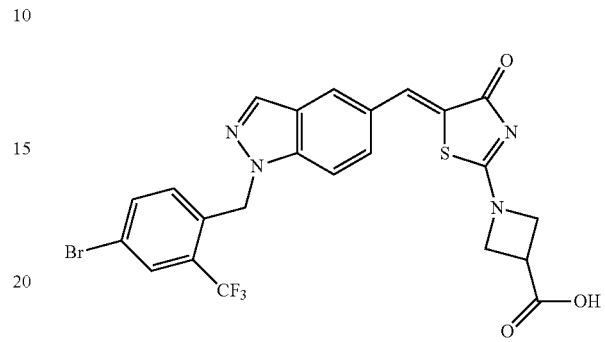

1-{5-[1-(4-Bromo-2-trifluoromethyl-benzyl)-1H-indazol-5-ylmethylene]-4-oxo-4,5-dihydro-thiazol-2-yl}-azetidine-3-carboxylic acid was prepared from 5-[1-(4-Bromo-2-trifluoromethyl-benzyl)-1H-indazol-5-ylmethylene]-2-methylsulfanyl-thiazol-4-one and azetidine-3-carboxylic acid following General Procedure C.

$^1$H NMR (400 MHz, CD$_3$OD): δ 8.26 (s, 1H), 8.09 (s, 1H), 7.93 (d, 1H), 7.84 (s, 1H), 7.65 (dd, 1H), 7.63 (dd, 1H), 7.56 (d, 1H), 6.59 (d, 1H), 5.84 (s, 2H), 4.43-4.58 (4H), 3.57 (m, 1H).

LC/MS: mass calcd. for C$_{23}$H$_{16}$BrF$_3$N$_4$O$_3$S (m/z), 564.0. found, 567.2 [M+H+2]$^+$.

Example 37

1-{5-[1-(2,4-Bis-trifluoromethyl-benzyl)-1H-indazol-5-ylmethylene]-4-oxo-4,5-dihydro-thiazol-2-yl}-piperidine-3-(S)-carboxylic acid

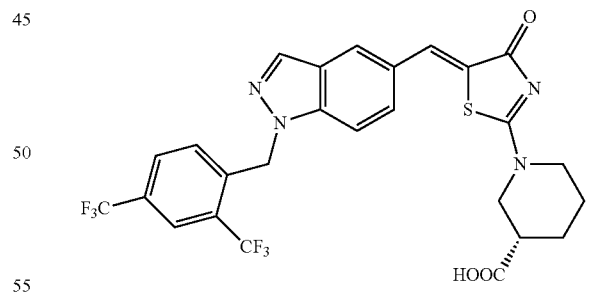

1-{5-[1-(2,4-Bis-trifluoromethyl-benzyl)-1H-indazol-5-ylmethylene]-4-oxo-4,5-dihydro-thiazol-2-yl}-piperidine-3-(S)-carboxylic acid was prepared from 5-[1-(2,4-bis-trifluoromethyl-benzyl)-1H-indazol-5-ylmethylene]-2-methylsulfanyl-thiazol-4-one and piperidine-3-(S)-carboxylic acid following General Procedure C.

$^1$H NMR (400 MHz, CD$_3$OD): δ 8.27 (d, 1H), 8.11 (d, 1H), 8.05 (s, 1H), 7.83 (d, 1H), 7.79 (d, 1H), 7.66 (m, 1H), 7.58 (m, 1H), 6.84 (d, 1H), 5.96 (s, 2H), 4.72 (m, 0.5H), 4.36 (m, 0.5H), 3.97 (m, 0.5H), 3.84 (m, 0.5H), 3.47-3.75 (3H), 2.65 (m, 1H), 1.65-2.22 (4H).

LC/MS: mass calcd. for $C_{26}H_{20}F_6N_4O_3S$ (m/z), 582.1. found, 583.3 [M+H]+.

Example 38

1-{5-[1-(2,4-Bis-trifluoromethyl-benzyl)-1H-indazol-5-ylmethylene]-4-oxo-4,5-dihydro-thiazol-2-yl}-piperidine-3-(R)-carboxylic acid

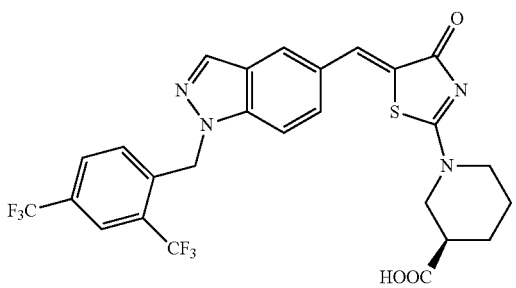 [SMILES: O=C1N=C(N2CCC[C@@H](C(=O)O)C2)S/C1=C\c1ccc2c(cnn2Cc2ccc(C(F)(F)F)cc2C(F)(F)F)c1]

1-{5-[1-(2,4-Bis-trifluoromethyl-benzyl)-1H-indazol-5-ylmethylene]-4-oxo-4,5-dihydro-thiazol-2-yl}-piperidine-3-(R)-carboxylic acid was prepared from 5-[1-(2,4-bis-trifluoromethyl-benzyl)-1H-indazol-5-ylmethylene]-2-methylsulfanyl-thiazol-4-one and piperidine-3-(R)-carboxylic acid following General Procedure C.

$^1$H NMR (400 MHZ, CD$_3$OD): δ 8.26 (d, 1H), 8.09 (d, 1H), 8.05 (s, 1H), 7.82 (s, 1H), 7.78 (d, 1H), 7.65 (m, 1H), 7.57 (m, 1H), 6.84 (d, 1H), 5.96 (s, 2H), 4.59 (m, 1H), 3.90 (m, 1H), 3.63 (m, 1H), 3.53 (m, 1H), 2.62 (m, 1H), 1.64-2.21 (4H).

LC/MS: mass calcd. for $C_{26}H_{20}F_6N_4O_3S$ (m/z), 582.1. found, 583.3 [M+H]+

Example 39

1-{5-[1-(4-Chloro-2-trifluoromethyl-benzyl)-1H-indazol-5-ylmethylene]-4-oxo-4,5-dihydro-thiazol-2-yl}-piperidine-4-carboxylic acid

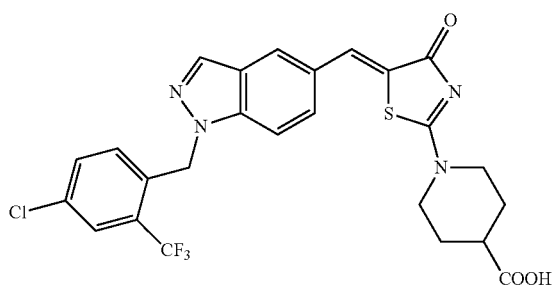 [SMILES: O=C1N=C(N2CCC(C(=O)O)CC2)S/C1=C\c1ccc2c(cnn2Cc2ccc(Cl)cc2C(F)(F)F)c1]

1-{5-[1-(4-Chloro-2-trifluoromethyl-benzyl)-1H-indazol-5-ylmethylene]-4-oxo-4,5-dihydro-thiazol-2-yl}piperidine-4-carboxylic acid was prepared from 5-[1-(4-chloro-2-trifluoromethyl-benzyl)-1H-indazol-5-ylmethylene]-2-ethylsulfanyl-thiazol-4-one and piperidine-4-carboxylic acid following General Procedure C.

$^1$H NMR (CDCl$_3$): δ 8.19 (s, 1H), 7.97 (s, 1H), 7.94 (s, 1H), 7.71 (s, 1H), 7.54 (d, 1H), 7.33 (d, 1H), 7.31 (d, 1H), 6.66 (d, 1H), 5.79 (s, 2H), 4.66 (m, 1H), 3.89 (m, 1H), 3.56 (m, 1H), 3.47 (m, 1H), 2.78 (m, 1H), 2.15 (m, 2H), 1.94 (m, 2H).

LC/MS: mass calcd. for $C_{25}H_{20}ClF_3N_4O_3S$ (m/z), 548.1. found, 549.3 [M+H]+.

Example 40

1-{5-[1-(4-Chloro-2-trifluoromethyl-benzyl)-1H-indazol-5-ylmethylene]-4-oxo-4,5-dihydro-thiazol-2-yl}-azetidine-3-carboxylic acid

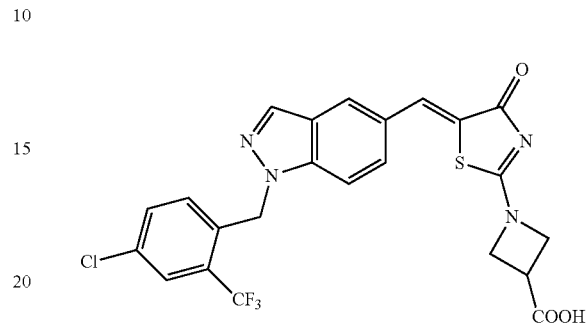

1-{5-[1-(4-Chloro-2-trifluoromethyl-benzyl)-1H-indazol-5-ylmethylene]-4-oxo-4,5-dihydro-thiazol-2-yl}-azetidine-3-carboxylic acid was prepared from 5-[1-(4-chloro-2-trifluoromethyl-benzyl)-1H-indazol-5-ylmethylene]-2-ethylsulfanyl-thiazol-4-one and azetidine-3-carboxylic acid following General Procedure C.

$^1$H NMR (400 MHZ, CD$_3$OD): δ 8.25 (d, 1H), 8.09 (m, 1H), 7.85 (s, 1H), 7.80 (d, 1H), 7.64 (dd, 1H), 7.56 (d, 1H), 7.48 (dd, 1H), 6.67 (d, 1H), 5.86 (s, 2H), 4.58 (m, 2H), 4.51 (m, 2H), 3.77 (m, 1H).

LC/MS: mass calcd. for $C_{23}H_{16}ClF_3N_4O_3S$ (m/z), 520.1. found, 521.3 [M+H]+.

Example 41

1-{5-[1-(4-Methoxy-2-trifluoromethyl-benzyl)-1H-indazol-5-ylmethylene]-4-oxo-4,5-dihydro-thiazol-2-yl}-piperidine-4-carboxylic acid

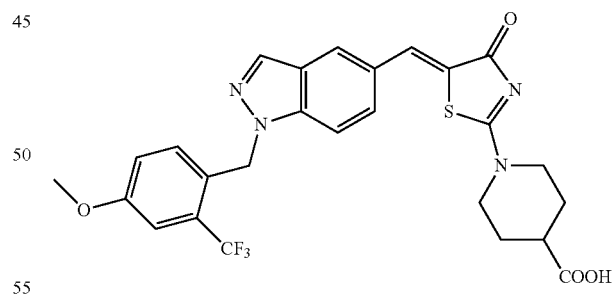

1-{5-[1-(4-Methoxy-2-trifluoromethyl-benzyl)-1H-indazol-5-ylmethylene]-4-oxo-4,5-dihydro-thiazol-2-yl}-piperidine-4-carboxylic acid was prepared from 5-[1-(4-methoxy-2-trifluoromethyl-benzyl)-1H-indazol-5-ylmethylene]-2-methylsulfanyl-thiazol-4-one and piperidine-4-carboxylic acid following General Procedure C.

$^1$H NMR (400 MHZ, DMSO-d$_6$): δ 8.27 (s, 1H), 8.09 (s, 1H), 7.73 (s, 1H), 7.69 (d, 1H), 7.64 (d, 1H), 7.25 (d, 1H), 7.11 (dd, 1H), 7.64 (d, 1H), 7.25 (d, 1H), 7.11 (dd, 1H), 6.77 (d, 1H), 5.75 (s, 2H), 4.37 (m, 1H), 3.77 (s, 3H), 2.65-3.63 (4H), 1.93 (m, 2H), 1.63 (m, 2H).

LC/MS: mass calcd. for $C_{26}H_{23}F_3N_4O_4S$ (m/z), 544.1. found, 545.5 [M+H]$^+$.

Example 42

5-[1-(2,4-Bis-trifluoromethyl-benzyl)-1H-indazol-5-ylmethylene]-2-(4-methyl-[1,4]diazepan-1-yl)-thiazol-4-one

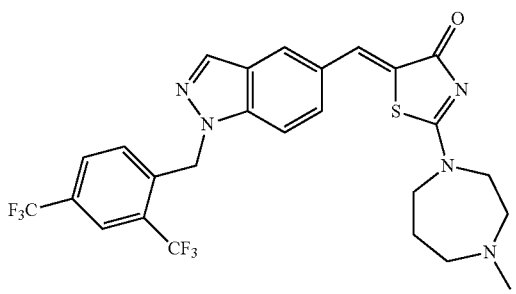 [SMILES: CN1CCCN(C2=NC(=O)/C(=C/c3ccc4c(cnn4Cc4ccc(C(F)(F)F)cc4C(F)(F)F)c3)S2)CC1]

5-[1-(2,4-Bis-trifluoromethyl-benzyl)-1H-indazol-5-ylmethylene]-2-(4-methyl-[1,4]diazepan-1-yl)-thiazol-4-one was prepared from 5-[1-(2,4-bis-trifluoromethyl-benzyl)-1H-indazol-5-ylmethylene]-2-methylsulfanyl-thiazol-4-one and 1-methyl-[1,4]diazepane following General Procedure C.

$^1$H NMR (400 MHZ, CDCl$_3$): δ 8.21 (m, 1H), 7.98 (s, 2H), 7.92 (s, 1H), 7.62 (d, 1H), 7.56 (dd, 1H), 7.31 (d, 1H), 6.81 (d, 1H), 5.88 (s, 2H), 4.15 (m, 1H), 4.08 (t, 1H), 3.77 (t, 1H), 3.75 (t, 1H), 2.82 (m, 2H), 2.70 (t, 1H), 2.66 (t, 1H), 2.43 (s, 3H), 2.17 (m, 2H), 2.05 (m, 2H).

LC/MS: mass calcd. for $C_{26}H_{23}F_6N_6OS$ (m/z), 567.2. found, 568.4 [M+H]$^+$.

Example 43

1-{5-[1-(2,4-Bis-trifluoromethyl-benzyl)-1H-indazol-5-ylmethylene]-4-oxo-4,5-dihydro-thiazol-2-yl}-pyrrolidine-2-(R)-carboxylic acid

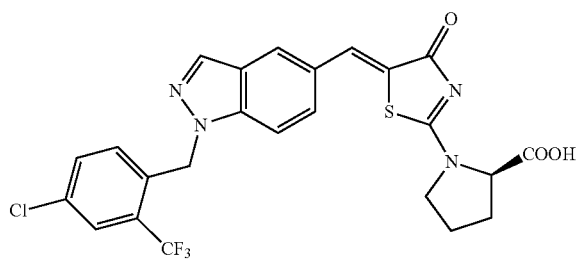 [SMILES: O=C1N=C(N2CCC[C@@H]2C(=O)O)S/C1=C\c1ccc2c(cnn2Cc2ccc(Cl)cc2C(F)(F)F)c1]

1-{5-[1-(2,4-Bis-trifluoromethyl-benzyl)-1H-indazol-5-ylmethylene]-4-oxo-4,5-dihydro-thiazol-2-yl}-pyrrolidine-2-(R)-carboxylic acid was prepared from 5-[1-(2,4-bis-trifluoromethyl-benzyl)-1H-indazol-5-ylmethylene]-2-methylsulfanyl-thiazol-4-one and pyrrolidine-2-(R)-carboxylic acid following General Procedure C.

$^1$H NMR (400 MHZ, CDCl$_3$): δ 8.22 (d, 1H), 7.98 (m, 2H), 7.95 (s, 1H), 7.63 (d, 1H), 7.53 (dd, 1H), 7.32 (d, 1H), 6.82 (d, 1H), 5.88 (s, 2H), 4.97 (dd, 1H), 3.83 (m, 1H), 3.68 (m, 1H), 2.51 (m, 1H), 2.23-2.41 (2H), 2.19 (m, 1H).

LC/MS: mass calcd. for $C_{25}H_{18}F_6N_4O_3S$ (m/z), 568.1. found, 569.4 [M+H]$^+$.

Example 44

1-{5-[1-(4-Chloro-2-trifluoromethyl-benzyl)-1H-indazol-5-ylmethylene]-4-oxo-4,5-dihydro-thiazol-2-yl}-pyrrolidine-2-(S)-carboxylic acid

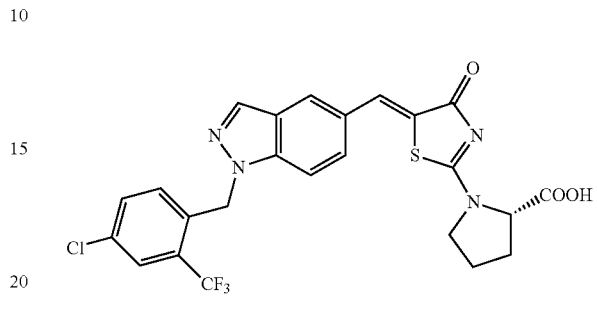

1-{5-[1-(4-Chloro-2-trifluoromethyl-benzyl)-1H-indazol-5-ylmethylene]-4-oxo-4,5-dihydro-thiazol-2-yl}-pyrrolidine-2-(S)-carboxylic acid was prepared from 5-[1-(2,4-bis-trifluoromethyl-benzyl)-1H-indazol-5-ylmethylene]-2-methylsulfanyl-thiazol-4-one and pyrrolidine-2-(S)-carboxylic acid following General Procedure C.

$^1$H NMR (400 MHZ, CDCl$_3$): δ 8.19 (s, 1H), 7.94 (d, 1H), 7.92 (s, 1H), 7.70 (d, 1H), 7.50 (dd, 1H), 7.33 (dd, 1H), 7.30 (d, 1H), 6.66 (d, 1H), 5.77 (s, 2H), 4.97 (dd, 1H), 3.83 (m, 1H), 3.68 (m, 1H), 2.47 (m, 1H), 2.37 (m, 1H), 2.27 (m, 1H), 2.18 (m, 1H).

LC/MS: mass calcd. for $C_{24}H_{18}ClF_3N_4O_3S$ (m/z), 534.1. found, 535.4 [M+H]$^+$.

Example 45

1-{5-[1-(4-Methoxy-2-trifluoromethyl-benzyl)-1H-indazol-5-ylmethylene]-4-oxo-4,5-dihydro-thiazol-2-yl}-pyrrolidine-2-(R)-carboxylic acid

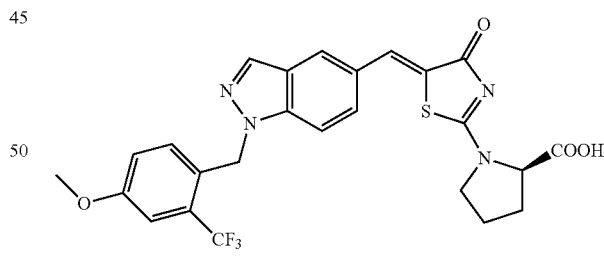

1-{5-[1-(4-Methoxy-2-trifluoromethyl-benzyl)-1H-indazol-5-ylmethylene]-4-oxo-4,5-dihydro-thiazol-2-yl}-pyrrolidine-2-(R)-carboxylic acid was prepared from 5-[1-(4-methoxy-2-trifluoromethyl-benzyl)-1H-indazol-5-ylmethylene]-2-methylsulfanyl-thiazol-4-one and pyrrolidine-2-(R)-carboxylic acid following General Procedure C.

$^1$H NMR (400 MHZ, CDCl$_3$): δ 8.17 (d, 1H), 7.93 (s, 2H), 7.49 (dd, 1H), 7.32 (d, 1H), 7.22 (d, 1H), 6.87 (dd, 1H), 6.70 (d, 1H), 5.74 (s, 2H), 4.97 (dd, 1H), 3.83 (m, 1H), 3.79 (s, 3H), 3.68 (m, 1H), 2.48 (m, 1H), 2.36 (m, 1H), 2.26 (m, 1H), 2.17 (m, 1H).

LC/MS: mass calcd. for $C_{25}H_{21}F_3N_4O_4S$ (m/z), 530.1. found, 531.5 [M+H]$^+$.

Example 46

1-{5-[1-(4-Chloro-2-trifluoromethyl-benzyl)-1H-indazol-5-ylmethylene]-4-oxo-4,5-dihydro-thiazol-2-yl}-pyrrolidine-2-(R)-carboxylic acid

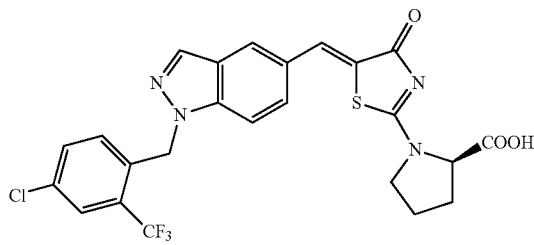 [SMILES: O=C1N=C(N2CCC[C@@H]2C(=O)O)S/C1=C\c1ccc2c(cnn2Cc2ccc(Cl)cc2C(F)(F)F)c1]

1-{5-[1-(4-Chloro-2-trifluoromethyl-benzyl)-1H-indazol-5-ylmethylene]-4-oxo-4,5-dihydro-thiazol-2-yl}-pyrrolidine-2-(R)-carboxylic acid was prepared from 5-[1-(4-chloro-2-trifluoromethyl-benzyl)-1H-indazol-5-ylmethylene]-2-ethylsulfanyl-thiazol-4-one and pyrrolidine-2-(R)-carboxylic acid following General Procedure C.

$^1$H NMR (400 MHZ, CDCl$_3$): δ 8.19 (s, 1H), 7.95 (s, 1H), 7.93 (s, 1H), 7.70 (d, 1H), 7.50 (dd, 1H), 7.33 (dd, 1H), 7.31 (d, 1H), 6.66 (d, 1H), 5.78 (s, 2H), 5.75 (m, 1H), 4.99 (dd, 1H), 3.83 (m, 1H), 3.68 (m, 1H), 2.47 (m, 1H), 2.38 (m, 1H), 2.26 (m, 1H), 2.18 (m, 1H).

LC/MS: mass calcd. for $C_{24}H_{18}ClF_3N_4O_3S$ (m/z), 534.1. found, 535.4 [M+H]$^+$.

Example 47

1-{5-[1-(2,4-Bis-trifluoromethyl-benzyl)-1H-indazol-5-ylmethylene]-4-oxo-4,5-dihydro-thiazol-2-yl}piperazine-2-(R)-carboxylic acid

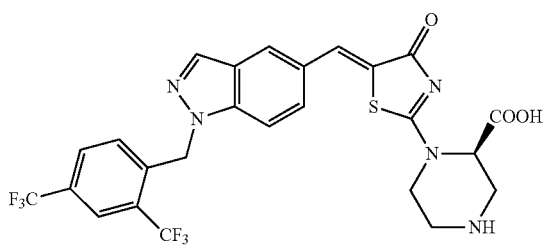 [SMILES: O=C1N=C(N2CCNC[C@@H]2C(=O)O)S/C1=C\c1ccc2c(cnn2Cc2ccc(C(F)(F)F)cc2C(F)(F)F)c1]

4-{5-[1-(2,4-Bis-trifluoromethyl-benzyl)-1H-indazol-5-ylmethylene]-4-oxo-4,5-dihydro-thiazol-2-yl}-piperazine-1,3-dicarboxylic acid 1-tert-butyl ester was prepared from 5-[1-(2,4-bis-trifluoromethyl-benzyl)-1H-indazol-5-ylmethylene]-2-methylsulfanyl-thiazol-4-one and piperazine-1,3-(R)-dicarboxylic acid 1-tert-butyl ester following General Procedure C. Compound was not isolated and 1-{5-[1-(2,4-Bis-trifluoromethyl-benzyl)-1H-indazol-5-ylmethylene]-4-oxo-4,5-dihydro-thiazol-2-yl}-piperazine-2-(R)-carboxylic acid was prepared following General Procedure H.

$^1$H NMR (400 MHZ, DMSO-d$_6$): δ 8.34 (s, 1H), 8.14 (d, 1H), 8.09 (s, 1H), 7.95 (d, 1H), 7.79 (d, 1H), 7.77 (d, 1H), 7.68 (m, 1H), 6.89 (dd, 1H), 5.96 (s, 2H), 5.06 (m, 1H), 2.50-4.20 (6H).

LC/MS: mass calcd. for $C_{25}H_{19}F_6N_5O_3S$ (m/z), 583.1. found, 584.4 [M+H]$^+$.

Example 48

1-{5-[1-(4-Chloro-2-trifluoromethyl-benzyl)-1H-indazol-5-ylmethylene]-4-oxo-4,5-dihydro-thiazol-2-yl}piperidine-3-(S)-carboxylic acid

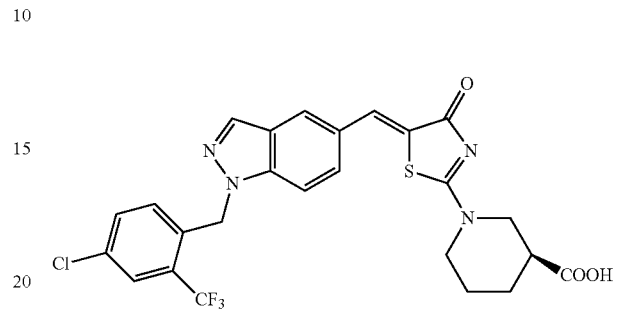

1-{5-[1-(4-Chloro-2-trifluoromethyl-benzyl)-1H-indazol-5-ylmethylene]-4-oxo-4,5-dihydro-thiazol-2-yl}-piperidine-3-(S)-carboxylic acid was prepared from 5-[1-(4-chloro-2-trifluoromethyl-benzyl)-1H-indazol-5-ylmethylene]-2-ethylsulfanyl-thiazol-4-one and piperidine-3-(R)-carboxylic acid following General Procedure C.

$^1$H NMR (400 MHZ, CDCl$_3$): δ 8.19 (d, 1H), 7.96 (d, 1H), 7.94 (d, 1H), 7.71 (t, 1H), 7.53 (dd, 1H), 7.33 (m, 1H), 7.30 (d, 1H), 6.66 (dd, 1H), 5.78 (s, 1H), 4.94 (dd, 1H), 4.53 (m, 0.5H), 3.95 (m, 0.5H), 3.80 (m, 0.5H), 3.67 (m, 0.5H), 3.39-3.58 (m, 2H), 2.76 (m, 1H), 2.25 (m, 1H), 1.67-2.06 (m, 2H).

LC/MS: mass calcd. for $C_{25}H_{20}ClF_3N_4O_3S$ (m/z), 548.1. found, 549.4 [M+H]$^+$.

Example 49

1-{5-[1-(2,4-Bis-trifluoromethyl-benzyl)-1H-indazol-5-ylmethylene]-4-oxo-4,5-dihydro-thiazol-2-yl}-azetidine-2-(S)-carboxylic acid

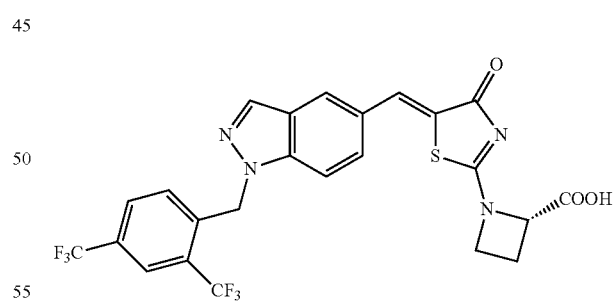

1-{5-[1-(2,4-Bis-trifluoromethyl-benzyl)-1H-indazol-5-ylmethylene]-4-oxo-4,5-dihydro-thiazol-2-yl}-azetidine-2-(S)-carboxylic acid was prepared from 5-[1-(2,4-bis-trifluoromethyl-benzyl)-1H-indazol-5-ylmethylene]-2-methylsulfanyl-thiazol-4-one and azetidine-2-(S)-carboxylic acid following General Procedure C.

$^1$H NMR (400 MHZ, CDCl$_3$): δ 8.22 (s, 1H), 7.98 (s, 1H), 7.95 (br, 2H), 7.63 (d, 1H), 7.50 (d, 1H), 7.32 (d, 1H), 6.82 (d, 1H), 6.07 (br, 1H), 5.87 (s, 2H), 5.27 (m, 1H), 4.38 (m, 1H), 4.28 (m, 1H), 2.80-2.97 (2H).

LC/MS: mass calcd. for $C_{24}H_{16}F_6N_4O_3S$ (m/z), 554.5. found, 555.4 [M+H]$^+$.

Example 50

1-{5-[1-(4-Methoxy-2-trifluoromethyl-benzyl)-1H-indazol-5-ylmethylene]-4-oxo-4,5-dihydro-thiazol-2-yl}-azetidine-2-(S)-carboxylic acid

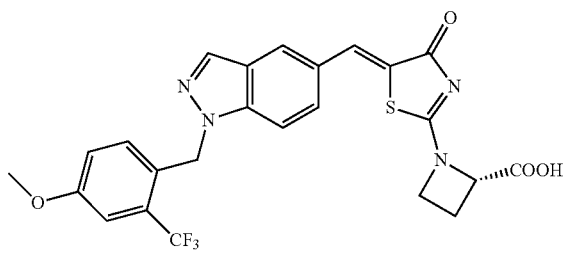 [SMILES: COc1ccc(Cn2ncc3cc(/C=C4\SC(N5CC[C@H]5C(=O)O)=NC4=O)ccc32)c(C(F)(F)F)c1]

1-{5-[1-(4-Methoxy-2-trifluoromethyl-benzyl)-1H-indazol-5-ylmethylene]-4-oxo-4,5-dihydro-thiazol-2-yl}-azetidine-2-(S)-carboxylic acid was prepared from 5-[1-(4-methoxy-2-trifluoromethyl-benzyl)-1H-indazol-5-ylmethylene]-2-methylsulfanyl-thiazol-4-one and azetidine-2-(S)-carboxylic acid following General Procedure C.

$^1$H NMR (400 MHZ, CD$_3$OD): δ 8.22 (d, 1H), 8.06 (d, 1H), 7.83 (s, 1H), 7.59 (d, 1H), 7.51 (m, 1H), 7.27 (m, 1H), 7.00 (m, 1H), 6.68 (m, 1H), 5.78 (s, 2H), 4.36 (m, 1H), 3.80 (s, 3H), 2.97 (m, 2H), 2.55 (m, 2H).

LC/MS: mass calcd. for $C_{24}H_{19}F_3N_4O_4S$ (m/z), 516.1. found, 517.5 [M+H]$^+$.

Example 51

2-(3-(S)-Amino-piperidin-1-yl)-5-[1-(4-methoxy-2-trifluoromethyl-benzyl)-1H-indazol-5-ylmethylene]-thiazol-4-one

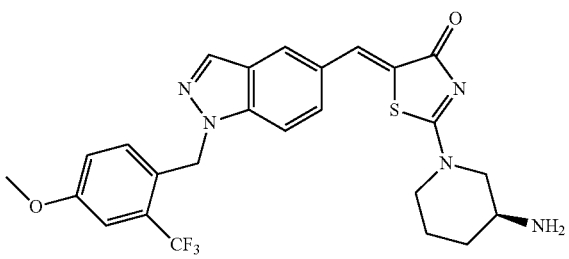 [SMILES: COc1ccc(Cn2ncc3cc(/C=C4\SC(N5CCC[C@H](N)C5)=NC4=O)ccc32)c(C(F)(F)F)c1]

(1-{5-[1-(4-Methoxy-2-trifluoromethyl-benzyl)-1H-indazol-5-ylmethylene]-4-oxo-4,5-dihydro-thiazol-2-yl}-piperidin-3-yl)-carbamic acid tert-butyl ester was prepared from 5-[1-(4-methoxy-2-trifluoromethyl-benzyl)-1H-indazol-5-ylmethylene]-2-methylsulfanyl-thiazol-4-one and piperidin-3-(S)-yl-carbamic acid tert-butyl ester following General Procedure C. The compound was used directly following General Procedure H to provide 2-(3-(S)-Amino-piperidin-1-yl)-5-[1-(4-methoxy-2-trifluoromethyl-benzyl)-1H-indazol-5-ylmethylene]-thiazol-4-one.

$^1$H NMR (400 MHZ, CD$_3$OD): δ 8.20 (d, 1H), 8.07 (s, 1H), 7.89 (s, 1H), 7.61 (dd, 1H), 7.48 (d, 1H), 7.27 (d, 1H), 7.00 (d, 1H), 6.70 (d, 1H), 5.77 (s, 2H), 4.42 (m, 1H), 3.96 (m, 1H), 3.81 (s, 3H), 3.50-3.80 (3H), 2.21 (m, 1H), 2.03 (m, 1H), 1.87 (m, 2H).

LC/MS: mass calcd. for $C_{25}H_{24}F_3N_5O_2S$ (m/z), 515.2. found, 516.5 [M+H]$^+$.

Example 52

2-(3-(S)-Amino-piperidin-1-yl)-5-[1-(2,4-bis-trifluoromethyl-benzyl)-1H-indazol-5-ylmethylene]-thiazol-4-one

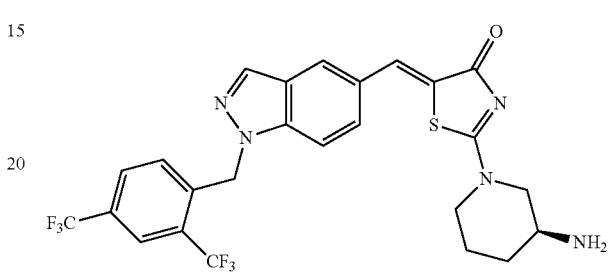

(1-{5-[1-(2,4-Bis-trifluoromethyl-benzyl)-1H-indazol-5-ylmethylene]-4-oxo-4,5-dihydro-thiazol-2-yl}-piperidin-3-yl)-carbamic acid tert-butyl ester was prepared from 5-[1-(2,4-Bis-trifluoromethyl-benzyl)-1H-indazol-5-ylmethylene]-2-methylsulfanyl-thiazol-4-one and piperidin-3-(S)-yl-carbamic acid tert-butyl ester following General Procedure C. The compound was used directly following General Procedure H to provide 2-(3-(S)-Amino-piperidin-1-yl)-5-[1-(2,4-bis-trifluoromethyl-benzyl)-1H-indazol-5-ylmethylene]-thiazol-4-one.

$^1$H NMR (400 MHZ, CD$_3$OD): δ 8.27 (dd, 1H), 8.11 (s, 1H), 8.06 (s, 1H), 7.85 (s, 1H), 7.79 (d, 1H), 7.67 (dt, 1H), 7.58 (d, 1H), 6.85 (dd, 1H), 5.97 (s, 1H), 4.49 (m, 1H), 3.85 (m, 1H), 3.46 (m, 1H), 3.25 (m, 1H), 2.94 (m, 1H), 1.88-2.10 (2H), 1.67 (m, 1H), 1.51 (m, 1H).

LC/MS: mass calcd. for $C_{25}H_{21}F_6N_5OS$ (m/z), 553.1. found, 554.5 [M+H]$^+$.

Example 53

2-(3-(R)-Amino-piperidin-1-yl)-5-[1-(2,4-bis-trifluoromethyl-benzyl)-1H-indazol-5-ylmethylene]-thiazol-4-one

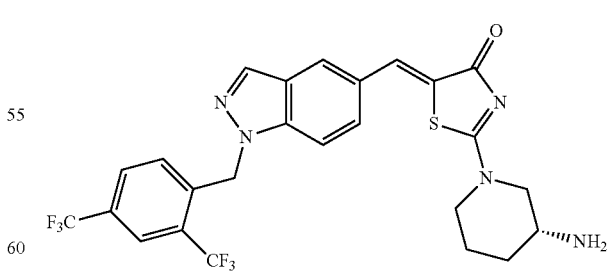

(1-{5-[1-(2,4-Bis-trifluoromethyl-benzyl)-1H-indazol-5-ylmethylene]-4-oxo-4,5-dihydro-thiazol-2-yl}-piperidin-3-yl)-carbamic acid tert-butyl ester was prepared prepared from 5-[1-(2,4-Bis-trifluoromethyl-benzyl)-1H-indazol-5-ylmethylene]-2-methylsulfanyl-thiazol-4-one and piperidin-3-

(R)-yl-carbamic acid tert-butyl ester following General Procedure C. The compound was used directly following General Procedure H to provide 2-(3-(R)-Amino-piperidin-1-yl)-5-[1-(2,4-bis-trifluoromethyl-benzyl)-1H-indazol-5-ylmethylene]-thiazol-4-one.

$^1$H NMR (400 MHZ, CDCl$_3$): δ 8.20 (dd, 1H), 7.98 (s, 1H), 7.97 (s, 1H), 7.91 (s, 1H), 7.62 (d, 1H), 7.55 (m, 1H), 7.30 (dd, 1H), 6.81 (d, 1H), 5.87 (s, 2H), 4.52 (m, 1H), 3.73 (m, 1H), 3.45 (m, 1H), 3.05-3.32 (2H), 1.45-2.12 (4H).

LC/MS: mass calcd. for C$_{25}$H$_{21}$F$_6$N$_5$OS (m/z), 553.1. found, 554.5 [M+H]$^+$.

Example 54

5-[1-(4-Chloro-2-trifluoromethyl-benzyl)-1H-indazol-5-ylmethylene]-2-[1,4]diazepan-1-yl-thiazol-4-one

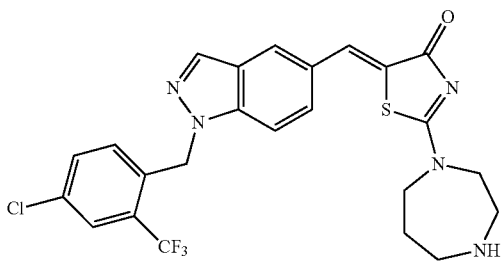 [SMILES: O=C1N=C(N2CCCNCC2)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-[1,4]diazepan-1-yl-thiazol-4-one was prepared from 5-[1-(4-Chloro-2-trifluoromethyl-benzyl)-1H-indazol-5-ylmethylene]-2-ethylsulfanyl-thiazol-4-one and [1,4]diazepane following General Procedure C.

$^1$H NMR (400 MHZ, CDCl$_3$): δ 8.19 (dd, 1H), 7.98 (d, 1H), 7.93 (d, 1H), 7.71 (d, 1H), 7.55 (m, 1H), 7.33 (dd, 1H), 7.31 (m, 1H), 6.65 (d, 1H), 5.79 (s, 2H), 4.09 (t, 1H), 4.06 (m, 1H), 3.79 (t, 1H), 3.71 (m, 1H), 3.14 (m, 1H), 3.09 (m, 1H), 2.94 (m, 2H), 1.98 (m, 2H).

LC/MS: mass calcd. for C$_{24}$H$_{21}$Cl$_3$N$_5$OS (m/z), 519.1. found, 520.5 [M+H]$^+$.

Example 55

5-[1-(2,4-Bis-trifluoromethyl-benzyl)-1H-indazol-5-ylmethylene]-2-[1,4]diazepan-1-yl-thiazol-4-one

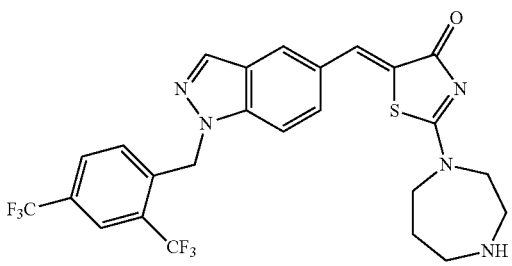 [SMILES: O=C1N=C(N2CCCNCC2)S/C1=C\c1ccc2c(cnn2Cc2ccc(C(F)(F)F)cc2C(F)(F)F)c1]

5-[1-(2,4-Bis-trifluoromethyl-benzyl)-1H-indazol-5-ylmethylene]-2-[1,4]diazepan-1-yl-thiazol-4-one was prepared from 5-[1-(2,4-bis-trifluoromethyl-benzyl)-1H-indazol-5-ylmethylene]-2-methylsulfanyl-thiazol-4-one and [1,4]diazepane following General Procedure C.

$^1$H NMR (400 MHZ, CDCl$_3$): δ 8.22 (m, 1H), 7.99 (m, 1H), 7.98 (s, 1H), 7.93 (s, 1H), 7.63 (d, 1H), 7.57 (d, 1H), 7.32 (d, 1H), 6.81 (d, 1H), 5.89 (s, 2H), 4.08 (m, 2H), 3.79 (t, 1H), 3.72 (t, 1H), 3.14 (m, 1H), 3.09 (m, 1H), 2.94 (m, 2H), 2.02 (m, 1H), 1.97 (m, 1H).

LC/MS: mass calcd. for C$_{25}$H$_{21}$F$_6$N$_5$OS (m/z), 553.1. found, 554.5 [M+H]$^+$.

Example 56

5-[1-(4-Chloro-2-trifluoromethyl-benzyl)-1H-indazol-5-ylmethylene]-2-[4-(2-methoxy-ethyl)-piperazin-1-yl]-thiazol-4-one

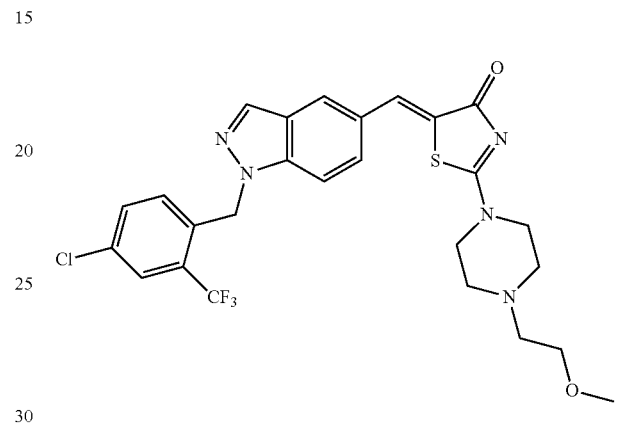

5-[1-(4-Chloro-2-trifluoromethyl-benzyl)-1H-indazol-5-ylmethylene]-2-[4-(2-methoxy-ethyl)-piperazin-1-yl]-thiazol-4-one was prepared from 5-[1-(4-chloro-2-trifluoromethyl-benzyl)-1H-indazol-5-ylmethylene]-2-ethylsulfanyl-thiazol-4-one and 1-(2-methoxy-ethyl)-piperazine following General Procedure C.

$^1$H NMR (400 MHZ, CD$_3$OD): δ 8.21 (d, 1H), 8.07 (m, 1H), 7.92 (s, 1H), 7.79 (d, 1H), 7.62 (dd, 1H), 7.52 (d, 1H), 7.47 (dd, 1H), 6.68 (d, 1H), 5.82 (s, 1H), 3.97 (br, 2H), 3.81 (t, 2H), 3.80 (br, 2H), 3.50 (t, 2H), 3.49 (br, 2H), 3.45 (s, 3H), 3.44 (br, 2H).

LC/MS: mass calcd. for C$_{26}$H$_{25}$ClF$_3$N$_5$O$_2$S (m/z), 563.1. found, 564.5 [M+H]$^+$.

Example 57

2-(4-Amino-piperidin-1-yl)-5-[1-(4-chloro-2-trifluoromethyl-benzyl)-1H-indazol-5-ylmethylene]-thiazol-4-one

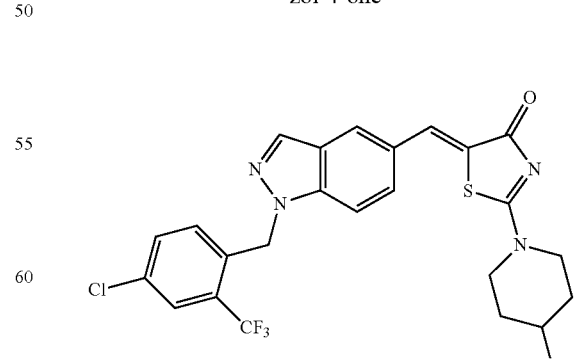

(1-{5-[1-(4-Chloro-2-trifluoromethyl-benzyl)-1H-indazol-5-ylmethylene]-4-oxo-4,5-dihydro-thiazol-2-yl}-piperidin-4-yl)-carbamic acid tert-butyl ester was prepared from 5-[1-(4-chloro-2-trifluoromethyl-benzyl)-1H-indazol-5-ylmethylene]-2-ethylsulfanyl-thiazol-4-one and piperidin-4-yl-carbamic acid tert-butyl ester following General Procedure C. The compound was used directly following General Procedure H to provide 2-(4-Amino-piperidin-1-yl)-5-[1-(4-chloro-2-trifluoromethyl-benzyl)-1H-indazol-5-ylmethylene]-thiazol-4-one.

$^1$H NMR (400 MHZ, CDCl$_3$): δ 8.19 (d, 1H), 7.97 (m, 1H), 7.92 (s, 1H), 7.71 (d, 1H), 7.54 (dd, 1H), 7.33 (dd, 1H), 7.31 (d, 1H), 6.65 (d, 1H), 5.79 (s, 2H), 4.76 (m, 1H), 3.90 (m, 1H), 3.42 9m, 2H), 3.12 (m, 1H), 2.02 (m, 2H), 1.28-1.68 (2H).

LC/MS: mass calcd. for C$_{24}$H$_{21}$ClF$_3$N$_5$OS (m/z), 519.1. found, 520.4 [M+H]$^+$.

Example 58

5-[1-(4-Chloro-2-trifluoromethyl-benzyl)-1H-indazol-5-ylmethylene]-2-[4-(2,2,2-trifluoro-ethyl)-piperazin-1-yl]-thiazol-4-one

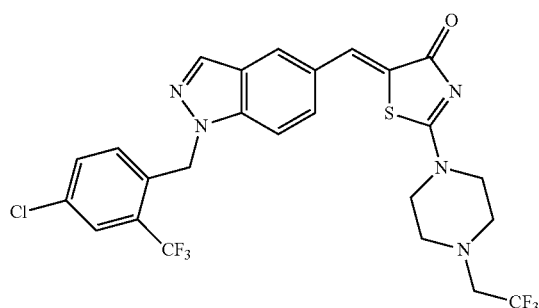

5-[1-(4-Chloro-2-trifluoromethyl-benzyl)-1H-indazol-5-ylmethylene]-2-[4-(2,2,2-trifluoro-ethyl)-piperazin-1-yl]-thiazol-4-one was prepared from 5-[1-(4-chloro-2-trifluoromethyl-benzyl)-1H-indazol-5-ylmethylene]-2-ethylsulfanyl-thiazol-4-one and 1-(2,2,2-trifluoro-ethyl)piperazine following General Procedure C.

$^1$H NMR (400 MHZ, CD$_3$OD): δ 8.27 (s, 1H), 8.16 (s, 1H), 8.02 (s, 1H), 7.80 (d, 1H), 7.67 (d, 1H), 7.59 (d, 1H), 7.49 (dd, 1H), 6.71 (d, 1H), 5.87 (s, 2H), 4.06 (t, 2H), 3.87 (t, 2H), 3.38 (q, 2H), 3.06 (t, 2H), 3.02 (t, 2H).

LC/MS: mass calcd. for C$_{25}$H$_{20}$ClF$_6$N$_5$OS (m/z), 587.1. found, 588.5 [M+H]$^+$.

Example 59

2-(3-(R)-Amino-piperidin-1-yl)-5-[1-(4-chloro-2-trifluoromethyl-benzyl)-1H-indazol-5-ylmethylene]-thiazol-4-one

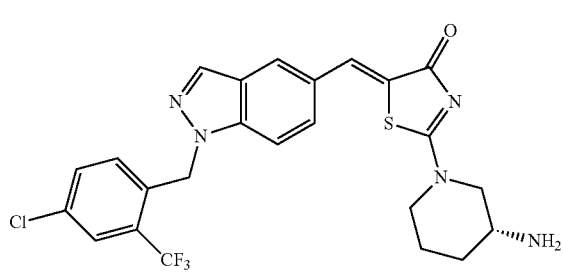 [SMILES: N[C@@H]1CCCN(C2=NC(=O)/C(=C/c3ccc4c(cnn4Cc4ccc(Cl)cc4C(F)(F)F)c3)S2)C1]

(1-{5-[1-(4-Chloro-2-trifluoromethyl-benzyl)-1H-indazol-5-ylmethylene]-4-oxo-4,5-dihydro-thiazol-2-yl}-piperidin-3-yl)-carbamic acid tert-butyl ester was prepared from 5-[1-(4-chloro-2-trifluoromethyl-benzyl)-1H-indazol-5-ylmethylene]-2-ethylsulfanyl-thiazol-4-one and piperidin-3-(R)-yl-carbamic acid tert-butyl ester following General Procedure C. The compound was used directly following General Procedure H to provide 2-(3-(R)-Amino-piperidin-1-yl)-5-[1-(4-chloro-2-trifluoromethyl-benzyl)-1H-indazol-5-ylmethylene]-thiazol-4-one.

$^1$H NMR (400 MHZ, CDCl$_3$): δ 8.19 (dd, 1H), 7.97 (s, 1H), 7.92 (s, 1H), 7.71 (d, 1H), 7.54 (dd, 1H), 7.33 (dd, 1H), 7.31 (d, 1H), 6.66 (d, 1H), 5.79 (s, 2H), 4.58 (m, 1H), 3.76 (m, 1H), 3.43 (m, 1H), 3.17 (m, 1H), 3.06 (m, 1H), 1.47-2.12 (4H).

LC/MS: mass calcd. for C$_{24}$H$_{21}$ClF$_3$N$_5$OS (m/z), 519.1. found, 520.5 [M+H]$^+$ Example 60

2-(3-(S)-Amino-piperidin-1-yl)-5-[1-(4-chloro-2-trifluoromethyl-benzyl)-1H-indazol-5-ylmethylene]-thiazol-4-one

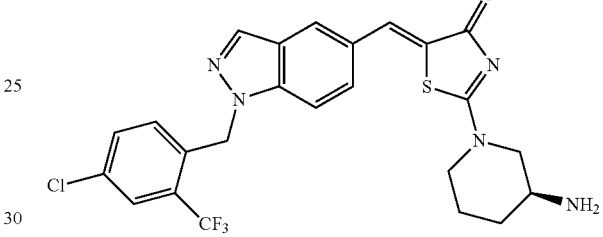

(1-{5-[1-(4-Chloro-2-trifluoromethyl-benzyl)-1H-indazol-5-ylmethylene]-4-oxo-4,5-dihydro-thiazol-2-yl}-piperidin-3-yl)-carbamic acid tert-butyl ester was prepared from 5-[1-(4-chloro-2-trifluoromethyl-benzyl)-1H-indazol-5-ylmethylene]-2-ethylsulfanyl-thiazol-4-one and piperidin-3-(S)-yl-carbamic acid tert-butyl ester following General Procedure C. The compound was used directly following General Procedure H to provide 2-(3-(S)-Amino-piperidin-1-yl)-5-[1-(4-chloro-2-trifluoromethyl-benzyl)-1H-indazol-5-ylmethylene]-thiazol-4-one.

$^1$H NMR (400 MHZ, CDCl$_3$): δ 8.19 (s, 1H), 7.96 (s, 1H), 7.88 (s, 1H), 7.71 (s, 1H), 7.53 (dd, 1H), 7.34 (m, 1H), 7.28 (m, 1H), 6.65 (m, 1H), 5.78 (s, 2H), 4.57 (m, 1H), 3.76 (m, 1H), 3.43 (m, 1H), 3.20 (m, 1H), 2.48 (br, 1H), 1.46-2.16 (4H).

LC/MS: mass calcd. for C$_{24}$H$_{21}$ClF$_3$N$_5$OS (m/z), 519.1. found, 520.5 [M+H]$^+$.

Example 61

5-[1-(4-Chloro-2-trifluoromethyl-benzyl)-1H-indazol-5-ylmethylene]-2-[4-(2,2-difluoro-ethyl)-piperazin-1-yl]-thiazol-4-one

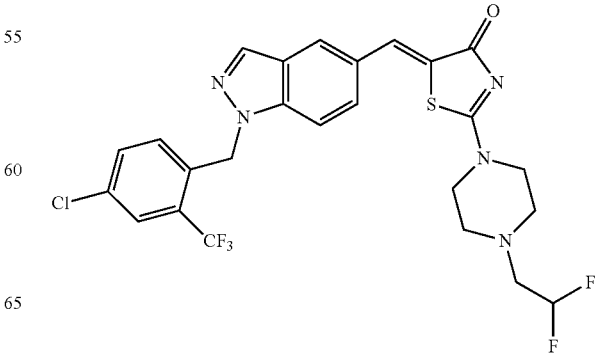

5-[1-(4-Chloro-2-trifluoromethyl-benzyl)-1H-indazol-5-ylmethylene]-2-[4-(2,2-difluoro-ethyl)-piperazin-1-yl]-thiazol-4-one was prepared from 5-[1-(4-chloro-2-trifluoromethyl-benzyl)-1H-indazol-5-ylmethylene]-2-ethylsulfanyl-thiazol-4-one and 1-(2,2-difluoro-ethyl)piperazine following General Procedure C.

¹H NMR (400 MHZ, CDCl₃): δ 8.18 (d, 1H), 7.96 (m, 1H), 7.93 (s, 1H), 7.71 (d, 1H), 7.54 (dd, 1H), 7.33 (dd, 1H), 7.31 (d, 1H), 6.66 (d, 1H), 5.99 (dt, 1H), 5.79 (s, 2H), 4.10 (t, 2H), 3.66 (t, 2H), 2.86 (m, 2H), 2.80 (t, 2H), 2.76 (t, 2H).

LC/MS: mass calcd. for $C_{25}H_{21}ClF_5N_5OS$ (m/z), 569.1. found, 570.5 [M+H]⁺.

Example 62

2-(3-(R)-Amino-pyrrolidin-1-yl)-5-[1-(4-chloro-2-trifluoromethyl-benzyl)-1H-indazol-5-ylmethylene]-thiazol-4-one

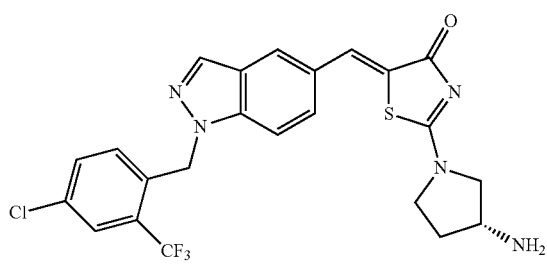 [SMILES: N[C@@H]1CCN(C2=NC(=O)/C(=C/c3ccc4c(cnn4Cc4ccc(Cl)cc4C(F)(F)F)c3)S2)C1]

(1-{5-[1-(4-Chloro-2-trifluoromethyl-benzyl)-1H-indazol-5-ylmethylene]-4-oxo-4,5-dihydro-thiazol-2-yl}-pyrrolidin-3-yl)-carbamic acid tert-butyl ester was prepared from 5-[1-(4-chloro-2-trifluoromethyl-benzyl)-1H-indazol-5-ylmethylene]-2-ethylsulfanyl-thiazol-4-one and pyrrolidin-3-(R)-yl-carbamic acid tert-butyl ester following General Procedure C. The compound was used directly following General Procedure H to provide 2-(3-(R)-Amino-pyrrolidin-1-yl)-5-[1-(4-chloro-2-trifluoromethyl-benzyl)-1H-indazol-5-ylmethylene]-thiazol-4-one.

¹H NMR (400 MHZ, CDCl₃): δ 8.17 (s, 1H), 7.94 (s, 1H), 7.89 (s, 1H), 7.71 (d, 1H), 7.52 (m, 1H), 7.33 (dd, 1H), 7.29 (d, 1H), 6.64 (d, 1H), 5.77 (s, 2H), 4.05 (m, ½H), 3.77-3.99 (3H), 3.67 (m, 1H), 3.35 (m, ½H), 2.27 (m, 1H), 1.92 (m, 1H).

LC/MS: mass calcd. for $C_{23}H_{19}ClF_3N_5OS$ (m/z), 505.1. found, 506.4 [M+H]⁺.

Example 63

5-[1-(4-Chloro-2-trifluoromethyl-benzyl)-1H-indazol-5-ylmethylene]-2-(4-ethyl-piperazin-1-yl)-thiazol-4-one

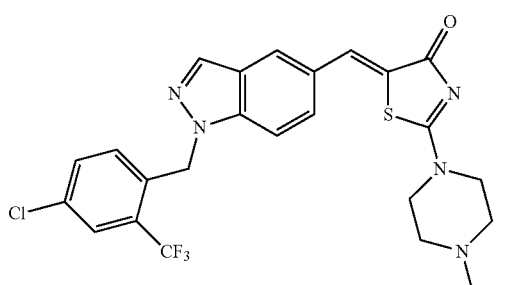

5-[1-(4-Chloro-2-trifluoromethyl-benzyl)-1H-indazol-5-ylmethylene]-2-(4-ethyl-piperazin-1-yl)-thiazol-4-one was prepared from 5-[1-(4-chloro-2-trifluoromethyl-benzyl)-1H-indazol-5-ylmethylene]-2-ethylsulfanyl-thiazol-4-one and 1-ethyl-piperazine following General Procedure C.

¹H NMR (400 MHZ, CDCl₃): δ 8.18 (d, 1H), 7.97 (m, 1H), 7.93 (s, 1H), 7.71 (d, 1H), 7.54 (dd, 1H), 7.33 (dd, 1H), 7.31 (d, 1H), 6.66 (d, 1H), 5.79 (s, 2H), 4.13 (br, 2H), 3.70 (t, 2H), 2.65 (m, 4H), 2.55 (q, 2H), 1.15 (t, 3H).

LC/MS: mass calcd. for $C_{25}H_{23}ClF_3N_5OS$ (m/z), 533.1. found, 534.5 [M+H]⁺.

Example 64

5-[1-(4-Chloro-2-trifluoromethyl-benzyl)-1H-indazol-5-ylmethylene]-2-(S)-(2-pyrrolidin-1-ylmethyl-pyrrolidin-1-yl)-thiazol-4-one

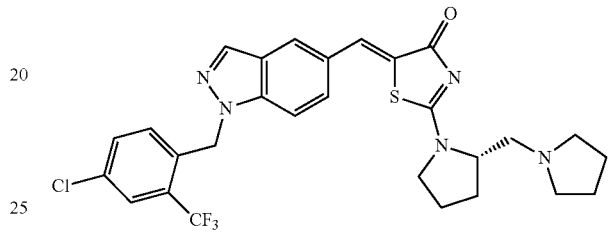

5-[1-(4-Chloro-2-trifluoromethyl-benzyl)-1H-indazol-5-ylmethylene]-2-(S)-(2-pyrrolidin-1-ylmethyl-pyrrolidin-1-yl)-thiazol-4-one was prepared from 5-[1-(4-chloro-2-trifluoromethyl-benzyl)-1H-indazol-5-ylmethylene]-2-ethylsulfanyl-thiazol-4-one and 2-((S)-1-methylpyrrolidino)-pyrrolidine following General Procedure C.

¹H NMR (400 MHZ, CDCl₃): δ 8.20 (d, 1H), 7.96 (m, 1H), 7.92 (s, 1H), 7.71 (d, 1H), 7.54 (m, 1H), 7.34 (m, 1H), 7.32 (m, 1H), 6.65 (m, 1H), 5.79 (s, 2H), 4.59 (m, ½H), 4.08 (m, ½H), 3.60-3.92 (2H), 2.88-3.20 (4H), 2.44-2.74 (2H), 2.05-2.31 (4H), 1.80-1.96 (4H).

LC/MS: mass calcd. for $C_{28}H_{27}ClF_3N_5OS$ (m/z), 573.2. found, 574.3 [M+H]⁺.

Example 65

5-[1-(4-Chloro-2-trifluoromethyl-benzyl)-1H-indazol-5-ylmethylene]-2-(2-(S),5-(S)-dimethyl-piperazin-1-yl)-thiazol-4-one

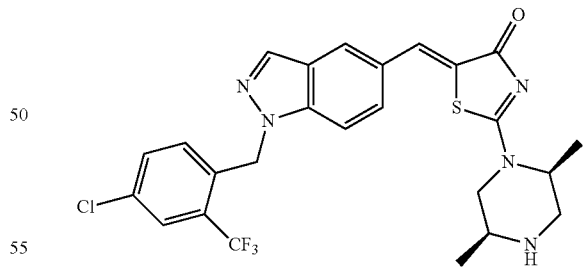

5-[1-(4-Chloro-2-trifluoromethyl-benzyl)-1H-indazol-5-ylmethylene]-2-(2,5-dimethyl-piperazin-1-yl)-thiazol-4-one one was prepared from 5-[1-(4-chloro-2-trifluoromethyl-benzyl)-1H-indazol-5-ylmethylene]-2-ethylsulfanyl-thiazol-4-one and 2-(S),5-(S)-Dimethyl-piperazine following General Procedure C.

¹H NMR (400 MHZ, CDCl₃): δ 8.19 (s, 1H), 7.97 (s, 1H), 7.93 (s, 1H), 7.71 (d, 1H), 7.55 (d, 1H), 7.33 (m, 1H), 7.32 (d, 1H), 6.66 (d, 1H), 5.79 (s, 2H), 4.99-5.20 (½H), 4.48-4.68 (½H), 3.18-4.10 (4H), 2.59-3.02 (1H), 0.99-1.99 (7H).

LC/MS: mass calcd. for $C_{25}H_{23}ClF_3N_5OS$ (m/z), 533.1. found, 534.4 [M+H]⁺.

Example 66

5-[1-(2,4-Bis-trifluoromethyl-benzyl)-1H-indazol-5-ylmethylene]-2-[4-(2-methoxy-ethyl)-piperazin-1-yl]-thiazol-4-one

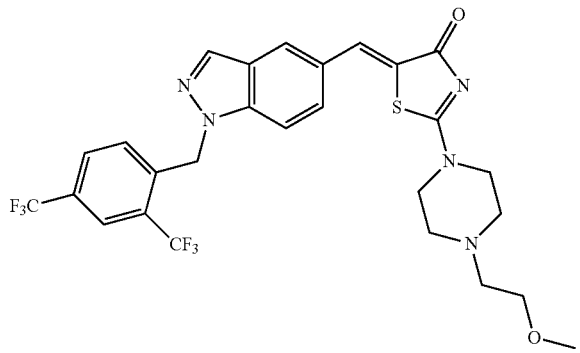 [SMILES: COCCN1CCN(C2=NC(=O)/C(=C/c3ccc4c(cnn4Cc4ccc(C(F)(F)F)cc4C(F)(F)F)c3)S2)CC1]

5-[1-(2,4-Bis-trifluoromethyl-benzyl)-1H-indazol-5-ylmethylene]-2-[4-(2-methoxy-ethyl)-piperazin-1-yl]-thiazol-4-one was prepared from 5-[1-(2,4-bis-trifluoromethyl-benzyl)-1H-indazol-5-ylmethylene]-2-methylsulfanyl-thiazol-4-one and 1-(2-methoxy-ethyl)-piperazine following General Procedure C.

$^1$H NMR (400 MHZ, CDCl$_3$): δ 8.21 (s, 1H), 7.98 (s, 2H), 7.91 (s, 1H), 7.62 (d, 1H), 7.55 (dd, 1H), 7.32 (d, 1H), 6.82 (d, 1H), 5.88 (s, 2H), 4.12 (t, 2H), 3.69 (t, 2H), 3.55 (t, 2H), 3.38 (s, 3H), 2.70 (t, 2H), 2.66 (m, 4H).

LC/MS: mass calcd. for $C_{27}H_{25}F_6N_5O_2S$ (m/z), 597.2. found, 598.5 [M+H]$^+$.

Example 67

5-[1-(2,4-Bis-trifluoromethyl-benzyl)-1H-indazol-5-ylmethylene]-2-(4-ethyl-piperazin-1-yl)-thiazol-4-one

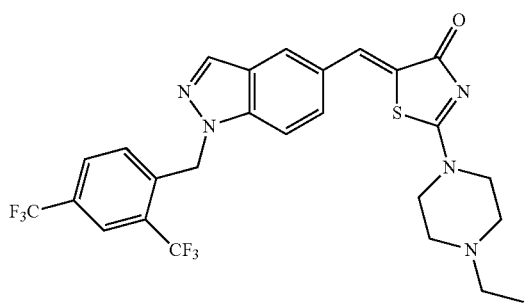 [SMILES: CCN1CCN(C2=NC(=O)/C(=C/c3ccc4c(cnn4Cc4ccc(C(F)(F)F)cc4C(F)(F)F)c3)S2)CC1]

5-[1-(2,4-Bis-trifluoromethyl-benzyl)-1H-indazol-5-ylmethylene]-2-(4-ethyl-piperazin-1-yl)-thiazol-4-one was prepared from 5-[1-(2,4-bis-trifluoromethyl-benzyl)-1H-indazol-5-ylmethylene]-2-methylsulfanyl-thiazol-4-one and 1-ethyl-piperazine following General Procedure C.

$^1$H NMR (400 MHZ, CDCl$_3$): δ 8.21 (d, 1H), 7.98 (s, 2H), 7.92 (s, 1H), 7.62 (d, 1H), 7.55 (dd, 1H), 7.32 (d, 1H), 6.82 (d, 1H), 5.89 (s, 2H), 4.10 (t, 2H), 3.67 (t, 2H), 2.62 (t, 2H), 2.58 (t, 2H), 2.50 (q, 2H), 1.13 (t, 3H).

LC/MS: mass calcd. for $C_{26}H_{23}F_6N_5OS$ (m/z), 567.2. found, 568.4 [M+H]$^+$.

Example 68

5-[1-(4-Chloro-2-trifluoromethyl-benzyl)-1H-indazol-5-ylmethylene]-2-(3-hydroxy-azetidin-1-yl)-thiazol-4-one

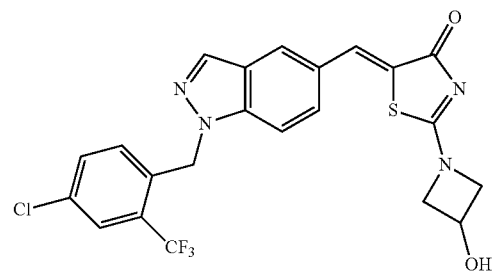 [SMILES: O=C1N=C(N2CC(O)C2)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-(3-hydroxy-azetidin-1-yl)-thiazol-4-one was prepared from 5-[1-(4-chloro-2-trifluoromethyl-benzyl)-1H-indazol-5-ylmethylene]-2-ethylsulfanyl-thiazol-4-one and azetidin-3-ol following General Procedure C.

$^1$H NMR (400 MHZ, DMSO-d$_6$): δ 8.34 (s, 1H), 8.10 (s, 1H), 7.88 (d, 1H), 7.77 (s, 1H), 7.75 (s, 1H), 7.67 (m, 1H), 7.64 (m, 1H), 6.76 (d, 1H), 6.13 (d, 1H), 5.85 (s, 2H), 4.72 (m, 1H), 4.53 (m, 2H), 4.08 (m, 2H).

LC/MS: mass calcd. for $C_{22}H_{16}ClF_3N_4O_2S$ (m/z), 492.1. found, 493.4 [M+H]$^+$.

Example 69

5-[1-(2,4-Bis-trifluoromethyl-benzyl)-1H-indazol-5-ylmethylene]-2-(2S,5S-diaza-bicyclo[2.2.1]hept-2-yl)-thiazol-4-one

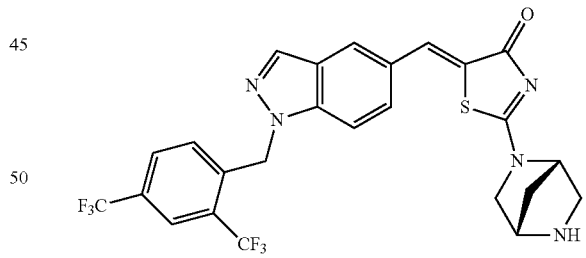

A. 5-{5-[1-(2,4-Bis-trifluoromethyl-benzyl)-1H-indazol-5-ylmethylene]-4-oxo-4,5-dihydro-thiazol-2-yl}-2,5-diaza-bicyclo[2.2.1]heptane-2-carboxylic acid tert-butyl ester was prepared from 5-[1-(2,4-bis-trifluoromethyl-benzyl)-1H-indazol-5-ylmethylene]-2-methylsulfanyl-thiazol-4-one and 2,5-diaza-bicyclo[2.2.1]heptane-2-carboxylic acid tert-butyl ester following General Procedure C.

LC/MS: mass calcd. for $C_{30}H_{27}F_6N_6O_3S$ (m/z), 651.2. found, 652.4 [M+H]$^+$.

B. 5-[1-(2,4-Bis-trifluoromethyl-benzyl)-1H-indazol-5-ylmethylene]-2-(2S,5S-diaza-bicyclo[2.2.1]hept-2-yl)-thiazol-4-one was prepared from 5-{5-[1-(2,4-Bis-trifluoromethyl-benzyl)-1H-indazol-5-ylmethylene]-4-oxo-4,5- dihydro-thiazol-2-yl}-2,5-diaza-bicyclo[2.2.1]heptane-2-carboxylic acid tert-butyl ester following General Procedure H.

¹H NMR (400 MHZ, CDCl₃): δ 8.22 (s, 1H), 7.98 (s, 2H), 7.93 (s, 1H), 7.62 (d, 1H), 7.55 (dd, 1H), 7.32 (d, 1H), 6.82 (d, 1H), 5.88 (s, 2H), 5.21 (s, ½H), 4.46 (s, ½H), 3.98 (d, 1H), 3.81 (dd, 1H), 3.70 (d, ½H), 3.47 (m, ½H), 3.17 (m, 2H), 1.98 (m, 2H).

LC/MS: mass calcd. for $C_{25}H_{19}F_6N_5OS$ (m/z), 551.1. found, 552.4 [M+H]⁺.

Example 70

5-[1-(2,4-Bis-trifluoromethyl-benzyl)-1H-indazol-5-ylmethylene]-2-(5-methyl-2S,5S-diaza-bicyclo[2.2.1]hept-2-yl)-thiazol-4-one

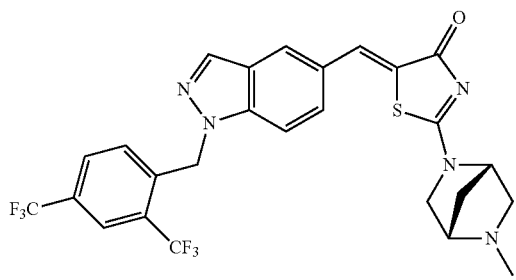 [SMILES: CN1C[C@@H]2C[C@H]1CN2C1=NC(=O)/C(=C/c2ccc3c(cnn3Cc3ccc(C(F)(F)F)cc3C(F)(F)F)c2)S1]

To a solution of 5-[1-(2,4-Bis-trifluoromethyl-benzyl)-1H-indazol-5-ylmethylene]-2-(2S,5S-diaza-bicyclo[2.2.1]hept-2-yl)-thiazol-4-one (50 mg, 0.091 mmol) in DCM (3 mL) was added 0.15 mL of 37% HCHO solution, followed by 150 mg of NaBH(OAc)₃. The mixture was stirred for 1 h and the solvents were removed under reduced pressure. The residue was purified by flash column chromatography on silica gel (0-20% gradient EtOAc/MeOH) to afford the title compound (40 mg, 78%).

¹H NMR (400 MHZ, CD₃OD): δ 8.26 (d, 1H), 8.11 (d, 1H), 8.06 (s, 1H), 7.97 (d, 1H), 7.79 (d, 1H), 7.65 (d, 1H), 7.58 (dd, 1H), 6.87 (m, 1H), 5.95 (s, 2H), 5.28 (s, ½H), 5.01 (s, ½H), 4.64 (m, 1H), 4.02-4.20 (3H), 3.40 (m, 1H), 3.08 (s, 3H), 2.63 (m, 1H), 2.48 (m, 1H).

LC/MS: mass calcd. for $C_{26}H_{21}F_6N_5OS$ (m/z), 565.1. found, 566.2 [M+H]⁺.

Example 71

5-[1-(2,4-Bis-trifluoromethyl-benzyl)-1H-indazol-5-ylmethylene]-2-[5-(2-hydroxy-ethyl)-2S,5S-diaza-bicyclo[2.2.1]hept-2-yl]-thiazol-4-one

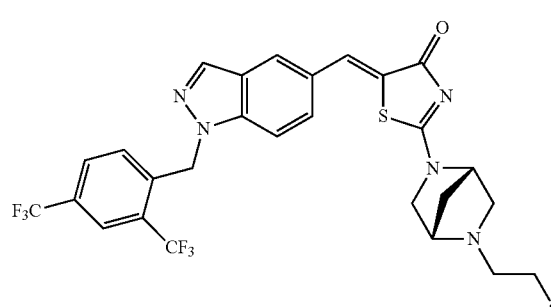

5-[1-(2,4-Bis-trifluoromethyl-benzyl)-1H-indazol-5-ylmethylene]-2-[5-(2-hydroxy-ethyl)-2S,5S-diaza-bicyclo[2.2.1]hept-2-yl]-thiazol-4-one was prepared from 5-[1-(2,4-bis-trifluoromethyl-benzyl)-1H-indazol-5-ylmethylene]-2-methylsulfanyl-thiazol-4-one and 2-(2S,5S-diaza-bicyclo[2.2.1]hept-2-yl)ethanol following General Procedure C.

¹H NMR (400 MHZ, CDCl₃): δ 8.21 (d, 1H), 7.98 (s, 1H), 7.97 (s, 1H), 7.93 (s, 1H), 7.62 (d, 1H), 7.54 (m, 1H), 7.31 (d, 1H), 6.82 (d, 1H), 5.88 (s, 2H), 5.15 (s, ½H), 4.40 (s, ½H), 3.49-4.07 (6H), 3.10 (m, 1H), 2.75-2.90 (3H), 1.95-2.17 (2H).

LC/MS: mass calcd. for $C_{27}H_{23}F_6N_5O_2S$ (m/z), 595.2. found, 596.5 [M+H]⁺.

Example 72

2-(4-{5-[1-(4-Chloro-2-trifluoromethyl-benzyl)-1H-indazol-5-ylmethylene]-4-oxo-4,5-dihydro-thiazol-2-yl}-piperazin-1-yl)-N,N-dimethyl-acetamide

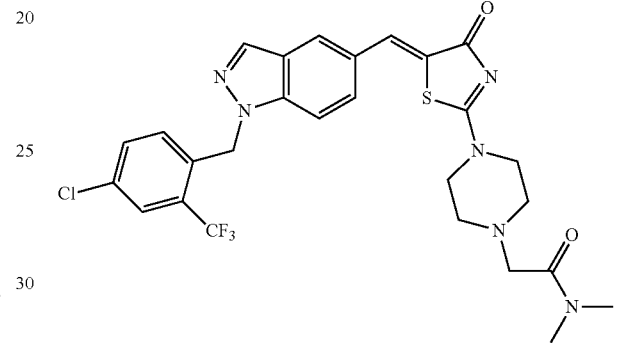

2-(4-{5-[1-(4-Chloro-2-trifluoromethyl-benzyl)-1H-indazol-5-ylmethylene]-4-oxo-4,5-dihydro-thiazol-2-yl}-piperazin-1-yl)-N,N-dimethyl-acetamide one was prepared from 5-[1-(4-chloro-2-trifluoromethyl-benzyl)-1H-indazol-5-ylmethylene]-2-ethylsulfanyl-thiazol-4-one and N,N-dimethyl-2-piperazin-1-yl-acetamide following General Procedure C.

¹H NMR (400 MHZ, CDCl₃): δ 8.19 (d, 1H), 7.97 (s, 1H), 7.93 (s, 1H), 7.71 (d, 1H), 7.54 (dd, 1H), 7.33 (dd, 1H), 7.31 (d, 1H), 6.66 (d, 1H), 5.79 (s, 2H), 4.14 (t, 2H), 3.69 (t, 2H), 3.28 (s, 2H), 3.06 (s, 3H), 2.98 (s, 3H), 2.78 (t, 2H), 2.72 (t, 2H).

LC/MS: mass calcd. for $C_{27}H_{26}ClF_3N_6O_2S$ (m/z), 590.2. found, 591.5 [M+H]⁺.

Example 73

5-[1-(2,4-Bis-trifluoromethyl-benzyl)-1H-indazol-5-ylmethylene]-2-[4-(2-ethoxy-ethyl)-piperazin-1-yl]-thiazol-4-one

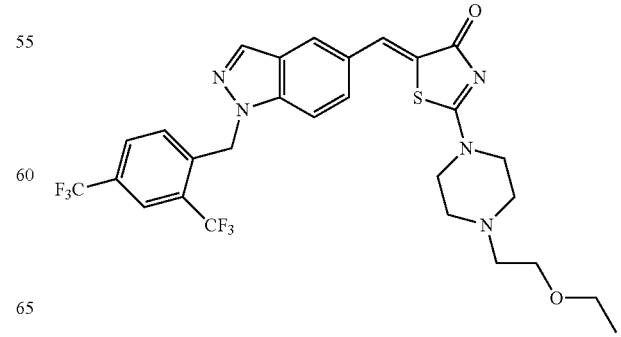

5-[1-(2,4-Bis-trifluoromethyl-benzyl)-1H-indazol-5-ylmethylene]-2-[4-(2-ethoxy-ethyl)-piperazin-1-yl]-thiazol-4-one was prepared from 5-[1-(2,4-bis-trifluoromethyl-benzyl)-1H-indazol-5-ylmethylene]-2-methylsulfanyl-thiazol-4-one and 1-(2-ethoxy-ethyl)-piperazine following General Procedure C.

$^1$H NMR (400 MHZ, CDCl$_3$): δ 8.21 (s, 1H), 7.98 (s, 2H), 7.93 (s, 1H), 7.63 (d, 1H), 7.55 (d, 1H), 7.31 (d, 1H), 6.81 (d, 1H), 5.88 (s, 2H), 4.11 (t, 2H), 3.67 (t, 2H), 3.59 (t, 2H), 3.52 (q, 2H), 2.71 (t, 2H), 2.66 (m, 4H), 1.22 (t, 3H).

LC/MS: mass calcd. for C$_{28}$H$_{27}$F$_6$N$_5$O$_2$S (m/z), 611.2. found, 612.5 [M+H]$^+$.

Example 74

1-{5-[1-(2,4-Bis-trifluoromethyl-benzyl)-1H-indazol-5-ylmethylene]-4-oxo-4,5-dihydro-thiazol-2-yl}-4-methyl-piperidine-4-carboxylic acid

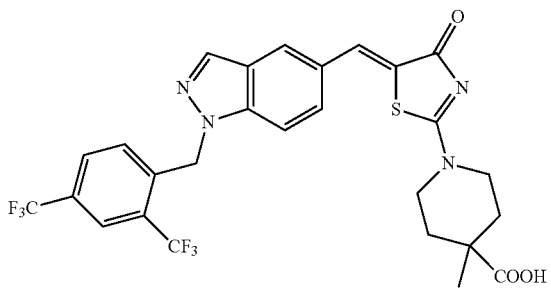 [SMILES: CC1(C(=O)O)CCN(C2=NC(=O)/C(=C/c3ccc4c(cnn4Cc4ccc(C(F)(F)F)cc4C(F)(F)F)c3)S2)CC1]

1-{5-[1-(2,4-Bis-trifluoromethyl-benzyl)-1H-indazol-5-ylmethylene]-4-oxo-4,5-dihydro-thiazol-2-yl}-4-methyl-piperidine-4-carboxylic acid was prepared from 5-[1-(2,4-bis-trifluoromethyl-benzyl)-1H-indazol-5-ylmethylene]-2-methylsulfanyl-thiazol-4-one and 4-methyl-piperidine-4-carboxylic acid following General Procedure C.

$^1$H NMR (400 MHZ, CDCl$_3$): δ 8.21 (s, 1H), 7.98 (s, 2H), 7.94 (s, 1H), 7.62 (d, 1H), 7.55 (dd, 1H), 7.31 (d, 1H), 6.82 (d, 1H), 5.87 (s, 2H), 4.69 (m, 1H), 3.74 (m, 1H), 3.56 (m, 1H), 3.45 (m, 1H), 2.32 (m, 2H), 1.60 (m, 2H), 1.35 (s, 3H).

LC/MS: mass calcd. for C$_{27}$H$_{22}$F$_6$N$_4$O$_3$S (m/z), 596.1. found, 597.4 [M+H]$^+$.

Example 75

1-{5-[1-(4-Chloro-2-trifluoromethyl-benzyl)-1H-indazol-5-ylmethylene]-4-oxo-4,5-dihydro-thiazol-2-yl}-4-methyl-piperidine-4-carboxylic acid

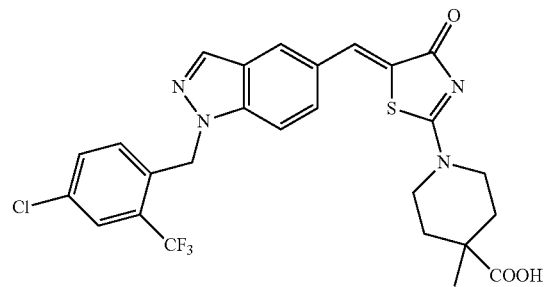 [SMILES: CC1(C(=O)O)CCN(C2=NC(=O)/C(=C/c3ccc4c(cnn4Cc4ccc(Cl)cc4C(F)(F)F)c3)S2)CC1]

1-{5-[1-(4-Chloro-2-trifluoromethyl-benzyl)-1H-indazol-5-ylmethylene]-4-oxo-4,5-dihydro-thiazol-2-yl}-4-methyl-piperidine-4-carboxylic acid was prepared from 5-[1-(4-chloro-2-trifluoromethyl-benzyl)-1H-indazol-5-ylmethylene]-2-ethylsulfanyl-thiazol-4-one and 4-methyl-piperidine-4-carboxylic acid following General Procedure C.

$^1$H NMR (400 MHZ, CDCl$_3$): δ 8.16 (s, 1H), 7.90 (s, 1H), 7.83 (s, 1H), 7.69 (m, 1H), 7.48 (d, 1H), 7.32 (d, 1H), 7.27 (d, 1H), 6.65 (d, 1H), 5.75 (s, 2H), 4.68 (br, 1H), 3.71 (m, 1H), 3.60 (m, 1H), 3.44 (m, 1H), 2.35 (m, 1H), 2.28 (m, 1H), 1.40-1.54 (2H), 1.43 (s, 3H).

LC/MS: mass calcd. for C$_{26}$H$_{22}$ClF$_3$N$_4$O$_3$S (m/z), 562.1. found, 563.3 [M+H]$^+$.

Example 76

5-[1-(4-Chloro-2-trifluoromethyl-benzyl)-1H-indazol-5-ylmethylene]-2-[4-(2-hydroxy-ethyl)-[1,4]diazepan-1-yl]-thiazol-4-one

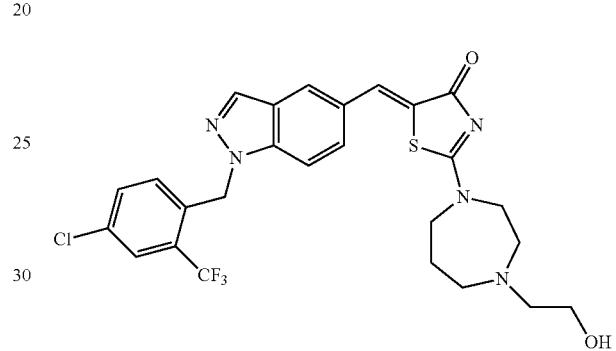

5-[1-(4-Chloro-2-trifluoromethyl-benzyl)-1H-indazol-5-ylmethylene]-2-[4-(2-hydroxy-ethyl)-[1,4]diazepan-1-yl]-thiazol-4-one was prepared from 5-[1-(4-chloro-2-trifluoromethyl-benzyl)-1H-indazol-5-ylmethylene]-2-ethylsulfanyl-thiazol-4-one and 2-[1,4]diazepan-1-yl-ethanol following General Procedure C.

$^1$H NMR (400 MHZ, CD$_3$OD): δ 8.19 (s, 1H), 8.01 (m, 1H), 7.77 (dd, 1H), 7.76 (d, 1H), 7.57 (dd, 1H), 7.48 (d, 1H), 7.45 (dd, 1H), 6.66 (d, 1H), 5.79 (s, 2H), 3.96-4.03 (2H), 3.78 (m, 2H), 3.65 (m, 2H), 3.00 (m, 1H), 2.92 (m, 1H), 2.78 (m, 2H), 2.69 (m, 2H), 2.05 (m, 1H), 1.96 (m, 1H).

LC/MS: mass calcd. for C$_{26}$H$_{25}$ClF$_3$N$_5$O$_2$S (m/z), 563.1. found, 564.3 [M+H]$^+$.

Example 77

2-(3-Amino-azetidin-1-yl)-5-[1-(2,4-bis-trifluoromethyl-benzyl)-1H-indazol-5-ylmethylene]-thiazol-4-one

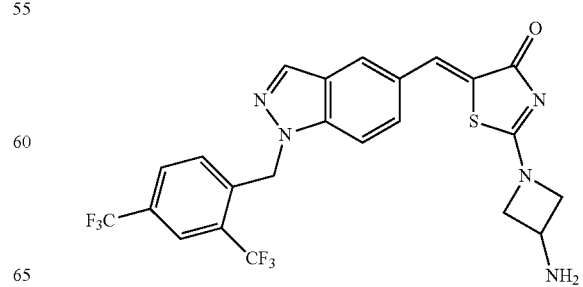

(1-{5-[1-(2,4-Bis-trifluoromethyl-benzyl)-1H-indazol-5-ylmethylene]-4-oxo-4,5-dihydro-thiazol-2-yl}-azetidin-3-yl)-carbamic acid tert-butyl ester was prepared from 5-[1-(2,4-Bis-trifluoromethyl-benzyl)-1H-indazol-5-ylmethylene]-2-methylsulfanyl-thiazol-4-one and azetidin-3-yl-carbamic acid tert-butyl ester following General Procedure C. The compound was used directly following General Procedure H to provide 2-(3-Amino-azetidin-1-yl)-5-[1-(2,4-bis-trifluoromethyl-benzyl)-1H-indazol-5-ylmethylene]-thiazol-4-one.

$^1$H NMR (400 MHZ, CD$_3$OD): δ 8.27 (s, 1H), 8.10 (s, 1H), 8.05 (s, 1H), 7.85 (s, 1H), 7.79 (d, 1H), 7.65 (dd, 1H), 7.58 (d, 1H), 6.85 (d, 1H), 5.97 (s, 1H), 4.52-4.62 (2H), 4.04-4.12 (3H).

LC/MS: mass calcd. for C$_{23}$H$_{17}$F$_6$N$_5$OS (m/z), 525.5. found, 526.3 [M+H]$^+$.

Example 78

5-[1-(4-Chloro-2-trifluoromethyl-benzyl)-1H-indazol-5-ylmethylene]-2-(5-methyl-2S,5S-diaza-bicyclo[2.2.1]hept-2-yl)-thiazol-4-one

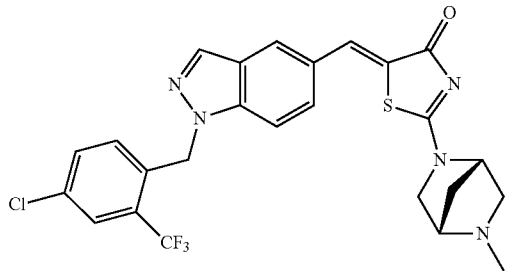 [SMILES: CN1C[C@@H]2C[C@H]1CN2C1=NC(=O)/C(=C/c2ccc3c(cnn3Cc3ccc(Cl)cc3C(F)(F)F)c2)S1]

5-[1-(4-Chloro-2-trifluoromethyl-benzyl)-1H-indazol-5-ylmethylene]-2-(5-methyl-2S,5S-diaza-bicyclo[2.2.1]hept-2-yl)-thiazol-4-one was prepared from 5-[1-(4-chloro-2-trifluoromethyl-benzyl)-1H-indazol-5-ylmethylene]-2-ethylsulfanyl-thiazol-4-one and 2-methyl-2S,5S-diaza-bicyclo[2.2.1]heptane following General Procedure C.

$^1$H NMR (400 MHZ, CDCl$_3$): δ 8.17 (d, 1H), 7.94 (s, 1H), 7.91 (d, 1H), 7.71 (d, 1H), 7.51 (m, 1H), 7.33 (dd, 1H), 7.29 (d, 1H), 6.66 (d, 1H), 5.77 (s, 2H), 5.17 (s, ½H), 4.40 (s, ½H), 4.14 (d, ½H), 3.89 (d, ½H), 2.79-3.86 (4H), 2.58 (d, 3H), 2.23 (m, 1H), 2.05 (m, 1H).

LC/MS: mass calcd. for C$_{25}$H$_{21}$ClF$_3$N$_5$OS (m/z), 531.1. found, 532.3 [M+H]$^+$.

Example 79

2-(4-{5-[1-(4-Chloro-2-trifluoromethyl-benzyl)-1H-indazol-5-ylmethylene]-4-oxo-4,5-dihydro-thiazol-2-yl}-piperazin-1-yl)-acetamide

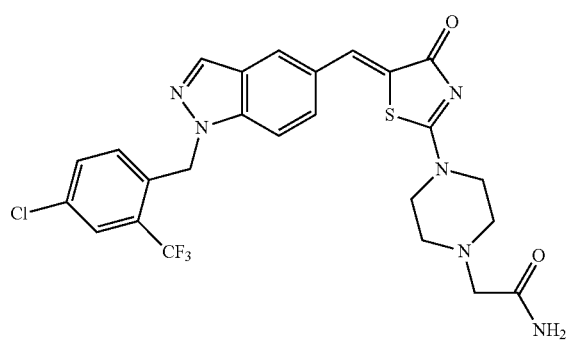 [SMILES: NC(=O)CN1CCN(C2=NC(=O)/C(=C/c3ccc4c(cnn4Cc4ccc(Cl)cc4C(F)(F)F)c3)S2)CC1]

2-(4-{5-[1-(4-Chloro-2-trifluoromethyl-benzyl)-1H-indazol-5-ylmethylene]-4-oxo-4,5-dihydro-thiazol-2-yl}-piperazin-1-yl)-acetamide was prepared from 5-[1-(4-chloro-2-trifluoromethyl-benzyl)-1H-indazol-5-ylmethylene]-2-ethylsulfanyl-thiazol-4-one and 2-piperazin-1-yl-acetamide following General Procedure C.

$^1$H NMR (400 MHZ, CD$_3$OD): δ 8.23 (s, 1H), 8.10 (s, 1H), 7.94 (s, 1H), 7.80 (s, 1H), 7.65 (d, 1H), 7.54 (d, 1H), 7.48 (d, 1H), 6.69 (d, 1H), 5.84 (s, 2H), 4.34 (br, 2H), 4.13 (s, 2H), 4.12 (br, 2H), 3.65 (br, 4H).

LC/MS: mass calcd. for C$_{25}$H$_{22}$ClF$_3$N$_6$O$_2$S (m/z), 562.1. found, 563.2 [M+H]$^+$.

Example 80

5-[1-(4-Chloro-2-trifluoromethyl-benzyl)-1H-indazol-5-ylmethylene]-2-[5-(2-hydroxy-ethyl)-2S,5S-diaza-bicyclo[2.2.1]hept-2-yl]-thiazol-4-one

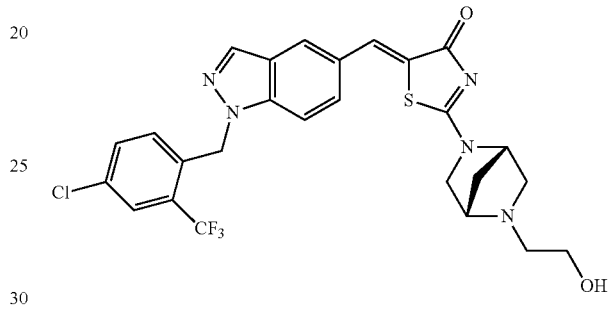

5-[1-(4-Chloro-2-trifluoromethyl-benzyl)-1H-indazol-5-ylmethylene]-2-[5-(2-hydroxy-ethyl)-2S,5S-diaza-bicyclo[2.2.1]hept-2-yl]-thiazol-4-one was prepared from 5-[1-(4-chloro-2-trifluoromethyl-benzyl)-1H-indazol-5-ylmethylene]-2-ethylsulfanyl-thiazol-4-one and 2-(2S,5S-diaza-bicyclo[2.2.1]hept-2-yl)ethanol following General Procedure C.

$^1$H NMR (400 MHZ, CD$_3$OD): δ 8.24 (s, 1H), 8.11 (s, 1H), 7.97 (d, 1H), 7.80 (d, 1H), 7.65 (d, 1H), 7.57 (d, 1H), 7.49 (d, 1H), 6.70 (m, 1H), 5.85 (s, 2H), 5.28 (s, ½H), 5.01 (m, ½H), 4.82-4.89 (1H), 3.40-4.31 (4H), 2.42-2.64 (2H).

LC/MS: mass calcd. for C$_{26}$H$_{23}$ClF$_3$N$_5$O$_2$S (m/z), 561.1. found, 562.2 [M+H]$^+$.

Example 81

5-[1-(4-Chloro-2-trifluoromethyl-benzyl)-1H-indazol-5-ylmethylene]-2-[4-(2-ethoxy-ethyl)-piperazin-1-yl]-thiazol-4-one

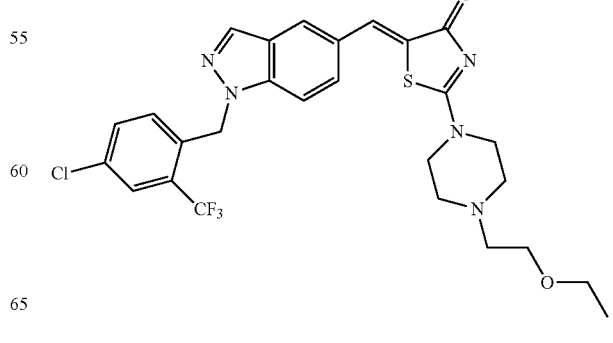

5-[1-(4-Chloro-2-trifluoromethyl-benzyl)-1H-indazol-5-ylmethylene]-2-[4-(2-ethoxy-ethyl)-piperazin-1-yl]-thiazol-4-one was prepared from 5-[1-(4-chloro-2-trifluoromethyl-benzyl)-1H-indazol-5-ylmethylene]-2-ethylsulfanyl-thiazol-4-one and 1-(2-ethoxy-ethyl)-piperazine following General Procedure C.

$^1$H NMR (400 MHZ, CDCl$_3$): δ 8.18 (m, 1H), 7.97 (s, 1H), 7.92 (s, 1H), 7.71 (d, 1H), 7.54 (dd, 1H), 7.33 (dd, 1H), 7.31 (d, 1H), 6.66 (d, 1H), 5.79 (s, 2H), 4.10 (t, 2H), 3.67 (t, 2H), 3.59 (t, 2H), 3.52 9q, 2H), 2.71 (t, 2H), 2.67 (m, 4H), 1.22 (t, 3H).

LC/MS: mass calcd. for C$_{27}$H$_{27}$ClF$_3$N$_5$O$_2$S (m/z), 577.2. found, 578.5 [M+H]$^+$.

Example 82

2-(4-{5-[1-(4-Chloro-2-trifluoromethyl-benzyl)-1H-indazol-5-ylmethylene]-4-oxo-4,5-dihydro-thiazol-2-yl}piperazin-1-yl)-N-methyl-acetamide

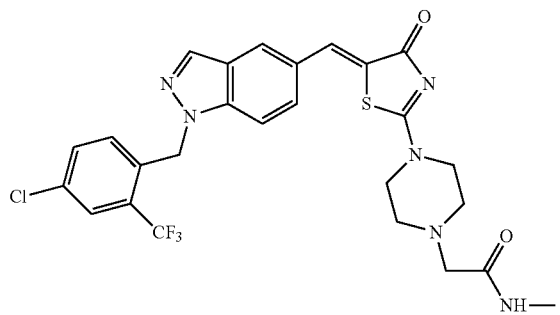 [SMILES: CNC(=O)CN1CCN(C2=NC(=O)/C(=C/c3ccc4c(cnn4Cc4ccc(Cl)cc4C(F)(F)F)c3)S2)CC1]

2-(4-{5-[1-(4-Chloro-2-trifluoromethyl-benzyl)-1H-indazol-5-ylmethylene]-4-oxo-4,5-dihydro-thiazol-2-yl}-piperazin-1-yl)-N-methyl-acetamide was prepared from 5-[1-(4-chloro-2-trifluoromethyl-benzyl)-1H-indazol-5-ylmethylene]-2-ethylsulfanyl-thiazol-4-one and N-methyl-2-piperazin-1-yl-acetamide following General Procedure C.

$^1$H NMR (400 MHZ, CD$_3$OD): δ 8.23 (d, 1H), 8.11 (m, 1H), 7.94 (s, 1H), 7.80 (d, 1H), 7.65 (dd, 1H), 7.55 (d, 1H), 7.48 (dd, 1H), 6.70 (d, 1H), 5.85 (s, 2H), 4.32 (br, 2H), 4.09 (br, 2H), 4.08 (s, 2H), 3.63 (m, 4H), 2.83 (s, 3H).

LC/MS: mass calcd. for C$_{26}$H$_{24}$ClF$_3$N$_6$O$_2$S (m/z), 576.1. found, 577.2 [M+H]$^+$.

Example 83

5-[1-(4-Chloro-2-trifluoromethyl-benzyl)-1H-indazol-5-ylmethylene]-2-(2-(R)-methyl-piperazin-1-yl)-thiazol-4-one

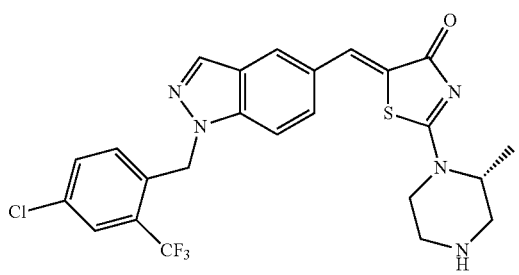 [SMILES: C[C@@H]1CNCCN1C1=NC(=O)/C(=C/c2ccc3c(cnn3Cc3ccc(Cl)cc3C(F)(F)F)c2)S1]

4-{5-[1-(4-Chloro-2-trifluoromethyl-benzyl)-1H-indazol-5-ylmethylene]-4-oxo-4,5-dihydro-thiazol-2-yl}-3-methyl-piperazine-1-carboxylic acid tert-butyl ester was prepared from 5-[1-(4-chloro-2-trifluoromethyl-benzyl)-1H-indazol-5-ylmethylene]-2-ethylsulfanyl-thiazol-4-one and 3-(R)-methyl-piperazine-1-carboxylic acid tert-butyl ester following General Procedure C. The compound was used directly following General Procedure H to provide 5-[1-(4-Chloro-2-trifluoromethyl-benzyl)-1H-indazol-5-ylmethylene]-2-(2-(R)-methyl-piperazin-1-yl)thiazol-4-one.

$^1$H NMR (400 MHZ, CD$_3$OD): δ 8.25 (d, 1H), 8.13 (m, 1H), 7.95 (s, 1H), 7.80 (d, 1H), 7.68 (dd, 1H), 7.57 (d, 1H), 7.49 (dd, 1H), 6.71 (d, 1H), 5.86 (s, 2H), 5.23 (br, 1H), 4.52 (br, 1H), 3.45-4.09 (5H), 1.54 (m, 3H).

LC/MS: mass calcd. for C$_{24}$H$_{21}$ClF$_3$N$_5$OS (m/z), 519.1. found, 520.2 [M+H]$^+$.

Example 84

2-(4-tert-Butyl-piperazin-1-yl)-5-[1-(4-chloro-2-trifluoromethyl-benzyl)-1H-indazol-5-ylmethylene]-thiazol-4-one

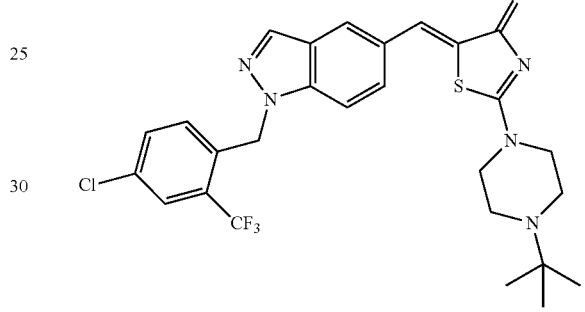

2-(4-tert-Butyl-piperazin-1-yl)-5-[1-(4-chloro-2-trifluoromethyl-benzyl)-1H-indazol-5-ylmethylene]-thiazol-4-one was prepared from 5-[1-(4-chloro-2-trifluoromethyl-benzyl)-1H-indazol-5-ylmethylene]-2-ethylsulfanyl-thiazol-4-one and 1-tert-butyl-piperazine following General Procedure C.

$^1$H NMR (400 MHZ, CDCl$_3$): δ 8.19 (m, 1H), 7.97 (s, 1H), 7.93 (s, 1H), 7.71 (d, 1H), 7.55 (dd, 1H), 7.33 (dd, 1H), 7.31 (d, 1H), 6.65 (d, 1H), 5.79 (s, 2H), 4.07 (t, 2H), 3.63 (t, 2H), 2.74 (t, 2H), 2.70 (t, 2H), 1.10 (s, 9H).

LC/MS: mass calcd. for C$_{27}$H$_{27}$ClF$_3$N$_5$OS (m/z), 561.2. found, 562.2 [M+H]$^+$.

Example 85

5-[1-(4-Chloro-2-trifluoromethyl-benzyl)-1H-indazol-5-ylmethylene]-2-[5-(2-methoxy-ethyl)-2S,5S-diaza-bicyclo[2.2.1]hept-2-yl]-thiazol-4-one

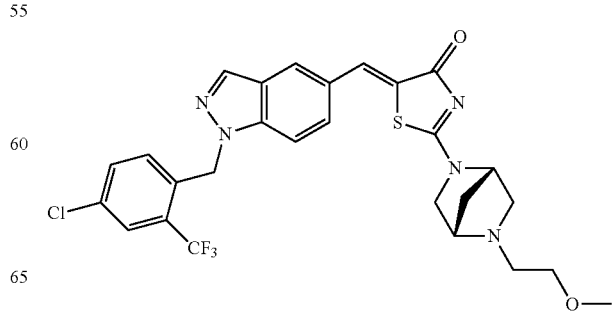

5-[1-(4-Chloro-2-trifluoromethyl-benzyl)-1H-indazol-5-ylmethylene]-2-[5-(2-methoxy-ethyl)-2S,5S-diaza-bicyclo[2.2.1]hept-2-yl]-thiazol-4-one was prepared from 5-[1-(4-chloro-2-trifluoromethyl-benzyl)-1H-indazol-5-ylmethylene]-2-ethylsulfanyl-thiazol-4-one and 2-(2-methoxy-ethyl)-2S,5S-diaza-bicyclo[2.2.1]heptane following General Procedure C.

$^1$H NMR (400 MHZ, CDCl$_3$): δ 8.19 (s, 1H), 7.96 (s, 1H), 7.92 (s, 1H), 7.71 (d, 1H), 7.53 (m, 1H), 7.33 (dd, 1H), 7.31 (d, 1H), 6.66 (d, 1H), 5.79 (s, 2H), 5.09 (s, ½H), 4.35 (s, ½H), 4.10 (dd, ½H), 3.80 (m, 1H), 3.66 (dd, ½H), 3.45-3.53 (3H), 3.36 (d, 3H), 3.24 (dd, ½H), 3.08 (dd, ½H), 2.72-2.86 (3H), 2.14 (dd, 1H), 1.94 (dd, 1H).

LC/MS: mass calcd. for $C_{27}H_{25}ClF_3N_5O_2S$ (m/z), 575.1. found, 576.2 [M+H]$^+$.

Example 86

5-[1-(2,4-Bis-trifluoromethyl-benzyl)-1H-indazol-5-ylmethylene]-2-(3-methyl-3,8-diaza-bicyclo[3.2.1]oct-8-yl)-thiazol-4-one

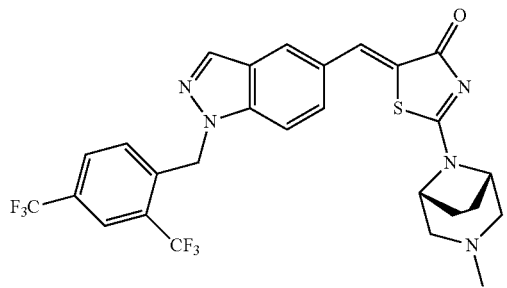 [SMILES: CN1C[C@H]2CC[C@@H](C1)N2C1=NC(=O)/C(=C/c2ccc3c(cnn3Cc3ccc(C(F)(F)F)cc3C(F)(F)F)c2)S1]

5-[1-(2,4-Bis-trifluoromethyl-benzyl)-1H-indazol-5-ylmethylene]-2-(3-methyl-3,8-diaza-bicyclo[3.2.1]oct-8-yl)-thiazol-4-one was prepared from 5-[1-(2,4-bis-trifluoromethyl-benzyl)-1H-indazol-5-ylmethylene]-2-methylsulfanyl-thiazol-4-one and 3-methyl-3,8-diaza-bicyclo[3.2.1]octane following General Procedure C.

$^1$H NMR (400 MHZ, CDCl$_3$): δ 8.21 (d, 1H), 7.98 (s, 1H), 7.93 (s, 1H), 7.62 (d, 1H), 7.55 (dd, 1H), 7.32 (d, 1H), 6.82 (d, 1H), 5.89 (s, 2H), 4.96 (m, 1H), 4.16 (m, 1H), 2.84 (dd, 1H), 2.76 (dd, 1H), 2.46 (dd, 1H), 2.40 (dd, 1H), 2.29 (s, 3H), 2.02-2.20 (4H).

LC/MS: mass calcd. for $C_{27}H_{23}F_6N_5OS$ (m/z), 579.2. found, 580.1 [M+H]$^+$.

Example 87

5-[1-(4-Chloro-2-trifluoromethyl-benzyl)-1H-indazol-5-ylmethylene]-2-(3-methyl-3,8-diaza-bicyclo[3.2.1]oct-8-yl)-thiazol-4-one

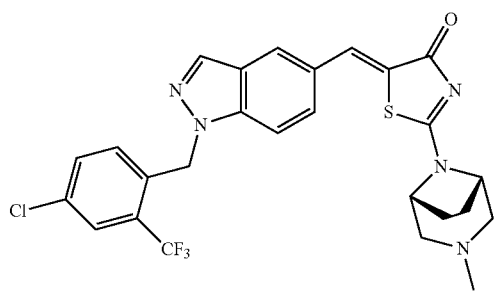 [SMILES: CN1C[C@H]2CC[C@@H](C1)N2C1=NC(=O)/C(=C/c2ccc3c(cnn3Cc3ccc(Cl)cc3C(F)(F)F)c2)S1]

5-[1-(4-Chloro-2-trifluoromethyl-benzyl)-1H-indazol-5-ylmethylene]-2-(3-methyl-3,8-diaza-bicyclo[3.2.1]oct-8-yl)-thiazol-4-one was prepared from 5-[1-(4-chloro-2-trifluoromethyl-benzyl)-1H-indazol-5-ylmethylene]-2-ethylsulfanyl-thiazol-4-one and 3-methyl-3,8-diaza-bicyclo[3.2.1]octane following General Procedure C.

$^1$H NMR (400 MHZ, CDCl$_3$): δ 8.19 (s, 1H), 7.96 (s, 1H), 7.92 (s, 1H), 7.71 (d, 1H), 7.54 (dd, 1H), 7.33 (dd, 1H), 7.31 (dd, 1H), 6.66 (d, 1H), 5.79 (s, 2H), 4.96 (m, 1H), 4.17 (m, 1H), 2.81 (dd, 2H), 2.43 (dd, 2H), 2.29 (s, 3H), 2.01-2.17 (4H).

LC/MS: mass calcd. for $C_{26}H_{23}ClF_3N_5OS$ (m/z), 545.1. found, 546.1 [M+H]$^+$.

Example 88

5-[1-(4-Chloro-2-trifluoromethyl-benzyl)-1H-indazol-5-ylmethylene]-2-[4-(2-methoxy-acetyl)cis-3,5-dimethyl-piperazin-1-yl]-thiazol-4-one

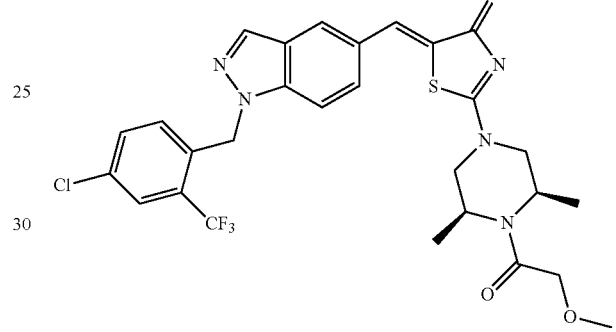

5-[1-(4-Chloro-2-trifluoromethyl-benzyl)-1H-indazol-5-ylmethylene]-2-[4-(2-methoxy-acetyl)-cis-3,5-dimethyl-piperazin-1-yl]-thiazol-4-one one was prepared from 5-[1-(4-chloro-2-trifluoromethyl-benzyl)-1H-indazol-5-ylmethylene]-2-ethylsulfanyl-thiazol-4-one and 1-(2,6-dimethyl-piperazin-1-yl)-2-methoxy-ethanone following General Procedure C.

$^1$H NMR (400 MHZ, CDCl$_3$): δ 8.21 (s, 1H), 7.97 (s, 2H), 7.71 (d, 1H), 7.54 (d, 1H), 7.33 (m, 2H), 6.68 (d, 1H), 5.79 (s, 2H), 4.87 (m, 2H), 4.08-4.24 (3H), 3.60-3.75 (2H), 3.47 (s, 3H), 3.37 (m, 1H).

LC/MS: mass calcd. for $C_{28}H_{27}ClF_3N_5O_3S$ (m/z), 605.2. found, 606.1 [M+H]$^+$.

Example 89

5-[1-(4-Chloro-2-trifluoromethyl-benzyl)-1H-indazol-5-ylmethylene]-2-[5-(2-methoxy-acetyl)-2S,5S-diaza-bicyclo[2.2.1]hept-2-yl]-thiazol-4-one

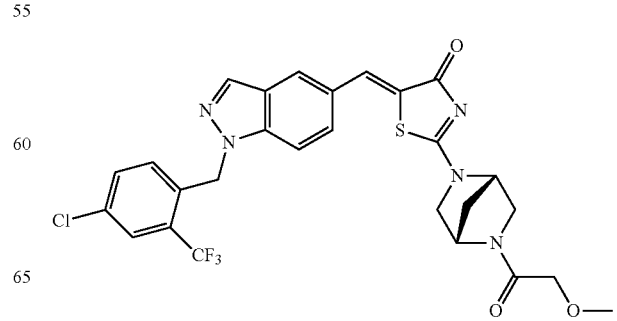

5-[1-(4-Chloro-2-trifluoromethyl-benzyl)-1H-indazol-5-ylmethylene]-2-[5-(2-methoxy-acetyl)-2S,5S-diaza-bicyclo[2.2.1]hept-2-yl]-thiazol-4-one was prepared from 5-[1-(4-chloro-2-trifluoromethyl-benzyl)-1H-indazol-5-ylmethylene]-2-ethylsulfanyl-thiazol-4-one and 1-(2,5-diaza-bicyclo[2.2.1]hept-2-yl)-2-methoxy-ethanone following General Procedure C.

$^1$H NMR (400 MHZ, CDCl$_3$): δ 8.17 (m, 1H), 7.94 (m, 1H), 7.90 (m, 1H), 7.70 (m, 1H), 7.50 (m, 1H), 7.33 (m, 1H), 7.30 (m, 1H), 6.66 (m, 1H), 5.77 (s, 2H), 5.34 (s, ½H), 5.17 (s, ½H), 4.98 (d, ½H), 4.62 (d, ½H), 3.40-4.22 (9H), 2.13 (m, 2H).

LC/MS: mass calcd. for C$_{27}$H$_{23}$ClF$_3$N$_5$O$_3$S (m/z), 589.1. found, 590.1 [M+H]$^+$.

Example 90

5-[1-(4-Chloro-2-trifluoromethyl-benzyl)-1H-indazol-5-ylmethylene]-2-[4-(2-methoxy-acetyl)-2-(R)-methyl-piperazin-1-yl]-thiazol-4-one

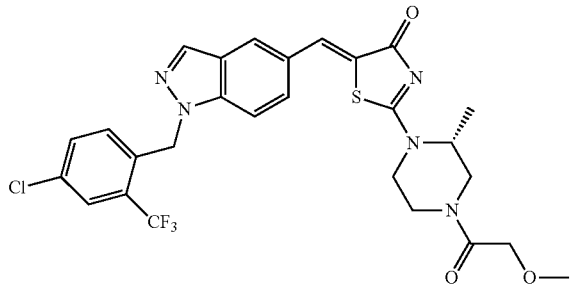 [SMILES: COCC(=O)N1CCN(C2=NC(=O)/C(=C/c3ccc4c(cnn4Cc4ccc(Cl)cc4C(F)(F)F)c3)S2)[C@H](C)C1]

5-[1-(4-Chloro-2-trifluoromethyl-benzyl)-1H-indazol-5-ylmethylene]-2-[4-(2-methoxy-acetyl)-2-(R)-methyl-piperazin-1-yl]-thiazol-4-one was prepared from 5-[1-(4-chloro-2-trifluoromethyl-benzyl)-1H-indazol-5-ylmethylene]-2-ethylsulfanyl-thiazol-4-one and 2-Methoxy-1-(3-(R)-methyl-piperazin-1-yl)-ethanone following General Procedure C.

$^1$H NMR (400 MHZ, CDCl$_3$): δ 8.20 (s, 1H), 7.98 (s, 1H), 7.96 (s, 1H), 7.71 (d, 1H), 7.54 (d, 1H), 7.34 (dd, 1H), 7.32 (m, 1H), 6.68 (d, 1H), 5.79 (s, 2H), 5.21 (m, 1H), 4.47-4.87 (2H), 3.87-4.29 (4H), 3.24-3.54 (7H), 2.86-3.11 (1H).

LC/MS: mass calcd. for C$_{27}$H$_{25}$ClF$_3$N$_5$O$_3$S (m/z), 591.1. found, 592.1 [M+H]$^+$.

Example 91

5-[1-(4-Chloro-2-trifluoromethyl-benzyl)-1H-indazol-5-ylmethylene]-2-[4-(2-methoxy-acetyl)-piperazin-1-yl]-thiazol-4-one

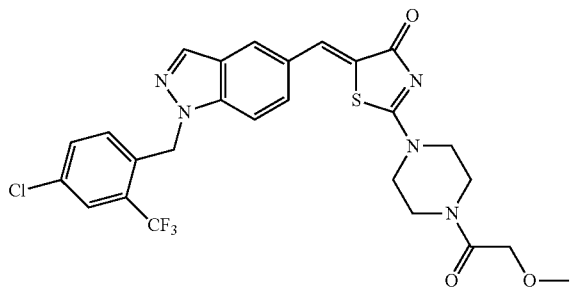 [SMILES: COCC(=O)N1CCN(C2=NC(=O)/C(=C/c3ccc4c(cnn4Cc4ccc(Cl)cc4C(F)(F)F)c3)S2)CC1]

5-[1-(4-Chloro-2-trifluoromethyl-benzyl)-1H-indazol-5-ylmethylene]-2-[4-(2-methoxy-acetyl)-piperazin-1-yl]-thiazol-4-one was prepared from 5-[1-(4-chloro-2-trifluoromethyl-benzyl)-1H-indazol-5-ylmethylene]-2-ethylsulfanyl-thiazol-4-one and 2-methoxy-1-piperazin-1-yl-ethanone following General Procedure C.

$^1$H NMR (400 MHZ, CDCl$_3$): δ 8.19 (s, 1H), 7.97 (s, 1H), 7.95 (s, 1H), 7.71 (d, 1H), 7.53 (d, 1H), 7.34 (dd, 1H), 7.31 (d, 1H), 6.67 (d, 1H), 5.78 (s, 2H), 4.17 (s, 2H), 4.11 (br, 2H), 3.49-3.86 (6H), 3.45 (s, 3H).

LC/MS: mass calcd. for C$_{26}$H$_{23}$ClF$_3$N$_5$O$_3$S (m/z), 577.1. found, 578.1 [M+H]$^+$.

Example 92

2-(3-Amino-azetidin-1-yl)-5-[1-(4-chloro-2-cyclopropyl-benzyl)-1H-indazol-5-ylmethylene]-thiazol-4-one

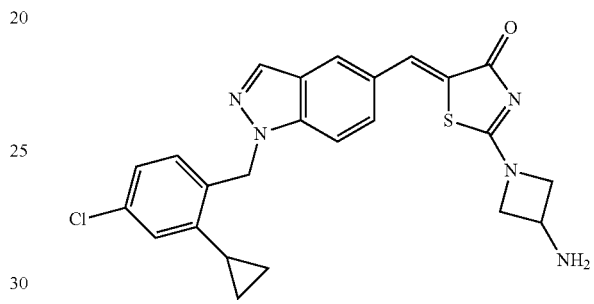

A. 2-Bromo-1-bromomethyl-4-chloro-benzene was prepared from 2-bromo-4-chloro-1-methyl-benzene following the procedure described for Example 9 (A).

B. 1-(2-Bromo-4-chloro-benzyl)-1H-indazole-5-carbaldehyde was prepared from 1H-indazole-5-carbaldehyde and 2-bromo-1-bromomethyl-4-chloro-benzene following General Procedure A.

$^1$H NMR (400 MHZ, CDCl$_3$): 10.03 (s, 1H), 8.27 (s, 1H), 8.24 (s, 1H), 7.91 (s, 1H), 7.59 (m, 1H), 7.45 (d, 1H), 7.14 (d, 1H), 6.69 (d, 1H), 5.78 (s, 2H).

LC/MS: mass calcd. for C$_{16}$H$_{10}$BrClN$_2$O, 349.61; m/z found, 349.0 [M+H]$^+$.

C. 1-(4-Chloro-2-cyclopropyl-benzyl)-1H-indazole-5-carbaldehyde

To a N$_2$ flushed vial was added 1-(2-bromo-4-chloro-benzyl)-1H-indazole-5-carbaldehyde (250 mg, 0.71 mmol), Pd$_2$(dba)$_3$ (47 mg, 0.05 mmol), biphenyl-2-yl-di-t-butyl-phosphane (42 mg, 0.14 mmol), Cs$_2$CO$_3$ (296 mg, 0.9 mmol) cyclopropaneboronic acid (86 mg, 1 mmol) and dioxane (3 mL). The resulting mixture was heated at 90° C. for 16 h. The resulting mixture was poured into water and extracted with EtOAc. The organic layer was dried and concentrated, and the residue was purified by preparative HPLC to yield 4-chloro-r-thiophen-3-yl-pyridine as a white solid.

$^1$H NMR (400 MHZ, CDCl$_3$): 10.04 (s, 1H), 8.28 (s, 1H), 8.22 (s, 1H), 7.89 (d, 1H), 7.38 (d, 1H), 7.07 (m, 2H), 6.72 (d, 1H), 5.78 (s, 2H), 1.91 (m, 1H), 0.95 (m, 2H), 0.69 (m, 2H).

LC/MS: mass calcd. for C$_{18}$H$_{11}$ClN$_2$O, 310.1; m/z found, 311.1 [M+H]$^+$.

D. (1-{5-[1-(4-Chloro-2-cyclopropyl-benzyl)-1H-indazol-5-ylmethylene]-4-oxo-4,5-dihydro-thiazol-2-yl}-azetidin-3-yl)-carbamic acid tert-butyl ester was prepared from 1-(4-Chloro-2-cyclopropyl-benzyl)-1H-indazole-5-carbaldehyde and azetidin-3-yl-carbamic acid tert-butyl ester following General Procedure C.

LC/MS: mass calcd. for C$_{29}$H$_{30}$ClN$_5$O$_3$S, 564.1; m/z found, 564.3 [M+H]$^+$.

E. 2-(3-Amino-azetidin-1-yl)-5-[1-(4-chloro-2-cyclopropyl-benzyl)-1H-indazol-5-ylmethylene]-thiazol-4-one was prepared from (1-{5-[1-(4-Chloro-2-cyclopropyl-benzyl)-1H-indazol-5-ylmethylene]-4-oxo-4,5-dihydro-thiazol-2-yl}-azetidin-3-yl)-carbamic acid tert-butyl ester following General Procedure H.

$^1$H NMR (400 MHZ, CDCl$_3$): 8.08 (s, 1H), 7.86 (s, 2H), 7.42 (d, 1H), 7.26 (d, 1H), 7.04 (m, 2H), 6.70 (d, 1H), 5.71 (s, 2H), 4.65 (t, 1H), 4.47 (t, 1H), 4.20-396 (m, 3H), 1.89 (m, 1H), 0.96 (m, 2H), 0.67 (m, 2H).

LC/MS: mass calcd. for C$_{24}$H$_{22}$ClN$_5$OS, 463.1; m/z found, 462.1 [M+H]$^+$.

Example 93

5-[1-(4-Chloro-2-cyclopropyl-benzyl)-1H-indazol-5-ylmethylene]-2-(4-methyl-piperazin-1-yl)-thiazol-4-one

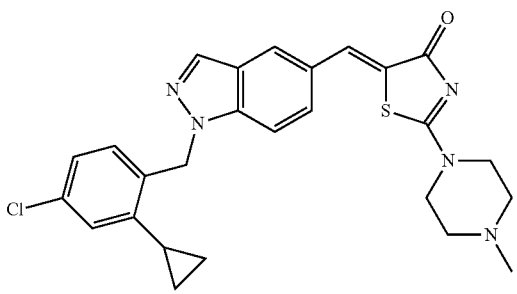 [SMILES: CN1CCN(C2=NC(=O)/C(=C/c3ccc4c(cnn4Cc4ccc(Cl)cc4C4CC4)c3)S2)CC1]

5-[1-(4-Chloro-2-cyclopropyl-benzyl)-1H-indazol-5-ylmethylene]-2-(4-methyl-piperazin-1-yl)-thiazol-4-one was prepared from 5-[1-(4-chloro-2-cyclopropyl-benzyl)-1H-indazol-5-ylmethylene]-2-methylsulfanyl-thiazol-4-one and 1-methyl-piperazine following General Procedure C.

$^1$H NMR (400 MHZ, CDCl$_3$): 8.14 (s, 1H), 7.96 (s, 1H), 7.93 (s, 1H), 7.51 (d, 1H), 7.32 (d, 1H), 7.07 (m, 2H), 6.73 (d, 1H), 5.76 (s, 2H), 4.11 (t, 2H), 3.65 (t, 2H), 2.56 (m, 4H), 2.37 (s, 3H), 1.91 (m, 1H), 0.97 (m, 2H), 0.70 (m, 2H).

LC/MS: mass calcd. for C$_{26}$H$_{26}$ClN$_5$OS, 491.2; m/z found, 492.3[M+H]$^+$.

Example 94

1-(5-[1-(4-Chloro-2-cyclopropyl-benzyl)-1H-indazol-5-ylmethylene]-4-oxo-dihydro-thiazol-2-yl)-azetidine-3-carboxylic acid

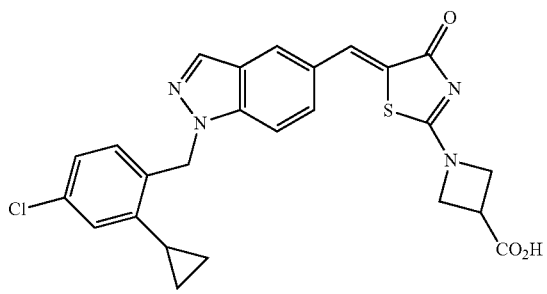 [SMILES: O=C1N=C(N2CC(C(=O)O)C2)S/C1=C\c1ccc2c(cnn2Cc2ccc(Cl)cc2C2CC2)c1]

1-(5-[1-(4-Chloro-2-cyclopropyl-benzyl)-1H-indazol-5-ylmethylene]-4-oxo-dihydro-thiazol-2-yl)-azetidine-3-carboxylic acid was prepared from 5-[1-(4-chloro-2-cyclopropyl-benzyl)-1H-indazol-5-ylmethylene]-2-methylsulfanyl-thiazol-4-one and azetidine-3-carboxylic acid following General Procedure C.

$^1$H NMR (400 MHZ, DMSO): 8.29 (s, 1H), 8.09 (s, 1H), 7.78 (s, 1H), 7.77 (d, 1H), 7.63 (d, 1H), 7.15 (dd, 1H), 7.07 (m, 1H), 6.74 (d, 1H), 5.85 (s, 2H), 4.52 (t, 2H), 4.38 (m, 2H), 3.71 (m, 1H), 2.12 (m, 1H), 0.90 (m, 2H), 0.70 (m, 2H).

LC/MS: mass calcd. for C$_{25}$H$_{21}$ClN$_4$O$_3$S, 492.1; m/z found, 493.4[M+H]$^+$.

Example 95

5-[1-(2-bromo-4-chlorobenzyl)-1H-indazol-5-ylmethylene]-2-(4-methyl-piperazin-1-yl)-thiazol-4-one

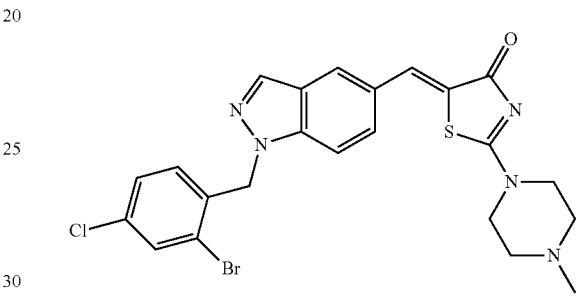

5-[1-(2-bromo-4-chlorobenzyl)-1H-indazol-5-ylmethylene]-2-(4-methyl-piperazin-1-yl)-thiazol-4-one was prepared from 5-[1-(2-bromo-4-chloro-benzyl)-1H-indazol-5-ylmethylene]-2-methylsulfanyl-thiazol-4-one and 1-methyl-piperazine following General Procedure C.

$^1$H NMR (400 MHZ, CDCl$_3$): 8.16 (s, 1H), 7.96 (d, 1H), 7.93 (s, 1H), 7.62 (d, 1H), 7.55 (dd, 1H), 7.41 (d, 1H), 7.16 (dd, 1H), 6.70 (d, 1H), 5.65 (s, 2H), 4.10 (t, 2H), 3.67 (t, 2H), 2.56 (m, 4H), 2.37 (s, 3H).

LC/MS: mass calcd. for C$_{23}$H$_{21}$BrClN$_5$OS, 529.0; m/z found, 530.4 [M+H]$^+$.

Example 96

5-[1-(4-Chloro-2-iodo-benzyl)-1H-indazol-5-ylmethylene]-2-(4-methyl-piperazin-1-yl)-thiazol-4-one

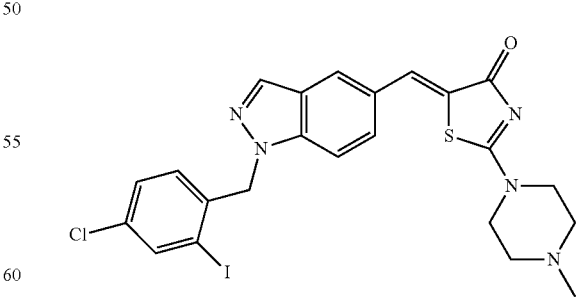

A. 1-Bromomethyl-4-chloro-2-iodo-benzene was prepared from 4-chloro-2-iodo-1-methyl-benzene following the procedure described for Example 9 (A).

$^1$H NMR (400 MHZ, CDCl$_3$): 7.85 (d, 1H), 7.39 (d, 1H), 7.32 (dd, 1H), 4.56 (s, 2H).

B. 1-(4-Chloro-2-iodo-benzyl)-1H-indazole-5-carbaldehyde was prepared from 1H-indazole-5-carbaldehyde and 1-Bromomethyl-4-chloro-2-iodo-benzene following General Procedure A.

C. 5-[1-(4-Chloro-2-iodo-benzyl)-1H-indazol-5-ylmethylene]-2-(4-methyl-piperazin-1-yl)-thiazol-4-one was prepared from 1-(4-Chloro-2-iodo-benzyl)-1H-indazole-5-carbaldehyde and 1-methyl-piperazine following General Procedure C.

$^1$H NMR (400 MHZ, CDCl$_3$): 8.17 (s, 1H), 7.96 (d, 1H), 7.94 (s, 1H), 7.89 (d, 1H), 7.55 (dd, 1H), 7.39 (d, 1H), 7.19 (dd, 1H), 6.59 (d, 1H), 5.60 (s, 2H), 4.10 (t, 2H), 3.67 (t, 2H), 2.57 (m, 4H), 2.37 (s, 3H).

LC/MS: mass calcd. for C$_{23}$H$_{21}$ClN$_5$OS, 577.0; m/z found, 578.2 [M+H]$^+$.

Example 97

5-[1-(2-Acetyl-4-chloro-benzyl)-1H-indazol-5-ylmethylene]-2-(4-methyl-piperazin-1-yl)-thiazol-4-one

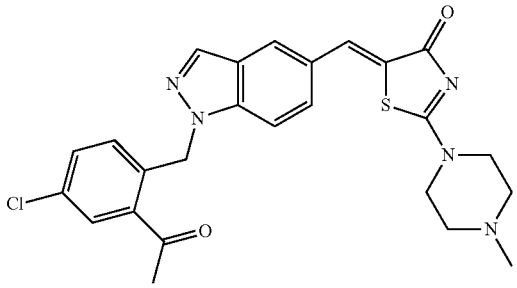 [SMILES: CC(=O)c1cc(Cl)ccc1Cn1ncc2cc(/C=C3\SC(N4CCN(C)CC4)=NC3=O)ccc21]

5-[1-(2-Acetyl-4-chloro-benzyl)-1H-indazol-5-ylmethylene]-2-(4-methyl-piperazin-1-yl)-thiazol-4-one was prepared following General Procedure G.

To a N$_2$ flushed vial was added 5-[1-(4-chloro-2-iodo-benzyl)-1H-indazol-5-ylmethylene]-2-(4-methyl-piperazin-1-yl)thiazol-4-one (100 mg, 0.15 mmol), Pd$_2$(dba)$_3$ (10 mg, 0.011 mmol), biphenyl-2-yl-di-t-butyl-phosphane (12 mg, 0.04 mmol), Tributyl-(1-ethoxy-vinyl)-stannane (86 mg, 0.23 mmol) and dioxane (2 mL). The resulting mixture was heated at 90° C. for 16 h. The resulting mixture was poured into water and extracted with EtOAc. The organic layer was dried and concentrated, and the residue was purified by preparative HPLC to yield a white solid which was treated 1 N hydrochloric acid in MeOH to yield the title compound.

$^1$H NMR (400 MHZ, CDCl$_3$): 8.14 (s, 1H), 7.95 (s, 1H), 7.93 (s, 1H), 7.81 (d, 1H), 7.53 (dd, 1H), 7.39 (d, 1H), 7.30 (dd, 1H), 6.56 (d, 1H), 5.91 (s, 2H), 4.09 (t, 2H), 3.66 (t, 2H), 2.62 (s, 3H), 2.55 (m, 4H), 2.36 (s, 3H).

LC/MS: mass calcd. for C$_{25}$H$_{24}$ClN$_5$O$_2$S, 493.1; m/z found, 494.3[M+H]$^+$.

Example 98

2-(3-Amino-azetidin-1-yl)-5-[1-(4-chloro-2-trifluoromethyl-benzyl)-1H-indazol-5-ylmethylene]-thiazol-4-one

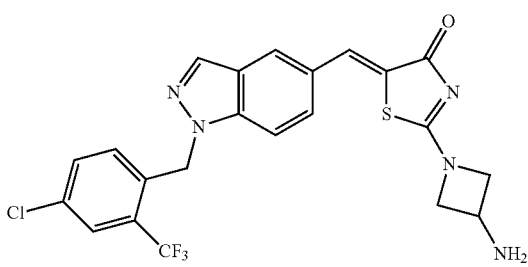 [SMILES: NC1CN(C2=NC(=O)/C(=C/c3ccc4c(cnn4Cc4ccc(Cl)cc4C(F)(F)F)c3)S2)C1]

A. (1-{5-[1-(4-Chloro-2-trifluoromethyl-benzyl)-1H-indazol-5-ylmethylene]-4-oxo-4,5-dihydro-thiazol-2-yl}-azetidin-3-yl)-carbamic acid tert-butyl ester was prepared from 5-[1-(4-chloro-2-trifluoromethyl-benzyl)-1H-indazol-5-ylmethylene]-2-ethylsulfanyl-thiazol-4-one and azetidin-3-yl-carbamic acid tert-butyl ester following General Procedure C.

LC/MS: mass calcd. for C$_{27}$H$_{25}$ClF$_3$N$_5$O$_3$S, 592.03; m/z found, 592.5 [M+H]$^+$.

B. 2-(3-Amino-azetidin-1-yl)-5-[1-(4-chloro-2-trifluoromethyl-benzyl)-1H-indazol-5-ylmethylene]-thiazol-4-one was prepared from (1-{5-[1-(4-Chloro-2-trifluoromethyl-benzyl)-1H-indazol-5-ylmethylene]-4-oxo-4,5-dihydro-thiazol-2-yl}-azetidin-3-yl)-carbamic acid tert-butyl ester following General Procedure H.

$^1$H NMR (400 MHZ, CDCl$_3$): 8.14 (s, 1H), 7.91 (s, 1H), 7.89 (s, 1H), 7.70 (d, 1H), 7.49 (dd, 1H), 7.32 (dd, 1H), 7.27 (d, 1H), 6.64 (d, 1H), 5.76 (s, 2H), 4.67 (t, 1H), 4.49 (t, 1H), 4.21-3.97 (m, 3H).

LC/MS: mass calcd. for C$_{22}$H$_{17}$ClF$_3$N$_5$OS, 491.1; m/z found, 492.5 [M+H]$^+$.

Example 99

5-[1-(4-Chloro-2-trifluoromethyl-benzyl)-1H-indazol-5-ylmethylene]-2-(3R,4R-dihydroxy-pyrrolidin-1-yl)-thiazol-4-one

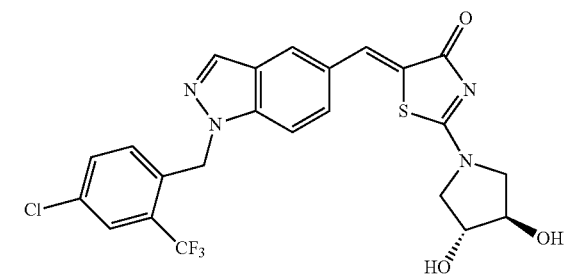 [SMILES: O=C1N=C(N2C[C@@H](O)[C@H](O)C2)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-(3,4-dihydroxy-pyrrolidin-1-yl)-thiazol-4-one was prepared from 5-[1-(4-chloro-2-trifluoromethyl-benzyl)-1H-indazol-5-ylmethylene]-2-ethylsulfanyl-thiazol-4-one and pyrrolidine-3R,4R-diol following General Procedure C.

$^1$H NMR (400 MHZ, DMSO): 8.23 (s, 1H), 8.11 (s, 1H), 7.87 (d, 1H), 7.77 (s, 1H), 7.67 (d, 1H), 7.67 (dd, 1H), 7.63 (dd, 1H), 6.74 (d, 1H), 5.85 (s, 2H), 5.53 (d, 1H), 5.46 (d, 1H), 4.11 (d, 2H), 3.83 (td, 2H), 3.67 (d, 1H), 3.47 (d, 1H).

LC/MS: mass calcd. for C$_{23}$H$_{18}$ClF$_3$N$_4$O$_3$S, 522.1; m/z found, 523.2 [M+H]$^+$.

Example 100

5-[1-(4-Chloro-2-trifluoromethyl-benzyl)-1H-indazol-5-ylmethylene]-2-(2S,5S-diaza-bicyclo[2.2.1]hept-2-yl)-thiazol-4-one

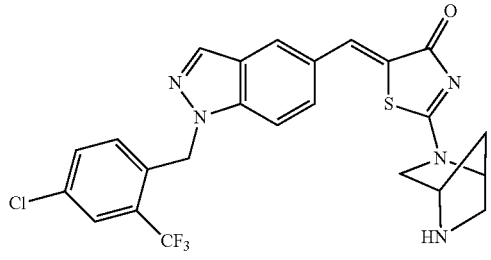 [SMILES: O=C1N=C(N2CC3CC2CN3)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-(2,5-diaza-bicyclo[2.2.1]hept-2-yl)-thiazol-4-one was prepared from 5-[1-(4-chloro-2-trifluoromethyl-benzyl)-1H-indazol-5-ylmethylene]-2-ethylsulfanyl-thiazol-4-one and 2S,5S-diaza-bicyclo[2.2.1]heptane following General Procedure C.

$^1$H NMR (400 MHZ, CDCl$_3$): 8.18 (s, 0.45H), 8.16 (s, 0.55H), 7.94 (m, 1H), 7.90 (s, 1H), 7.70 (d, 1H), 7.51 (m, 1H), 7.34-7.27 (m, 2H), 7.27 (d, 1H), 6.64 (d, 0.45H), 6.63 (d, 0.55H), 5.78 (s, 0.9H), 5.77 (s, 1.1H), 5.20 (s, 0.55H), 4.45 (s, 0.45H), 3.97-3.12 (m, 5H), 2.02 (m, 2H).

LC/MS: mass calcd. for C$_{24}$H$_{19}$ClF$_3$N$_5$OS, 517.1; m/z found, 518.4 [M+H]$^+$.

Example 101

5-[1-(4-Chloro-2-trifluoromethyl-benzyl)-1H-indazol-5-ylmethylene]-2-(8-methyl-3,8-diaza-bicyclo[3.2.1]oct-3-yl)-thiazol-4-one

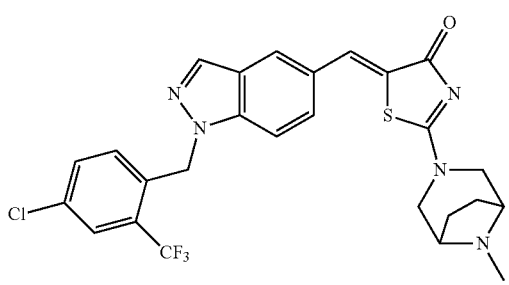 [SMILES: CN1C2CCC1CN(C1=NC(=O)/C(=C/c3ccc4c(cnn4Cc4ccc(Cl)cc4C(F)(F)F)c3)S1)C2]

5-[1-(4-Chloro-2-trifluoromethyl-benzyl)-1H-indazol-5-ylmethylene]-2-(8-methyl-3,8-diaza-bicyclo[3.2.1]oct-3-yl)-thiazol-4-one was prepared from 5-[1-(4-chloro-2-trifluoromethyl-benzyl)-1H-indazol-5-ylmethylene]-2-ethylsulfanyl-thiazol-4-one and 8-methyl-3,8-diaza-bicyclo[3.2.1]octane following General Procedure C.

$^1$H NMR (400 MHZ, CDCl$_3$): 8.18 (s, 1H), 7.96 (s, 1H), 7.92 (s, 1H), 7.70 (d, 1H), 7.54 (dd, 1H), 7.30 (m, 2H), 6.66 (d, 1H), 5.79 (s, 2H), 4.96 (s, 1H), 3.16 (s, 1H), 2.79 (dd, 2H), 2.43 (dd, 2H), 2.28 (s, 3H), 2.25-2.05 (m, 4H).

LC/MS: mass calcd. for C$_{26}$H$_{23}$ClF$_3$N$_5$OS, 545.1; m/z found, 546.4 [M+H]$^+$.

Example 102

5-[1-(4-Chloro-2-trifluoromethyl-benzyl)-1H-indazol-5-ylmethylene]-2-(3-oxo-azetidin-1-yl)-thiazol-4-one

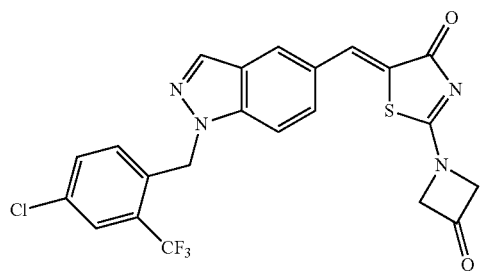 [SMILES: O=C1CN(C2=NC(=O)/C(=C/c3ccc4c(cnn4Cc4ccc(Cl)cc4C(F)(F)F)c3)S2)C1]

5-[1-(4-Chloro-2-trifluoromethyl-benzyl)-1H-indazol-5-ylmethylene]-2-(3-oxo-azetidin-1-yl)-thiazol-4-one was prepared from 5-[1-(4-chloro-2-trifluoromethyl-benzyl)-1H-indazol-5-ylmethylene]-2-ethylsulfanyl-thiazol-4-one and azetidin-3-one following General Procedure C.

$^1$H NMR (400 MHZ, CDCl$_3$): 8.19 (s, 1H), 7.99 (s, 1H), 7.96 (s, 1H), 7.71 (d, 1H), 7.52 (dd, 1H), 7.33 (m, 2H), 6.68 (d, 1H), 5.79 (s, 2H), 5.22 (s, 2H), 5.09 (s, 2H).

LC/MS: mass calcd. for C$_{22}$H$_{14}$ClF$_3$N$_4$O$_2$S, 490.1; m/z found, 491.1 [M+H]$^+$.

Example 103

5-[1-(2,4-Bis-trifluoromethyl-benzyl)-1H-indazol-5-ylmethylene]-2-(8-methyl-3,8-diaza-bicyclo[3.2.1]oct-3-yl)-thiazol-4-one

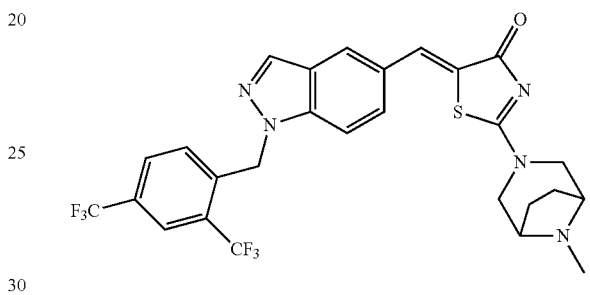

5-[1-(2,4-Bis-trifluoromethyl-benzyl)-1H-indazol-5-ylmethylene]-2-(8-methyl-3,8-diaza-bicyclo[3.2.1]oct-3-yl)-thiazol-4-one was prepared from 5-[1-(2,4-bis-trifluoromethyl-benzyl)-1H-indazol-5-ylmethylene]-2-methylsulfanyl-thiazol-4-one and 8-methyl-3,8-diaza-bicyclo[3.2.1]octane following General Procedure C.

$^1$H NMR (400 MHZ, CDCl$_3$): 8.21 (s, 1H), 7.98 (s, 2H), 7.93 (s, 1H), 7.62 (d, 1H), 7.55 (d, 1H), 7.31 (d, 1H), 6.82 (d, 1H), 5.88 (s, 2H), 4.97 (s, 1H), 4.16 (s, 1H), 2.79 (dd, 2H), 2.43 (dd, 2H), 2.29 (s, 3H), 2.24-2.06 (m, 4H).

LC/MS: mass calcd. for C$_{27}$H$_{23}$F$_6$N$_5$OS, 579.2; m/z found, 530.4[M+H]$^+$.

Example 104

5-[1-(2,4-Bis-trifluoromethyl-benzyl)-1H-indazol-5-ylmethylene]-2-(2-hydroxymethyl-piperazin-1-yl)-thiazol-4-one

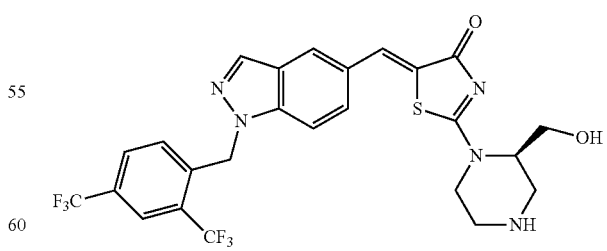

A. 4-{5-[1-(2,4-Bis-trifluoromethyl-benzyl)-1H-indazol-5-ylmethylene]-4-oxo-4,5-dihydro-thiazol-2-yl}-3-hydroxymethyl-piperazine-1-carboxylic acid tert-butyl ester was prepared from 5-[1-(2,4-bis-trifluoromethyl-benzyl)-1H-indazol-5-ylmethylene]-2-methylsulfanyl-thiazol-4-one and 3-(R)-hydroxymethyl-piperazine-1-carboxylic acid tert-butyl ester following General Procedure C.

LC/MS: mass calcd. for $C_{30}H_{29}F_6N_5O_4S$, 669.6; m/z found, 670.2 [M+H]$^+$.

B. 5-[1-(2,4-Bis-trifluoromethyl-benzyl)-1H-indazol-5-ylmethylene]-2-(2-hydroxymethyl-piperazin-1-yl)-thiazol-4-one was prepared from 4-{5-[1-(2,4-Bis-trifluoromethyl-benzyl)-1H-indazol-5-ylmethylene]-4-oxo-4,5-dihydro-thiazol-2-yl}-3-hydroxymethyl-piperazine-1-carboxylic acid tert-butyl ester following General Procedure H.

$^1$H NMR (400 MHZ, CDCl$_3$): 8.20 (m, 1H), 7.98-7.89 (m, 3H), 7.63-7.51 (m, 2H), 7.30 (m, 1H), 6.80 (m, 1H), 5.86 (m, 2H), 4.89-4.79 (m, 1H), 4.23-2.88 (m, 10H).

LC/MS: mass calcd. for $C_{25}H_{21}F_6N_5O_2S$, 569.1; m/z found, 570.2 [M+H]$^+$.

Example 105

5-[1-(4-Chloro-2-trifluoromethyl-benzyl)-1H-indazol-5-ylmethylene]-2-(2-hydroxymethyl-piperazin-1-yl)-thiazol-4-one

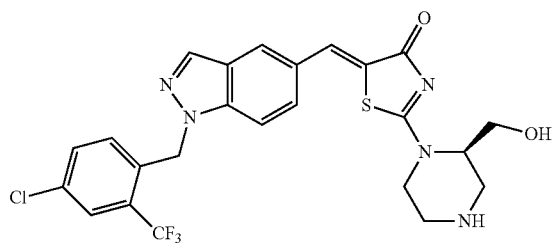 [SMILES: O=C1N=C(N2CCNC[C@@H]2CO)S/C1=C\c1ccc2c(cnn2Cc2ccc(Cl)cc2C(F)(F)F)c1]

A. 4-{5-[1-(4-Chloro-2-trifluoromethyl-benzyl)-1H-indazol-5-ylmethylene]-4-oxo-4,5-dihydro-thiazol-2-yl}-3-hydroxymethyl-piperazine-1-carboxylic acid tert-butyl ester was prepared from 5-[1-(4-chloro-2-trifluoromethyl-benzyl)-1H-indazol-5-ylmethylene]-2-ethylsulfanyl-thiazol-4-one and 3-(R)-hydroxymethyl-piperazine-1-carboxylic acid tert-butyl ester following General Procedure C.

LC/MS: mass calcd. for $C_{29}H_{29}ClF_3N_5O_4S$, 636.09; m/z found, 636.3 [M+H]$^+$.

B. 5-[1-(4-Chloro-2-trifluoromethyl-benzyl)-1H-indazol-5-ylmethylene]-2-(2-hydroxymethyl-piperazin-1-yl)-thiazol-4-one was prepared from 4-{5-[1-(4-Chloro-2-trifluoromethyl-benzyl)-1H-indazol-5-ylmethylene]-4-oxo-4,5-dihydro-thiazol-2-yl}-3-hydroxymethyl-piperazine-1-carboxylic acid tert-butyl ester following General Procedure H.

$^1$H NMR (400 MHZ, CDCl$_3$): 8.14 (m, 1H), 7.92-7.85 (m, 2H), 7.70 (m, 1H), 7.51-7.47 (m, 1H), 7.33-7.22 (m, 2H), 6.64 (m, 1H), 5.73 (m, 2H), 4.85-4.74 (m, 1H), 4.22-2.86 (m, 10H).

LC/MS: mass calcd. for $C_{24}H_{21}ClF_3N_5O_2S$, 535.1; m/z found, 536.1 [M+H]$^+$.

Example 106

1-{5-[1-(2,4-Bis-trifluoromethyl-benzyl)-1H-indazol-5-ylmethylene]-4-oxo-4,5-dihydro-thiazol-2-yl}-piperidine-4-carboxylic acid amide

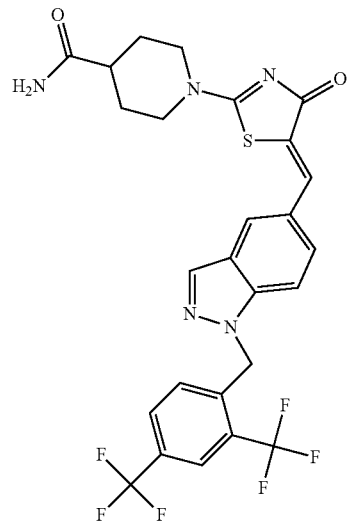 [SMILES: NC(=O)C1CCN(C2=NC(=O)/C(=C/c3ccc4c(cnn4Cc4ccc(C(F)(F)F)cc4C(F)(F)F)c3)S2)CC1]

1-{5-[1-(2,4-Bis-trifluoromethyl-benzyl)-1H-indazol-5-ylmethylene]-4-oxo-4,5-dihydro-thiazol-2-yl}-piperidine-4-carboxylic acid amide was prepared from 5-[1-(2,4-Bis-trifluoromethyl-benzyl)-1H-indazol-5-ylmethylene]-2-methylsulfanyl-thiazol-4-one and piperidine-4-carboxylic acid amide following General Procedure B.

$^1$H NMR (400 MHz, DMSO) δ 8.35 (s, 1H), 8.16-8.11 (m, 2H), 7.97 (d, 1H), 7.81-7.77 (m, 2H), 7.72-7.70 (dd, 1H), 7.38 (br s, 1H), 6.92-6.90 (m, 2H), 5.98 (s, 2H), 4.58-4.55 (m, 1H), 3.90-3.85 (m, 1H), 3.54-3.47 (m, 1H), 3.38-3.30 (m, 2H), 1.96-1.86 (m, 2H), 1.66-1.56 (m, 2H).

LC/MS (m/z) [M+1]$^+$ 582.2 (calculated for $C_{26}H_{21}F_6N_5O_2S$, 581.53).

Example 107

5-[1-(2,4-Bis-trifluoromethyl-benzyl)-1H-indazol-5-ylmethylene]-2-(4-isocyano-piperidin-1-yl)-thiazol-4-one

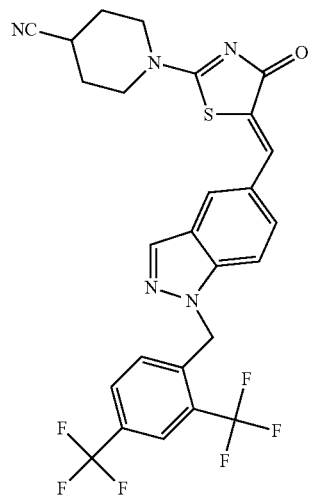 [SMILES: N#CC1CCN(C2=NC(=O)/C(=C/c3ccc4c(cnn4Cc4ccc(C(F)(F)F)cc4C(F)(F)F)c3)S2)CC1]

5-[1-(2,4-Bis-trifluoromethyl-benzyl)-1H-indazol-5-ylm-ethylene]-2-(4-isocyano-piperidin-1-yl)-thiazol-4-one was prepared from 5-[1-(2,4-Bis-trifluoromethyl-benzyl)-1H-indazol-5-ylmethylene]-2-methylsulfanyl-thiazol-4-one and 4-Isocyano-piperidine following General Procedure B.

$^1$H NMR (400 MHz, DMSO) δ 8.35 (s, 1H), 8.16-8.12 (m, 2H), 7.97 (d, 1H), 7.82-7.79 (m, 2H), 7.72-7.70 (dd, 1H), 6.91 (d, 1H), 5.98 (s, 2H), 4.22-4.16 (m, 1H), 3.82-3.72 (m, 2H), 3.66-3.61 (m, 1H), 3.30-3.25 (m, 1H), 2.13-1.02 (m, 2H), 1.96-1.84 (m, 2H).

LC/MS (m/z) [M+1]$^+$ 564.3 (calculated for $C_{26}H_{19}F_6N_5OS$, 563.52).

Example 108

N-(1-{5-[1-(2,4-Bis-trifluoromethyl-benzyl)-1H-indazol-5-ylmethylene]-4-oxo-4,5-dihydro-thiazol-2-yl}-piperidin-4-yl)-acetamide

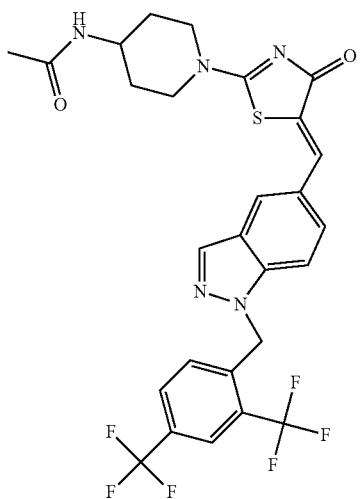 [SMILES: CC(=O)NC1CCN(C2=NC(=O)/C(=C/c3ccc4c(cnn4Cc4ccc(C(F)(F)F)cc4C(F)(F)F)c3)S2)CC1]

N-(1-{5-[1-(2,4-Bis-trifluoromethyl-benzyl)-1H-indazol-5-ylmethylene]-4-oxo-4,5-dihydro-thiazol-2-yl}-piperidin-4-yl)-acetamide was prepared from 5-[1-(2,4-Bis-trifluoromethyl-benzyl)-1H-indazol-5-ylmethylene]-2-methylsulfanyl-thiazol-4-one and N-Piperidin-4-yl-acetamide following General Procedure B.

$^1$H NMR (400 MHz, CD$_3$CN) δ 8.24 (s, 1H), 8.10-8.08 (m, 2H), 7.80 (s, 1H), 7.76-7.74 (m, 1H), 7.67-7.64 (dd, 1H), 7.56-7.64 (m, 1H), 6.85 (d, 1H), 6.70-6.68 (m, 1H), 5.92 (s, 2H), 4.63-4.58 (m, 1H), 4.01-3.96 (m, 1H), 3.86-3.81 (m, 1H), 3.54-3.38 (m, 2H), 2.08-1.96 (m, 2H), 1.95 (s, 3H), 1.59-1.50 (m, 2H).

LC/MS (m/z) [M+1]$^+$ 596.2 (calculated for $C_{27}H_{23}F_6N_5O_2S$, 595.56).

Example 109

5-[1-(2,4-Bis-trifluoromethyl-benzyl)-1H-indazol-5-ylmethylene]-2-[4-(1H-tetrazol-5-yl)piperidin-1-yl]-thiazol-4-one

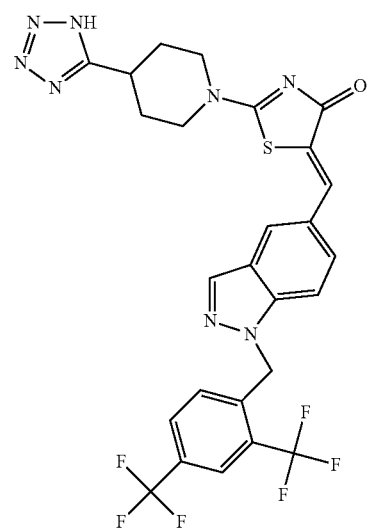 [SMILES: O=C1N=C(N2CCC(c3nnn[nH]3)CC2)S/C1=C\c1ccc2c(cnn2Cc2ccc(C(F)(F)F)cc2C(F)(F)F)c1]

A. 4-(1H-Tetrazol-5-yl)-piperidine-1-carboxylic acid benzyl ester

A mixture of 4-cyano-piperidine-1-carboxylic acid benzyl ester (0.73 g, 3.0 mmol), sodium azide (0.39 g, 6.0 mmol) and zinc bromide (0.33 g, 1.5 mmol) in 2-propanol (5 mL) and water (10 mL) was stirred at 120° C. for 3 days into a pressure tube. The reaction mixture was then partitioned between aqueous 3.0N HCl (1.5 mL) and ethyl acetate and then stirred vigorously until 2 clear phases were obtained. Aqueous layer was then extracted with ethyl acetate and combined ethyl acetate layers dried over Na$_2$SO$_4$, filtered, and the solvent evaporated in vacuo to yield a crude residue. The residue was dissolved in ethyl acetate (10 mL) and washed with 0.25N aqueous sodium hydroxide. Aqueous layer was acidified to pH=1 with aqueous 3.0N HCl and extracted with ethyl acetate. Ethyl acetate layer was dried over Na$_2$SO$_4$, filtered, and the solvent evaporated in vacuo to yield a crude gum. The gum was purified via flash chromatography (4% methanol in dichloromethane) to yield 4-(1H-Tetrazol-5-yl)-piperidine-1-carboxylic acid benzyl ester as a gum (1.14 g, 66%).

$^1$H NMR (400 MHz, CDCl$_3$) δ 7.36-7.29 (m, 5H), 5.16 (br s, 2H), 4.27-4.24 (m, 2H), 3.34-3.27 (m, 1H), 3.06-2.98 (m, 2H), 2.16-2.06 (m, 2H), 1.82-1.77 (m, 2H)

LC/MS (m/z) [M+1]$^+$ 288.3 (calculated for $C_{14}H_{17}N_5O_2$, 287.32).

B. 4-(1H-Tetrazol-5-yl)-piperidine

A mixture of 4-(1H-Tetrazol-5-yl)-piperidine-1-carboxylic acid benzyl ester (0.6 g, 2.08 mmol) and activated 10 wt. % palladium on carbon (0.065 g) in ethanol (35 mL) was stirred vigorously under 1 atmosphere hydrogen atmosphere for 4 hours. The reaction mixture was then filtered through a microglass filter paper and the solid washed abundantly with methanol and water. The solvent was evaporated in vacuo to yield the 4-(1H-tetrazol-5-yl)-piperidine as a white solid (0.30 g, 94%).

¹H NMR (400 MHz, CDCl₃) δ 3.32-3.27 (m, 2H), 3.15-3.08 (m, 2H), 3.04-2.97 (m, 2H), 2.01-2.05 (m, 2H), 1.87-1.77 (m, 2H).

LC/MS (m/z) [M+1]⁺ 154.2 (calculated for C₆H₁₁N₅, 153.19).

C. 5-[1-(2,4-Bis-trifluoromethyl-benzyl)-1H-indazol-5-ylmethylene]-2-[4-(1H-tetrazol-5-A-piperidin-1-yl]-thiazol-4-one 5-[1-(2,4-Bis-trifluoromethyl-benzyl)-1H-indazol-5-ylmethylene]-2-[4-(1H-tetrazol-5-yl)-piperidin-1-yl]-thiazol-4-one was prepared from 5-[1-(2,4-Bis-trifluoromethyl-benzyl)-1H-indazol-5-ylmethylene]-2-methylsulfanyl-thiazol-4-one and 4-(1H-tetrazol-5-yl)-piperidine following General Procedure B.

¹H NMR (400 MHz, DMSO) δ 8.28 (s, 1H), 8.14 (s, 1H), 8.07 (s, 1H), 7.89 (s, 1H), 7.79-7.77 (m, 1H), 7.69 (dd, 1H), 7.60-7.58 (m, 1H), 6.87-6.84 (m, 1H), 5.96 (s, 2H), 4.80-4.74 (m, 1H), 4.05-4.02 (m, 1H), 3.72-3.65 (m, 1H), 3.59-3.47 (m, 2H), 2.35-2.23 (m, 2H), 2.03-1.92 (m, 2H).

LC/MS (m/z) [M+1]⁺ 607.1 (calculated for C₂₆H₂₀F₆N₈OS, 606.55).

Example 110

5-[1-(4-Chloro-2-trifluoromethyl-benzyl)-1H-indazol-5-ylmethylene]-2-[4-(1H-tetrazol-5-yl)-piperidin-1-yl]-thiazol-4-one

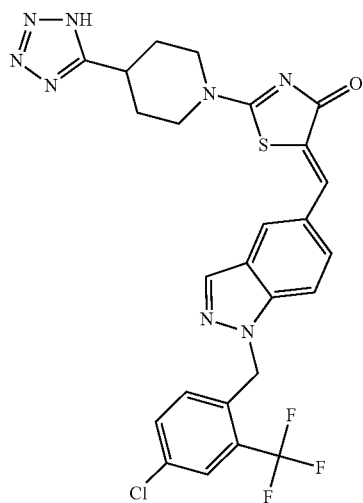 [SMILES: O=C1N=C(N2CCC(c3nnn[nH]3)CC2)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-[4-(1H-tetrazol-5-yl)-piperidin-1-yl]-thiazol-4-one was prepared from 5-[1-(4-Chloro-2-trifluoromethyl-benzyl)-1H-indazol-5-ylmethylene]-2-methylsulfanyl-thiazol-4-one and 4-(1H-tetrazol-5-yl)-piperidine following General Procedure B.

¹H NMR (00 MHz, DMSO) δ 8.32 (s, 1H), 8.15 (s, 1H), 7.89-7.88 (m, 1H), 7.81 (s, 1H), 7.79-7.76 (m, 1H), 7.70 (dd, 1H), 7.67-7.65 (m, 1H), 6.78-6.76 (m, 1H), 5.87 (s, 2H), 4.62-4.58 (m, 1H), 3.97-3.93 (m, 1H), 3.72-3.67 (m, 1H), 3.59-3.47 (m, 2H), 2.26-2.17 (m, 2H), 1.90-1.82 (m, 2H).

LC/MS (m/z) [M+1]⁺ 573.0 (calculated for C₂₅H₂₀ClF₃N₈OS, 572.99).

Example 111

N-(1-{5-[1-(4-Chloro-2-trifluoromethyl-benzyl)-1H-indazol-5-ylmethylene]-4-oxo-4,5-dihydro-thiazol-2-yl}-piperidin-4-yl)-methanesulfonamide

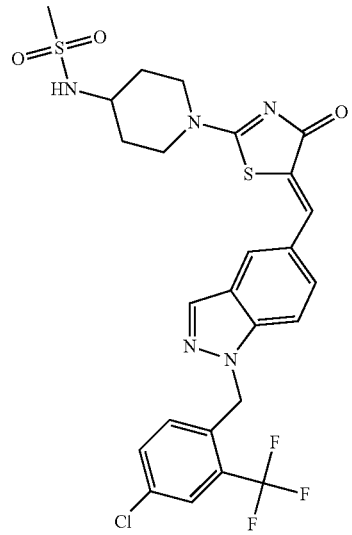

N-(1-{5-[1-(4-Chloro-2-trifluoromethyl-benzyl)-1H-indazol-5-ylmethylene]-4-oxo-4,5-dihydro-thiazol-2-yl}-piperidin-4-yl)-methanesulfonamide was prepared from 5-[1-(4-Chloro-2-trifluoromethyl-benzyl)-1H-indazol-5-ylmethylene]-2-methylsulfanyl-thiazol-4-one and N-piperidin-4-yl-methanesulfonamide following General Procedure B.

¹H NMR (400 MHz, CDCl₃) δ 8.18 (s, 1H), 7.96-7.94 (m, 2H), 7.71 (d, 1H), 7.53 (dd, 1H), 7.34-7.28 (m, 2H), 6.67-6.65 (m, 1H), 5.78 (s, 2H), 4.83-4.79 (m, 1H), 4.70 (d, 1H), 3.90-3.86 (m, 1H), 3.72-3.68 (m, 1H), 3.52-3.36 (m, 2H), 3.05 (s, 3H), 2.29-2.14 (m, 2H), 1.75-1.66 (m, 2H).

LC/MS (m/z) [M+1]⁺ 598.2 (calculated for C₂₅H₂₃ClF₃N₅O₃S₂, 598.06).

Example 112

5-[1-(4-Chloro-2-trifluoromethyl-benzyl)-1H-indazol-5-ylmethylene]-2-(4-methoxy-piperidin-1-yl)-thiazol-4-one

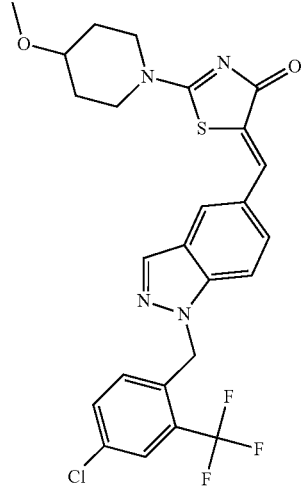 [SMILES: COC1CCN(C2=NC(=O)/C(=C/c3ccc4c(cnn4Cc4ccc(Cl)cc4C(F)(F)F)c3)S2)CC1]

5-[1-(4-Chloro-2-trifluoromethyl-benzyl)-1H-indazol-5-ylmethylene]-2-(4-methoxy-piperidin-1-yl)-thiazol-4-one was prepared from 5-[1-(4-Chloro-2-trifluoromethyl-benzyl)-1H-indazol-5-ylmethylene]-2-methylsulfanyl-thiazol-4-one and 4-methoxy-piperidine following General Procedure B.

$^1$H NMR (400 MHz, CDCl$_3$) δ 8.18 (s, 1H), 7.97 (s, 1H), 7.92 (s, 1H), 7.71 (d, 1H), 7.54 (dd, 1H), 7.34-7.29 (m, 2H), 6.66-6.64 (m, 1H), 5.79 (s, 2H), 4.19-4.00 (m, 2H), 3.83-3.77 (m, 1H), 3.63-3.58 (m, 1H), 3.56-3.49 (m, 1H), 3.40 (s, 3H), 1.98-1.82 (m, 4H).

LC/MS (m/z) [M+1]$^+$ 535.2 (calculated for C$_{25}$H$_{22}$ClF$_3$N$_4$O$_2$S, 534.98).

Example 113

5-[1-(4-Chloro-2-trifluoromethyl-benzyl)-1H-indazol-5-ylmethylene]-2-(3-methoxy-azetidin-1-yl)-thiazol-4-one

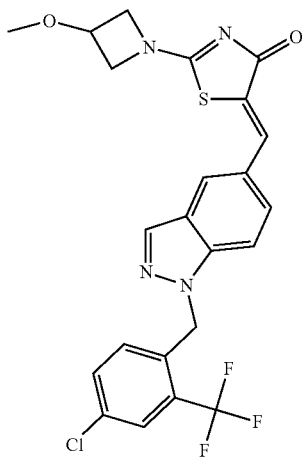 [SMILES: COC1CN(C2=NC(=O)/C(=C/c3ccc4c(cnn4Cc4ccc(Cl)cc4C(F)(F)F)c3)S2)C1]

5-[1-(4-Chloro-2-trifluoromethyl-benzyl)-1H-indazol-5-ylmethylene]-2-(3-methoxy-azetidin-1-yl)-thiazol-4-one was prepared from 5-[1-(4-Chloro-2-trifluoromethyl-benzyl)-1H-indazol-5-ylmethylene]-2-methylsulfanyl-thiazol-4-one and 3-methoxy-azetidine following General Procedure B.

$^1$H NMR (400 MHz, CDCl$_3$) δ 8.18 (s, 1H), 7.94-7.92 (m, 2H), 7.71 (d, 1H), 7.52 (dd, 1H), 7.34-7.29 (m, 2H), 6.66-6.64 (m, 1H), 5.79 (s, 2H), 4.61-4.57 (m, 1H), 4.48-4.41 (m, 2H), 4.32-4.29 (m, 1H), 4.20-4.17 (m, 1H), 3.38 (s, 3H).

LC/MS (m/z) [M+1]$^+$ 507.1 (calculated for C$_{23}$H$_{18}$ClF$_3$N$_4$O$_2$S, 506.93).

Example 114

1-{5-[1-(4-Chloro-2-trifluoromethyl-benzyl)-1H-indazol-5-ylmethylene]-4-oxo-4,5-dihydro-thiazol-2-yl}-[1,4]diazepan-5-one

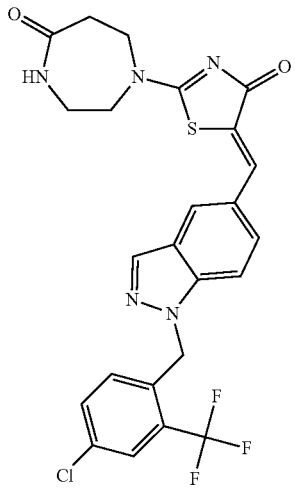 [SMILES: O=C1CCN(C2=NC(=O)/C(=C/c3ccc4c(cnn4Cc4ccc(Cl)cc4C(F)(F)F)c3)S2)CCN1]

1-{5-[1-(4-Chloro-2-trifluoromethyl-benzyl)-1H-indazol-5-ylmethylene]-4-oxo-4,5-dihydro-thiazol-2-yl}-[1,4]diazepan-5-one was prepared from 5-[1-(4-Chloro-2-trifluoromethyl-benzyl)-1H-indazol-5-ylmethylene]-2-methylsulfanyl-thiazol-4-one and [1,4]diazepan-5-one following General Procedure B.

$^1$H NMR (400 MHz, CDCl$_3$) δ 8.20 (dd, 1H), 7.98 (br s, 2H), 7.71 (d, 1H), 7.56-7.53 (m, 1H), 7.35-7.31 (m, 2H), 6.69-6.67 (m, 1H), 6.12 (br s, 1H), 5.79 (s, 2H), 4.27-4.24 (m, 2H), 3.84-3.82 (m, 2H), 3.53-3.45 (m, 2H), 2.84-2.78 (m, 2H).

LC/MS (m/z) [M+1]$^+$ 534.1 (calculated for C$_{24}$H$_{19}$ClF$_3$N$_5$O$_2$S, 533.95).

Example 115

5-[1-(4-Chloro-2-trifluoromethyl-benzyl)-1H-indazol-5-ylmethylene]-2-(3-methylamino-pyrrolidin-1-yl)-thiazol-4-one

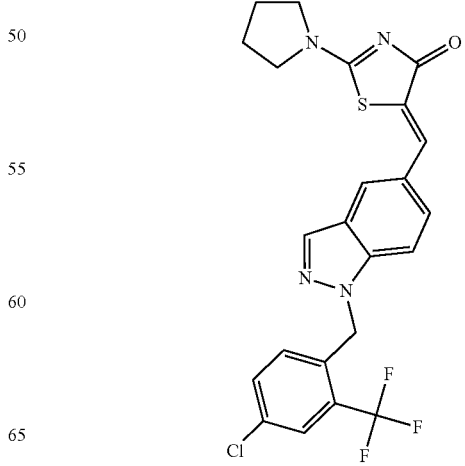

A. (1-{5-[1-(4-Chloro-2-trifluoromethyl-benzyl)-1H-indazol-5-ylmethylene]-4-oxo-4,5-dihydro-thiazol-2-yl}-pyrrolidin-3-yl)-methyl-carbamic acid tert-butyl ester was prepared from 5-[1-(4-chloro-2-trifluoromethyl-benzyl)-1H-indazol-5-ylmethylene]-2-methylsulfanyl-thiazol-4-one and methyl-pyrrolidin-3-yl-carbamic acid tert-butyl ester following General Procedure B.

$^1$H NMR (400 MHz, CDCl$_3$) δ 8.19 (dd, 1H), 7.97-7.94 (m, 2H), 7.71 (d, 1H), 7.56-7.52 (m, 1H), 7.34-7.30 (m, 2H), 6.66-6.64 (m, 1H), 5.79 (s, 2H), 4.18-4.05 (m, 1H), 3.85-3.74 (m, 2H), 3.69-3.49 (m, 2H), 2.84 (d, 3H), 2.34-2.17 (m, 2H), 1.49 (d, 9H).

LC/MS (m/z) [M+1]$^+$ 620.0 (calculated for C$_{29}$H$_{29}$ClF$_3$N$_5$O$_3$S, 620.09).

B. 5-[1-(4-Chloro-2-trifluoromethyl-benzyl)-1H-indazol-5-ylmethylene]-2-(3-methylamino-pyrrolidin-1-yl)-thiazol-4-one was prepared from (1-{5-[1-(4-Chloro-2-trifluoromethyl-benzyl)-1H-indazol-5-ylmethylene]-4-oxo-4,5-dihydro-thiazol-2-yl}-pyrrolidin-3-yl)-methyl-carbamic acid tert-butyl ester following General Procedure I.

$^1$H NMR (400 MHz, DMSO) δ 8.35 (s, 1H), 8.14 (s, 1H), 7.89 (d, 1H), 7.83-7.78 (m, 2H), 7.71-7.65 (m, 2H), 6.78-6.76 (m, 1H), 5.87 (s, 2H), 4.06-3.75 (m, 5H), 2.64-2.62 (m, 3H), 2.45-2.32 (m, 2H).

LC/MS (m/z) [M+1]$^+$ 520.1 (calculated for C$_{24}$H$_{21}$ClF$_3$N$_5$OS, 519.97).

Example 116

N-(1-{5-[1-(4-Chloro-2-trifluoromethyl-benzyl)-1H-indazol-5-ylmethylene]-4-oxo-4,5-dihydro-thiazol-2-yl}-pyrrolidin-3-yl)-2,2,2-trifluoro-acetamide

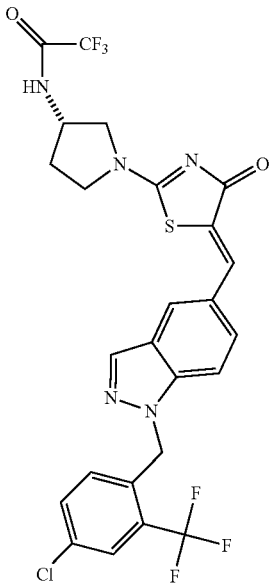 [SMILES: O=C1N=C(N2CC[C@H](NC(=O)C(F)(F)F)C2)S/C1=C\c1ccc2c(cnn2Cc2ccc(Cl)cc2C(F)(F)F)c1]

N-(1-{5-[1-(4-Chloro-2-trifluoromethyl-benzyl)-1H-indazol-5-ylmethylene]-4-oxo-4,5-dihydro-thiazol-2-yl}-pyrrolidin-3-yl)-2,2,2-trifluoro-acetamide was prepared from 5-[1-(4-Chloro-2-trifluoromethyl-benzyl)-1H-indazol-5-ylmethylene]-2-methylsulfanyl-thiazol-4-one and 2,2,2-Trifluoro-N-pyrrolidin-3-yl-acetamide following General Procedure B.

$^1$H NMR (400 MHz, DMSO) δ 8.35 (dd, 1H), 8.14 (br s, 2H), 7.89 (s, 1H), 7.80-7.76 (m, 2H), 7.71-7.65 (m, 2H), 6.77-6.75 (m, 1H), 5.88 (s, 2H), 4.59-4.55 (m, 1H), 4.0-3.95 (m, 1H), 3.86-3.75 (m, 2H), 3.66-3.62 (m, 1H), 2.39-2.29 (m, 1H), 2.13-2.07 (m, 1H).

LC/MS (m/z) [M+1]$^+$ 602.2 (calculated for C$_{25}$H$_{18}$ClF$_6$N$_5$O$_2$S, 601.95).

Example 117

4-{5-[1-(4-Chloro-2-trifluoromethyl-benzyl)-1H-indazol-5-ylmethylene]-4-oxo-4,5-dihydro-thiazol-2-yl}-piperazin-1-yl)-acetic acid

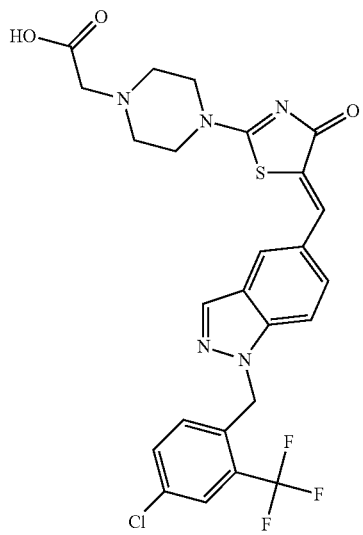 [SMILES: O=C(O)CN1CCN(C2=NC(=O)/C(=C/c3ccc4c(cnn4Cc4ccc(Cl)cc4C(F)(F)F)c3)S2)CC1]

(4-{5-[1-(4-Chloro-2-trifluoromethyl-benzyl)-1H-indazol-5-ylmethylene]-4-oxo-4,5-dihydro-thiazol-2-yl}-piperazin-1-yl)-acetic acid was prepared from 5-[1-(4-Chloro-2-trifluoromethyl-benzyl)-1H-indazol-5-ylmethylene]-2-methylsulfanyl-thiazol-4-one and piperazin-1-yl-acetic acid following General Procedure B.

$^1$H NMR (400 MHz, DMSO) δ 8.32 (s, 1H), 8.14 (s, 2H), 7.89 (d, 1H), 7.80-7.77 (m, 2H), 7.71-7.64 (m, 2H), 6.78-6.75 (d, 1H), 5.87 (s, 2H), 3.97 (br s, 2H), 3.72 (br s, 2H), 3.4 (br s, 2H), 2.84-2.80 (m, 4H).

LC/MS (m/z) [M+1]+ 564.2 (calculated for $C_{25}H_{21}ClF_3N_5O_3S$, 563.98).

Example 118

1-{5-[1-(2,4-Bis-trifluoromethyl-benzyl)-1H-indazol-5-ylmethylene]-4-oxo-4,5-dihydro-thiazol-2-yl}-[1,4]diazepan-5-one

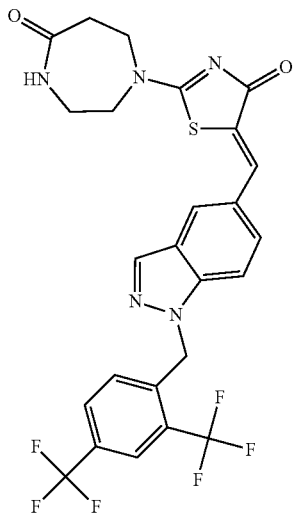 [SMILES: O=C1CCN(C2=NC(=O)/C(=C/c3ccc4c(cnn4Cc4ccc(C(F)(F)F)cc4C(F)(F)F)c3)S2)CCN1]

1-{5-[1-(2,4-Bis-trifluoromethyl-benzyl)-1H-indazol-5-ylmethylene]-4-oxo-4,5-dihydro-thiazol-2-yl}-[1,4]diazepan-5-one was prepared from 5-[1-(2,4-Bis-trifluoromethyl-benzyl)-1H-indazol-5-ylmethylene]-2-methylsulfanyl-thiazol-4-one and [1,4]diazepan-5-one following General Procedure B.

$^1$H NMR (400 MHz, DMSO) δ 8.36 (d, 1H), 8.16 (s, 1H), 8.12 (s, 1H), 7.97 (d, 1H), 7.88-7.780 (m, 3H), 7.72-7.68 (m, 1H), 6.92 (d, 1H), 5.98 (s, 2H), 4.08-4.05 (m, 2H), 3.84-3.78 (m, 2H), 3.39-3.31 (m, 2H), 2.71-2.62 (m, 2H).

LC/MS (m/z) [M+1]+ 568.1 (calculated for $C_{25}H_{19}F_6N_5O_2S$, 567.51).

Example 119

4-{5-[1-(2,4-Bis-trifluoromethyl-benzyl)-1H-indazol-5-ylmethylene]-4-oxo-4,5-dihydro-thiazol-2-yl}-piperazin-1-yl)-acetic acid

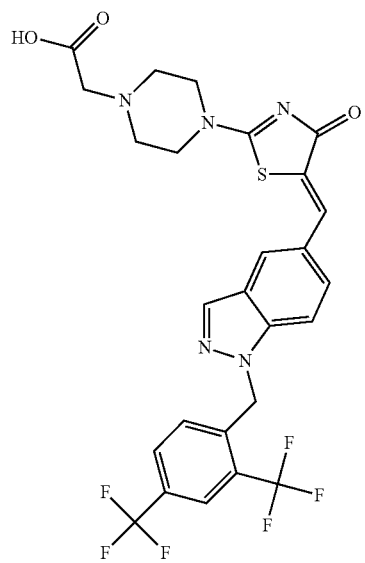 [SMILES: O=C(O)CN1CCN(C2=NC(=O)/C(=C/c3ccc4c(cnn4Cc4ccc(C(F)(F)F)cc4C(F)(F)F)c3)S2)CC1]

(4-{5-[1-(2,4-Bis-trifluoromethyl-benzyl)-1H-indazol-5-ylmethylene]-4-oxo-4,5-dihydro-thiazol-2-yl}-piperazin-1-yl)-acetic acid was prepared from 5-[1-(2,4-Bis-trifluoromethyl-benzyl)-1H-indazol-5-ylmethylene]-2-methylsulfanyl-thiazol-4-one and piperazin-1-yl-acetic acid following General Procedure B.

$^1$H NMR (400 MHz, DMSO) δ 8.36 (s, 1H), 8.16 (s, 1H), 8.12 (s, 1H), 7.98 (d, 1H), 7.84-7.81 (m, 2H), 7.70 (dd, 1H), 6.92 (d, 1H), 5.99 (s, 2H), 4.10-3.99 (m, 2H), 3.84-3.82 (m, 2H), 3.65-3.50 (m, 4H), 3.10-3.05 (br s, 2H).

LC/MS (m/z) [M+1]+ 598.2 (calculated for $C_{26}H_{21}F_6N_5O_3S$, 597.53).

Example 120

N-(1-{5-[1-(2,4-Bis-trifluoromethyl-benzyl)-1H-indazol-5-ylmethylene]-4-oxo-4,5-dihydro-thiazol-2-yl}-piperidin-4-yl)-methanesulfonamide

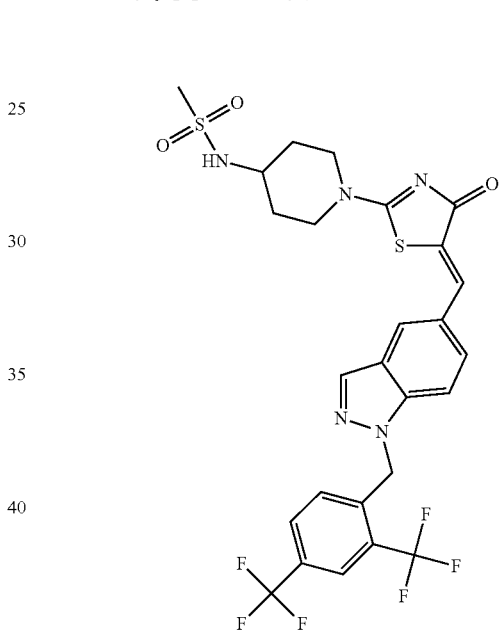

N-(1-{5-[1-(2,4-Bis-trifluoromethyl-benzyl)-1H-indazol-5-ylmethylene]-4-oxo-4,5-dihydro-thiazol-2-yl}-piperidin-4-yl)-methanesulfonamide was prepared from 5-[1-(2,4-Bis-trifluoromethyl-benzyl)-1H-indazol-5-ylmethylene]-2-methylsulfanyl-thiazol-4-one and N-piperidin-4-yl-methanesulfonamide following General Procedure B.

$^1$H NMR (400 MHz, DMSO) δ 8.33 (s, 1H), 8.14-8.10 (m, 2H), 7.96 (d, 1H), 7.79-7.77 (m, 2H), 7.69 (dd, 1H), 7.28 (d, 1H), 6.92 (d, 1H), 5.99 (s, 2H), 4.44-4.41 (m, 1H), 3.84-3.81 (m, 1H), 3.58-3.43 (m, 3H), 2.95 (s, 3H), 2.07-1.97 (m, 2H), 1.55-1.47 (m, 2H).

LC/MS (m/z) [M+1]+ 632.2 (calculated for $C_{26}H_{23}F_6N_5O_3S_2$, 631.62).

Example 121

5-[1-(4-Chloro-2-trifluoromethyl-benzyl)-1H-indazol-5-ylmethylene]-2-(4-cyclopropyl-piperazin-1-yl)-thiazol-4-one

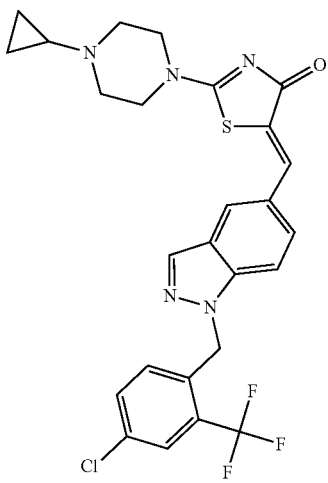 [SMILES: O=C1N=C(N2CCN(C3CC3)CC2)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-(4-cyclopropyl-piperazin-1-yl)-thiazol-4-one was prepared from 5-[1-(4-Chloro-2-trifluoromethyl-benzyl)-1H-indazol-5-ylmethylene]-2-methylsulfanyl-thiazol-4-one and 1-cyclopropyl-piperazine following General Procedure B.

$^1$H NMR (400 MHz, CDCl$_3$) δ 8.19 (s, 1H), 7.97 (s, 1H), 7.93 (s, 1H), 7.71 (d, 1H), 7.54 (dd, 1H), 7.34-7.30 (m, 2H), 6.65 (d, 1H), 5.79 (s, 2H), 4.06-4.03 (m, 2H), 3.61-3.59 (m, 2H), 2.79-2.73 (m, 4H), 1.73-1.68 (m, 1H), 0.55-0.51 (m, 2H), 0.49-0.44 (m, 2H).

LC/MS (m/z) [M+1]$^+$ 546.2 (calculated for C$_{26}$H$_{23}$ClF$_3$N$_5$OS, 546.01).

Example 122

5-[1-(2,4-Bis-trifluoromethyl-benzyl)-1H-indazol-5-ylmethylene]-2-(4-cyclopropyl-piperazin-1-yl)-thiazol-4-one

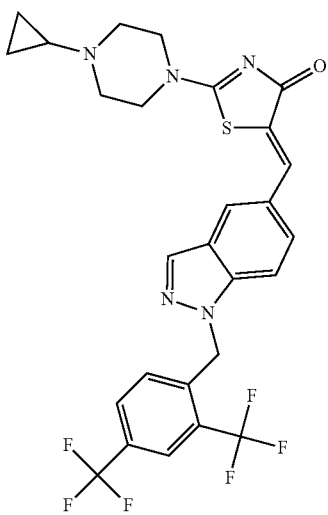 [SMILES: O=C1N=C(N2CCN(C3CC3)CC2)S/C1=C\c1ccc2c(cnn2Cc2ccc(C(F)(F)F)cc2C(F)(F)F)c1]

5-[1-(2,4-Bis-trifluoromethyl-benzyl)-1H-indazol-5-ylm-ethylene]-2-(4-cyclopropyl-piperazin-1-yl)-thiazol-4-one methanesulfonamide was prepared from 5-[1-(2,4-Bis-trifluoromethyl-benzyl)-1H-indazol-5-ylmethylene]-2-methyl-sulfanyl-thiazol-4-one and 1-cyclopropyl-piperazine following General Procedure B.

$^1$H NMR (400 MHz, CDCl$_3$) δ 8.21 (s, 1H), 7.99 br (s, 2H), 7.93 (s, 1H), 7.62 (d, 1H), 7.56 (dd, 1H), 7.32-1.30 (m, 1H), 6.81 (d, 1H), 5.88 (s, 2H), 4.06-4.03 (m, 2H), 3.61-3.59 (m, 2H), 2.79-2.74 (m, 4H), 1.73-1.69 (m, 1H), 0.55-0.50 (m, 2H), 0.49-0.46 (m, 2H).

LC/MS (m/z) [M+1]$^+$ 580.2 (calculated for C$_{27}$H$_{23}$F$_6$N$_5$OS, 579.56).

Example 123

5-[1-(4-Chloro-2-trifluoromethyl-benzyl)-1H-indazol-5-ylmethylene]-2-(3-ethyl-piperazin-1-yl)-thiazol-4-one

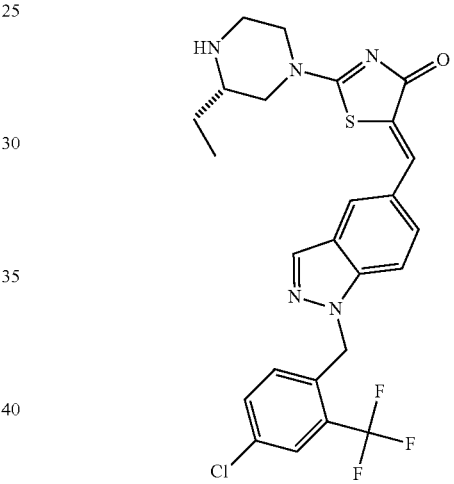

A. 4-{5-[1-(4-Chloro-2-trifluoromethyl-benzyl)-1H-indazol-5-ylmethylene]-4-oxo-4,5-dihydro-thiazol-2-yl}-2-ethyl-piperazine-1-carboxylic acid tert-butyl ester.

4-{5-[1-(4-Chloro-2-trifluoromethyl-benzyl)-1H-indazol-5-ylmethylene]-4-oxo-4,5-dihydro-thiazol-2-yl}-2-ethyl-piperazine-1-carboxylic acid tert-butyl ester was prepared from 5-[1-(2,4-Bis-trifluoromethyl-benzyl)-1H-indazol-5-ylmethylene]-2-methylsulfanyl-thiazol-4-one and 2-ethyl-piperazine-1-carboxylic acid tert-butyl ester following General Procedure B.

$^1$H NMR (400 MHz, CD$_3$OD) δ 8.21 (s, 1H), 8.05 (s, 1H), 7.82 (s, 1H), 7.78 (s, 1H), 7.62-7.59 (m, 1H), 7.53-7.45 (m, 2H), 6.67 (d, 1H), 5.82 (s, 2H), 4.67-4.64 (m, 1H), 4.30-4.21 (m, 1H), 4.13-4.05 (m, 1H), 3.88-3.65 (m, 2H), 3.56-3.43 (m, 1H), 3.19-3.12 (m, 1H), 1.62-1.56 (m, 2H), 1.49 (br s, 9H), 0.92 (t, 3H).

LC/MS (m/z) [M+1]$^+$ 634.0 (calculated for C$_{30}$H$_{31}$ClF$_3$N$_5$O$_3$S, 634.11).

B. 5-[1-(4-Chloro-2-trifluoromethyl-benzyl)-1H-indazol-5-ylmethylene]-2-(3-ethyl-piperazin-1-yl)-thiazol-4-one was prepared from 4-{5-[1-(4-Chloro-2-trifluoromethyl-benzyl)-1H-indazol-5-ylmethylene]-4-oxo-4,5-dihydro-thiazol-2-yl}-2-ethyl-piperazine-1-carboxylic acid tert-butyl ester following General Procedure I.

$^1$H NMR (400 MHz, DMSO) δ 8.33 (s, 1H), 8.15 (s, 1H), 7.89 (d, 1H), 7.86 (s, 1H), 7.81-7.78 (m, 1H), 7.71-7.65 (m, 2H), 6.81-6.78 (m, 1H), 5.87 (s, 2H), 4.68-4.62 (m, 1H), 4.03-3.98 (m, 1H), 3.77-3.71 (m, 1H), 3.62-3.25 (m, 4H), 1.71-1.63 (m, 2H), 1.03-0.97 (m, 3H).

LC/MS (m/z) [M+1]$^+$ 534.2 (calculated for $C_{25}H_{23}ClF_3N_5OS$, 534.0).

Example 124

5-[1-(2,4-Bis-trifluoromethyl-benzyl)-1H-indazol-5-ylmethylene]-2-(3-ethyl-piperazin-1-yl)-thiazol-4-one

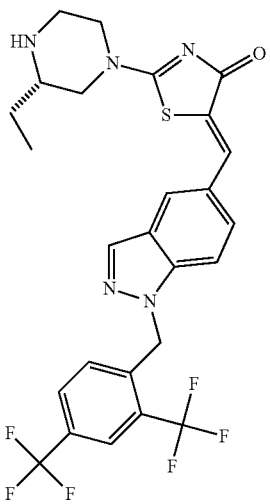

A. 4-{5-[1-(2,4-Bis-trifluoromethyl-benzyl)-1H-indazol-5-ylmethylene]-4-oxo-4,5-dihydro-thiazol-2-yl}-2-ethyl-piperazine-1-carboxylic acid tert-butyl ester.

4-{5-[1-(2,4-Bis-trifluoromethyl-benzyl)-1H-indazol-5-ylmethylene]-4-oxo-4,5-dihydro-thiazol-2-yl}-2-ethyl-piperazine-1-carboxylic acid tert-butyl ester was prepared from 5-[1-(2,4-Bis-trifluoromethyl-benzyl)-1H-indazol-5-ylmethylene]-2-methylsulfanyl-thiazol-4-one and 2-ethyl-piperazine-1-carboxylic acid tert-butyl ester following General Procedure B.

$^1$H NMR (400 MHz, CD$_3$OD) δ 8.23 (d, 1H), 8.06-8.04 (m, 2H), 7.82 (s, 1H), 7.77 (d, 1H), 7.64-7.59 (m, 1H), 7.55-7.53 (m, 1H), 6.85 (d, 1H), 5.93 (s, 2H), 4.67-4.64 (m, 1H), 4.30-4.23 (m, 1H), 4.13-4.04 (m, 1H), 3.88-3.65 (m, 2H), 3.56-3.42 (m, 1H), 3.19-3.12 (m, 1H), 1.62-1.56 (m, 2H), 1.49 (br s, 9H), 0.92 (t, 3H).

LC/MS (m/z) [M+1]$^+$ 667.9 (calculated for $C_{31}H_{31}F_6N_5O_3S$, 667.67).

B. 5-[1-(2,4-Bis-trifluoromethyl-benzyl)-1H-indazol-5-ylmethylene]-2-(3-ethyl-piperazin-1-yl)thiazol-4-one was prepared from 4-{5-[1-(2,4-Bis-trifluoromethyl-benzyl)-1H-indazol-5-ylmethylene]-4-oxo-4,5-dihydro-thiazol-2-yl}-2-ethyl-piperazine-1-carboxylic acid tert-butyl ester following General Procedure I.

$^1$H NMR (400 MHz, DMSO) δ 8.36 (s, 1H), 8.17 (s, 1H), 8.13 (s, 1H), 7.98 (d, 1H), 7.87 (s, 1H), 7.84-7.81 (m, 1H), 7.73-7.70 (m, 1H), 6.96-6.93 (m, 1H), 5.99 (s, 2H), 4.68-4.62 (m, 1H), 4.03-3.99 (m, 1H), 3.77-3.71 (m, 1H), 3.62-3.25 (m, 4H), 1.71-1.62 (m, 2H), 1.03-0.97 (m, 3H).

LC/MS (m/z) [M+1]$^+$ 568.2 (calculated for $C_{26}H_{23}F_6N_5OS$, 567.55).

Example 125

5-[1-(4-Chloro-2-trifluoromethyl-benzyl)-1H-indazol-5-ylmethylene]-2-(6-hydroxy-[1,4]diazepan-1-yl)-thiazol-4-one

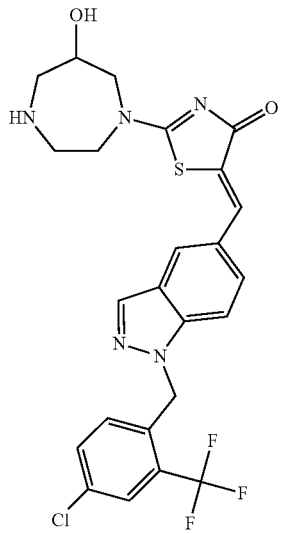 [SMILES: O=C1N=C(N2CCNCC(O)C2)S/C1=C\c1ccc2c(cnn2Cc2ccc(Cl)cc2C(F)(F)F)c1]

A. 5-[1-(4-Chloro-2-trifluoromethyl-benzyl)-1H-indazol-5-ylmethylene]-2-propylsulfanyl-thiazol-4-one was prepared from 1-(4-Chloro-2-trifluoromethyl-benzyl)-1H-indazole-5-carbaldehyde following General Procedure B.

$^1$H NMR (400 MHz, CDCl$_3$) δ 8.21 (s, 1H), 7.99-7.98 (m, 2H), 7.71 (d, 1H), 7.53 (dd, 1H), 7.35-7.32 (m, 2H), 6.66 (d, 1H), 5.79 (s, 2H), 3.42 (t, 2H), 1.91-1.82 (m, 2H), 1.07 (t, 3H).

LC/MS (m/z) [M+1]$^+$ 496.1 (calculated for $C_{22}H_{17}ClF_3N_3OS_2$, 495.97).

B. 5-[1-(4-Chloro-2-trifluoromethyl-benzyl)-1H-indazol-5-ylmethylene]-2-(6-hydroxy-[1,4]diazepan-1-yl)-thiazol-4-one.

5-[1-(4-Chloro-2-trifluoromethyl-benzyl)-1H-indazol-5-ylmethylene]-2-(6-hydroxy-[1,4]diazepan-1-yl)-thiazol-4-one was prepared from 5-[1-(4-Chloro-2-trifluoromethyl-benzyl)-1H-indazol-5-ylmethylene]-2-propylsulfanyl-thiazol-4-one and [1,4]diazepan-6-ol following General Procedure B.

$^1$H NMR (400 MHz, CDCl$_3$) δ 8.19 (s, 1H), 7.98 (s, 1H), 7.93 (d, 1H), 7.71 (s, 1H), 7.54 (dd, 1H), 7.35-7.27 (m, 2H), 6.68-6.64 (m, 1H), 5.79 (s, 2H), 4.29-4.07 (m, 2H), 3.95-3.77 (m, 2H), 3.70-3.64 (m, 1H), 3.35-3.31 (m, 1H), 3.17-2.87 (m, 4H).

LC/MS (m/z) [M+1]+ 536.2 (calculated for $C_{24}H_{21}ClF_3N_5O_2S$, 535.97).

Example 126

5-[1-(4-Chloro-2-trifluoromethyl-benzyl)-1H-indazol-5-ylmethylene]-2-isoxazolidin-2-yl-thiazol-4-one

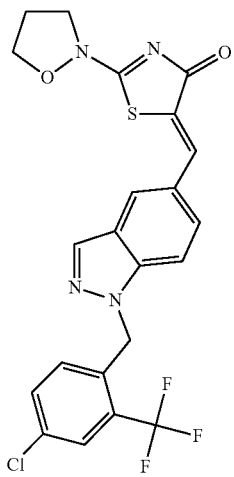 [SMILES: O=C1N=C(N2CCCO2)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-isoxazolidin-2-yl-thiazol-4-one was prepared from 5-[1-(4-Chloro-2-trifluoromethyl-benzyl)-1H-indazol-5-ylmethylene]-2-ethylsulfanyl-thiazol-4-one and isoxazolidine following General Procedure B.

$^1$H NMR (400 MHz, DMSO) δ 8.35 (s, 1H), 8.14 (s, 1H), 7.89 (d, 1H), 7.82 (s, 1H), 7.78-7.76 (m, 1H), 7.70-7.64 (m, 2H), 6.74 (d, 1H), 5.86 (s, 2H), 4.27 (t, 2H), 4.03 (t, 2H), 2.52-2.45 (m, 2H).

LC/MS (m/z) [M+1]+ 493.0 (calculated for $C_{22}H_{16}ClF_3N_4O_2S$, 492.9).

Example 127

4-{5-[1-(4-Chloro-2-trifluoromethyl-benzyl)-1H-indazol-5-ylmethylene]-4-oxo-4,5-dihydro-thiazol-2-yl}-piperazin-1-yl)-acetic acid ethyl ester

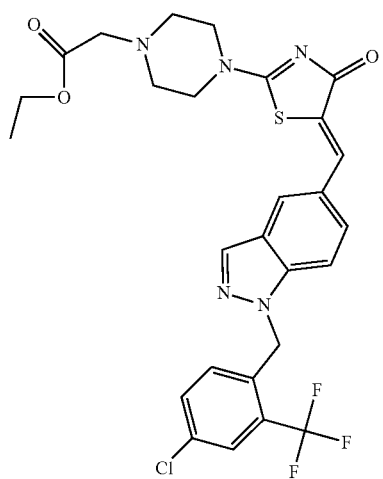 [SMILES: CCOC(=O)CN1CCN(C2=NC(=O)/C(=C/c3ccc4c(cnn4Cc4ccc(Cl)cc4C(F)(F)F)c3)S2)CC1]

(4-{5-[1-(4-Chloro-2-trifluoromethyl-benzyl)-1H-indazol-5-ylmethylene]-4-oxo-4,5-dihydro-thiazol-2-yl}-piperazin-1-yl)-acetic acid ethyl ester was prepared from 5-[1-(4-Chloro-2-trifluoromethyl-benzyl)-1H-indazol-5-ylmethylene]-2-ethylsulfanyl-thiazol-4-one and piperazin-1-yl-acetic acid ethyl ester following General Procedure B.

$^1$H NMR (400 MHz, DMSO) δ 8.32 (s, 1H), 8.14 (s, 1H), 7.89 (d, 1H), 7.82 (s, 1H), 7.79-7.77 (m, 1H), 7.70-7.65 (m, 2H), 6.77 (d, 1H), 5.86 (s, 2H), 4.15 (q, 2H), 4.03 (br s, 2H), 3.79-3.66 (m, 4H), 3.04-2.90 (m, 4H), 1.22 (t, 3H).

LC/MS (m/z) [M+1]+ 592.2 (calculated for $C_{27}H_{25}ClF_3N_5O_3S$, 592.03).

Example 128

4-{5-[1-(4-Chloro-2-trifluoromethyl-benzyl)-1H-indazol-5-ylmethylene]-4-oxo-4,5-dihydro-thiazol-2-yl}-[1,4]diazepane-1-carboxylic acid ethyl ester

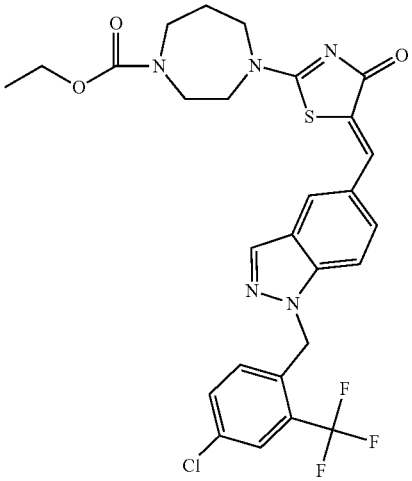 [SMILES: CCOC(=O)N1CCCN(C2=NC(=O)/C(=C/c3ccc4c(cnn4Cc4ccc(Cl)cc4C(F)(F)F)c3)S2)CC1]

A. 2-Methylsulfanyl-thiazol-4-one was prepared following General Procedure E.

$^1$H NMR (400 MHz, CDCl$_3$) δ4.0 (s, 2H), 2.75 (s, 3H) (compound described: J. Heterocyclic Chem. 2002 39 1153).

B. 2-[1,4]-Diazepan-1-yl-thiazol-4-one was prepared from 2-Methylsulfanyl-thiazol-4-one and [1,4]diazepane following General Procedure E $^1$H NMR (400 MHz, CDCl$_3$) δ4.01-3.94 (m, 4H), 3.68-3.65 (m, 1H), 3.61-3.58 (m, 1H), 3.09-3.07 (m, 1H), 3.05-3.02 (m, 1H), 2.94-2.89 (m, 2H), 1.99-1.88 (m, 2H), 1.71 (br s, 1H).

LC/MS (m/z) [M+1]+ 200.2 (calculated for $C_8H_{13}N_3OS$, 199.27).

C. 4-(4-Oxo-4,5-dihydro-thiazol-2-yl)-[1,4]diazepane-1-carboxylic acid ethyl ester.

To a solution of 2-[1,4]diazepan-1-yl-thiazol-4-one (105 mg, 0.52 mmol) in dichloromethane (8 mL) was added ethyl chloroformate (68 mg, 0.63 mmol) followed by triethylamine (64 mg, 0.63 mmol). The reaction mixture was stirred at room temperature for 4 hours and partitioned between saturated aqueous hydrogenocarbonate solution and dichloromethane. The dichloromethane layer was washed with brine, dried over Na$_2$SO$_4$, filtered, and the solvent evaporated in vacuo to yield a crude solid. The crude solid was purified via flash chromatography (2.5% methanol in dichloromethane) to yield the title compound (125 mg, 88%).

$^1$H NMR (400 MHz, CDCl$_3$) δ4.19-4.14 (m, 2H), 4.00-3.89 (m, 4H), 3.67-3.61 (m, 4H), 3.53-3.44 (m, 2H), 2.06-1.98 (m, 2H), 1.27 (t, 3H).

LC/MS (m/z) [M+1]+ 272.1 (calculated for $C_{11}H_{17}N_3O_3S$, 271.34).

D. 4-{5-[1-(4-Chloro-2-trifluoromethyl-benzyl)-1H-indazol-5-ylmethylene]-4-oxo-4,5-dihydro-thiazol-2-yl}-[1,4]diazepane-1-carboxylic acid ethyl ester.

4-(4-oxo-4,5-dihydro-thiazol-2-yl)-[1,4]diazepane-1-carboxylic acid ethyl ester was prepared from 5-[1-(4-Chloro-2-trifluoromethyl-benzyl)-1H-indazol-5-ylmethylene]-2-ethylsulfanyl-thiazol-4-one and 1-(4-Chloro-2-trifluoromethyl-benzyl)-1H-indazole-5-carbaldehyde following General Procedure E.

$^1$H NMR (400 MHz, CDCl$_3$) δ 8.20 (s, 1H), 7.97-7.94 (m, 2H), 7.71 (d, 1H), 7.55-7.53 (m, 1H), 7.35-7.31 (m, 2H), 6.66 (d, 1H), 5.79 (s, 2H), 4.19-3.99 (m, 4H), 3.78-3.68 (m, 4H), 3.57-3.47 (m, 2H), 2.12-2.04 (m, 2H), 1.27 (q, 3H).

LC/MS (m/z) [M+1]$^+$ 592.2 (calculated for C$_{27}$H$_{25}$ClF$_3$N$_5$O$_3$S, 592.03).

Example 129

4-{5-[1-(2,4-Bis-trifluoromethyl-benzyl)-1H-indazol-5-ylmethylene]-4-oxo-4,5-dihydro-thiazol-2-yl}-[1,4]diazepane-1-carboxylic acid ethyl ester

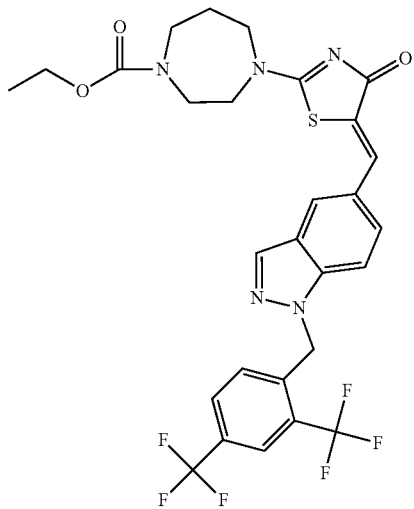 [SMILES: CCOC(=O)N1CCCN(C2=NC(=O)/C(=C/c3ccc4c(cnn4Cc4ccc(C(F)(F)F)cc4C(F)(F)F)c3)S2)CC1]

4-{5-[1-(2,4-Bis-trifluoromethyl-benzyl)-1H-indazol-5-ylmethylene]-4-oxo-4,5-dihydro-thiazol-2-yl}-[1,4]diazepane-1-carboxylic acid ethyl ester was prepared from 5-[1-(4-Chloro-2-trifluoromethyl-benzyl)-1H-indazol-5-ylmethylene]-2-ethylsulfanyl-thiazol-4-one and 1-(2,4-Bis-trifluoromethyl-benzyl)-1H-indazole-5-carbaldehyde following General Procedure E.

$^1$H NMR (400 MHz, CDCl$_3$) δ 8.22 (s, 1H), 7.98 (br s, 2H), 7.96-7.94 (m, 1H), 7.57-7.54 (m, 1H), 7.34-7.31 (m, 1H), 6.82 (d, 1H), 5.89 (s, 2H), 4.19-4.00 (m, 4H), 3.78-3.68 (m, 4H), 3.57-3.47 (m, 2H), 2.12-2.04 (m, 2H), 1.26 (q, 3H).

LC/MS (m/z) [M+1]$^+$ 526.2 (calculated for C$_{28}$H$_{25}$F$_6$N$_5$O$_3$S, 625.59).

Example 130

1-{5-[1-(4-Chloro-2-trifluoromethyl-benzyl)-1H-indazol-5-ylmethylene]-4-oxo-4,5-dihydro-thiazol-2-yl}piperidin-4-yloxy)-acetic acid methyl ester

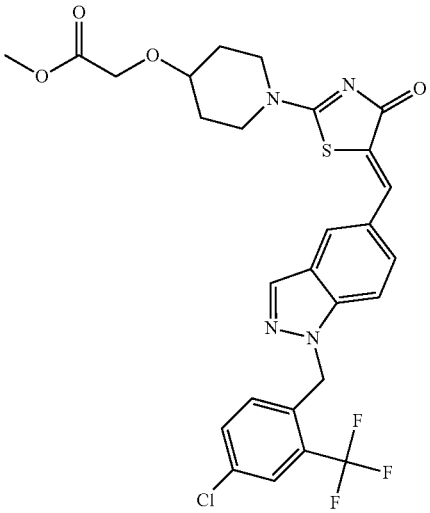 [SMILES: COC(=O)COC1CCN(C2=NC(=O)/C(=C/c3ccc4c(cnn4Cc4ccc(Cl)cc4C(F)(F)F)c3)S2)CC1]

(1-{5-[1-(4-Chloro-2-trifluoromethyl-benzyl)-1H-indazol-5-ylmethylene]-4-oxo-4,5-dihydro-thiazol-2-yl}piperidin-4-yloxy)-acetic acid methyl ester was prepared from 5-[1-(4-Chloro-2-trifluoromethyl-benzyl)-1H-indazol-5-ylmethylene]-2-ethylsulfanyl-thiazol-4-one and (piperidin-4-yloxy)-acetic acid methyl ester following General Procedure B.

$^1$H NMR (400 MHz, CDCl$_3$) δ 8.19 (s, 1H), 7.97 (s, 1H), 7.93 (s, 1H), 7.71 (d, 1H), 7.54 (dd, 1H), 7.34-7.29 (m, 2H), 6.65 (d, 1H), 5.79 (s, 2H), 4.23-4.17 (m, 3H), 4.13-4.05 (m, 1H), 3.89-3.80 (m, 2H), 3.78 (s, 3H), 3.57-3.48 (m, 1H), 2.01-1.88 (m, 4H).

LC/MS (m/z) [M+1]$^+$ 593.2 (calculated for C$_{27}$H$_{24}$ClF$_3$N$_4$O$_4$S, 593.02).

Example 131

1-{5-[1-(4-Chloro-2-trifluoromethyl-benzyl)-1H-indazol-5-ylmethylene]-4-oxo-4,5-dihydro-thiazol-2-yl}-piperidin-4-yloxy)-acetic acid

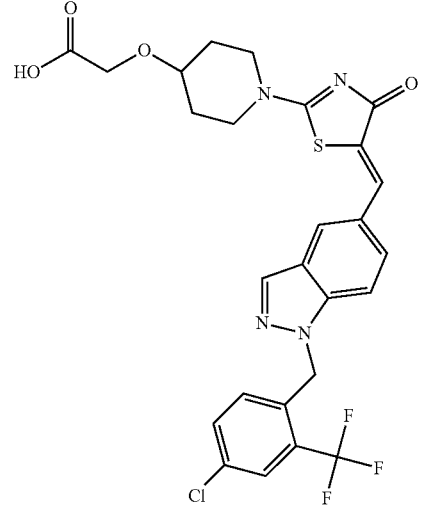 [SMILES: O=C(O)COC1CCN(C2=NC(=O)/C(=C/c3ccc4c(cnn4Cc4ccc(Cl)cc4C(F)(F)F)c3)S2)CC1]

A solution of (1-{5-[1-(4-Chloro-2-trifluoromethyl-benzyl)-1H-indazol-5-ylmethylene]-4-oxo-4,5-dihydro-thiazol-2-yl}-piperidin-4-yloxy)-acetic acid methyl ester (0.043 g, 0.072 mmol) in THF/methanol (3 mL, 2/1) was treated with an aqueous solution of lithium hydroxide (1 mL, 6.9 mg, 0.29 mmol) and stirred at room temperature for 1 hour. The reaction mixture was concentrated and acidified with aqueous 0.3 mM HCl. The precipitate obtained was washed with water, dried and purified using semi-preparative reverse phase HPLC (YMC ODS A, 100×30 mm, 50 μM I.D., 0.05% TFA acetonitrile/0.05% TFA water=30/70 to 100/0) to yield the title compound as a flocculent solid.

$^1$H NMR (400 MHz, DMSO) δ 8.32 (s, 1H), 8.14 (s, 1H), 7.89 (s, 1H), 7.78-7.76 (m, 2H), 7.71-7.65 (m, 2H), 6.76 (d, 1H), 5.87 (s, 2H), 4.12 (s, 2H), 4.10-4.06 (m, 1H), 3.82-5.53 (m, 4H), 2.02-1.93 (m, 2H), 1.72-1.63 (m, 2H).

LC/MS (m/z) [M+1]$^+$ 579.2 (calculated for $C_{26}H_{22}ClF_3N_4O_4S$, 578.99).

Example 132

5-[1-(4-Chloro-2-trifluoromethyl-benzyl)-1H-indazol-5-ylmethylene]-2-(3-(R)-hydroxymethyl-piperazin-1-yl)-thiazol-4-one

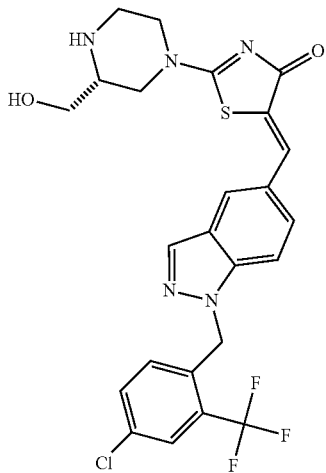 [SMILES: O=C1N=C(N2CCN[C@@H](CO)C2)S/C1=C\c1ccc2c(cnn2Cc2ccc(Cl)cc2C(F)(F)F)c1]

A. 4-{5-[1-(4-Chloro-2-trifluoromethyl-benzyl)-1H-indazol-5-ylmethylene]-4-oxo-4,5-dihydro-thiazol-2-yl}-2-(R)-hydroxymethyl-piperazine-1-carboxylic acid tert-butyl ester was prepared from 5-[1-(4-Chloro-2-trifluoromethyl-benzyl)-1H-indazol-5-ylmethylene]-2-ethylsulfanyl-thiazol-4-one and 2-Hydroxymethyl-piperazine-1-carboxylic acid tert-butyl ester following General Procedure B.

LC/MS (m/z) [M+1]$^+$ 636.0 (calculated for $C_{29}H_{29}ClF_3N_5O_4S$, 636.09).

B. 5-[1-(4-Chloro-2-trifluoromethyl-benzyl)-1H-indazol-5-ylmethylene]-2-(3-(R)-hydroxymethyl-piperazin-1-yl)-thiazol-4-one was prepared from 4-{5-[1-(4-Chloro-2-trifluoromethyl-benzyl)-1H-indazol-5-ylmethylene]-4-oxo-4,5-dihydro-thiazol-2-yl}-2-(R)-hydroxymethyl-piperazine-1-carboxylic acid tert-butyl ester following General Procedure I.

$^1$H NMR (400 MHz, DMSO) δ 8.33 (s, 1H), 8.15 (s, 1H), 7.89 (s, 1H), 7.86 (s, 1H), 7.79 (dd, 1H), 7.71-7.65 (m, 2H), 6.80 (dd, 1H), 5.87 (s, 2H), 5.63 (br s, 1H), 4.73-4.66 (m, 1H), 4.06-4.00 (m, 1H), 3.75-3.63 (m, 4H), 3.59-3.34 (m, 3H).

LC/MS (m/z) [M+1]$^+$ 536.2 (calculated for $C_{24}H_{21}ClF_3N_5O_2S$, 535.97).

Example 133

5-[1-(4-Chloro-2-trifluoromethyl-benzyl)-1H-indazol-5-ylmethylene]-2-[4-(2-fluoro-ethyl)-[1,4]diazepan-1-yl]-thiazol-4-one

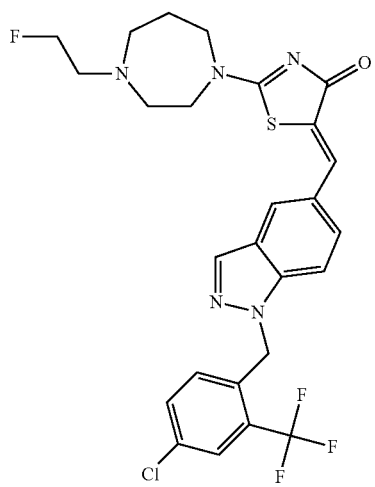 [SMILES: O=C1N=C(N2CCCN(CCF)CC2)S/C1=C\c1ccc2c(cnn2Cc2ccc(Cl)cc2C(F)(F)F)c1]

A. 5-[1-(4-Chloro-2-trifluoromethyl-benzyl)-1H-indazol-5-ylmethylene]-2-[1,4]diazepan-1-yl-thiazol-4-one.

5-[1-(4-Chloro-2-trifluoromethyl-benzyl)-1H-indazol-5-ylmethylene]-2-[1,4]diazepan-1-yl-thiazol-4-one was prepared from 5-[1-(4-Chloro-2-trifluoromethyl-benzyl)-1H-indazol-5-ylmethylene]-2-methylsulfanyl-thiazol-4-one and [1,4]diazepane following General Procedure D.

$^1$H NMR (400 MHz, CDCl$_3$) δ 8.19 (dd, 1H), 7.97 (s, 1H), 7.92 (s, 1H), 7.71 (s, 1H), 7.56-7.53 (m, 1H), 7.34-7.26 (m, 2H), 6.65 (d, 1H), 5.79 (s, 2H), 4.10-4.05 (m, 2H), 3.80-3.77 (m, 1H), 3.72-3.69 (m, 1H), 3.15-3.12 (m, 1H), 3.10-3.08 (m, 1H), 2.96-2.92 (m, 2H), 2.05-1.95 (m, 2H).

LC/MS (m/z) [M+1]$^+$ 520.3 (calculated for $C_{24}H_{21}ClF_3N_5OS$, 519.97).

B. 5-[1-(4-Chloro-2-trifluoromethyl-benzyl)-1H-indazol-5-ylmethylene]-2-[4-(2-fluoro-ethyl)-[1,4]diazepan-1-yl]-thiazol-4-one.

A solution 5-[1-(4-Chloro-2-trifluoromethyl-benzyl)-1H-indazol-5-ylmethylene]-2-[1,4]diazepan-1-yl-thiazol-4-one (0.016 g, 0.03 mmol) in acetonitrile (1.5 mL) was treated with potassium carbonate (0.022 g, 0.15 mmol) and 1-bromo-2-fluoro-ethane (0.04 g, 0.3 mmol). Reaction mixture was stirred at 70° C. for 18 hours and the solvent evaporated in vacuo. The residue was partitioned between dichloromethane and water. The dichloromethane layer was washed with brine, dried over Na$_2$SO$_4$, filtered, and the solvent evaporated in vacuo to yield a crude solid. The crude solid was purified via flash chromatography (5% methanol in dichloromethane) to yield the title compound (17 mg, 100%).

$^1$H NMR (400 MHz, CDCl$_3$) δ 8.19 (s, 1H), 7.98 (s, 1H), 7.93 (s, 1H), 7.71 (s, 1H), 7.56-7.54 (m, 1H), 7.34-7.30 (m, 2H), 6.65 (d, 1H), 5.79 (s, 2H), 4.63-4.58 (m, 1H), 4.51-4.46 (m, 1H), 4.12-4.06 (m, 2H), 3.76-3.73 (m, 2H), 3.04-3.02 (m, 1H), 2.95-2.90 (m, 2H), 2.88-2.79 (m, 3H), 2.11-1.98 (m, 2H).

LC/MS (m/z) [M+1]+ 566.2 (calculated for $C_{26}H_{24}ClF_4N_5OS$, 566.01).

Example 134

5-[1-(4-Chloro-2-trifluoromethyl-benzyl)-1H-indazol-5-ylmethylene]-2-(4-methanesulfonyl-[1,4]diazepan-1-yl)-thiazol-4-one

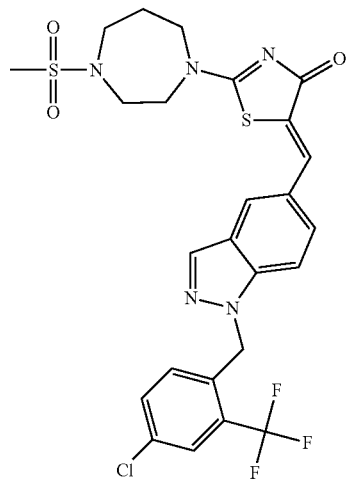 [SMILES: CS(=O)(=O)N1CCCN(C2=NC(=O)/C(=C/c3ccc4c(cnn4Cc4ccc(Cl)cc4C(F)(F)F)c3)S2)CC1]

5-[1-(4-Chloro-2-trifluoromethyl-benzyl)-1H-indazol-5-ylmethylene]-2-(4-methanesulfonyl-[1,4]diazepan-1-yl)-thiazol-4-one was prepared from 5-[1-(4-Chloro-2-trifluoromethyl-benzyl)-1H-indazol-5-ylmethylene]-2-[1,4]diazepan-1-yl-thiazol-4-one and methane sulfonyl chloride according to Example 133.

$^1$H NMR (400 MHz, CDCl$_3$) δ 8.20 (dd, 1H), 7.97-7.95 (m, 2H), 7.71 (s, 1H), 7.55-7.52 (m, 1H), 7.35-7.31 (m, 2H), 6.67 (d, 1H), 5.79 (s, 2H), 4.19-4.12 (m, 2H), 3.90-3.87 (m, 1H), 3.84-3.82 (m, 1H), 3.64-3.62 (m, 1H), 3.57-3.55 (m, 1H), 3.43-3.39 (m, 2H), 2.89 (d, 3H), 2.22-2.16 (m, 2H).

LC/MS (m/z) [M+1]+ 598.2 (calculated for $C_{25}H_{23}ClF_3N_5O_3S_2$, 598.06).

Example 135

5-[1-(4-Chloro-2-trifluoromethyl-benzyl)-1H-indazol-5-ylmethylene]-2-[4-(2,2,2-trifluoro-ethyl)-[1,4]diazepan-1-yl]-thiazol-4-one

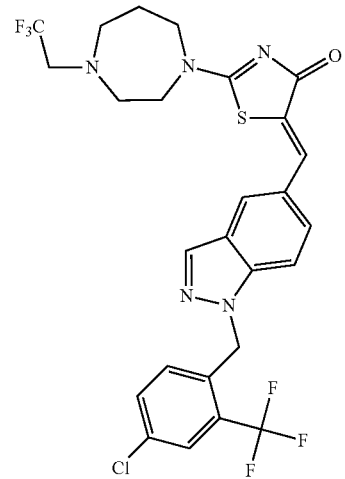 [SMILES: O=C1N=C(N2CCCN(CC(F)(F)F)CC2)S/C1=C\c1ccc2c(cnn2Cc2ccc(Cl)cc2C(F)(F)F)c1]

A solution of 5-[1-(4-Chloro-2-trifluoromethyl-benzyl)-1H-indazol-5-ylmethylene]-2-[1,4]diazepan-1-yl-thiazol-4-one (0.051 g, 0.098 mmol) in DMSO (2.2 mL) was treated with potassium carbonate (0.045 g, 0.32 mmol) and methanesulfonic acid 2,2,2-trifluoro-ethyl ester (0.06 g, 0.32 mmol). Reaction mixture was stirred at 70° C. for 1 hour and partitioned between dichloromethane and water. The dichloromethane layer was dried over Na$_2$SO$_4$, filtered, and the solvent evaporated in vacuo to yield a crude solid. The crude solid was purified using semi-preparative reverse phase HPLC (YMC ODS A, 100×30 mm, 50 μM I.D., 0.05% TFA acetonitrile/0.05% TFA water=30/70 to 100/0) to yield the title compound as a flocculent solid.

$^1$H NMR (400 MHz, CD$_3$OD) δ 8.25 (s, 1H), 8.11 (s, 1H), 7.86 (s, 1H), 7.79 (d, 1H), 7.66 (dd, 1H), 7.56 (d, 1H), 7.48 (dd, 1H), 6.68 (d, 1H), 5.86 (s, 2H), 4.05-4.0 (m, 2H), 3.85-3.79 (m, 2H), 3.36-3.30 (m, 2H), 3.20-3.18 (m, 1H), 3.14-3.11 (m, 1H), 3.0-2.96 (m, 2H), 2.06-2.01 (m, 1H), 2.0-1.92 (m, 1H).

LC/MS (m/z) [M+1]+ 602.3 (calculated for $C_{26}H_{22}ClF_6N_5OS$, 602.0).

Example 136

4-{5-[1-(4-Chloro-2-trifluoromethyl-benzyl)-1H-indazol-5-ylmethylene]-4-oxo-4,5-dihydro-thiazol-2-yl}[1,4]diazepane-1-carboxylic acid 2,2,2-trifluoro-ethyl ester

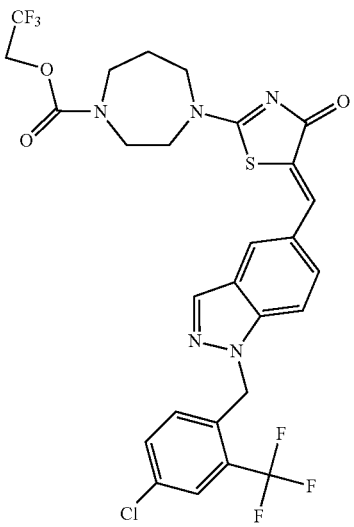 [SMILES: O=C1N=C(N2CCCN(C(=O)OCC(F)(F)F)CC2)S/C1=C\c1ccc2c(cnn2Cc2ccc(Cl)cc2C(F)(F)F)c1]

4-{5-[1-(4-Chloro-2-trifluoromethyl-benzyl)-1H-indazol-5-ylmethylene]-4-oxo-4,5-dihydro-thiazol-2-yl}-[1,4]diazepane-1-carboxylic acid 2,2,2-trifluoro-ethyl ester was prepared from 5-[1-(4-Chloro-2-trifluoromethyl-benzyl)-1H-indazol-5-ylmethylene]-2-[1,4]diazepan-1-yl-thiazol-4-one and 2,2,2-Trifluoroethyl chloroformate according to Example 133.

$^1$H NMR (400 MHz, CD$_3$OD) δ 8.24 (s, 1H), 8.08 (s, 1H), 7.85 (s, 1H), 7.79 (s, 1H), 7.65-7.62 (m, 1H), 7.55-7.53 (m, 1H), 7.48-7.46 (m, 1H), 6.67 (d, 1H), 5.84 (s, 2H), 4.64-4.57 (m, 2H), 4.11-4.08 (m, 1H), 4.02 (br s, 1H), 3.89-3.75 (m, 4H), 3.63-3.57 (m, 2H), 2.03-1.93 (m, 2H).

LC/MS (m/z) [M+1]+ 646.3 (calculated for $C_{27}H_{22}ClF_6N_5O_3S$, 646.0).

Example 137

1-{5-[1-(4-Chloro-2-trifluoromethyl-benzyl)-1H-indazol-5-ylmethylene]-4-oxo-4,5-dihydro-thiazol-2-yl}-pyrrolidine-3-carboxylic acid

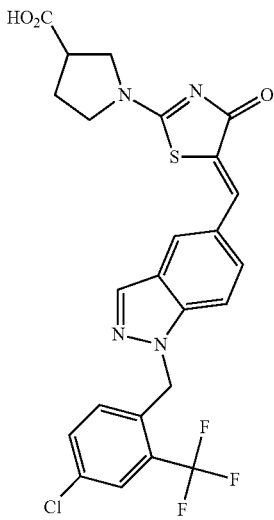 [SMILES: O=C1N=C(N2CCC(C(=O)O)C2)S/C1=C\c1ccc2c(cnn2Cc2ccc(Cl)cc2C(F)(F)F)c1]

1-{5-[1-(4-Chloro-2-trifluoromethyl-benzyl)-1H-indazol-5-ylmethylene]-4-oxo-4,5-dihydro-thiazol-2-yl}-pyrrolidine-3-carboxylic acid was prepared from 5-[1-(4-Chloro-2-trifluoromethyl-benzyl)-1H-indazol-5-ylmethylene]-2-methylsulfanyl-thiazol-4-one and pyrrolidine-3-carboxylic acid following General Procedure B.

$^1$H NMR (400 MHz, DMSO) δ 8.34 (s, 1H), 8.14-8.12 (m, 1H), 7.89 (d, 1H), 7.79-7.76 (m, 2H), 7.71-7.64 (m, 2H), 6.75 (d, 1H), 5.86 (s, 2H), 3.93-3.66 (m, 4H), 3.37-3.27 (m, 1H), 2.36-2.18 (m, 2H).

LC/MS (m/z) [M+1]$^+$ 535.2 (calculated for $C_{24}H_{18}ClF_3N_4O_3S$, 534.94).

Example 138

2-[4-(2-Amino-acetyl)-[1,4]diazepan-1-yl]-5-[1-(4-chloro-2-trifluoromethyl-benzyl)-1H-indazol-5-ylmethylene]-thiazol-4-one

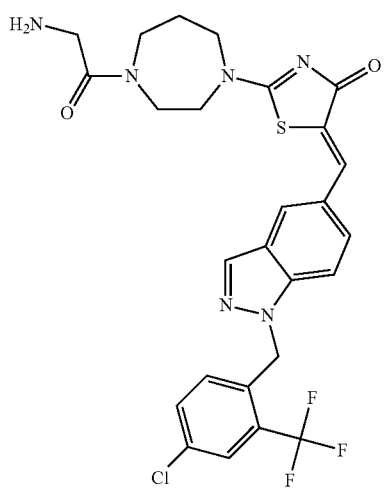 [SMILES: NCC(=O)N1CCCN(C2=NC(=O)/C(=C/c3ccc4c(cnn4Cc4ccc(Cl)cc4C(F)(F)F)c3)S2)CC1]

A. [2-(4-{5-[1-(4-Chloro-2-trifluoromethyl-benzyl)-1H-indazol-5-ylmethylene]-4-oxo-4,5-dihydro-thiazol-2-yl}-[1,4]diazepan-1-yl)-2-oxo-ethyl]-carbamic acid tert-butyl ester.

A solution 5-[1-(4-Chloro-2-trifluoromethyl-benzyl)-1H-indazol-5-ylmethylene]-2-[1,4]diazepan-1-yl-thiazol-4-one (0.026 g, 0.05 mmol) and tert-butoxycarbonylamino-acetic acid (0.0087 g, 0.05 mmol) in dichloromethane (3 mL) was treated with EDCI (0.0104 g, 0.055 mmol) and triethylamine (0.006 g, 0.06 mmol). Reaction mixture was stirred at room temperature for 18 hours and was then partitioned between dichloromethane and an aqueous saturated hydrogenocarbonate solution. The dichloromethane layer was then washed with aqueous 10% citric acid, brine, dried over $Na_2SO_4$, filtered, and the solvent evaporated in vacuo to yield a crude solid. The crude solid was purified via flash chromatography (5% methanol in dichloromethane) to yield the title compound (26 mg, 77%).

$^1$H NMR (400 MHz, CDCl$_3$) δ 8.20 (s, 1H), 7.96-7.94 (m, 2H), 7.71 (s, 1H), 7.55-7.52 (m, 1H), 7.35-7.30 (m, 2H), 6.66 (dd, 1H), 5.79 (s, 2H), 5.36 (br s, 1H), 4.16-4.05 (m, 2H), 4.03-3.96 (m, 2H), 3.89-3.62 (m, 4H), 3.55-3.50 (m, 2H), 2.18-2.07 (m, 2H), 1.44 (s, 9H).

LC/MS (m/z) [M+1]$^+$ 676.7 (calculated for $C_{31}H_{32}ClF_3N_6O_4S$, 677.14).

B. 2-[4-(2-Amino-acetyl)-[1,4]diazepan-1-yl]-5-[1-(4-chloro-2-trifluoromethyl-benzyl)-1H-indazol-5-ylmethylene]-thiazol-4-one. 2-[4-(2-Amino-acetyl)-[1,4]diazepan-1-yl]-5-[1-(4-chloro-2-trifluoromethyl-benzyl)-1H-indazol-5-ylmethylene]-thiazol-4-one was prepared from [2-(4-{5-[1-(4-Chloro-2-trifluoromethyl-benzyl)-1H-indazol-5-ylmethylene]-4-oxo-4,5-dihydro-thiazol-2-yl}-[1,4]diazepan-1-yl)-2-oxo-ethyl]-carbamic acid tert-butyl ester following General Procedure I.

$^1$H NMR (400 MHz, CD$_3$OD) δ 8.25-8.22 (m, 1H), 8.18-8.09 (m, 1H), 7.89 (s, 1H), 7.80 (s, 1H), 7.66-7.63 (m, 1H), 7.58-7.55 (m, 1H), 7.48 (dd, 1H), 6.71-6.69 (m, 1H), 5.85 (s, 2H), 4.19-4.09 (m, 2H), 4.0-3.86 (m, 5H), 3.80-3.75 (m, 2H), 3.64-3.59 (m, 1H), 2.03-1.95 (m, 2H).

LC/MS (m/z) [M+1]$^+$ 577.2 (calculated for $C_{26}H_{24}ClF_3N_6O_2S$, 577.02).

Example 139

5-[1-(2,4-Bis-trifluoromethyl-benzyl)-1H-indazol-5-ylmethylene]-2-(3-(R)-hydroxymethyl-piperazin-1-yl)-thiazol-4-one

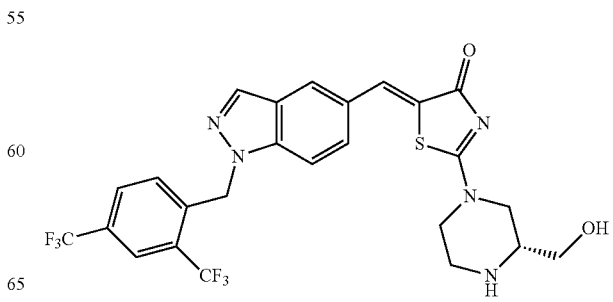

A. 4-{5-[1-(2,4-Bis-trifluoromethyl-benzyl)-1H-indazol-5-ylmethylene]-4-oxo-4,5-dihydro-thiazol-2-yl}-2-(R)-hydroxymethyl-piperazine-1-carboxylic acid tert-butyl ester was prepared from 5-[1-(2,4-Bis-trifluoromethyl-benzyl)-1H-indazol-5-ylmethylene]-2-ethylsulfanyl-thiazol-4-one and (2R)-Hydroxymethyl-piperazine-1-carboxylic acid tert-butyl ester following General Procedure C.

LC/MS: mass calcd. for $C_{30}H_{29}F_6N_5O_4S$: 669.18. found 670.3 $[M+H]^+$.

B. 5-[1-(2,4-Bis-trifluoromethyl-benzyl)-1H-indazol-5-ylmethylene]-2-(3-hydroxymethyl-piperazin-1-yl)thiazol-4-one was prepared from 4-{5-[1-(2,4-Bis-trifluoromethyl-benzyl)-1H-indazol-5-ylmethylene]-4-oxo-4,5-dihydro-thiazol-2-yl}-2-(R)-hydroxymethyl-piperazine-1-carboxylic acid tert-butyl ester following General Procedure I.

$^1$H NMR (400 MHZ, CDCl3): δ 8.22 (dd, 1H), 7.99 (br, 2H), 7.94 (s, 1H), 7.63 (d, 1H), 7.56 (m, 1H), 7.32 (d, 1H), 6.82 (d, 1H), 5.88 (s, 2H), 4.77 (m, 1H), 3.78-3.72 (2H), 3.70-3.55 (1H), 3.53-3.15 (3H), 3.05-2.92 (2H), 2.01 (br, 1H).

LC/MS: mass calcd. for $C_{25}H_{21}F_6N_5O_2S$: 569.13. found 570.5 $[M+H]^+$.

Example 140

5-[1-(2,4-Bis-trifluoromethyl-benzyl)-1H-indazol-5-ylmethylene]-2-((2S)-hydroxymethyl-morpholin-4-yl)-thiazol-4-one

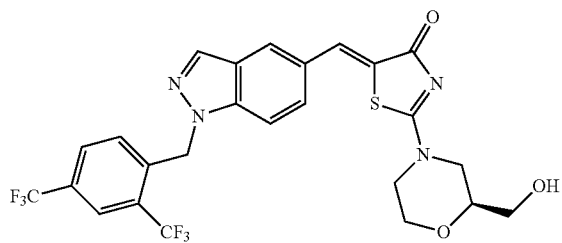 [SMILES: O=C1N=C(N2CCO[C@H](CO)C2)S/C1=C\c1ccc2c(cnn2Cc2ccc(C(F)(F)F)cc2C(F)(F)F)c1]

5-[1-(2,4-Bis-trifluoromethyl-benzyl)-1H-indazol-5-ylmethylene]-2-((2S)-hydroxymethyl-morpholin-4-yl)-thiazol-4-one was prepared from 5-[1-(2,4-Bis-trifluoromethyl-benzyl)-1H-indazol-5-ylmethylene]-2-ethylsulfanyl-thiazol-4-one and (2S)-Morpholin-2-yl-methanol following General Procedure C.

$^1$H NMR (400 MHZ, CDCl$_3$): δ 8.22 (d, 1H), 7.99 (br, 2H), 7.96 (s, 1H), 7.63 (d, 1H), 7.55 (m, 1H), 7.32 (d, 1H), 6.82 (d, 1H), 5.89 (s, 2H), 4.81 (m, 1H), 4.11 (m, 1H), 3.84-3.25 (9H).

LC/MS: mass calcd. for $C_{25}H_{20}F_6N_4O_3S$: 570.12. found 571.4 $[M+H]^+$.

Example 141

5-[1-(2,4-Bis-trifluoromethyl-benzyl)-1H-indazol-5-ylmethylene]-2-(3(R)-hydroxymethyl-morpholin-4-yl)-thiazol-4-one

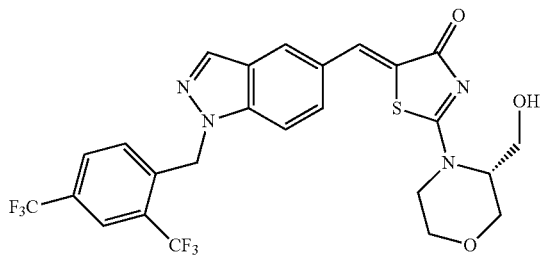 [SMILES: O=C1N=C(N2CCOC[C@H]2CO)S/C1=C\c1ccc2c(cnn2Cc2ccc(C(F)(F)F)cc2C(F)(F)F)c1]

5-[1-(2,4-Bis-trifluoromethyl-benzyl)-1H-indazol-5-ylmethylene]-2-((2S)-hydroxymethyl-morpholin-4-yl)-thiazol-4-one was prepared from 5-[1-(2,4-Bis-trifluoromethyl-benzyl)-1H-indazol-5-ylmethylene]-2-ethylsulfanyl-thiazol-4-one and (3R)-Morpholin-3-yl-methanol following General Procedure C.

$^1$H NMR (400 MHZ, CDCl$_3$): δ 8.21-8.20 (1H), 7.98-7.96 (2H), 7.96-7.92 (1H), 7.65-7.60 (1H), 7.56-7.51 (1H), 7.33-7.30 (1H), 6.82, (m, 1H), 5.88-5.86 (2H), 4.92-4.70 (1H), 4.16-3.97 (4H), 3.86-3.50 (4H), 2.42-2.14 (1H).

LC/MS: mass calcd. for $C_{25}H_{20}F_6N_4O_3S$: 570.12. found 571.4 $[M+H]^+$.

Example 142

5-[1-(4-Chloro-2-trifluoromethyl-benzyl)-1H-indazol-5-ylmethylene]-2-(3(R)-hydroxymethyl-morpholin-4-yl)-thiazol-4-one

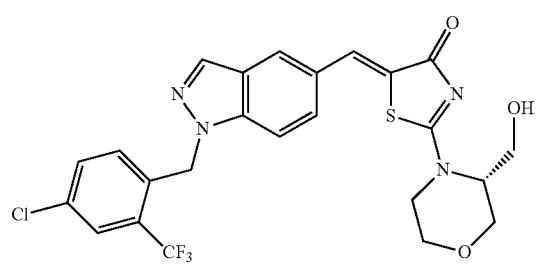 [SMILES: O=C1N=C(N2CCOC[C@H]2CO)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-(3(R)-hydroxymethyl-morpholin-4-yl)-thiazol-4-one was prepared from 5-[1-(4-Chloro-2-trifluoromethyl-benzyl)-1H-indazol-5-ylmethylene]-2-ethylsulfanyl-thiazol-4-one and (3R)-Morpholin-3-yl-methanol following General Procedure C.

$^1$H NMR (400 MHZ, CDCl$_3$): δ 8.19 (s, 1H), 7.97 (d, 1H), 7.95 (d, 1H), 7.71 (d, 1H), 7.53 (m, 1H), 7.36-7.28 (2H), 6.66 (m, 1H), 5.79 (d, 2H), 4.92-3.49 (9H).

LC/MS: mass calcd. for $C_{24}H_{20}ClF_3N_4O_3S$: 536.09. found 537.5 $[M+H]^+$.

Example 143

5-({1-[2,4-Bis(trifluoromethyl)benzyl]-1H-indazol-5-yl}methylidene)-2-[2(S)-(tert-butoxymethyl)morpholin-4-yl]-1,3-thiazol-4(5H)-one

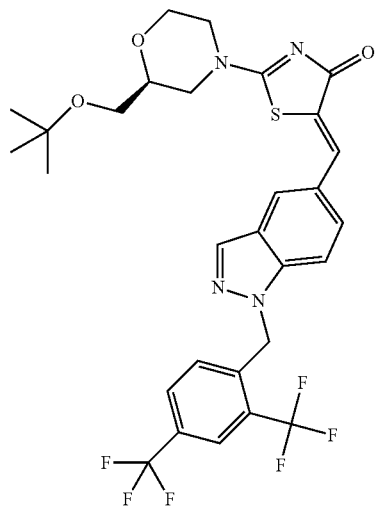 [SMILES: CC(C)(C)OC[C@@H]1CN(C2=NC(=O)/C(=C/c3ccc4c(cnn4Cc4ccc(C(F)(F)F)cc4C(F)(F)F)c3)S2)CCO1]

5-({1-[2,4-Bis(trifluoromethyl)benzyl]-1H-indazol-5-yl}methylidene)-2-[2(S)-(tert-butoxymethyl)morpholin-4-yl]-1,3-thiazol-4(5H)-one was obtained as a side-product during the synthesis of 5-[1-(2,4-Bis-trifluoromethyl-benzyl)-1H-indazol-5-ylmethylene]-2-((2S)-hydroxymethyl-morpholin-4-yl)-thiazol-4-one (see example 140).

$^1$H NMR (400 MHz, CDCl$_3$) δ 8.22 (d, 1H), 8.00-7.95 (m, 3H), 7.63 (d, 1H), 7.56 (m, 1H), 7.33 (m, 1H), 6.82 (d, 1H), 5.89 (s, 2H), 4.87-4.74 (m, 1H), 4.16-3.24 (m, 9H), 1.22 (d, 9H).

LC/MS (m/z) [M+1]$^+$ 627.0 (calculated for C$_{29}$H$_{28}$F$_6$N$_4$O$_3$S, 626.2).

Example 144

5-{5-[1-(4-Chloro-2-trifluoromethyl-benzyl)-1H-indazol-5-ylmethylene]-4-oxo-4,5-dihydro-thiazol-2-yl}-hexahydro-furo[3,4-c]pyrrol-1-one

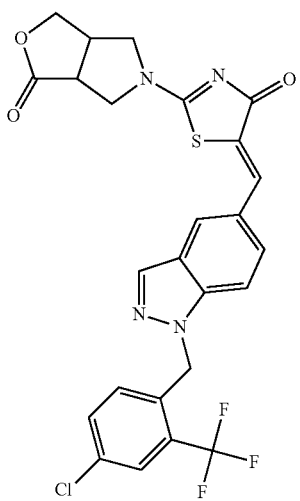 [SMILES: O=C1N=C(N2CC3COC(=O)C3C2)S/C1=C\c1ccc2c(cnn2Cc2ccc(Cl)cc2C(F)(F)F)c1]

5-{5-[1-(4-Chloro-2-trifluoromethyl-benzyl)-1H-indazol-5-ylmethylene]-4-oxo-4,5-dihydro-thiazol-2-yl}-hexahydro-furo[3,4-c]pyrrol-1-one was prepared from 5-[1-(4-Chloro-2-trifluoromethyl-benzyl)-1H-indazol-5-ylmethylene]-2-propylsulfanyl-thiazol-4-one and hexahydro-furo[3,4-c]pyrrol-1-one following General Procedure B.

$^1$H NMR (400 MHz, DMSO) δ 8.34 (s, 1H), 8.14-8.12 (m, 1H), 7.88 (d, 1H), 7.80-7.76 (m, 2H), 7.7-7.64 (m, 2H), 6.76 (d, 1H), 5.86 (s, 2H), 4.5-4.45 (m, 1H), 4.37-4.33 (m, 1H), 4.19-4.14 (m, 0.5H), 4.1-3.98 (m, 2H), 3.91-3.88 (m, 0.5H), 3.7-3.59 (m, 2H), 3.51-3.41 (m, 1H).

LC/MS (m/z) [M+1]$^+$ 547.2 (calculated for C$_{25}$H$_{18}$ClF$_3$N$_4$O$_3$S, 546.07).

Example 145

(1-{5-[1-(4-Chloro-2-trifluoromethyl-benzyl)-1H-indazol-5-ylmethylene]-4-oxo-4,5-dihydro-thiazol-2-yl}-pyrrolidin-3-yl)-acetic acid

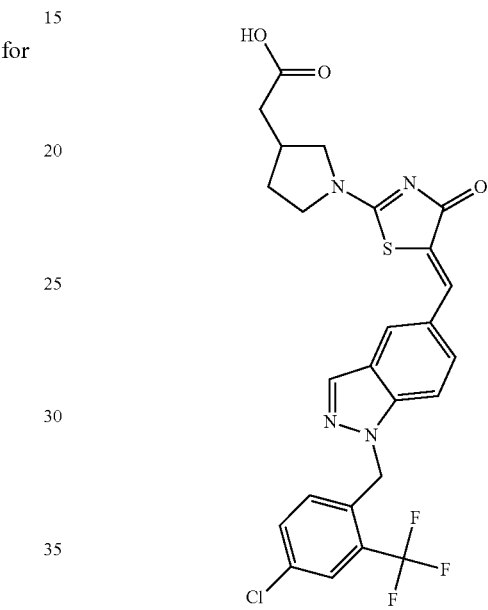

(1-{5-[1-(4-Chloro-2-trifluoromethyl-benzyl)-1H-indazol-5-ylmethylene]-4-oxo-4,5-dihydro-thiazol-2-yl}-pyrrolidin-3-yl)-acetic acid was prepared from 5-[1-(4-Chloro-2-trifluoromethyl-benzyl)-1H-indazol-5-ylmethylene]-2-propylsulfanyl-thiazol-4-one and pyrrolidin-3-yl-acetic acid following General Procedure B.

$^1$H NMR (400 MHz, DMSO) δ 8.35 (d, 1H), 8.12 (d, 1H), 7.89 (d, 1H), 7.72-7.82 (m, 2H), 7.61-7.72 (m, 2H), 6.75 (d, 1H), 5.86 (s, 2H), 3.98 (dd, 0.5H), 3.89-3.85 (m, 1H), 3.77-3.71 (m, 0.5H), 3.69-3.62 (m, 1H), 3.39-3.33 (m, 1H), 2.66 (td, 1H), 2.48-2.45 (m, 1H), 2.25-2.16 (m, 1H), 1.84-1.65 (m, 1H).

LC/MS (m/z) [M+1]$^+$ 549.2 (calculated for C$_{25}$H$_{20}$ClF$_3$N$_4$O$_3$S, 548.09).

Example 146

5-[1-(4-Chloro-2-trifluoromethyl-benzyl)-1H-indazol-5-ylmethylene]-2-(1,1-dioxidothiomorpholin-4-yl)-thiazol-4-one

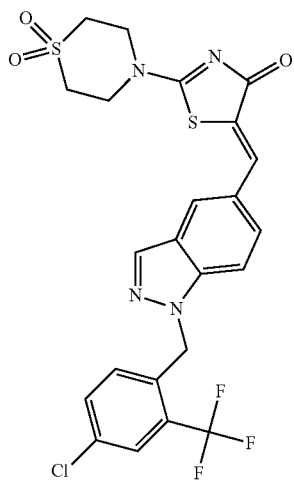 [SMILES: O=C1N=C(N2CCS(=O)(=O)CC2)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-(1,1-dioxidothiomorpholin-4-yl)-thiazol-4-one was prepared from 5-[1-(4-Chloro-2-trifluoromethyl-benzyl)-1H-indazol-5-ylmethylene]-2-propylsulfanyl-thiazol-4-one and thiomorpholine 1,1-dioxide following General Procedure B.

$^1$H NMR (400 MHz, DMSO) δ 8.33 (d, 1H), 8.16 (d, 1H), 7.89 (d, 1H), 7.86 (s, 1H), 7.80-7.77 (m, 1H), 7.71 (dd, 1H), 7.66 (dd, 1H), 6.78 (d, 1H), 5.87 (s, 2H), 4.34-4.31 (m, 2H), 4.09-4.07 (m, 2H), 3.47-3.45 (m, 2H), 3.42-3.39 (m, 2H).

LC/MS (m/z) [M+1]$^+$ 555.2 (calculated for $C_{23}H_{18}ClF_3N_4O_3S_2$, 554.05).

Example 147

5-[1-(4-Chloro-2-trifluoromethyl-benzyl)-1H-indazol-5-ylmethylene]-2-[4-(3,5-dimethyl-[1,2,4]triazol-4-yl)-piperidin-1-yl]-thiazol-4-one

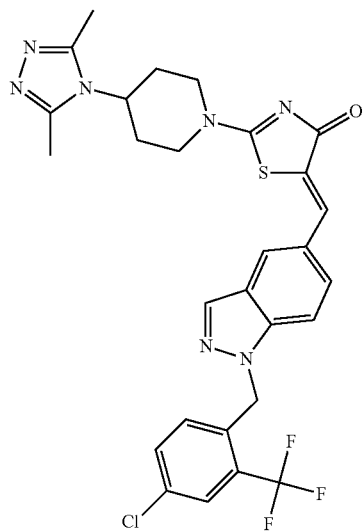 [SMILES: Cc1nnc(C)n1C1CCN(C2=NC(=O)/C(=C/c3ccc4c(cnn4Cc4ccc(Cl)cc4C(F)(F)F)c3)S2)CC1]

5-[1-(4-Chloro-2-trifluoromethyl-benzyl)-1H-indazol-5-ylmethylene]-2-[4-(3,5-dimethyl-[1,2,4]triazol-4-yl)-piperidin-1-yl]-thiazol-4-one was prepared from 5-[1-(4-Chloro-2-trifluoromethyl-benzyl)-1H-indazol-5-ylmethylene]-2-propylsulfanyl-thiazol-4-one and 4-(3,5-Dimethyl-[1,2,4]triazol-4-yl)piperidine following General Procedure B.

$^1$H NMR (400 MHz, DMSO) δ 8.32 (d, 1H), 8.15 (d, 1H), 7.89 (d, 1H), 7.81 (s, 1H), 7.78-7.76 (m, 1H), 7.71 (dd, 1H), 7.66 (dd, 1H), 6.77 (d, 1H), 5.87 (s, 2H), 4.81-4.77 (m, 1H), 4.48-4.42 (m, 1H), 4.01-3.98 (m, 1H), 3.70-3.64 (m, 1H), 3.42-3.12 (m, 1H), 2.4 (s, 6H).

LC/MS (m/z) [M+1]$^+$ 600.2 (calculated for $C_{28}H_{25}ClF_3N_7OS$, 599.15).

Example 148

5-[1-(4-Chloro-2-trifluoromethyl-benzyl)-1H-indazol-5-ylmethylene]-2-thiomorpholin-4-yl-thiazol-4-one

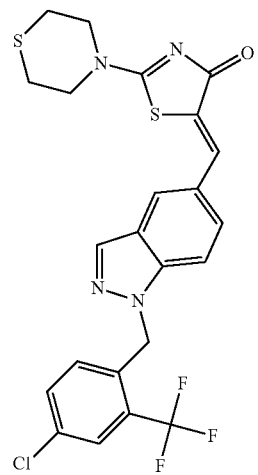 [SMILES: O=C1N=C(N2CCSCC2)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-thiomorpholin-4-yl-thiazol-4-one was prepared from 5-[1-(4-Chloro-2-trifluoromethyl-benzyl)-1H-indazol-5-ylmethylene]-2-propylsulfanyl-thiazol-4-one and thiomorpholine following General Procedure B.

$^1$H NMR (400 MHz, DMSO) δ 8.33 (d, 1H), 8.14 (d, 1H), 7.89 (d, 1H), 7.81 (s, 1H), 7.78-7.75 (m, 1H), 7.69 (dd, 1H), 7.66 (dd, 1H), 6.77 (d, 1H), 5.86 (s, 2H), 4.20-4.18 (m, 2H), 3.95-3.92 (m, 2H), 2.84-2.82 (m, 2H), 2.79-2.77 (m, 2H).

LC/MS (m/z) [M+1]$^+$ 523.2 (calculated for $C_{23}H_{18}ClF_3N_4OS_2$, 522.06).

Example 149

5-[1-(4-Chloro-2-trifluoromethyl-benzyl)-1H-indazol-5-ylmethylene]-2-(3-fluoro-azetidin-1-yl)-thiazol-4-one

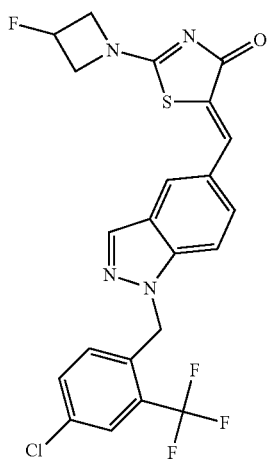 [SMILES: O=C1N=C(N2CC(F)C2)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-(3-fluoro-azetidin-1-yl)-thiazol-4-one was prepared from 5-[1-(4-Chloro-2-trifluoromethyl-benzyl)-1H-indazol-5-ylmethylene]-2-methylsulfanyl-thiazol-4-one and 3-fluoro-azetidine following General Procedure B.

$^1$H NMR (400 MHz, DMSO) δ 8.34 (d, 1H), 8.11 (d, 1H), 7.89 (d, 1H), 7.80 (s, 1H), 7.78-7.76 (m, 1H), 7.68-7.64 (m, 2H), 6.75 (d, 1H), 5.86 (s, 2H), 5.70-5.67 (m, 0.5H), 5.56-5.53 (m, 0.5H), 4.72-4.62 (m, 2H), 4.54-4.39 (m, 2H).

LC/MS (m/z) [M+1]$^+$ 495.2 (calculated for $C_{22}H_{15}ClF_4N_4OS$, 494.06).

Example 150

5-[1-(4-Chloro-2-trifluoromethyl-benzyl)-1H-indazol-5-ylmethylene]-2-(4-tetrazol-1-yl-piperidin-1-yl)-thiazol-4-one

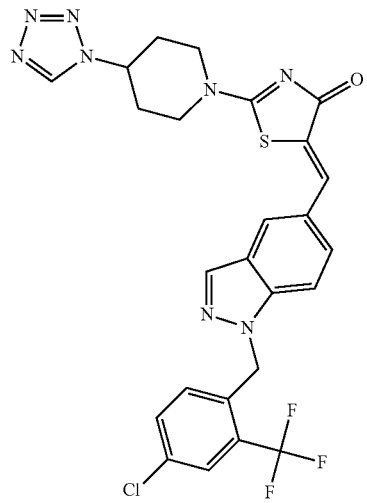 [SMILES: O=C1N=C(N2CCC(n3cnnn3)CC2)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-(4-tetrazol-1-yl-piperidin-1-yl)-thiazol-4-one was prepared from 5-[1-(4-Chloro-2-trifluoromethyl-benzyl)-1H-indazol-5-ylmethylene]-2-propylsulfanyl-thiazol-4-one and 4-tetrazol-1-yl-piperidine following General Procedure B.

$^1$H NMR (400 MHz, DMSO) δ 9.03 (s, 1H), 8.33 (d, 1H), 8.15 (s, 1H), 7.89 (d, 1H), 7.82 (s, 1H), 7.79-7.77 (m, 1H), 7.70 (dd, 2H), 7.66 (dd, 1H), 6.76 (d, 1H), 5.87 (s, 2H), 5.38-5.33 (m, 1H), 4.63-4.59 (m, 1H), 4.01-3.98 (m, 1H), 3.80-3.74 (m, 1H), 3.70-3.63 (m, 1H), 2.48-2.40 (m, 2H), 2.25-2.15 (m, 2H).

LC/MS (m/z) [M+1]$^+$ 572.9 (calculated for $C_{25}H_{20}ClF_3N_8OS$, 572.11).

Example 151

5-[1-(2,4-Bis-trifluoromethyl-benzyl)-1H-indazol-5-ylmethylene]-2-(6-hydroxy-[1,4]diazepan-1-yl)thiazol-4-one

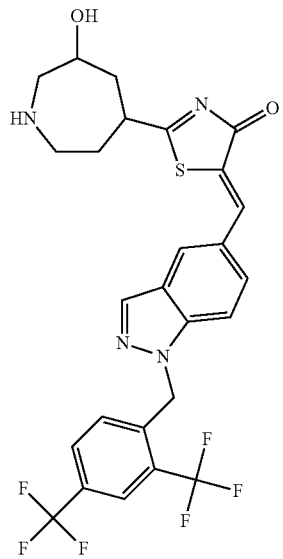

5-[1-(2,4-Bis-trifluoromethyl-benzyl)-1H-indazol-5-ylmethylene]-2-(6-hydroxy-[1,4]diazepan-1-yl)-thiazol-4-one was prepared from 5-[1-(2,4-Bis-trifluoromethyl-benzyl)-1H-indazol-5-ylmethylene]-2-ethylsulfanyl-thiazol-4-one and [1,4]Diazepan-6-ol following General Procedure B.

$^1$H NMR (400 MHz, CDCl$_3$) δ 8.21 (d, 1H), 7.98 (br s, 2H), 7.93 (d, 1H), 7.62 (d, 1H), 7.55 (dd, 1H), 7.31 (dd, 1H), 6.81 (t, 1H), 5.88 (s, 2H), 4.28-4.07 (m, 2.5H), 3.94-3.77 (m, 1.5H), 3.70-3.64 (m, 1H), 3.36-3.29 (m. 0.5H), 3.21-2.86 (m, 3.5H).

LC/MS (m/z) [M+1]+ 570.2 (calculated for C25H21F6N5O2S, 569.13).

Example 152

3-[(1-{5-[1-(4-Chloro-2-trifluoromethyl-benzyl)-1H-indazol-5-ylmethylene]-4-oxo-4,5-dihydro-thiazol-2-yl}-azetidine-3-carbonyl)-amino]-propionic acid methyl ester

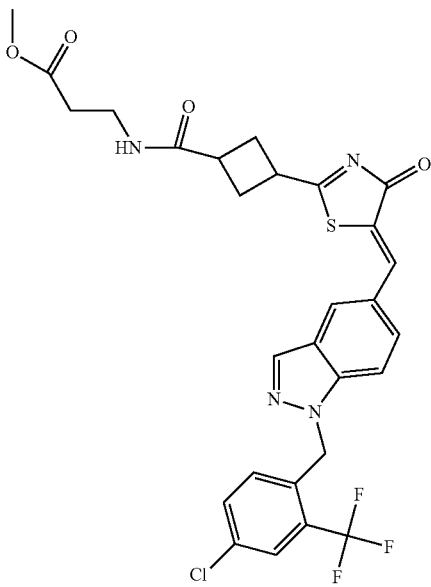

A. 3-(2-Methoxycarbonyl-ethylcarbamoyl)-azetidine-1-carboxylic acid tert-butyl ester A solution of azetidine-1,3-dicarboxylic acid mono-tert-butyl ester (0.4 g, 1.98 mmol) and 3-amino-propionic acid methyl ester hydrochloride (0.277 g, 1.98 mmol) in dichloromethane (16 mL) and THF (6 mL) was treated with diisopropylethylamine (0.256 g, 1.98 mmol); it was then added EDCI (0.42 g, 2.18 mmol) and dimethylaminopyridine (0.073 g, 0.59 mmol). The reaction mixture was stirred at room temperature for 50 hours and rotavapored to dryness. The residue was dissolved in dichloromethane. The dichloromethane layer was then successively washed with aqueous 5% citric acid, aqueous saturated hydrogenocarbonate solution, brine, dried over Na2SO4, filtered, and the solvent evaporated in vacuo to yield the title compound as a gum (551 mg, 97%).

$^1$H NMR (400 MHz, CDCl3) δ 6.16 (br s, 1H), 4.10-4.01 (m, 4H), 3.71 (s, 3H), 3.55 (q, 2H), 3.18-3.11 (m, 1H), 2.56 (t, 2H), 1.43 (s, 9H).

LC/MS (m/z) [MNa]+ 309.3 (calculated for C13H22N2O5, 286.15).

B. 3-[(Azetidine-3-carbonyl)-amino]-propionic acid methyl ester hydrochloride

A solution of 3-(2-Methoxycarbonyl-ethylcarbamoyl)-azetidine-1-carboxylic acid tert-butyl ester (0.55 g, 1.92 mmol) in MeOH (4 mL) and THF (2 mL) was treated with 4.0N HCl in 1,4-dioxane (4 mL) and stirred at 0° C. for 30 minutes and at room temperature for 5 hours. The solvent was removed in vacuo to yield the title compound as a gum (100%).

$^1$H NMR (400 MHz, D2O) δ 4.05-4.03 (m, 4H), 3.51 (s, 3H), 3.45-3.43 (m, 1H), 3.29 (t, 2H), 2.46 (t, 2H).

LC/MS (m/z) [M+1]+ 187.2 (calculated for C8H14N2O3, 186.10).

C. 3-{[1-(4-Oxo-4,5-dihydro-thiazol-2-yl)-azetidine-3-carbonyl]-amino}-propionic acid methyl ester was prepared from 3-[(Azetidine-3-carbonyl)-amino]-propionic acid methyl ester and 2-Methylsulfanyl-thiazol-4-one following General Procedure D.

$^1$H NMR (400 MHz, CDCl3) δ 6.55 (br s, 1H), 4.51-4.42 (m, 3H), 4.25 (t, 1H), 3.96 (s, 2H), 3.71 (s, 3H), 3.67-3.64 (m, 1H), 3.59-3.54 (m, 1H), 3.53-3.45 (m, 1H), 2.58 (t, 2H).

LC/MS (m/z) [M+1]+ 286.1 (calculated for C11H15N3O4S, 285.08).

D. 3-[(1-{5-[1-(4-Chloro-2-trifluoromethyl-benzyl)-1H-indazol-5-ylmethylene]-4-oxo-4,5-dihydro-thiazol-2-yl}-azetidine-3-carbonyl)-amino]-propionic acid methyl ester was prepared from 3-{[1-(4-oxo-4,5-dihydro-thiazol-2-yl)-azetidine-3-carbonyl]-amino}-propionic acid methyl ester and 1-(4-Chloro-2-trifluoromethyl-benzyl)-1H-indazole-5-carbaldehyde following General Procedure D.

$^1$H NMR (400 MHz, CDCl3) δ 8.21 (d, 1H), 7.93 (br s, 1H), 7.93 (d, 1H), 7.84 (s, 1H), 7.50 (dd, 1H), 7.34-7.31 (m, 2H), 6.64 (d, 1H), 6.34 (br s, 1H), 5.79 (s, 2H), 4.21-4.16 (m, 1H), 3.93-3.88 (m, 1H), 3.79-3.73 (m, 2H), 3.72 (s, 3H), 3.60-3.52 (m, 2H), 2.66-2.60 (m, 1H), 2.57 (t, 2H).

LC/MS (m/z) [M+1]+ 606.2 (calculated for C27H23ClF3N5O4S, 605.11).

Example 153

3-[(1-{5-[1-(2,4-Bis-trifluoromethyl-benzyl)-1H-indazol-5-ylmethylene]-4-oxo-4,5-dihydro-thiazol-2-yl}-azetidine-3-carbonyl)-amino]-propionic acid methyl ester

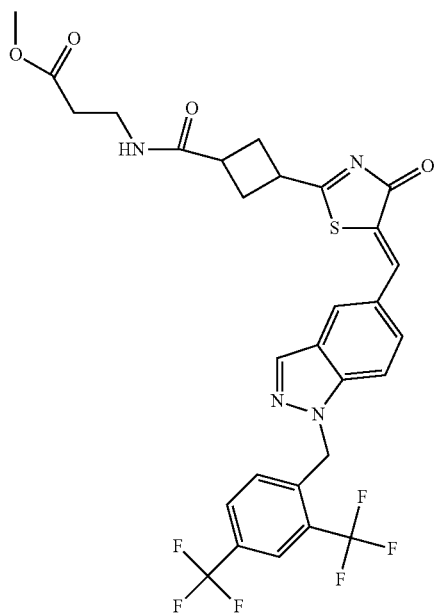

3-[(1-{5-[1-(2,4-Bis-trifluoromethyl-benzyl)-1H-indazol-5-ylmethylene]-4-oxo-4,5-dihydro-thiazol-2-yl}-azetidine-3-carbonyl)-amino]-propionic acid methyl ester was prepared from 3-{[1-(4-oxo-4,5-dihydro-thiazol-2-yl)- azetidine-3-carbonyl]-amino}-propionic acid methyl ester and 1-(2,4-Bis-trifluoromethyl-benzyl)-1H-indazole-5-carbaldehyde following General Procedure D.

$^1$H NMR (400 MHz, CDCl$_3$) δ 8.23 (d, 1H), 7.93 (s, 1H), 7.94 (d, 1H), 7.85 (s, 1H), 7.62 (d, 1H), 7.51 (dd, 1H), 7.34 (d, 1H), 6.79 (d, 1H), 6.35 (br s, 1H), 5.89 (s, 2H), 4.21-4.17 (m, 1H), 3.94-3.88 (m, 1H), 3.79-3.73 (m, 2H), 3.72 (s, 3H), 3.60-3.53 (m, 2H), 2.66-2.60 (m, 1H), 2.57 (t, 2H).

LC/MS (m/z) [M+1]$^+$ 640.2 (calculated for C$_{28}$H$_{23}$F$_6$N$_5$O$_4$S, 639.14).

Example 154

4-Amino-1-{5-[1-(4-chloro-2-trifluoromethyl-benzyl)-1H-indazol-5-ylmethylene]-4-oxo-4,5-dihydro-thiazol-2-yl}-piperidine-4-carboxylic acid

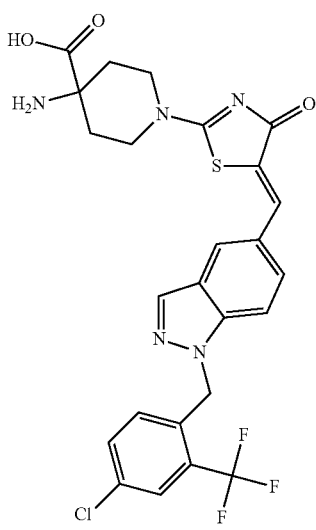 [SMILES: NC1(C(=O)O)CCN(C2=NC(=O)/C(=C/c3ccc4c(cnn4Cc4ccc(Cl)cc4C(F)(F)F)c3)S2)CC1]

4-Amino-1-{5-[1-(4-chloro-2-trifluoromethyl-benzyl)-1H-indazol-5-ylmethylene]-4-oxo-4,5-dihydro-thiazol-2-yl}-piperidine-4-carboxylic acid was prepared from 5-[1-(4-Chloro-2-trifluoromethyl-benzyl)-1H-indazol-5-ylmethylene]-2-propylsulfanyl-thiazol-4-one and 4-aminopiperidine-4-carboxylic acid following General Procedure B.

$^1$H NMR (400 MHz, DMSO) δ 8.30 (d, 1H), 8.13 (s, 1H), 7.87 (d, 1H), 7.80 (s, 1H), 7.76 (d, 1H), 7.69 (dd, 1H), 7.64 (dd, 1H), 6.75 (d, 1H), 5.85 (s, 2H), 4.29-4.24 (m. 0.5H), 3.99-3.89 (m, 1H), 3.84-3.81 (m, 0.5H), 3.23-3.20 (m, 2H), 2.26-2.20 (m, 2H), 1.99-1.96 (m, 2H).

LC/MS (m/z) [M+1]$^+$ 564.2 (calculated for C$_{25}$H$_{21}$ClF$_3$N$_5$O$_3$S, 563.1).

Example 155

N-(1-{5-[1-(4-Chloro-2-trifluoromethyl-benzyl)-1H-indazol-5-ylmethylene]-4-oxo-4,5-dihydro-thiazol-2-yl}-piperidin-4-yl)-N-methyl-acetamide

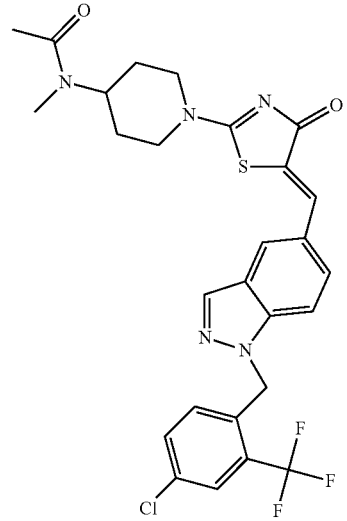 [SMILES: CC(=O)N(C)C1CCN(C2=NC(=O)/C(=C/c3ccc4c(cnn4Cc4ccc(Cl)cc4C(F)(F)F)c3)S2)CC1]

N-(1-{5-[1-(4-Chloro-2-trifluoromethyl-benzyl)-1H-indazol-5-ylmethylene]-4-oxo-4,5-dihydro-thiazol-2-yl}-piperidin-4-yl)-N-methyl-acetamide was prepared from 5-[1-(4-Chloro-2-trifluoromethyl-benzyl)-1H-indazol-5-ylmethylene]-2-propylsulfanyl-thiazol-4-one and N-Methyl-N-piperidin-4-yl-acetamide following General Procedure B.

$^1$H NMR (400 MHz, DMSO) δ 8.18 (d, 1H), 7.97 (d, 1H), 7.93 (s, 1H), 7.71 (d, 1H), 7.54 (dd, 1H), 7.34-7.30 (m, 2H), 6.66 (d, 1H), 5.79 (s, 2H), 5.11-5.06 (m, 1H), 4.89-4.83 (m, 1H), 3.96-3.92 (m, 1H), 3.50 (td, 1H), 2.87 (s, 3H), 2.12 (s, 3H), 1.90-1.72 (m, 4H).

LC/MS (m/z) [M+1]$^+$ 576.2 (calculated for C$_{27}$H$_{25}$ClF$_3$N$_5$O$_2$S, 575.14).

Example 156

4-Amino-1-{5-[1-(4-chloro-2-trifluoromethyl-benzyl)-1H-indazol-5-ylmethylene]-4-oxo-4,5-dihydro-thiazol-2-yl}-piperidine-4-carboxylic acid ethyl ester

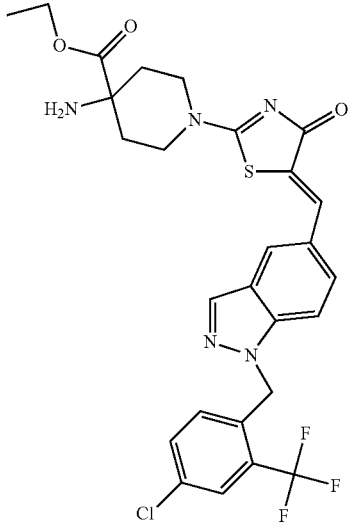 [SMILES: CCOC(=O)C1(N)CCN(C2=NC(=O)/C(=C/c3ccc4c(cnn4Cc4ccc(Cl)cc4C(F)(F)F)c3)S2)CC1]

4-Amino-1-{5-[1-(4-chloro-2-trifluoromethyl-benzyl)-1H-indazol-5-ylmethylene]-4-oxo-4,5-dihydro-thiazol-2-yl}-piperidine-4-carboxylic acid ethyl ester was prepared from 5-[1-(4-Chloro-2-trifluoromethyl-benzyl)-1H-indazol-5-ylmethylene]-2-propylsulfanyl-thiazol-4-one and 4-amino-piperidine-4-carboxylic acid ethyl ester following General Procedure B.

$^1$H NMR (400 MHz, DMSO) δ 8.32 (d, 1H), 8.15 (s, 1H), 7.89 (d, 1H), 7.84 (s, 1H), 7.79 (d, 1H), 7.70 (dd, 1H), 7.66 (dd, 1H), 6.78 (d, 1H), 5.87 (s, 2H), 4.29 (q, 2H), 3.91-3.68 (m, 4H), 2.38-2.26 (m, 2H), 2.06-1.94 (m, 2H), 1.29 (t, 3H).

LC/MS (m/z) [M+1]$^+$ 592.2 (calculated for $C_{27}H_{25}ClF_3N_5O_3S$, 591.13).

Example 157

5-[1-(4-Chloro-2-trifluoromethyl-benzyl)-1H-indazol-5-ylmethylene]-2-(4-pyrazol-1-yl-piperidin-1-yl)-thiazol-4-one

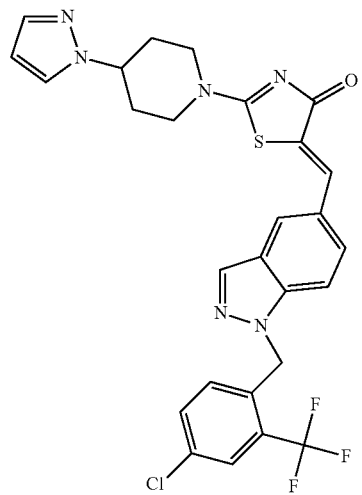 [SMILES: O=C1N=C(N2CCC(n3cccn3)CC2)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-(4-pyrazol-1-yl-piperidin-1-yl)-thiazol-4-one was prepared from 5-[1-(4-Chloro-2-trifluoromethyl-benzyl)-1H-indazol-5-ylmethylene]-2-propylsulfanyl-thiazol-4-one and 4-Pyrazol-1-yl-piperidine following General Procedure B.

$^1$H NMR (400 MHz, DMSO) δ 8.32 (d, 1H), 8.15 (t, 1H), 7.89 (d, 1H), 7.83 (d, 1H), 7.81 (s, 1H), 7.77 (d, 1H), 7.71 (dd, 1H), 7.66 (dd, 1H), 7.46 (dd, 1H), 6.77 (d, 1H), 6.26 (t, 1H), 5.87 (s, 2H), 4.71-4.60 (m, 2H), 4.0-3.96 (m, 1H), 3.68 (td, 1H), 3.49 (td, 1H), 2.25-2.16 (m, 2H), 2.08-2.00 (m, 2H).

LC/MS (m/z) [M+1]$^+$ 571.2 (calculated for $C_{27}H_{22}ClF_3N_6OS$, 570.12).

Example 158

5-[1-(4-Chloro-2-trifluoromethyl-benzyl)-1H-indazol-5-ylmethylene]-2-(4-[1,2,4]triazol-1-yl-piperidin-1-yl)-thiazol-4-one

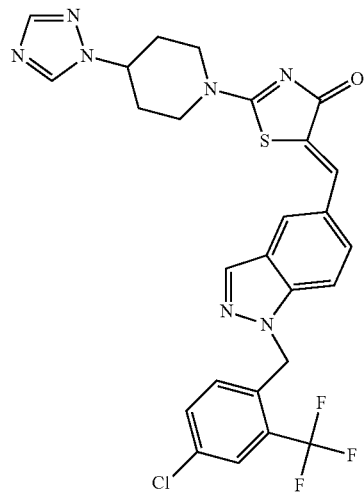 [SMILES: O=C1N=C(N2CCC(n3cncn3)CC2)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-(4-[1,2,4]triazol-1-yl-piperidin-1-yl)-thiazol-4-one was prepared from 5-[1-(4-Chloro-2-trifluoromethyl-benzyl)-1H-indazol-5-ylmethylene]-2-propylsulfanyl-thiazol-4-one and 4-[1,2,4]Triazol-1-yl-piperidine following General Procedure B.

$^1$H NMR (400 MHz, DMSO) δ 8.63 (s, 1H), 8.33 (d, 1H), 8.15 (br s, 1H), 8.0 (s, 1H), 7.89 (d, 1H), 7.81 (s, 1H), 7.77 (d, 1H), 7.70 (dd, 1H), 7.66 (dd, 1H), 6.77 (d, 1H), 5.87 (s, 2H), 4.78-4.67 (m, 2H), 4.01-3.97 (m, 1H), 3.69 (td, 1H), 3.50 (td, 1H), 2.33-2.22 (m, 2H), 2.09-2.02 (m, 2H).

LC/MS (m/z) [M+1]$^+$ 572.2 (calculated for $C_{26}H_{21}ClF_3N_7OS$, 571.12).

Example 159

5-[1-(4-Chloro-2-trifluoromethyl-benzyl)-1H-indazol-5-ylmethylene]-2-(4-imidazol-1-yl-piperidin-1-yl)-thiazol-4-one

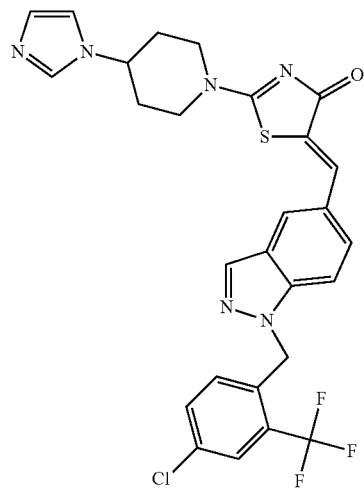 [SMILES: O=C1N=C(N2CCC(n3ccnc3)CC2)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-(4-imidazol-1-yl-piperidin-1-yl)-thiazol-4-one was prepared from 5-[1-(4-Chloro-2-trifluoromethyl-benzyl)-1H-indazol-5-ylmethylene]-2-propylsulfanyl-thiazol-4-one and 4-Imidazol-1-yl-piperidine following General Procedure B.

$^1$H NMR (400 MHz, CDCl$_3$) δ 8.16 (d, 1H), 7.97 (m, 1H), 7.96 (s, 1H), 7.71 (d, 1H), 7.62 (br s, 1H), 7.54 (dd, 1H), 7.35-7.30 (m, 2H), 7.14 (br s 1H), 7.03 (br s, 1H), 6.67 (d, 1H), 5.79 (s, 2H), 5.17-5.13 (m, 1H), 4.39-4.33 (m, 1H), 4.06-4.02 (m, 1H), 3.55 (td, 1H), 3.31 (td, 1H), 2.37-2.28 (m, 2H), 2.12-2.03 (m, 2H).

LC/MS (m/z) [M+1]$^+$ 571.2 (calculated for C$_{27}$H$_{22}$ClF$_3$N$_6$OS, 570.12).

Example 160

1-(1-{5-[1-(2,4-Bis-trifluoromethyl-benzyl)-1H-indazol-5-ylmethylene]-4-oxo-4,5-dihydro-thiazol-2-yl}-piperidin-4-yl)-3-ethyl-urea

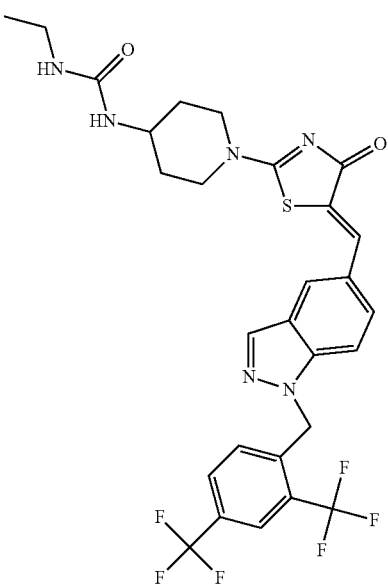 [SMILES: CCNC(=O)NC1CCN(C2=NC(=O)/C(=C/c3ccc4c(cnn4Cc4ccc(C(F)(F)F)cc4C(F)(F)F)c3)S2)CC1]

1-(1-{5-[1-(2,4-Bis-trifluoromethyl-benzyl)-1H-indazol-5-ylmethylene]-4-oxo-4,5-dihydro-thiazol-2-yl}-piperidin-4-yl)-3-ethyl-urea was prepared from 5-[1-(2,4-Bis-trifluoromethyl-benzyl)-1H-indazol-5-ylmethylene]-2-ethylsulfanyl-thiazol-4-one and 1-Ethyl-3-piperidin-4-yl-urea following General Procedure B.

$^1$H NMR (400 MHz, DMSO) δ 8.35 (d, 1H), 8.15 (d, 1H), 8.11 (s, 1H), 7.98-7.96 (m, 1H), 7.81-7.79 (m, 2H), 7.70 (dd, 1H), 6.91 (d, 1H), 5.98 (s, 2H), 5.92 (d, 1H), 5.76 (t, 1H), 4.47-4.43 (m, 1H), 3.83-3.73 (m, 2H), 3.59-3.52 (m, 1H), 3.49-3.42 (m, 1H), 3.04-2.97 (m, 2H), 1.99-1.98 m, 2H), 1.46-1.39 (m, 2H), 0.98 (t, 3H).

LC/MS (m/z) [M+1]$^+$ 625.1 (calculated for C$_{28}$H$_{26}$F$_6$N$_6$O$_2$S, 624.17).

Example 161
5-[1-(4-Chloro-2-trifluoromethyl-benzyl)-1H-indazol-5-ylmethylene]-2-(3-methylamino-azepan-1-yl)-thiazol-4-one

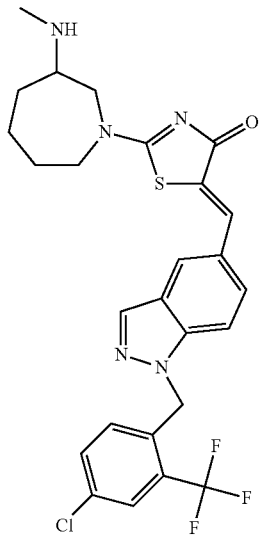 [SMILES: CNC1CCCCN(C2=NC(=O)/C(=C/c3ccc4c(cnn4Cc4ccc(Cl)cc4C(F)(F)F)c3)S2)C1]

5-[1-(4-Chloro-2-trifluoromethyl-benzyl)-1H-indazol-5-ylmethylene]-2-(3-methylamino-azepan-1-yl)-thiazol-4-one was prepared from 5-[1-(4-Chloro-2-trifluoromethyl-benzyl)-1H-indazol-5-ylmethylene]-2-propylsulfanyl-thiazol-4-one and Azepan-3-yl-methyl-amine following General Procedure B.

$^1$H NMR (400 MHz, CDCl$_3$) δ 8.20-8.17 (m, 1H), 7.98-7.89 (m, 2H), 7.71 (d, 1H), 7.56-7.51 (m, 1H), 7.34-7.27 (m, 2H), 6.65 (dd, 1H), 5.78 (d, 1H), 4.33-4.22 (m, 1H), 3.91-3.84 (m, 1H), 3.78-3.70 (m, 1H), 3.39 (dd, 0.5H), 3.12 (br s, 1H), 2.93-2.90 (m. 0.5H), 2.57 (s, 3H), 2.45 (br s, 1H), 2.04-1.92 (m, 3H), 1.68-1.48 (m, 2H).

LC/MS (m/z) [M+1]$^+$ 548.2 (calculated for C$_{26}$H$_{25}$ClF$_3$N$_5$OS, 547.14).

Example 162
5-[1-(4-Chloro-2-trifluoromethyl-benzyl)-1H-indazol-5-ylmethylene]-2-pyrrolidin-1-yl-thiazol-4-one

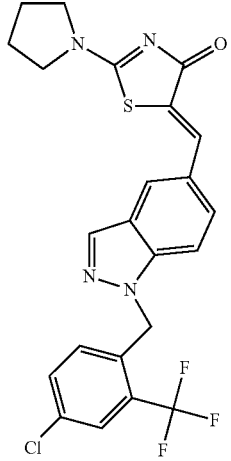 [SMILES: O=C1N=C(N2CCCC2)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-pyrrolidin-1-yl-thiazol-4-one was prepared from 5-[1-(4-Chloro-2-trifluoromethyl-benzyl)-1H-indazol-5-ylmethylene]-2-propylsulfanyl-thiazol-4-one and pyrrolidine following General Procedure B.

$^1$H NMR (400 MHz, DMSO) δ 8.34 (d, 1H), 8.12 (m, 1H), 7.89 (d, 1H), 7.78-7.76 (m, 2H), 7.69-7.64 (m, 2H), 6.75 (d, 1H), 5.86 (s, 2H), 3.72 (t, 2H), 3.65 (t, 2H), 2.04-1.99 (m, 4H).

LC/MS (m/z) [M+1]$^+$ 491.2 (calculated for C$_{23}$H$_{18}$ClF$_3$N$_4$OS, 490.08).

Example 163

5-[1-(4-Chloro-2-trifluoromethyl-benzyl)-1H-indazol-5-ylmethylene]-2-(4-dimethylaminomethyl-4-hydroxy-piperidin-1-yl)-thiazol-4-one

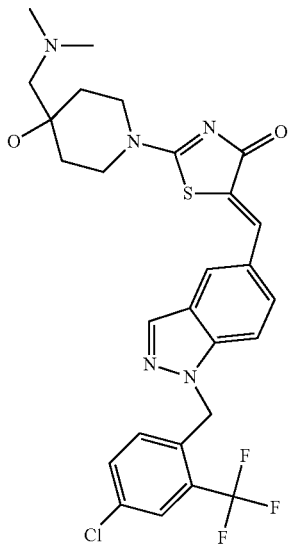 [SMILES: CN(C)CC1(O)CCN(C2=NC(=O)/C(=C/c3ccc4c(cnn4Cc4ccc(Cl)cc4C(F)(F)F)c3)S2)CC1]

5-[1-(4-Chloro-2-trifluoromethyl-benzyl)-1H-indazol-5-ylmethylene]-2-(4-dimethylaminomethyl-4-hydroxy-piperidin-1-yl)-thiazol-4-one was prepared from 5-[1-(4-Chloro-2-trifluoromethyl-benzyl)-1H-indazol-5-ylmethylene]-2-propylsulfanyl-thiazol-4-one and 4-Dimethylaminomethyl-piperidin-4-ol following General Procedure B.

$^1$H NMR (400 MHz, CD$_3$OD) δ 8.23 (d, 1H), 8.08 (s, 1H), 7.86 (s, 1H), 7.79 (d, 1H), 7.64 (dd, 1H), 7.54 (d, 1H), 7.48 (dd, 1H), 6.68 (d, 1H), 5.84 (s, 2H), 4.65-4.61 (m, 1H), 3.85-3.82 (m, 2H), 3.68-3.61 (m, 1H), 3.26 (s, 2H), 3.0 (s, 6H), 1.96-1.78 (m, 4H).

LC/MS (m/z) [M+1]$^+$ 578.2 (calculated for C$_{27}$H$_{27}$ClF$_3$N$_5$O$_2$S, 577.15).

Example 164

5-[1-(4-Chloro-2-trifluoromethyl-benzyl)-1H-indazol-5-ylmethylene]-2-(4-hydroxy-4-imidazol-1-ylmethyl-piperidin-1-yl)-thiazol-4-one

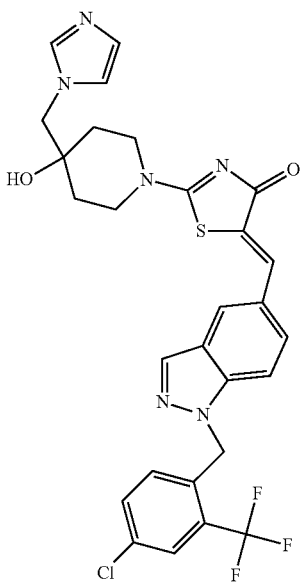 [SMILES: O=C1N=C(N2CCC(O)(Cn3ccnc3)CC2)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-(4-hydroxy-4-imidazol-1-ylmethyl-piperidin-1-yl)-thiazol-4-one was prepared from 5-[1-(4-Chloro-2-trifluoromethyl-benzyl)-1H-indazol-5-ylmethylene]-2-propylsulfanyl-thiazol-4-one and 4-Imidazol-1-ylmethyl-piperidin-4-ol following General Procedure B.

$^1$H NMR (400 MHz, DMSO) δ 8.232 (d, 1H), 8.13 (s, 1H), 7.89 (d, 1H), 7.78-7.75 (m, 2H), 7.70-7.65 (m, 2H), 7.55 (d, 1H), 7.11 (s, 1H), 6.88 (s, 1H), 6.76 (d, 1H), 5.86 (s, 2H), 4.46-4.42 (m, 1H), 3.98 (s, 2H), 3.74-3.62 (m, 2H), 3.52-3.46 (m, 1H), 1.70-1.59 (m, 2H), 1.50-1.47 (m, 2H).

LC/MS (m/z) [M+1]$^+$ 601.2 (calculated for C$_{28}$H$_{24}$ClF$_3$N$_6$O$_2$S, 600.13).

Example 165

5-[1-(4-Chloro-2-trifluoromethyl-benzyl)-1H-indazol-5-ylmethylene]-2-(3-ethyl-3-hydroxy-piperidin-1-yl)-thiazol-4-one

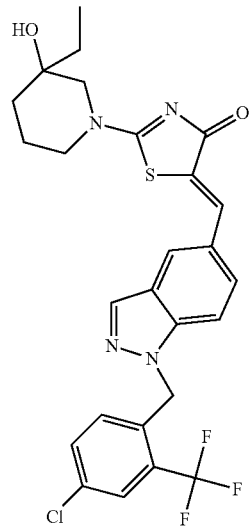 [SMILES: CCC1(O)CCCN(C2=NC(=O)/C(=C/c3ccc4c(cnn4Cc4ccc(Cl)cc4C(F)(F)F)c3)S2)C1]

5-[1-(4-Chloro-2-trifluoromethyl-benzyl)-1H-indazol-5-ylmethylene]-2-(3-ethyl-3-hydroxy-piperidin-1-yl)-thiazol-4-one was prepared from 5-[1-(4-Chloro-2-trifluoromethyl-benzyl)-1H-indazol-5-ylmethylene]-2-propylsulfanyl-thiazol-4-one and 3-Ethyl-piperidin-3-ol following General Procedure B.

$^1$H NMR (400 MHz, DMSO) δ 8.33 (d, 1H), 8.05 (s, 1H), 7.89 (d, 1H), 7.79 (d, 1H), 7.72 (s, 1H), 7.66-7.61 (m, 2H), 6.73 (d, 1H), 5.86 (s, 2H), 4.44 (t, 1H), 3.53 (br s, 2H), 3.40-3.35 (m, 2H), 1.45-1.42 (m, 6H), 0.83 (t, 3H).

LC/MS (m/z) [M+1]$^+$ 549.1 (calculated for C$_{26}$H$_{24}$ClF$_3$N$_4$O$_2$S, 548.13).

Example 166

5-[1-(4-Chloro-2-trifluoromethyl-benzyl)-1H-indazol-5-ylmethylene]-2-(3-hydroxy-[1,4']bipiperidinyl-1'-yl)-thiazol-4-one

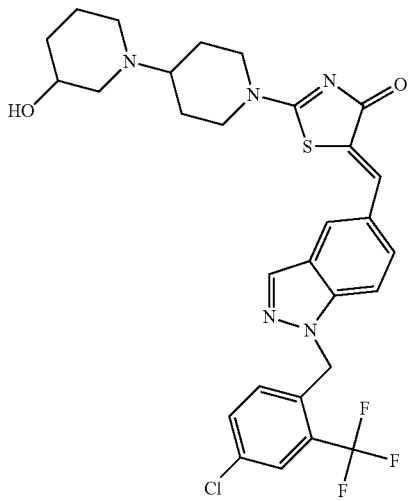 [SMILES: O=C1N=C(N2CCC(N3CCCC(O)C3)CC2)S/C1=C\c1ccc2c(cnn2Cc2ccc(Cl)cc2C(F)(F)F)c1]

5-[1-(4-Chloro-2-trifluoromethyl-benzyl)-1H-indazol-5-ylmethylene]-2-(3-hydroxy-[1,4']bipiperidinyl-1'-yl)-thiazol-4-one was prepared from 5-[1-(4-Chloro-2-trifluoromethyl-benzyl)-1H-indazol-5-ylmethylene]-2-propylsulfanyl-thiazol-4-one and [1,4']Bipiperidinyl-3-ol following General Procedure B.

$^1$H NMR (400 MHz, CD$_3$OD) δ 8.21 (s, 1H), 8.07 (s, 1H), 7.86 (s, 1H), 7.79 (d, 1H), 7.62 (dd, 1H), 7.52 (d, 1H), 7.47 (dd, 1H), 6.68 (d, 1H), 5.83 (s, 2H), 4.98-4.94 (m, 1H), 4.13-4.10 (m, 1H), 3.59-3.53 (m, 2H), 3.45-3.42 (m, 2H), 3.33-3.13 (m, 4H), 2.36-2.20 (m, 3H), 1.99-1.70 (m, 5H).

LC/MS (m/z) [M+1]$^+$ 604.2 (calculated for C$_{29}$H$_{29}$ClF$_3$N$_5$O$_2$S, 603.17).

Example 167

8-{5-[1-(4-Chloro-2-trifluoromethyl-benzyl)-1H-indazol-5-ylmethylene]-4-oxo-4,5-dihydro-thiazol-2-yl}-1,3,8-triaza-spiro[4.5]decan-4-one

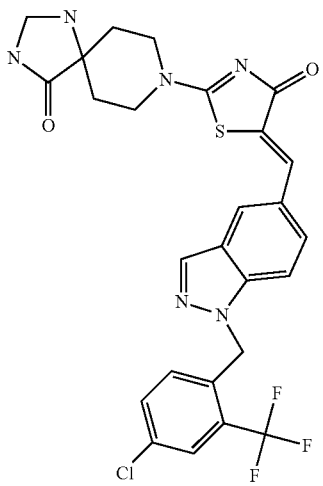 [SMILES: O=C1N=C(N2CCC3(CC2)NCNC3=O)S/C1=C\c1ccc2c(cnn2Cc2ccc(Cl)cc2C(F)(F)F)c1]

8-{5-[1-(4-Chloro-2-trifluoromethyl-benzyl)-1H-indazol-5-ylmethylene]-4-oxo-4,5-dihydro-thiazol-2-yl}-1,3,8-triaza-spiro[4.5]decan-4-one was prepared from 5-[1-(4-Chloro-2-trifluoromethyl-benzyl)-1H-indazol-5-ylmethylene]-2-propylsulfanyl-thiazol-4-one and 1,3,8-Triaza-spiro[4.5]decan-4-one following General Procedure B.

$^1$H NMR (400 MHz, CD$_3$OD) δ 8.23 (d, 1H), 8.09 (s, 1H), 7.87 (s, 1H), 7.79 (d, 1H), 7.65 (dd, 1H), 7.54 (d, 1H), 7.47 (dd, 1H), 6.68 (d, 1H), 5.84 (s, 2H), 4.61 (s, 2H), 4.40-4.35 (m, 1H), 4.14-4.04 (m, 2H), 3.89-3.82 (m, 1H), 2.28-2.17 (m, 2H), 2.09-1.97 (m, 2H).

LC/MS (m/z) [M+1]$^+$ 575.2 (calculated for C$_{26}$H$_{22}$ClF$_3$N$_6$O$_2$S, 574.12).

Example 168

5-[1-(2,4-Bis-trifluoromethyl-benzyl)-1H-indazol-5-ylmethylene]-2-[3-(2-hydroxy-ethyl)-4-methyl-piperazin-1-yl]-thiazol-4-one

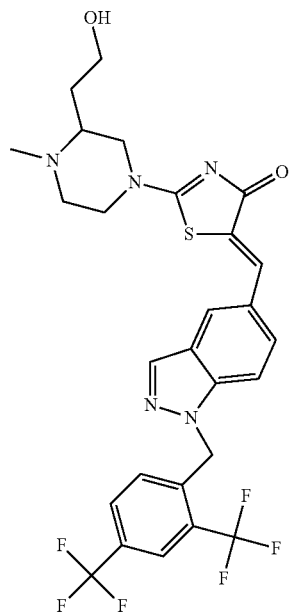 [SMILES: CN1CCN(C2=NC(=O)/C(=C/c3ccc4c(cnn4Cc4ccc(C(F)(F)F)cc4C(F)(F)F)c3)S2)CC1CCO]

5-[1-(2,4-Bis-trifluoromethyl-benzyl)-1H-indazol-5-ylmethylene]-2-[3-(2-hydroxy-ethyl)-4-methyl-piperazin-1-yl]-thiazol-4-one was prepared from 5-[1-(2,4-Bis-trifluoromethyl-benzyl)-1H-indazol-5-ylmethylene]-2-ethylsulfanyl-thiazol-4-one and 2-(1-Methyl-piperazin-2-yl)-ethanol following General Procedure B.

$^1$H NMR (400 MHz, CDCl$_3$) δ 8.22-8.21 (m, 1H), 7.98 (br s, 2H), 7.93 (s, 1H), 7.63 (d, 1H), 7.56-7.54 (m, 1H), 7.32 (d, 1H), 6.82 (d, 1H), 5.88 (s, 2H), 4.57 (d, 1H), 3.91-3.71 (m, 3H), 3.63-3.51 (m, 2H), 3.10-2.96 (m, 2H), 2.57 (br s, 1H), 2.45 (s, 3H), 1.94-1.84 (m, 2H).

LC/MS (m/z) [M+1]$^+$ 598.3 (calculated for C$_{27}$H$_{25}$F$_6$N$_5$O$_2$S, 597.16).

Example 169
5-[1-(2,4-Bis-trifluoromethyl-benzyl)-1H-indazol-5-ylmethylene]-2-(3,4-dihydro-1H-pyrrolo[1,2-a]pyrazin-2-yl)-thiazol-4-one

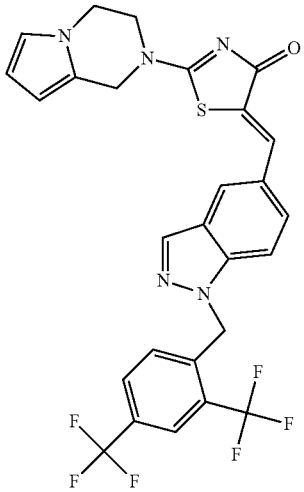 [SMILES: O=C1N=C(N2CCn3cccc3C2)S/C1=C\c1ccc2c(cnn2Cc2ccc(C(F)(F)F)cc2C(F)(F)F)c1]

5-[1-(2,4-Bis-trifluoromethyl-benzyl)-1H-indazol-5-ylmethylene]-2-(3,4-dihydro-1H-pyrrolo[1,2-a]pyrazin-2-yl)-thiazol-4-one was prepared from 5-[1-(2,4-Bis-trifluoromethyl-benzyl)-1H-indazol-5-ylmethylene]-2-ethylsulfanyl-thiazol-4-one and 1,2,3,4-Tetrahydro-pyrrolo[1,2-a]pyrazine following General Procedure B.

$^1$H NMR (400 MHz, DMSO) δ 8.37 (dd, 1H), 8.19-8.17 (m, 1H), 8.12 (s, 1H), 7.97 (d, 1H), 7.84-7.81 (m, 2H), 7.74-7.71 (m, 1H), 6.92 (dd, 1H), 6.79 (t, 1H), 6.07-6.04 (m, 1H), 5.99-5.96 (m, 3H), 5.06 (s, 1H), 4.94 (s, 1H), 4.28-4.25 (m, 1H), 4.23-4.21 (m, 1H), 4.17-4.15 (m, 1H), 4.07-4.04 (m, 1H).

LC/MS (m/z) [M+1]$^+$ 576.3 (calculated for $C_{27}H_{19}F_6N_5OS$, 575.12).

Example 170
4-{5-[1-(2,4-Bis-trifluoromethyl-benzyl)-1H-indazol-5-ylmethylene]-4-oxo-4,5-dihydro-thiazol-2-yl}-1,3-dimethyl-piperazin-2-one

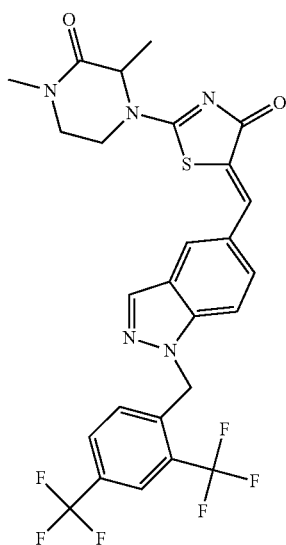 [SMILES: CC1C(=O)N(C)CCN1C1=NC(=O)/C(=C/c2ccc3c(cnn3Cc3ccc(C(F)(F)F)cc3C(F)(F)F)c2)S1]

4-{5-[1-(2,4-Bis-trifluoromethyl-benzyl)-1H-indazol-5-ylmethylene]-4-oxo-4,5-dihydro-thiazol-2-yl}-1,3-dimethyl-piperazin-2-one was prepared from 5-[1-(2,4-Bis-trifluoromethyl-benzyl)-1H-indazol-5-ylmethylene]-2-ethylsulfanyl-thiazol-4-one and 1,3-Dimethyl-piperazin-2-one following General Procedure B.

$^1$H NMR (400 MHz, CDCl$_3$) δ 8.24-8.22 (m, 1H), 7.99-7.97 (m, 3H), 7.63 (d, 1H), 7.55 (dd, 1H), 7.34 (d, 1H), 6.82 (d, 1H), 5.89 (s, 2H), 5.02-4.98 (m, 1H), 4.45 (q, 1H), 3.88-3.86 (m, 1H), 3.73-3.60 (m, 3H), 3.43-3.39 (m, 1H), 3.35-3.32 (m, 1H), 1.69 (d, 3H).

LC/MS (m/z) [M+1]$^+$ 582.3 (calculated for $C_{26}H_{21}F_6N_5O_2S$, 581.13).

Example 171
5-[1-(2,4-Bis-trifluoromethyl-benzyl)-1H-indazol-5-ylmethylene]-2-(2-dimethylaminomethyl-morpholin-4-yl)-thiazol-4-one

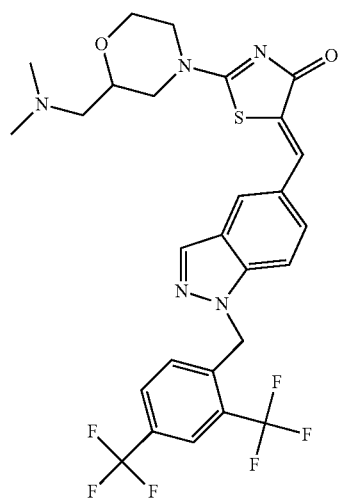 [SMILES: CN(C)CC1CN(C2=NC(=O)/C(=C/c3ccc4c(cnn4Cc4ccc(C(F)(F)F)cc4C(F)(F)F)c3)S2)CCO1]

5-[1-(2,4-Bis-trifluoromethyl-benzyl)-1H-indazol-5-ylmethylene]-2-(2-dimethylaminomethyl-morpholin-4-yl)-thiazol-4-one was prepared from 5-[1-(2,4-Bis-trifluoromethyl-benzyl)-1H-indazol-5-ylmethylene]-2-ethylsulfanyl-thiazol-4-one and Dimethyl-morpholin-2-ylmethyl-amine following General Procedure B.

$^1$H NMR (400 MHz, CDCl$_3$) δ 8.22 (dd, 1H), 7.99-7.98 (m, 2H), 7.95 (s, 1H), 7.62 (d, 1H), 7.55 (ddd, 1H), 7.32 (dd, 1H), 6.82 (d, 1H), 5.88 (s, 2H), 4.86-4.75 (m, 1H), 4.14-4.04 (m, 1H), 3.79-3.57 (m, 3H), 3.41-3.35 (m, 0.5H), 3.29-3.23 (m, 0.5H), 3.07-3.01 (m, 0.5H), 2.59-2.51 (m, 1H), 2.41 (dd, 0.5H), 2.31 (s, 3H), 2.28 (s, 3H), 2.28-2.23 (m, 1H).

LC/MS (m/z) [M+1]$^+$ 598.3 (calculated for $C_{27}H_{25}F_6N_5O_2S$, 597.16).

Example 172

5-[1-(2,4-Bis-trifluoromethyl-benzyl)-1H-indazol-5-ylmethylene]-2(R)-(2-hydroxymethyl-morpholin-4-yl)-thiazol-4-one

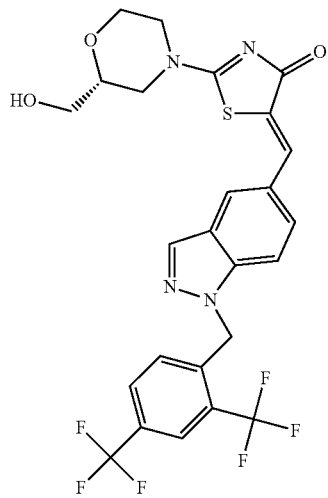 [SMILES: O=C1N=C(N2CCO[C@@H](CO)C2)S/C1=C\c1ccc2c(cnn2Cc2ccc(C(F)(F)F)cc2C(F)(F)F)c1]

A. 2-(2-Hydroxymethyl-morpholin-4-A-thiazol-4-one was prepared from 2-Methylsulfanyl-thiazol-4-one and Morpholin-2-yl-methanol following general procedure D.

$^1$H NMR (400 MHz, CDCl$_3$) δ 4.72-4.66 (m, 1H), 4.11-4.00 (m, 1H), 3.97 (s, 2H), 3.80-3.56 (m, 4H), 3.51-3.26 (m, 2H), 3.19 (dd, 1H), 1.96-1.91 (m, 1H).

LC/MS (m/z) [M+1]$^+$ 217.2 (calculated for C$_8$H$_{12}$N$_2$O$_3$S, 216.06).

B. 5-[1-(2,4-Bis-trifluoromethyl-benzyl)-1H-indazol-5-ylmethylene]-2(R)-(2-hydroxymethyl-morpholin-4-yl)-thiazol-4-one was prepared from 1-(2,4-Bis-trifluoromethyl-benzyl)-1H-indazole-5-carbaldehyde and 2(R)-(2-Hydroxymethyl-morpholin-4-yl)-thiazol-4-one following General Procedure D.

$^1$H NMR (400 MHz, CDCl$_3$) δ 8.22-8.21 (m, 1H), 7.98 (br s, 2H), 7.95 (s, 1H), 7.62 (d, 1H), 7.56-7.53 (m, 1H), 7.32 (d, 1H), 6.83 (d, 1H), 5.88 (s, 2H), 4.84-4.78 (m, 1H), 4.16-4.06 (m, 1H), 3.84-3.49 (6H), 3.41-3.25 (m, 1H), 1.99-1.93 (m, 1H).

LC/MS (m/z) [M+1]$^+$ 571.2 (calculated for C$_{25}$H$_{20}$F$_6$N$_4$O$_3$S, 570.12).

Example 173

Pyrrolidine-1-sulfonic acid (1-{5-[1-(2,4-bis-trifluoromethyl-benzyl)-1H-indazol-5-ylmethylene]-4-oxo-4,5-dihydro-thiazol-2-yl}-piperidine-4-carbonyl)-amide

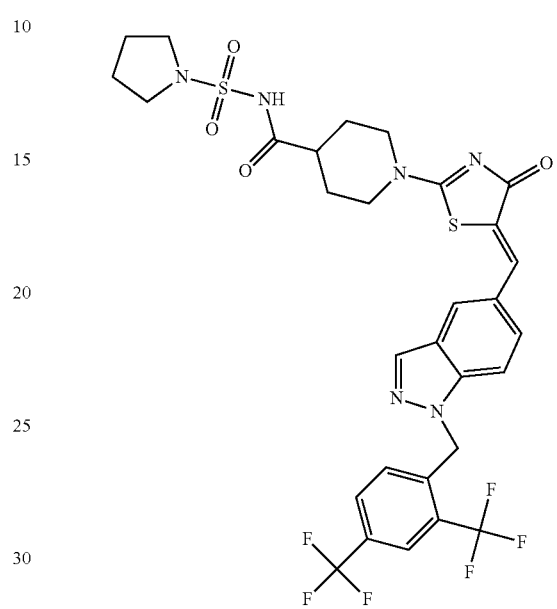

A. 1-(4-Oxo-4,5-dihydro-thiazol-2-yl)-piperidine-4-carboxylic acid

To a solution of 2-methylsulfanyl-thiazol-4-one (4.4 g, 30 mmol) in MeOH (60 mL) was added piperidine-4-carboxylic acid (3.9 g, 30 mmol). The mixture was stirred at room temperature for 16 hours. The resulting solid was collected by filtration, washed with fresh MeOH and dried to give the title compound.

$^1$H NMR (400 MHz, DMSO): 12.43 (s, 1H), 4.36 (m, 1H), 3.99 (s, 2H), 3.66 (m, 1H), 3.34 (m, 2H), 2.61 (m, 1H), 1.94 (m, 2H), 1.56 (m, 2H).

LC/MS (m/z) [M+1]$^+$ 229.1 (calculated for C$_9$H$_{12}$N$_2$O$_3$S, 228.1).

B. Pyrrolidine-1-sulfonic acid [1-(4-oxo-4,5-dihydro-thiazol-2-A-piperidine-4-carbonyl]-amide A solution of 1-(4-Oxo-4,5-dihydro-thiazol-2-yl)piperidine-4-carboxylic acid (0.075 g, 0.33 mmol) and carbonyl diimidazole (0.107 g, 0.65 mmol) in THF (3 mL) was heated under stirring at 45 to 50° C. for 3 hours. It was then added to the homogenous reaction mixture a solution of Pyrrolidine-1-sulfonic acid amide (0.099 g, 0.65 mmol) in THF (1 mL) containing Diazabicyclo[5.4.0]undec-7-ene (0.15 g, 0.98 mmol). The resulting reaction mixture was stirred at 45-50° C. for 30 minutes then at room temperature for 12 hours, diluted with dichloromethane and quenched with 10% aqueous HCl. The dichloromethane layer was then successively washed with water, brine, dried over Na$_2$SO$_4$, filtered, and the solvent evaporated in vacuo to yield the title compound as a gum (64 mg, 54%).

$^1$H NMR (400 MHz, CDCl$_3$) δ 3.99 (s, 3H), 3.53-3.42 (m, 4H), 3.37-3.30 (m, 4H), 2.72-2.66 (m, 1H), 1.96-1.81 (m, 8H).

LC/MS (m/z) [M+1]+ 361.2 (calculated for $C_{13}H_{20}H_4O_4S_2$, 360.09).

C. Pyrrolidine-1-sulfonic acid (1-{5-[1-(2,4-bis-trifluoromethyl-benzyl)-1H-indazol-5-ylmethylene]-4-oxo-4,5-dihydro-thiazol-2-yl}-piperidine-4-carbonyl)-amide was prepared from 1-(2,4-Bis-trifluoromethyl-benzyl)-1H-indazole-5-carbaldehyde and Pyrrolidine-1-sulfonic acid [1-(4-oxo-4,5-dihydro-thiazol-2-yl)-piperidine-4-carbonyl]-amide following General Procedure E.

$^1$H NMR (400 MHz, CDCl$_3$) δ 9.31 (br s, 1H), 8.19 (d, 1H), 7.98-7.96 (m, 2H), 7.93 (s, 1H), 7.62 (d, 1H), 7.53 (dd, 1H), 7.28 (d, 1H), 6.81 (d, 1H), 5.86 (s, 2H), 4.78-4.75 (m, 1H), 3.95-3.92 (m, 1H), 3.55-3.39 (m, 6H), 2.79-2.74 (m, 1H), 2.11-2.08 (m, 2H), 2.04-1.90 (m, 8H).

LC/MS (m/z) [M+1]+ 715.3 (calculated for $C_{30}H_{28}F_6N_6O_4S_2$, 714.15).

Example 174

Pyrrolidine-1-sulfonic acid (1-{5-[1-(4-chloro-2-trifluoromethyl-benzyl)-1H-indazol-5-ylmethylene]-4-oxo-4,5-dihydro-thiazol-2-yl}-piperidine-4-carbonyl)-amide

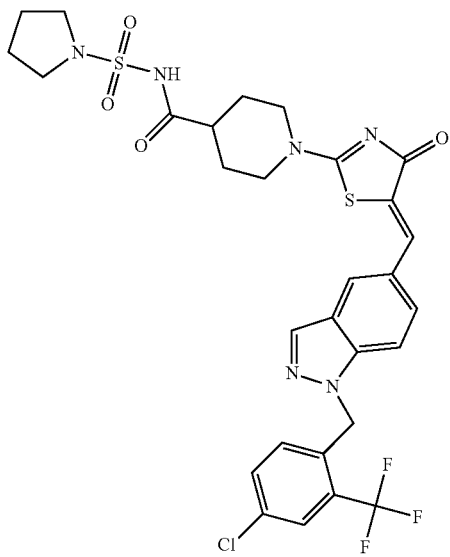 [SMILES: O=C1N=C(N2CCC(C(=O)NS(=O)(=O)N3CCCC3)CC2)S/C1=C\c1ccc2c(cnn2Cc2ccc(Cl)cc2C(F)(F)F)c1]

A. 1-(4-Oxo-4,5-dihydro-thiazol-2-yl)-piperidine-4-carboxylic acid

To a solution of 2-methylsulfanyl-thiazol-4-one (4.4 g, 30 mmol) in MeOH (60 mL) was added piperidine-4-carboxylic acid (3.9 g, 30 mmol). The mixture was stirred at room temperature for 16 hours. The resulting solid was collected by filtration and washed with fresh MeOH.

$^1$H NMR (400 MHz, DMSO): 12.43 (s, 1H), 4.36 (m, 1H), 3.99 (s, 2H), 3.66 (m, 1H), 3.34 (m, 2H), 2.61 (m, 1H), 1.94 (m, 2H), 1.56 (m, 2H).

LC/MS (m/z) [M+1]+ 229.1 (calculated for $C_9H_{12}N_2O_3S$, 228.1).

B. Pyrrolidine-1-sulfonic acid [1-(4-oxo-4,5-dihydro-thiazol-2-A-piperidine-4-carbonyl]-amide A solution of 1-(4-Oxo-4,5-dihydro-thiazol-2-yl)-piperidine-4-carboxylic acid (0.075 g, 0.33 mmol) and carbonyl diimidazole (0.107 g, 0.65 mmol) in THF (3 mL) was heated under stirring at 45 to 50° C. for 3 hours. It was then added to the homogenous reaction mixture a solution of Pyrrolidine-1-sulfonic acid amide (0.099 g, 0.65 mmol) in THF (1 mL) containing Diazabicyclo[5.4.0]undec-7-ene (0.15 g, 0.98 mmol). The resulting reaction mixture was stirred at 45-50° C. for 30 minutes then at room temperature for 12 hours, diluted with dichloromethane and quenched with 10% aqueous HCl. The dichloromethane layer was then successively washed with water, brine, dried over Na$_2$SO$_4$, filtered, and the solvent evaporated in vacuo to yield the title compound as a gum (64 mg, 54%).

$^1$H NMR (400 MHz, CDCl$_3$) δ 3.99 (s, 3H), 3.53-3.42 (m, 4H), 3.37-3.30 (m, 4H), 2.72-2.66 (m, 1H), 1.96-1.81 (m, 8H).

LC/MS (m/z) [M+1]+ 361.2 (calculated for $C_{13}H_{20}H_4O_4S_2$, 360.09).

C. Pyrrolidine-1-sulfonic acid (1-{5-[1-(4-chloro-2-trifluoromethyl-benzyl)-1H-indazol-5-ylmethylene]-4-oxo-4,5-dihydro-thiazol-2-yl}-piperidine-4-carbonyl)-amide was prepared from 1-(4-Chloro-2-trifluoromethyl-benzyl)-1H-indazole-5-carbaldehyde and Pyrrolidine-1-sulfonic acid [1-(4-oxo-4,5-dihydro-thiazol-2-yl)-piperidine-4-carbonyl]-amide following General Procedure E.

$^1$H NMR (400 MHz, CDCl$_3$) δ 8.16 (d, 1H), 7.94-7.92 (m, 2H), 7.70 (d, 1H), 7.50 (dd, 1H), 7.33 (dd, 1H), 7.27-7.25 (m, 1H), 6.65 (d, 1H), 5.75 (s, 2H), 4.77-4.74 (m, 1H), 3.94-3.91 (m, 1H), 3.54-3.38 (m, 6H), 2.84-2.77 (m, 1H), 2.11-2.08 (m, 2H), 2.04-1.86 (m, 8H).

LC/MS (m/z) [M+1]+ 715.3 (calculated for $C_{30}H_{28}F_6N_6O_4S_2$, 714.15).

Example 175

5-[1-(2,4-Bis-trifluoromethyl-benzyl)-3-iodo-1H-indazol-5-ylmethylene]-2(S)-(2-hydroxymethyl-morpholin-4-yl)-thiazol-4-one

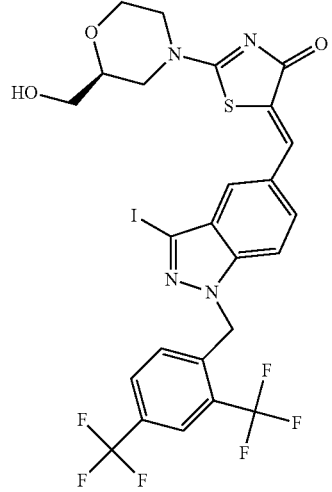 [SMILES: O=C1N=C(N2CCO[C@H](CO)C2)S/C1=C\c1ccc2c(c1)c(I)nn2Cc1ccc(C(F)(F)F)cc1C(F)(F)F]

A. 2-(2-Hydroxymethyl-morpholin-4-yl)-thiazol-4-one was prepared from 2-Methylsulfanyl-thiazol-4-one and Morpholin-2-yl-methanol following general procedure E.

$^1$H NMR (400 MHz, CDCl$_3$) δ 4.72-4.66 (m, 1H), 4.11-4.00 (m, 1H), 3.97 (s, 2H), 3.80-3.56 (m, 4H), 3.51-3.26 (m, 2H), 3.19 (dd, 1H), 1.96-1.91 (m, 1H).

LC/MS (m/z) [M+1]+ 217.2 (calculated for $C_8H_{12}N_2O_3S$, 216.06).

B. 1-(2,4-Bis-trifluoromethyl-benzyl)-3-iodo-1H-indazole-5-carbaldehyde was prepared from 3-Iodo-1H-indazole-5-carbaldehyde and 1-Bromomethyl-2,4-bis-trifluoromethyl-benzene following general procedure A.

¹H NMR (400 MHz, CDCl₃) δ 10.10 (s, 1H), 8.09 (dd, 1H), 8.01-7.99 (m, 2H), 7.66 (d, 1H), 7.34 (d, 1H), 6.91 (d, 1H), 5.91 (s, 2H).

LC/MS (m/z) [M+1]⁺ 497.9 (calculated for $C_{17}H_9F_6IN_2O$, 497.97).

C. 5-[1-(2,4-Bis-trifluoromethyl-benzyl)-3-iodo-1H-indazol-5-ylmethylene]-2(S)-(2-hydroxymethyl-morpholin-4-yl)-thiazol-4-one was prepared from 1-(2,4-Bis-trifluoromethyl-benzyl)-3-iodo-1H-indazole-5-carbaldehyde and 2-(2-Hydroxymethyl-morpholin-4-yl)-thiazol-4-one following General Procedure E.

¹H NMR (400 MHz, CDCl₃) δ 7.98-7.95 (m, 2H), 7.69 (s, 1H), 7.65 (d, 1H), 7.61-7.57 (m, 1H), 7.28 (d, 1H), 6.90 (d, 1H), 5.88 (s, 2H), 4.85-4.78 (m, 1H), 4.17-4.07 (m, 1H), 3.84-3.49 (m, 6H), 3.42-3.26 (m, 1H).

LC/MS (m/z) [M+1]⁺ 697.0 (calculated for $C_{25}H_{19}F_6IN_4O_3S$, 696.01).

Example 176

1-{5-[1-(4-Fluoro-2-trifluoromethyl-benzyl)-1H-indazol-5-ylmethylene]-4-oxo-4,5-dihydro-thiazol-2-yl}-piperidine-4-carboxylic acid

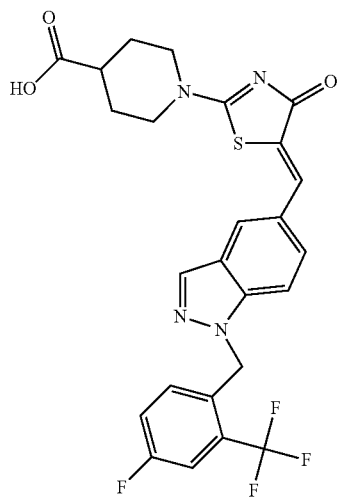 [SMILES: O=C1N=C(N2CCC(C(=O)O)CC2)S/C1=C\c1ccc2c(cnn2Cc2ccc(F)cc2C(F)(F)F)c1]

A. 1-(4-Fluoro-2-trifluoromethyl-benzyl)-1H-indazole-5-carbaldehyde was prepared from 1H-Indazole-5-carbaldehyde and 1-Bromomethyl-4-fluoro-2-trifluoromethyl-benzene following General Procedure A.

¹H NMR (400 MHz, CDCl₃): δ 10.09 (s, 1H), 8.34 (s, 1H), 8.30 (s, 1H), 7.96 (dd, 1H), 7.47 (dd, 1H), 7.40 (d, 1H), 6.77 (dd, 1H), 5.86 (s, 2H).

LC/MS (m/z) [M+1]⁺ 323.3 (calculated for $C_{16}H_{10}F_4N_2O$, 322.2).

B. 1-{5-[1-(4-Fluoro-2-trifluoromethyl-benzyl)-1H-indazol-5-ylmethylene]-4-oxo-4,5-dihydro-thiazol-2-yl}-piperidine-4-carboxylic acid was prepared from 1-(4-Fluoro-2-trifluoromethyl-benzyl)-1H-indazole-5-carbaldehyde and 1-(4-Oxo-4,5-dihydro-thiazol-2-yl)piperidine-4-carboxylic acid following General Procedure E.

¹H NMR (400 MHz, DMSO): δ 12.4 (br s, 1H), 8.31 (d, 1H), 8.13 (s, 1H), 7.78-7.76 (m, 2H), 7.73 (dd, 1H), 7.69 (dd, 1H), 7.45 (td, 1H), 6.85 (dd, 1H), 5.85 (s, 2H), 4.48-4.45 (m, 1H), 3.85-3.81 (m, 1H), 3.58-3.51 (m, 1H), 3.48-3.41 (m, 1H), 2.72-2.66 (m, 1H), 2.09-1.98 (m, 2H), 1.7-1.61 (m, 2H). LC/MS (m/z) [M+1]⁺ 533.2 (calculated for $C_{25}H_{20}F_4N_4O_3S$, 532.12).

Example 177

5-[1-(4-Fluoro-2-trifluoromethyl-benzyl)-1H-indazol-5-ylmethylene]-2-((2S)-2-hydroxymethyl-morpholin-4-yl)-thiazol-4-one

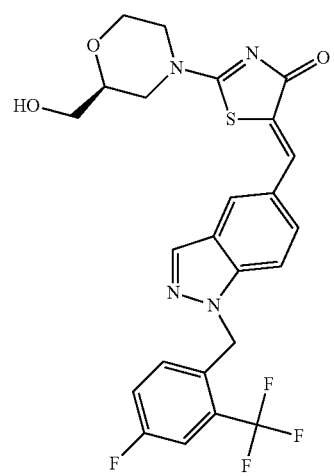 [SMILES: O=C1N=C(N2CCO[C@H](CO)C2)S/C1=C\c1ccc2c(cnn2Cc2ccc(F)cc2C(F)(F)F)c1]

5-[1-(4-Fluoro-2-trifluoromethyl-benzyl)-1H-indazol-5-ylmethylene]-2-((2S)-2-hydroxymethyl-morpholin-4-yl)-thiazol-4-one was prepared from 5-[1-(4-Fluoro-2-trifluoromethyl-benzyl)-1H-indazol-5-ylmethylene]-2-propylsulfanyl-thiazol-4-one and (2S) Morpholin-2-yl-methanol following General Procedure B.

¹H NMR (400 MHz, CDCl₃): δ 8.19 (dd, 1H), 7.97-7.95 (m, 2H), 7.54-7.52 (m, 1H), 7.44 (dd, 1H), 7.32 (d, 1H), 7.07 (td, 1H), 6.74 (dd, 1H), 5.78 (s, 2H), 4.84-4.78 (m, 1H), 4.16-4.06 (m, 1H), 3.84-3.49 (m, 6H), 3.41-3.25 (m, 1H), 2.06-1.99 (m, 1H). LC/MS (m/z) [M+1]⁺ 521.2 (calculated for $C_{24}H_{20}F_4N_4O_3S$, 520.12).

Example 178

5-[1-(4-Fluoro-2-trifluoromethyl-benzyl)-1H-indazol-5-ylmethylene]-2-((3R)-3-hydroxymethyl-piperazin-1-yl)-thiazol-4-one

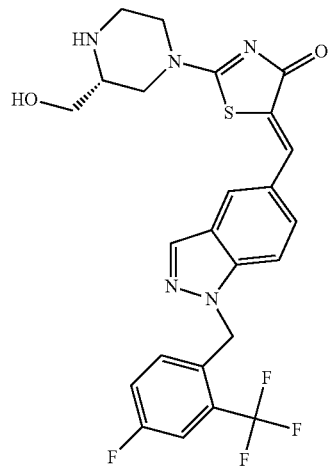 [SMILES: O=C1N=C(N2CCN[C@@H](CO)C2)S/C1=C\c1ccc2c(cnn2Cc2ccc(F)cc2C(F)(F)F)c1]

A. 4-{5-[1-(4-Fluoro-2-trifluoromethyl-benzyl)-1H-indazol-5-ylmethylene]-4-oxo-4,5-dihydro-thiazol-2-yl}-2-(R)-hydroxymethyl-piperazine-1-carboxylic acid tert-butyl ester was prepared from 1-(4-Fluoro-2-trifluoromethyl-benzyl)-1H-indazole-5-carbaldehyde and 2(R)-Hydroxymethyl-4-(4-oxo-4,5-dihydro-thiazol-2-yl)piperazine-1-carboxylic acid tert-butyl ester following general procedure D.

$^1$H NMR (400 MHz, CDCl$_3$): δ 8.16-8.13 (m, 1H), 7.91-7.86 (m, 2H), 7.49-7.43 (m, 2H), 7.29-7.23 (m, 1H), 7.09-7.43 (m, 1H), 6.77-6.71 (m, 1H), 5.77-5.74 (m, 2H), 4.92-4.88 (m, 0.5H), 4.76-4.72 (m, 0.5H), 4.38 (br s, 1H), 4.18-4.13 (m. 0.5H), 4.07-4.02 (m, 1H), 3.81-3.51 (m, 3.5H), 3.45-3.32 (m, 1H), 3.23-3.17 (m, 1H), 1.49 (d, 9H).

LC/MS (m/z) [M+1]$^+$ 619.9 (calculated for C$_{29}$H$_{29}$F$_4$N$_5$O$_4$S, 619.19).

B. 5-[1-(4-Fluoro-2-trifluoromethyl-benzyl)-1H-indazol-5-ylmethylene]-2-((3R)-3-hydroxymethyl-piperazin-1-yl)-thiazol-4-one was prepared from 4-{5-[1-(4-Fluoro-2-trifluoromethyl-benzyl)-1H-indazol-5-ylmethylene]-4-oxo-4,5-dihydro-thiazol-2-yl}-2-(R)-hydroxymethyl-piperazine-1-carboxylic acid tert-butyl ester following general procedure H.

$^1$H NMR (400 MHz, CDCl$_3$): δ 8.19 (d, 1H), 7.97-7.93 (m, 2H), 7.54 (d, 1H), 7.44 (dd, 1H), 7.32 (d, 1H), 7.07 (td, 1H), 6.74 (dd, 1H), 5.79 (s, 2H), 4.79-4.74 (m, 1H), 3.77-3.73 (m, 2H), 3.69-3.65 (m, 0.5H), 3.60-3.56 (m, 0.5H), 3.52-3.45 (m, 0.5H), 3.36-3.29 (m, 1H), 3.25-3.15 (m, 1.5H), 3.04-2.94 (m, 2H).

LC/MS (m/z) [M+1]$^+$ 520.1 (calculated for C$_{24}$H$_{21}$F$_4$N$_5$O$_2$S, 519.14).

Example 179

5-[1-(2,4-Bis-trifluoromethyl-benzyl)-1H-indazol-5-ylmethylene]-2-(4,7-diaza-spiro[2.5]oct-7-yl)-thiazol-4-one

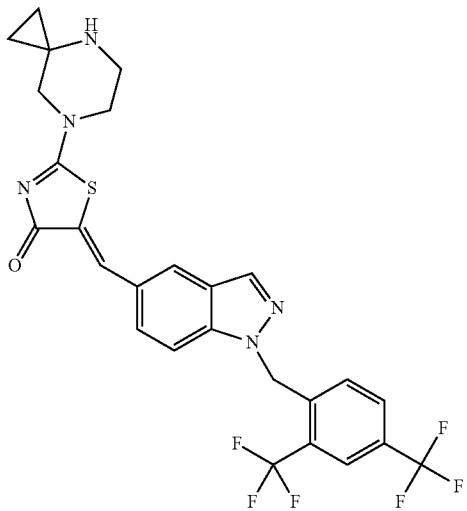 [SMILES: O=C1N=C(N2CCNC3(CC3)C2)S/C1=C\c1ccc2c(cnn2Cc2ccc(C(F)(F)F)cc2C(F)(F)F)c1]

A. 7-{5-[1-(2,4-Bis-trifluoromethyl-benzyl)-1H-indazol-5-ylmethylene]-4-oxo-4,5-dihydro-thiazol-2-yl}-4,7-diaza-spiro[2.5]octane-4-carboxylic acid tert-butyl ester was prepared from 5-[1-(2,4-Bis-trifluoromethyl-benzyl)-1H-indazol-5-ylmethylene]-2-propylsulfanyl-thiazol-4-one and 4,7-Diaza-spiro[2.5]octane-4-carboxylic acid tert-butyl ester following general procedure B.

$^1$H NMR (400 MHz, CDCl$_3$): δ 8.22 (s, 1H), 7.99-7.94 (m, 3H), 7.63-7.61 (m, 1H), 7.57-7.52 (m, 1H), 7.33-7.30 (m, 1H), 6.82 (d, 1H), 5.88 (s, 2H), 4.11-4.09 (m, 1H), 3.93 (s, 1H), 3.74-3.72 (m, 1H), 3.68-3.63 (m, 2H), 3.45 (s, 1H), 1.5 (s, 9H), 1.21-1.10 (m, 1H), 1.05-1.02 (m, 1H), 0.95 (br s, 2H).

LC/MS (m/z) [M+1]$^+$ 666.9 (calculated for C$_{31}$H$_{29}$F$_6$N$_5$O$_3$S, 665.19).

B. 5-[1-(2,4-Bis-trifluoromethyl-benzyl)-1H-indazol-5-ylmethylene]-2-(4,7-diaza-spiro[2.5]oct-7-yl)-thiazol-4-one was prepared from 7-{5-[1-(2,4-Bis-trifluoromethyl-benzyl)-1H-indazol-5-ylmethylene]-4-oxo-4,5-dihydro-thiazol-2-yl}-4,7-diaza-spiro[2.5]octane-4-carboxylic acid tert-butyl ester following general procedure H.

$^1$H NMR (400 MHz, CDCl$_3$): δ 8.21 (d, 1H), 7.98-7.96 (m, 2H), 7.93 (s, 1H), 7.62 (d, 1H), 7.55 (td, 1H), 7.31 (dd, 1H), 6.81 (d, 1H), 5.88 (s, 2H), 4.09-4.06 (m, 1H), 3.94 (s, 1H), 3.64-3.62 (m, 1H), 3.47 (s, 1H), 3.15-3.12 (m, 1H), 3.09-3.07 (m, 1H), 0.75-0.65 (m, 4H).

LC/MS (m/z) [M+1]$^+$ 566.1 (calculated for C$_{26}$H$_{21}$F$_6$N$_5$OS, 565.14).

Example 180

5-[1-(2,4-Bis-trifluoromethyl-benzyl)-3-methyl-1H-indazol-5-ylmethylene]-2-(2-(S)-hydroxymethyl-morpholin-4-yl)-thiazol-4-one

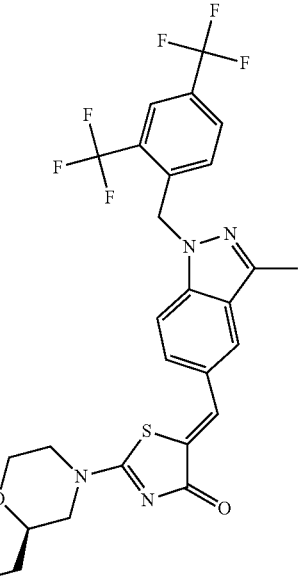

A. 3-Methyl-1H-indazole-5-carbaldehyde

To an Argon flushed flask of anhydrous THF (81 mL) cooled to −78° C. was added a 1.7M solution of tert-butyl-lithium in n-pentane (27 mL, 45.6 mmol). After stirring the solution at −78° C. for 15 minutes, a solution of 5-Bromo-3-methyl-1H-indazole (3 g, 14.2 mmol) in THF (42 mL) was added dropwise such that the temperature of the solution did not exceed −70° C. After stirring the solution at −78° C. for 30 minutes, anhydrous DMF (3.15 g, 43.09 mmol) was added dropwise. The reaction mixture was then stirred at −78° C. for 30 minutes, warmed to room temperature and stirred for 1.5 hours. The reaction mixture was cooled down to 0° C. and it was added carefully water (36 mL) and ethyl acetate. The ethyl acetate layer was washed with brine, dried over Na$_2$SO$_4$, filtered, and the solvent evaporated in vacuo. The residue was purified by flash column chromatography on silica gel (heptane/EtOAc 6:4 v/v) to afford white solid (1.6 g, 70%).

$^1$H NMR (400 MHz, CDCl$_3$) δ10.09 (br s, 1H), 10.07 (s, 1H), 8.24 (s, 1H), 7.95 (dd, 1H), 7.52 (d, 1H), 2.66 (s, 3H).

LC/MS (m/z) [M+1]$^+$ 161.1 (calculated for C$_9$H$_8$N$_2$O, 160.06).

(compound described: WO 2008071451)

B. 1-(2,4-Bis-trifluoromethyl-benzyl)-3-methyl-1H-indazole-5-carbaldehyde was prepared from 3-Methyl-1H-indazole-5-carbaldehyde and 1-Bromomethyl-2,4-bis-trifluoromethyl-benzene following general procedure A.

$^1$H NMR (400 MHz, CDCl$_3$) δ 10.03 (s, 1H), 8.19 (d, 1H), 7.99 (s, 1H), 7.86 (dd, 1H), 7.74 (d, 1H), 6.68 (d, 1H), 5.88 (s, 2H), 2.61 (s, 3H).

LC/MS (m/z) [M+1]$^+$ 387.1 (calculated for C$_{18}$H$_{12}$F$_8$N$_2$O, 386.09).

C. 5-[1-(2,4-Bis-trifluoromethyl-benzyl)-3-methyl-1H-indazol-5-ylmethylene]-2-(2-(S)-hydroxymethyl-morpholin-4-yl)-thiazol-4-one was prepared from 5-[1-(2,4-Bis-trifluoromethyl-benzyl)-3-methyl-1H-indazol-5-ylmethylene]-2-propylsulfanyl-thiazol-4-one and 2-(S)-Morpholin-2-yl-methanol following general procedure B.

$^1$H NMR (400 MHz, CDCl$_3$): δ 7.97 (s, 2H), 7.88 (s, 1H), 7.61 (d, 1H), 7.55-7.52 (m, 1H), 7.25 (d, 1H), 6.81 (d, 1H), 5.80 (s, 2H), 4.84-4.78 (m, 1H), 4.16-4.06 (m, 1H), 3.82-3.49 (m, 6H), 3.41-3.25 (m, 1H), 2.67 (d, 3H), 1.92-1.86 (m, 1H).

LC/MS (m/z) [M+1]$^+$ 585.2 (calculated for C$_{26}$H$_{22}$F$_6$N$_4$O$_3$S, 584.13).

Example 181

5-[1-(4-Chloro-2-trifluoromethyl-benzyl)-3-methyl-1H-indazol-5-ylmethylene]-2-(2-(S)-hydroxymethyl-morpholin-4-yl)-thiazol-4-one

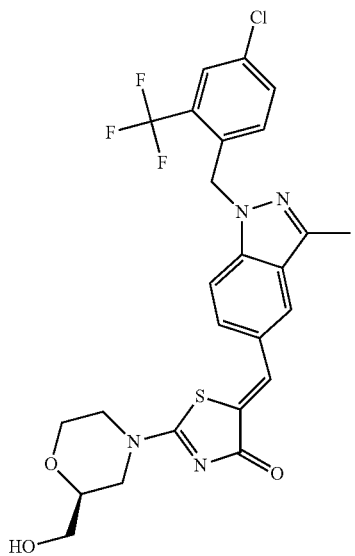 [SMILES: Cc1nn(Cc2ccc(Cl)cc2C(F)(F)F)c2ccc(/C=C3\SC(N4CCO[C@H](CO)C4)=NC3=O)cc12]

A. 1-(4-Chloro-2-trifluoromethyl-benzyl)-3-methyl-1H-indazole-5-carbaldehyde was prepared from 3-Methyl-1H-indazole-5-carbaldehyde and 1-Bromomethyl-4-chloro-2-trifluoromethyl-benzene following general procedure A.

$^1$H NMR (400 MHz, CDCl$_3$) δ 10.06 (s, 1H), 8.25 (d, 1H), 7.91 (dd, 1H), 7.71 (d, 1H), 7.33 (dd, 1H), 7.29 (d, 1H), 6.65 (d, 1H), 5.74 (s, 2H), 2.68 (s, 3H).

LC/MS (m/z) [M+1]$^+$ 353.0 (calculated for C$_{17}$H$_{12}$ClF$_3$N$_2$O, 352.06).

B. 5-[1-(4-Chloro-2-trifluoromethyl-benzyl)-3-methyl-1H-indazol-5-ylmethylene]-2-(2-(S)-hydroxymethyl-morpholin-4-yl)-thiazol-4-one was prepared from 5-[1-(4-Chloro-2-trifluoromethyl-benzyl)-3-methyl-1H-indazol-5-ylmethylene]-2-propylsulfanyl-thiazol-4-one and 2-(S)-Morpholin-2-yl-methanol following general procedure B.

$^1$H NMR (400 MHz, CDCl$_3$): δ 7.96 (s, 1H), 7.85 (s, 1H), 7.69 (d, 1H), 7.53-7.50 (m, 1H), 7.32 (dd, 1H), 7.23 (d, 1H), 6.64 (d, 1H), 5.71 (s, 2H), 4.84-4.77 (m, 1H), 4.16-4.06 (m, 1H), 3.88-3.48 (m, 6H), 3.41-3.24 (m, 1H), 2.65 (d, 3H), 2.10-2.04 (m, 1H).

LC/MS (m/z) [M+1]$^+$ 551.2 (calculated for C$_{25}$H$_{22}$ClF$_3$N$_4$O$_3$S, 550.11).

Example 182

5-[1-(2,4-Bis-trifluoromethyl-benzyl)-3-methyl-1H-indazol-5-ylmethylene]-2-(3-(R)-hydroxymethyl-piperazin-1-yl)-thiazol-4-one

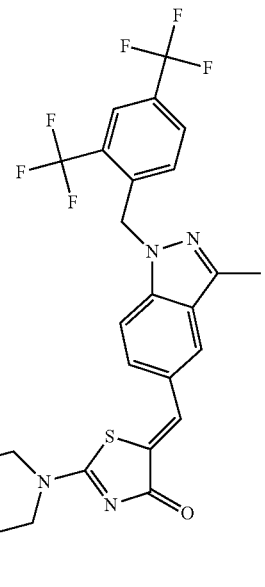

A. 4-{5-[1-(2,4-Bis-trifluoromethyl-benzyl)-3-methyl-1H-indazol-5-ylmethylene]-4-oxo-4,5-dihydro-thiazol-2-yl}-2-(R)-hydroxymethyl-piperazine-1-carboxylic acid tert-butyl ester was prepared from 1-(2,4-Bis-trifluoromethyl-benzyl)-3-methyl-1H-indazole-5-carbaldehyde and 2-(R)-Hydroxymethyl-4-(4-oxo-4,5-dihydro-thiazol-2-yl)-piperazine-1-carboxylic acid tert-butyl ester following general procedure D.

$^1$H NMR (400 MHz, CDCl$_3$): δ 7.96-7.94 (m, 2H), 7.86-7.84 (m, 1H), 7.62-7.60 (m, 1H), 7.52-7.50 (m, 1H), 7.25-7.22 (m, 1H), 6.83-6.79 (m, 1H), 5.81-5.79 (m, 2H), 4.93-4.88 (m, 0.5H), 4.79-4.74 (m, 0.5H), 4.37 (br s, 1H), 4.19-4.15 (m. 0.5H), 4.04-3.99 (m, 1H), 3.82-3.51 (m, 3.5H), 3.46-3.32 (m, 1H), 3.22-3.16 (m, 1H), 2.66 (d, 3H), 1.49 (d, 9H).

LC/MS (m/z) [M+1]$^+$ 683.9 (calculated for C$_{31}$H$_{31}$F$_6$N$_5$O$_4$S, 683.20).

B. 5-[1-(2,4-Bis-trifluoromethyl-benzyl)-3-methyl-1H-indazol-5-ylmethylene]-2-(3-(R)-hydroxymethyl-piperazin- 1-yl)-thiazol-4-one was prepared from 4-{5-[1-(2,4-Bis-trifluoromethyl-benzyl)-3-methyl-1H-indazol-5-ylmethylene]-4-oxo-4,5-dihydro-thiazol-2-yl}-2-(R)-hydroxymethyl-piperazine-1-carboxylic acid tert-butyl ester following general procedure H.

$^1$H NMR (400 MHz, CDCl$_3$): δ 7.97-7.94 (m, 2H), 7.87 (s, 1H), 7.61 (d, 1H), 7.55-7.52 (m, 1H), 7.24 (d, 1H), 6.80 (d, 1H), 5.80 (s, 2H), 4.79-4.74 (m, 1H), 3.77-3.74 (m, 2H), 3.69-3.65 (m, 0.5H), 3.61-3.56 (m, 0.5H), 3.53-3.45 (m, 0.5H), 3.37-3.29 (m, 1H), 3.27-3.16 (m, 1.5H), 3.04-2.97 (m, 2H), 2.67 (s, 3H).

LC/MS (m/z) [M+1]$^+$ 584.2 (calculated for C$_{26}$H$_{23}$F$_6$N$_5$O$_2$S, 583.15).

Example 183

5-[1-(4-Chloro-2-trifluoromethyl-benzyl)-3-methyl-1H-indazol-5-ylmethylene]-2-(3-(R)-hydroxymethyl-piperazin-1-yl)-thiazol-4-one

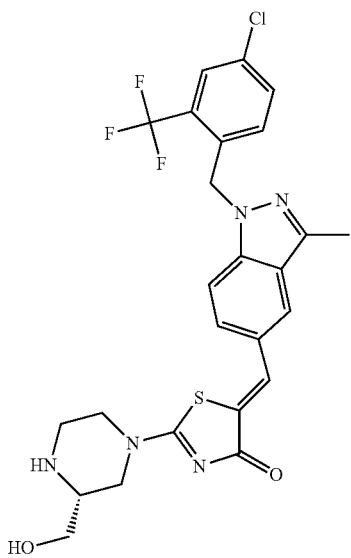 [SMILES: Cc1nn(Cc2ccc(Cl)cc2C(F)(F)F)c2ccc(/C=C3\SC(N4CCN[C@@H](CO)C4)=NC3=O)cc12]

A. 4-{5-[1-(4-Chloro-2-trifluoromethyl-benzyl)-3-methyl-1H-indazol-5-ylmethylene]-4-oxo-4,5-dihydro-thiazol-2-yl}-2-(R)-hydroxymethyl-piperazine-1-carboxylic acid tert-butyl ester was prepared from 1-(4-Chloro-2-trifluoromethyl-benzyl)-3-methyl-1H-indazole-5-carbaldehyde and 2-(R)-Hydroxymethyl-4-(4-oxo-4,5-dihydro-thiazol-2-yl)-piperazine-1-carboxylic acid tert-butyl ester following general procedure D.

$^1$H NMR (400 MHz, CDCl$_3$): δ 7.95-7.93 (m, 1H), 7.84-7.82 (m, 1H), 7.69 (s, 1H), 7.51-7.48 (m, 1H), 7.33-7.30 (m, 1H), 7.23-7.19 (m, 1H), 6.66-6.62 (m, 1H), 5.71-5.69 (m, 2H), 4.93-4.88 (m, 0.5H), 4.78-4.74 (m, 0.5H), 4.38 (br s, 1H), 4.18-4.12 (m. 0.5H), 4.04-3.99 (m, 1H), 3.82-3.70 (m, 1.5H), 3.64-3.31 (m, 3H), 3.22-3.15 (m, 1H), 2.65 (d, 3H), 1.49 (d, 9H).

LC/MS (m/z) [M+1]$^+$ 650.0 (calculated for C$_{30}$H$_{31}$ClF$_3$N$_5$O$_4$S, 649.17).

B. 5-[1-(4-Chloro-2-trifluoromethyl-benzyl)-3-methyl-1H-indazol-5-ylmethylene]-2-(3-(R)-hydroxymethyl-piperazin-1-yl)-thiazol-4-one was prepared from 4-{5-[1-(4-Chloro-2-trifluoromethyl-benzyl)-3-methyl-1H-indazol-5-ylmethylene]-4-oxo-4,5-dihydro-thiazol-2-yl}-2-(R)-hydroxymethyl-piperazine-1-carboxylic acid tert-butyl ester following general procedure H.

$^1$H NMR (400 MHz, CDCl$_3$): δ 7.94 (s, 1H), 7.86 (s, 1H), 7.69 (d, 1H), 7.54-7.51 (m, 1H), 7.32 (dd, 1H), 7.23 (d, 1H), 6.64 (d, 1H), 5.71 (s, 2H), 4.79-4.74 (m, 1H), 3.77-3.73 (m, 2H), 3.69-3.65 (m, 0.5H), 3.60-3.56 (m, 0.5H), 3.52-3.45 (m, 0.5H), 3.37-3.29 (m, 1H), 3.27-3.15 (m, 1.5H), 3.04-2.93 (m, 2H), 2.66 (s, 3H).

LC/MS (m/z) [M+1]$^+$ 550.2 (calculated for C$_{25}$H$_{23}$ClF$_3$N$_5$O$_2$S, 549.12).

Example 184

5-[1-(2,4-Bis-trifluoromethyl-benzyl)-3-chloro-1H-indazol-5-ylmethylene]-2-(2-(S)-hydroxymethyl-morpholin-4-yl)-thiazol-4-one

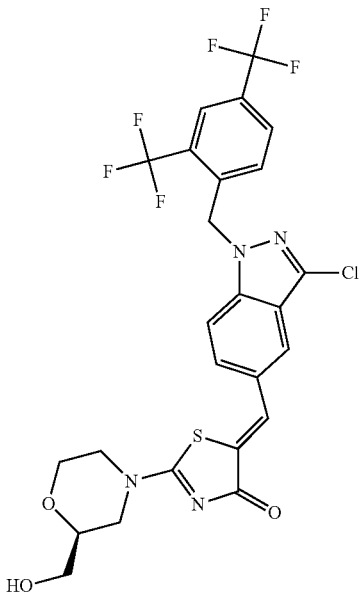 [SMILES: O=C1N=C(N2CCO[C@H](CO)C2)S/C1=C\c1ccc2c(c1)c(Cl)nn2Cc1ccc(C(F)(F)F)cc1C(F)(F)F]

A. 3-Chloro-1H-indazole-5-carbaldehyde

To a solution of 1H-Indazole-5-carbaldehyde (3.2 g, 21.89 mmol) in acetonitrile (140 mL) was added N-Chlorosuccinimide (3.5 g, 26.27 mmol). After stirring for 50 hours at 65 to 70° C., the precipitate was filtered, washed with cold acetonitrile, abundantly with water and dried to afford the title compound as a white solid (2.15 g, 54%).

$^1$H NMR (400 MHz, CDCl$_3$) δ13.78 (s, 1H), 10.08 (s, 1H), 8.37 (d, 1H), 7.92 (dd, 1H), 7.72 (d, 1H).

LC/MS (m/z) [M+1]$^+$ 181.2 (calculated for C$_8$H$_5$ClN$_2$O, 180.01).

B. 1-(2,4-Bis-trifluoromethyl-benzyl)-3-chloro-1H-indazole-5-carbaldehyde was prepared from 3-Chloro-1H-indazole-5-carbaldehyde and 1-Bromomethyl-2,4-bis-trifluoromethyl-benzene following general procedure A.

$^1$H NMR (400 MHz, CDCl$_3$) δ 10.09 (s, 1H), 8.28 (s, 1H), 8.01-7.99 (m, 2H), 7.68 (d, 1H), 7.36 (d, 1H), 6.98 (d, 1H), 5.83 (s, 2H).

LC/MS (m/z) [M+1]$^+$ 405.9 (calculated for C$_{17}$H$_9$ClF$_6$N$_2$O, 406.03).

C. 5-[1-(2,4-Bis-trifluoromethyl-benzyl)-3-chloro-1H-indazol-5-ylmethylene]-2-(2-(S)-hydroxymethyl-morpholin-4-yl)-thiazol-4-one was prepared from 1-(2,4-Bis-trifluoromethyl-benzyl)-3-chloro-1H-indazole-5-carbaldehyde and 2-(2-(S)-Hydroxymethyl-morpholin-4-yl)-thiazol-4-one following general procedure D.

$^1$H NMR (400 MHz, CDCl$_3$): δ 7.98 (s, 1H), 7.94 (s, 1H), 7.89 (s, 1H), 7.67 (d, 1H), 7.60-7.57 (m, 1H), 7.31 (d, 1H), 6.97 (d, 1H), 5.81 (s, 2H), 4.84-4.79 (m, 1H), 4.17-4.07 (m, 1H), 3.85-3.48 (m, 6H), 3.41-3.26 (m, 1H), 1.91-1.85 (m, 1H).

LC/MS (m/z) [M+1]$^+$ 605.2 (calculated for C$_{25}$H$_{19}$ClF$_6$N$_4$O$_3$S, 604.08).

Example 185

5-[3-Chloro-1-(4-chloro-2-trifluoromethyl-benzyl)-1H-indazol-5-ylmethylene]-2-(2-(S)-hydroxymethyl-morpholin-4-yl)-thiazol-4-one

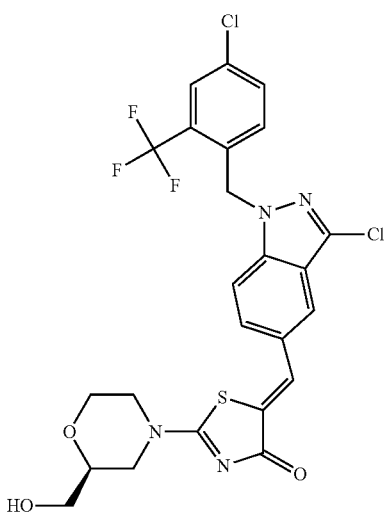 [SMILES: O=C1N=C(N2CCO[C@H](CO)C2)S/C1=C\c1ccc2c(c1)c(Cl)nn2Cc1ccc(Cl)cc1C(F)(F)F]

A. 3-Chloro-1-(4-chloro-2-trifluoromethyl-benzyl)-1H-indazole-5-carbaldehyde was prepared from 3-Chloro-1H-indazole-5-carbaldehyde and 1-Bromomethyl-4-chloro-2-trifluoromethyl-benzene following general procedure A.

$^1$H NMR (400 MHz, CDCl$_3$) δ 10.09 (s, 1H), 8.29-8.28 (dd, 1H), 8.01-7.99 (m, 2H), 7.68 (d, 1H), 7.36 (d, 1H), 6.98 (d, 1H), 5.84 (s, 2H).

LC/MS (m/z) [M+1]$^+$ 372.0 (calculated for C$_{16}$H$_9$Cl$_2$F$_3$N$_2$O, 372.0).

B. 5-[3-Chloro-1-(4-chloro-2-trifluoromethyl-benzyl)-1H-indazol-5-ylmethylene]-2-(2-hydroxymethyl-morpholin-4-yl)-thiazol-4-one was prepared from 3-Chloro-1-(4-chloro-2-trifluoromethyl-benzyl)-1H-indazole-5-carbaldehyde and 2-(2-(S)-Hydroxymethyl-morpholin-4-yl)-thiazol-4-one following general procedure D.

$^1$H NMR (400 MHz, CDCl$_3$): δ 7.92 (s, 1H), 7.86 (s, 1H), 7.89 (s, 1H), 7.71 (d, 1H), 7.58-7.55 (m, 1H), 7.38 (dd, 1H), 7.29 (d, 1H), 6.81 (d, 1H), 5.72 (s, 2H), 4.84-4.78 (m, 1H), 4.17-4.07 (m, 1H), 3.85-3.48 (m, 6H), 3.42-3.26 (m, 1H), 2.06-1.99 (m, 1H).

LC/MS (m/z) [M+1]$^+$ 571.3 (calculated for C$_{24}$H$_{19}$Cl$_2$F$_3$N$_4$O$_3$S, 570.05).

Example 186

5-[1-(2,4-Bis-trifluoromethyl-benzyl)-3-chloro-1H-indazol-5-ylmethylene]-2-(3-(R)-hydroxymethyl-piperazin-1-yl)-thiazol-4-one

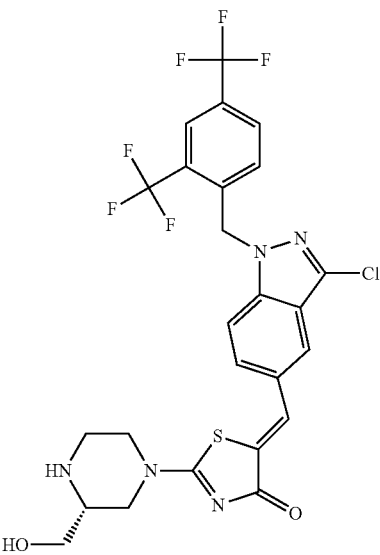 [SMILES: O=C1N=C(N2CCN[C@@H](CO)C2)S/C1=C\c1ccc2c(c1)c(Cl)nn2Cc1ccc(C(F)(F)F)cc1C(F)(F)F]

A. 4-{5-[1-(2,4-Bis-trifluoromethyl-benzyl)-3-chloro-1H-indazol-5-ylmethylene]-4-oxo-4,5-dihydro-thiazol-2-yl}-2-(R)-hydroxymethyl-piperazine-1-carboxylic acid tert-butyl ester was prepared from 1-(2,4-Bis-trifluoromethyl-benzyl)-3-chloro-1H-indazole-5-carbaldehyde and 2-(R)-Hydroxymethyl-4-(4-oxo-4,5-dihydro-thiazol-2-yl)-piperazine-1-carboxylic acid tert-butyl ester following general procedure D.

$^1$H NMR (400 MHz, CDCl$_3$): δ 7.98 (s, 1H), 7.89-7.87 (m, 1H), 7.83-7.80 (m, 1H), 7.68-7.66 (m, 1H), 7.54 (dd, 1H), 7.29-7.25 (m, 1H), 6.98-6.94 (m, 1H), 5.80-5.78 (m, 2H), 4.93-4.89 (m, 0.5H), 4.76-4.73 (m, 0.5H), 4.37 (br s, 1H), 4.19-4.14 (m. 0.5H), 4.06-4.00 (m, 1H), 3.84-3.52 (m, 3.5H), 3.46-3.33 (m, 1H), 3.23-3.21 (m, 1H), 1.49 (d, 9H).

LC/MS (m/z) [M+1]$^+$ 704.0 (calculated for C$_{30}$H$_{28}$ClF$_6$N$_5$O$_4$S, 703.15).

B. 5-[1-(2,4-Bis-trifluoromethyl-benzyl)-3-chloro-1H-indazol-5-ylmethylene]-2-(3-(R)-hydroxymethyl-piperazin-1-yl)-thiazol-4-one was prepared from 4-{5-[1-(2,4-Bis-trifluoromethyl-benzyl)-3-chloro-1H-indazol-5-ylmethylene]-4-oxo-4,5-dihydro-thiazol-2-yl}-2-(R)-hydroxymethyl-piperazine-1-carboxylic acid tert-butyl ester following general procedure H.

$^1$H NMR (400 MHz, CDCl$_3$): δ 7.98 (s, 1H), 7.90-7.87 (m, 2H), 7.67 (d, 1H), 7.59-7.56 (m, 1H), 7.30 (d, 1H), 6.96 (d, 1H), 5.80 (s, 2H), 4.79-4.74 (m, 1H), 3.78-3.73 (m, 2H), 3.70-3.66 (m, 0.5H), 3.61-3.57 (m, 0.5H), 3.54-3.47 (m, 0.5H), 3.38-3.30 (m, 1H), 3.28-3.16 (m, 1.5H), 3.05-2.93 (m, 2H).

LC/MS (m/z) [M+1]+ 604.2 (calculated for $C_{25}H_{20}ClF_6N_5O_2S$, 603.09).

Example 187

5-[3-Chloro-1-(4-chloro-2-trifluoromethyl-benzyl)-1H-indazol-5-ylmethylene]-2-(3-(R)-hydroxymethyl-piperazin-1-yl)-thiazol-4-one

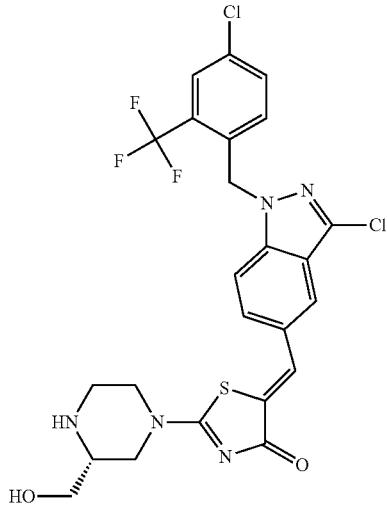 [SMILES: O=C1N=C(N2CCN[C@@H](CO)C2)S/C1=C\c1ccc2c(c1)c(Cl)nn2Cc1ccc(Cl)cc1C(F)(F)F]

A. 4-{5-[3-Chloro-1-(4-chloro-2-trifluoromethyl-benzyl)-1H-indazol-5-ylmethylene]-4-oxo-4,5-dihydro-thiazol-2-yl}-2-(R)-hydroxymethyl-piperazine-1-carboxylic acid tert-butyl ester was prepared from 3-Chloro-1-(4-chloro-2-trifluoromethyl-benzyl)-1H-indazole-5-carbaldehyde and 2-(R)-Hydroxymethyl-4-(4-oxo-4,5-dihydro-thiazol-2-yl)-piperazine-1-carboxylic acid tert-butyl ester following general procedure D.

$^1$H NMR (400 MHz, CDCl$_3$): δ 7.92-7.89 (m, 1H), 7.84-7.81 (m, 1H), 7.71 (s, 1H), 7.56-7.53 (m, 1H), 7.39-7.36 (m, 1H), 7.29-7.27 (m, 1H), 6.82-6.78 (m, 1H), 5.71-5.70 (m, 2H), 4.93-4.89 (m, 0.5H), 4.78-4.74 (m, 0.5H), 4.39 (br s, 1H), 4.20-4.15 (m. 0.5H), 4.05-4.0 (m, 1H), 3.84-3.72 (m, 1.5H), 3.65-3.32 (m, 3H), 3.23-3.17 (m, 1H), 1.49 (d, 9H).

LC/MS (m/z) [M+1]+ 669.9 (calculated for $C_{29}H_{28}Cl_2F_3N_5O_4S$, 669.12).

B. 5-[3-Chloro-1-(4-chloro-2-trifluoromethyl-benzyl)-1H-indazol-5-ylmethylene]-2-(3-(R)-hydroxymethyl-piperazin-1-yl)-thiazol-4-one was prepared from 4-{5-[3-Chloro-1-(4-chloro-2-trifluoromethyl-benzyl)-1H-indazol-5-ylmethylene]-4-oxo-4,5-dihydro-thiazol-2-yl}-2-(R)-hydroxymethyl-piperazine-1-carboxylic acid tert-butyl ester following general procedure H.

$^1$H NMR (400 MHz, CDCl$_3$): δ 7.90 (s, 1H), 7.86 (s, 1H), 7.71 (d, 1H), 7.56 (d, 1H), 7.38 (d, 1H), 7.29 (d, 1H), 6.80 (d, 1H), 5.71 (s, 2H), 4.79-4.74 (m, 1H), 3.79-3.74 (m, 2H), 3.70-3.66 (m, 0.5H), 3.61-3.57 (m, 0.5H), 3.54-3.47 (m, 0.5H), 3.38-3.30 (m, 1H), 3.27-3.16 (m, 1.5H), 3.05-2.93 (m, 2H).

LC/MS (m/z) [M+1]+ 570.2 (calculated for $C_{24}H_{20}Cl_2F_3N_5O_2S$, 569.07).

Example 188

4-[5-({1-[2,4-Bis(trifluoromethyl)benzyl]-1H-indazol-5-yl}methylidene)-4-oxo-4,5-dihydro-1,3-thiazol-2-yl]morpholine-2-carboxylic acid

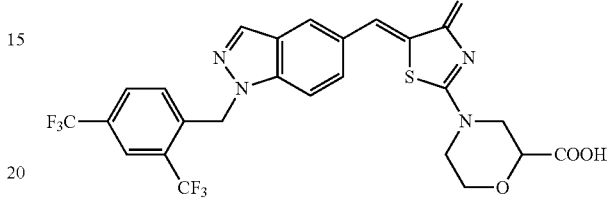

4-[5-({1-[2,4-Bis(trifluoromethyl)benzyl]-1H-indazol-5-yl}methylidene)-4-oxo-4,5-dihydro-1,3-thiazol-2-yl]morpholine-2-carboxylic acid was prepared from 5-[1-(2,4-bis-trifluoromethyl-benzyl)-1H-indazol-5-ylmethylene]2-methylsulfanyl-thiazol-4-one and morpholine-2-carboxylic acid following General Procedure C.

$^1$H NMR (400 MHz, CD$_3$OD) δ 8.29 (dd, 1H), 8.15 (d, 1H), 8.06 (s, 1H), 7.91 (s, 1H), 7.80 (d, 1H), 7.69 (ddd, 1H), 7.60 (dd, 1H), 6.86 (d, 1H), 5.98 (s, 2H), 4.76 (m, ½H), 4.44 (m, ½H), 4.30-4.37 (1H), 4.01-4.19 (1H), 3.67-3.86 (4H).

LC/MS (m/z) [M+1]+ 585.1 (calculated for $C_{26}H_{19}F_6N_4O_3S$, 584.1).

Example 189

1-[5-({1-[4-Chloro-2-(trifluoromethyl)benzyl]-1H-indazol-5-yl}methylidene)-4-oxo-4,5-dihydro-1,3-thiazol-2-yl]-4-(S)-fluoro-L-proline

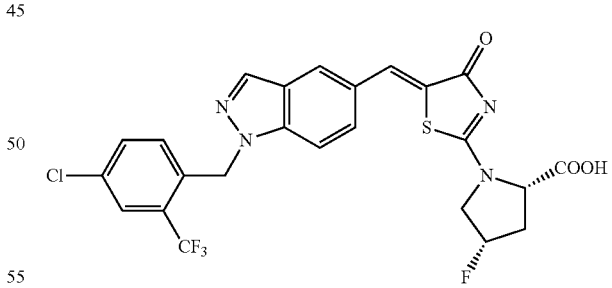

1-[5-({1-[4-Chloro-2-(trifluoromethyl)benzyl]-1H-indazol-5-yl}methylidene)-4-oxo-4,5-dihydro-1,3-thiazol-2-yl]-4-(S)-fluoro-L-proline was prepared from 5-[1-(4-Chloro-2-trifluoromethyl-benzyl)-1H-indazol-5-ylmethylene]-2-ethylsulfanyl-thiazol-4-one and 4-(S)-Fluoro-pyrrolidine-2-(S)-carboxylic acid following General Procedure C.

$^1$H NMR (400 MHz, CDCl$_3$) δ 10.61 (br s, 1H), 8.14 (d, 1H), 7.86 (m, 1H), 7.78 (m, 1H), 7.67 (m, 1H), 7.41 (t, 1H), 7.31 (dd, 1H), 7.24 (m, 1H), 6.63 (t, 1H), 5.71 (d, 2H), 5.38 (m, 1H), 4.91 (dd, 1H), 3.88-4.31 (2H), 2.50-3.69 (2H).

LC/MS (m/z) [M+1]+ 553.0 (calculated for C24H17ClF4N4O3S, 552.1).

Example 190

Methyl 1-[5-({1-[2,4-bis(trifluoromethyl)benzyl]-1H-indazol-5-yl}methylidene)-4-oxo-4,5-dihydro-1,3-thiazol-2-yl]piperidine-4-carboxylate

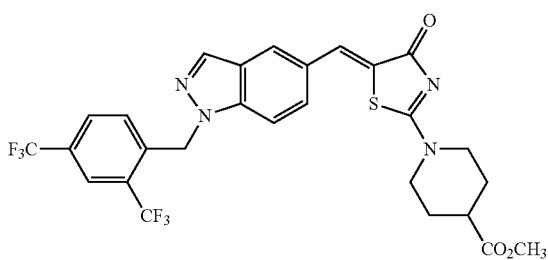 [SMILES: COC(=O)C1CCN(C2=NC(=O)/C(=C/c3ccc4c(cnn4Cc4ccc(C(F)(F)F)cc4C(F)(F)F)c3)S2)CC1]

Methyl 1-[5-({1-[2,4-bis(trifluoromethyl)benzyl]-1H-indazol-5-yl}methylidene)-4-oxo-4,5-dihydro-1,3-thiazol-2-yl]piperidine-4-carboxylate was prepared from 5-[1-(2,4-Bis-trifluoromethyl-benzyl)-1H-indazol-5-ylmethylene]-2-ethylsulfanyl-thiazol-4-one and Piperidine-4-carboxylic acid methyl ester following General Procedure C.

$^1$H NMR (400 MHz, CDCl$_3$) δ 8.22 (s, 1H), 7.99 (br s, 2H), 7.95 (s, 1H), 7.63 (d, 1H), 7.56 (dd, 1H), 7.32 (d, 1H), 7.56 (dd, 1H), 7.32 (d, 1H), 6.82 (d, 1H), 5.89 (s, 2H), 4.67 (m, ½H), 3.92 (s, 3H), 3.89 (m, ½H), 3.44-3.60 (2H), 2.79 (m, 1H), 2.16 (m, 2H), 1.88-1.98 (3H).

LC/MS (m/z) [M+1]+ 597.0 (calculated for C27H22F8N4O3S, 596.1).

Example 191

1-[5-({1-[2,4-Bis(trifluoromethyl)benzyl]-3-iodo-1H-indazol-5-yl}methylidene)-4-oxo-4,5-dihydro-1,3-thiazol-2-yl]piperidine-4-carboxylic acid

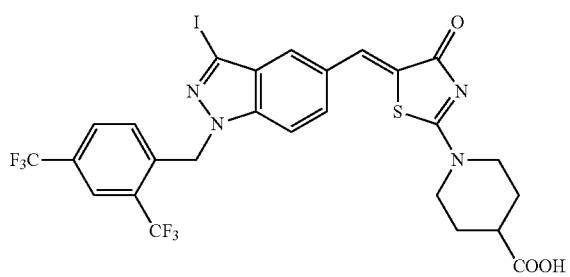 [SMILES: O=C1N=C(N2CCC(C(=O)O)CC2)S/C1=C\c1ccc2c(c1)c(I)nn2Cc1ccc(C(F)(F)F)cc1C(F)(F)F]

A. 3-Iodo-1H-indazole-5-carbaldehyde

To a solution of 1H-indazole-5-carboxaldehyde (670.2 mg, 4.59 mmol) in DMF (5 mL) were added iodine (2.33 g, 9.17 mmol) and potassium hydroxide pellets (1.03 g, 18.36 mmol) at room temperature under stirring. After 4 h, the mixture was quenched with aqueous Na$_2$S$_2$O$_3$ solution and extracted with EtOAc. The combined extracts were washed with brine, dried, and evaporated to afford the title product.

$^1$H NMR (400 MHz, CD$_3$OD) δ10.05 (s, 1H), 8.10 (m, 1H), 7.99 (dd, 1H), 7.65 (d, 1H).

LC/MS (m/z) [M+1]+ 272.9 (calculated for C8H5IN2O, 271.94).

B. 1-(2,4-Bis-trifluoromethyl-benzyl)-3-iodo-1H-indazole-5-carbaldehyde was prepared from 3-Iodo-1H-indazole-5-carbaldehyde and 1-Bromomethyl-2,4-bis-trifluoromethyl-benzene following General Procedure A.

$^1$H NMR (400 MHz, CDCl$_3$) δ 10.10 (s, 1H), 8.09 (m, 1H), 8.01 (d, 1H), 7.99 (d, 1H), 7.67 (d, 1H), 7.35 (d, 1H), 6.92 (d, 1H), 5.91 (s, 2H).

LC/MS (m/z) [M+1]+ 498.9 (calculated for C17H9F6IN2O, 497.97).

C. 1-[5-({1-[2,4-Bis(trifluoromethyl)benzyl]-3-iodo-1H-indazol-5-yl}methylidene)-4-oxo-4,5-dihydro-1,3-thiazol-2-yl]piperidine-4-carboxylic acid was prepared from 5-[1-(2,4-Bis-trifluoromethyl-benzyl)-3-iodo-1H-indazol-5-ylmethylene]-2-ethylsulfanyl-thiazol-4-one and Piperidine-4-carboxylic acid following general procedure C.

$^1$H NMR (400 MHz, CDCl$_3$) δ 7.98 (br s, 1H), 7.94 (s, 1H), 7.71 (s, 1H), 7.66 (d, 1H), 7.60 (dd, 1H), 7.28 (m, 1H), 6.90 (d, 1H), 5.89 (s, 2H), 4.68 (m, ½H), 3.90 (m, ½H), 3.46-3.62 (2H), 2.11-2.84 (2H), 1.49-2.02 (4H).

LC/MS (m/z) [M+1]+ 709.0 (calculated for C26H19F6IN4O3S, 708.43).

Example 192

5-({1-[2,4-Bis(trifluoromethyl)benzyl]-1H-indazol-5-yl}methylidene)-2-(2-(R),4-dimethylpiperazin-1-yl)-1,3-thiazol-4(5H)-one

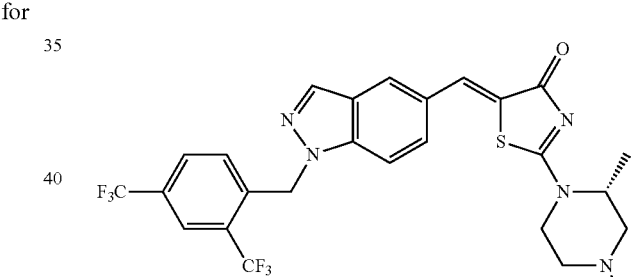

5-({1-[2,4-Bis(trifluoromethyl)benzyl]-1H-indazol-5-yl}methylidene)-2-(2-(R),4-dimethylpiperazin-1-yl)-1,3-thiazol-4(5H)-one was prepared from 5-[1-(2,4-Bis-trifluoromethyl-benzyl)-1H-indazol-5-ylmethylene]-2-ethylsulfanyl-thiazol-4-one and 1,3-(R)-Dimethyl-piperazine following general procedure C.

$^1$H NMR (400 MHz, CD$_3$OD) δ 8.23 (s, 1H), 8.04 (s, 1H), 8.03 (s, 1H), 7.78 (s, 1H), 7.76 (d, 1H), 7.60 (dd, 1H), 7.53 (d, 1H), 6.84 (d, 1H), 5.92 (s, 2H), 4.91 (m, ½H), 4.56 (d, ½H), 4.13 (br s, ½H), 3.72 (m, 1H), 3.49 (m, ½H), 2.79-2.99 (2H), 2.31 (s, 3H), 2.30 (m, 1H), 2.14 (m, 1H), 1.46 (dd, 3H).

LC/MS (m/z) [M+1]+ 568.1 (calculated for C26H23F6N5OS, 567.1).

Example 193

5-({1-[4-Chloro-2-(trifluoromethyl)benzyl]-1H-indazol-5-yl}methylidene)-2-(2-(R),4-dimethylpiperazin-1-yl)-1,3-thiazol-4(5H)-one

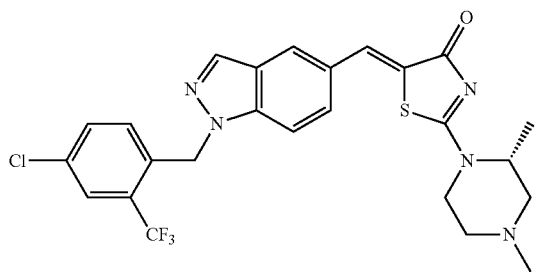 [SMILES: C[C@@H]1CN(C)CCN1C1=NC(=O)/C(=C/c2ccc3c(cnn3Cc3ccc(Cl)cc3C(F)(F)F)c2)S1]

5-({1-[4-Chloro-2-(trifluoromethyl)benzyl]-1H-indazol-5-yl}methylidene)-2-(2(R),4-dimethylpiperazin-1-yl)-1,3-thiazol-4(5H)-one was prepared from 5-[1-(4-Chloro-2-trifluoromethyl-benzyl)-1H-indazol-5-ylmethylene]-2-ethylsulfanyl-thiazol-4-one and 1,3-(R)-Dimethyl-piperazine following general procedure C.

$^1$H NMR (400 MHz, CDCl$_3$) δ 8.18 (s, 1H), 7.96 (s, 1H), 7.92 (s, 1H), 7.70 (d, 1H), 7.53 (dd, 1H), 7.33 (dd, 1H), 7.30 (d, 1H), 6.66 (d, 1H), 5.77 (s, 2H), 5.10 (br s, ½H), 4.74 (d, ½H), 4.03 (br s, ½H), 3.76 (m, ½H), 3.47-3.61 (1H), 2.95 (m, 1H), 2.80 (m, 1H), 2.37 (m, 1H), 2.35 (s, 3H), 2.19 (m, 1H), 1.49 (dd, 3H).

LC/MS (m/z) [M+1]$^+$ 534.1 (calculated for C$_{25}$H$_{23}$ClF$_3$N$_5$OS, 533.13).

Example 194

4-[5-({1-[4-Chloro-2-(trifluoromethyl)benzyl]-1H-indazol-5-yl}methylidene)-4-oxo-4,5-dihydro-1,3-thiazol-2-yl]morpholine-3-(R)-carboxylic acid

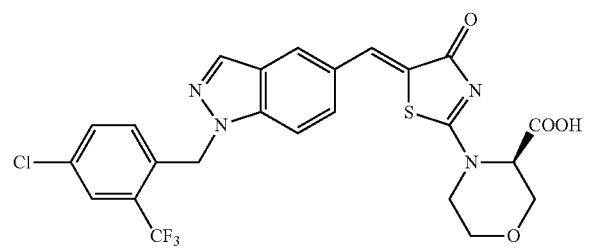 [SMILES: O=C1N=C(N2CCOC[C@@H]2C(=O)O)S/C1=C\c1ccc2c(cnn2Cc2ccc(Cl)cc2C(F)(F)F)c1]

4-[5-({1-[4-Chloro-2-(trifluoromethyl)benzyl]-1H-indazol-5-yl}methylidene)-4-oxo-4,5-dihydro-1,3-thiazol-2-yl]morpholine-3-(R)-carboxylic acid was prepared from 5-[1-(4-Chloro-2-trifluoromethyl-benzyl)-1H-indazol-5-ylmethylene]-2-ethylsulfanyl-thiazol-4-one and Morpholine-3-(R)-carboxylic acid following general procedure C.

$^1$H NMR (400 MHz, CD$_3$OD) δ 8.10 (s, 1H), 7.80 (d, 1H), 7.68 (s, 1H), 7.57 (d, 1H), 7.39 (d, 1H), 7.35 (d, 1H), 7.32 (d, 1H), 6.61 (d, 1H), 5.68 (s, 2H), 5.20 (m, ½H), 4.56 (m, ½H), 4.38-4.53 (1H), 3.55-4.02 (5H).

LC/MS (m/z) [M+1]$^+$ 551.2 (calculated for C$_{24}$H$_{18}$ClF$_3$N$_4$O$_4$S, 550.07).

Example 195

5-({1-[2,4-Bis(trifluoromethyl)benzyl]-1H-indazol-5-yl}methylidene)-2-[3-(R)-(hydroxymethyl)-4-methylpiperazin-1-yl]-1,3-thiazol-4(5H)-one

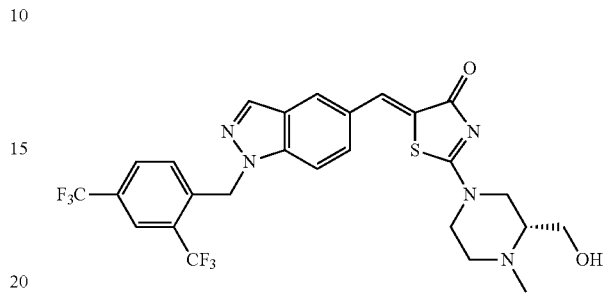

To 4 mL of CH$_2$Cl$_2$ was added 5-({1-[2,4-bis(trifluoromethyl)benzyl]-1H-indazol-5-yl}methylidene)-2-[3-(R)-(hydroxymethyl)-piperazin-1-yl]-1,3-thiazol-4(5H)-one (Example 139, 50 mg), followed by 50 mg of 37% HCHO. The mixture was stirred at room temperature for 20 min, then 50 mg of NaBH(OAc)$_3$ was added. The reaction mixture was kept stirring for 1 h and partitioned between CH$_2$Cl$_2$ and water. The combined organic extracts were washed with brine, dried, and evaporated. The residue was purified by flash column chromatography on silica gel, eluting with EtOAc to MeOH/EtOAc (10/90) to afford the title product.

$^1$H NMR (400 MHz, CD$_3$OD) δ 8.22 (s, 1H), 8.04 (s, 1H), 8.02 (s, 1H), 7.78 (s, 1H), 7.77 (d, 1H), 7.59 (d, 1H), 7.52 (d, 1H), 6.84 (d, 1H), 5.92 (s, 2H), 4.51-4.69 (1H), 3.56-3.93 (4H), 3.49 (m, 1H), 3.00 (m, 1H), 2.30-2.55 (5H).

LC/MS (m/z) [M+1]$^+$ 584.1 (calculated for C$_{26}$H$_{23}$F$_6$N$_5$O$_2$S, 583.15).

Example 196

5-({1-[4-Chloro-2-(trifluoromethyl)benzyl]-1H-indazol-5-yl}methylidene)-2-[3-(R)-(hydroxymethyl)-4-methylpiperazin-1-yl]-1,3-thiazol-4(5H)-one

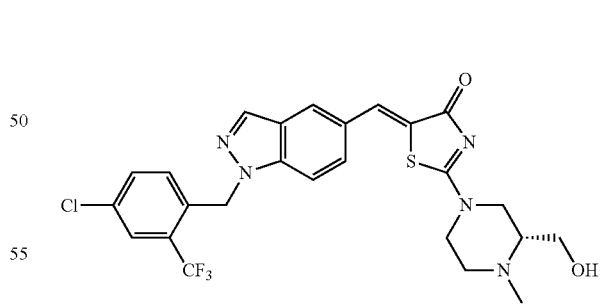

5-({1-[4-Chloro-2-(trifluoromethyl)benzyl]-1H-indazol-5-yl}methylidene)-2-[3-(R)-(hydroxymethyl)-4-methylpiperazin-1-yl]-1,3-thiazol-4(5H)-one was prepared from 5-[1-(4-Chloro-2-trifluoromethyl-benzyl)-1H-indazol-5-ylmethylene]-2-(3-(R)-hydroxymethyl-piperazin-1-yl)-thiazol-4-one and formaldehyde following procedure used for compound of example 195.

$^1$H NMR (400 MHz, CDCl$_3$) δ 8.19 (d, 1H), 7.96 (s, 1H), 7.93 (s, 1H), 7.71 (d, 1H), 7.53 (dd, 1H), 7.33 (d, 1H), 7.31 (d,

1H), 6.66 (d, 1H), 5.78 (d, 2H), 4.72 (m, 1H), 3.91 (dd, 1H), 3.40-3.80 (4H), 2.98 (m, 1H), 2.30-2.53 (5H).
LC/MS (m/z) [M+1]$^+$ 550.1 (calculated for $C_{25}H_{23}ClF_3N_5O_2S$, 549.12).

Example 197

5-({1-[4-Chloro-2-(trifluoromethyl)benzyl]-1H-indazol-5-yl}methylidene)-2-(3-hydroxy-4,7-dihydroisoxazolo[5,4-c]pyridin-6(5H)-yl)-1,3-thiazol-4(5H)-one

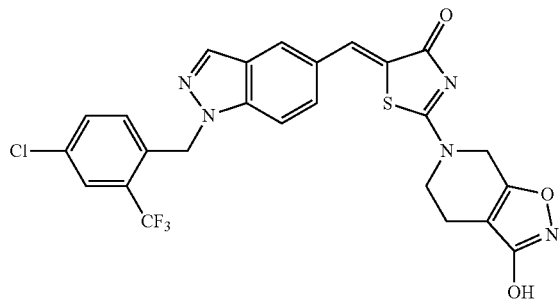 [SMILES: O=C1N=C(N2CCc3c(O)noc3C2)S/C1=C\c1ccc2c(cnn2Cc2ccc(Cl)cc2C(F)(F)F)c1]

5-({1-[4-Chloro-2-(trifluoromethyl)benzyl]-1H-indazol-5-yl}methylidene)-2-(3-hydroxy-4,7-dihydroisoxazolo[5,4-c]pyridin-6(5H)-yl)-1,3-thiazol-4(5H)-one was prepared from 5-[1-(4-Chloro-2-trifluoromethyl-benzyl)-1H-indazol-5-ylmethylene]-2-ethylsulfanyl-thiazol-4-one and 4,5,6,7-Tetrahydro-isoxazolo[5,4-c]pyridin-3-ol following general procedure C.
$^1$H NMR (400 MHz, CD$_3$OD) δ 8.26 (s, 1H), 8.14 (s, 1H), 7.91 (d, 1H), 7.80 (d, 1H), 7.69 (dd, 1H), 7.57 (d, 1H), 7.49 (dd, 1H), 6.69 (d, 1H), 5.87 (s, 2H), 5.05 (s, 1H), 4.84 (s, 1H), 4.28 (t, ½H), 3.98 (t, 3/2H), 2.68 (t, 1H), 2.63 (t, 1H).
LC/MS (m/z) [M+1]$^+$ 560.0 (calculated for $C_{25}H_{17}ClF_3N_5O_3S$, 559.07).

Example 198

1-[5-({1-[4-Chloro-2-(trifluoromethyl)benzyl]-1H-indazol-5-yl}methylidene)-4-oxo-4,5-dihydro-1,3-thiazol-2-yl]-1,2,3,6-tetrahydropyridine-4-carboxylic acid

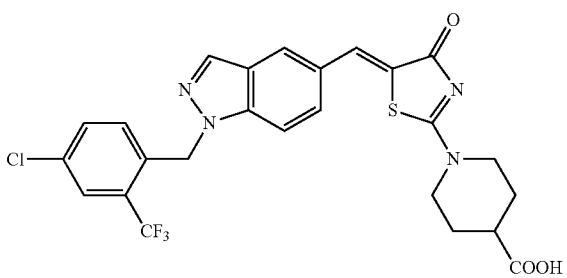 [SMILES: O=C1N=C(N2CCC(C(=O)O)CC2)S/C1=C\c1ccc2c(cnn2Cc2ccc(Cl)cc2C(F)(F)F)c1]

1-[5-({1-[4-Chloro-2-(trifluoromethyl)benzyl]-1H-indazol-5-yl}methylidene)-4-oxo-4,5-dihydro-1,3-thiazol-2-yl]-1,2,3,6-tetrahydropyridine-4-carboxylic acid was prepared from 5-[1-(4-Chloro-2-trifluoromethyl-benzyl)-1H-indazol-5-ylmethylene]-2-ethylsulfanyl-thiazol-4-one and 1,2,3,6-Tetrahydro-pyridine-4-carboxylic acid following general procedure C.

$^1$H NMR (400 MHz, CD$_3$OD) δ 8.26 (m, 1H), 8.14 (s, 1H), 7.90 (d, 1H), 7.80 (d, 1H), 7.69 (d, 1H), 7.58 (d, 1H), 7.49 (dd, 1H), 6.98 (m, 1H), 6.69 (d, 1H), 5.87 (s, 2H), 4.63 (m, 2H), 4.42 (m, ½H), 4.15 (m, ½H), 3.86 (t, 1H), 2.55-2.66 (2H).
LC/MS (m/z) [M+1]$^+$ 547.0 (calculated for $C_{25}H_{18}ClF_3N_4O_3S$, 546.07).

Example 199

5-({1-[4-Chloro-2-(trifluoromethyl)benzyl]-1H-indazol-5-yl}methylidene)-2-[4-(2-methoxyethyl)-2-(R)-methylpiperazin-1-yl]-1,3-thiazol-4(5H)-one

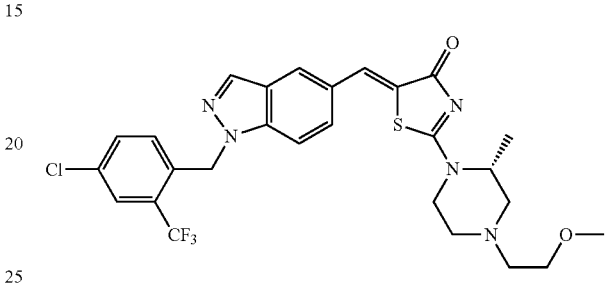

5-({1-[4-Chloro-2-(trifluoromethyl)benzyl]-1H-indazol-5-yl}methylidene)-2-[4-(2-methoxyethyl)-2-(R)-methylpiperazin-1-yl]-1,3-thiazol-4(5H)-one was prepared from 5-[1-(4-Chloro-2-trifluoromethyl-benzyl)-1H-indazol-5-ylmethylene]-2-ethylsulfanyl-thiazol-4-one and 1-(2-Methoxy-ethyl)-3-(R)-methyl-piperazine following general procedure C.
$^1$H NMR (400 MHz, CD$_3$OD) δ 8.24 (s, 1H), 8.09 (s, 1H), 7.84 (s, 1H), 7.80 (d, 1H), 7.65 (dd, 1H), 7.55 (d, 1H), 7.48 (dd, 1H), 6.68 (d, 1H), 5.85 (s, 2H), 4.56 (d, ½H), 4.13 (m, ½H), 3.72 (m, 1H), 3.47-3.59 (3H), 3.37 (s, 3H), 3.06 (dd, 1H), 2.96 (dd, 1H), 2.54-2.67 (2H), 2.39 (m, 1H), 2.26 (m, 1H), 1.48 (dd, 3H).
LC/MS (m/z) [M+1]$^+$ 578.2 (calculated for $C_{27}H_{27}ClF_3N_5O_2S$, 577.15).

Example 200

5-({1-[2,4-Bis(trifluoromethyl)benzyl]-1H-indazol-5-yl}methylidene)-2-[3-(S)-(hydroxymethyl)piperazin-1-yl]-1,3-thiazol-4(5H)-one

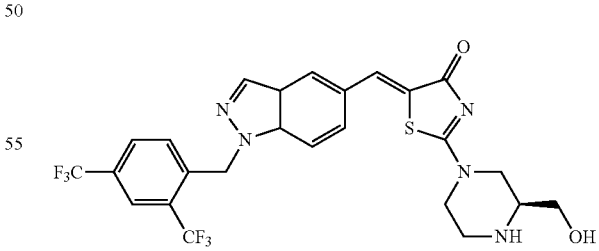

A. 4-{5-[1-(2,4-Bis-trifluoromethyl-benzyl)-1H-indazol-5-ylmethylene]-4-oxo-4,5-dihydro-thiazol-2-yl}-2-(S)-hydroxymethyl-piperazine-1-carboxylic acid tert-butyl ester was prepared from 5-[1-(2,4-Bis-trifluoromethyl-benzyl)-1H-indazol-5-ylmethylene]-2-ethylsulfanyl-thiazol-4-one and 2-(S)-Hydroxymethyl-piperazine-1-carboxylic acid tert-butyl ester following general procedure C.

LC/MS (m/z) [M+1]+ 670.3 (calculated for $C_{30}H_{29}F_6N_5O_4S$, 669.18).

B. 5-({1-[2,4-Bis(trifluoromethyl)benzyl]-1H-indazol-5-yl}methylidene)-2-[3-(S)-(hydroxymethyl)piperazin-1-yl]-1,3-thiazol-4(5H)-one was prepared from 4-{5-[1-(2,4-Bis-trifluoromethyl-benzyl)-1H-indazol-5-ylmethylene]-4-oxo-4,5-dihydro-thiazol-2-yl}-2-(S)-hydroxymethyl-piperazine-1-carboxylic acid tert-butyl ester following General Procedure H.

$^1$H NMR (400 MHz, CD$_3$OD) δ 8.27 (s, 1H), 8.14 (s, 1H), 8.06 (s, 1H), 7.94 (s, 1H), 7.80 (d, 1H), 7.68 (d, 1H), 7.59 (d, 1H), 6.88 (d, 1H), 5.97 (s, 2H), 4.83-4.94 (1H), 4.14 (m, 1H), 3.71-3.92 (3H), 3.51-3.68 (3H), 3.35-3.46 (1H).

LC/MS (m/z) [M+1]+ 570.3 (calculated for $C_{25}H_{21}F_6N_5O_2S$, 569.13).

Example 201

2-[2-(Aminomethyl)morpholin-4-yl]-5-({1-[2,4-bis(trifluoromethyl)benzyl]-1H-indazol-5-yl}methylidene)-1,3-thiazol-4(5H)-one

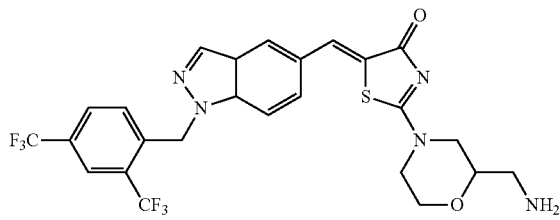 [SMILES: NCC1CN(C2=NC(=O)/C(=C/C3=CC4C=NN(Cc5ccc(C(F)(F)F)cc5C(F)(F)F)C4C=C3)S2)CCO1]

A. (4-{5-[1-(2,4-Bis-trifluoromethyl-benzyl)-1H-indazol-5-ylmethylene]-4-oxo-4,5-dihydro-thiazol-2-yl}-morpholin-2-ylmethyl)-carbamic acid tert-butyl ester was prepared from 5-[1-(2,4-Bis-trifluoromethyl-benzyl)-1H-indazol-5-ylmethylene]-2-ethylsulfanyl-thiazol-4-one and Morpholin-2-ylmethyl-carbamic acid tert-butyl ester following General Procedure C.

LC/MS (m/z) [M+1]+ 670.3 (calculated for $C_{30}H_{29}F_6N_5O_4S$, 669.18).

B. 2-[2-(Aminomethyl)morpholin-4-yl]-5-({1-[2,4-bis(trifluoromethyl)benzyl]-1H-indazol-5-yl}methylidene)-1,3-thiazol-4(5H)-one was prepared from (4-{5-[1-(2,4-Bis-trifluoromethyl-benzyl)-1H-indazol-5-ylmethylene]-4-oxo-4,5-dihydro-thiazol-2-yl}-morpholin-2-ylmethyl)-carbamic acid tert-butyl ester following General Procedure H.

$^1$H NMR (400 MHz, CD$_3$OD) δ 8.28 (d, 1H), 8.15 (s, 1H), 8.06 (s, 1H), 7.93 (s, 1H), 7.80 (d, 1H), 7.69 (dd, 1H), 7.60 (dd, 1H), 6.88 (d, 1H), 5.98 (s, 2H), 4.70 (m, 1H), 4.16 (m, 1H), 3.01-3.99 (7H).

LC/MS (m/z) [M+1]+ 570.3 (calculated for $C_{25}H_{21}F_6N_5O_2S$, 569.13).

Example 202

5-({1-[2,4-Bis(trifluoromethyl)benzyl]-1H-indazol-5-yl}methylidene)-2-[3-(2,6-cis-dimethylmorpholin-4-yl)azetidin-1-yl]-1,3-thiazol-4(5H)-one

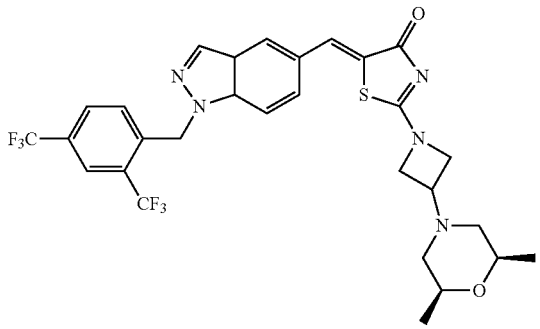 [SMILES: C[C@@H]1CN(C2CN(C3=NC(=O)/C(=C/C4=CC5C=NN(Cc6ccc(C(F)(F)F)cc6C(F)(F)F)C5C=C4)S3)C2)C[C@H](C)O1]

A. 3-(2,6-cis-Dimethyl-morpholin-4-A-azetidine-1-carboxylic acid tert-butyl ester To a CH$_2$Cl$_2$ solution containing 1-Boc-azetidine (459.3 mg, 2.68 mmol) was added 2,6-cis-dimethylmorpholine (311 mg, 2.7 mmol). The mixture was stirred for 20 min, NaBH(OAc)$_3$ (572.2 mg, 2.70 mmol) was added and the resulting mixture was kept stirring for 2 h. It was then partitioned between CH$_2$Cl$_2$ and water. The organic extracts were washed with brine, dried, and evaporated to afford the Boc-protected intermediate.

$^1$H NMR (400 MHz, CDCl$_3$) δ 3.92 (t, 2H), 3.83 (dd, 2H), 3.66-3.74 (2H), 3.05 (m, 1H), 2.66 (d, 2H), 2.09 (d, 2H), 1.44 (s, 9H), 1.18 (d, 6H).

B. 4-Azetidin-3-yl-2,6-(cis)-dimethyl-morpholine was prepared as a TFA salt from 3-(2,6-(cis)-Dimethyl-morpholin-4-yl)-azetidine-1-carboxylic acid tert-butyl ester following General Procedure H.

$^1$H NMR (400 MHz, CD$_3$OD) δ 4.49 (m, 2H), 4.33 (m, 2H), 4.18 (m, 1H), 3.85-3.93 (2H), 3.37 (d, 2H), 2.45 (t, 2H), 1.22 (d, 6H).

LC/MS (m/z) [M+1]+ 171.2 (calculated for $C_9H_{18}N_2O$, 170.14).

C. 5-({1-[2,4-Bis(trifluoromethyl)benzyl]-1H-indazol-5-yl}methylidene)-2-[3-(2,6-cis-dimethylmorpholin-4-yl)azetidin-1-yl]-1,3-thiazol-4(5H)-one was prepared from 5-[1-(2,4-Bis-trifluoromethyl-benzyl)-1H-indazol-5-ylmethylene]-2-ethylsulfanyl-thiazol-4-one and 4-Azetidin-3-yl-2,6-(cis)-dimethyl-morpholine following General Procedure C.

$^1$H NMR (400 MHz, CDCl$_3$) δ 8.21 (d, 1H), 7.99 (s, 1H), 7.97 (s, 1H), 7.92 (s, 1H), 7.63 (dd, 1H), 7.54 (dd, 1H), 7.32 (d, 1H), 6.81 (d, 1H), 5.89 (s, 2H), 4.44 (dd, 1H), 4.30 (dd, 1H), 4.28 (dd, 1H), 4.19 (dd, 1H), 3.70 (m, 2H), 3.45 (m, 1H), 2.67 (m, 2H), 1.76 (dd, 1H), 1.73 (dd, 1H), 1.20 (d, 6H).

LC/MS (m/z) [M+1]+ 624.5 (calculated for $C_{29}H_{27}F_6N_5O_2S$, 623.18).

Example 203

5-({1-[4-Chloro-2-(trifluoromethyl)benzyl]-1H-indazol-5-yl}methylidene)-2-[3-(2,6-cis-dimethylmorpholin-4-yl)azetidin-1-yl]-1,3-thiazol-4(5H)-one

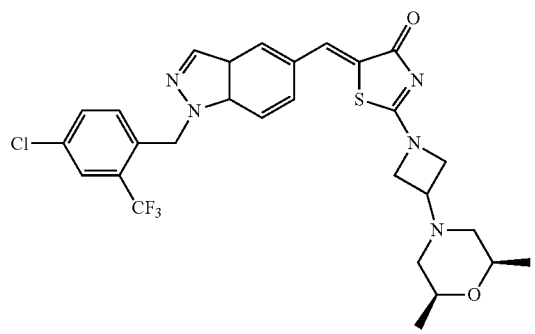 [SMILES: C[C@@H]1CN(C2CN(C3=NC(=O)/C(=C/C4=CC5C=NN(Cc6ccc(Cl)cc6C(F)(F)F)C5C=C4)S3)C2)C[C@H](C)O1]

5-({1-[4-Chloro-2-(trifluoromethyl)benzyl]-1H-indazol-5-yl}methylidene)-2-[3-(2,6-cis-dimethylmorpholin-4-yl)azetidin-1-yl]-1,3-thiazol-4(5H)-one was prepared from 5-[1-(4-Chloro-2-trifluoromethyl-benzyl)-1H-indazol-5-yl-methylene]-2-ethylsulfanyl-thiazol-4-one and 4-Azetidin-3-yl-2,6-(cis)-dimethyl-morpholine following General Procedure C.

¹H NMR (400 MHz, CDCl₃) δ 8.19 (d, 1H), 7.95 (m, 1H), 7.92 (s, 1H), 7.71 (d, 1H), 7.52 (dd, 1H), 7.30-7.35 (2H), 6.65 (d, 1H), 5.79 (s, 2H), 4.44 (m, 1H), 4.30 (dd, 1H), 4.27 (dd, 1H), 4.18 (m, 1H), 3.70 (m, 2H), 3.45 (m, 1H), 2.67 (m, 2H), 1.76 (dd, 1H), 1.73 (dd, 1H), 1.20 (d, 6H).

LC/MS (m/z) [M+1]⁺ 590.4 (calculated for $C_{28}H_{27}ClF_3N_5O_2S$, 589.15).

Example 204

5-({1-[2,4-Bis(trifluoromethyl)benzyl]-1H-indazol-5-yl}methylidene)-2-(3-morpholin-4-ylazetidin-1-yl)-1,3-thiazol-4(5H)-one

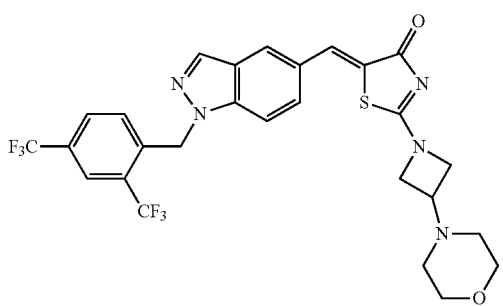 [SMILES: O=C1N=C(N2CC(N3CCOCC3)C2)S/C1=C\c1ccc2c(cnn2Cc2ccc(C(F)(F)F)cc2C(F)(F)F)c1]

5-({1-[2,4-Bis(trifluoromethyl)benzyl]-1H-indazol-5-yl}methylidene)-2-(3-morpholin-4-ylazetidin-1-yl)-1,3-thiazol-4(5H)-one was prepared from 5-[1-(2,4-Bis-trifluoromethyl-benzyl)-1H-indazol-5-ylmethylene]-2-ethylsulfanyl-thiazol-4-one and 4-Azetidin-3-yl-morpholine following General Procedure C.

¹H NMR (400 MHz, CDCl₃) δ 8.22 (d, 1H), 7.99 (d, 1H), 7.97 (m, 1H), 7.93 (s, 1H), 7.63 (dd, 1H), 7.54 (dd, 1H), 7.32 (d, 1H), 6.81 (d, 1H), 5.89 (s, 2H), 4.45 (m, 1H), 4.27-4.33 (2H), 4.18 (m, 1H), 3.77 (t, 4H), 3.49 (m, 1H), 2.45 (m, 4H).

LC/MS (m/z) [M+1]⁺ 596.4 (calculated for $C_{27}H_{23}F_6N_5O_2S$, 595.15).

Example 205

5-({1-[4-Chloro-2-(trifluoromethyl)benzyl]-1H-indazol-5-yl}methylidene)-2-(3-morpholin-4-ylazetidin-1-yl)-1,3-thiazol-4(5H)-one

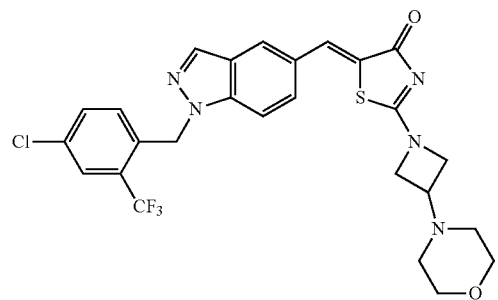 [SMILES: O=C1N=C(N2CC(N3CCOCC3)C2)S/C1=C\c1ccc2c(cnn2Cc2ccc(Cl)cc2C(F)(F)F)c1]

5-({1-[4-Chloro-2-(trifluoromethyl)benzyl]-1H-indazol-5-yl}methylidene)-2-(3-morpholin-4-ylazetidin-1-yl)-1,3-thiazol-4(5H)-one was prepared from 5-[1-(4-Chloro-2-trifluoromethyl-benzyl)-1H-indazol-5-ylmethylene]-2-ethylsulfanyl-thiazol-4-one and 4-Azetidin-3-yl-morpholine following General Procedure C.

¹H NMR (400 MHz, CDCl₃) δ 8.19 (d, 1H), 7.95 (m, 1H), 7.92 (s, 1H), 7.71 (d, 1H), 7.52 (dd, 1H), 7.33 (dd, 1H), 7.31 (d, 1H), 6.65 (d, 1H), 5.79 (s, 2H), 4.45 (dd, 1H), 4.26-4.32 (2H), 4.18 (dd, 1H), 3.77 (t, 4H), 3.48 (m, 1H), 2.45 (m, 4H).

LC/MS (m/z) [M+1]⁺ 562.3 (calculated for $C_{26}H_{23}ClF_3N_5O_2S$, 561.12).

Example 206

5-({1-[4-Chloro-2-(trifluoromethyl)benzyl]-1H-indazol-5-yl}methylidene)-2-[3-(S)-(hydroxymethyl)piperazin-1-yl]-1,3-thiazol-4(5H)-one

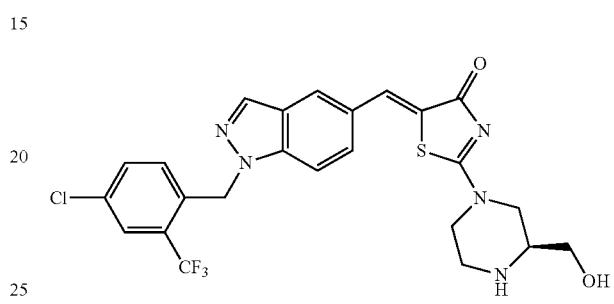

A. 4-{5-[1-(4-Chloro-2-trifluoromethyl-benzyl)-1H-indazol-5-ylmethylene]-4-oxo-4,5-dihydro-thiazol-2-yl}-2-(S)-hydroxymethyl-piperazine-1-carboxylic acid tert-butyl ester was prepared from 5-[1-(4-Chloro-2-trifluoromethyl-benzyl)-1H-indazol-5-ylmethylene]-2-ethylsulfanyl-thiazol-4-one and 2-(S)-Hydroxymethyl-piperazine-1-carboxylic acid tert-butyl ester following General Procedure C.

LC/MS (m/z) [M+1]⁺ 636.3 (calculated for $C_{24}H_{21}ClF_3N_5O_2S$, 635.16).

B. 5-({1-[4-Chloro-2-(trifluoromethyl)benzyl]-1H-indazol-5-yl}methylidene)-2-[3-(S)-(hydroxymethyl)piperazin-1-yl]-1,3-thiazol-4(5H)-one was prepared from 4-{5-[1-(4-Chloro-2-trifluoromethyl-benzyl)-1H-indazol-5-ylmethylene]-4-oxo-4,5-dihydro-thiazol-2-yl}-2-(S)-hydroxymethyl-piperazine-1-carboxylic acid tert-butyl ester following General Procedure H.

¹H NMR (400 MHz, CDCl₃) δ 8.15 (d, 1H), 7.92 (s, 1H), 7.87 (d, 1H), 7.70 (dd, 1H), 7.49 (dd, 1H), 7.32 (m, 1H), 7.27 (dd, 1H), 6.65 (dd, 1H), 5.74 (d, 2H), 4.73 (d, 1H), 3.74 (m, 2H), 3.46-3.69 (2H), 3.13-3.37 (2H), 2.92-3.07 (2H).

LC/MS (m/z) [M+1]⁺ 536.4 (calculated for $C_{24}H_{21}ClF_3N_5O_2S$, 535.11).

Example 207

5-({1-[2,4-Bis(trifluoromethyl)benzyl]-1H-indazol-5-yl}methylidene)-2-[4-tert-butyl-3-(R)-(hydroxymethyl)piperazin-1-yl]-1,3-thiazol-4(5H)-one

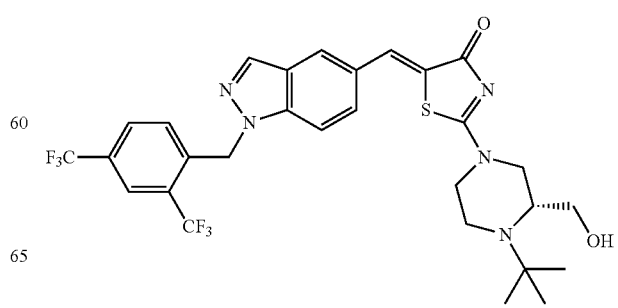

5-({1-[2,4-Bis(trifluoromethyl)benzyl]-1H-indazol-5-yl}methylidene)-2-[4-tert-butyl-3-(R)-(hydroxymethyl)piperazin-1-yl]-1,3-thiazol-4(5H)-one was obtained from 4-{5-[1-(2,4-Bis-trifluoromethyl-benzyl)-1H-indazol-5-ylmethylene]-4-oxo-4,5-dihydro-thiazol-2-yl}-2-(R)-hydroxymethyl-piperazine-1-carboxylic acid tert-butyl ester using General Procedure H.

$^1$H NMR (400 MHz, CDCl$_3$) δ 8.22 (dd, 1H), 7.98-8.00 (2H), 7.94 (s, 1H), 7.63 (d, 1H), 7.56 (dt, 1H), 7.32 (d, 1H), 6.81 (d, 1H), 5.89 (s, 2H), 4.80 (d, 1H), 3.72 (dd, 1H), 2.89-3.52 (7H), 1.19-1.22 (9H).

LC/MS (m/z) [M+1]$^+$ 626.5 (calculated for C$_{29}$H$_{29}$F$_6$N$_5$O$_2$S, 625.19).

Example 208

5-({1-[4-Chloro-2-(trifluoromethyl)benzyl]-1H-indazol-5-yl}methylidene)-2-[3-(R)-(methoxymethyl)piperazin-1-yl]-1,3-thiazol-4(5H)-one

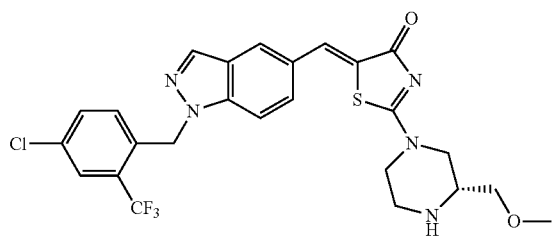 [SMILES: COC[C@H]1CN(C2=NC(=O)/C(=C/c3ccc4c(cnn4Cc4ccc(Cl)cc4C(F)(F)F)c3)S2)CCN1]

A. 4-{5-[1-(4-Chloro-2-trifluoromethyl-benzyl)-1H-indazol-5-ylmethylene]-4-oxo-4,5-dihydro-thiazol-2-yl}-2-(R)-methoxymethyl-piperazine-1-carboxylic acid tert-butyl ester was prepared from 5-[1-(4-Chloro-2-trifluoromethyl-benzyl)-1H-indazol-5-ylmethylene]-2-ethylsulfanyl-thiazol-4-one and 2-(R)-Methoxymethyl-piperazine-1-carboxylic acid tert-butyl ester following General Procedure C.

LC/MS (m/z) [M+1]$^+$ 650.6 (calculated for C$_{30}$H$_{31}$ClF$_3$N$_5$O$_4$S, 649.17).

B. 5-({1-[4-Chloro-2-(trifluoromethyl)benzyl]-1H-indazol-5-yl}methylidene)-2-[3-(R)-(methoxymethyl)piperazin-1-yl]-1,3-thiazol-4(5H)-one was prepared from 4-{5-[1-(4-Chloro-2-trifluoromethyl-benzyl)-1H-indazol-5-ylmethylene]-4-oxo-4,5-dihydro-thiazol-2-yl}-2-(R)-methoxymethyl-piperazine-1-carboxylic acid tert-butyl ester following General Procedure H.

$^1$H NMR (400 MHz, CDCl$_3$) δ 8.18 (s, 1H), 7.95 (s, 1H), 7.91 (d, 1H), 7.71 (d, 1H), 7.52 (dd, 1H), 7.33 (dd, 1H), 7.30 (d, 1H), 6.66 (d, 1H), 5.77 (s, 2H), 4.81 (m, 1H), 3.81 (d, 1H), 3.43-3.71 (5H), 3.39 (d, 3H), 3.02-3.36 (2H).

LC/MS (m/z) [M+1]$^+$ 550.5 (calculated for C$_{25}$H$_{23}$ClF$_3$N$_5$O$_2$S, 549.12).

Example 209

5-({1-[4-Chloro-2-(trifluoromethyl)benzyl]-1H-indazol-5-yl}methylidene)-2-[3-(S)-(methoxymethyl)piperazin-1-yl]-1,3-thiazol-4(5H)-one

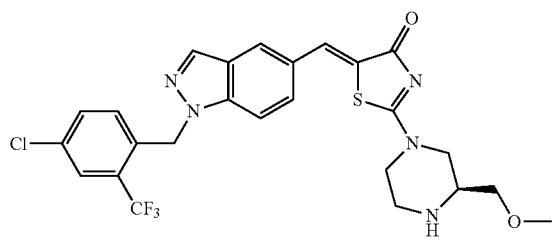 [SMILES: COC[C@@H]1CN(C2=NC(=O)/C(=C/c3ccc4c(cnn4Cc4ccc(Cl)cc4C(F)(F)F)c3)S2)CCN1]

A. 4-{5-[1-(4-Chloro-2-trifluoromethyl-benzyl)-1H-indazol-5-ylmethylene]-4-oxo-4,5-dihydro-thiazol-2-yl}-2-(S)-methoxymethyl-piperazine-1-carboxylic acid tert-butyl ester was prepared from 5-[1-(4-Chloro-2-trifluoromethyl-benzyl)-1H-indazol-5-ylmethylene]-2-ethylsulfanyl-thiazol-4-one and 2-(S)-Methoxymethyl-piperazine-1-carboxylic acid tert-butyl ester following General Procedure C.

LC/MS (m/z) [M+1]$^+$ 650.6 (calculated for C$_{30}$H$_{31}$ClF$_3$N$_5$O$_4$S, 649.17).

B. 5-({1-[4-Chloro-2-(trifluoromethyl)benzyl]-1H-indazol-5-yl}methylidene)-2-[3-(S)-(methoxymethyl)piperazin-1-yl]-1,3-thiazol-4(5H)-one was prepared from 4-{5-[1-(4-Chloro-2-trifluoromethyl-benzyl)-1H-indazol-5-ylmethylene]-4-oxo-4,5-dihydro-thiazol-2-yl}-2-(S)-methoxymethyl-piperazine-1-carboxylic acid tert-butyl ester following General Procedure H.

$^1$H NMR (400 MHz, CDCl$_3$) δ 8.19 (dd, 1H), 7.97 (br s, 1H), 7.93 (s, 1H), 7.71 (d, 1H), 7.54 (dt, 1H), 7.33 (d, 1H), 7.31 (d, 1H), 6.66 (d, 1H), 5.79 (s, 2H), 4.79 (d, 1H), 3.74 (m, 1H), 3.40-3.51 (2H), 3.39 (d, 3H), 3.02-3.35 (4H), 2.94 (m, 1H).

LC/MS (m/z) [M+1]$^+$ 550.5 (calculated for C$_{25}$H$_{23}$ClF$_3$N$_5$O$_2$S, 549.12).

Example 210

5-({1-[2,4-Bis(trifluoromethyl)benzyl]-1H-indazol-5-yl}methylidene)-2-[3-(R)-(methoxymethyl)piperazin-1-yl]-1,3-thiazol-4(5H)-one

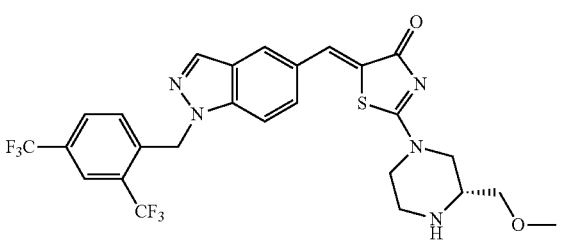 [SMILES: COC[C@H]1CN(C2=NC(=O)/C(=C/c3ccc4c(cnn4Cc4ccc(C(F)(F)F)cc4C(F)(F)F)c3)S2)CCN1]

A. 4-{5-[1-(2,4-Bis-trifluoromethyl-benzyl)-1H-indazol-5-ylmethylene]-4-oxo-4,5-dihydro-thiazol-2-yl}-2-(R)-methoxymethyl-piperazine-1-carboxylic acid tert-butyl ester was prepared from 5-[1-(2,4-Bis-trifluoromethyl-benzyl)-

1H-indazol-5-ylmethylene]-2-ethylsulfanyl-thiazol-4-one and 2-(R)-Methoxymethyl-piperazine-1-carboxylic acid tert-butyl ester following General Procedure C.

LC/MS (m/z) [M+1]+ 684.6 (calculated for $C_{31}H_{31}F_6N_5O_4S$, 683.20).

B. 5-({1-[2,4-Bis(trifluoromethyl)benzyl]-1H-indazol-5-yl}methylidene)-2-[3-(R)-(methoxymethyl)piperazin-1-yl]-1,3-thiazol-4(5H)-one was prepared from 4-{5-[1-(2,4-Bis-trifluoromethyl-benzyl)-1H-indazol-5-ylmethylene]-4-oxo-4,5-dihydro-thiazol-2-yl}-2-(R)-methoxymethyl-piperazine-1-carboxylic acid tert-butyl ester following General Procedure H.

$^1$H NMR (400 MHz, $CD_3OD$) δ 8.26 (s, 1H), 8.11 (d, 1H), 8.05 (s, 1H), 7.96 (s, 1H), 7.80 (d, 1H), 7.65 (d, 1H), 7.58 (d, 1H), 6.88 (d, 1H), 5.94 (s, 2H), 4.80 (t, 1H), 4.24 (m, 1H), 3.52-4.02 (7H), 3.49 (d, 3H).

LC/MS (m/z) [M+1]+ 584.5 (calculated for $C_{26}H_{23}F_6N_5O_2S$, 583.15).

Example 211

5-({1-[2,4-Bis(trifluoromethyl)benzyl]-1H-indazol-5-yl}methylidene)-2-[3-(S)-(methoxymethyl)piperazin-1-yl]-1,3-thiazol-4(5H)-one

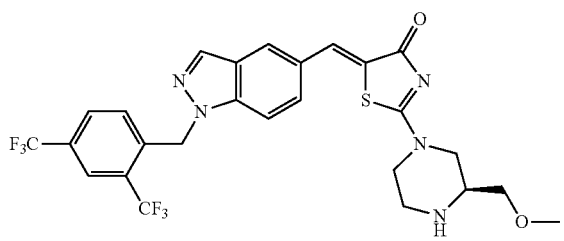 [SMILES: COC[C@@H]1CN(C2=NC(=O)/C(=C/c3ccc4c(cnn4Cc4ccc(C(F)(F)F)cc4C(F)(F)F)c3)S2)CCN1]

A. 4-{5-[1-(2,4-Bis-trifluoromethyl-benzyl)-1H-indazol-5-ylmethylene]-4-oxo-4,5-dihydro-thiazol-2-yl}-2-(S)-methoxymethyl-piperazine-1-carboxylic acid tert-butyl ester was prepared from 5-[1-(2,4-Bis-trifluoromethyl-benzyl)-1H-indazol-5-ylmethylene]-2-ethylsulfanyl-thiazol-4-one and 2-(S)-Methoxymethyl-piperazine-1-carboxylic acid tert-butyl ester following General Procedure C.

LC/MS (m/z) [M+1]+ 684.6 (calculated for $C_{31}H_{31}F_6N_5O_4S$, 683.20).

B. 5-({1-[2,4-Bis(trifluoromethyl)benzyl]-1H-indazol-5-yl}methylidene)-2-[3-(S)-(methoxymethyl)piperazin-1-yl]-1,3-thiazol-4(5H)-one was prepared from 4-{5-[1-(2,4-Bis-trifluoromethyl-benzyl)-1H-indazol-5-ylmethylene]-4-oxo-4,5-dihydro-thiazol-2-yl}-2-(S)-methoxymethyl-piperazine-1-carboxylic acid tert-butyl ester following General Procedure H.

$^1$H NMR (400 MHz, $CD_3OD$) δ 8.21 (s, 1H), 8.04 (br s, 2H), 7.89 (s, 1H), 7.76 (d, 1H), 7.60 (d, 1H), 7.52 (d, 1H), 6.84 (d, 1H), 5.90 (s, 2H), 4.80 (m, 1H), 4.19 (br, 1H), 3.54-3.98 (7H), 3.49 (d, 3H).

LC/MS (m/z) [M+1]+ 584.5 (calculated for $C_{26}H_{23}F_6N_5O_2S$, 583.15).

Example 212

5-({1-[4-Chloro-2-(trifluoromethyl)benzyl]-1H-indazol-5-yl}methylidene)-2-[2-(S)-(hydroxymethyl)morpholin-4-yl]-1,3-thiazol-4(5H)-one

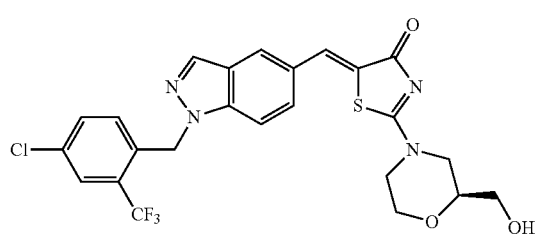 [SMILES: O=C1N=C(N2CCO[C@H](CO)C2)S/C1=C\c1ccc2c(cnn2Cc2ccc(Cl)cc2C(F)(F)F)c1]

5-({1-[4-Chloro-2-(trifluoromethyl)benzyl]-1H-indazol-5-yl}methylidene)-2-[2-(S)-(hydroxymethyl)morpholin-4-yl]-1,3-thiazol-4(5H)-one was prepared from 5-[1-(4-Chloro-2-trifluoromethyl-benzyl)-1H-indazol-5-ylmethylene]-2-ethylsulfanyl-thiazol-4-one and (S)-Morpholin-2-yl-methanol following General Procedure C.

$^1$H NMR (400 MHz, $CDCl_3$) δ 8.20 (dd, 1H), 7.98 (br s, 1H), 7.96 (s, 1H), 7.72 (d, 1H), 7.54 (m, 1H), 7.34 (dd, 1H), 7.32 (d, 1H), 6.67 (d, 1H), 5.79 (s, 2H), 4.82 (m, 1H), 4.12 (m, 1H), 3.25-3.85 (7H).

LC/MS (m/z) [M+1]+ 537.4 (calculated for $C_{24}H_{20}ClF_3N_4O_3S$, 536.09).

Example 213

Methyl {1-[5-({1-[2,4-bis(trifluoromethyl)benzyl]-1H-indazol-5-yl}methylidene)-4-oxo-4,5-dihydro-1,3-thiazol-2-yl]-5-(R)-(hydroxymethyl)pyrrolidin-3-(R)-yl}carbamate

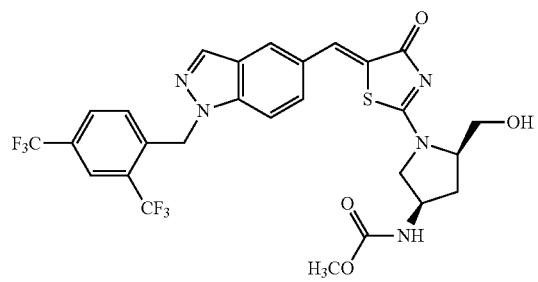 [SMILES: COC(=O)N[C@@H]1C[C@H](CO)N(C2=NC(=O)/C(=C/c3ccc4c(cnn4Cc4ccc(C(F)(F)F)cc4C(F)(F)F)c3)S2)C1]

Methyl {1-[5-({1-[2,4-bis(trifluoromethyl)benzyl]-1H-indazol-5-yl}methylidene)-4-oxo-4,5-dihydro-1,3-thiazol-2-yl]-5-(R)-(hydroxymethyl)pyrrolidin-3-(R)-yl}carbamate was prepared from 5-[1-(2,4-Bis-trifluoromethyl-benzyl)-1H-indazol-5-ylmethylene]-2-ethylsulfanyl-thiazol-4-one and (5-(R)-Methyl-pyrrolidin-3-(R)-yl)-carbamic acid methyl ester following General Procedure C.

$^1$H NMR (400 MHz, $CD_3OD$) δ 8.29 (dd, 1H), 8.14 (m, 1H), 8.06 (br s, 1H), 7.88 (s, 1H), 7.79 (d, 1H), 7.68 (m, 1H), 7.60 (d, 1H), 6.86 (d, 1H), 5.98 (s, 2H), 4.02-4.45 (3H), 3.69 (m, 1H), 3.66 (s, 3H), 3.50 (m, 1H), 2.59 (m, 1H), 2.10 (m, 1H).

LC/MS (m/z) [M+1]+ 628.1 (calculated for $C_{27}H_{23}F_6N_5O_4S$, 627.14).

Example 214

(1R,6R)-7-[5-({1-[2,4-Bis(trifluoromethyl)benzyl]-1H-indazol-5-yl}methylidene)-4-oxo-4,5-dihydro-1,3-thiazol-2-yl]-4-oxa-2,7-diazabicyclo[4.2.1]nonan-3-one

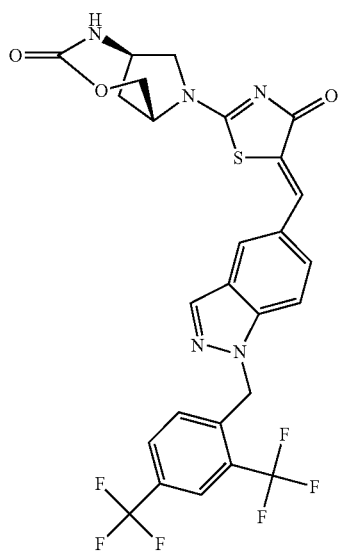 [SMILES: O=C1N[C@@H]2C[C@H](CO1)N(C1=NC(=O)/C(=C/c3ccc4c(cnn4Cc4ccc(C(F)(F)F)cc4C(F)(F)F)c3)S1)C2]

(1R,6R)-7-[5-({1-[2,4-Bis(trifluoromethyl)benzyl]-1H-indazol-5-yl}methylidene)-4-oxo-4,5-dihydro-1,3-thiazol-2-yl]-4-oxa-2,7-diazabicyclo[4.2.1]nonan-3-one was obtained from Methyl {1-[5-({1-[2,4-bis(trifluoromethyl)benzyl]-1H-indazol-5-yl}methylidene)-4-oxo-4,5-dihydro-1,3-thiazol-2-yl]-5-(R)-(hydroxymethyl)pyrrolidin-3-(R)-yl}carbamate (example 213) following General Procedure H.

$^1$H NMR (400 MHz, CDCl$_3$) δ 8.22 (m, 1H), 7.98-7.97 (m, 3H), 7.63 (d, 1H), 7.55 (d, 1H), 7.33 (d, 1H), 6.82 (dd, 1H), 6.57 (d, 1H), 5.88 (s, 2H), 5.06 (s, 1H), 4.80-4.72 (m, 1H) 4.15-3.78 (m, 4H), 2.48-2.15 (m, 2H).

LC/MS (m/z) [M+1]+ 595.1 (calculated for $C_{26}H_{19}F_6N_5O_3S$, 596.1).

Example 215

5-({1-[2,4-Bis(trifluoromethyl)benzyl]-1H-indazol-5-yl}methylidene)-2-[4-(cyclopropylcarbonyl)-3-(R)-(hydroxymethyl)piperazin-1-yl]-1,3-thiazol-4(5H)-one

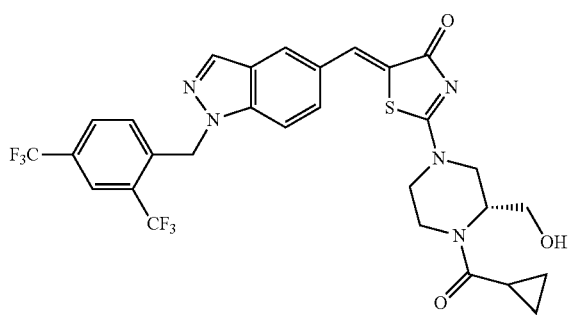 [SMILES: O=C1N=C(N2CCN(C(=O)C3CC3)[C@@H](CO)C2)S/C1=C\c1ccc2c(cnn2Cc2ccc(C(F)(F)F)cc2C(F)(F)F)c1]

5-({1-[2,4-Bis(trifluoromethyl)benzyl]-1H-indazol-5-yl}methylidene)-2-[4-(cyclopropylcarbonyl)-3-(R)-(hydroxymethyl)piperazin-1-yl]-1,3-thiazol-4(5H)-one was prepared from 5-[1-(2,4-Bis-trifluoromethyl-benzyl)-1H-indazol-5-ylmethylene]-2-(3-(R)-hydroxymethyl-piperazin-1-yl)-thiazol-4-one (example 139) and Cyclopropanecarbonyl chloride.

$^1$H NMR (400 MHz, CDCl$_3$) δ 8.19 (s, 1H), 7.99 (br s, 2H), 7.92 (d, 1H), 7.63 (d, 1H), 7.50 (d, 1H), 7.28 (d, 1H), 6.82 (t, 1H), 5.87 (s, 2H), 4.45-5.08 (3H), 3.00-4.26 (6H), 1.81 (m, 1H), 1.05 (m, 2H), 0.87 (m, 2H).

LC/MS (m/z) [M+1]+ 638.5 (calculated for $C_{29}H_{25}F_6N_5O_3S$, 637.16).

Example 216

Methyl 4-[5-({1-[2,4-bis(trifluoromethyl)benzyl]-1H-indazol-5-yl}methylidene)-4-oxo-4,5-dihydro-1,3-thiazol-2-yl]-2-(R)-(hydroxymethyl)piperazine-1-carboxylate

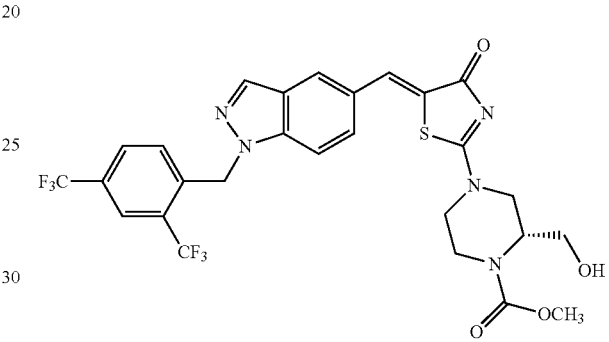

Methyl 4-[5-({1-[2,4-bis(trifluoromethyl)benzyl]-1H-indazol-5-yl}methylidene)-4-oxo-4,5-dihydro-1,3-thiazol-2-yl]-2-(R)-(hydroxymethyl)piperazine-1-carboxylate was prepared from 5-[1-(2,4-Bis-trifluoromethyl-benzyl)-1H-indazol-5-ylmethylene]-2-(3-(R)-hydroxymethyl-piperazin-1-yl)-thiazol-4-one (example 139) and Methyl chloroformate.

$^1$H NMR (400 MHz, CDCl$_3$) δ 8.18-8.20 (1H), 7.98 (s, 1H), 7.91-7.94 (1H), 7.88-7.90 (1H), 7.62 (d, 1H), 7.50 (dd, 1H), 7.29 (d, 1H), 6.80-6.84 (1H), 5.84-5.87 (2H), 4.85 (dd, 1H), 4.43 (br s, 1H), 4.05-4.29 (2H), 3.23-3.84 (8H).

LC/MS (m/z) [M+1]+ 628.5 (calculated for $C_{27}H_{23}F_6N_5O_4S$, 627.14).

Example 217

1-[2,4-Bis(trifluoromethyl)benzyl]-5-({2-[3-(R)-(hydroxymethyl)piperazin-1-yl]-4-oxo-1,3-thiazol-5(4H)-ylidene}methyl)-1H-indazole-3-carbonitrile

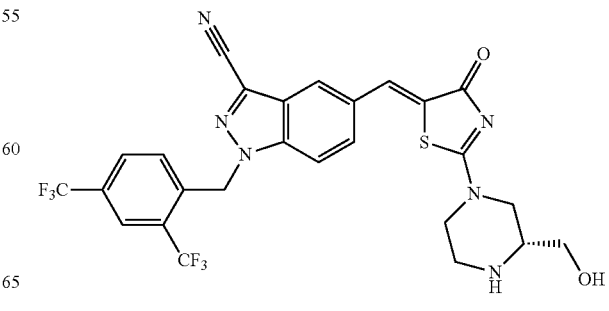

A. 1-(2,4-Bis-trifluoromethyl-benzyl)-5-formyl-1H-indazole-3-carbonitrile

A 5 mL microwave reaction vessel was charged with 1-(2,4-Bis-trifluoromethyl-benzyl)-3-iodo-1H-indazole-5-carbaldehyde (300 mg, 0.6 mmol), copper (I) cyanide (135 mg, 1.5 mmol), and N,N-dimethylformamide (4 mL). The vessel was sealed and subjected to microwave irradiation at 185° C. for 15 min. The reaction mixture was partitioned between EtOAc and water. The organic layers were washed with brine, dried over $Na_2SO_4$, and evaporated. The crude residue was purified by flash column chromatography on silica gel, eluting with EtOAc/hexanes (1:4 v/v), to afford the title compound as a white solid.

$^1$H NMR (400 MHz, $CDCl_3$) δ 10.15 (s, 1H), 8.44 (s, 1H), 8.30 (s, 1H), 8.07 (m, 1H), 7.74 (m, 1H), 7.51 (d, 1H), 7.00 (d, 1H), 5.96 (s, 2H).

B. 4-{5-[1-(2,4-Bis-trifluoromethyl-benzyl)-3-cyano-1H-indazol-5-ylmethylene]-4-oxo-4,5-dihydro-thiazol-2-yl}-2-(R)-hydroxymethyl-piperazine-1-carboxylic acid tert-butyl ester was prepared from 1-(2,4-Bis-trifluoromethyl-benzyl)-5-(2-ethylsulfanyl-4-oxo-4H-thiazol-5-ylidenemethyl)-1H-indazole-3-carbonitrile and 2-(R)-Hydroxymethyl-piperazine-1-carboxylic acid tert-butyl ester following General Procedure C.

LC/MS (m/z) [M+1]$^+$ 695.3 (calculated for $C_{31}H_{28}F_6N_6O_4S$, 694.18).

C. 1-[2,4-Bis(trifluoromethyl)benzyl]-5-({2-[3-(R)-(hydroxymethyl)piperazin-1-yl]-4-oxo-1,3-thiazol-5(4H)-ylidene}methyl)-1H-indazole-3-carbonitrile was prepared from 4-{5-[1-(2,4-Bis-trifluoromethyl-benzyl)-3-cyano-1H-indazol-5-ylmethylene]-4-oxo-4,5-dihydro-thiazol-2-yl}-2-(R)-hydroxymethyl-piperazine-1-carboxylic acid tert-butyl ester following General Procedure H.

$^1$H NMR (400 MHz, $CD_3OD$) δ 8.07 (s, 1H), 7.89 (d, 1H), 7.86 (d, 1H), 7.78 (d, 1H), 7.74 (d, 1H), 7.71 (br s, 1H), 7.13 (d, 1H), 6.04 (s, 2H), 4.84 (m, 1H), 4.19 (m, 1H), 3.42-3.98 (7H).

LC/MS (m/z) [M+1]$^+$ 595.2 (calculated for $C_{26}H_{20}F_6N_6O_2S$, 594.1).

Example 218

1-[2,4-Bis(trifluoromethyl)benzyl]-5-({2-[3-(S)-(hydroxymethyl)piperazin-1-yl]-4-oxo-1,3-thiazol-5(4H)-ylidene}methyl)-1H-indazole-3-carbonitrile

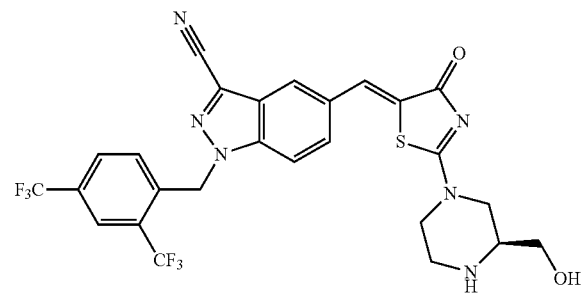 [SMILES: N#Cc1nn(Cc2ccc(C(F)(F)F)cc2C(F)(F)F)c2ccc(/C=C3\SC(N4CCN[C@H](CO)C4)=NC3=O)cc12]

A. 4-{5-[1-(2,4-Bis-trifluoromethyl-benzyl)-3-cyano-1H-indazol-5-ylmethylene]-4-oxo-4,5-dihydro-thiazol-2-yl}-2-(S)-hydroxymethyl-piperazine-1-carboxylic acid tert-butyl ester was prepared from 1-(2,4-Bis-trifluoromethyl-benzyl)-5-(2-ethylsulfanyl-4-oxo-4H-thiazol-5-ylidenemethyl)-1H-indazole-3-carbonitrile and 2-(S)-Hydroxymethyl-piperazine-1-carboxylic acid tert-butyl ester following General Procedure C.

LC/MS (m/z) [M+1]$^+$ 695.3 (calculated for $C_{31}H_{28}F_6N_6O_4S$, 694.18).

B. 1-[2,4-Bis(trifluoromethyl)benzyl]-5-({2-[3-(S)-(hydroxymethyl)piperazin-1-yl]-4-oxo-1,3-thiazol-5(4H)-ylidene}methyl)-1H-indazole-3-carbonitrile was prepared from 4-{5-[1-(2,4-Bis-trifluoromethyl-benzyl)-3-cyano-1H-indazol-5-ylmethylene]-4-oxo-4,5-dihydro-thiazol-2-yl}-2-(S)-hydroxymethyl-piperazine-1-carboxylic acid tert-butyl ester following General Procedure H.

$^1$H NMR (400 MHz, $CD_3OD$) δ 8.07 (s, 1H), 7.86 (d, 1H), 7.83 (d, 1H), 7.74 (d, 1H), 7.67 (d, 1H), 7.66 (d, 1H), 7.12 (d, 1H), 6.03 (s, 2H), 4.86 (m, 1H), 4.16 (m, 1H), 3.41-3.98 (7H).

LC/MS (m/z) [M+1]$^+$ 595.2 (calculated for $C_{26}H_{20}F_6N_6O_2S$, 594.1).

Example 219

5-({1-[2,4-Bis(trifluoromethyl)benzyl]-1H-indazol-5-yl}methylidene)-2-(3,3,4-trimethylpiperazin-1-yl)-1,3-thiazol-4(5H)-one

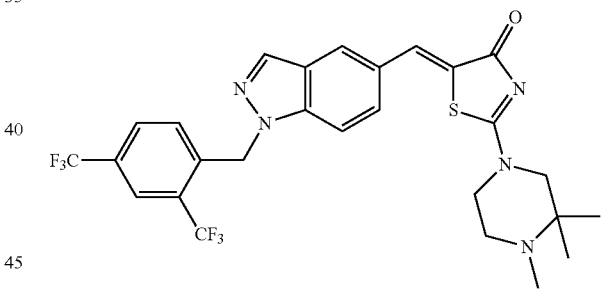

5-({1-[2,4-Bis(trifluoromethyl)benzyl]-1H-indazol-5-yl}methylidene)-2-(3,3,4-trimethylpiperazin-1-yl)-1,3-thiazol-4(5H)-one was prepared from 5-[1-(2,4-Bis-trifluoromethyl-benzyl)-1H-indazol-5-ylmethylene]-2-ethylsulfanyl-thiazol-4-one and 1,2,2-Trimethyl-piperazine following General Procedure C.

$^1$H NMR (400 MHz, $CDCl_3$) δ 8.28 (d, 1H), 8.16 (s, 1H), 8.06 (s, 1H), 7.96 (s, 1H), 7.80 (d, 1H), 7.70 (d, 1H), 7.61 (d, 1H), 6.89 (d, 1H), 5.98 (s, 2H), 3.49-4.21 (6H), 2.91 (s, 3H), 1.29-1.60 (6H).

LC/MS (m/z) [M+1]$^+$ 582.1 (calculated for $C_{27}H_{25}F_6N_5OS$, 581.1).

Example 220

4-[5-({1-[2,4-Bis(trifluoromethyl)benzyl]-1H-indazol-5-yl}methylidene)-4-oxo-4,5-dihydro-1,3-thiazol-2-yl]-N-tert-butylpiperazine-2-(S)-carboxamide

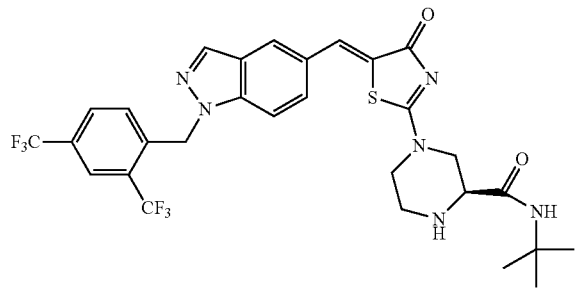 [SMILES: CC(C)(C)NC(=O)[C@@H]1CN(C2=NC(=O)/C(=C/c3ccc4c(cnn4Cc4ccc(C(F)(F)F)cc4C(F)(F)F)c3)S2)CCN1]

4-[5-({1-[2,4-Bis(trifluoromethyl)benzyl]-1H-indazol-5-yl}methylidene)-4-oxo-4,5-dihydro-1,3-thiazol-2-yl]-N-tert-butylpiperazine-2-(S)-carboxamide was prepared from 5-[1-(2,4-Bis-trifluoromethyl-benzyl)-1H-indazol-5-ylmethylene]-2-ethylsulfanyl-thiazol-4-one and piperazine-2-(S)-carboxylic acid tert-butylamide following General Procedure C.

$^1$H NMR (400 MHz, CD$_3$OD) δ 8.25-8.27 (1H), 8.11-8.13 (1H), 8.05 (1H), 7.94 (s, 1H), 7.78 (d, 1H), 7.66 (m, 1H), 7.57 (d, 1H), 6.87 (d, 1H), 5.95 (s, 2H), 4.71-4.95 (1H), 4.30 (m, 1H), 4.16 (m, 1H), 3.88 (m, 1H), 3.62-3.80 (2H), 3.48 (m, 1H), 1.36-1.41 (9H).

LC/MS (m/z) [M+1]$^+$ 639.1 (calculated for C$_{29}$H$_{28}$F$_6$N$_6$O$_2$S, 638.1).

Example 221

5-({1-[4-Chloro-2-(trifluoromethyl)benzyl]-1H-indazol-5-yl}methylidene)-2-(3,3,4-trimethylpiperazin-1-yl)-1,3-thiazol-4(5H)-one

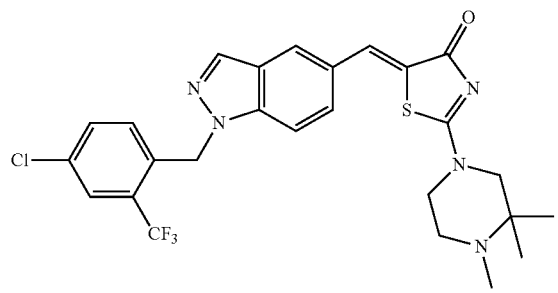 [SMILES: CN1CCN(C2=NC(=O)/C(=C/c3ccc4c(cnn4Cc4ccc(Cl)cc4C(F)(F)F)c3)S2)CC1(C)C]

5-({1-[4-Chloro-2-(trifluoromethyl)benzyl]-1H-indazol-5-yl}methylidene)-2-(3,3,4-trimethylpiperazin-1-yl)-1,3-thiazol-4(5H)-one was prepared from 5-[1-(4-Chloro-2-trifluoromethyl-benzyl)-1H-indazol-5-ylmethylene]-2-ethylsulfanyl-thiazol-4-one and 1,2,2-Trimethyl-piperazine following General Procedure C.

$^1$H NMR (400 MHz, CD$_3$OD) δ 8.25 (d, 1H), 8.15 (s, 1H), 7.96 (s, 1H), 7.81 (d, 1H), 7.69 (d, 1H), 7.58 (dd, 1H), 7.49 (dd, 1H), 6.72 (d, 1H), 5.87 (s, 2H), 3.19-3.62 (6H), 2.92 (s, 3H), 1.39-1.60 (6H).

LC/MS (m/z) [M+1]$^+$ 548.1 (calculated for C$_{26}$H$_{25}$ClF$_3$N$_5$OS, 547.1).

Example 222

1-[4-Chloro-2-(trifluoromethyl)benzyl]-5-{[4-oxo-2-(3,3,4-trimethylpiperazin-1-yl)-1,3-thiazol-5(4H)-ylidene]methyl}-1H-indazole-3-carbonitrile

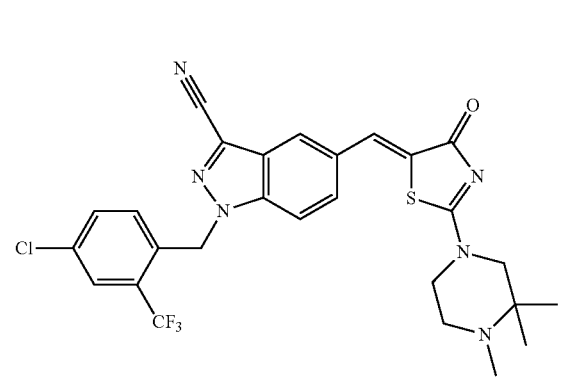 [SMILES: CN1CCN(C2=NC(=O)/C(=C/c3ccc4c(c3)c(C#N)nn4Cc3ccc(Cl)cc3C(F)(F)F)S2)CC1(C)C]

1-[4-Chloro-2-(trifluoromethyl)benzyl]-5-{[4-oxo-2-(3,3,4-trimethylpiperazin-1-yl)-1,3-thiazol-5(4H)-ylidene]methyl}-1H-indazole-3-carbonitrile was prepared from 1-(4-Chloro-2-trifluoromethyl-benzyl)-5-(2-ethylsulfanyl-4-oxo-4H-thiazol-5-ylidenemethyl)-1H-indazole-3-carbonitrile and 1,2,2-Trimethyl-piperazine following General Procedure C.

$^1$H NMR (400 MHz, CD$_3$OD) δ 8.14 (br s, 1H), 7.98 (s, 1H), 7.84 (d, 1H), 7.81 (s, 1H), 7.80 (d, 1H), 7.58 (dd, 1H), 7.00 (d, 1H), 5.97 (s, 2H), 3.10-3.72 (6H), 2.91 (s, 3H), 1.38-1.58 (6H).

LC/MS (m/z) [M+1]$^+$ 573.1 (calculated for C$_{27}$H$_{24}$ClF$_3$N$_6$OS, 572.1).

Example 223

1-[4-Chloro-2-(trifluoromethyl)benzyl]-5-{[2-(4-methylpiperazin-1-yl)-4-oxo-1,3-thiazol-5(4H)-ylidene]methyl}-1H-indazole-3-carbonitrile

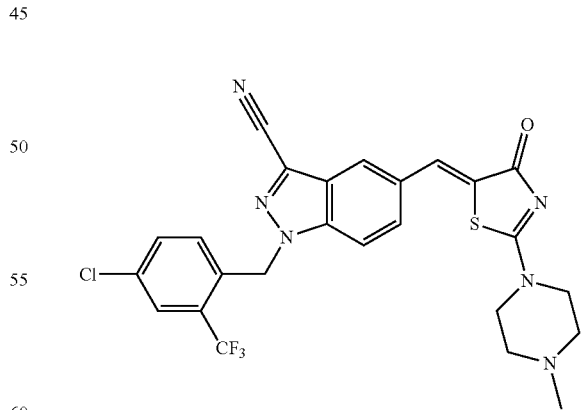

1-[4-Chloro-2-(trifluoromethyl)benzyl]-5-{[2-(4-methylpiperazin-1-yl)-4-oxo-1,3-thiazol-5(4H)-ylidene]methyl}-1H-indazole-3-carbonitrile was prepared from 1-(4-Chloro-2-trifluoromethyl-benzyl)-5-(2-ethylsulfanyl-4-oxo-4H-thiazol-5-ylidenemethyl)-1H-indazole-3-carbonitrile and 1-Methyl-piperazine following General Procedure C.

¹H NMR (400 MHz, CD₃OD) δ 8.00 (s, 1H), 7.86 (s, 1H), 7.83 (d, 1H), 7.76 (br s, 2H), 7.57 (dd, 1H), 6.98 (d, 1H), 5.94 (s, 2H), 4.25 (m, 1H), 3.92 (m, 1H), 3.67-3.78 (3H), 3.35-3.49 (3H), 3.02 (s, 3H).

LC/MS (m/z) [M+1]⁺ 545.2 (calculated for $C_{25}H_{20}ClF_3N_6OS$, 544.1).

Example 224

1-[4-Chloro-2-(trifluoromethyl)benzyl]-5-({2-[4-(cyclopropylmethyl)piperazin-1-yl]-4-oxo-1,3-thiazol-5(4H)-ylidene}methyl)-1H-indazole-3-carbonitrile

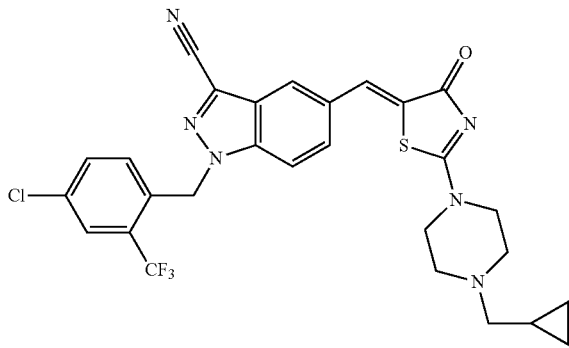 [SMILES: N#Cc1nn(Cc2ccc(Cl)cc2C(F)(F)F)c2ccc(/C=C3\SC(N4CCN(CC5CC5)CC4)=NC3=O)cc12]

1-[4-Chloro-2-(trifluoromethyl)benzyl]-5-({2-[4-(cyclopropylmethyl)piperazin-1-yl]-4-oxo-1,3-thiazol-5(4H)-ylidene}methyl)-1H-indazole-3-carbonitrile was prepared from 1-(4-Chloro-2-trifluoromethyl-benzyl)-5-(2-ethylsulfanyl-4-oxo-4H-thiazol-5-ylidenemethyl)-1H-indazole-3-carbonitrile and 1-Cyclopropylmethyl-piperazine following General Procedure C.

¹H NMR (400 MHz, CD₃OD) δ 7.99 (s, 1H), 7.85 (s, 1H), 7.83 (d, 1H), 7.76 (br s, 2H), 7.57 (dd, 1H), 6.98 (d, 1H), 5.94 (s, 2H), 3.16-4.30 (10H), 1.18-1.40 (1H), 0.80-0.86 (2H), 0.51 (m, 2H).

LC/MS (m/z) [M+1]⁺ 585.2 (calculated for $C_{28}H_{24}ClF_3N_6OS$, 584.1).

Example 225

(5Z)-5-({1-[2,4-Bis(trifluoromethyl)benzyl]-1H-indazol-5-yl}methylidene)-2-[(3S,4S)-3-hydroxy-4-morpholin-4-ylpyrrolidin-1-yl]-1,3-thiazol-4(5H)-one

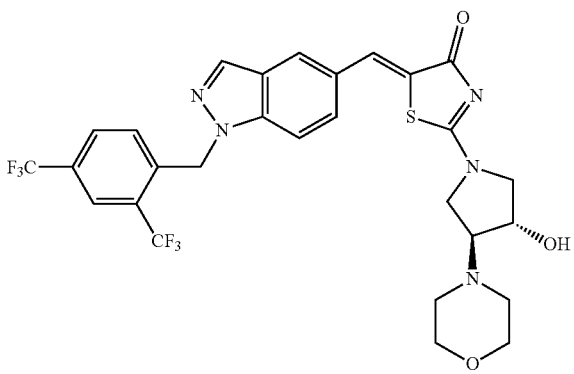 [SMILES: O=C1N=C(N2C[C@H](O)[C@@H](N3CCOCC3)C2)S/C1=C\c1ccc2c(cnn2Cc2ccc(C(F)(F)F)cc2C(F)(F)F)c1]

5-({1-[2,4-Bis(trifluoromethyl)benzyl]-1H-indazol-5-yl}methylidene)-2-[(3S,4S)-3-hydroxy-4-morpholin-4-ylpyrrolidin-1-yl]-1,3-thiazol-4(5H)-one was prepared from 5-[1-(2,4-Bis-trifluoromethyl-benzyl)-1H-indazol-5-ylmethylene]-2-ethylsulfanyl-thiazol-4-one and 4-(3S,4S)-Morpholin-4-yl-pyrrolidin-3-ol following General Procedure C.

¹H NMR (400 MHz, DMSO-d6) δ 8.38 (m, 1H), 8.16 (m, 1H), 8.12 (s, 1H), 7.98 (d, 1H), 7.84 (m, 1H), 7.82 (d, 1H), 7.71 (m, 1H), 6.92 (dd, 1H), 5.99 (s, 2H), 4.86-5.00 (2H), 4.25 (m, 1H), 4.05-4.20 (2H), 3.80-4.05 (5H), 3.71 (m, 1H), 3.55 (m, 1H), 3.19-3.50 (2H).

LC/MS (m/z) [M+1]⁺ 626.2 (calculated for $C_{28}H_{25}F_6N_5O_3S$, 625.14).

Example 226

(2R)-4-[5-({1-[4-Chloro-2-(trifluoromethyl)benzyl]-1H-indazol-5-yl}methylidene)-4-oxo-4,5-dihydro-1,3-thiazol-2-yl]-N-methylpiperazine-2-carboxamide

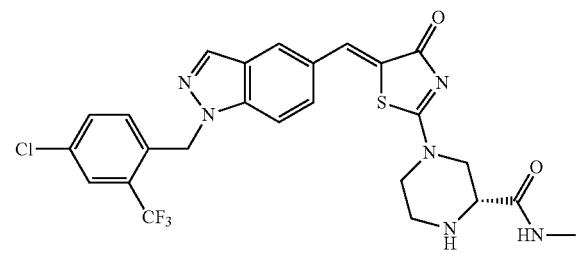 [SMILES: CNC(=O)[C@H]1CN(C2=NC(=O)/C(=C/c3ccc4c(cnn4Cc4ccc(Cl)cc4C(F)(F)F)c3)S2)CCN1]

(2R)-4-[(5Z)-5-({1-[4-Chloro-2-(trifluoromethyl)benzyl]-1H-indazol-5-yl}methylidene)-4-oxo-4,5-dihydro-1,3-thiazol-2-yl]-N-methylpiperazine-2-carboxamide was prepared from 5-[1-(4-Chloro-2-trifluoromethyl-benzyl)-1H-indazol-5-ylmethylene]-2-ethylsulfanyl-thiazol-4-one and (2R)-piperazine-2-carboxylic acid methylamide following General Procedure C.

¹H NMR (400 MHz, CD₃OD) δ 8.15 (d, 1H), 7.99 (d, 1H), 7.85 (d, 1H), 7.76 (d, 1H), 7.53 (d, 1H), 7.44 (s, 1H), 7.43 (s, 1H), 6.64 (d, 1H), 5.74 (m, 2H), 5.04 (m, ½H), 4.77 (m, ½H), 4.53 (m, ½H), 4.41 (m, 1H), 4.20 (m, ½H), 3.94 (m, 1H), 3.67-3.87 (2H), 3.58 (m, 1H), 2.87 (m, 3H).

LC/MS (m/z) [M+1]⁺ 563.1 (calculated for $C_{25}H_{22}ClF_3N_6O_2S$, 562.12).

Example 227

(2R)-4-[5-({1-[2,4-Bis(trifluoromethyl)benzyl]-1H-indazol-5-yl}methylidene)-4-oxo-4,5-dihydro-1,3-thiazol-2-yl]-N-methylpiperazine-2-carboxamide

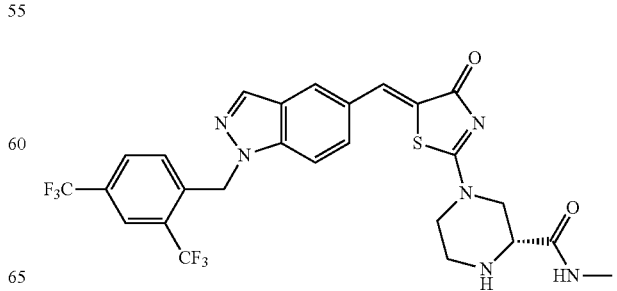

(2R)-4-[5-({1-[2,4-Bis(trifluoromethyl)benzyl]-1H-indazol-5-yl}methylidene)-4-oxo-4,5-dihydro-1,3-thiazol-2-yl]-N-methylpiperazine-2-carboxamide was prepared from 5-[1-(2,4-Bis-trifluoromethyl-benzyl)-1H-indazol-5-ylmethylene]-2-ethylsulfanyl-thiazol-4-one and (2R)-piperazine-2-carboxylic acid methylamide following General Procedure C.

¹H NMR (400 MHz, CD₃OD) δ 8.17 (d, 1H), 8.02 (s, 1H), 8.00 (d, 1H), 7.85 (d, 1H), 7.75 (d, 1H), 7.56 (d, 1H), 7.48 (m, 1H), 6.82 (d, 1H), 5.86 (m, 2H), 5.07 (m, ½H), 4.78 (m, ½H), 4.53 (m, ½H), 4.41 (m, 1H), 4.21 (m, ½H), 3.94 (m, 1H), 3.67-3.87 (2H), 3.58 (m, 1H), 2.87 (m, 3H).

LC/MS (m/z) [M+1]⁺ 597.1 (calculated for $C_{26}H_{22}F_6N_6O_2S$, 596.14).

Example 228

(2S)—N-tert-Butyl-4-[5-({1-[4-chloro-2-(trifluoromethyl)benzyl]-1H-indazol-5-yl}methylidene)-4-oxo-4,5-dihydro-1,3-thiazol-2-yl]piperazine-2-carboxamide

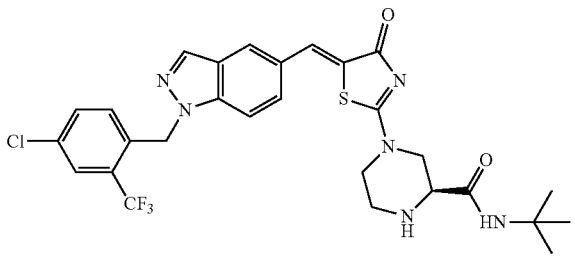 [SMILES: CC(C)(C)NC(=O)[C@@H]1CN(C2=NC(=O)/C(=C/c3ccc4c(cnn4Cc4ccc(Cl)cc4C(F)(F)F)c3)S2)CCN1]

(2S)-4-[5-({1-[4-Chloro-2-(trifluoromethyl)benzyl]-1H-indazol-5-yl}methylidene)-4-oxo-4,5-dihydro-1,3-thiazol-2-yl]-N-methylpiperazine-2-carboxamide was prepared from 5-[1-(4-Chloro-2-trifluoromethyl-benzyl)-1H-indazol-5-ylmethylene]-2-ethylsulfanyl-thiazol-4-one and (2S)-piperazine-2-carboxylic acid methylamide following General Procedure C.

¹H NMR (400 MHz, CD₃OD) δ 8.21 (d, 1H), 8.05 (d, 1H), 7.89 (s, 1H), 7.77 (s, 1H), 7.57 (d, 1H), 7.49 (d, 1H), 7.45 (d, 1H), 6.67 (d, 1H), 5.77 (s, 2H), 4.99 (m, ½H), 4.71 (m, ½H), 4.20-4.44 (2H), 3.53-3.98 (4H), 1.41 (m, 9H).

LC/MS (m/z) [M+1]⁺ 605.2 (calculated for $C_{28}H_{28}Cl_3F_3N_6O_2S$, 604.16).

Example 229

5-({1-[2-Chloro-4-(1-hydroxy-1-methylethyl)benzyl]-1H-indazol-5-yl}methylidene)-2-[3-(R)-(hydroxymethyl)piperazin-1-yl]-1,3-thiazol-4(5H)-one

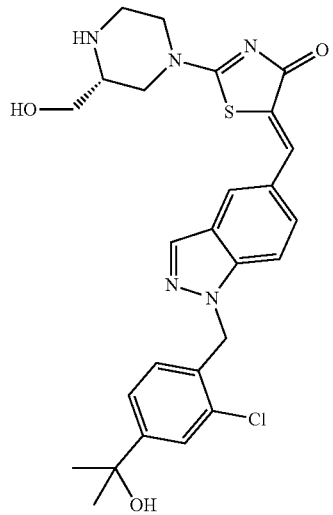 [SMILES: CC(C)(O)c1ccc(Cn2ncc3cc(/C=C4\SC(N5CCN[C@@H](CO)C5)=NC4=O)ccc32)c(Cl)c1]

A. 2-(3-Chloro-4-methyl-phenyl)-propan-2-ol

To a solution of 4-bromo-2-chlorotoluene (10 g, 48.7 mmol) in THF was added n-BuLi at −78° C. After the reaction mixture was stirred at −78° C. for 30 minutes, dry acetone was slowly added. The resulting content was maintained at −78° C. for 3 hours and slowly warmed up to RT overnight. The reaction mixture was then partitioned between ethyl acetate and water. The ethyl acetate layer was then washed with brine, dried over Na₂SO₄, filtered, and the solvent evaporated in vacuo to yield a crude oil. The crude solid was purified via flash chromatography (30% EtOAc in n-hexane) yielded the title compound as an oil (7.2 g, 80%)

¹H NMR (400 MHz, CDCl₃) δ 7.46 (d, 1H), 7.24 (dd, 1H), 7.16 (d, 1H), 2.33 (s, 3H), 1.53 (s, 6H).

B. 2-(4-Bromomethyl-3-chloro-phenyl)-propan-2-ol was prepared following procedure described for example 9-A.

¹H NMR (400 MHz, CDCl3) δ 7.53 (d, 1H), 7.40 (d, 1H), 7.35 (dd, 1H), 4.59 (s, 2H), 1.56 (s, 6H).

C. 4-(5-{1-[2-Chloro-4-(1-hydroxy-1-methyl-ethyl)-benzyl]-1H-indazol-5-ylmethylene}-4-oxo-4,5-dihydro-thiazol-2-yl)-2-(R)-hydroxymethyl-piperazine-1-carboxylic acid tert-butyl ester was prepared from 5-{1-[2-Chloro-4-(1-hydroxy-1-methyl-ethyl)-benzyl]-1H-indazol-5-ylmethylene}-2-ethylsulfanyl-thiazol-4-one and 2-(R)-Hydroxymethyl-piperazine-1-carboxylic acid tert-butyl ester following General Procedure C.

LC/MS (m/z) [M+1]⁺ 626.4 (calculated for $C_{31}H_{36}ClN_5O_5S$, 625.21).

D. 5-({1-[2-Chloro-4-(1-hydroxy-1-methylethyl)benzyl]-1H-indazol-5-yl}methylidene)-2-[3-(R)-(hydroxymethyl)piperazin-1-yl]-1,3-thiazol-4(5H)-one was prepared from 4-(5-{1-[2-Chloro-4-(1-hydroxy-1-methyl-ethyl)-benzyl]-1H-indazol-5-ylmethylene}-4-oxo-4,5-dihydro-thiazol-2-yl)-2-(R)-hydroxymethyl-piperazine-1-carboxylic acid tert-butyl ester following General Procedure H.

¹H NMR (400 MHz, CDCl₃) δ 8.16 (m, 1H), 7.95 (s, 1H), 7.94 (s, 1H), 7.57-7.53 (m, 2H), 7.47 (d, 1H), 7.23 (dd, 1H), 6.83 (d, 1H), 5.70 (s, 2H), 4.76 (t, 1H), 3.78-2.92 (m, 8H), 1.53 (s, 6H).

LC/MS (m/z) [M+1]⁺ 526.1 (calculated for $C_{26}H_{28}ClN_5O_3S$, 525.2).

Example 230

5-({1-[2-Chloro-4-(1-methylethenyl)benzyl]-1H-indazol-5-yl}methylidene)-2-[3-(R)-(hydroxymethyl)piperazin-1-yl]-1,3-thiazol-4(5H)-one

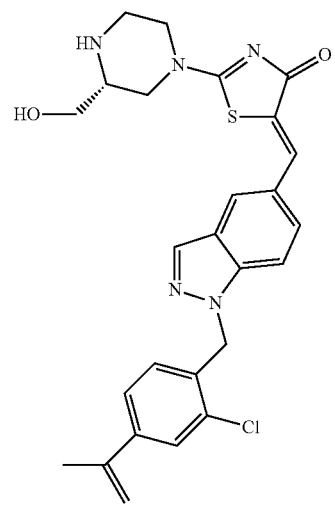 [SMILES: C=C(C)c1ccc(Cn2ncc3cc(/C=C4\SC(N5CCN[C@@H](CO)C5)=NC4=O)ccc32)c(Cl)c1]

407

5-({1-[2-Chloro-4-(1-methylethenyl)benzyl]-1H-indazol-5-yl}methylidene)-2-[3-(R)-(hydroxymethyl)piperazin-1-yl]-1,3-thiazol-4(5H)-one was obtained as a side product during the deprotection of the Boc protecting group of 4-(5-{1-[2-Chloro-4-(1-hydroxy-1-methyl-ethyl)-benzyl]-1H-indazol-5-ylmethylene}-4-oxo-4,5-dihydro-thiazol-2-yl)-2-(R)-hydroxymethyl-piperazine-1-carboxylic acid tert-butyl ester (example 229) following General Procedure H.

$^1$H NMR (400 MHz, CDCl$_3$) δ 8.15 (m, 1H), 7.94 (s, 1H), 7.92 (s, 1H), 7.53 (dd, 1H), 7.49 (d, 1H), 7.44 (d, 1H), 7.23 (dd, 1H), 6.81 (d, 1H), 5.69 (s, 2H), 5.34 (s, 1H), 5.10 (m, 1H) 4.76 (t, 1H), 3.77-2.92 (m, 8H), 2.07 (s, 3H).

LC/MS (m/z) [M+1]$^+$ 506.1 (calculated for C$_{26}$H$_{26}$ClN$_5$O$_2$S, 507.2).

Example 231

5-({1-[2-Chloro-4-(1-hydroxy-1-methylethyl)benzyl]-1H-indazol-5-yl}methylidene)-2-[2-(R)-(hydroxymethyl)morpholin-4-yl]-1,3-thiazol-4(5H)-one

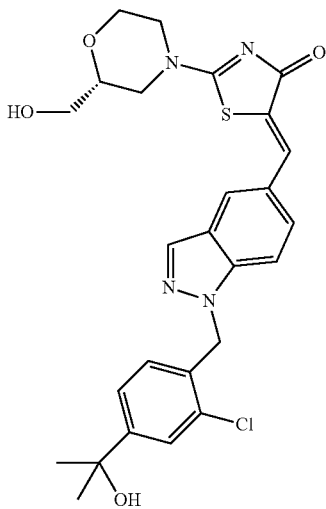 [SMILES: CC(C)(O)c1ccc(Cn2ncc3cc(/C=C4\SC(N5CCO[C@@H](CO)C5)=NC4=O)ccc32)c(Cl)c1]

5-({1-[2-Chloro-4-(1-hydroxy-1-methylethyl)benzyl]-1H-indazol-5-yl}methylidene)-2-[2-(R)-(hydroxymethyl)morpholin-4-yl]-1,3-thiazol-4(5H)-one was prepared from 5-{1-[2-Chloro-4-(1-hydroxy-1-methyl-ethyl)-benzyl]-1H-indazol-5-ylmethylene}-2-ethylsulfanyl-thiazol-4-one and (2R) Morpholin-2-yl-methanol following General Procedure C.

$^1$H NMR (400 MHz, CDCl$_3$) δ 8.12 (s, 1H), 7.91 (br s, 2H), 7.56 (d, 1H), 7.49 (d, 1H), 7.41 (dd, 1H), 7.22 (dd, 1H), 6.81 (d, 1H), 5.66 (d, 2H), 4.77 (t, 1H), 4.04 (d, 1H), 3.79-3.22 (m, 7H), 2.42 (br s, 1H), 1.52 (s, 6H).

LC/MS (m/z) [M+1]$^+$ 527.1 (calculated for C$_{26}$H$_{27}$ClN$_4$O$_4$S, 526.1).

408

Example 232

5-({1-[2-Chloro-4-(1-hydroxy-1-methylethyl)benzyl]-1H-indazol-5-yl}methylidene)-2-(4-methylpiperazin-1-yl)-1,3-thiazol-4(5H)-one

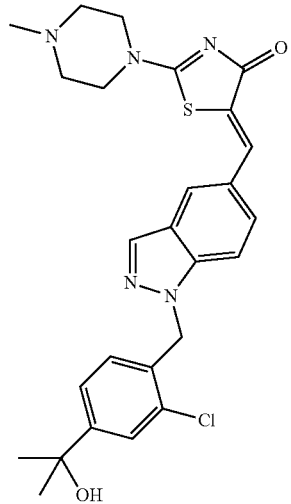 [SMILES: CN1CCN(C2=NC(=O)/C(=C/c3ccc4c(cnn4Cc4ccc(C(C)(C)O)cc4Cl)c3)S2)CC1]

5-({1-[2-Chloro-4-(1-hydroxy-1-methylethyl)benzyl]-1H-indazol-5-yl}methylidene)-2-(4-methylpiperazin-1-yl)-1,3-thiazol-4(5H)-one was prepared from 5-{1-[2-Chloro-4-(1-hydroxy-1-methyl-ethyl)benzyl]-1H-indazol-5-ylmethylene}-2-ethylsulfanyl-thiazol-4-one and 1-Methylpiperazine following General Procedure C.

$^1$H NMR (400 MHz, CDCl$_3$) δ 8.15 (s, 1H), 7.95 (s, 1H), 7.93 (s, 1H), 7.57 (d, 1H), 7.5 (dd, 1H), 7.46 (d, 1H), 7.22 (dd, 1H), 6.82 (d, 1H), 5.69 (s, 2H), 4.08 (t, 2H), 3.66 (t, 3H), 2.56 (m, 4H), 2.36 (s, 3H), 1.86 (br s, 1H), 1.53 (s, 6H).

LC/MS (m/z) [M+1]$^+$ 510.2 (calculated for C$_{26}$H$_{28}$ClN$_5$O$_2$S, 509.1).

Example 233

5-({1-[2-Chloro-4-(1-hydroxy-1-methylethyl)benzyl]-1H-indazol-5-yl}methylidene)-2-(3,5-(cis)-dimethylpiperazin-1-yl)-1,3-thiazol-4(5H)-one

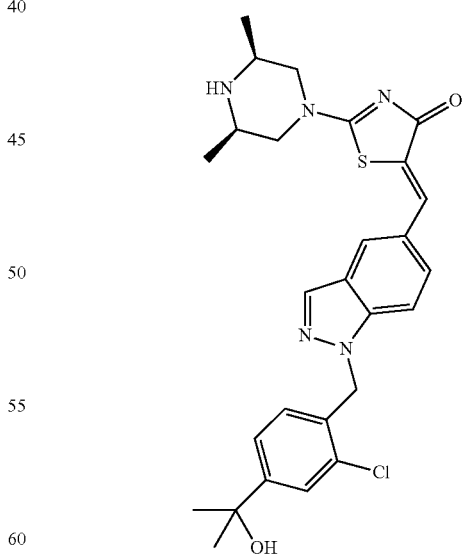

5-({1-[2-Chloro-4-(1-hydroxy-1-methylethyl)benzyl]-1H-indazol-5-yl}methylidene)-2-(3,5-(cis)-dimethylpiperazin-1-yl)-1,3-thiazol-4(5H)-one was prepared from 5-{1-[2-Chloro-4-(1-hydroxy-1-methyl-ethyl)-benzyl]-1H-indazol-5-ylmethylene}-2-ethylsulfanyl-thiazol-4-one and 2,6-(cis)-Dimethyl-piperazine following General Procedure C.

¹H NMR (400 MHz, CDCl₃) δ 8.14 (s, 1H), 7.94 (s, 1H), 7.91 (s, 1H), 7.56 (d, 1H), 7.53 (dd, 1H), 7.45 (d, 1H), 7.22 (dd, 1H), 6.82 (d, 1H), 5.68 (s, 2H), 4.84 (d, 1H), 3.65 (d, 1H), 3.12-2.95 (m, 2H), 2.72 (t, 1H), 1.67 (br s, 2H), 1.52 (s, 6H), 1.18 (d, 3H), 1.12 (d, 3H).
LC/MS (m/z) [M+1]⁺ 524.2 (calculated for C₂₇H₃₀ClN₅O₂S, 523.2).

Example 234

5-({1-[2,4-Bis(trifluoromethyl)benzyl]-1H-indazol-5-yl}methylidene)-2-[2-(S)-(methoxymethyl)morpholin-4-yl]-1,3-thiazol-4(5H)-one

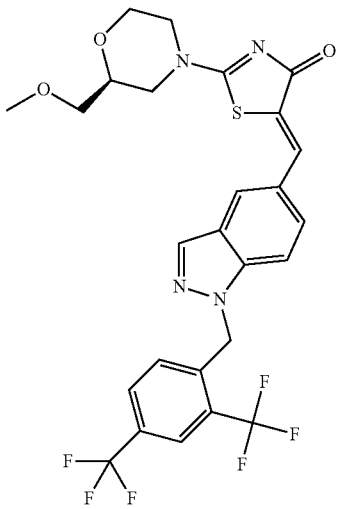 [SMILES: COC[C@@H]1CN(C2=NC(=O)/C(=C/c3ccc4c(cnn4Cc4ccc(C(F)(F)F)cc4C(F)(F)F)c3)S2)CCO1]

A. (2S)-2-Methoxymethyl-morpholine was prepared as described in *J. Med. Chem.* 1994, 37, 2791-2796.
B. 5-({1-[2,4-Bis(trifluoromethyl)benzyl]-1H-indazol-5-yl}methylidene)-2-[2-(S)-(methoxymethyl)morpholin-4-yl]-1,3-thiazol-4(5H)-one was prepared from 5-[1-(2,4-Bis-trifluoromethyl-benzyl)-1H-indazol-5-ylmethylene]-2-ethylsulfanyl-thiazol-4-one and (2S)-2-Methoxymethyl-morpholine following General Procedure C.
¹H NMR (400 MHz, CDCl₃) δ 8.23 (d, 1H), 8.00-7.96 (m, 3H), 7.64 (d, 1H), 7.56 (m, 1H), 7.33 (d, 1H), 6.83 (d, 1H), 5.89 (s, 2H), 4.81 (dd, 1H), 4.11 (dd, 1H), 3.81-3.24 (m, 11H).
LC/MS (m/z) [M+1]⁺ 585.2 (calculated for C₂₆H₂₂F₆N₄O₃S, 584.1).

Example 235

5-({1-[4-Chloro-2-(trifluoromethyl)benzyl]-1H-indazol-5-yl}methylidene)-2-[2-(S)-(methoxymethyl)morpholin-4-yl]-1,3-thiazol-4(5H)-one

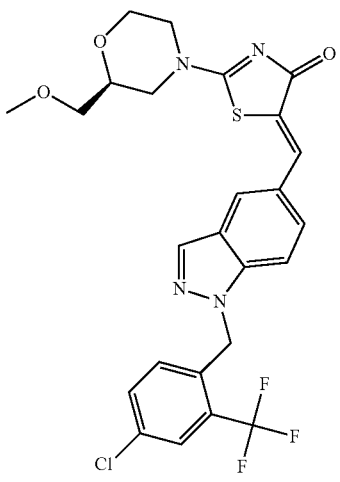 [SMILES: COC[C@@H]1CN(C2=NC(=O)/C(=C/c3ccc4c(cnn4Cc4ccc(Cl)cc4C(F)(F)F)c3)S2)CCO1]

5-({1-[4-Chloro-2-(trifluoromethyl)benzyl]-1H-indazol-5-yl}methylidene)-2-[2-(S)-(methoxymethyl)morpholin-4-yl]-1,3-thiazol-4(5H)-one was prepared from 5-[1-(4-Chloro-2-trifluoromethyl-benzyl)-1H-indazol-5-ylmethylene]-2-ethylsulfanyl-thiazol-4-one and (2S)-2-Methoxymethyl-morpholine following General Procedure C.
¹H NMR (400 MHz, CDCl₃) δ 8.19 (d, 1H), 7.98-7.95 (m, 2H), 7.71 (s, 1H), 7.54 (dd, 1H), 7.35-7.30 (m, 2H), 6.67 (d, 1H), 5.79 (s, 2H), 4.81 (dd, 1H), 4.10 (dd, 1H), 3.79-3.23 (m, 11H).
LC/MS (m/z) [M+1]⁺ 551.2 (calculated for C₂₅H₂₂ClF₃N₄O₃S, 550.1).

Example 236

5-({1-[4-Hydroxy-2-(trifluoromethyl)benzyl]-1H-indazol-5-yl}methylidene)-2-[2(S)-(methoxymethyl)morpholin-4-yl]-1,3-thiazol-4(5H)-one

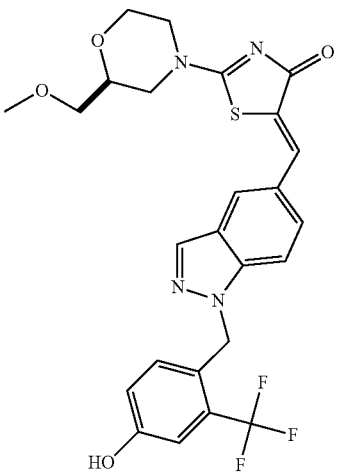 [SMILES: COC[C@@H]1CN(C2=NC(=O)/C(=C/c3ccc4c(cnn4Cc4ccc(O)cc4C(F)(F)F)c3)S2)CCO1]

5-({1-[4-Hydroxy-2-(trifluoromethyl)benzyl]-1H-indazol-5-yl}methylidene)-2-[2(S)-(methoxymethyl)morpholin-4-yl]-1,3-thiazol-4(5H)-one was prepared from 2-Ethylsulfanyl-5-[1-(4-hydroxy-2-trifluoromethyl-benzyl)-1H-indazol-5-ylmethylene]-thiazol-4-one and (2S)-2-Methoxymethyl-morpholine following General Procedure C.
¹H NMR (400 MHz, CDCl₃) δ 10.19 (s, 1H), 8.29 (d, 1H), 8.13 (s, 1H), 7.80 (s, 1H), 7.73-7.66 (m, 2H), 7.12 (d, 1H), 6.92 (dd, 1H), 6.71 (dd, 1H), 5.73 (s, 2H), 4.49 (dd, 1H), 4.98 (t, 1H), 3.80-3.16 (m, 11H).
LC/MS (m/z) [M+1]⁺ 533.2 (calculated for C₂₅H₂₃ClF₃N₄O₄S, 532.1).

Example 237

5-({1-[4-Bromo-2-bis(trifluoromethyl)benzyl]-1H-indazol-5-yl}methylidene)-2-[2-(R)-(hydroxymethyl)morpholin-4-yl]-1,3-thiazol-4(5H)-one

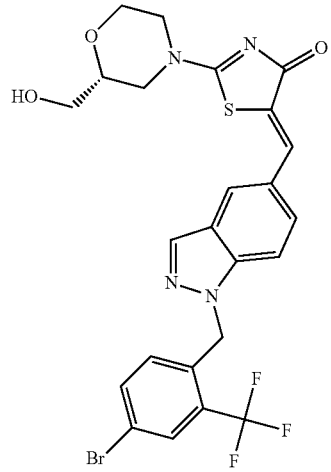 [SMILES: O=C1N=C(N2CCO[C@@H](CO)C2)S/C1=C\c1ccc2c(cnn2Cc2ccc(Br)cc2C(F)(F)F)c1]

5-({1-[4-Bromo-2-bis(trifluoromethyl)benzyl]-1H-indazol-5-yl}methylidene)-2-[2-(R)-(hydroxymethyl)morpholin-4-yl]-1,3-thiazol-4(5H)-one was prepared from 5-[1-(4-Bromo-2-trifluoromethyl-benzyl)-1H-indazol-5-ylmethylene]-2-ethylsulfanyl-thiazol-4-one and (2R)-2-Methoxymethyl-morpholine following General Procedure C.

$^1$H NMR (400 MHz, CDCl$_3$) δ 8.19 (d, 1H), 7.97 (s, 1H), 7.94 (s, 1H), 7.86 (d, 1H), 7.53 (d, 1H), 7.48 (dd, 1H), 7.31 (d, 1H), 6.59 (d, 1H), 5.76 (s, 2H), 4.80 (t, 1H), 4.11 (dd, 1H), 3.85-3.25 (m, 7H).

LC/MS (m/z) [M+1]$^+$ 581.3 (calculated for C$_{24}$H$_{20}$BrF$_3$N$_4$O$_3$S, 580.0).

Example 238

5-({1-[2,4-(trifluoromethyl)benzyl]-1H-indazol-5-yl}methylidene)-2-(3,5-(cis)-dimethylpiperazin-1-yl)-1,3-thiazol-4(5H)-one

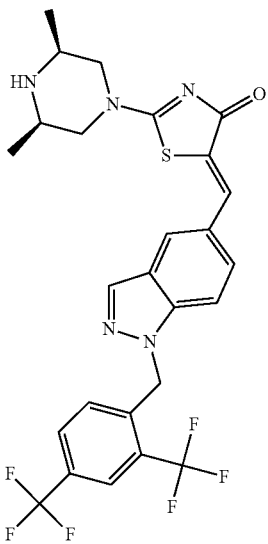

5-({1-[2,4-(trifluoromethyl)benzyl]-1H-indazol-5-yl}methylidene)-2-(3,5-(cis)-dimethylpiperazin-1-yl)-1,3-thiazol-4(5H)-one was prepared from 5-[1-(2,4-Bis-trifluoromethyl-benzyl)-1H-indazol-5-ylmethylene]-2-ethylsulfanyl-thiazol-4-one and 2,6-(cis)-Dimethyl-piperazine following General Procedure C.

$^1$H NMR (400 MHz, CDCl$_3$) δ 8.23 (s, 1H), 7.98 (br s, 2H), 7.91 (s, 1H), 7.63 (d, 1H), 7.55 (dd, 1H), 7.32 (d, 1H), 6.83 (d, 1H), 5.89 (s, 2H), 4.84 (d, 1H), 3.63 (d, 1H), 3.12-2.95 (m, 2H), 2.81 (t, 1H), 2.10 (br s, 1H), 1.21 (d, 3H), 1.15 (d, 3H).

LC/MS (m/z) [M+1]$^+$ 568.2 (calculated for C$_{26}$H$_{23}$F$_6$N$_5$OS, 567.2).

Example 239
5-({1-[2,4-Bis(trifluoromethyl)benzyl]-1H-indazol-5-yl}methylidene)-2-((3R,5S)-3,4,5-trimethylpiperazin-1-yl)-1,3-thiazol-4(5H)-one

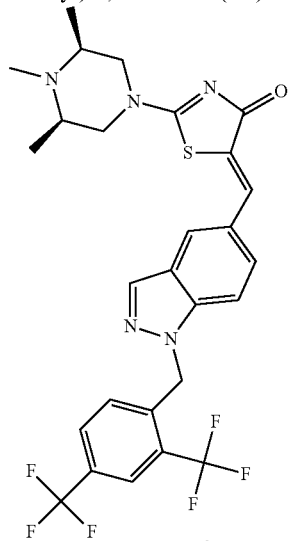

To 4 mL of THF was added 5-({1-[2,4-(trifluoromethyl)benzyl]-1H-indazol-5-yl}methylidene)-2-(3,5-(cis)-dimethylpiperazin-1-yl)-1,3-thiazol-4(5H)-one (example 238, 45 mg), followed by 50 mg of 37% HCHO. The mixture was stirred at room temperature for 20 min, and then 15 mg of NaBH$_3$CN was added. The reaction mixture was kept stirring for 3 h, concentrated in vacuo and partitioned between CH$_2$Cl$_2$ and water. The combined organic extracts were washed with brine, dried, and evaporated. The residue was purified by flash column chromatography on silica gel, eluting with MeOH/Dichloromethane (10/90) to afford the title product.

$^1$H NMR (400 MHz, CDCl$_3$) δ 8.24 (s, 1H), 7.99-7.97 (br s, 2H), 7.91 (s, 1H), 7.63 (d, 1H), 7.55 (dd, 1H), 7.32 (d, 1H), 6.83 (d, 1H), 5.89 (s, 2H), 4.81 (d, 1H), 3.64 (d, 1H), 3.14-2.95 (m, 3H), 2.85 (t, 1H), 2.47 (s, 3H), 1.20 (d, 3H), 1.14 (d, 3H).

LC/MS (m/z) [M+1]$^+$ 582.2 (calculated for C$_{27}$H$_{25}$F$_6$N$_5$OS, 581.2).

Example 240
(2R,6S)-4-[5-({1-[2,4-Bis(trifluoromethyl)benzyl]-1H-indazol-5-yl}methylidene)-4-oxo-4,5-dihydro-1,3-thiazol-2-yl]-1,1,2,6-tetramethylpiperazin-1-ium chloride

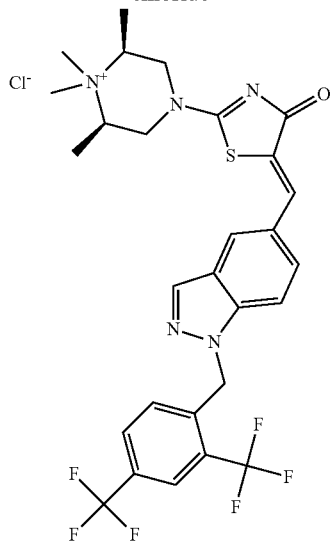

To a solution of 5-({1-[2,4-(trifluoromethyl)benzyl]-1H-indazol-5-yl}methylidene)-2-(3,5-(cis)-dimethylpiperazin-1-yl)-1,3-thiazol-4(5H)-one (50 mg, 0.088 mmol) in DMF (2 mL) was added potassium carbonate (21.2 mg, 0.15 mmol) and methyl iodide (30 mg, 0.21 mmol). After stirring for at room temperature for 15 h, the solid formed was collected by filtration, dried, dissolved in MeOH/dichloromethane and precipitated out with a 1.0M solution of HCl in diethyl ether to give the title compound as a solid.

$^1$H NMR (400 MHz, DMSO-d$_6$) δ 8.33 (s, 1H), 8.16 (s, 1H), 8.10 (s, 1H), 7.96 (d, 1H), 7.85 (s, 1H), 7.81 (d, 1H), 7.70 (d, 1H), 6.94 (d, 1H), 5.97 (s, 2H), 4.63 (d, 1H), 4.02-3.86 (m, 4H), 3.49-3.35 (m, 4h), 3.10 (s, 3H), 2.91 (s, 3H), 2.48 (m, 6H)

LC/MS (m/z) M$^+$ 596.2 (calculated for C$_{28}$H$_{28}$F$_6$N$_6$OS, 596.0).

Example 241

5-({1-[4-Chloro-2-(trifluoromethyl)benzyl]-1H-indazol-5-yl}methylidene)-2-((3R,5S)-3,5-dimethylpiperazin-1-yl)-1,3-thiazol-4(5H)-one

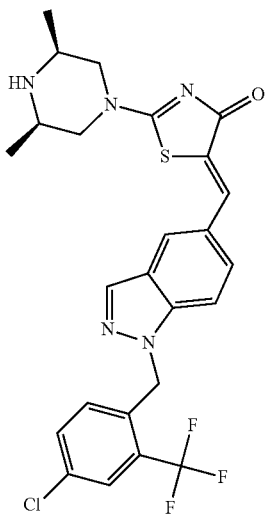 [SMILES: C[C@@H]1CN(C2=NC(=O)/C(=C/c3ccc4c(cnn4Cc4ccc(Cl)cc4C(F)(F)F)c3)S2)C[C@H](C)N1]

5-({1-[4-Chloro-2-(trifluoromethyl)benzyl]-1H-indazol-5-yl}methylidene)-2-((3R,5S)-3,5-dimethylpiperazin-1-yl)-1,3-thiazol-4(5H)-one was prepared from 5-[1-(4-Chloro-2-trifluoromethyl-benzyl)-1H-indazol-5-ylmethylene]-2-ethylsulfanyl-thiazol-4-one and (2R,6S) 2,6-Dimethyl-piperazine following General Procedure C.

$^1$H NMR (400 MHz, CDCl$_3$) δ 8.19 (s, 1H), 7.97 (s, 1H), 7.93 (s, 1H), 7.71 (d, 1H), 7.55 (d, 1H), 7.35-7.30 (m, 2H), 6.66 (d, 1H), 5.79 (s, 2H), 4.85 (d, 1H), 3.64 (d, 1H), 3.05-2.95 (m, 3H), 2.75 (t, 1H), 1.80 (br s, 1H), 1.19 (d, 3H), 1.14 (d, 3H).

LC/MS (m/z) [M+1]$^+$ 568.2 (calculated for C$_{25}$H$_{23}$ClF$_3$N$_5$OS, 567.2).

Example 242

5-({1-[4-(1-Hydroxy-1-methylethyl)-2-(trifluoromethyl)benzyl]-1H-indazol-5-yl}methylidene)-2-(4-methylpiperazin-1-yl)-1,3-thiazol-4(5H)-one

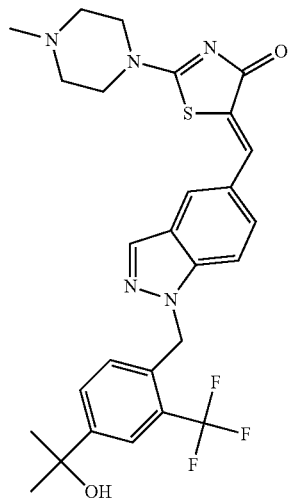 [SMILES: CN1CCN(C2=NC(=O)/C(=C/c3ccc4c(cnn4Cc4ccc(C(C)(C)O)cc4C(F)(F)F)c3)S2)CC1]

A. 2-(4-Methyl-3-trifluoromethyl-phenyl)-propan-2-ol

To a solution of 4-Bromo-1-methyl-2-trifluoromethyl-benzene (3.4 g, 14.2 mmol) in THF was added n-BuLi at −78° C. After the reaction mixture was stirred at −78° C. for 30 minutes, dry acetone was slowly added. The resulting content was maintained at −78° C. for 3 hours and slowly warmed up to RT overnight. The reaction mixture was then partitioned between ethyl acetate and water. The ethyl acetate layer was then washed with brine, dried over Na$_2$SO$_4$, filtered, and the solvent evaporated in vacuo to yield a crude oil. The crude solid was purified via flash chromatography (15% EtOAc in n-hexane) yielded the title compound as an oil (2.7 g, 86%).

$^1$H NMR (400 MHz, CDCl3) δ 7.73 (d, 1H), 7.53 (dd, 1H), 7.25 (d, 1H), 2.47 (q, 3H), 1.58 (s, 6H).

B. 2-(4-Bromomethyl-3-trifluoromethyl-phenyl)-propan-2-ol was prepared following procedure described for example 9-A.

$^1$H NMR (400 MHz, CDCl3) δ 7.78 (d, 1H), 7.65 (dd, 1H), 7.55 (d, 1H), 4.63 (s, 2H), 1.59 (s, 6H).

C. 5-({1-[4-(1-Hydroxy-1-methylethyl)-2-(trifluoromethyl)benzyl]-1H-indazol-5-yl}methylidene)-2-(4-methylpiperazin-1-yl)-1,3-thiazol-4(5H)-one was prepared from 2-Ethylsulfanyl-5-{1-[4-(1-hydroxy-1-methyl-ethyl)-2-trifluoromethyl-benzyl]-1H-indazol-5-ylmethylene}-thiazol-4-one and 1-Methyl-piperazine following General Procedure C.

$^1$H NMR (400 MHz, CDCl$_3$) δ 8.18 (s, 1H), 7.98 (s, 1H), 7.93 (s, 1H), 7.87 (d, 1H), 7.53 (dd, 1H), 7.45 (dd, 1H), 7.34 (d, 1H), 6.66 (d, 1H), 5.82 (s, 2H), 4.10 (t, 2H), 3.65 (t, 3H), 2.57 (m, 4H), 2.37 (s, 3H), 1.55 (s, 6H).

LC/MS (m/z) [M+1]+ 544.2 (calculated for $C_{27}H_{28}F_3N_5O_2S$, 543.2).

Example 243

2-((3R,5S)-3,5-Dimethylpiperazin-1-yl)-5-({1-[4-(1-hydroxy-1-methylethyl)-2-(trifluoromethyl)benzyl]-1H-indazol-5-yl}methylidene)-1,3-thiazol-4(5H)-one

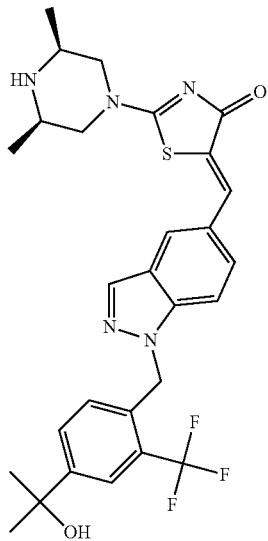 [SMILES: C[C@@H]1CN(C2=NC(=O)/C(=C/c3ccc4c(cnn4Cc4ccc(C(C)(C)O)cc4C(F)(F)F)c3)S2)C[C@H](C)N1]

2-((3R,5S)-3,5-Dimethylpiperazin-1-yl)-5-({1-[4-(1-hydroxy-1-methylethyl)-2-(trifluoromethyl)benzyl]-1H-indazol-5-yl}methylidene)-1,3-thiazol-4(5H)-one was prepared from 2-Ethylsulfanyl-5-{1-[4-(1-hydroxy-1-methyl-ethyl)-2-trifluoromethyl-benzyl]-1H-indazol-5-ylmethylene}-thiazol-4-one and (2R,6S) 2,6-Dimethyl-piperazine following General Procedure C.

$^1$H NMR (400 MHz, CDCl$_3$) δ 8.16 (s, 1H), 7.94 (s, 1H), 7.89 (s, 1H), 7.85 (s, 1H), 7.50 (d, 1H), 7.42 (d, 1H), 7.31 (d, 1H), 6.63 (d, 1H), 5.79 (s, 2H), 4.82 (d, 1H), 3.62 (d, 1H), 3.01-2.91 (m, 2H), 2.70 (t, 1H), 2.15 (br s, 1H), 1.53 (s, 6H), 1.17 (d, 3H), 1.10 (d, 3H).

LC/MS (m/z) [M+1]+ 558.3 (calculated for $C_{28}H_{30}F_3N_5O_2S$, 557.2).

Example 244

5-({1-[4-(1-Hydroxy-1-methylethyl)-2-(trifluoromethyl)benzyl]-1H-indazol-5-yl}methylidene)-2-[2-(S)-(hydroxymethyl)morpholin-4-yl]-1,3-thiazol-4(5H)-one

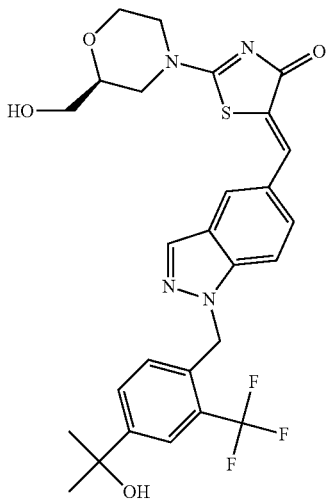 [SMILES: CC(C)(O)c1ccc(Cn2ncc3cc(/C=C4\SC(N5CCO[C@H](CO)C5)=NC4=O)ccc32)c(C(F)(F)F)c1]

5-({1-[4-(1-Hydroxy-1-methylethyl)-2-(trifluoromethyl)benzyl]-1H-indazol-5-yl}methylidene)-2-[2-(S)-(hydroxymethyl)morpholin-4-yl]-1,3-thiazol-4(5H)-one was prepared from 2-Ethylsulfanyl-5-{1-[4-(1-hydroxy-1-methyl-ethyl)-2-trifluoromethyl-benzyl]-1H-indazol-5-ylmethylene}-thiazol-4-one and (2S) Morpholin-2-yl-methanol following General Procedure C.

$^1$H NMR (400 MHz, CDCl$_3$) δ 8.15 (s, 1H), 7.92 (s, 1H), 7.90 (s, 1H), 7.87 (s, 1H), 7.48-7.44 (m, 2H), 7.29 (dd, 1H), 6.64 (d, 1H), 5.79-5.77 (2H), 4.75 (dd, 1H), 4.08 (dd, 1H), 3.79-2.75 (m, 8H), 1.54 (s, 6H).

LC/MS (m/z) [M+1]+ 561.3 (calculated for $C_{27}H_{27}ClF_3N_4O_4S$, 560.2).

Example 245

4-[(5Z)-5-({1-[4-(1-Hydroxy-1-methylethyl)-2-(trifluoromethyl)benzyl]-1H-indazol-5-yl}methylidene)-4-oxo-4,5-dihydro-1,3-thiazol-2-yl]piperazine-1-carboxylic acid

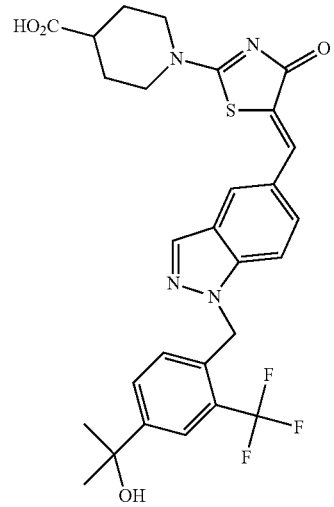 [SMILES: CC(C)(O)c1ccc(Cn2ncc3cc(/C=C4\SC(N5CCC(C(=O)O)CC5)=NC4=O)ccc32)c(C(F)(F)F)c1]

4-[(5Z)-5-({1-[4-(1-Hydroxy-1-methylethyl)-2-(trifluoromethyl)benzyl]-1H-indazol-5-yl}methylidene)-4-oxo-4,5-dihydro-1,3-thiazol-2-yl]piperazine-1-carboxylic acid was prepared from 2-Ethylsulfanyl-5-{1-[4-(1-hydroxy-1-methyl-ethyl)-2-trifluoromethyl-benzyl]-1H-indazol-5-ylmethylene}-thiazol-4-one and Piperidine-4-carboxylic acid following General Procedure C.

$^1$H NMR (400 MHz, CDCl$_3$) δ 8.19 (s, 1H), 7.96 (s, 1H), 7.94 (s, 1H), 7.87 (s, 1H), 7.52 (d, 1H), 7.45 (dd, 1H), 7.33 (d, 1H), 6.65 (d, 1H), 5.81 (s, 2H), 4.63 (dd, 1H), 3.87 (dd, 1H), 3.59-3.44 (m, 2H), 2.76 (m, 1H), 2.18-2.07 (m, 2H), 1.99-1.87 (m, 2H), 1.55 (s, 6H).

LC/MS (m/z) [M+1]+ 561.3 (calculated for $C_{27}H_{27}ClF_3N_4O_4S$, 560.2).

Example 246

5-({1-[4-(1-Hydroxy-1-methylethyl)-2-(trifluoromethyl)benzyl]-1H-indazol-5-yl}methylidene)-2-[3-(R)-(hydroxymethyl)piperazin-1-yl]-1,3-thiazol-4(5H)-one

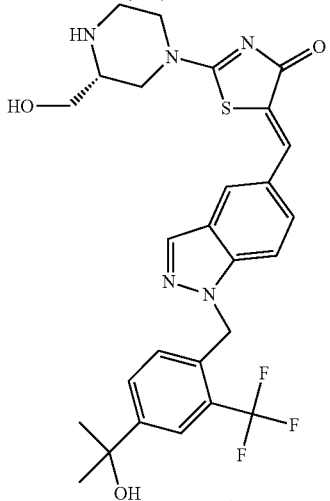 [SMILES: CC(C)(O)c1ccc(Cn2ncc3cc(/C=C4\SC(N5CCN[C@@H](CO)C5)=NC4=O)ccc32)c(C(F)(F)F)c1]

A. (2R)-2-Hydroxymethyl-4-(5-{1-[4-(1-hydroxy-1-methyl-ethyl)-2-trifluoromethyl-benzyl]-1H-indazol-5-ylmethylene}-4-oxo-4,5-dihydro-thiazol-2-yl)-piperazine-1-carboxylic acid tert-butyl ester was prepared from 2-Ethylsulfanyl-5-{1-[4-(1-hydroxy-1-methyl-ethyl)-2-trifluoromethyl-benzyl]-1H-indazol-5-ylmethylene}-thiazol-4-one and (2R)2-Hydroxymethyl-piperazine-1-carboxylic acid tert-butyl ester following General Procedure C.

LC/MS (m/z) [M+1]⁺ 660.3 (calculated for C₃₂H₃₆F₃N₅O₅S, 659.24).

B. 5-({1-[4-(1-Hydroxy-1-methylethyl)-2-(trifluoromethyl)benzyl]-1H-indazol-5-yl}methylidene)-2-[3-(R)-(hydroxymethyl)piperazin-1-yl]-1,3-thiazol-4(5H)-one was prepared from (2R)2-Hydroxymethyl-4-(5-{1-[4-(1-hydroxy-1-methyl-ethyl)-2-trifluoromethyl-benzyl]-1H-indazol-5-ylmethylene}-4-oxo-4,5-dihydro-thiazol-2-yl)-piperazine-1-carboxylic acid tert-butyl ester following General Procedure H.

¹H NMR (400 MHz, CD₃OD) δ 8.23 (s, 1H), 8.11 (s, 1H), 7.92 (br s, 2H), 7.64 (d, 1H), 7.52-7.50 (d, 2H), 6.64 (d, 1H), 5.85 (s, 2H), 4.14 (d, 1H), 3.92-3.34 (m, 8H), 1.49 (s, 6H).

LC/MS (m/z) [M+1]⁺ 560.3 (calculated for C₂₇H₂₇ClF₃N₄O₄S, 559.2).

Example 247

2-[3-(R)-(Hydroxymethyl)piperazin-1-yl]-5-({1-[4-(1-methylethenyl)-2-(trifluoromethyl)benzyl]-1H-indazol-5-yl}methylidene)-1,3-thiazol-4(5H)-one

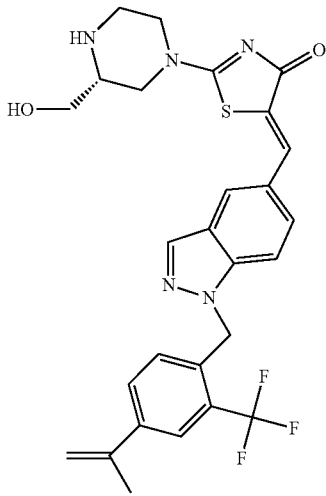 [SMILES: C=C(C)c1ccc(Cn2ncc3cc(/C=C4\SC(N5CCN[C@@H](CO)C5)=NC4=O)ccc32)c(C(F)(F)F)c1]

2-[3-(R)-(Hydroxymethyl)piperazin-1-yl]-5-({1-[4-(1-methylethenyl)-2-(trifluoromethyl)benzyl]-1H-indazol-5-yl}methylidene)-1,3-thiazol-4(5H)-one was obtained as a side product during the deprotection of the Boc protecting group of (2R)2-Hydroxymethyl-4-(5-{1-[4-(1-hydroxy-1-methyl-ethyl)-2-trifluoromethyl-benzyl]-1H-indazol-5-ylmethylene}-4-oxo-4,5-dihydro-thiazol-2-yl)-piperazine-1-carboxylic acid tert-butyl ester (example 246) following General Procedure H.

¹H NMR (400 MHz, CDCl₃) δ 8.18 (m, 1H), 7.96 (s, 1H), 7.92 (s, 1H), 7.78 (s, 1H), 7.52 (dd, 1H), 7.42 (d, 1H), 7.32 (dd, 1H), 6.66 (d, 1H), 5.83-5.81 (2H), 5.38 (s, 1H), 5.15 (s, 1H) 4.49-4.72 (m, 1H), 3.80-2.91 (m, 9H), 2.11 (s, 3H).

LC/MS (m/z) [M+1]⁺ 542.3 (calculated for C₂₆H₂₆ClN₅O₂S, 541.2).

Example 248

2-[3-(R)-(Hydroxymethyl)piperazin-1-yl]-5-({1-[4-methoxy-2-(trifluoromethyl)benzyl]-1H-indazol-5-yl}methylidene)-1,3-thiazol-4(5H)-one

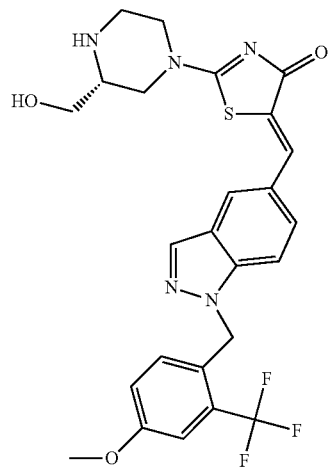 [SMILES: COc1ccc(Cn2ncc3cc(/C=C4\SC(N5CCN[C@@H](CO)C5)=NC4=O)ccc32)c(C(F)(F)F)c1]

A. (2R)2-Hydroxymethyl-4-{5-[1-(4-methoxy-2-trifluoromethyl-benzyl)-1H-indazol-5-ylmethylene]-4-oxo-4,5-dihydro-thiazol-2-yl}-piperazine-1-carboxylic acid tert-butyl ester was prepared from 2-Ethylsulfanyl-5-[1-(4-methoxy-2-trifluoromethyl-benzyl)-1H-indazol-5-ylmethylene]-thiazol-4-one and (2R)2-Hydroxymethyl-piperazine-1-carboxylic acid tert-butyl ester following General Procedure C.

LC/MS (m/z) [M+1]⁺ 632.3 (calculated for C₃₀H₃₂F₃N₆O₆S, 631.21).

B. 2-[3-(R)-(Hydroxymethyl)piperazin-1-yl]-5-({1-[4-methoxy-2-(trifluoromethyl)benzyl]-1H-indazol-5-yl}methylidene)-1,3-thiazol-4(5H)-one was prepared from (2R)2-Hydroxymethyl-4-{5-[1-(4-methoxy-2-trifluoromethyl-benzyl)-1H-indazol-5-ylmethylene]-4-oxo-4,5-dihydro-thiazol-2-yl}-piperazine-1-carboxylic acid tert-butyl ester following General Procedure H.

¹H NMR (400 MHz, DMSO-d₆) δ 8.15 (s, 1H), 7.94-7.83 (m, 2H), 7.47 (d, 1H), 7.32-7.21 (m, 2H), 6.87 (d, 1H), 6.69 (d, 1H), 5.72 (s, 2H), 4.77 (d, 1H), 3.85-2.92 (m, 13H).

LC/MS (m/z) [M+1]⁺ 532.3 (calculated for C₂₆H₂₄F₃N₆O₃S, 531.2).

Example 249

2-[(2R)-2-(Hydroxymethyl)morpholin-4-yl]-5-({1-[4-hydroxy-2-(trifluoromethyl)benzyl]-1H-indazol-5-yl}methylidene)-1,3-thiazol-4(5H)-one

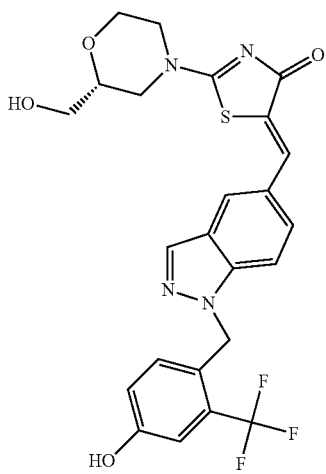 [SMILES: O=C1N=C(N2CCO[C@@H](CO)C2)S/C1=C\c1ccc2c(cnn2Cc2ccc(O)cc2C(F)(F)F)c1]

2-[(2R)-2-(Hydroxymethyl)morpholin-4-yl]-5-({1-[4-hydroxy-2-(trifluoromethyl)benzyl]-1H-indazol-5-yl}methylidene)-1,3-thiazol-4(5H)-one was prepared from 2-Ethylsulfanyl-5-[1-(4-hydroxy-2-trifluoromethyl-benzyl)-1H-indazol-5-ylmethylene]-thiazol-4-one and (2R) Morpholin-2-yl-methanol following General Procedure C.

$^1$H NMR (400 MHz, DMSO-d$_6$) δ 10.17 (s, 1H), 8.29 (s, 1H), 8.12 (s, 1H), 7.81 (s, 1H), 7.83-7.66 (m, 2H), 7.12 (d, 1H), 6.92 (dd, 1H), 6.71 (d, 1H), 5.73 (s, 2H), 5.00-4.94 (m, 1H), 4.52 (dd, 1H), 4.02-3.13 (m, 7H).

LC/MS (m/z) [M+1]$^+$ 519.1 (calculated for C$_{24}$H$_{21}$F$_3$N$_4$O$_4$S, 518.1).

Example 250

2-[(3R)-3-(Hydroxymethyl)piperazin-1-yl]-5-({1-[4-hydroxy-2-(trifluoromethyl)benzyl]-1H-indazol-5-yl}methylidene)-1,3-thiazol-4(5H)-one

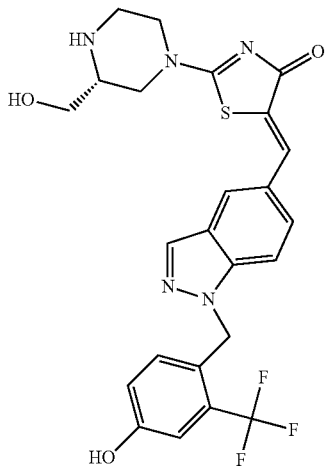 [SMILES: O=C1N=C(N2CCN[C@@H](CO)C2)S/C1=C\c1ccc2c(cnn2Cc2ccc(O)cc2C(F)(F)F)c1]

A. (2R)2-Hydroxymethyl-4-{5-[1-(4-hydroxy-2-trifluoromethyl-benzyl)-1H-indazol-5-ylmethylene]-4-oxo-4,5-dihydro-thiazol-2-yl}-piperazine-1-carboxylic acid tert-butyl ester was prepared from 2-Ethylsulfanyl-5-[1-(4-hydroxy-2-trifluoromethyl-benzyl)-1H-indazol-5-ylmethylene]-thiazol-4-one and (2R)2-Hydroxymethyl-piperazine-1-carboxylic acid tert-butyl ester following General Procedure C.

LC/MS (m/z) [M+1]$^+$ 618.3 (calculated for C$_{30}$H$_{32}$F$_3$N$_5$O$_5$S, 617.19).

B. 2-[(3R)-3-(Hydroxymethyl)piperazin-1-yl]-5-({1-[4-hydroxy-2-(trifluoromethyl)benzyl]-1H-indazol-5-yl}methylidene)-1,3-thiazol-4(5H)-one was prepared from (2R)2-Hydroxymethyl-4-{5-[1-(4-hydroxy-2-trifluoromethyl-benzyl)-1H-indazol-5-ylmethylene]-4-oxo-4,5-dihydro-thiazol-2-yl}-piperazine-1-carboxylic acid tert-butyl ester following General Procedure H.

$^1$H NMR (400 MHz, CD$_3$OD) δ 8.20 (s, 1H), 8.07 (s, 1H), 7.86 (s, 1H), 7.60 (d, 1H), 7.46 (d, 1H), 7.06 (d, 1H), 6.73 (dd, 1H), 6.55 (d, 1H), 5.70 (s, 2H), 4.74-4.56 (m, 2H), 3.95-3.84 (m, 1H), 3.63-3.45 (m, 2H), 3.25-2.84 (m, 4H).

LC/MS (m/z) [M+1]$^+$ 518.2 (calculated for C$_{24}$H$_{22}$F$_3$N$_5$O$_3$S, 517.1).

Example 251

2-[(2S)-2-(Hydroxymethyl)morpholin-4-yl]-5-({1-[4-hydroxy-2-(trifluoromethyl)benzyl]-1H-indazol-5-yl}methylidene)-1,3-thiazol-4(5H)-one

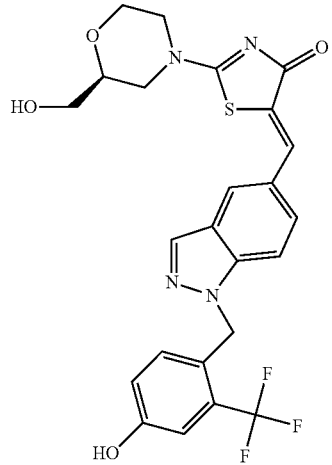 [SMILES: O=C1N=C(N2CCO[C@H](CO)C2)S/C1=C\c1ccc2c(cnn2Cc2ccc(O)cc2C(F)(F)F)c1]

2-[(2S)-2-(Hydroxymethyl)morpholin-4-yl]-5-({1-[4-hydroxy-2-(trifluoromethyl)benzyl]-1H-indazol-5-yl}methylidene)-1,3-thiazol-4(5H)-one was prepared from 2-Ethylsulfanyl-5-[1-(4-hydroxy-2-trifluoromethyl-benzyl)-1H-indazol-5-ylmethylene]-thiazol-4-one and (2S) Morpholin-2-yl-methanol following General Procedure C.

$^1$H NMR (400 MHz, CD$_3$OD) δ 8.20 (s, 1H), 8.08 (s, 1H), 7.87 (s, 1H), 7.62 (d, 1H), 7.49 (d, 1H), 7.14 (d, 1H), 6.82 (dd, 1H), 6.60 (d, 1H), 5.74 (s, 2H), 4.64 (dd, 1H), 4.14-3.39 (m, 8H).

LC/MS (m/z) [M+1]+ 519.2 (calculated for $C_{24}H_{21}F_3N_4O_4S$, 518.1).

Example 252

5-({1-[2,4-Bis(trifluoromethyl)benzyl]-1H-indazol-5-yl}methylidene)-2-[(3R)-3-(dimethylamino)pyrrolidin-1-yl]-1,3-thiazol-4(5H)-one

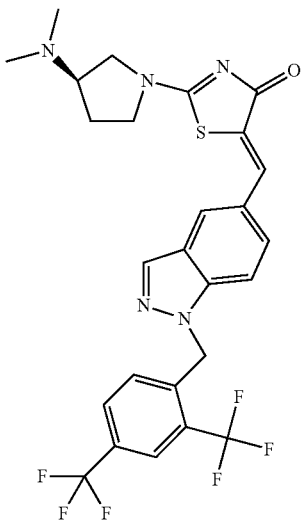 [SMILES: CN(C)[C@@H]1CCN(C2=NC(=O)/C(=C/c3ccc4c(cnn4Cc4ccc(C(F)(F)F)cc4C(F)(F)F)c3)S2)C1]

5-({1-[2,4-Bis(trifluoromethyl)benzyl]-1H-indazol-5-yl}methylidene)-2-[(3R)-3-(dimethylamino)pyrrolidin-1-yl]-1,3-thiazol-4(5H)-one was prepared from 5-[1-(2,4-Bis-trifluoromethyl-benzyl)-1H-indazol-5-ylmethylene]-2-ethylsulfanyl-thiazol-4-one and (3R)Dimethyl-pyrrolidin-3-yl-amine following General Procedure C.

$^1$H NMR (400 MHz, CDCl$_3$) δ 8.21 (s, 1H), 7.97 (br s, 2H), 7.90 (s, 1H), 7.61 (d, 1H), 7.54 (dd, 1H), 7.30 (d, 1H), 6.80 (d, 1H), 5.87 (s, 2H), 4.19-4.09 (m, 1H), 3.81-3.42 (m, 3H), 3.00-2.82 (m, 1H), 2.31 (s, 3H), 2.29 (s, 3H), 2.12-1.81 (m, 2H).

LC/MS (m/z) [M+1]+ 568.2 (calculated for $C_{26}H_{23}F_6N_5OS$, 567.2).

Example 253

5-({1-[2,4-Bis(trifluoromethyl)benzyl]-1H-indazol-5-yl}methylidene)-2-[(2R)-2-(hydroxymethyl)-4-methylpiperazin-1-yl]-1,3-thiazol-4(5H)-one

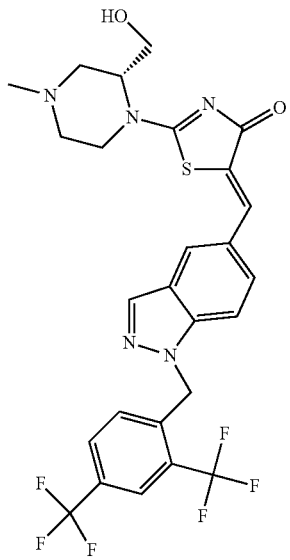 [SMILES: CN1CCN(C2=NC(=O)/C(=C/c3ccc4c(cnn4Cc4ccc(C(F)(F)F)cc4C(F)(F)F)c3)S2)[C@@H](CO)C1]

5-({1-[2,4-Bis(trifluoromethyl)benzyl]-1H-indazol-5-yl}methylidene)-2-[(2R)-2-(hydroxymethyl)-4-methylpiperazin-1-yl]-1,3-thiazol-4(5H)-one was prepared from 5-[1-(2,4-Bis-trifluoromethyl-benzyl)-1H-indazol-5-ylmethylene]-2-ethylsulfanyl-thiazol-4-one and (2R) (4-Methyl-piperazin-2-yl)-methanol following General Procedure C.

$^1$H NMR (400 MHz, CDCl$_3$) δ 8.19 (m, 1H), 7.98-7.90 (m, 3H), 7.64-7.50 (m, 2H), 7.32-7.26 (m, 1H), 6.80-6.79 (m, 1H), 5.88-5.85 (m, 2H), 4.95-4.80 (m, 1H), 4.23-3.62 (m, 4H), 3.11-2.90 (m, 2H), 2.45-2.17 (m, 5H).

LC/MS (m/z) [M+1]+ 584.2 (calculated for $C_{26}H_{23}F_6N_5O_2S$, 583.2).

Example 254

5-({1-[4-Chloro-2-(trifluoromethyl)benzyl]-1H-indazol-5-yl}methylidene)-2-[(2R)-2-(hydroxymethyl)-4-methylpiperazin-1-yl]-1,3-thiazol-4(5H)-one

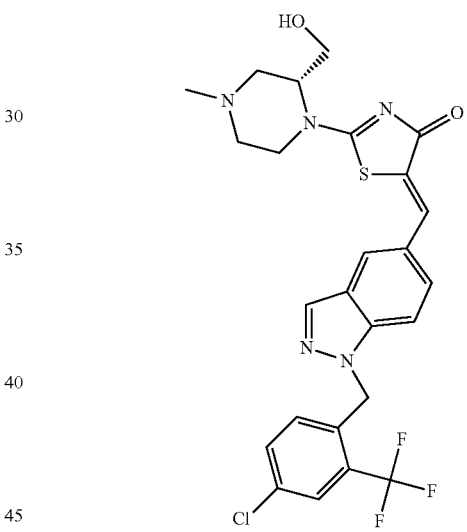

5-({1-[4-Chloro-2-(trifluoromethyl)benzyl]-1H-indazol-5-yl}methylidene)-2-[(2R)-2-(hydroxymethyl)-4-methylpiperazin-1-yl]-1,3-thiazol-4(5H)-one was prepared from 5-[1-(4-Chloro-2-trifluoromethyl-benzyl)-1H-indazol-5-ylmethylene]-2-ethylsulfanyl-thiazol-4-one and (2R) (4-Methyl-piperazin-2-yl)-methanol following General Procedure C.

$^1$H NMR (400 MHz, CDCl$_3$) δ 8.18 (m, 1H), 7.98-7.91 (m, 2H), 7.71-7.50 (m, 2H), 7.35-7.29 (m, 2H), 6.68-6.64 (m, 1H), 5.79-5.77 (m, 2H), 4.97-4.81 (m, 1H), 4.20-3.66 (m, 4H), 3.14-2.91 (m, 2H), 2.48-2.19 (m, 5H).

LC/MS (m/z) [M+1]+ 550.1 (calculated for $C_{25}H_{23}ClF_3N_5O_2S$, 549.1).

Example 255

5-({1-[4-Chloro-2-(trifluoromethyl)benzyl]-1H-indazol-5-yl}methylidene)-2-(2S)-2-ethylpiperazin-1-yl)-1,3-thiazol-4(5H)-one

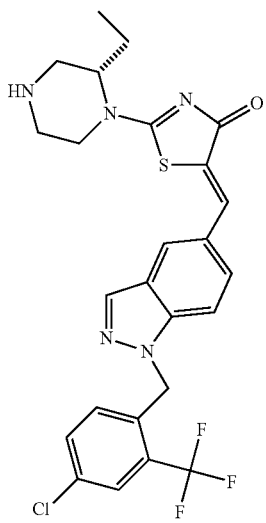 [SMILES: CC[C@H]1CNCCN1C1=NC(=O)/C(=C/c2ccc3c(cnn3Cc3ccc(Cl)cc3C(F)(F)F)c2)S1]

A. 4-{5-[1-(4-Chloro-2-trifluoromethyl-benzyl)-1H-indazol-5-ylmethylene]-4-oxo-4,5-dihydro-thiazol-2-yl}-3-ethyl-piperazine-1-carboxylic acid tert-butyl ester was prepared from 5-[1-(4-Chloro-2-trifluoromethyl-benzyl)-1H-indazol-5-ylmethylene]-2-ethylsulfanyl-thiazol-4-one and (3S)-3-Ethyl-piperazine-1-carboxylic acid tert-butyl ester following General Procedure C.

LC/MS (m/z) [M+1]$^+$ 634.2 (calculated for $C_{30}H_{31}ClF_3N_5O_3S$, 633.18).

B. 5-({1-[4-Chloro-2-(trifluoromethyl)benzyl]-1H-indazol-5-yl}methylidene)-2-((2S)-2-ethyl piperazin-1-yl)-1,3-thiazol-4(5H)-one was prepared from 4-{5-[1-(4-Chloro-2-trifluoromethyl-benzyl)-1H-indazol-5-ylmethylene]-4-oxo-4,5-dihydro-thiazol-2-yl}-3-ethyl-piperazine-1-carboxylic acid tert-butyl ester following General Procedure H.

$^1$H NMR (400 MHz, CDCl$_3$) δ 8.22-8.20 (m, 1H), 7.98-7.93 (m, 2H), 7.71-7.55 (m, 2H), 7.36-7.31 (m, 2H), 6.66 (d, 1H), 5.80 (s, 2H), 4.93-4.77 (m, 1H), 3.70-3.58 (m, 1H), 3.38-2.83 (m, 5H), 2.13-1.77 (m, 2H), 1.05-0.95 (m, 3H).

LC/MS (m/z) [M+1]$^+$ 534.1 (calculated for $C_{25}H_{23}ClF_3N_5OS$, 533.1).

Example 256

5-({1-[4-Chloro-2-(trifluoromethyl)benzyl]-1H-indazol-5-yl}methylidene)-2-((2S)-2-ethyl-4-methylpiperazin-1-yl)-1,3-thiazol-4(5H)-one

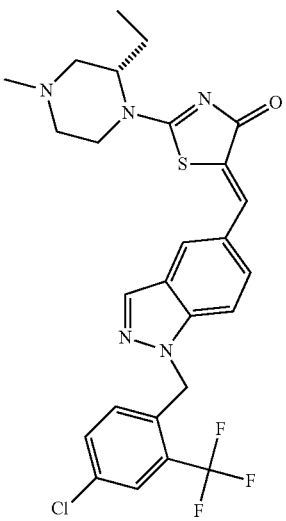 [SMILES: CC[C@H]1CN(C)CCN1C1=NC(=O)/C(=C/c2ccc3c(cnn3Cc3ccc(Cl)cc3C(F)(F)F)c2)S1]

5-({1-[4-Chloro-2-(trifluoromethyl)benzyl]-1H-indazol-5-yl}methylidene)-2-((2S)-2-ethyl-4-methylpiperazin-1-yl)-1,3-thiazol-4(5H)-one was prepared from 5-({1-[4-Chloro-2-(trifluoromethyl)benzyl]-1H-indazol-5-yl}methylidene)-2-((2S)-2-ethylpiperazin-1-yl)-1,3-thiazol-4(5H)-one and formaldehyde following procedure used as in example 195.

$^1$H NMR (400 MHz, CDCl$_3$) δ 8.20-8.18 (m, 1H), 7.97-7.92 (m, 2H), 7.71-7.54 (m, 2H), 7.35-7.30 (m, 2H), 6.66 (d, 1H), 5.79 (s, 2H), 4.93-4.72 (m, 2H), 3.75-2.87 (m, 5H), 2.33 (s, 3H), 2.09-1.88 (m, 2H), 1.02-0.94 (m, 3H).

LC/MS (m/z) [M+1]$^+$ 548.2 (calculated for $C_{26}H_{25}ClF_3N_5OS$, 547.1).

Example 257

2-[(2R,4R)-4-Amino-2-(hydroxymethyl)pyrrolidin-1-yl]-5-({1-[4-chloro-2-(trifluoromethyl)benzyl]-1H-indazol-5-yl}methylidene)-1,3-thiazol-4(5H)-one

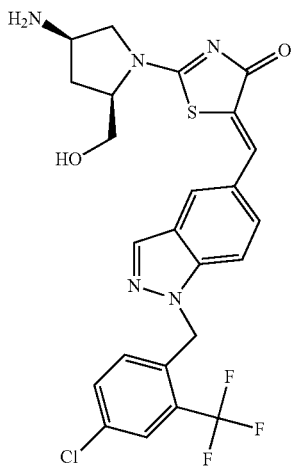 [SMILES: N[C@@H]1C[C@H](CO)N(C2=NC(=O)/C(=C/c3ccc4c(cnn4Cc4ccc(Cl)cc4C(F)(F)F)c3)S2)C1]

A. (1-{(3R,5R)-5-[1-(4-Chloro-2-trifluoromethyl-benzyl)-1H-indazol-5-ylmethylene]-4-oxo-4,5-dihydro-thiazol-2-yl}-5-hydroxymethyl-pyrrolidin-3-yl)-carbamic acid tert-butyl ester was prepared from 5-[1-(4-Chloro-2-trifluoromethyl-benzyl)-1H-indazol-5-ylmethylene]-2-ethylsulfanyl-thiazol-4-one and (3R,5R) (5-Hydroxymethyl-pyrrolidin-3-yl)-carbamic acid tert-butyl ester following General Procedure C.

LC/MS (m/z) [M+1]$^+$ 636.2 (calculated for $C_{29}H_{29}ClF_3N_5O_4S$, 635.16).

B. 2-[(2R,4R)-4-Amino-2-(hydroxymethyl)pyrrolidin-1-yl]-5-({1-[4-chloro-2-(trifluoromethyl)benzyl]-1H-indazol-5-yl}methylidene)-1,3-thiazol-4(5H)-one was prepared from (1-{(3R,5R)-5-[1-(4-Chloro-2-trifluoromethyl-benzyl)-1H-indazol-5-ylmethylene]-4-oxo-4,5-dihydro-thiazol-2-yl}-5-hydroxymethyl-pyrrolidin-3-yl)-carbamic acid tert-butyl ester following General Procedure H.

¹H NMR (400 MHz, CDCl₃) δ 8.18-8.16 (m, 1H), 7.94-7.90 (m, 2H), 7.73 (d, 1H), 7.51 (d, 1H), 7.34-7.27 (m, 2H), 6.65 (d, 1H), 5.77 (m, 2H), 4.64-3.46 (m, 8H), 2.65-2.55 (m, 1H), 1.97-1.83 (m, 2H).

LC/MS (m/z) [M+1]⁺ 536.2 (calculated for C₂₄H₂₁ClF₃N₅O₂S, 535.1).

Example 258

2-[(2R,4R)-4-Amino-2-(hydroxymethyl)pyrrolidin-1-yl]-5-({1-[2,4-bis(trifluoromethyl)benzyl]-1H-indazol-5-yl}methylidene)-1,3-thiazol-4(5H)-one

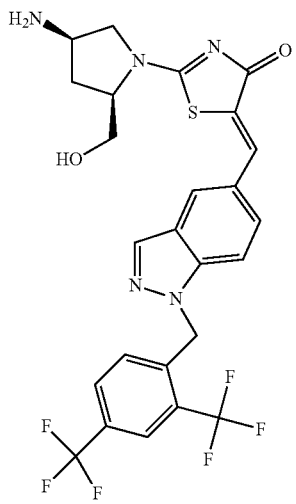 [SMILES: N[C@@H]1C[C@H](CO)N(C2=NC(=O)/C(=C/c3ccc4c(cnn4Cc4ccc(C(F)(F)F)cc4C(F)(F)F)c3)S2)C1]

A. (1-{(3R,5R)-5-[1-(2,4-Bis-trifluoromethyl-benzyl)-1H-indazol-5-ylmethylene]-4-oxo-4,5-dihydro-thiazol-2-yl}-5-hydroxymethyl-pyrrolidin-3-yl)-carbamic acid tert-butyl ester was prepared from 5-[1-(2,4-Bis-trifluoromethyl-benzyl)-1H-indazol-5-ylmethylene]-2-ethylsulfanyl-thiazol-4-one and (3R,5R) (5-Hydroxymethyl-pyrrolidin-3-yl)-carbamic acid tert-butyl ester following General Procedure C.

LC/MS (m/z) [M+1]⁺ 670.3 (calculated for C₃₀H₂₉F₆N₅O₄S, 669.18).

B. 2-[(2R,4R)-4-Amino-2-(hydroxymethyl)pyrrolidin-1-yl]-5-({1-[2,4-bis(trifluoromethyl)benzyl]-1H-indazol-5-yl}methylidene)-1,3-thiazol-4(5H)-one was prepared from (1-{(3R,5R)-5-[1-(2,4-Bis-trifluoromethyl-benzyl)-1H-indazol-5-ylmethylene]-4-oxo-4,5-dihydro-thiazol-2-yl}-5-hydroxymethyl-pyrrolidin-3-yl)-carbamic acid tert-butyl ester following General Procedure H.

¹H NMR (400 MHz, CDCl₃) δ 8.22-8.20 (m, 1H), 7.98-7.92 (m, 3H), 7.63 (d, 1H), 7.54 (d, 1H), 7.31 (d, 1H), 6.81 (d, 1H), 5.87 (s, 2H), 4.66-3.46 (m, 8H), 2.66-2.54 (m, 1H), 1.98-1.82 (m, 2H).

LC/MS (m/z) [M+1]⁺ 570.1 (calculated for C₂₅H₂₁F₆N₅O₂S, 569.1).

Example 259

N-{1-[(3R,5R)-5-({1-[2,4-Bis(trifluoromethyl)benzyl]-1H-indazol-5-yl}methylidene)-4-oxo-4,5-dihydro-1,3-thiazol-2-yl]-5-(hydroxymethyl)pyrrolidin-3-yl}acetamide

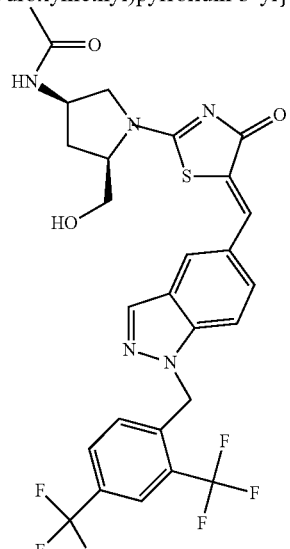

N-{(3R,5R)-1-[5-({1-[2,4-Bis(trifluoromethyl)benzyl]-1H-indazol-5-yl}methylidene)-4-oxo-4,5-dihydro-1,3-thiazol-2-yl]-5-(hydroxymethyl)pyrrolidin-3-yl}acetamide was prepared from 2-[(2R,4R)-4-Amino-2-(hydroxymethyl)pyrrolidin-1-yl]-5-({1-[2,4-bis(trifluoromethyl)benzyl]-1H-indazol-5-yl}methylidene)-1,3-thiazol-4(5H)-one (example 258) and acetic anhydride.

¹H NMR (400 MHz, CDCl₃) δ 8.13-8.11 (m, 1H), 7.97 (s, 1H), 7.91 (s, 1H), 7.69 (s, 1H), 7.62-7.57 (m, 1H), 7.28 (d, 1H), 6.98 (d, 1H), 6.71 (d, 1H), 5.71-5.60 (m, 3H), 4.91-4.79 (m, 2H), 4.50 (d, 1H), 3.97 (dd, 1H), 3.72-3.61 (m, 2H), 2.73-2.64 (m, 1H), 2.10-2.00 (m, 4H).

LC/MS (m/z) [M+1]⁺ 612.2 (calculated for C₂₇H₂₃F₆N₅O₃S, 611.1).

Example 260

N-{(3R,5R)-1-[5-({1-[2,4-Bis(trifluoromethyl)benzyl]-1H-indazol-5-yl}methylidene)-4-oxo-4,5-dihydro-1,3-thiazol-2-yl]-5-(hydroxymethyl)pyrrolidin-3-yl}cyclopropanecarboxamide

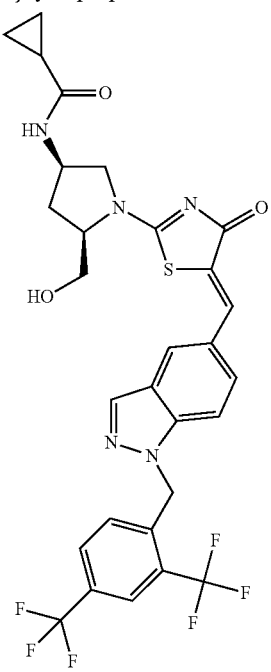

N-{(3R,5R)-1-[5-({1-[2,4-Bis(trifluoromethyl)benzyl]-1H-indazol-5-yl}methylidene)-4-oxo-4,5-dihydro-1,3-thiazol-2-yl]-5-(hydroxymethyl)pyrrolidin-3-yl}cyclopropanecarboxamide was prepared from 2-[(2R,4R)-4-Amino-2-(hydroxymethyl)pyrrolidin-1-yl]-5-({1-[2,4-bis(trifluoromethyl)benzyl]-1H-indazol-5-yl}methylidene)-1,3-thiazol-4(5H)-one (example 258) and Cyclopropylcarbonyl chloride.

$^1$H NMR (400 MHz, CDCl$_3$) δ 8.28-8.25 (m, 1H), 7.96 (s, 1H), 7.91 (s, 1H), 7.68 (s, 1H), 7.61-7.57 (m, 1H), 7.27 (d, 1H), 6.98 (d, 1H), 6.70 (d, 1H), 5.87-5.64 (m, 3H), 4.86 (br s, 2H), 4.50 (d, 1H), 3.97 (dd, 1H), 3.71-3.63 (m, 2H), 2.75-2.62 (m, 1H), 2.20-1.86 (m, 2H), 1.47 (br s, 1H), 1.01 (m, 2H), 0.80 (m, 2H).

LC/MS (m/z) [M+1]$^+$ 638.2 (calculated for C$_{29}$H$_{25}$F$_6$N$_5$O$_3$S, 637.2).

Example 261

N-{(3R,5R)-1-[5-({1-[4-Chloro-2-(trifluoromethyl)benzyl]-1H-indazol-5-yl}methylidene)-4-oxo-4,5-dihydro-1,3-thiazol-2-yl]-5-(hydroxymethyl)pyrrolidin-3-yl}acetamide

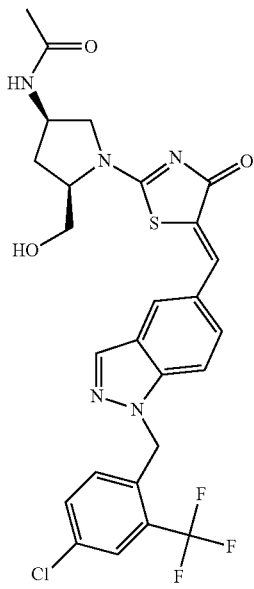 [SMILES: CC(=O)N[C@@H]1C[C@H](CO)N(C2=NC(=O)/C(=C/c3ccc4c(cnn4Cc4ccc(Cl)cc4C(F)(F)F)c3)S2)C1]

N-{(3R,5R)-1-[5-({1-[4-Chloro-2-(trifluoromethyl)benzyl]-1H-indazol-5-yl}methylidene)-4-oxo-4,5-dihydro-1,3-thiazol-2-yl]-5-(hydroxymethyl)pyrrolidin-3-yl}acetamide was prepared from 2-[(2R,4R)-4-Amino-2-(hydroxymethyl)pyrrolidin-1-yl]-5-({1-[4-chloro-2-(trifluoromethyl)benzyl]-1H-indazol-5-yl}methylidene)-1,3-thiazol-4(5H)-one (example 257) and acetic anhydride.

$^1$H NMR (400 MHz, CDCl$_3$) δ 8.08-8.06 (m, 1H), 7.90 (s, 1H), 7.70 (s, 1H), 7.61 (s, 1H), 7.31-7.24 (m, 2H), 6.97 (d,1H), 6.55 (d, 1H), 5.67-5.56 (m, 2H), 4.90-4.80 (m, 2H), 4.50 (d, 1H), 3.97 (dd, 1H), 3.71-3.62 (m, 2H), 2.72-2.64 (m, 1H), 2.09-2.00 (m, 5H).

LC/MS (m/z) [M+1]$^+$ 578.2 (calculated for C$_{26}$H$_{23}$ClF$_3$N$_5$O$_3$S, 577.1).

Example 262

N-{(2R,4R)-1-[2,4-Bis(trifluoromethyl)benzyl]-1H-indazol-5-yl}methylidene)-2-{2-(hydroxymethyl)-4-[(1-methylethyl)amino]pyrrolidin-1-yl}-1,3-thiazol-4(5H)-one

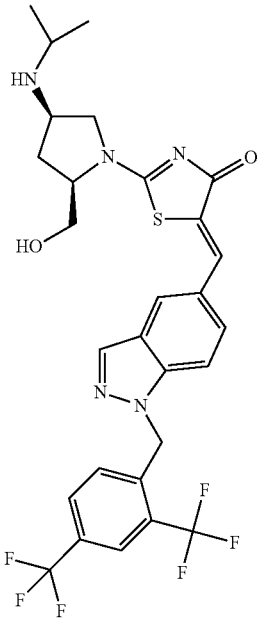 [SMILES: CC(C)N[C@@H]1C[C@H](CO)N(C2=NC(=O)/C(=C/c3ccc4c(cnn4Cc4ccc(C(F)(F)F)cc4C(F)(F)F)c3)S2)C1]

To a solution of CH$_2$Cl$_2$ (1 mL) and acetic acid (50 μL) was added 2-[(2R,4R)-4-Amino-2-(hydroxymethyl)pyrrolidin-1-yl]-5-({1-[2,4-bis(trifluoromethyl)benzyl]-1H-indazol-5-yl}methylidene)-1,3-thiazol-4(5H)-one (example 258, 35 mg, 0.061 mmol), followed by acetone (20 mg, 0.34 mmol). After stirring the mixture at room temperature for 20 min, it was added NaBH(OAc)$_3$ (29 mg, 0.14 mmol). The reaction mixture was kept stirring for 48 h and partitioned between CH$_2$Cl$_2$ and water. The combined organic extracts were washed with brine, dried, and evaporated. The residue was purified by reverse phase semi-preparative HPLC to afford the title product.

$^1$H NMR (400 MHz, CDCl$_3$) δ 8.20-8.18 (m, 1H), 7.98-7.90 (m, 3H), 7.63 (d, 1H), 7.53 (d, 1H), 7.31-7.28 (m, 1H), 6.81 (d, 1H), 5.87-5.85 (m, 2H), 4.63-3.52 (m, 6H), 2.92 (m, 1H), 2.61-2.50 (m, 1H), 2.07-1.89 (m, 1H), 1.18-1.14 (m, 6H).

LC/MS (m/z) [M+1]$^+$ 612.5 (calculated for C$_{28}$H$_{27}$F$_6$N$_5$O$_2$S, 611.2).

Example 263

N-{(2R,4R)-1-[4-Chloro-2-(trifluoromethyl)benzyl]-1H-indazol-5-yl}methylidene)-2-{2-(hydroxymethyl)-4-[(1-methylethyl)amino]pyrrolidin-1-yl}-1,3-thiazol-4(5H)-one

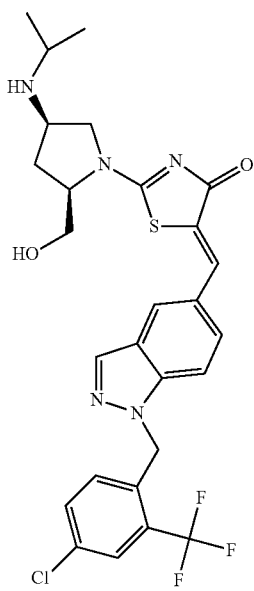 [SMILES: CC(C)N[C@@H]1C[C@H](CO)N(C2=NC(=O)/C(=C/c3ccc4c(cnn4Cc4ccc(Cl)cc4C(F)(F)F)c3)S2)C1]

N-{(2R,4R)-1-[4-Chloro-2-(trifluoromethyl)benzyl]-1H-indazol-5-yl}methylidene)-2-{2-(hydroxymethyl)-4-[(1-methylethyl)amino]pyrrolidin-1-yl}-1,3-thiazol-4(5H)-one was prepared from 2-[(2R,4R)-4-Amino-2-(hydroxymethyl)pyrrolidin-1-yl]-5-({1-[4-chloro-2-(trifluoromethyl)benzyl]-1H-indazol-5-yl}methylidene)-1,3-thiazol-4(5H)-one (example 257) and acetone following procedure used in example 262.

$^1$H NMR (400 MHz, CDCl$_3$) δ 8.16-8.14 (m, 1H), 7.92-7.87 (m, 2H), 7.71 (d, 1H), 7.50 (dd, 1H), 7.33 (dd, 1H), 7.29-7.26 (m, 1H), 6.64 (d, 1H), 5.77-5.86 (m, 2H), 4.62-3.52 (m, 6H), 2.92 (m, 1H), 2.62-2.50 (m, 1H), 2.07-1.89 (m, 1H), 1.17-1.14 (m, 6H).

LC/MS (m/z) [M+1]$^+$ 578.4 (calculated for C$_{27}$H$_{27}$ClF$_3$N$_5$O$_2$S, 577.2).

Example 264

N-2-{(3S)-1-[5-({1-[2,4-Bis(trifluoromethyl)benzyl]-1H-indazol-5-yl}methylidene)-4-oxo-4,5-dihydro-1,3-thiazol-2-yl]pyrrolidin-3-yl}alaninamide

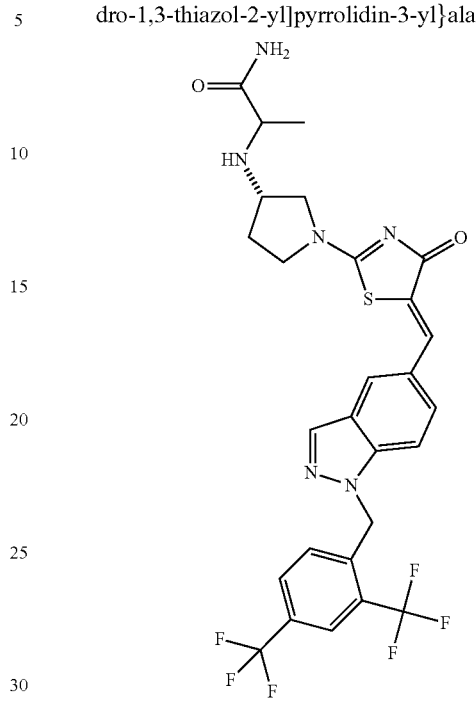

A. (3S)-3-(1-Carbamoyl-ethylamino)-pyrrolidine-1-carboxylic acid tert-butyl ester To a solution of MeCN (3 mL) was added 3-Amino-pyrrolidine-1-carboxylic acid tert-butyl ester (0.186 g, 1 mmol), 2-Bromo-propionamide (0.15 g, 1 mmol) and potassium carbonate (0.153 g, 1.1 mmol). The resulting mixture was heated at 80° C. overnight and partitioned between dichloromethane and water. The combined organic extracts were washed with brine, dried, and evaporated. The residue was purified by flash column chromatography on silica gel, eluting with MeOH/CH$_2$Cl$_2$ (20/80) to afford the title product.

$^1$H NMR (400 MHz, CDCl$_3$) δ 7.02 (br s, 1H), 6.27 (br s, 1H), 3.52-2.96 (m, 6H), 2.08-1.53 (m, 3H), 1.40-1.25 (m, 12H).

B. (2S)-2-(Pyrrolidin-3-ylamino)-propionamide was prepared from (3S)-3-(1-Carbamoyl-ethylamino)-pyrrolidine-1-carboxylic acid tert-butyl ester following General Procedure H and used directly into the next step.

C. N-2-{(3S)-1-[5-({1-[2,4-Bis(trifluoromethyl)benzyl]-1H-indazol-5-yl}methylidene)-4-oxo-4,5-dihydro-1,3-thiazol-2-yl]pyrrolidin-3-yl}alaninamide was prepared from 5-[1-(2,4-Bis-trifluoromethyl-benzyl)-1H-indazol-5-ylmethylene]-2-ethylsulfanyl-thiazol-4-one and (2S)-2-(Pyrrolidin-3-ylamino)-propionamide following General Procedure C.

$^1$H NMR (400 MHz, CDCl$_3$) δ 8.18-8.10 (1H), 7.97 (br s, 1H), 7.91-7.85 (2H), 7.62-7.60 (1H), 7.51-7.47 (1H), 7.26-7.21 (1H), 7.06-6.94 (1H), 6.81-6.77 (1H), 5.93-5.66 (3H), 4.07-3.08 (6H), 2.39-1.83 (3H), 1.53-1.36 (3H).

LC/MS (m/z) [M+1]+ 611.5 (calculated for C$_{27}$H$_{24}$F$_6$N$_6$O$_2$S, 610.2).

Example 265

N-2-{(3S)-1-[5-({1-[4-Chloro-2-(trifluoromethyl)benzyl]-1H-indazol-5-yl}methylidene)-4-oxo-4,5-dihydro-1,3-thiazol-2-yl]pyrrolidin-3-yl}alaninamide

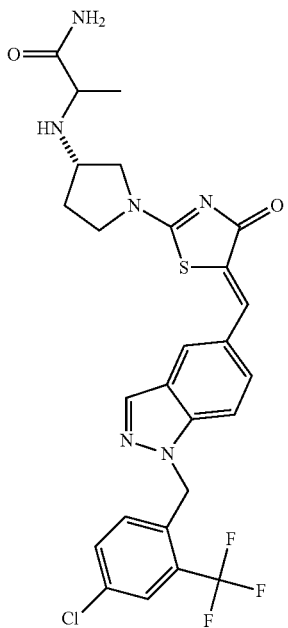 [SMILES: CC(N[C@H]1CCN(C2=NC(=O)/C(=C/c3ccc4c(cnn4Cc4ccc(Cl)cc4C(F)(F)F)c3)S2)C1)C(N)=O]

N-2-{(3S)-1-[5-({1-[4-Chloro-2-(trifluoromethyl)benzyl]-1H-indazol-5-yl}methylidene)-4-oxo-4,5-dihydro-1,3-thiazol-2-yl]pyrrolidin-3-yl}alaninamide was prepared from 5-[1-(4-Chloro-2-trifluoromethyl-benzyl)-1H-indazol-5-yl-methylene]-2-ethylsulfanyl-thiazol-4-one and (2S)-2-(Pyrrolidin-3-ylamino)-propionamide following General Procedure C.

$^1$H NMR (400 MHz, CDCl$_3$) δ 8.14-8.06 (1H), 7.89-7.83 (2H), 7.70 (br 1H), 7.48-7.42 (1H), 7.36-7.18 (2H), 7.15-6.89 (1H), 6.66-6.81 (1H), 6.02, 6.08 (1H), 5.75-5.69 (2H), 4.08-3.07 (6H), 2.39-1.96 (3H), 1.56-1.37 (3H).

LC/MS (m/z) [M+1]+ 577.5 (calculated for C$_{26}$H$_{24}$ClF$_3$N$_6$O$_2$S, 576.1).

Example 266

5-({1-[2,4-Bis(trifluoromethyl)benzyl]-1H-indazol-5-yl}methylidene)-2-{(3S)-3-[(2,2-difluoroethyl)amino]piperidin-1-yl}-1,3-thiazol-4(5H)-one

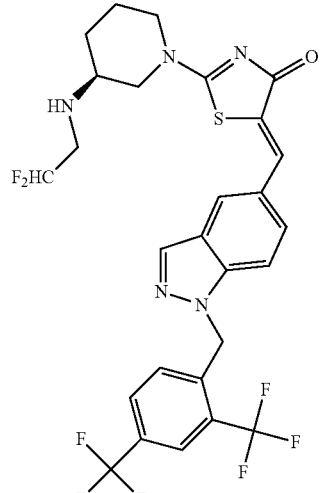

To a solution of DMF (1 mL) was added 2-(3-(S)-Amino-piperidin-1-yl)-5-[1-(2,4-bis-trifluoromethyl-benzyl)-1H-indazol-5-ylmethylene]-thiazol-4-one (0.03 g, 0.05 mmol), Trifluoro-methanesulfonic acid 2,2-difluoro-ethyl ester (0.02 g, 0.09 mmol) and potassium carbonate (0.014 g, 0.1 mmol). The resulting mixture was heated at 70° C. overnight and partitioned between dichloromethane and water. The combined organic extracts were washed with brine, dried, and evaporated. The residue was purified by flash column chromatography on silica gel, eluting with MeOH/CH$_2$Cl$_2$ (7/93) to afford the title product.

$^1$H NMR (400 MHz, CDCl$_3$) δ 8.23-8.21 (m, 1H), 7.98 (br s, 2H), 7.93 (s, 1H), 7.63 (d, 1H), 7.56 (d, 1H), 6.82 (d, 1H), 6.00-5.68 (m, 3H), 4.52-4.44 (m, 1H), 3.84-2.84 (m, 6H), 2.14-1.46 (m, 4H).

LC/MS (m/z) [M+1]+ 618.2 (calculated for C$_{27}$H$_{23}$F$_8$N$_5$OS, 617.2).

Example 267

5-({1-[2,4-Bis(trifluoromethyl)benzyl]-1H-indazol-5-yl}methylidene)-2-{3-[(2-hydroxyethyl)amino]piperidin-1-yl}-1,3-thiazol-4(5H)-one

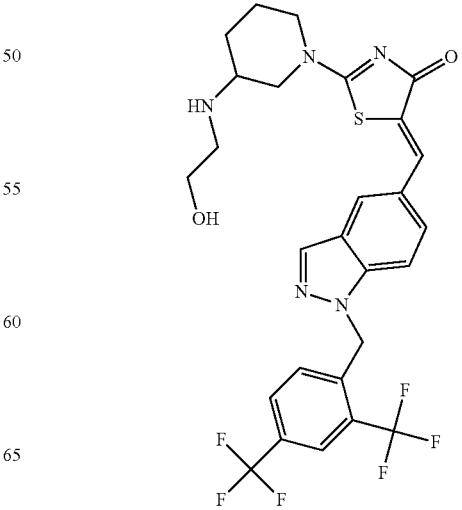

A. 3-(2-Hydroxy-ethylamino)-piperidine-1-carboxylic acid tert-butyl ester

To a solution of 3-Oxo-piperidine-1-carboxylic acid tert-butyl ester (0.2 g, 1 mmol) in dichloromethane (5 mL) was added 2-Amino ethanol (0.073 mg, 1.2 mmol) and NaBH(OAc)$_3$ (0.3 g, 1.4 mmol). The resulting mixture was stirred at room temperature overnight and partitioned between dichloromethane and water. The combined organic extracts were washed with brine, dried, and evaporated. The residue was directly used into the next step without further purification.

LC/MS (m/z) [M]$^+$ 245.3 (calculated for $C_{12}H_{24}N_2O_3$, 244.2).

B. 2-(Piperidin-3-ylamino)-ethanol was prepared from 3-(2-Hydroxy-ethylamino)-piperidine-1-carboxylic acid tert-butyl ester following General Procedure H.

C. 5-({1-[2,4-Bis(trifluoromethyl)benzyl]-1H-indazol-5-yl}methylidene)-2-{(3S)-3-[(2-hydroxyethyl)amino]piperidin-1-yl}-1,3-thiazol-4(5H)-one was prepared from 5-[1-(2,4-Bis-trifluoromethyl-benzyl)-1H-indazol-5-ylmethylene]-2-ethylsulfanyl-thiazol-4-one and 2-(Piperidin-3-ylamino)-ethanol following General Procedure C.

$^1$H NMR (400 MHz, DMSO-d$_6$) δ 8.34-8.32 (1H), 8.15-8.10 (m, 2H), 7.96 (d, 1H), 7.82-7.78 (m, 2H), 7.69 (d, 1H), 6.91 (d, 1H), 6.00 (s, 2H), 5.37-5.29 (m, 1H), 4.56 (d, 1H), 4.34-4.15 (m, 1H), 3.80-3.36 (m, 4H), 3.16-3.00 (m, 2H), 2.21-1.56 (m, 4H).

LC/MS (m/z) [M+1]$^+$ 598.3 (calculated for $C_{27}H_{25}F_6N_5O_2S$, 597.2).

Example 268

1-[5-({1-[4-Chloro-2-(trifluoromethyl)benzyl]-1H-indazol-5-yl}methylidene)-4-oxo-4,5-dihydro-1,3-thiazol-2-yl]-4-hydroxypiperidine-4-carboxylic acid

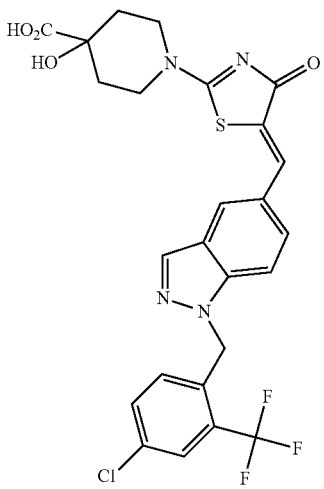 [SMILES: O=C1N=C(N2CCC(O)(C(=O)O)CC2)S/C1=C\c1ccc2c(cnn2Cc2ccc(Cl)cc2C(F)(F)F)c1]

1-[5-({1-[4-Chloro-2-(trifluoromethyl)benzyl]-1H-indazol-5-yl}methylidene)-4-oxo-4,5-dihydro-1,3-thiazol-2-yl]-4-hydroxypiperidine-4-carboxylic acid was prepared from 5-[1-(4-Chloro-2-trifluoromethyl-benzyl)-1H-indazol-5-ylmethylene]-2-ethylsulfanyl-thiazol-4-one and 4-Hydroxy-piperidine-4-carboxylic acid following General Procedure C.

$^1$H NMR (400 MHz, DMSO-d$_6$) δ 8.30 (s, 1H), 8.12 (s, 1H), 7.96 (s, 1H), 7.86 (d, 1H), 7.77 (s, 1H), 7.74 (d, 1H), 7.67 (dd, 1H), 7.63 (dd, 1H), 7.35 (d, 1H), 7.22 (d, 1H), 6.75 (d, 1H), 5.84 (s, 2H), 4.48 (d, 1H), 3.78-3.63 (m, 2H), 3.44-3.30 (m, 1H), 2.04-1.91 (m, 2H), 21.71-1.60 (m, 2H).

LC/MS (m/z) [M]$^+$ 564.3 (calculated for $C_{25}H_{20}ClF_3N_4O_4S$, 564.1).

Example 269

1-[5-({1-[2,4-Bis(trifluoromethyl)benzyl]-1H-indazol-5-yl}methylidene)-4-oxo-4,5-dihydro-1,3-thiazol-2-yl]-4-hydroxypiperidine-4-carboxylic acid

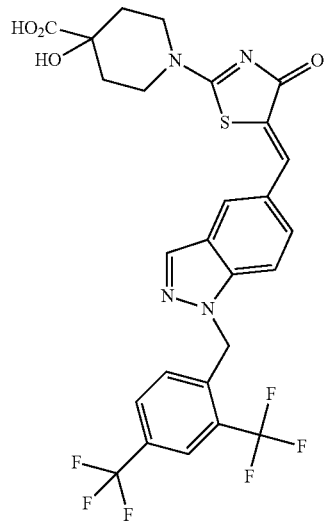 [SMILES: O=C1N=C(N2CCC(O)(C(=O)O)CC2)S/C1=C\c1ccc2c(cnn2Cc2ccc(C(F)(F)F)cc2C(F)(F)F)c1]

1-[5-({1-[2,4-Bis(trifluoromethyl)benzyl]-1H-indazol-5-yl}methylidene)-4-oxo-4,5-dihydro-1,3-thiazol-2-yl]-4-hydroxypiperidine-4-carboxylic acid was prepared from 5-[1-(2,4-Bis-trifluoromethyl-benzyl)-1H-indazol-5-ylmethylene]-2-ethylsulfanyl-thiazol-4-one and 4-Hydroxy-piperidine-4-carboxylic acid following General Procedure C.

$^1$H NMR (400 MHz, DMSO-d$_6$) δ 8.33 (s, 1H), 8.13 (s, 1H), 8.10 (s, 1H), 7.95 (d, 1H), 7.79-7.76 (m, 2H), 7.69 (d, 1H), 7.35 (d, 1H), 7.35 (d, 1H), 7.22 (d, 1H), 6.90 (d, 1H), 5.96 (s, 2H), 4.48 (d, 1H), 3.78-3.62 (m, 2H), 3.49-3.24 (m, 1H), 2.05-1.91 (m, 2H), 21.71-1.61 (m, 2H).

LC/MS (m/z) [M]$^+$ 598.1 (calculated for $C_{26}H_{20}F_6N_4O_4S$, 598.1).

Example 270

5-({1-[4-Chloro-2-(trifluoromethyl)benzyl]-1H-indazol-5-yl}methylidene)-2-[3-(methylamino)azetidin-1-yl]-1,3-thiazol-4(5H)-one

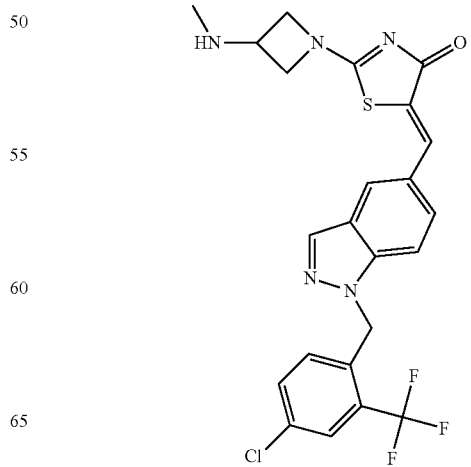

A. 5-({1-[4-Chloro-2-(trifluoromethyl)benzyl]-1H-indazol-5-yl}methylidene)-2-[3-(methylamino)azetidin-1-yl]-1,3-thiazol-4(5H)-one was prepared from 5-[1-(4-Chloro-2-trifluoromethyl-benzyl)-1H-indazol-5-ylmethylene]-2-ethylsulfanyl-thiazol-4-one and Azetidin-3-yl-methyl-amine following General Procedure C.

$^1$H NMR (400 MHz, CDCl$_3$) δ 8.13 (s, 1H), 7.90 (s, 1H), 7.88 (s, 1H), 7.71 (d, 1H), 7.48 (dd, 1H), 7.32 (dd, 1H), 7.27 (d, 1H), 6.64 (d, 1H), 5.76 (s, 2H), 4.59 (dd, 1H), 4.43 (dd, 1H), 4.18 (dd, 1H), 4.04 (dd, 1H), 3.94-3.88 (m, 1H), 2.47 (s, 3H).

LC/MS (m/z) [M+1]$^+$ 506.1 (calculated for C$_{23}$H$_{19}$ClF$_3$N$_5$OS, 505.1).

Example 271

4-[5-({1-[4-Chloro-2-(trifluoromethyl)benzyl]-1H-indazol-5-yl}methylidene)-4-oxo-4,5-dihydro-1,3-thiazol-2-yl]-N-methoxypiperazine-2-carboxamide

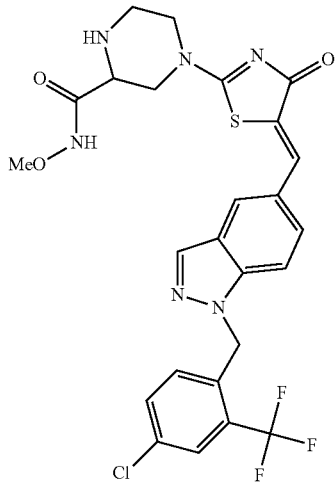 [SMILES: CONC(=O)C1CN(C2=NC(=O)/C(=C/c3ccc4c(cnn4Cc4ccc(Cl)cc4C(F)(F)F)c3)S2)CCN1]

A. 2-Methoxycarbamoyl-piperazine-1,4-dicarboxylic acid 4-benzyl ester 1-tert-butyl ester To a solution of piperazine-1,2,4-tricarboxylic acid 4-benzyl ester 1-tert-butyl ester (0.364 g, 1 mmol) in dichloromethane (3 mL) was added O-Methyl Hydroxylamine HCl (95 mg, 1.13 mmol), EDC HCl (0.3 g, 1.57 mmol) and DIEA (0.28 g, 2.17 mmol). The resulting mixture was stirred at room temperature overnight and partitioned between dichloromethane and water. The combined organic extracts were washed with brine, dried, and evaporated. The residue was purified by flash column chromatography on silica gel, eluting with EtOAc/n-Hexane (30/70) to afford the title product.

LC/MS (m/z) [M]$^+$ 394.2 (calculated for C$_{19}$H$_{27}$N$_3$O$_6$, 393.19).

B. 2-Methoxycarbamoyl-piperazine-1-carboxylic acid tert-butyl ester

A mixture of 2-Methoxycarbamoyl-piperazine-1,4-dicarboxylic acid 4-benzyl ester 1-tert-butyl ester (0.23 g, 0.58 mmol) and activated 10 wt. % palladium on carbon (0.048 g) in methanol (8 mL) was stirred vigorously under 40 psi hydrogen atmosphere for 2 hours. The reaction mixture was then filtered through a microglass filter paper and the solid washed abundantly with methanol. The solvent was evaporated in vacuo to yield the title compound.

LC/MS (m/z) [M]$^+$ 260.3 (calculated for C$_{11}$H$_{21}$N$_3$O$_4$, 259.15).

C. 4-{5-[1-(4-Chloro-2-trifluoromethyl-benzyl)-1H-indazol-5-ylmethylene]-4-oxo-4,5-dihydro-thiazol-2-yl}-2-methoxycarbamoyl-piperazine-1-carboxylic acid tert-butyl ester was prepared from 5-[1-(4-Chloro-2-trifluoromethyl-benzyl)-1H-indazol-5-ylmethylene]-2-ethylsulfanyl-thiazol-4-one and 2-Methoxycarbamoyl-piperazine-1-carboxylic acid tert-butyl ester following General Procedure C.

LC/MS (m/z) [M]$^+$ 679.3 (calculated for C$_{30}$H$_{30}$ClF$_3$N$_6$O$_6$S, 678.16).

D. 4-[5-({1-[4-Chloro-2-(trifluoromethyl)benzyl]-1H-indazol-5-yl}methylidene)-4-oxo-4,5-dihydro-1,3-thiazol-2-yl]-N-methoxypiperazine-2-carboxamide was prepared from 4-{5-[1-(4-Chloro-2-trifluoromethyl-benzyl)-1H-indazol-5-ylmethylene]-4-oxo-4,5-dihydro-thiazol-2-yl}-2-methoxycarbamoyl-piperazine-1-carboxylic acid tert-butyl ester following General Procedure H.

$^1$H NMR (400 MHz, DMSO-d$_6$) δ 11.50-11.30 (br s, 1H), 8.33, 8.30 (s, 1H), 8.11 (s, 1H), 7.86 (d, 1H), 7.77-7.73 (m, 2H), 7.69-7.62 (m, 2H), 6.73 (d, 1H), 5.84 (s, 2H), 4.45-3.42 (m, 7H), 3.10-2.67 (m, 3H).

LC/MS (m/z) [M]$^+$ 579.2 (calculated for C$_{26}$H$_{22}$ClF$_3$N$_6$O$_3$S, 578.1).

Example 272

4-[5-({1-[2,4-Bis(trifluoromethyl)benzyl]-1H-indazol-5-yl}methylidene)-4-oxo-4,5-dihydro-1,3-thiazol-2-yl]-N-methoxypiperazine-2-carboxamide

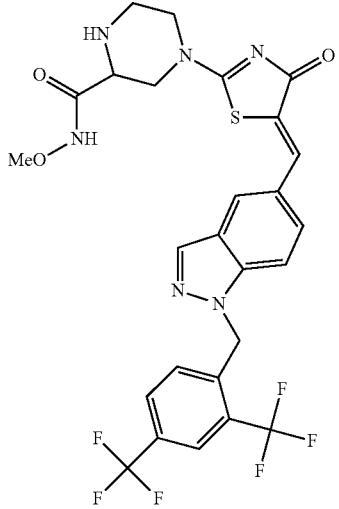 [SMILES: CONC(=O)C1CN(C2=NC(=O)/C(=C/c3ccc4c(cnn4Cc4ccc(C(F)(F)F)cc4C(F)(F)F)c3)S2)CCN1]

A. 4-{5-[1-(2,4-Bis-trifluoromethyl-benzyl)-1H-indazol-5-ylmethylene]-4-oxo-4,5-dihydro-thiazol-2-yl}-2-methoxycarbamoyl-piperazine-1-carboxylic acid tert-butyl ester was prepared from 5-[1-(2,4-Bis-trifluoromethyl-benzyl)-1H-indazol-5-ylmethylene]-2-ethylsulfanyl-thiazol-4-one and 2-Methoxycarbamoyl-piperazine-1-carboxylic acid tert-butyl ester following General Procedure C.

LC/MS (m/z) [M]$^+$ 713.4 (calculated for C$_{31}$H$_{30}$F$_6$N$_6$O$_5$S, 712.19).

B. 4-[5-({1-[2,4-Bis(trifluoromethyl)benzyl]-1H-indazol-5-yl}methylidene)-4-oxo-4,5-dihydro-1,3-thiazol-2-yl]-N-methoxypiperazine-2-carboxamide was prepared from 4-{5-[1-(2,4-Bis-trifluoromethyl-benzyl)-1H-indazol-5-ylmethylene]-4-oxo-4,5-dihydro-thiazol-2-yl}-2-methoxycarbamoyl-piperazine-1-carboxylic acid tert-butyl ester following General Procedure H.

¹H NMR (400 MHz, DMSO-d₆) δ 11.52-11.35 (br s, 1H), 8.40, 8.37 (s, 1H), 8.19 (s, 1H), 8.11 (s, 1H), 7.97 (d, 2H), 7.84-7.81 (m, 2H), 7.72 (dd, 1H), 6.90 (d, 1H), 5.96 (s, 2H), 4.48-3.46 (m, 7H), 3.10-2.67 (m, 3H).
LC/MS (m/z) [M]⁺ 613.2 (calculated for C₂₆H₂₂ClF₃N₆O₃S, 612.1).

Example 273
4-[5-({1-[4-Chloro-2-(trifluoromethyl)benzyl]-1H-indazol-5-yl}methylidene)-4-oxo-4,5-dihydro-1,3-thiazol-2-yl]piperazine-2-carboxamide

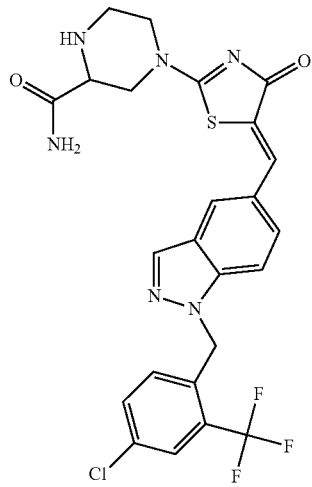 [SMILES: NC(=O)C1CN(C2=NC(=O)/C(=C/c3ccc4c(cnn4Cc4ccc(Cl)cc4C(F)(F)F)c3)S2)CCN1]

4-[5-({1-[4-Chloro-2-(trifluoromethyl)benzyl]-1H-indazol-5-yl}methylidene)-4-oxo-4,5-dihydro-1,3-thiazol-2-yl]piperazine-2-carboxamide was prepared from 5-[1-(4-Chloro-2-trifluoromethyl-benzyl)-1H-indazol-5-ylmethylene]-2-ethylsulfanyl-thiazol-4-one and piperazine-2-carboxylic acid amide following General Procedure C.
¹H NMR (400 MHz, CDCl₃) δ 8.22, 8.18 (s, 1H), 7.99-7.92 (m, 2H), 7.71 (d, 1H), 7.54 (dd, 2H), 7.35-7.29 (m, 2H), 6.99-6.61 (m, 2H), 5.79 (s, 2H), 5.55 (br s, 1H), 4.71-4.23 (m, 1H), 3.93-2.98 (m, 6H).
LC/MS (m/z) [M]⁺ 549.1 (calculated for C₂₄H₂₀ClF₃N₆O₂S, 548.1).

Example 274
4-[5-({1-[2,4-Bis(trifluoromethyl)benzyl]-1H-indazol-5-yl}methylidene)-4-oxo-4,5-dihydro-1,3-thiazol-2-yl]piperazine-2-carboxamide

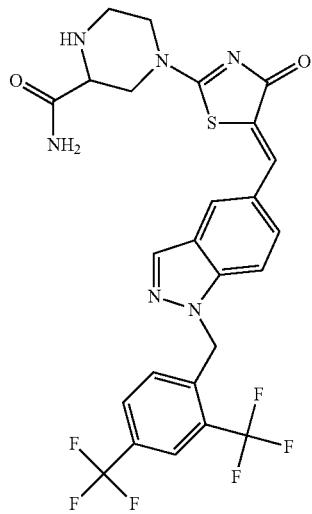 [SMILES: NC(=O)C1CN(C2=NC(=O)/C(=C/c3ccc4c(cnn4Cc4ccc(C(F)(F)F)cc4C(F)(F)F)c3)S2)CCN1]

4-[5-({1-[2,4-Bis(trifluoromethyl)benzyl]-1H-indazol-5-yl}methylidene)-4-oxo-4,5-dihydro-1,3-thiazol-2-yl]piperazine-2-carboxamide was prepared from 5-[1-(2,4-Bis-trifluoromethyl-benzyl)-1H-indazol-5-ylmethylene]-2-ethylsulfanyl-thiazol-4-one and piperazine-2-carboxylic acid amide following General Procedure C.
¹H NMR (400 MHz, CDCl₃) δ 8.25, 8.21 (s, 1H), 8.01-7.93 (m, 3H), 7.63 (d, 1H), 7.31 (d, 1H), 6.99-6.58 (m, 2H), 5.88 (s, 2H), 5.54 (br s1H), 4.70-4.22 (m, 1H), 3.93-2.98 (m, 6H).
LC/MS (m/z) [M]⁺ 583.1 (calculated for C₂₅H₂₀F₆N₆O₂S, 582.1).

Example 275
2-[(2R)-2-(Hydroxymethyl)morpholin-4-yl]-5-({1-[4-(1-methylethenyl)-2-(trifluoromethyl)benzyl]-1H-indazol-5-yl}methylidene)-1,3-thiazol-4(5H)-one

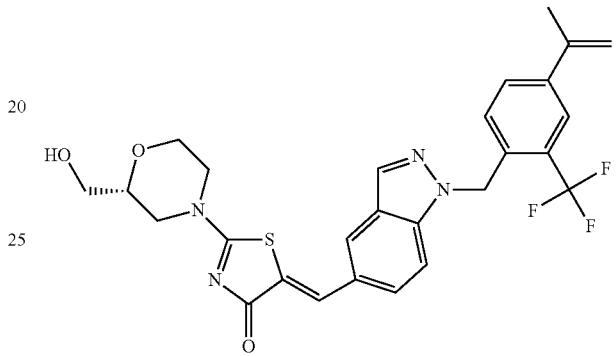

A solution of 5-{1-[4-(1-Hydroxy-1-methyl-ethyl)-2-trifluoromethyl-benzyl]-1H-indazol-5-ylmethylene}-2-(2-hydroxymethyl-morpholin-4-yl)-thiazol-4-one (400 mg, 0.71 mmol) in dichloromethane (2 mL) was treated with TFA (2 mL). The reaction mixture was stirred at room temperature for 1.5 hour and partitioned between water and dichloromethane. The dichloromethane layer was washed with aqueous saturated sodium carbonate, brine, dried over Na₂SO₄, filtered, and the solvent evaporated in vacuo to yield a crude solid. The crude solid was purified via flash chromatography (90% ethyl acetate in Heptane) to yield the title compound as a solid (94 mg, 24% yield).
¹H NMR (400 MHz, CDCl₃) δ 8.19 (d, 1H), 7.97 (s, 1H), 7.96 (s, 1H), 7.79 (d, 1H), 7.52 (d, 1H), 7.42 (dd, 1H), 7.33 (d, 1H), 6.66 (d, 1H), 5.83 (s, 2H), 5.38 (s, 1H), 5.15 (t, 1H), 4.81 (t, 1H), 4.11 (ddd, 1H), 3.84-3.25 (m, 7H), 2.11 (d, 3H).
LC/MS (m/z) [M]⁺ 543.3 (calculated for C₂₇H₂₅F₃N₄O₃S, 542.16).

Example 276
1-[5-({1-[4-Chloro-2-(trifluoromethyl)benzyl]-3-methyl-1H-indazol-5-yl}methylidene)-4-oxo-4,5-dihydro-1,3-thiazol-2-yl]piperidine-4-carboxylic acid

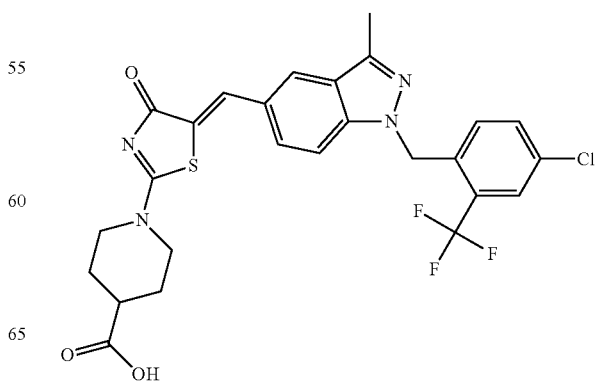

1-[5-({1-[4-Chloro-2-(trifluoromethyl)benzyl]-3-methyl-1H-indazol-5-yl}methylidene)-4-oxo-4,5-dihydro-1,3-thiazol-2-yl]piperidine-4-carboxylic acid was prepared from 5-[1-(4-Chloro-2-trifluoromethyl-benzyl)-3-methyl-1H-indazol-5-ylmethylene]-2-ethylsulfanyl-thiazol-4-one and Piperidine-4-carboxylic acid following General Procedure C. The compound was then prepared as an ethanolamine salt.

$^1$H NMR (400 MHz, CD$_3$OD): δ 8.02 (s, 1H), 7.86 (s, 1H), 7.79 (d, 1H), 7.67 (dd, 1H), 7.50 (d, 1H), 7.48 (d, 1H), 6.65 (d, 1H), 5.78 (s, 2H), 4.65 and 3.96 (d, 1H, rotamer), 3.71 (t, 2H, ethanolamine salt), 3.53 (t, 1H), 3.43 (t, 1H), 2.98 (m, 2H, ethanolamine salt), 2.63 (s, 3H), 2.51 (br, 1H), 2.00-2.13 (3H), 1.81 (m, 2H).

LC/MS (m/z) [M]$^+$ 563.25 (calculated for C$_{26}$H$_{22}$ClF$_3$N$_4$O$_3$S, 562.11).

Example 277

5-({1-[4-Chloro-2-(trifluoromethyl)benzyl]-3-methyl-1H-indazol-5-yl}methylidene)-2-[(3S)-3-(hydroxymethyl)piperazin-1-yl]-1,3-thiazol-4(5H)-one

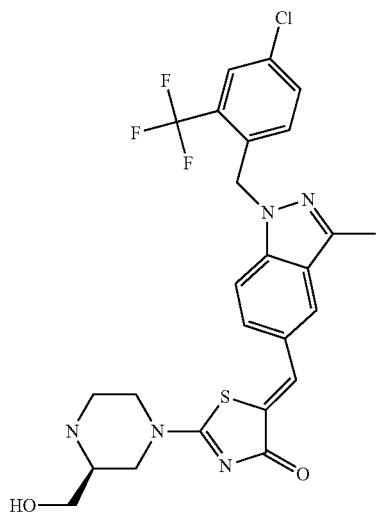 [SMILES: Cc1nn(Cc2ccc(Cl)cc2C(F)(F)F)c2ccc(/C=C3\SC(N4CCN[C@H](CO)C4)=NC3=O)cc12]

A. 4-{5-[1-(4-Chloro-2-trifluoromethyl-benzyl)-3-methyl-1H-indazol-5-ylmethylene]-4-oxo-4,5-dihydro-thiazol-2-yl}-2-hydroxymethyl-piperazine-1-carboxylic acid tert-butyl ester was prepared from 5-[1-(4-Chloro-2-trifluoromethyl-benzyl)-3-methyl-1H-indazol-5-ylmethylene]-2-ethylsulfanyl-thiazol-4-one and 2-Hydroxymethyl-piperazine-1-carboxylic acid tert-butyl ester following General Procedure C.

LC/MS (m/z) [M]$^+$ 650.3 (calculated for C$_{30}$H$_{31}$ClF$_3$N$_5$O$_4$S, 649.17).

B. 5-({1-[4-Chloro-2-(trifluoromethyl)benzyl]-3-methyl-1H-indazol-5-yl}methylidene)-2-[(3S)-3-(hydroxymethyl)piperazin-1-yl]-1,3-thiazol-4(5H)-one was prepared from 4-{5-[1-(4-Chloro-2-trifluoromethyl-benzyl)-3-methyl-1H-indazol-5-ylmethylene]-4-oxo-4,5-dihydro-thiazol-2-yl}-2-hydroxymethyl-piperazine-1-carboxylic acid tert-butyl ester following General Procedure H.

$^1$H NMR (400 MHz, CD$_3$OD): δ 8.06 (s, 1H), 7.97 (s, 1H), 7.80 (s, 1H), 7.68 (d, 1H), 7.51 (d, 1H), 7.48 (d, 1H), 6.69 (d, 1H), 5.78 (s, 2H), 4.16 (m, 1H), 3.87 (m, 1H), 3.76 (m, 2H), 3.65-3.12 (5H), 2.62 (s, 3H).

LC/MS (m/z) [M]$^+$ 550.8 (calculated for C$_{25}$H$_{23}$ClF$_3$N$_5$O$_2$S, 549.12).

Example 278

5-({1-[4-Chloro-2-(trifluoromethyl)benzyl]-3-methyl-1H-indazol-5-yl}methylidene)-2-(3,3,4-trimethylpiperazin-1-yl)-1,3-thiazol-4(5H)-one

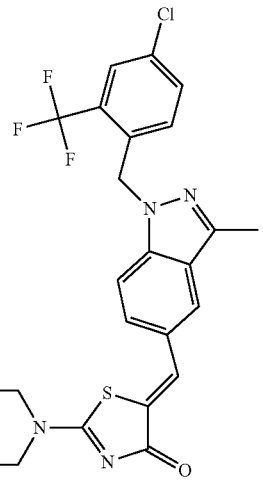

5-({1-[4-Chloro-2-(trifluoromethyl)benzyl]-3-methyl-1H-indazol-5-yl}methylidene)-2-(3,3,4-trimethylpiperazin-1-yl)-1,3-thiazol-4(5H)-one was prepared from 5-[1-(4-Chloro-2-trifluoromethyl-benzyl)-3-methyl-1H-indazol-5-ylmethylene]-2-ethylsulfanyl-thiazol-4-one and 1,2,2-Trimethyl-piperazine following General Procedure C.

$^1$H NMR (400 MHz, CD$_3$OD): δ 7.98 (s, 1H), 7.95 (d, 1H), 7.78 (d, 1H), 7.62 (d, 1H), 7.48 (d, 1H), 7.46 (d, 1H), 6.68 (t, 1H), 5.73 (d, 2H, rotamers), 4.82 and 4.70 (d, 1H, rotamers), 4.23 and 3.73 (d, 1H, rotamers), 4.13 (m, 1H), 3.93 (m, 1H), 3.61 (m, 2H), 2.91 (s, 3H), 2.60 (d, 3H, rotamers), 1.62 (d, 3H, rotamers), 1.46 (d, 3H, rotamers).

LC/MS (m/z) [M]$^+$ 562.20 (calculated for C$_{27}$H$_{27}$ClF$_3$N$_5$OS, 561.16).

Example 279 tert-Butyl (2R)-4-[5-({1-[2,4-bis(trifluoromethyl)benzyl]-3-iodo-1H-indazol-5-yl}methylidene)-4-oxo-4,5-dihydro-1,3-thiazol-2-yl]-2-(hydroxymethyl)piperazine-1-carboxylate

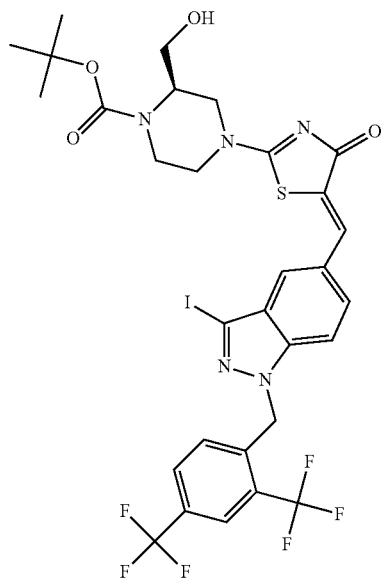 [SMILES: CC(C)(C)OC(=O)N1CCN(C2=NC(=O)/C(=C/c3ccc4c(c3)c(I)nn4Cc3ccc(C(F)(F)F)cc3C(F)(F)F)S2)C[C@@H]1CO]

4-{5-[1-(2,4-Bis-trifluoromethyl-benzyl)-3-iodo-1H-indazol-5-ylmethylene]-4-oxo-4,5-dihydro-thiazol-2-yl}-2-hydroxymethyl-piperazine-1-carboxylic acid tert-butyl ester was prepared from 1-(2,4-Bis-trifluoromethyl-benzyl)-3-iodo-1H-indazole-5-carbaldehyde and 2-Hydroxymethyl-4-(4-oxo-4,5-dihydro-thiazol-2-yl)-piperazine-1-carboxylic acid tert-butyl ester following General Procedure D.

$^1$H NMR (400 MHz, CD$_3$OD): δ 8.00 (s, 1H), 7.75 (br, 1H), 7.61 (d, 1H), 7.54 (d, 1H), 7.45 (m, 1H), 7.40 (m, 1H), 6.88 (t, 1H), 5.83 (s, 2H), 4.70 and 4.54 (d, 1H, rotamers), 4.31 (br, 1H), 4.11 and 3.82 (d, 1H, rotamers), 4.04 (d, 1H), 3.54-3.74 (3H), 3.42 (m, 1H), 3.25 (br, 1H), 1.50 (s, 9H).

LC/MS (m/z) [M]$^+$ 796.05 (calculated for C$_{30}$H$_{28}$F$_{61}$N$_5$O$_4$S, 795.08).

Example 280

{(2S)-4-[5-({1-[2,4-Bis(trifluoromethyl)benzyl]-1H-indazol-5-yl}methylidene)-4-oxo-4,5-dihydro-1,3-thiazol-2-yl]morpholin-2-yl}methyl acetate

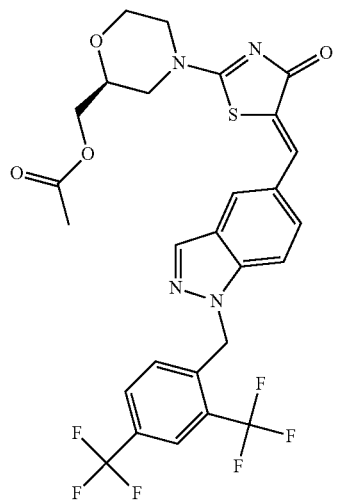 [SMILES: CC(=O)OC[C@@H]1CN(C2=NC(=O)/C(=C/c3ccc4c(cnn4Cc4ccc(C(F)(F)F)cc4C(F)(F)F)c3)S2)CCO1]

{(2S)-4-[5-({1-[2,4-Bis(trifluoromethyl)benzyl]-1H-indazol-5-yl}methylidene)-4-oxo-4,5-dihydro-1,3-thiazol-2-yl]morpholin-2-yl}methyl acetate was prepared from 1-(2,4-Bis-trifluoromethyl-benzyl)-1H-indazole-5-carbaldehyde and Morpholin-2-yl-methanol following General Procedure E.

$^1$H NMR (400 MHz, CDCl$_3$) δ 8.22 (d, 1H), 7.99 (br s, 2H), 7.97 (s, 1H), 7.63 (d, 1H), 7.56 (d, 1H), 7.33-7.31 (m, 1H), 6.83 (d, 1H), 5.89 (s, 2H), 4.89 (d, 0.5H), 4.79 (d, 0.5H), 4.25-4.08 (m, 3H), 3.84-3.81 (m, 1H), 3.76-3.67 (m, 2H), 3.64-3.57 (m, 0.5H), 3.43-3.37 (m, 0.5H), 3.22-3.17 (m, 0.5H), 2.15 and 2.12 (2s, 3H).

LC/MS (m/z) [M+1]$^+$ 613.2 (calculated for C$_{27}$H$_{22}$F$_6$N$_4$O$_4$S, 612.13).

Example 281

2-[(2S)-2-(Hydroxymethyl)morpholin-4-yl]-5-[(1-{[3-(trifluoromethyl)pyridin-2-yl]methyl}-1H-indazol-5-yl)methylidene]-1,3-thiazol-4(5H)-one

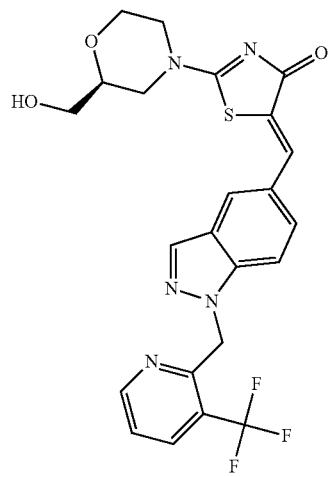 [SMILES: O=C1N=C(N2CCO[C@H](CO)C2)S/C1=C\c1ccc2c(cnn2Cc2ncccc2C(F)(F)F)c1]

A. 1-(3-Trifluoromethyl-pyridin-2-ylmethyl)-1H-indazole-5-carbaldehyde was prepared from 1H-Indazole-5-carbaldehyde and 2-Chloromethyl-3-trifluoromethyl-pyridine following General Procedure A.

$^1$H NMR (400 MHz, CDCl$_3$) δ 10.06 (s, 1H), 8.59 (d, 1H), 8.29 (s, 1H), 8.25 (s, 1H), 8.03 (d, 1H), 7.94 (d, 1H), 7.48 (d, 1H), 7.37-7.33 (m, 1H), 5.94 (s, 2H).

LC/MS (m/z) [M+1]$^+$ 306.1 (calculated for C$_{15}$H$_{10}$F$_3$N$_3$O, 305.08).

B. 2-[(2S)-2-(Hydroxymethyl)morpholin-4-yl]-5-[(1-{[3-(trifluoromethyl)pyridin-2-yl]methyl}-1H-indazol-5-yl)methylidene]-1,3-thiazol-4(5H)-one was prepared from 1-(3-Trifluoromethyl-pyridin-2-ylmethyl)-1H-indazole-5-carbaldehyde and 2(S)-(2-Hydroxymethyl-morpholin-4-yl)-thiazol-4-one following General Procedure D.

$^1$H NMR (400 MHz, CDCl$_3$) δ 8.61 (d, 1H), 8.16 (d, 1H), 8.02 (d, 1H), 7.96 (br s, 2H), 7.53 (d, 1H), 7.44 (d, 1H), 7.36-7.33 (m, 1H), 5.91 (s, 2H), 4.84-4.78 (m, 1H), 4.15-4.06 (ddd, 1H), 3.85-3.56 (m, 5.5H), 3.52-3.46 (m, 0.5H), 3.41-3.33 (m, 0.5H), 3.30-3.24 (m, 0.5H), 1.94-1.88 (m, 1H).

LC/MS (m/z) [M+1]+ 504.1 (calculated for $C_{23}H_{20}F_3N_5O_3S$, 503.12).

Example 282

Methyl N-({(2S)-4-[5-({1-[2,4-bis(trifluoromethyl)benzyl]-1H-indazol-5-yl}methylidene)-4-oxo-4,5-dihydro-1,3-thiazol-2-yl]morpholin-2-yl}carbonyl)glycinate

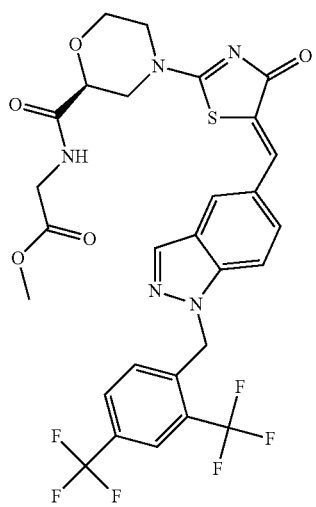 [SMILES: COC(=O)CNC(=O)[C@@H]1CN(C2=NC(=O)/C(=C/c3ccc4c(cnn4Cc4ccc(C(F)(F)F)cc4C(F)(F)F)c3)S2)CCO1]

A. 2-(Methoxycarbonylmethyl-carbamoyl)-morpholine-4-carboxylic acid tert-butyl ester.

To a solution of Morpholine-2,4-dicarboxylic acid 4-tert-butyl ester (0.3 g, 1.29 mmol), glycine methyl ester hydrochloride (0.162 g, 1.29 mmol) and diisopropylethylamine (0.167 g, 1.29 mmol) in dichloromethane (8 mL) and THF (4 mL) was added EDCI (0.274 g, 1.43 mmol) followed by DMAP (0.048 g, 0.39 mmol).

The reaction mixture was stirred at room temperature for 48 hours and the solvent evaporated in vacuo to give a solid. The solid was partitioned between dichloromethane and an aqueous 5% citric acid solution. The dichloromethane layer was washed with aqueous saturated sodium carbonate, brine, dried over $Na_2SO_4$, filtered, and the solvent evaporated in vacuo to yield the title compound as a colorless gum (0.25 g, 64% yield).

$^1$H NMR (400 MHz, CDCl$_3$) δ 7.06 (br s, 1H), 4.33 (br s, 1H), 4.07 (d, 2H), 3.99-3.93 (m, 3H), 3.77 (s, 3H), 2.93-2.91 (m, 1H), 2.81-2.75 (m, 1H), 1.47 (s, 9H).

LC/MS (m/z) [MNa]+ 325.2 (calculated for $C_{13}H_{22}N_2O_6$, 302.15).

B. [(Morpholine-2-carbonyl)-amino]-acetic acid methyl ester was prepared following General Procedure I.

$^1$H NMR (400 MHz, D$_2$O) δ 4.37 (dd, 1H), 4.13-4.09 (m, 1H), 3.95 (s, 2H), 3.87-3.79 (m, 1H), 3.62 (s, 3H), 3.52-3.49 (m, 1H), 3.27-3.24 (m, 1H), 3.15-3.06 (m, 2H).

LC/MS (m/z) [M]+ 203.1 (calculated for $C_8H_{14}N_2O_4$, 202.1).

C. Methyl N-({(2S)-4-[5-({1-[2,4-bis(trifluoromethyl)benzyl]-1H-indazol-5-yl}methylidene)-4-oxo-4,5-dihydro-1,3-thiazol-2-yl]morpholin-2-yl}carbonyl)glycinate was prepared from 5-[1-(2,4-Bis-trifluoromethyl-benzyl)-1H-indazol-5-ylmethylene]-2-propylsulfanyl-thiazol-4-one and [(Morpholine-2-carbonyl)-amino]-acetic acid methyl ester following General Procedure B.

$^1$H NMR (400 MHz, CDCl$_3$) δ 8.26 (d, 1H), 8.01-7.95 (m, 3H), 7.63 (d, 1H), 7.55 (d, 1H), 7.33 (d, 1H), 7.12-7.10 (m, 1H), 6.82 (d, 1H), 5.89 (s, 2H), 4.79-4.75 (m, 1H), 4.19-4.11 (m, 5H), 3.81-3.76 (m, 4H), 3.50-3.40 (m, 2H).

LC/MS (m/z) [M+1]+ 656.2 (calculated for $C_{28}H_{23}F_6N_5O_5S$, 655.13).

Example 283

5-[1-(2,4-Bis-trifluoromethyl-benzyl)-1H-indazol-5-ylmethylene]-2-(3-(S)-hydroxymethyl-piperazin-1-yl)-thiazol-4-one

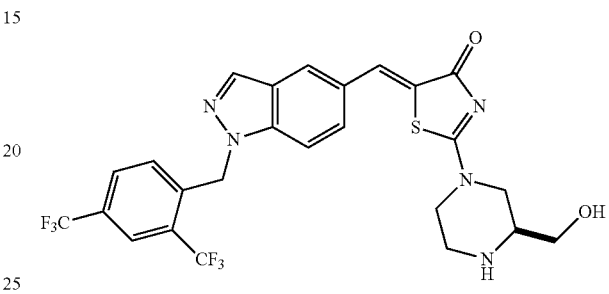

A. 4-{5-[1-(2,4-Bis-trifluoromethyl-benzyl)-1H-indazol-5-ylmethylene]-4-oxo-4,5-dihydro-thiazol-2-yl}-2-(S)-hydroxymethyl-piperazine-1-carboxylic acid tert-butyl ester was prepared from 5-[1-(2,4-Bis-trifluoromethyl-benzyl)-1H-indazol-5-ylmethylene]-2-ethylsulfanyl-thiazol-4-one and (2S)-Hydroxymethyl-piperazine-1-carboxylic acid tert-butyl ester following General Procedure C.

LC/MS (m/z) [M+1]+ 670.3 (calculated for $C_{30}H_{29}F_6N_5O_4S$, 669.18).

B. 5-[1-(2,4-Bis-trifluoromethyl-benzyl)-1H-indazol-5-ylmethylene]-2-(3-(S)-hydroxymethyl-piperazin-1-yl)thiazol-4-one was prepared from 4-{5-[1-(2,4-Bis-trifluoromethyl-benzyl)-1H-indazol-5-ylmethylene]-4-oxo-4,5-dihydro-thiazol-2-yl}-2-(S)-hydroxymethyl-piperazine-1-carboxylic acid tert-butyl ester following General Procedure H.

$^1$H NMR (400 MHz, CDCl$_3$): δ 8.22 (dd, 1H), 7.99 (br, 2H), 7.94 (s, 1H), 7.63 (d, 1H), 7.56 (m, 1H), 7.32 (d, 1H), 6.82 (d, 1H), 5.88 (s, 2H), 4.77 (m, 1H), 3.78-3.72 (2H), 3.70-3.55 (1H), 3.53-3.15 (3H), 3.05-2.92 (2H), 2.01 (br s, 1H).

LC/MS (m/z) [M+1]+ 570.5 (calculated for $C_{25}H_{21}F_6N_5O_2S$, 569.13).

D) General Administration, Formulation, and Dosages

The present compounds are ERR-α modulators and are therefore useful in treating, preventing, or inhibiting the progression of ERR-α mediated conditions including but not limited to ankylosing spondylitis, artherosclerosis, arthritis (such as rheumatoid arthritis, infectious arthritis, childhood arthritis, psoriatic arthritis, reactive arthritis), bone-related diseases (including those related to bone formation), breast cancer (including those unresponsive to anti-estrogen therapy), cardiovascular disorders, cartilage-related disease (such as cartilage injury/loss, cartilage degeneration, and those related to cartilage formation), chondrodysplasia, chondrosarcoma, chronic back injury, chronic bronchitis, chronic inflammatory airway disease, chronic obstructive pulmonary disease, diabetes, disorders of energy homeostasis, gout, pseudogout, lipid disorders, metabolic syndrome, multiple myeloma, obesity, osteoarthritis, osteogenesis imperfecta, osteolytic bone metastasis, osteomalacia, osteoporosis, Paget's disease, periodontal disease, polymyalgia rheumatica, Reiter's syndrome, repetitive stress injury, hyperglycemia, elevated blood glucose level, and insulin resistance and other disorders, diseases, or conditions related thereto.

The invention features a method for treating a subject with an ERR-α mediated disease, said method comprising administering to the subject a therapeutically effective amount of a pharmaceutical composition comprising a compound of the invention. In particular, the invention also provides a method for treating or inhibiting the progression of breast cancer, arthritis, inflammatory airway disease, or metabolic disorders, and associated symptoms or complications thereof in a subject, wherein the method comprises administering to the subject a therapeutically effective amount of a pharmaceutical composition comprising a compound of the invention.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts in vivo to the specified compound after administration to the subject. Conventional procedures for the selection and preparation of suitable prodrug derivatives are described, for example, in "*Design of Prodrugs*", ed. H. Bundgaard, Elsevier, 1985.

Some of the crystalline forms for the compounds may exist as polymorphs and as such are intended to be included in the present invention. In addition, some of the compounds may form solvates with water (i.e., hydrates) or common organic solvents, and such solvates are intended to be encompassed within the scope of this invention.

Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, cis-trans isomers, and enantiomers thereof are encompassed within the scope of the present invention.

E) Use

1. Dosages

Those of skill in the treatment of disorders, diseases, or conditions mediated by ERR-α can determine the effective daily amount from the test results presented hereinafter and other information. The exact dosage and frequency of administration depends on the particular compound of invention used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines in practicing the present invention.

Preferably, the method for the treatment of the ERR-α disorders described in the present invention using any of the compounds as defined herein, the dosage form will contain a pharmaceutically acceptable carrier containing between from about 0.1 mg to about 5000 mg; particularly from about 0.5 mg to about 1000 mg; and, more particularly, from about 1 mg to about 100 mg of the compound, and may be constituted into any form suitable for the mode of administration selected. The dosages, however, may be varied depending upon the requirement of the subjects, the severity of the condition being treated and the compound being employed. The use of either daily administration or post-periodic dosing may be employed.

The pharmaceutical compositions herein will contain, per unit dosage unit, e.g., tablet, capsule, powder, injection, suppository, teaspoonful and the like, of from about 0.001 mg/kg/day to about 10 mg/kg/day (particularly from about 0.01 mg/kg/day to about 1 mg/kg/day; and, more particularly, from about 0.1 mg/kg/day to about 0.5 mg/kg/day) and may be given at a dosage of from about 0.001 mg/kg/day to about 30 mg/kg/day (particularly from about 0.01 mg/kg/day to about 2 mg/kg/day, more particularly from about 0.1 mg/kg/day to about 1 mg/kg/day and even more particularly from about 0.5 mg/kg/day to about 1 mg/kg/day).

Preferably these compositions are in unit dosage forms from such as tablets, pills, capsules, dry powders for reconstitution or inhalation, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, dry powder inhaler or other inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W.R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active form of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetllitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

The daily dose of a pharmaceutical composition of the present invention may be varied over a wide range from about 0.1 mg to about 5000 mg; preferably, the dose will be in the range of from about 1 mg to about 100 mg per day for an average human. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 or 500 milligrams of the active ingredient for the symptomatic adjustment of the dosage to the subject to be treated. Advantageously, a compound of the present invention may be administered in a single daily dose or the total daily dosage may be administered in divided doses of two, three or four times daily.

It is also apparent to one skilled in the art that the therapeutically effective dose for active compounds of the invention or a pharmaceutical composition thereof will vary according to the desired effect. Therefore, optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as ERR-α modulators is required for a subject in need thereof.

2. Formulations

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

The compounds of the present invention may be formulated into various pharmaceutical forms for administration purposes. Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

3. Combination Therapy

The compounds of the present invention may be used in combination with one or more pharmaceutically active agents. These include anti-diabetic agents, anti-obesity agents, other lipid lowering agents, direct thrombin inhibitor (DTI), as well as lipid lowering agents such as statin drugs and the fibrates.

Other agents useful for the combination therapy of the present invention include glucokinase modulators such as:

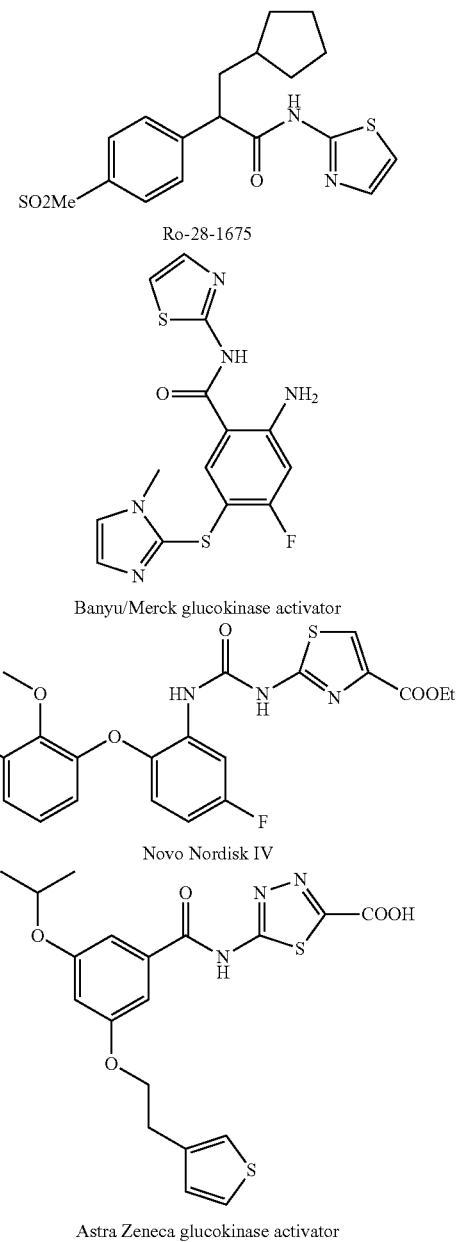

Ro-28-1675

Banyu/Merck glucokinase activator

Novo Nordisk IV

Astra Zeneca glucokinase activator

Anti-Diabetic Agents Include RXR Modulators Such as:
(1) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455);
(2) 9-cis-retinoic acid;
(3) AGN-4326 (also known as ALRT-4204, AGN-4204, ALRT-326, ALRT-324, or LGD 1324);
(4) LGD 1324 (ALRT 324);
(5) LG 100754;
(6) LY-510929;
(7) LGD 1268 (6-(1,1,4,4,6-pentamethyl-1,2,3,4-tetrahydro-naphth-7-ylcycloprop-1-yl)nicotinic acid, known as ALRT 268 or LG 100268); and
(8) LG 100264.

Anti-diabetic agents also include thiazolidinedione and non-thiazolidinedione insulin sensitizers, which decrease peripheral insulin resistance by enhancing the effects of insulin at target organs and tissues.

The following agents are known to bind and activate the nuclear receptor peroxisome proliferator-activated receptor-gamma (PPARγ) which increases transcription of specific insulin-responsive genes. Examples of PPAR-gamma agonists are thiazolidinediones such as:

(1) rosiglitazone (2,4-thiazolidinedione,5-((4-(2-(methyl-2-pyridinylamino) ethoxy)phenyl)methyl)-, (Z)-2-butenedioate (1:1) or 5-((4-(2-(methyl-2-pyridinylamino) ethoxy)phenyl)methyl)-2,4-thiazolidinedione, known as AVANDIA; also known as BRL 49653, BRL 49653C, BRL 49653c, SB 210232, or rosiglitazone maleate);

(2) pioglitazone (2,4-thiazolidinedione, 5-((4-(2-(5-ethyl-2-pyridinyl)ethoxy)phenyl)methyl)-, monohydrochloride, (+-)- or 5-((4-(2-(5-ethyl-2-pyridyl)ethoxy)phenyl)methy)-2,4-thiazolidinedione, known as ACTOS, ZACTOS, or GLUSTIN; also known as AD 4833, U 72107, U 72107A, U 72107E, pioglitazone hydrochloride (USAN));

(3) troglitazone (5-((4-((3,4-dihydro-6-hydroxy-2,5,7,8-tetramethyl-2H-1-benzopyran-2-yl)methoxy)phenyl) methyl)-2,4-thiazolidinedione, known as NOSCAL, REZULIN, ROMOZIN, or PRELAY; also known as CI-991, CS 045, GR 92132, GR 92132×);

(4) isaglitazone ((+)-5-[[6-[(2-fluorophenyl)methoxy]-2-naphthalenyl]methyl]-2,4-thiazolidinedione or 5-((6-((2-fluorophenyl)methoxy)-2-naphthalenyl)methyl-2,4-thiazolidinedione or 5-(6-(2-fluorobenzyloxy) naphthalen-2-ylmethyl) thiazolidine-2,4-dione, also known as MCC-555 or neoglitazone); and (5) 5-BTZD.

Additionally, the non-thiazolidinediones that act as insulin sensitizing agents include, but are not limited to:

(1) JT-501 (JTT 501, PNU-1827, PNU-7,6-MET-0096, or PNU 182716: isoxazolidine-3,5-dione, 4-((4-(2-phenyl-5-methyl)-1,3-oxazolyl)ethylphenyl-4) methyl-);

(2) KRP-297 (5-(2,4-dioxothiazolidin-5-ylmethyl)-2-methoxy-N-(4-(trifluoromethyl)benzyl)benzamide or 5-((2,4-dioxo-5-thiazolidinyl)methyl)-2-methoxy-N-((4-(trifluoromethyl)phenyl)methyl)benzamide); and (3) Farglitazar (L-tyrosine, N-(2-benzoylphenyl)-o-(2-(5-methyl-2-phenyl-4-oxazolyl)ethyl)- or N-(2-benzoylphenyl)-O-(2-(5-methyl-2-phenyl-4-oxazolyl)ethyl)-L-tyrosine, or GW2570 or GI-262570).

Other anti-diabetic agents have also been shown to have PPAR modulator activity such as PPAR gamma, SPPAR gamma, and/or PPAR delta/gamma agonist activity. Examples are listed below:

(1) AD 5075;
(2) R 119702 ((+-)-5-(4-(5-Methoxy-1H-benzimidazol-2-ylmethoxy)benzyl) thiazolin-2,4-dione hydrochloride, or Cl 1037 or CS 011);
(3) CLX-0940 (peroxisome proliferator-activated receptor alpha agonist/peroxisome proliferator-activated receptor gamma agonist);
(4) LR-90 (2,5,5-tris(4-chlorophenyl)-1,3-dioxane-2-carboxylic acid, PPARdelta/γ agonist);
(5) Tularik (PPARγ agonist);
(6) CLX-0921 (PPARγ agonist);
(7) CGP-52608 (PPAR agonist);
(8) GW-409890 (PPAR agonist);
(9) GW-7845 (PPAR agonist);
(10) L-764406 (PPAR agonist);
(11) LG-101280 (PPAR agonist);
(12) LM-4156 (PPAR agonist);
(13) Risarestat (CT-112);
(14) YM 440 (PPAR agonist);
(15) AR-H049020 (PPAR agonist);
(16) GW 0072 (4-(4-((2S,5S)-5-(2-(bis(phenylmethyl) amino)-2-oxoethyl)-2-heptyl-4-oxo-3-thiazolidinyl) butyl)benzoic acid);
(17) GW 409544 (GW-544 or GW-409544);
(18) NN 2344 (DRF 2593);
(19) NN 622 (DRF 2725);
(20) AR-H039242 (AZ-242);
(21) GW 9820 (fibrate);
(22) GW 1929 (N-(2-benzoylphenyl)-O-(2-(methyl-2-pyridinylamino) ethyl)-L-tyrosine, known as GW 2331, PPAR alpha/γ agonist);
(23) SB 219994 ((S)-4-(2-(2-benzoxazolylmethylamino) ethoxy)-alpha-(2,2,2-trifluoroethoxy)benzenepropanoic acid or 3-(4-(2-(N-(2-benzoxazolyl)-N-methylamino)ethoxy)phenyl)-2(S)-(2,2,2-trifluoroethoxy) propionic acid or benzenepropanoic acid,4-(2-(2-benzoxazolylmethylamino)ethoxy)-alpha-(2,2,2-trifluoroethoxy)-, (alphaS)-, PPARalpha/γ agonist);
(24) L-796449 (PPAR alpha/γ agonist);
(25) Fenofibrate (Propanoic acid, 2-[4-(4-chlorobenzoyl) phenoxy]-2-methyl-, 1-methylethyl ester, known as TRICOR, LIPCOR, LIPANTIL, LIPIDIL MICRO PPAR alpha agonist);
(26) GW-9578 (PPAR alpha agonist);
(27) GW-2433 (PPAR alpha/γ agonist);
(28) GW-0207 (PPARγ agonist);
(29) LG-100641 (PPARγ agonist);
(30) LY-300512 (PPARγ agonist);
(31) NID525-209 (NID-525);
(32) VDO-52 (VDO-52);
(33) LG 100754 (peroxisome proliferator-activated receptor agonist);
(34) LY-510929 (peroxisome proliferator-activated receptor agonist);
(35) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455); and
(36) GW-1536 (PPAR alpha/γ agonist).

Other insulin sensitizing agents include, but are not limited to:

(1) INS-1 (D-chiro inositol or D-1,2,3,4,5,6-hexahydroxycyclohexane);
(2) protein tyrosine phosphatase 1 B (PTP-1B) inhibitors;
(3) glycogen synthase kinase-3 (GSK3) inhibitors;
(4) beta 3 adrenoceptor agonists such as ZD 2079 ((R)—N-(2-(4-(carboxymethyl)phenoxy)ethyl)-N-(2-hydroxy-2-phenethyl) ammonium chloride, also known as ICI D 2079) or AZ 40140;
(5) glycogen phosphorylase inhibitors;
(6) fructose-1,6-bisphosphatase inhibitors;
(7) chromic picolinate, vanadyl sulfate (vanadium oxysulfate);
(8) KP 102 (organo-vanadium compound);
(9) chromic polynicotinate;
(10) potassium channel agonist NN 414;
(11) YM 268 (5,5'-methylene-bis(1,4-phenylene)bismethylenebis(thiazolidine-2,4-dione);
(12) TS 971;
(13) T 174 ((+-)-5-(2,4-dioxothiazolidin-5-ylmethyl)-2-(2-naphthylmethyl)benzoxazole);

(14) SDZ PGU 693 ((+)-trans-2 (S-((4-chlorophenoxy) methyl)-7alpha-(3,4-dichlorophenyl)tetrahydropyrrolo (2,1-b)oxazol-5(6H)-one);
(15) S15261 ((−)-4-(2-((9H-fluoren-9-ylacetyl)amino) ethyl)benzoic acid 2-((2-methoxy-2-(3-(trifluoromethyl)phenyl)ethyl)amino) ethyl ester);
(16) AZM 134 (Alizyme);
(17) ARIAD;
(18) R 102380;
(19) PNU 140975 (1-(hydrazinoiminomethyl) hydrazino) acetic acid;
(20) PNU 106817 (2-(hydrazinoiminomethyl) hydrazino) acetic acid;
(21) NC 2100 (5-((7-(phenylmethoxy)-3-quinolinyl)methyl)-2,4-thiazolidinedione;
(22) MXC 3255;
(23) MBX 102;
(24) ALT 4037;
(25) AM 454;
(26) JTP 20993 (2-(4-(2-(5-methyl-2-phenyl-4-oxazolyl) ethoxy)benzyl)-malonic acid dimethyl diester);
(27) Dexlipotam (5(R)-(1,2-dithiolan-3-yl)pentanoic acid, also known as (R)-alpha lipoic acid or (R)-thioctic acid);
(28) BM 170744 (2,2-Dichloro-12-(p-chlorophenyl)dodecanoic acid);
(29) BM 152054 (5-(4-(2-(5-methyl-2-(2-thienyl)oxazol-4-yl)ethoxy)benzothien-7-ylmethyl)thiazolidine-2,4-dione);
(30) BM 131258 (5-(4-(2-(5-methyl-2-phenyloxazol-4-yl) ethoxy)benzothien-7-ylmethyl)thiazolidine-2,4-dione);
(31) CRE 16336 (EML 16336);
(32) HQL 975 (3-(4-(2-(5-methyl-2-phenyloxazol-4-yl) ethoxy)phenyl)-2(S)-(propylamino)propionic acid);
(33) DRF 2189 (5-((4-(2-(1-Indolyl)ethoxy)phenyl)methyl)thiazolidine-2,4-dione);
(34) DRF 554158;
(35) DRF-NPCC;
(36) CLX 0100, CLX 0101, CLX 0900, or CLX 0901;
(37) IkappaB Kinase (IKK B) Inhibitors;
(38) mitogen-activated protein kinase (MAPK) inhibitors p38 MAPK Stimulators;
(39) phosphatidyl-inositide triphosphate;
(40) insulin recycling receptor inhibitors;
(41) glucose transporter 4 modulators;
(42) TNF-α antagonists;
(43) plasma cell differentiation antigen-1 (PC-1) Antagonists;
(44) adipocyte lipid-binding protein (ALBP/aP2) inhibitors;
(45) phosphoglycans;
(46) Galparan;
(47) Receptron;
(48) islet cell maturation factor;
(49) insulin potentiating factor (IPF or insulin potentiating factor-1);
(50) somatomedin C coupled with binding protein (also known as IGF-BP3, IGF-BP3, SomatoKine);
(51) Diab II (known as V-411) or Glucanin, produced by Biotech Holdings Ltd. or Volque Pharmaceutical;
(52) glucose-6 phosphatase inhibitors;
(53) fatty acid glucose transport protein;
(54) glucocorticoid receptor antagonists; and
(55) glutamine:fructose-6-phosphate amidotransferase (GFAT) modulators.

Anti-diabetic agents can further include biguanides, which decreases liver glucose production and increases the uptake of glucose. Examples of biguanides include metformin such as:
(1) 1,1-dimethylbiguanide (e.g., Metformin—DepoMed, Metformin—Biovail Corporation, or METFORMIN GR (metformin gastric retention polymer)); and
(2) metformin hydrochloride (N,N-dimethylimidodicarbonimidic diamide monohydrochloride, also known as LA 6023, BMS 207150, GLUCOPHAGE, or GLUCOPHAGE XR.

Additionally, anti-diabetic agents include alpha-glucosidase inhibitors, which inhibit alpha-glucosidase. Alpha-glucosidase converts fructose to glucose, thereby delaying the digestion of carbohydrates. The undigested carbohydrates are subsequently broken down in the gut, reducing the postprandial glucose peak. Examples of alpha-glucosidase inhibitors include, but are not limited to:
(1) acarbose (D-glucose, O-4,6-dideoxy-4-(((1S-(1alpha, 4alpha,5beta,6alpha))-4,5,6-trihydroxy-3-(hydroxymethyl)-2-cyclohexen-1-yl)amino)-alpha-D-glucopyranosyl-(1-4)-O-alpha-D-glucopyranosyl-(1-4)-, also known as AG-5421, Bay-g-542, BAY-g-542, GLUCOBAY, PRECOSE, GLUCOR, PRANDASE, GLUMIDA, or ASCAROSE);
(2) Miglitol (3,4,5-piperidinetriol, 1-(2-hydroxyethyl)-2-(hydroxymethyl)-, (2R(2alpha, 3beta, 4alpha, 5beta))- or (2R,3R,4R,5S)-1-(2-hydroxyethyl)-2-(hydroxymethyl-3,4,5-piperidinetriol), also known as BAY 1099, BAY M 1099, BAY-m-1099, BAYGLITOL, DIASTABOL, GLYSET, MIGLIBAY, MITOLBAY, PLUMAROL);
(3) CKD-711 (0-4-deoxy-4-((2,3-epoxy-3-hydroxymethyl-4,5,6-trihydroxycyclohexane-1-yl)amino)-alpha-b-glucopyranosyl-(1-4)-alpha-D-glucopyranosyl-(1-4)-D-glucopyranose);
(4) emiglitate (4-(2-((2R,3R,4R,5S)-3,4,5-trihydroxy-2-(hydroxymethyl)-1-piperidinyl)ethoxy)benzoic acid ethyl ester, also known as BAY o 1248 or MKC 542);
(5) MOR14 (3,4,5-piperidinetriol, 2-(hydroxymethyl)-1-methyl-, (2R-(2alpha,3beta,4alpha,5beta))-, also known as N-methyldeoxynojirimycin or N-methylmoranoline); and
(6) Voglibose (3,4-dideoxy-4-((2-hydroxy-1-(hydroxymethyl)ethyl)amino)-2-C-(hydroxymethyl)-D-epi-inositol or D-epi-Inositol, 3,4-dideoxy-4-((2-hydroxy-1-(hydroxymethyl)ethyl)amino)-2-C-(hydroxymethyl)-, also known as A 71100, AO 128, BASEN, GLUSTAT, VOGLISTAT.

Anti-diabetic agents also include insulins such as regular or short-acting, intermediate-acting, and long-acting insulins, non-injectable or inhaled insulin, tissue selective insulin, glucophosphokinin (D-chiroinositol), insulin analogues such as insulin molecules with minor differences in the natural amino acid sequence and small molecule mimics of insulin (insulin mimetics), and endosome modulators. Examples include, but are not limited to:
(1) Biota;
(2) LP 100;
(3) (SP-5-21)-oxobis(1-pyrrolidinecarbodithioato-S,S') vanadium;
(4) insulin aspart (human insulin (28B-L-aspartic acid) or B28-Asp-insulin, also known as insulin X14, INA-X14, NOVORAPID, NOVOMIX, or NOVOLOG);
(5) insulin detemir (Human 29B-(N-6-(1-oxotetradecyl)-L-lysine)-(1A-21A), (1B-29B)—Insulin or NN 304);

(6) insulin lispro ("28B-L-lysine-29B-L-proline human insulin, or Lys(B28), Pro(B29) human insulin analog, also known as lys-pro insulin, LY 275585, HUMALOG, HUMALOG MIX 75/25, or HUMALOG MIX 50/50);

(7) insulin glargine (human (A21-glycine, B31-arginine, B32-arginine) insulin HOE 901, also known as LANTUS, OPTISULIN);

(8) Insulin Zinc Suspension, extended (Ultralente), also known as HUMULIN U or ULTRALENTE;

(9) Insulin Zinc suspension (Lente), a 70% crystalline and 30% amorphous insulin suspension, also known as LENTE ILETIN II, HUMULIN L, or NOVOLIN L;

(10) HUMULIN 50/50 (50% isophane insulin and 50% insulin injection);

(11) HUMULIN 70/30 (70% isophane insulin NPH and 30% insulin injection), also known as NOVOLIN 70/30, NOVOLIN 70/30 PenFill, NOVOLIN 70/30 Prefilled;

(12) insulin isophane suspension such as NPH ILETIN II, NOVOLIN N, NOVOLIN N PenFill, NOVOLIN N Prefilled, HUMULIN N;

(13) regular insulin injection such as ILETIN II Regular, NOVOLIN R, VELOSULIN BR, NOVOLIN R PenFill, NOVOLIN R Prefilled, HUMULIN R, or Regular U-500 (Concentrated);

(14) ARIAD;

(15) LY 197535;

(16) L-783281; and

(17) TE-17411.

Anti-diabetic agents can also include insulin secretion modulators such as:

(1) glucagon-like peptide-1 (GLP-1) and its mimetics;

(2) glucose-insulinotropic peptide (GIP) and its mimetics;

(3) exendin and its mimetics;

(4) dipeptidyl protease (DPP or DPPIV) inhibitors such as (4a) DPP-728 or LAF 237 (2-pyrrolidinecarbonitrile,1-(((2-((5-cyano-2-pyridinyl)amino) ethyl)amino) acetyl), known as NVP-DPP-728, DPP-728A, LAF-237);

(4b) Sitagliptin, also known as Januvia;

(4c) Saxagliptin;

(4d) Linagliptin;

(4e) Alogliptin;

(4f) KRP-104;

(4g) AMG-222;

(4h) P 3298 or P32/98 (di-(3N-((2S,3S)-2-amino-3-methyl-pentanoyl)-1,3-thiazolidine) fumarate);

(4i) TSL 225 (tryptophyl-1,2,3,4-tetrahydroisoquinoline-3-carboxylic acid);

(4j) Valine pyrrolidide (valpyr);

(4k) 1-aminoalkylisoquinolinone-4-carboxylates and analogues thereof;

(4l) SDZ 272-070 (1-(L-Valyl)pyrrolidine);

(4m) TMC-2A, TMC-2B, or TMC-2C;

(4n) Dipeptide nitriles (2-cyanopyrrolodides);

(4o) CD26 inhibitors; and (4p) SDZ 274-444;

(5) GPR119 modulators;

(6) glucagon antagonists such as AY-279955; and (7) amylin agonists which include, but are not limited to, pramlintide (AC-137, Symlin, tripro-amylin or pramlintide acetate).

Other anti-diabetic agents have also been shown to have sodium glucose cotransporter-2 (SGLT-2) inhibition activity. Examples are listed below:

(1) Dapagliflozin;

(2) Remogliflozin;

(3) TA-7284;

(4) LX-4211;

(5) BI-44847;

(6) BI-10773;

(7) ASP-1941; and (8) ISIS 388626.

Well-known anti-diabetic agents include insulin, sulfonylureas, biguanides, meglitinides, AGI's (Alpha-Glucosidase Inhibitors; e.g., Glyset), PPAR alpha agonists, and PPAR gamma agonists, and dual PPAR alpha/gamma agonists.

Anti-obesity agents can be classified into several categories based upon the mechanism of action. These agents include selective serotonin reuptake inhibitors (SSRIs), serotonin agonists, serotonin and norepinephrine reuptake inhibitors, pancreatic lipase inhibitors, β3-adrenoreceptor agonists, NPY antagonists, melanocortin receptor agonists, leptin-targeted agents, CB1 antagonists (e.g. Rimonabant), monoamine reuptake inhibotors (e.g. Sibutramine), microsomal triglyceride transfer protein (MTP) inhibitors and lipase inhibitors (e.g. Orlistat).

Serotonin agonist agents such as dexfenfluramine and fenfluramine were reported to cause cardiac valvular abnormalities when used at the prescribed dosage in combination with phentermine. Selective serotonin reuptake inhibitors (SSRIs) are generally used for the treatment of depression. These agents include fluoxetine (Prozac), paroxetine, fluvoxamine and sertraline.

Representative serotonin modulators are listed below:

(A) Selective serotonin reuptake inhibitors (SSRIs)

1. Citalopram (1-(3-(dimethylamino) propyl)-1-(4-fluorophenyl)-1,3-dihydro-5-isobenzofurancarbonitrile, also known as citalopram hydrobromide (USAN), nitalopram, nitalapram, ZD 211, LU 10171, Lu10-171, LU 10171-B, CIPRAMIL, SEROPRAM, CIPRAM, ELOPRAM, LUPRAM, SEPRAM, PRISDAL, or CELEXA);

2. Fluoxetine (benzenepropanamine, N-Methyl-gamma-[4-(trifluoromethyl)phenoxy]-, (±) hydrochloride, also known as LY 110140, RENEURON, SARAFEM, or PROZAC);

3. Fluvoxamine (5-methoxy-1-(4-(trifluoromethyl)phenyl)-1-pentanone (E)-O—(2-aminoethyl) oxime, also known as fluvoxamine maleate (USAN), DU 23000, MK 264, SME 3110, FEVARIN, FLOXYFRAL, LUVOX, DUMYROX, DUMIROX, FLAVOXYL, FAVERIN, or DEPROMEL);

4. Indeloxazine ((+,−)-2-((indel-7-yloxy)methyl) morpholine, also known as ideloxazine, YM 08054, CI-874, ELEN, or NOIN);

5. Paroxetine hydrochloride ((3S,4R)-3-((1,3-benzodioxol-5-yloxy)methyl)-4-(4-fluorophenyl)piperidine hydrochloride, or piperidine, 3-((1,3-benzodioxol-5-yloxy)methyl)-4-(4-fluorophenyl)-, (3S-trans)-, also known as FR 7051, FG-7051, BRL 29060, BRL 29060A, NNC 207051, S1211103, CASBOL, SEROXAT, AROPAX, PAXIL, TAGONIS, FROSINOR, DEROXAT, SEREUPIN, MOTIVAN, or PAXIL CR);

6. Sertraline (1-naphthalenamine, 4-(3,4-dichlorophenyl)-1,2,3,4-tetrahydro-N-methyl-, (1S-cis)- or 1-Naphthalenamine,4-(3,4-dichlorophenyl)-1,2,3,4-tetrahydro-N-methyl-, (1S-cis), also known as CP 51974, CP 51974 01, AREMIS, BESITRAN, GLADEM, LUSTRAL, SERAD, SERLAIN, SERLIFT, TATIG, or ZOLOFT);

7. Tianeptine (7-((3-chloro-6,11-dihydro-6-methyldibenzo (c,f)(1,2)thiazepin-11-yl)amino) heptanoic acid S, S-dioxide, also known as S 1574, or STABLON);

8. Centpropazine (1-(p-propionylphenoxy)-3-(Nsup(4)-henylpiperazynyl)-propan-2-01);
9. Paroxetine (GEOMATRIX drug delivery system) (piperidine,3-((1,3-benzodioxol-5-yloxy)methyl)-4-(4-fluorophenyl)-, (3S-trans)-, also known as paroxetine, GEOMATRIX, PAXIL CR);
10. Escitalopram ((1S)-1-(3-(dimethylamino) propyl)-1-(4-fluorophenyl)-1,3-dihydro-5-isobenzofuran carbonitrile, or 5-Isobenzofurancarbonitrile,1-(3-(dimethylamino) propyl)-1-(4-fluorophenyl)-1,3-dihydro-, (S)—, also known as escitalopram, xalate (USAN), citalopram, (S)(+)-citalopram, LU 26042, LU 26054, Lu26-054, or CIPRALEX);
11. Litoxetine (4-[(2-Naphthalenyl)methoxy]piperidine, also known as SL 810385);
12. (S)-Fluoxetine((S)—N-methyl-gamma-(4-(trifluoromethyl)phenoxy)benzenepropanamine);
13. Cericlamine((+,−)-3,4-dichloro-beta-(dimethylamino)-beta-methylbenzenepropanol, also known as JO 1017(+,−), JO 1239(−), or JO 1240(+));
14. Dapoxetine ((+)-(S)—N,N-dimethyl-alpha-(2-(1-naphthyl-oxy)ethyl)benzylamine HCl, also known as LY-210448 or LY-243917);
15. 6-Nitroquipazine derivatives;
16. Series of substituted 6-nitroquipazines (Pharmaprojects No. 3391);
17. AAL 13 (2-(4-(3-chloropropyl)-1-piperazinyl) quinoline);
18. Depression therapy (by Vita Invest, Spain);
19. DUP 631 ($C_{13}H_{23}NO_2S$);
20. FI 4503 (by Ferrer, Spain);
21. Series of indolylcyclohexylamines (Pharmaprojects No. 6443, American Home Products);
22. LY 280253 (N-Methyl-N-[3-[4-(methylthio)phenoxy)-3-phenylpropyl]amine);
23. LY 285974 (by Lilly);
24. Omiloxetine (Ethanone,2-((3R,4S)-3-((1,3-benzodioxol-5-yloxy)methyl)-4-(4-fluorophenyl)-1-piperidinyl)-1-(4-fluorophenyl)-, rel-, also known as Fl-4500, Fl-4501, Fl-4503); and
25. WF 31 (8-Methyl-2beta-propanoyl-3beta-(4-(1-methylethyl)-phenyl)-8-azabicyclo[3.2.1]);

(B) Serotonin agonists and partial agonists
1. Dexfenfluramine; and
2. Fenfluramine;

(C) Serotonin reuptake inhibitor with serotonin agonist activity
1. EMD-68843 (2-benzofurancarboxamide, 5-(4-(4-(5-cyano-1H-indol-3-yl) butyl)-1-piperazinyl)-, also known as SB-659746-A);
2. OPC-14523 (2 (1H)-quinolinone, 1-(3-(4-(3-chlorophenyl)-1-piperazinyl)propyl)-3,4-dihydro-5-methoxy);
3. Vilazodone (5-{4-[4-(5-Cyano-3-indolyl)-butyl]-1-piperazinyl}-benzofuran-2-carboxamide, also known as EMD 68843 or SB 659746A);
4. Series of condensed thiazoles (3-(benzo(b)thiophen-3-yl)-5,6-dihydroimidazo(2,1-b)thiazolemonohydrobromide dihydrate, Pharmaprojects No. 5274, Abbott); and
5. VN-2222 (VN-8522, by Vita Invest, Spain).

Preferred examples of serotonin modulators include selective serotonin reuptake inhibitors such as Citalopram, Fluoxetine, Fluvoxamine, Indeloxazine, Paroxetine hydrochloride, Sertraline, Tianeptine, Centpropazine, Paroxetine, Escitalopram, and Litoxetine.

The following are also anti-obesity agents useful in the combination therapies of the present invention:

(A) Amylin and Amylin Analogs
1. Pramlintide (l-Lysyl-l-cysteinyl-l-asparaginyl-l-threonyl-alanyl-l-threonyl-l-cysteinyl-l-alanyl-l-threonyl-l-glutaminyl-l-arginyl-l-leucyl-l-alanyl-l-asparaginyl-l-phenylalanyl-l-leucyl-l-valyl-l-histidyl-l-seryl-l-seryl-l-asparaginyl-l-asparaginyl-l-phenylalanylglycyl-l-prolyl-l-isoleucyl-l-leucyl-l-prolyl-l-prolyl-l-threonyl-l-asparaginyl-l-valylglycyl-l-seryl-l-asparaginyl-l-threonyl-l-tyrosinamide cyclic (2-7)-disulfide, also known as pramlintide acetate, AC 137, ACO 137, AC 0137, SYMLIN, Tripro-amylin, or NORMYLIN);
2. Amylin agonists;
3. ACO 253 (AC 253, GG 747, GR 1150747A, or ANTAM);

(B) Ciliary Neurotrophic Factors (CNTF)
1. AXOKINE;
2. PEG-AXOKINE;
3. Peptide mimic of ciliary neurotrophic factor (CNTF mimic, also known as MYELOS);
4. Ciliary neurotrophic factor (CNTF by Fidia, Italy);

(C) Glucagon-Like Peptide—1
1. AC-2993 (also known as exendin-4, AC-2993 LAR, Medisord Exendin, AC-2993, Medisorb, or extendin-4, Amylin);
2. Exendin 4 (His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-amide, also known as AC 2993, AC 2993 LAR, Medisord Exendin, or AC-2993, Medisorb);
3. GLP-1 (Glucagon-like peptide-17-36 amide);
4. Glucagon-like peptide-1 oral transmucosal formulation;
5. Exendin 3 (His-Ser-Asp-Gly-Thr-Phe-Thr-Ser-Asp-Leu-Ser-Lys-Gln-Met-Glu-Glu-Glu-Ala-V-al-Arg-Leu-Phe-Ile-Glu-Trp-Leu-Lys-Asn-Gly-Gly-Pro-Ser-Ser-Gly-Ala-Pro-Pro-Pro-Ser-amide);

(D) Leptin & Leptin Mimetics
1. Leptin (2nd-generation);
2. Leptin agonists;
3. Leptin expression modulators;
4. Leptin signalling pathway modulators;
5. Leptin modulator;
6. Leptin (by IC Innovations, UK);
7. Leptin receptor, Monoclonal antibodies;
8. Recombinant native leptin;
9. LY-355101;
10. Leptin, Amylin;

(E) Melanocortin Receptor Agonist (MC4)
1. HP-228 (Glycinamide, N-acetyl-L-norleucyl-L-glutaminyl-L-histidyl-D-phenylalanyl-L-arginyl-D-tryptophyl-);
2. Melanocortin-4 receptor agonist (by Palatin, USA);
3. Melanocortin 4 agonist (by Pharmacopeia, Roche);
4. MC-4 agonists (by Millennium, Chiron);
5. Melanocortin-4 agonist (by Melacure Therapeutics, Sweden);
6. Melanocortin receptor modulators (Pharmaprojects No. 5224, Neurocrine Biosciences, US);
7. Pharmaprojects No. 5967, Trega/Novartis;

(F) NPY Antagonists
1. AXC 0216;
2. AXC 1829;
3. SA-0204 (Neuropeptide γ antagonist, Apoptosis stimulator, Lipid metabolism modulator);

4. Alpha-trinositol (D-myo-Inositol, 1,2,6-tris(dihydrogen phosphate), also known as PP-56);
5. H 40922 (H 409/22);
6. BMS-192548 (1,11(4H,5H)-naphthacenedione,2-acetyl-4-a,12a-dihydro-3,4-a,10,12,12a-pentahydroxy-8-methoxy-, TAN 1612 isomer);
7. Alanex (1,4-bis{(4-amino-6-methoxyphenylamino-1,2-dihydro-1,3,5-triazin-2-yl)-4-phenoxymethyl}benzene, Neuropeptide Y derivatives);
8. PD-160170 (6-(2-isopropyl-benzenesulfonyl)-5-nitroquinolin-8-ylamine);
9. 2,4-Diaminopyridine derivatives (6-(5-ethyl-1,3,4-thiadiazol-2-ylthiomethyl)-4-morpholino-2-(3-(2-propenyloxycarbonylamino)benzylamino) pyridine, Pharmaprojects No. 5618, Banyu/Merck);
10. Arpromidine analogs;
11. Neuropeptide γ antagonist (Pharmaprojects No. 4990, Pfizer);
12. 4 Methyl substituted benzimidazoles (NPY-1 antagonist, NPY-2 antagonist);
13. LY-366337 (Neuropeptide Y1 antagonist);
14. S-2501, S-25579, S-25584, S-25585, S-19528, S-34354 (all Neuropeptide Y1/5 antagonists);
15. Neuropeptide γ antagonist (subtypes 1 and 5) and Galanin receptor antagonist (Pharmaprojects No. 4897, Bristol-Myers Squibb);
16. Benzylamine derivatives (1-arylpiperazinyl-1-alkyloxyphenyl-4-alkylcycloalkanes);
17. J-104870 (Neuropeptide Y1 antagonist, Appetite suppressant);
18. LY-357897 (Neuropeptide Y1 antagonist);
19. Neuropeptide Y1 antagonist (Pfizer/Neurogen);
20. 5R-120107A (Neuropeptide Y1 antagonist);
21. BIBO-3304 ((R)—N-((4-(aminocarbonylaminomethyl)-phenyl)methyl)-N2-(diphenylacetyl)-argininamide trifluoroacetate);
22. BIBP 3226 ((R)—N-(4-((aminoiminomethyl)amino)-1-((((4-hydroxyphenyl)methyl)amino) carbonyl) butyl)-alpha-phenylbenzeneacetamide, or benzeneacetamide, N-((1R)-4-((aminoiminomethyl)amino)-1-((((4-hydroxyphenyl)methyl)amino)carbonyl)butyl)-alpha-phenyl-);
23. SR 120819A (benzenepropanamide, N-(1-((4-((((4-((dimethylamino) methyl)cyclohexyl)methyl)amino) iminomethyl)phenyl)methyl)-2-oxo-2-(1-pyrrolidinyl) ethyl)-alpha-((2-naphthalenylsulfonyl)amino)-, (alphaR-(N(R*(cis)), alphaR*))-);
24. NGD-95-1 (CP-422935, NGD 951);
25. Compounds with benzazepine nuclei (Neuropeptide Y1 antagonist);
26. Neuropeptide Y1 antagonist (by Yamanouchi Pharmaceutical);
27. GI-264879A (Neuropeptide Y1 antagonist);
28. GW-1229 ([2',4],[2,4']homodimer of Ile-Glu-Pro-Dpr-Tyr-Arg-Leu-Arg-Tyr-CONH2, where Dpr is diaminopropionic acid, also known as 1229U91, MN-24, GR-231118);
29. BIIE-0246 (Cyclopentaneacetamide, N-[(1S)-4-[(aminoiminomethyl)amino]-1-[[[2-(3,5-dioxo-1,2-diphenyl-1,2,4-triazolidin-4-yl)ethyl]amino]carbonyl]butyl]-1-[2-[4-(6,11-dihydro-6-oxo-5H-dibenz[b,e]azepin-11-yl)-1-piperazinyl]-2-oxoethyl]-);
30. Neuropeptide Y2 antagonist (by Neurogen, USA);
31. Amide derivatives (Neuropeptide Y5 antagonist);
32. Neuropeptide γ agonist and antagonist-subtypes 1 and 5 (Schering-Plough);
33. N-(sulfonamido)alkyl-[3a,4,5,9b-tetrahydro-1H-benzo[e]indol-2-yl]amine (RWJPRI);
34. Neuropeptide Y5 antagonist (by Novartis);
35. Neuropeptide Y5 antagonist (by Pfizer/Neurogen);
36. Pyrrolo[3,2-d]pyrimidine based neuropeptide Y5 antagonists;
37. CGP-71683 (Pharmaprojects No. 5651, CGP-71683A);
38. Neuropeptide Y5 agonist/antagonist (Pharmaprojects No. 5664, Bayer);

(G) Histamine H3 Receptor Antagonists
1. GT-2331 (3-((1R,2R)-2-(5,5-dimethyl-1-hexynyl)cyclopropyl)-1H-imidazole, also known as PERCEPTIN);
2. Ciproxifan (Cyclopropyl-(4-(3-1H-imidazol-4-yl) propyloxy)phenyl)methanone, also known as BP 2359 or Compound 359);
3. Compound 421 (imidazoylpropanol derivative, INSERM (France)/Bioprojet);
4. FUB 181 (3-(4-chlorophenyl) propyl-3-(1H-imidazol-4-yl) propyl ether);
5. GR 175737 (3-((4-chlorophenyl)methyl)-5-(2-(1H-imidazol-4-yl)ethyl)-1,2-oxadiazole);
6. GT 2227 (4-(6-cyclohexyl-3(Z)-hexenyl) imidazole maleate);
7. GT 2394 ((1R,2R)— (trans-2-Imidazol-4-ylcyclopropyl)-(cyclohexylmethoxy) carboxamide);
8. GT-2016 (piperidine, 1-(5-cyclohexyl-1-oxopentyl)-4-(1H-imidazol-4-yl)-);
9. Imoproxifan (1-(4-(3-(1H-imidazol-4-yl) propoxy)phenyl)ethan-1-one oxime);
10. Impentamine (by Berlin Free University);
11. Abbott Laboratories H3 antagonist for Attention deficit Hyperactivity Disorder (ADHD);
12. Gliatech (USA) H3 antagonist for eating disorder;
13. Series of novel carbamates as derivatives of 3-(1H-imidazol-4-yl)propanol with an N-alkyl chain;
14. Series of analogs with a neutral linker leading to 4-(1H-imidazol-4-ylmethyl)benzene;
15. Urea, N-4-(1H-imidazol-4-ylmethyl)phenylmethyl-N'-(3,5-dichlorophenyl)-, monohydrochloride;
16. Sch-50971 (1H-imidazole, 4-[(3R,4R)-4-methyl-3-pyrrolidinyl]-);
17. Thioperamide (N-cyclohexyl-4-(1H-imidazol-4-yl)-1-piperidinecarbothioamide, also known as MR 12842);
18. UCL-1283 (by University College London);
19. UCL-1390 (4-(3-(1H-imidazol-4-yl) propoxy)benzonitrile);
20. UCL-1409 ((phenoxyalkyl)imidazoles);
21. UCL-1972 (by University College London);
22. Verongamine (benzenepropanamide, 3-bromo-.alpha.-(hydroxyimino)-N-[2-(1H-imidazol-4-yl)ethyl]-4-methoxy-, (E)-);
23. VUF-9153 (Carbamimidothioic acid, [(4-chlorophenyl)methyl]-, 3-(1H-imidazol-4-yl)propyl ester, also known as Clobenpropit);

(H) Pancreatic lipase inhibitors
1. Orlistat (L-Leucine, N-formyl-, 1-((3-hexyl-4-oxo-2-oxetanyl)methyl) dodecyl ester, (2S-(2alpha (R*), 3beta))-, or N-formyl-L-leucine (2S-(2alpha(R*), 3beta))-1-((3-hexyl-4-oxo-2-oxetanyl)methyl) dodecyl ester, also known as Orlipastat, RO 180647, Tetrahydrolipstatin (THL), XENICAL, or ZENICAL);
2. ATL 962 (also known as AZM 119 or Alizyme);
3. GelTex (Anti-obesity therapeutics);
4. AZM-131 (by Yakurigaku Chuo Kenkyusho/Institute of Food Research);

5. RED 103004 (XiMed Group (United Kingdom)/BioClin);

(I) Alpha Melanocyte Stimulating Hormone Analogues
1. Melanotan II (acetyl-norleucyl-aspartyl-histidyl-D-phenylalanyl-arginyl-tryptophyl-lysinamide C-4,2-N-6.7-lactam, also known as MT II);
2. MBU-23, MBU-23, MBU-24, MBU-27, MBU-28 and MBU-29 (all described in WO 1998027113);
3. MSH fusion toxin (also known as DAB389MSH, anti-melanoma, chimaera);
4. SHU-9119 (L-Lysinamide, N-acetyl-L-norleucyl-L-.alpha.-aspartyl-L-histidyl-3-(2-naphthalenyl)-D-alanyl-L-arginyl-L-tryptophyl-, (2.fwdarw.7)-lactam, also known as MBX 36);
5. SHU-9005 (a substituted derivative of alpha-MSH);
6. ZYC-200 (alpha-MSH, Schepens/ZYCOS with BIOTOPE expression cassette system);

(J) Mixed Serotonin Reuptake Inhibitor with Serotonin or Alpha Adrenergic Antagonist Activity
1. Nefazodone (2-(3-(4-(3-chlorophenyl)-1-piperazinyl)propyl)-5-ethyl-2,4-dihydro-4-(2-phenoxyethyl)-3H-1,2,4-triazol-3-one, also known as MJ 13754, MS13754, BMY 13754, BMY 137541, SERZONE, DUTONIN, RESERIL, NEFADAR, NIFEREL, MENFAZONA, RULIVAN, DEPREFAX, or SERZONIL);
2. YM 992 ((S)-2-(((7-fluoro-2,3-dihydro-1H-inden-4-yl)oxy)methyl) morpholine hydrochloride, or (S)-2-(((7-fluoro-2,3-dihydro-1H-inden-4-yl)oxy)methyl)morpholine hydrochloride, also known as YM 35992);
3. A 80426 ((R)—N-methyl-N-((1,2,3,4-tetrahydro-5-methoxy-1-naphthalenyl)methyl)-6-benzofuranethanamine);
4. 5-HT1A antagonist (by Vita-Invest, Spain);
5. Nefazodone metabolite (by Sepracor, USA);
6. Serotonin reuptake inhibitors/serotonin 1A antagonists (Wyeth-Ayerst);

(K) Appetite-Suppressants Acting Through Adrenergic Mechanisms
1. benzphetamine;
2. phenmetrazine;
3. phentermine;
4. diethylpropion;
5. mazindol;
6. sibutramine;
7. phenylpropanolamine;
8. ephedrine;

(L) Mixed Serotonin & Dopamine Reuptake Inhibitors
1. BL-1834 (1-propanamine, 3-dibenz(b,e)oxepin-11(6H)-ylidene-N,N-dimethyl);
2. NS-2389 or NS-2347 (GW-650250A, GW 650250);
3. (R)-Sibutramine;
4. NS-2359 (by NeuroSearch, Denmark);
5. RTI-112 or RTI-113 or RTI-177 (8-Azabicyclo(3.2.1)octane-2-carboxylic acid,3-(4-chloro-3-methylphenyl)-8-methyl-, methyl ester, hydrochloride, (1R,2S,3S,5S));
6. BSF-74681(Abbott);
7. Hyperforin trimethoxybenzoate (IDN-5491);

(M) Mixed Serotonin Reuptake Inhibitors and Dopamine Antagonist
1. SLV-310 (Solvay, Belgium);
2. EMD 86006 (3-(2-(3-(4-fluorophenyl)benzylamino)ethoxy)benzonitrile);
3. SLV 301 (by Solvay);

(N) Norepinephrine & Serotonin Reuptake Inhibitors (NSRI)
1. Milnacipran (Cyclopropanecarboxamide, 2-(aminomethyl)-N,N-diethyl-1-phenyl-, cis-(+/−)-, or (±)-cis-2-(Aminomethyl)-N-diethyl-1-phenyl cyclopropane carboxamide hydrochloride, also known as F-2207, F-2641, TN-912, DALCIPRAN, IXEL, MIDACIPRAN, MIDALCIPRAN, MILNACIPRAN SR, TOLEDOMIN);
2. Tramadol, Purdue (cyclohexanol, 2-((dimethylamino)methyl)-1-(3-methoxyphenyl)-, cis-(+/−), also known as TRAMADOL, Tramadol, CR, or Toray);
3. Milnacipran (drug delivery system, sustained release);
4. Duloxetine ((S)—N-methyl-gamma-(1-naphthalenyloxy)-2-thiophenepropanamine, or (+)-(S)—N-Methyl-gamma-(1-naphthyloxy)-2-thiophene-propylamine hydrochloride, also known as LY 248686, duloxetine oxalate, LY-223332, LY-223743, LY-223994, LY-227750, LY-227942, LY-228993, LY-248686, LY-264452, LY-264453, LY-267826;
5. Naltrexone+tramadol (morphinan-6-one,17-(cyclopropylmethyl)-4,5-epoxy-3,14-dihydroxy-, (5alpha)-, mixt with cyclohexanol, 2-((dimethylamino)methyl)-1-(3-methoxyphenyl)-, cis-(+/+)-, also known as PTI-601, tramadol+naltrexone, Pain T);
6. (S) sibutramine ((S)-1-(4-chlorophenyl)-N,N-dimethyl-alpha-(2-methylpropyl)cyclobutanemethanamine);
7. Tramadol, Labopharm (cyclohexanol, 2-((dimethylamino) methyl)-1-(3-methoxyphenyl)-, cis-(+/−), also known as tramadol, Contramid);
8. F 98214TA (by FAES, Spain);
9. S 33005 ((−)-1-(1-Dimethylaminomethyl-5-methoxybenzocyclobutan-1-yl)cyclopentanol);
10. Tacrine analogues, SIDR;

(O) Serotonin, Norepinephrine and Dopamine Reuptake Inhibitors
1. Sibutramine (cyclobutanemethanamine,1-(4-chlorophenyl)-N,N-dimethyl-alpha-(2-methylpropyl)-, or 1-(4-chlorophenyl)-N,N-dimethyl-alpha-(2-methylpropyl)cyclobutanemethanamine hydrochloride monohydrate, also known as Sibutramine hydrochloride monohydrate, BTS-54354, BTS-54505, BTS-54524, KES-524, MERIDIA, REDUCTIL, RADUCTIL, REDUCTASE, PLENTY, ECTIVA);
2. Venlafaxine (cyclohexanol, 1-[2-(dimethylamino)-1-(4-methoxyphenyl)ethyl], also known as WY 45030, WY 45651, WY 45655, DOBUPAL, EFECTIN, EFEXOR, EFFEXOR, ELAFAX, VANDRAL, TREVILOR);
3. Venlafaxine XR (cyclohexanol, 1-(2-(dimethylamino)-1-(4-methoxyphenyl)ethyl)-, hydrochloride, also known as EFFEXOR XR, I EFFEXOR ER, EFFEXOR XL, EFFEXOR LP, DOBUPAL RETARD, VANDRAL RETARD, EFFEXOR-EXEL 75, EFEXOR XR, EFEXOR DEPOT, ELAFAX XR);
4. Venlafaxine (drug delivery system, OROS oral controlled release, also known as venlafaxine, OROS, or EFEXOR XR);
5. (+)-Desmethylsibutramine (also known as DDMS, Didesmethylsibutramine—Sepracor);
6. BTS-74398 (1-[1-(3,4-Dichlorophenyl)cyclobutyl]-2-(3-dimethylaminopropylthio)ethanone, Abbott Pharmaprojects No. 6247);
7. Desmethylvenlafaxine (by Sepracor);

(P) Appetite-Suppressant Agents Acting Through Dopamine Mechanisms
1. Apomorphine;

(Q) Selective Norepinephrine (Noradrenaline) Reuptake Inhibitors
1. Reboxetine ((2S)-rel-2-((R)— (2-ethoxyphenoxy)phenylmethyl) morpholine, or morpholine, 2-[(2-ethoxyphenoxy)phenylmethyl]-, (R,S)—, methanesulfonate, also known as reboxetine mesylate (USAN), FCE 20124, FCE 21684, PNU 155950E, EDRONAX, PROLIFT, VESTRA, IRENON, NOREBOX);
2. Tomoxetine ((gamma.R)-N-methyl-gamma-(2-methylphenoxy)benzenepropanamine, or (−)-N-Methyl-3-phenyl-3-(o-tolyloxy)-propylamine hydrochloride, also known as LY 139603, LY 135252, LY 139602);
3. Hydroxynortriptyline ((E)-10-11-dihydro-5-(3-(methylamino) propylidene)-5H-dibenzo-(a,d)cyclohepten-10-ol);
4. LY 368975 ((R)—N-Methyl-3-[2-(methylsulfanyl)phenoxy]-3-phenyl-propylamine hydrochloroide);

(R) Combined Norepinephrine and Dopamine Reuptake Inhibitors
1. Bupropion (1-(3-chlorophenyl)-2-((1,1-dimethylethyl) amino)-1-propanone, also known as bupropion hydrochloride (USAN), bupropin, amfebutamone, BW 323U, WELLBUTRIN, QUOMEM, or ZYBAN);
2. GW 320659 ((2S-(2alpha,3alpha,5alpha))-2-(3,5-difluorophenyl)-3,5-dimethyl-2-morpholinol hydrochloride, also known as 1555, 1555U88, BW 1555U88);
3. Hydroxy bupropion (also known as bupropion, R—, or R-bupropion);
4. (−)Didesmethylsibutramine (also known as (S)-didesmethylsibutramine, desmethylsibutramine, (−)-DDMS or MERIDIA (urogenital));

(S) Mixed Norepinephrine Reuptake Inhibitor and Other Neurotransmitter Antagonists
1. Zotepine (2-((8-chlorodibenzo(b,f)thiepin-10-yl)oxy)-N,N-dimethylethylamine, also known as LODOPIN, NIPOLEPT, ZOLEPTIL, ZOPITE, SETOUS, MAJORPIN);
2. MC1-225 (4-(2-fluorophenyl)-2-methyl-6-(piperazin-1-yl)-3a,7a-dihydrothieno(2,3-d)pyrimidine, or 4-(2-Fluorophenyl)-6-methyl-2-piperazinothieno[2,3-d]pyrimidine hydrochloride hydrate);
3. A 75200 ((R*, R*)-(+,−)-3-phenyl-1-((6,7,8,9-tetrahydronaphtho(1,2-d)-1,3-dioxol-6-yl)methyl)pyrrolidine);

(T) Combined Serotonin Reuptake Inhibitors and Sigma Receptor Antagonists
1. E-5296 (by Esteve, Spain);
2. E-6276 (by Esteve, Spain);
3. E-5842 (pyridine, 4-(4-fluorophenyl)-1,2,3,6-tetrahydro-1-(4-(1H-1,2,4-triazol-1-yl) butyl)-, 2-hydroxy-1,2,3-propanetricarboxylate (1:1));
4. E 5826 (citrate salt of E-5842);

(U) Other Neurotransmitter Modulators with Serotonin or Norepinephrine Uptake Inhibitor Activity
1. Pirlindole (1H-pyrazino (3,2,1-jk) carbazole, 2,3,3a,4,5,6-hexahydro-8-methyl-, also known as CAS-125, Pyrazidol, pirazidol, LIFRIL, IMPLEMENTOR);
2. NS-2330 (by NeuroSearch, Denmark);
3. VAN-H36 (by Vita-Invest, Spain);
4. UR 1827 (2-(1-Benzylpiperidin-4-yl)-1-[4-(5-methylpyrimidin-4-ylamino)phenyl]-1-ethanone);

(v) C-75 (Fatty Acid Synthase Inhibitor)
(W) S 15261 (L-4-(2-(2-(9-Fluorenyl)acetamido) ethyl) benzoic acid 2-(2-methoxy-2-(3-(trifluoromethyl)phenyl) ethylamino) ethyl ester)
(X) S100B (Neurotrophic Factor)
(Y) Stimulators of Uncoupling Protein Function
(Z) Cholecystokinin Agonists
(AA) Androgens
1. dehydroepiandrosterone;
2. dehydroepiandrosterone derivatives (such as etiocholandione);

(BB) Testosterone
(CC) Anabolic Steroids (eg, Oxandrolone)
(DD) Steroidal Hormones
(EE) Amylase Inhibitors
(FF) Enterostatin Agonists/Mimetics
(GG) Orexin/Hypocretin Antagonists
(HH) Urocortin Antagonists
(II) Bombesin Agonists
(JJ) Modulators of Protein Kinase A
(KK) Corticotropin-Releasing Factor Mimetics
(LL) Cocaine- and Amphetamine-Regulated Transcript Mimetics
(MM) Calcitonin-Gene Related Peptide Mimetics
(NN) Nizatidine (Axid).

Examples of lipid lowering agents include bile acid sequestrants, fibric acid derivatives, nicotinic acid, and HMGCoA reductase inhibitors. Specific examples include statins such as LIPITOR®, ZOCOR®, PRAVACHOL®, LESCOL®, CRESTOR®, and MEVACOR®, and pitavastatin (nisvastatin) (Nissan, Kowa Kogyo, Sankyo, Novartis) and extended release forms thereof, such as ADX-159 (extended release lovastatin), as well as Colestid, Locholest, Questran, Atromid, Lopid, and Tricor.

Examples of blood pressure lowering agents include antihypertensive agents, such as angiotensin-converting enzyme (ACE) inhibitors (Accupril, Altace, Captopril, Lotensin, Mavik, Monopril, Prinivil, Univasc, Vasotec, and Zestril), adrenergic blockers (such as Cardura, Dibenzyline, Hylorel, Hytrin, Minipress, and Minizide) alpha/beta adrenergic blockers (such as Coreg, Normodyne, and Trandate), calcium channel blockers (such as Adalat, Calan, Cardene, Cardizem, Covera-HS, Dilacor, DynaCirc, Isoptin, Nimotop, Norvace, Plendil, Procardia, Procardia XL, Sula, Tiazac, Vascor, and Verelan), diuretics, angiotensin II receptor antagonists (such as Atacand, Avapro, Cozaar, and Diovan), beta adrenergic blockers (such as Betapace, Blocadren, Brevibloc, Cartrol, Inderal, Kerlone, Lavatol, Lopressor, Sectral, Tenormin, Toprol-XL, and Zebeta), vasodilators (such as Deponit, Dilatrate, SR, Imdur, Ismo, Isordil, Isordil Titradose, Monoket, Nitro-Bid, Nitro-Dur, Nitrolingual Spray, Nitrostat, and Sorbitrate), and combinations thereof (such as Lexxel, Lotrel, Tarka, Teczem, Lotensin HCT, Prinzide, Uniretic, Vaseretic, Zestoretic).

F) Biological Example

TR-FRET Assay

Time-Resolved Fluorescence Resonance Energy Transfer (TR-FRET) experiments were performed to examine the functional response of ERR1 (also known as ERR-α or ERR-1) ligands. The TR-FRET assay described herein relied on the conformation of ERR1 for binding to a co-activator peptide: when a test compound binds to ERR1 and alters its conformation, it can disrupt the binding of the co-activator peptide. The components of this homogeneous secondary assay included: the $^6$His-tagged-ERR1LBD, a GST-labeled-hSRC2 co-activator polypeptide and a fluorescent donor/acceptor pair from CIS bio international htrf/bioassays (Bedford, Mass.) using both an α-GST Europium Cryptate (Eu) label and an α$^6$His-XL665 (allophycocyanin) fluorophore.

For TR-FRET measurements, the reaction was buffered in 25 mM Tris pH 8, 2.5 mM Hepes, 20 mM KCl, 1 mM DTT, and 0.05 mg/mL BSA (-lipids). The final concentrations of reagents were 6 nM of ERR1LBD, 6 nM GST-SRC-2 peptide, 30 nM Eu cryptate, and 7.5 nM XL665. Reactions were allowed to reach equilibrium at 25° C. for 4-18 hours before collecting data on the Analyst from LJL Biosystems (Molecular Devices Sunnyvale, Calif.). As a time-resolved method, the samples were excited at 340 nM and emission was collected for 1 ms at both 615 and 665 nm with delays of 400 and 75 μs, respectively. Dose response curves were fitted using a hyperbolic equation and the data reported is the average of 3 independent experiments.

Compounds listed in Tables II below were tested in the above assay, and they are all active modulators of ERR1.

TABLE II

TR-FRET data

| COMPOUND # | $EC_{50}$ TR-FRET (μM) |
|---|---|
| 1 | 0.0101 |
| 2 | 0.0072 |
| 3 | 0.0210 |
| 4 | 0.0920 |
| 5 | 0.0420 |
| 6 | 0.0090 |
| 7 | 0.0380 |
| 8 | 0.0070 |
| 9 | 0.0575 |
| 10 | 0.1990 |
| 11 | 0.0570 |
| 12 | 0.0046 |
| 13 | 0.0047 |
| 14 | 0.0680 |
| 15 | 0.5300 |
| 16 | 0.4500 |
| 17 | >4.00037 |
| 18 | >4.00037 |
| 19 | 0.3500 |
| 20 | 0.3000 |
| 21 | 0.0030 |
| 22 | 0.0114 |
| 23 | 0.0104 |
| 24 | 0.5200 |
| 25 | 0.0680 |
| 26 | 0.0048 |
| 27 | 0.0110 |
| 28 | 0.0590 |
| 29 | 0.0380 |
| 30 | 0.0230 |
| 31 | 0.0046 |
| 32 | 0.0100 |
| 33 | 0.0044 |
| 34 | 0.0075 |
| 35 | 0.0143 |
| 36 | 0.0054 |
| 37 | 0.0053 |
| 38 | 0.0090 |
| 39 | 0.0032 |
| 40 | 0.0080 |
| 41 | 0.0150 |
| 42 | 0.0042 |
| 43 | 0.0110 |
| 44 | 0.0032 |
| 45 | 0.0340 |
| 46 | 0.0270 |
| 47 | 0.0082 |
| 48 | 0.0143 |
| 49 | 0.0060 |
| 50 | 0.0078 |
| 51 | 0.0090 |
| 52 | 0.0045 |
| 53 | 0.0130 |
| 54 | 0.0131 |
| 55 | 0.0610 |
| 56 | 0.0157 |
| 57 | 0.0121 |
| 58 | 0.0420 |
| 59 | 0.0230 |
| 60 | 0.0197 |
| 61 | 0.0196 |
| 62 | 0.0173 |
| 63 | 0.0540 |
| 64 | 0.0250 |
| 65 | 0.0170 |
| 66 | 0.0249 |
| 67 | 0.0210 |
| 68 | 0.0096 |
| 69 | 0.0260 |
| 70 | 0.0110 |
| 71 | 0.0164 |
| 72 | 0.0133 |
| 73 | 0.1725 |
| 74 | 0.0562 |
| 75 | 0.0734 |
| 76 | 0.0183 |
| 77 | 0.0587 |
| 78 | 0.0045 |
| 79 | 0.0090 |
| 80 | 0.0057 |
| 81 | 0.0688 |
| 82 | 0.0076 |
| 83 | 0.0150 |
| 84 | 0.0390 |
| 85 | 0.0086 |
| 86 | 0.0200 |
| 87 | 0.0150 |
| 88 | 0.0130 |
| 89 | 0.0047 |
| 90 | 0.0034 |
| 91 | 0.0087 |
| 92 | 0.0490 |
| 93 | 0.0144 |
| 94 | 0.0260 |
| 95 | 0.0110 |
| 96 | 0.0640 |
| 97 | 0.0290 |
| 98 | 0.0150 |
| 99 | 0.0028 |
| 100 | 0.0140 |
| 101 | 0.0214 |
| 102 | 0.0220 |
| 103 | 0.0122 |
| 104 | 0.0182 |
| 105 | 0.0409 |
| 106 | 0.0210 |
| 107 | 0.2230 |
| 108 | 0.0302 |
| 109 | 0.0360 |
| 110 | 0.0186 |
| 111 | 0.0069 |
| 112 | 0.0290 |
| 113 | 0.0140 |
| 114 | 0.0130 |
| 115 | 0.0084 |
| 116 | 0.0110 |
| 117 | 0.0083 |
| 118 | 0.0073 |
| 119 | 0.0140 |
| 120 | 0.0270 |
| 121 | 0.0253 |
| 122 | 0.0418 |
| 123 | 0.0050 |
| 124 | 0.0090 |
| 125 | 0.0100 |
| 126 | 0.0240 |
| 127 | 0.0290 |
| 128 | 0.0320 |
| 129 | 0.0280 |
| 130 | 0.0320 |
| 131 | 0.0078 |
| 132 | 0.0107 |
| 133 | 0.0041 |
| 134 | 0.0050 |
| 135 | 0.0520 |
| 136 | 0.0340 |
| 137 | 0.0140 |
| 138 | 0.0190 |
| 139 | 0.0160 |
| 140 | 0.0190 |
| 141 | 0.0370 |

TABLE II-continued

TR-FRET data

| COMPOUND # | EC$_{50}$ TR-FRET (µM) |
|---|---|
| 142 | 0.0200 |
| 143 | 0.0560 |
| 144 | 0.0140 |
| 145 | 0.0210 |
| 146 | 0.0140 |
| 147 | 0.0110 |
| 148 | 0.0330 |
| 149 | 0.0550 |
| 150 | 0.0480 |
| 151 | 0.0257 |
| 152 | 0.0240 |
| 153 | 0.0440 |
| 154 | 0.0262 |
| 155 | 0.0340 |
| 156 | 0.0580 |
| 157 | 0.0350 |
| 158 | 0.0320 |
| 159 | 0.0360 |
| 160 | 0.0220 |
| 161 | 0.0248 |
| 162 | 0.0270 |
| 163 | 0.0260 |
| 164 | 0.0120 |
| 165 | 0.0180 |
| 166 | 0.0190 |
| 167 | 0.0160 |
| 168 | 0.0090 |
| 169 | 0.2250 |
| 170 | 0.0300 |
| 171 | 0.0380 |
| 172 | 0.0140 |
| 173 | 0.0710 |
| 174 | 0.0581 |
| 175 | 0.0050 |
| 176 | 0.1387 |
| 177 | 0.0550 |
| 178 | 0.0520 |
| 179 | 0.0170 |
| 180 | 0.0210 |
| 181 | 0.0160 |
| 182 | 0.0108 |
| 183 | 0.0049 |
| 184 | 0.0030 |
| 185 | 0.0030 |
| 186 | 0.0050 |
| 187 | 0.0127 |
| 188 | 0.0197 |
| 189 | 0.0240 |
| 190 | 0.0530 |
| 191 | 0.0036 |
| 192 | 0.0160 |
| 193 | 0.0110 |
| 194 | 0.0235 |
| 195 | 0.0200 |
| 196 | 0.0160 |
| 197 | 0.0290 |
| 198 | 0.0150 |
| 199 | 0.0110 |
| 200 | 0.0130 |
| 201 | 0.0470 |
| 202 | 0.0597 |
| 203 | 0.0388 |
| 204 | 0.0420 |
| 205 | 0.0300 |
| 206 | 0.0280 |
| 207 | 0.0380 |
| 208 | 0.0060 |
| 209 | 0.0060 |
| 210 | 0.0248 |
| 211 | 0.0310 |
| 212 | 0.0200 |
| 213 | 0.0210 |
| 214 | 0.0080 |
| 215 | 0.0480 |
| 216 | 0.0150 |
| 217 | 0.0270 |
| 218 | 0.0360 |
| 219 | 0.0230 |
| 220 | 0.0214 |
| 221 | 0.0070 |
| 222 | 0.0200 |
| 223 | 0.0134 |
| 224 | 0.0700 |
| 225 | 0.0180 |
| 226 | 0.0080 |
| 227 | 0.0150 |
| 228 | 0.0260 |
| 229 | 0.5800 |
| 230 | 0.1340 |
| 231 | 0.4900 |
| 232 | 0.7951 |
| 233 | 0.1270 |
| 234 | 0.0160 |
| 235 | 0.0050 |
| 236 | 0.0030 |
| 237 | 0.0060 |
| 238 | 0.0110 |
| 239 | 0.0180 |
| 240 | 0.0090 |
| 241 | 0.0040 |
| 242 | 0.0300 |
| 243 | 0.0380 |
| 244 | 0.1100 |
| 245 | 0.2350 |
| 246 | 0.2300 |
| 247 | 0.0410 |
| 248 | 0.0140 |
| 249 | 0.0040 |
| 250 | 0.1900 |
| 251 | 0.0040 |
| 252 | 0.1900 |
| 253 | 0.0050 |
| 254 | 0.0065 |
| 255 | 0.0280 |
| 256 | 0.0490 |
| 257 | 0.0960 |
| 258 | 0.0300 |
| 259 | 0.0300 |
| 260 | 0.2900 |
| 261 | 0.0200 |
| 262 | 0.0640 |
| 263 | 0.0420 |
| 264 | 0.0470 |
| 265 | 0.0380 |
| 266 | 0.0240 |
| 267 | 0.0430 |
| 268 | 0.0150 |
| 269 | 0.0150 |
| 270 | 0.0080 |
| 271 | 0.0090 |
| 272 | 0.0350 |
| 273 | 0.0060 |
| 274 | 0.0080 |
| 275 | 0.0110 |
| 276 | 0.0240 |
| 277 | 0.0090 |
| 278 | 0.0170 |
| 279 | 0.0110 |
| 280 | 0.0030 |
| 281 | 0.59 |
| 282 | >4.001 |
| 283 | 0.013 |

Zucker fa/fa Rat Model Assay

Zucker fa/fa is a monogenic model of frank diabetes due to a mutation on the fa gene truncating the leptin receptor and preventing its interaction with its peptide hormone. This mutation results in a hyperphagic phenotype and the rodent develops obesity, hyperlipidemia, fasting hyperglycemia and insulin resistance. Zucker fa/fa male rats were received at four weeks of age and allowed to acclimate for one week. At five weeks of age the animals were single housed in cages in a temperature-controlled room with 12-hour light/dark cycle. The rats were allowed ad libitum access to water and food and throughout the study were maintained on a Purina 5008 diet. Animals were sorted based primarily on fed insulin levels and circulating triglycerides. Animals were dosed orally once a day in the morning for 4 days. The vehicle used was either 20% HPβCD (Hydroxypropyl Beta Cyclodextrin) or 15% Vitamin E/30% PEG-400 (Polyethylene Glycol 400). Fed insulin and triglycerides were measured using blood collected from the tail vein at day 5. Serum plasma samples were prepared by centrifugation in EDTA (Ethylenediaminetetraacetic acid) containing tubes, transferred into 96 well plates and stored at −80° C. Results are summarized in Table III.

TABLE III

Zucker fa/fa Rat Model Data

| COMPOUND # | % Lowering Fed Insulin Levels | % Lowering Fed Triglyceride Levels |
|---|---|---|
| 1 | 58 | 37 |
| 35 | 45 | 20 |
| 39 | 58 | 35 |
| 40 | 75 | 60 |
| 52 | 86 | 55 |
| 54 | 60 | 27 |
| 56 | 70 | 68 |
| 62 | 48 | 36 |
| 64 | 46 | 51 |
| 71 | 37 | 25 |
| 72 | 62 | 57 |
| 98 | 51 | 22 |
| 125 | 30 | N/A |
| 139 | 82 | 58 |
| 140 | 59 | 67 |
| 141 | 49 | 76 |
| 142 | 63 | 55 |
| 186 | 75 | 56 |
| 188 | 81 | 59 |
| 197 | 27 | 2 |
| 198 | 35 | 21 |
| 213 | 42 | 30 |
| 223 | 77 | 85 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A method of treating a subject suffering from or diagnosed with a disease, disorder, or condition mediated by ERR-α activity, comprising administering to the subject a therapeutically effective amount of at least one compound of Formula (I)

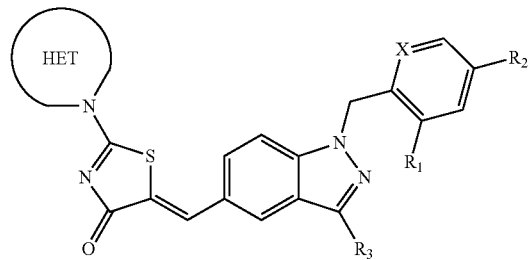

wherein
X is —CH— or N;
$R_1$ is $C_{1-3}$alkyl, halo, cycloalkyl, and —C(O)—$C_{1-4}$alkyl; wherein said $C_{1-3}$alkyl may be substituted with halo;
$R_2$ is —H, halo, cyano, $C_{1-3}$alkyl, $C_{2-3}$alkenyl, $C_{1-4}$alkoxy, hydroxyl, cycloalkyl, —C(O)O—$C_{1-4}$alkyl, —C(O)NH_2, —OS(O_2)—$C_{1-4}$alkyl, —O—$C_{1-4}$alkyl-O—$C_{1-4}$alkyl, heterocyclyl, heteroaryl, or —S(O_2)—$C_{1-4}$alkyl; wherein said $C_{1-3}$alkyl may be substituted with halo or hydroxyl;
$R_3$ is —H, halo, cyano, or $C_{1-3}$alkyl; and

is a 4 to 9 membered heterocyclyl bonded to the rest of the molecule through a ring nitrogen atom and optionally containing 1-2 heteroatoms in addition to said ring nitrogen atom, wherein the optional 1-2 additional heteroatoms are independently selected from the group consisting of N, O and S;
wherein said 4 to 9 membered heterocyclyl may be substituted with $C_{1-4}$alkyl, $C_{2-4}$alkenyl, $C_{2-4}$alkynyl, halo, oxo, cyano, hydroxyl, —$OR^5$, —O—$C_{1-4}$alkyl-C(O)$OR^5$, cycloalkyl, heteroaryl, heterocyclyl, —C(O)$OR^5$, —C(O)N($R^5$)($R^6$), —C(O)N($R^5$)($OR^6$), —C(O)$R^5$, —C(O)—$C_{1-4}$alkyl-N($R^5$)($R^6$), —C(O)—$C_{1-4}$alkyl-O—$C_{1-4}$alkyl, —C(O)N($R^5$)—S(O)_2($R^6$), —C(O)N($R^5$)—$OR^6$, —C(O)N($R^5$)S(O)_2N($R^5$)($R^6$), —C(O)N($R^5$)—$C_{1-4}$alkyl-C(O)$OR^6$,
—N($R^5$)($R^6$), —N($R^5$)—$C_{1-4}$alkyl-$OR^6$, —N($R^5$)C(O)$R^6$, —N($R^5$)C(O)$OR^6$, —N($R^5$)S(O)_2$R^6$, —N($R^5$)C(O)—NH($R^6$),
—N($R^5$)—$C_{1-4}$alkyl-C(O)—NH($R^6$), —$SR^5$, —S(O)_2$R^5$, or —S(O)_2—N($R^5$)($R^6$);
wherein said $C_{1-4}$alkyl may be substituted with —OH, —O—$C_{1-4}$alkyl, —C(O)$OR^5$, —C(O)N($R^5$)($R^6$), —N($R^5$)($R^6$), —N($R^5$)C(O)$OR^6$, heterocyclyl, heteroaryl, cycloalkyl, or halo;
wherein said heteroaryl may be substituted with $C_{1-4}$alkyl, halo, cyano, —$CF_3$, alkoxy or hydroxyl;
wherein said heterocyclyl may be substituted with $C_{1-4}$alkyl, oxo, halo, amino, alkoxy, or hydroxyl;
wherein said $C_{2-4}$alkenyl and said $C_{2-4}$alkynyl may be independently substituted with oxo, heterocyclyl, hydroxyl, or halo;
wherein $R^5$ and $R^6$ are each independently —H, $C_{1-4}$alkyl, cycloalkyl, or heterocyclyl, wherein said $C_{1-4}$alkyl may be substituted with halo or hydroxyl; or alternatively $R^5$ and $R^6$ are linked together to form a 5-7 membered ring;
or an optical isomer, enantiomer, diastereomer, cis-trans isomer, racemate, or pharmaceutically acceptable salt thereof wherein the disease, disorder or condition is selected from the group consisting of bone-related disease, bone formation, cartilage formation, cartilage loss, cartilage degeneration, cartilage injury, ankylosing spondylitis, chronic back injury, gout, osteoporosis, osteolytic bone metastasis, multiple myeloma, chondrosarcoma, chrondrodysplasia, osteogenesis imperfecta, osteomalacia, Paget's disease, polymyalgia rheumatica, pseudogout, arthritis, rheumatoid arthritis, infectious arthritis, osteoarthritis, psoriatic arthritis, reactive arthritis, childhood arthritis, Reiter's syndrome, repetitive stress injury, periodontal disease, chronic inflammatory airway disease, chronic bronchitis, chronic obstructive pulmonary disease, breast cancer, metabolic syndrome, obesity, disorders of energy homeostasis, diabetes, lipid disorders, cardiovascular disorders, artherosclerosis, hyperglycemia, elevated blood glucose level, and insulin resistance.

2. A method according to claim 1, wherein the disease, disorder, or medical condition is selected from the group consisting of bone-related disease, bone formation, cartilage formation, cartilage loss, cartilage degeneration, cartilage injury, ankylosing spondylitis, chronic back injury, gout, osteoporosis, osteolytic bone metastasis, multiple myeloma, chondrosarcoma, chondrodysplasia, osteogenesis imperfecta, osteomalacia, Paget's disease, polymyalgia rheumatica, pseudogout, arthritis, rheumatoid arthritis, infectious arthritis, osteoarthritis, psoriatic arthritis, reactive arthritis, childhood arthritis, Reiter's syndrome, and repetitive stress injury.

3. A method according to claim 1, wherein the disease, disorder, or condition is selected from the group consisting of periodontal disease, chronic inflammatory airway disease, chronic bronchitis, and chronic obstructive pulmonary disease.

4. A method according to claim 1, wherein the disease, disorder, or condition is breast cancer.

5. A method according to claim 1, wherein the disease, disorder, or condition is selected from the group consisting of metabolic syndrome, obesity, disorders of energy homeostasis, diabetes, lipid disorders, cardiovascular disorders, artherosclerosis, hyperglycemia, elevated blood glucose level, and insulin resistance.

6. The method of claim 1 comprising administering to the subject a therapeutically effective amount of (a) at least one compound of claim 1; and (b) at least one additional agent selected from an anti-diabetic agent, an anti-obesity agent, a lipid lowering agent, an anti-thrombotic agent, direct thrombin inhibitor, and a blood pressure lowering agent, said administration being in any order.

7. The method of claim 6 wherein the additional agent in (b) is an anti-obesity agent selected from CB1 antagonists, monoamine reuptake inhibitors, MTP inhibitors and lipase inhibitors.

8. The method of claim 6 wherein the additional agent in (b) is an anti-diabetic agent selected from metformin, DPP-IV inhibitors, GLP-1 mimetics, glucokinase modulators, glucagon antagonists, SGLT2 inhibitors, PPARγ agonists and GPR119 modulators.

9. The method of claim 6 wherein the additional agent in (b) is selected from Metformin, Sitagliptin and Pioglitazone.

10. A method for inhibiting the progression of an ERR-α-mediated condition in a subject in need thereof, comprising administering to said subject a therapeutically effective amount of at least one compound according to Formula (I)

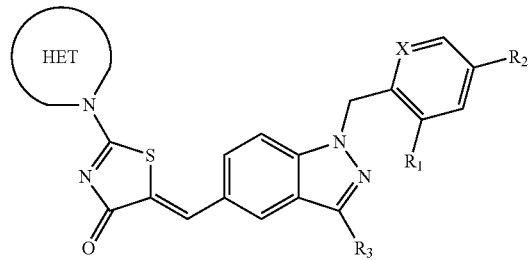

(I)

wherein
X is —CH— or N;
$R_1$ is $C_{1-3}$alkyl, halo, cycloalkyl, and —C(O)—$C_{1-4}$alkyl; wherein said $C_{1-3}$alkyl may be substituted with halo;
$R_2$ is —H, halo, cyano, $C_{1-3}$alkyl, $C_{2-3}$alkenyl, $C_{1-4}$alkoxy, hydroxyl, cycloalkyl, —C(O)O—$C_{1-4}$alkyl, —C(O)NH$_2$, —OS(O$_2$)—$C_{1-4}$alkyl, —O—$C_{1-4}$alkyl-O—$C_{1-4}$alkyl, heterocyclyl, heteroaryl, or —S(O$_2$)—$C_{1-4}$alkyl; wherein said $C_{1-3}$alkyl may be substituted with halo or hydroxyl;
$R_3$ is —H, halo, cyano, or $C_{1-3}$alkyl; and

is a 4 to 9 membered heterocyclyl bonded to the rest of the molecule through a ring nitrogen atom and optionally containing 1-2 heteroatoms in addition to said ring nitrogen atom, wherein the optional 1-2 additional heteroatoms are independently selected from the group consisting of N, O and S;
wherein said 4 to 9 membered heterocyclyl may be substituted with $C_{1-4}$alkyl, $C_{2-4}$alkenyl, $C_{2-4}$alkynyl, halo, oxo, cyano, hydroxyl, —OR$^5$, —O—$C_{1-4}$alkyl-C(O)OR$^5$, cycloalkyl, heteroaryl, heterocyclyl, —C(O)OR$^5$, —C(O)N(R$^5$)(R$^6$), —C(O)N(R$^5$)(OR$^6$), —C(O)R$^5$, —C(O)—$C_{1-4}$alkyl-N(R$^5$)(R$^6$), —C(O)—$C_{1-4}$alkyl-O—$C_{1-4}$alkyl, —C(O)N(R$^5$)—S(O)$_2$(R$^6$), —C(O)N(R$^5$)—OR$^6$, —C(O)N(R$^5$)S(O)$_2$N(R$^5$)(R$^6$), —C(O)N(R$^5$)—$C_{1-4}$alkyl-C(O)OR$^6$,
—N(R$^5$)(R$^6$), —N(R$^5$)—$C_{1-4}$alkyl-OR$^6$, —N(R$^5$)C(O)R$^6$, —N(R$^5$)C(O)OR$^6$, —N(R$^5$)S(O)$_2$R$^6$, —N(R$^5$)C(O)—NH(R$^6$),
—N(R$^5$)—$C_{1-4}$alkyl-C(O)—NH(R$^6$), —SR$^5$, —S(O)$_2$R$^5$, or —S(O)$_2$—N(R$^5$)(R$^6$);
wherein said $C_{1-4}$alkyl may be substituted with —OH, —O—$C_{1-4}$alkyl, —C(O)OR$^5$, —C(O)N(R$^5$)(R$^6$), —N(R$^5$)(R$^6$), —N(R$^5$)C(O)OR$^6$, heterocyclyl, heteroaryl, cycloalkyl, or halo;
wherein said heteroaryl may be substituted with $C_{1-4}$alkyl, halo, cyano, —CF$_3$, alkoxy or hydroxyl;
wherein said heterocyclyl may be substituted with $C_{1-4}$alkyl, oxo, halo, amino, alkoxy, or hydroxyl;
wherein said $C_{2-4}$alkenyl and said $C_{2-4}$alkynyl may be independently substituted with oxo, heterocyclyl, hydroxyl, or halo;
wherein R$^5$ and R$^6$ are each independently —H, $C_{1-4}$alkyl, cycloalkyl, or heterocyclyl, wherein said $C_{1-4}$alkyl may be substituted with halo or hydroxyl; or alternatively R$^5$ and R$^6$ are linked together to form a 5-7 membered ring;

or an optical isomer, enantiomer, diastereomer, cis-trans isomer, racemate, or pharmaceutically acceptable salt thereof.

11. A method for treating a prediabetic condition in a subject in need thereof, comprising administering to said subject a therapeutically effective amount of at least one compound according to Formula (I)

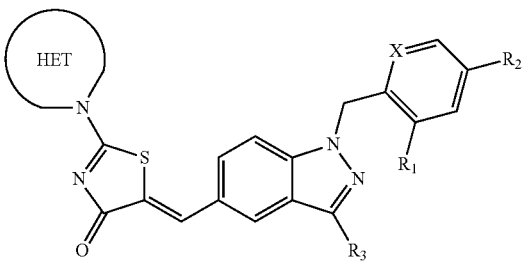

wherein
- X is —CH— or N;
- $R_1$ is $C_{1-3}$alkyl, halo, cycloalkyl, and —C(O)—$C_{1-4}$alkyl; wherein said $C_{1-3}$alkyl may be substituted with halo;
- $R_2$ is —H, halo, cyano, $C_{1-3}$alkyl, $C_{2-3}$alkenyl, $C_{1-4}$alkoxy, hydroxyl, cycloalkyl, —C(O)O—$C_{1-4}$alkyl, —C(O)NH_2, —OS(O_2)—$C_{1-4}$alkyl, —O—$C_{1-4}$alkyl-O—$C_{1-4}$alkyl, heterocyclyl, heteroaryl, or —S(O_2)—$C_{1-4}$alkyl; wherein said $C_{1-3}$alkyl may be substituted with halo or hydroxyl;
- $R_3$ is —H, halo, cyano, or $C_{1-3}$alkyl; and

is a 4 to 9 membered heterocyclyl bonded to the rest of the molecule through a ring nitrogen atom and optionally containing 1-2 heteroatoms in addition to said ring nitrogen atom, wherein the optional 1-2 additional heteroatoms are independently selected from the group consisting of N, O and S;

wherein said 4 to 9 membered heterocyclyl may be substituted with $C_{1-4}$alkyl, $C_{2-4}$alkenyl, $C_{2-4}$alkynyl, halo, oxo, cyano, hydroxyl, —$OR^5$, —O—$C_{1-4}$alkyl-C(O)$OR^5$, cycloalkyl, heteroaryl, heterocyclyl, —C(O)$OR^5$, —C(O)N($R^5$)($R^6$), —C(O)N($R^5$)($OR^6$), —C(O)$R^5$, —C(O)—$C_{1-4}$alkyl-N($R^5$)($R^6$), —C(O)—$C_{1-4}$alkyl-O—$C_{1-4}$alkyl, —C(O)N($R^5$)—S(O)_2($R^6$), —C(O)N($R^5$)—$OR^6$, —C(O)N($R^5$)S(O)_2N($R^5$)($R^6$), —C(O)N($R^5$)—$C_{1-4}$alkyl-C(O)$OR^6$, —N($R^5$)($R^6$), —N($R^5$)—$C_{1-4}$alkyl-$OR^6$, —N($R^5$)C(O)$R^6$, —N($R^5$)C(O)$OR^6$, —N($R^5$)S(O)_2$R^6$, —N($R^5$)C(O)—NH($R^6$), —N($R^5$)—$C_{1-4}$alkyl-C(O)—NH($R^6$), —$SR^5$, —S(O)_2$R^5$, or —S(O)_2—N($R^5$)($R^6$);

wherein said $C_{1-4}$alkyl may be substituted with —OH, —O—$C_{1-4}$alkyl, —C(O)$OR^5$, —C(O)N($R^5$)($R^6$), —N($R^5$)($R^6$), —N($R^5$)C(O)$OR^6$, heterocyclyl, heteroaryl, cycloalkyl, or halo;

wherein said heteroaryl may be substituted with $C_{1-4}$alkyl, halo, cyano, —$CF_3$, alkoxy or hydroxyl;

wherein said heterocyclyl may be substituted with $C_{1-4}$alkyl, oxo, halo, amino, alkoxy, or hydroxyl;

wherein said $C_{2-4}$alkenyl and said $C_{2-4}$alkynyl may be independently substituted with oxo, heterocyclyl, hydroxyl, or halo;

wherein $R^5$ and $R^6$ are each independently —H, $C_{1-4}$alkyl, cycloalkyl, or heterocyclyl, wherein said $C_{1-4}$alkyl may be substituted with halo or hydroxyl; or alternatively $R^5$ and $R^6$ are linked together to form a 5-7 membered ring;

or an optical isomer, enantiomer, diastereomer, cis-trans isomer, racemate, or pharmaceutically acceptable salt thereof.

12. The method of claim 1 wherein the therapeutically effective amount of the compound of Formula I is from about 0.1 mg/dose to about 5000 mg/dose.

13. The method of claim 1 wherein the therapeutically effective amount of the compound of Formula I is from about 0.5 mg/dose to about 1000 mg/dose.

14. The method of claim 1 wherein the therapeutically effective amount of the compound of Formula I is from about 1 mg/dose to about 100 mg/dose.

* * * * *